United States Patent
Chen et al.

(10) Patent No.: US 8,095,350 B2
(45) Date of Patent: Jan. 10, 2012

(54) THREE-DIMENSIONAL STRUCTURE OF THE APOBEC 2 STRUCTURE, USES THEREOF, AND METHODS FOR TREATING CHRONIC AND INFECTIOUS DISEASES

(76) Inventors: Xiaojiang Chen, Los Angeles, CA (US); Myron Goodman, La Canada, CA (US); Courtney Prochnow, Culver City, CA (US); Ronda Bransteitter, Culver City, CA (US)

(*) Notice: Subject to any disclaimer, the term of this patent is extended or adjusted under 35 U.S.C. 154(b) by 101 days.

(21) Appl. No.: 12/340,526

(22) Filed: Dec. 19, 2008

(65) Prior Publication Data

US 2009/0163422 A1 Jun. 25, 2009

Related U.S. Application Data

(60) Provisional application No. 61/016,172, filed on Dec. 21, 2007.

(51) Int. Cl.
*G06G 7/58* (2006.01)
*G01N 23/00* (2006.01)

(52) U.S. Cl. .......................................... 703/11; 702/19

(58) Field of Classification Search .................. None
See application file for complete search history.

(56) References Cited

OTHER PUBLICATIONS

McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Ginalski et al., Comparative Modeling for Protein Structure Prediction. Current Opinion in Structural Biololgy, 2006. vol. 16, pp. 172-177.*
Prochnow et al. "The APOBEC-2 crystal structure and functional implications for the deaminase AID", Nature, vol. 445, pp. 447-451—published on-line Dec. 24, 2006.*
Böhm et al., Journal of Computer-Aided Molecular Design, 1992, vol. 6, pp. 61-78.*
Goodsell et al., Journal of Molecular Recognition, 1996, vol. 9, pp. 1-5.*

(Continued)

*Primary Examiner* — Suzanne M. Noakes
(74) *Attorney, Agent, or Firm* — Beverly W. Lubit; Greenberg Traurig, LLP

(57) ABSTRACT

Three-dimensional structure of APOBEC-2 and other structure models of APOBEC proteins obtained by computer modeling that bear similarity with a root-mean-square deviation (RMSD) of 2.0 with the APOBEC-2 monomer, dimer or tetramer. Uses of the three-dimensional structure of APOBEC-2 and models of APOBEC proteins particularly for structure-based drug design of compounds, peptides or mutant APOBEC proteins designed to treat Hyper-IgM-2 Syndrome, B cell lymphomas and lentivirus infections, particularly the human immunodeficiency virus (HIV) infection. Methods for identifying a compound that binds to any fragment of an APOBEC protein. The method includes obtaining the three dimensional structure of the APOBEC-2 monomer, dimer or tetramer and identifying or designing one or more compounds that bind, mimic, enhance, disrupt, or compete with interactions of APOBEC family proteins with themselves, their nucleic acid substrates and other cellular or viral proteins based on the three dimensional structure of the APOBEC-2 protein.

20 Claims, 80 Drawing Sheets
(4 of 80 Drawing Sheet(s) Filed in Color)

OTHER PUBLICATIONS

Pham, P. et al., "Reward versus Risk: DNA Cytidine Deaminases Triggering Immunity and Disease", Biochemistry, (Mar. 1, 2005), vol. 44, No. 8, pp. 2703-2715.

Conticello, S.G. et al., "Evolution of the AID/APOBEC Family of Polynucleotide (Deoxy)cytidine Deaminases", Molecular Biology and Evolution, (2005), vol. 22, No. 2, pp. 367-377.

Bransteitter, R. et al., "First AID (Activation-induced Cytidine Deaminase) Is Needed to Produce High Affinity Isotype-switched Antibodies", Journal of Biological Chemistry (Jun. 23, 2006), vol. 281, No. 25, pp. 16833-16836.

Chiu, Y.L. et al., "Multifaceted antiviral actions of APOBEC3 cytidine deaminases", Trends in Immunology, (Jun. 2006), vol. 27, No. 6, pp. 291-297.

Cullen, B.R., "Role and Mechanism of Action of the APOBEC3 Family of Antiretroviral Resistance Factors", Journal of Virology, (Feb. 2006), vol. 80, pp. 1067-1076.

Franca, R. et al., "APOBEC deaminases as cellular antiviral factors: A novel natural host defense mechanism", Med. Sci. Monit., (2006), vol. 12, pp. RA92-RA98.

Bonvin, M. et al., "Interferon-inducible Expression of APOBEC3 Editing Enzymes in Human Hepatocytes and Inhibition of Hepatitis B Virus Replication", Hepatology, (2006), vol. 43, No. 6, pp. 1364-1374.

Johansson, E. et al., "Crystal structure of the tetrameric cytidine deaminase from Bacillus subtilis at 2.0 A resolution", Biochemistry, (2002), vol. 41, No. 8, pp. 2563-2570.

Xie, K. K et al., "The structure of a yeast RNA-editing deaminase provides insight into the fold and function of activation-induced deaminase and APOBEC-1", Proc. Natl. Acad. Sci. USA, (May 25, 2004), vol. 101, No. 21, pp. 8114-8119.

Teh, A. et al., "The 1.48 A Resolution Crystal Structure of the Homotetrameric Cytidine Deaminase from Mouse", Biochemistry, (2006), vol. 45, No. 25, pp. 7825-7833.

Chung, S.J. et al., "Structure of human cytidine deaminase bound to a potent inhibitor", Journal of Medicinal Chemistry, (2005), vol. 48, No. 3, pp. 658-660.

Betts, L. et al., "Cytidine deaminase. The 2.3 A crystal structure of an enzyme: transition-state analog complex", Journal of Molecular Biology, (Jan. 13, 1994), vol. 235, No. 2, pp. 635-656.

Smith, A.A. et al., "Mutations Affecting Transition-State Stabilization by Residues Coordinating Zinc at the Active Site of Cytidine Deaminase", Biochemistry, (1994), vol. 33, No. 21, pp. 6468-6474.

Durandy, A. et al., "Hyper-IgM syndromes", Current Opinion in Rheumatology, (Jul. 2006), vol. 18, No. 4, pp. 369-376.

Minegishi, Y. et al., "Mutations in Activation-induced Cytidine Deaminase in Patients with Hyper IgM Syndrome", Clinical Immunology, (Dec. 2000), vol. 97, No. 3, pp. 203-210.

Anant, S. et al., "ARCD-1, an APOBEC-1-related cytidine deaminase, exerts a dominant negative effect on C to U RNA editing", American Journal of Cell Physiology, (Dec. 1, 2001), vol. 281, pp. C1904-C1916.

Jarmuz, A. et al., "An anthropoid-specific locus of orphan C to U RNA-editing enzymes on chromosome 22", Genomics, (Mar. 2002), vol. 79, No. 3, pp. 285-296.

Shindo, K. et al., "The enzymatic activity of CEM15/APOBEC-3G is essential for the regulation of the infectivity of HIV-1 virion but not a sole determinant of its antiviral activity", Journal of Biological Chemistry, (Nov. 7, 2003), vol. 278, No. 45, pp. 44412-44416.

Wiegand, H.L. et al., "A second human antiretroviral factor, APOBEC3F, is suppressed by the HIV-1 and HIV-2 Vif proteins", The EMBO Journal, (Jun. 16, 2004), vol. 23, No. 12, pp. 2451-2458.

Opi, S. et al., "Monomeric APOBEC3G is catalytically active and has antiviral activity", Journal of Virology, (May 2006), vol. 80, No. 10, pp. 4673-4682.

Navarro, F. et al., "Complementary function of the two catalytic domains of APOBEC3G", Virology, (Mar. 15, 2005), vol. 333, No. 2, pp. 374-386.

Wang, J. et al., "Identification of a Specific Domain Required for Dimerization of Activation-induced Cytidine Deaminase", Journal of Biological Chemistry, (2006), vol. 281, pp. 19115-19123, withdrawn, (2008), vol. 283, No. 1, pp. 660.

Teng, B. et al., "Mutational analysis of apolipoprotein B mRNA editing enzyme (APOBEC1): structure-function relationships of RNA editing and dimerization", Journal of Lipid Research, (1999), vol. 40, No. 4, pp. 623-635.

Otwinowski, Z. et al., "Processing of X-ray Diffraction Data Collected in Oscillation Mode", Methods in Enzymology, (1997), vol. 276, pp. 307-326.

Terwilliger, T.C. et al., "Automated MAD and MIR structure solution", Acta Crystallographica, (1999), vol. 55, pp. 849-861.

Schneider, T.R. et al., "Substructure solution with SHELXD", Acta Crystallographica, (2002), vol. 58, pp. 1772-1779.

Terwilliger, T.C., "Maximum-likelihood density modification", Acta Crystallographica, (2000), vol. 56, pp. 965-972.

Bransteitter, R. et al."Activation-induced cytidine deaminase deaminates deoxycytidine on single-stranded DNA but requires the action of RNase", Proc. Natl. Acad. Sci. USA, (2003), vol. 100, pp. 4102-4107.

Okazaki, I.M. et al., "Role of AID in Tumorogenesis", Adv. Immunol., (2007), vol. 94, pp. 245-273.

* cited by examiner

Supplementary Materials

Supplementary Table 1 Data collection, phasing and refinement statistics (MIR)

|  | Native ($\lambda = 0.9774$ Å) | Peak Se ($\lambda = 0.9796$ Å) | Inflection Se ($\lambda = 0.9798$ Å) |
|---|---|---|---|
| Data collection | | | |
| Space group | $P2_12_12_1$ | $P2_12_12_1$ | $P2_12_12_1$ |
| Cell dimensions | | | |
| $a, b, c$ (Å) | 37.841, 89.41, 245.77 | 37.862, 88.952, 244.533 | 37.888, 89.016, 244.644 |
| $\alpha, \beta, \gamma$ (°) | 90.0, 90.0, 90.0 | 90.0, 90.0, 90.0 | 90.0, 90.0, 90.0 |
| Resolution (Å) | 50-2.5 (2.59-2.50)* | 50-2.8 (2.90-2.80) | 50-2.8 (2.90-2.80) |
| Observations | 383,800 | 547,891 | 540,462 |
| $R_{merge}$ | 15.1(33.3) | 10.7(32.2) | 10.2(35.5) |
| $I / \sigma I$ | 17.7(2.5) | 21.9(4.3) | 21.1(3.8) |
| Completeness (%) | 96.3(85.5) | 96.4(83.0) | 96.9(85.2) |
| Refinement | | | |
| Resolution (Å) | 50-2.5 | | |
| No. reflections | 24,699 | | |
| $R_{work} / R_{free}$ | 24.56/29.54 | | |
| No. atoms | | | |
| Protein | 5,994 | | |
| Zinc | 4 | | |
| Water | 88 | | |
| $B$-factors (Averaged) | | | |
| Protein | 29.97 | | |
| Zinc | 34.35 | | |
| Water | 26.97 | | |
| R.m.s deviations | | | |
| Bond lengths (Å) | .009299 | | |
| Bond angles (°) | 1.01753 | | |

Table contains data collection statistics obtained from a total of two crystals. *Highest-resolution shell is shown in parentheses.

FIG. 6 (con't)

FIG. 6 (con't)

FIG. 6 (con't)

```
REMARK 465   GLY D   35
REMARK 465   SER D   36
REMARK 465   GLY D   37
REMARK 465   GLY D   38
REMARK 465   GLY D   39
REMARK 465   GLU D  196
REMARK 465   GLY D  197
REMARK 465   GLU D  198
REMARK 465   SER D  199
REMARK 465   LYS D  200
REMARK 465   ALA D  201
REMARK 470
REMARK 470 MISSING ATOM
REMARK 470 THE FOLLOWING RESIDUES HAVE MISSING ATOMS(M=MODEL
NUMBER;
REMARK 470 RES=RESIDUE NAME; C=CHAIN IDENTIFIER; SSEQ=SEQUENCE
NUMBER;
REMARK 470 I=INSERTION CODE):
REMARK 470   M RES CSSEQI  ATOMS
REMARK 470     GLU A 196    CG   CD   OE1  OE2
REMARK 470     GLU B 196    CG   CD   OE1  OE2
REMARK 470     GLU B 198    CG   CD   OE1  OE2
REMARK 470     SER B 199    OG
REMARK 470     LYS B 200    CG   CD   CE   NZ
REMARK 470     GLU C 196    CG   CD   OE1  OE2
REMARK 470     GLU C 198    CG   CD   OE1  OE2
REMARK 470     SER C 199    OG
REMARK 470     LYS C 200    CG   CD   CE   NZ
REMARK 500
REMARK 500 GEOMETRY AND STEREOCHEMISTRY
REMARK 500 SUBTOPIC: COVALENT BOND LENGTHS
REMARK 500
REMARK 500 THE STEREOCHEMICAL PARAMETERS OF THE FOLLOWING
RESIDUES
REMARK 500 HAVE VALUES WHICH DEVIATE FROM EXPECTED VALUES BY
MORE
REMARK 500 THAN 6*RMSD (M=MODEL NUMBER; RES=RESIDUE NAME;
C=CHAIN
REMARK 500 IDENTIFIER; SSEQ=SEQUENCE NUMBER; I=INSERTION CODE).
REMARK 500
REMARK 500 STANDARD TABLE:
REMARK 500 FORMAT: (10X,I3,1X,2(A3,1X,A1,I4,A1,1X,A4,3X),F6.3)
REMARK 500
REMARK 500 EXPECTED VALUES: ENGH AND HUBER, 1991
REMARK 500
REMARK 500   M RES CSSEQI ATM1   RES CSSEQI ATM2   DEVIATION
REMARK 500     MET A  40   SD    MET A  40   CE    0.158
REMARK 500     MET A 156   SD    MET A 156   CE   -0.094
REMARK 500     MET A 179   SD    MET A 179   CE   -0.176
REMARK 500     MET B 179   SD    MET B 179   CE   -0.069
REMARK 500     MET C 179   SD    MET C 179   CE   -0.090
REMARK 500
REMARK 500 GEOMETRY AND STEREOCHEMISTRY
REMARK 500 SUBTOPIC: COVALENT BOND ANGLES
REMARK 500
REMARK 500 THE STEREOCHEMICAL PARAMETERS OF THE FOLLOWING
RESIDUES
REMARK 500 HAVE VALUES WHICH DEVIATE FROM EXPECTED VALUES BY
MORE
REMARK 500 THAN 6*RMSD (M=MODEL NUMBER; RES=RESIDUE NAME;
C=CHAIN
REMARK 500 IDENTIFIER; SSEQ=SEQUENCE NUMBER; I=INSERTION CODE).
REMARK 500
REMARK 500 STANDARD TABLE:
REMARK 500 FORMAT: (10X,I3,1X,A3,1X,A1,I4,A1,3(1X,A4,2X),12X,F5.1)
REMARK 500
REMARK 500 EXPECTED VALUES: ENGH AND HUBER, 1991
REMARK 500
REMARK 500   M RES CSSEQI ATM1   ATM2   ATM3
REMARK 500     MET A  40   CB  - CG  - SD    ANGL. DEV. =-12.2 DEGREES
REMARK 500     GLU B 206   N   - CA  - C     ANGL. DEV. = 6.5 DEGREES
REMARK 500     GLU C 206   N   - CA  - C     ANGL. DEV. = 7.1 DEGREES
REMARK 500     ARG D 116   N   - CA  - C     ANGL. DEV. =-6.1 DEGREES
DBREF  2NYT A   41   224  UNP    Q9Y235   ABEC2_HUMAN     41    224
DBREF  2NYT B   41   224  UNP    Q9Y235   ABEC2_HUMAN     41    224
DBREF  2NYT C   41   224  UNP    Q9Y235   ABEC2_HUMAN     41    224
DBREF  2NYT D   41   224  UNP    Q9Y235   ABEC2_HUMAN     41    224
SEQADV 2NYT GLY A   35  UNP  Q9Y235              CLONING ARTIFACT
SEQADV 2NYT SER A   36  UNP  Q9Y235              CLONING ARTIFACT
SEQADV 2NYT GLY A   37  UNP  Q9Y235              CLONING ARTIFACT
SEQADV 2NYT GLY A   38  UNP  Q9Y235              CLONING ARTIFACT
SEQADV 2NYT GLY A   39  UNP  Q9Y235              CLONING ARTIFACT
SEQADV 2NYT MET A   40  UNP  Q9Y235              CLONING ARTIFACT
SEQADV 2NYT GLY B   35  UNP  Q9Y235              CLONING ARTIFACT
SEQADV 2NYT SER B   36  UNP  Q9Y235              CLONING ARTIFACT
SEQADV 2NYT GLY B   37  UNP  Q9Y235              CLONING ARTIFACT
```

```
ATOM   3036  C   ILE C  41      11.435  -5.341  19.099  1.00 20.52           C
ATOM   3037  O   ILE C  41      11.856  -6.471  18.860  1.00 20.78           O
ATOM   3038  CB  ILE C  41       9.396  -5.927  20.405  1.00 21.61           C
ATOM   3039  CG1 ILE C  41       7.889  -5.723  20.551  1.00 19.60           C
ATOM   3040  CG2 ILE C  41      10.089  -5.510  21.702  1.00 19.91           C
ATOM   3041  CD1 ILE C  41       7.251  -6.532  21.677  1.00 16.52           C
ATOM   3042  N   VAL C  42      12.236  -4.293  19.257  1.00 20.64           N
ATOM   3043  CA  VAL C  42      13.697  -4.416  19.186  1.00 20.29           C
ATOM   3044  C   VAL C  42      14.224  -4.545  20.624  1.00 20.11           C
ATOM   3045  O   VAL C  42      14.022  -3.647  21.430  1.00 19.10           O
ATOM   3046  CB  VAL C  42      14.323  -3.163  18.509  1.00 19.89           C
ATOM   3047  CG1 VAL C  42      15.832  -3.335  18.329  1.00 18.15           C
ATOM   3048  CG2 VAL C  42      13.657  -2.932  17.165  1.00 18.58           C
ATOM   3049  N   THR C  43      14.874  -5.670  20.933  1.00 21.59           N
ATOM   3050  CA  THR C  43      15.428  -5.918  22.266  1.00 22.96           C
ATOM   3051  C   THR C  43      16.779  -6.589  22.197  1.00 23.91           C
ATOM   3052  O   THR C  43      17.124  -7.196  21.189  1.00 23.38           O
ATOM   3053  CB  THR C  43      14.554  -6.852  23.054  1.00 21.69           C
ATOM   3054  OG1 THR C  43      13.201  -6.504  22.797  1.00 27.90           O
ATOM   3055  CG2 THR C  43      14.827  -6.728  24.541  1.00 20.23           C
ATOM   3056  N   GLY C  44      17.533  -6.493  23.287  1.00 25.76           N
ATOM   3057  CA  GLY C  44      18.836  -7.116  23.327  1.00 26.74           C
ATOM   3058  C   GLY C  44      18.753  -8.537  23.846  1.00 28.98           C
ATOM   3059  O   GLY C  44      19.575  -9.377  23.488  1.00 29.38           O
ATOM   3060  N   GLU C  45      17.754  -8.821  24.685  1.00 29.06           N
ATOM   3061  CA  GLU C  45      17.603 -10.157  25.252  1.00 29.67           C
ATOM   3062  C   GLU C  45      17.468 -11.190  24.141  1.00 30.23           C
ATOM   3063  O   GLU C  45      16.804 -10.955  23.136  1.00 30.67           O
ATOM   3064  CB  GLU C  45      16.398 -10.198  26.190  1.00 29.86           C
ATOM   3065  CG  GLU C  45      16.234 -11.512  26.915  1.00 30.83           C
ATOM   3066  CD  GLU C  45      17.528 -12.012  27.515  1.00 31.53           C
ATOM   3067  OE1 GLU C  45      18.136 -11.294  28.343  1.00 33.73           O
ATOM   3068  OE2 GLU C  45      17.936 -13.137  27.157  1.00 31.19           O
ATOM   3069  N   ARG C  46      18.108 -12.334  24.319  1.00 31.50           N
ATOM   3070  CA  ARG C  46      18.071 -13.366  23.301  1.00 32.25           C
ATOM   3071  C   ARG C  46      17.139 -14.501  23.682  1.00 31.30           C
ATOM   3072  O   ARG C  46      16.416 -15.011  22.835  1.00 30.77           O
ATOM   3073  CB  ARG C  46      19.480 -13.914  23.085  1.00 35.44           C
ATOM   3074  CG  ARG C  46      19.743 -14.461  21.696  1.00 41.03           C
ATOM   3075  CD  ARG C  46      20.051 -13.333  20.724  1.00 45.37           C
ATOM   3076  NE  ARG C  46      20.255 -13.809  19.353  1.00 49.76           N
ATOM   3077  CZ  ARG C  46      21.239 -14.613  18.954  1.00 51.47           C
ATOM   3078  NH1 ARG C  46      22.152 -15.058  19.812  1.00 52.53           N
ATOM   3079  NH2 ARG C  46      21.295 -14.985  17.685  1.00 52.71           N
ATOM   3080  N   LEU C  47      17.174 -14.891  24.959  1.00 30.33           N
ATOM   3081  CA  LEU C  47      16.358 -15.989  25.487  1.00 30.61           C
ATOM   3082  C   LEU C  47      14.933 -15.564  25.835  1.00 29.07           C
ATOM   3083  O   LEU C  47      14.726 -14.557  26.514  1.00 27.58           O
ATOM   3084  CB  LEU C  47      17.006 -16.601  26.740  1.00 32.78           C
ATOM   3085  CG  LEU C  47      16.150 -17.597  27.555  1.00 36.71           C
ATOM   3086  CD1 LEU C  47      16.008 -18.931  26.776  1.00 36.83           C
ATOM   3087  CD2 LEU C  47      16.771 -17.808  28.963  1.00 35.00           C
ATOM   3088  N   PRO C  48      13.931 -16.341  25.378  1.00 27.60           N
ATOM   3089  CA  PRO C  48      12.528 -16.025  25.653  1.00 26.20           C
ATOM   3090  C   PRO C  48      12.260 -15.877  27.152  1.00 25.50           C
ATOM   3091  O   PRO C  48      11.697 -14.881  27.592  1.00 24.81           O
ATOM   3092  CB  PRO C  48      11.789 -17.219  25.059  1.00 24.82           C
ATOM   3093  CG  PRO C  48      12.650 -17.610  23.927  1.00 25.93           C
ATOM   3094  CD  PRO C  48      14.025 -17.548  24.538  1.00 26.99           C
ATOM   3095  N   ALA C  49      12.676 -16.877  27.925  1.00 24.55           N
ATOM   3096  CA  ALA C  49      12.456 -16.865  29.364  1.00 23.55           C
ATOM   3097  C   ALA C  49      12.899 -15.566  30.006  1.00 23.21           C
ATOM   3098  O   ALA C  49      12.196 -15.007  30.849  1.00 23.67           O
ATOM   3099  CB  ALA C  49      13.168 -18.016  30.007  1.00 22.92           C
ATOM   3100  N   ASN C  50      14.076 -15.091  29.626  1.00 22.90           N
ATOM   3101  CA  ASN C  50      14.583 -13.841  30.159  1.00 21.05           C
ATOM   3102  C   ASN C  50      13.725 -12.653  29.703  1.00 19.93           C
ATOM   3103  O   ASN C  50      13.448 -11.754  30.483  1.00 17.95           O
ATOM   3104  CB  ASN C  50      16.029 -13.613  29.727  1.00 23.78           C
ATOM   3105  CG  ASN C  50      17.028 -14.352  30.591  1.00 25.53           C
ATOM   3106  OD1 ASN C  50      16.987 -14.264  31.819  1.00 27.43           O
ATOM   3107  ND2 ASN C  50      17.944 -15.073  29.959  1.00 28.14           N
ATOM   3108  N   PHE C  51      13.319 -12.642  28.433  1.00 18.81           N
ATOM   3109  CA  PHE C  51      12.509 -11.548  27.901  1.00 17.02           C
ATOM   3110  C   PHE C  51      11.197 -11.415  28.663  1.00 16.85           C
ATOM   3111  O   PHE C  51      10.883 -10.354  29.221  1.00 17.16           O
ATOM   3112  CB  PHE C  51      12.223 -11.772  26.413  1.00 16.69           C
ATOM   3113  CG  PHE C  51      11.214 -10.826  25.837  1.00 13.42           C
ATOM   3114  CD1 PHE C  51      11.549  -9.504  25.578  1.00 13.59           C
ATOM   3115  CD2 PHE C  51       9.899 -11.237  25.631  1.00 13.42           C
ATOM   3116  CE1 PHE C  51      10.588  -8.597  25.137  1.00 13.61           C
ATOM   3117  CE2 PHE C  51       8.929 -10.343  25.184  1.00 12.96           C
ATOM   3118  CZ  PHE C  51       9.273  -9.020  24.942  1.00 12.62           C
ATOM   3119  N   PHE C  52      10.437 -12.498  28.700  1.00 17.51           N
ATOM   3120  CA  PHE C  52       9.141 -12.470  29.368  1.00 19.77           C
ATOM   3121  C   PHE C  52       9.187 -12.269  30.868  1.00 21.23           C
```

FIG. 6 (con't)

FIG. 6 (con't)

FIG. 6 (con't)

| | | | | | | | | |
|---|---|---|---|---|---|---|---|---|
| ATOM | 24 | CG MET A 40 | -6.560 -9.748 74.122 1.00 34.33 | C | ATOM | 3294 | CA TYR C 72 | -1.606 -5.761 21.117 1.00 14.20 | C |
| ATOM | 25 | SD MET A 40 | -5.122 -10.626 73.644 1.00 35.10 | S | ATOM | 3295 | C TYR C 72 | -1.861 -6.188 19.677 1.00 13.90 | C |
| ATOM | 26 | CE MET A 40 | -4.743 -11.654 75.256 1.00 35.47 | C | ATOM | 3296 | O TYR C 72 | -0.949 -6.256 18.839 1.00 12.83 | O |
| ATOM | 27 | N ILE A 41 | -9.716 -10.323 72.366 1.00 27.95 | N | ATOM | 3297 | CB TYR C 72 | -2.286 -4.421 21.391 1.00 15.01 | C |
| ATOM | 28 | CA ILE A 41 | -10.388 -9.766 71.211 1.00 25.80 | C | ATOM | 3298 | CG TYR C 72 | -1.751 -3.288 20.540 1.00 17.85 | C |
| ATOM | 29 | C ILE A 41 | -11.877 -10.047 71.277 1.00 24.30 | C | ATOM | 3299 | CD1 TYR C 72 | -2.137 -3.149 19.206 1.00 17.20 | C |
| ATOM | 30 | O ILE A 41 | -12.276 -11.209 71.304 1.00 23.96 | O | ATOM | 3300 | CD2 TYR C 72 | -0.834 -2.379 21.057 1.00 17.95 | C |
| ATOM | 31 | CB ILE A 41 | -9.867 -10.404 69.915 1.00 24.92 | C | ATOM | 3301 | CE1 TYR C 72 | -1.615 -2.130 18.402 1.00 20.96 | C |
| ATOM | 32 | CG1 ILE A 41 | -8.355 -10.185 69.796 1.00 25.08 | C | ATOM | 3302 | CE2 TYR C 72 | -0.305 -1.358 20.267 1.00 18.98 | C |
| ATOM | 33 | CG2 ILE A 41 | -10.568 -9.804 68.725 1.00 23.59 | C | ATOM | 3303 | CZ TYR C 72 | -0.695 -1.237 18.951 1.00 21.32 | C |
| ATOM | 34 | CD1 ILE A 41 | -7.707 -10.772 68.525 1.00 20.84 | C | ATOM | 3304 | OH TYR C 72 | -0.170 -0.222 18.176 1.00 22.85 | O |
| ATOM | 35 | N VAL A 42 | -12.691 -8.994 71.305 1.00 23.41 | N | ATOM | 3305 | N VAL C 73 | -3.129 -6.483 19.414 1.00 13.88 | N |
| ATOM | 36 | CA VAL A 42 | -14.155 -9.137 71.343 1.00 22.08 | C | ATOM | 3306 | CA VAL C 73 | -3.611 -6.879 18.095 1.00 14.76 | C |
| ATOM | 37 | C VAL A 42 | -14.679 -9.043 69.905 1.00 22.86 | C | ATOM | 3307 | C VAL C 73 | -5.009 -6.273 17.860 1.00 15.24 | C |
| ATOM | 38 | O VAL A 42 | -14.486 -8.024 69.241 1.00 23.94 | O | ATOM | 3308 | O VAL C 73 | -5.901 -6.412 18.692 1.00 16.12 | O |
| ATOM | 39 | CB VAL A 42 | -14.794 -8.024 72.217 1.00 20.15 | C | ATOM | 3309 | CB VAL C 73 | -3.703 -8.426 17.956 1.00 13.53 | C |
| ATOM | 40 | CG1 VAL A 42 | -16.297 -8.251 72.370 1.00 18.38 | C | ATOM | 3310 | CG1 VAL C 73 | -4.434 -8.763 16.694 1.00 13.14 | C |
| ATOM | 41 | CG2 VAL A 42 | -14.135 -8.000 73.579 1.00 18.94 | C | ATOM | 3311 | CG2 VAL C 73 | -2.303 -9.045 17.879 1.00 15.17 | C |
| ATOM | 42 | N THR A 43 | -15.322 -10.105 69.424 1.00 22.77 | N | ATOM | 3312 | N VAL C 74 | -5.192 -5.592 16.734 1.00 16.75 | N |
| ATOM | 43 | CA THR A 43 | -15.881 -10.141 68.073 1.00 22.69 | C | ATOM | 3313 | CA VAL C 74 | -6.485 -4.991 16.435 1.00 17.84 | C |
| ATOM | 44 | C THR A 43 | -17.234 -10.827 68.032 1.00 23.62 | C | ATOM | 3314 | C VAL C 74 | -7.033 -5.464 15.097 1.00 20.23 | C |
| ATOM | 45 | O THR A 43 | -17.581 -11.575 68.939 1.00 23.01 | O | ATOM | 3315 | O VAL C 74 | -6.315 -5.498 14.099 1.00 21.94 | O |
| ATOM | 46 | CB THR A 43 | -14.996 -10.906 67.129 1.00 22.17 | C | ATOM | 3316 | CB VAL C 74 | -6.402 -3.450 16.403 1.00 16.51 | C |
| ATOM | 47 | OG1 THR A 43 | -13.646 -10.544 67.406 1.00 28.17 | O | ATOM | 3317 | CG1 VAL C 74 | -7.748 -2.869 16.024 1.00 14.53 | C |
| ATOM | 48 | CG2 THR A 43 | -15.309 -10.568 65.685 1.00 20.20 | C | ATOM | 3318 | CG2 VAL C 74 | -5.963 -2.922 17.755 1.00 13.66 | C |
| ATOM | 49 | N GLY A 44 | -17.978 -10.575 66.960 1.00 23.82 | N | ATOM | 3319 | N GLU C 75 | -8.301 -5.842 15.088 1.00 23.04 | N |
| ATOM | 50 | CA GLY A 44 | -19.275 -11.182 66.813 1.00 24.08 | C | ATOM | 3320 | CA GLU C 75 | -8.947 -6.298 13.864 1.00 25.68 | C |
| ATOM | 51 | C GLY A 44 | -19.191 -12.501 66.067 1.00 25.62 | C | ATOM | 3321 | C GLU C 75 | -10.373 -5.762 13.815 1.00 25.92 | C |
| ATOM | 52 | O GLY A 44 | -20.002 -13.398 66.283 1.00 25.79 | O | ATOM | 3322 | O GLU C 75 | -11.197 -6.116 14.650 1.00 23.58 | O |
| ATOM | 53 | N GLU A 45 | -18.203 -12.625 65.190 1.00 25.75 | N | ATOM | 3323 | CB GLU C 75 | -8.955 -7.820 13.802 1.00 27.24 | C |
| ATOM | 54 | CA GLU A 45 | -18.038 -13.845 64.429 1.00 27.88 | C | ATOM | 3324 | CG GLU C 75 | -7.557 -8.418 13.823 1.00 33.29 | C |
| ATOM | 55 | C GLU A 45 | -17.896 -15.039 65.376 1.00 28.91 | C | ATOM | 3325 | CD GLU C 75 | -7.559 -9.908 13.532 1.00 36.25 | C |
| ATOM | 56 | O GLU A 45 | -17.236 -14.942 66.403 1.00 29.04 | O | ATOM | 3326 | OE1 GLU C 75 | -8.349 -10.633 14.167 1.00 38.19 | O |
| ATOM | 57 | CB GLU A 45 | -16.821 -13.735 63.520 1.00 28.06 | C | ATOM | 3327 | OE2 GLU C 75 | -6.758 -10.350 12.678 1.00 39.93 | O |
| ATOM | 58 | CG GLU A 45 | -16.651 -14.917 62.609 1.00 30.62 | C | ATOM | 3328 | N ALA C 76 | -10.648 -4.896 12.836 1.00 27.55 | N |
| ATOM | 59 | CD GLU A 45 | -17.947 -15.312 61.937 1.00 31.52 | C | ATOM | 3329 | CA ALA C 76 | -11.973 -4.313 12.661 1.00 29.35 | C |
| ATOM | 60 | OE1 GLU A 45 | -18.569 -14.448 61.284 1.00 32.36 | O | ATOM | 3330 | C ALA C 76 | -12.629 -4.812 11.378 1.00 31.61 | C |
| ATOM | 61 | OE2 GLU A 45 | -18.342 -16.497 62.066 1.00 32.94 | O | ATOM | 3331 | O ALA C 76 | -12.005 -4.854 10.318 1.00 32.23 | O |
| ATOM | 62 | N ARG A 46 | -18.520 -16.159 65.028 1.00 30.75 | N | ATOM | 3332 | CB ALA C 76 | -11.882 -2.799 12.644 1.00 28.53 | C |
| ATOM | 63 | CA ARG A 46 | -18.474 -17.341 65.871 1.00 32.60 | C | ATOM | 3333 | N GLN C 77 | -13.895 -5.196 11.487 1.00 35.17 | N |
| ATOM | 64 | C ARG A 46 | -17.531 -18.414 65.311 1.00 32.42 | C | ATOM | 3334 | CA GLN C 77 | -14.669 -5.692 10.355 1.00 38.73 | C |
| ATOM | 65 | O ARG A 46 | -16.793 -19.051 66.063 1.00 32.04 | O | ATOM | 3335 | C GLN C 77 | -15.856 -4.756 10.133 1.00 39.92 | C |
| ATOM | 66 | CB ARG A 46 | -19.882 -17.923 65.998 1.00 36.08 | C | ATOM | 3336 | O GLN C 77 | -16.458 -4.272 11.090 1.00 40.27 | O |
| ATOM | 67 | CG ARG A 46 | -20.144 -18.681 67.276 1.00 40.89 | C | ATOM | 3337 | CB GLN C 77 | -15.160 -7.111 10.650 1.00 41.13 | C |
| ATOM | 68 | CD ARG A 46 | -20.455 -17.716 68.408 1.00 45.55 | C | ATOM | 3338 | CG GLN C 77 | -16.495 -7.464 9.992 1.00 46.73 | C |
| ATOM | 69 | NE ARG A 46 | -20.654 -18.398 69.686 1.00 49.81 | N | ATOM | 3339 | CD GLN C 77 | -17.373 -8.356 10.869 1.00 50.10 | C |
| ATOM | 70 | CZ ARG A 46 | -21.637 -19.254 69.955 1.00 52.19 | C | ATOM | 3340 | OE1 GLN C 77 | -18.535 -8.626 10.544 1.00 51.62 | O |
| ATOM | 71 | NH1 ARG A 46 | -22.554 -19.555 69.037 1.00 52.84 | N | ATOM | 3341 | NE2 GLN C 77 | -16.817 -8.818 11.987 1.00 52.36 | N |
| ATOM | 72 | NH2 ARG A 46 | -21.689 -19.825 71.151 1.00 53.17 | N | ATOM | 3342 | N GLY C 78 | -16.189 -4.503 8.871 1.00 41.78 | N |
| ATOM | 73 | N LEU A 47 | -17.567 -18.605 63.989 1.00 31.06 | N | ATOM | 3343 | CA GLY C 78 | -17.309 -3.628 8.554 1.00 43.14 | C |
| ATOM | 74 | CA LEU A 47 | -16.740 -19.604 63.308 1.00 30.16 | C | ATOM | 3344 | C GLY C 78 | -18.136 -4.183 7.415 1.00 45.00 | C |
| ATOM | 75 | C LEU A 47 | -15.319 -19.108 63.042 1.00 28.29 | C | ATOM | 3345 | O GLY C 78 | -17.604 -4.544 6.361 1.00 44.86 | O |
| ATOM | 76 | O LEU A 47 | -15.127 -17.987 62.571 1.00 27.10 | O | ATOM | 3346 | N LYS C 79 | -19.447 -4.248 7.623 1.00 46.65 | N |
| ATOM | 77 | CB LEU A 47 | -17.388 -20.006 61.970 1.00 33.05 | C | ATOM | 3347 | CA LYS C 79 | -20.349 -4.783 6.610 1.00 47.68 | C |
| ATOM | 78 | CG LEU A 47 | -16.509 -20.838 61.010 1.00 37.28 | C | ATOM | 3348 | C LYS C 79 | -20.340 -3.875 5.392 1.00 46.97 | C |
| ATOM | 79 | CD1 LEU A 47 | -16.346 -22.281 61.551 1.00 36.15 | C | ATOM | 3349 | O LYS C 79 | -21.162 -2.967 5.275 1.00 48.03 | O |
| ATOM | 80 | CD2 LEU A 47 | -17.125 -20.806 59.591 1.00 35.68 | C | ATOM | 3350 | CB LYS C 79 | -21.771 -4.908 7.189 1.00 49.30 | C |
| ATOM | 81 | N PRO A 48 | -14.306 -19.941 63.349 1.00 26.74 | N | ATOM | 3351 | CG LYS C 79 | -22.689 -5.870 6.432 1.00 51.79 | C |
| ATOM | 82 | CA PRO A 48 | -12.898 -19.586 63.136 1.00 25.76 | C | ATOM | 3352 | CD LYS C 79 | -23.497 -6.733 7.395 1.00 53.28 | C |
| ATOM | 83 | C PRO A 48 | -12.624 -19.188 61.692 1.00 25.17 | C | ATOM | 3353 | CE LYS C 79 | -24.307 -7.786 6.655 1.00 54.43 | C |
| ATOM | 84 | O PRO A 48 | -12.045 -18.134 61.430 1.00 25.26 | O | ATOM | 3354 | NZ LYS C 79 | -25.042 -8.674 7.603 1.00 56.65 | N |
| ATOM | 85 | CB PRO A 48 | -12.161 -20.861 63.521 1.00 23.74 | C | ATOM | 3355 | N GLY C 80 | -19.391 -4.114 4.494 1.00 45.55 | N |
| ATOM | 86 | CG PRO A 48 | -13.012 -21.405 64.605 1.00 22.93 | C | ATOM | 3356 | CA GLY C 80 | -19.294 -3.316 3.291 1.00 44.65 | C |
| ATOM | 87 | CD PRO A 48 | -14.399 -21.241 64.034 1.00 26.04 | C | ATOM | 3357 | C GLY C 80 | -17.960 -3.494 2.603 1.00 44.50 | C |
| ATOM | 88 | N ALA A 49 | -13.050 -20.041 60.766 1.00 25.16 | N | ATOM | 3358 | O GLY C 80 | -17.658 -2.810 1.622 1.00 45.83 | O |
| ATOM | 89 | CA ALA A 49 | -12.845 -19.805 59.340 1.00 24.41 | C | ATOM | 3359 | N GLY C 81 | -17.160 -4.427 3.111 1.00 42.91 | N |
| ATOM | 90 | C ALA A 49 | -13.306 -18.437 58.904 1.00 23.89 | C | ATOM | 3360 | CA GLY C 81 | -15.844 -4.672 2.546 1.00 40.31 | C |
| ATOM | 91 | O ALA A 49 | -12.634 -17.782 58.119 1.00 24.84 | O | ATOM | 3361 | C GLY C 81 | -14.729 -3.910 3.260 1.00 39.13 | C |
| ATOM | 92 | CB ALA A 49 | -13.552 -20.854 58.528 1.00 24.69 | C | ATOM | 3362 | O GLY C 81 | -13.583 -3.961 2.820 1.00 38.82 | O |
| ATOM | 93 | N ASN A 50 | -14.469 -18.012 59.389 1.00 23.87 | N | ATOM | 3363 | N GLN C 82 | -15.063 -3.208 4.349 1.00 37.19 | N |
| ATOM | 94 | CA ASN A 50 | -14.977 -16.689 59.039 1.00 21.61 | C | ATOM | 3364 | CA GLN C 82 | -14.091 -2.434 5.133 1.00 35.54 | C |
| ATOM | 95 | C ASN A 50 | -14.119 -15.593 59.677 1.00 20.06 | C | ATOM | 3365 | C GLN C 82 | -13.374 -3.351 6.131 1.00 33.75 | C |
| ATOM | 96 | O ASN A 50 | -13.817 -14.589 59.044 1.00 19.10 | O | ATOM | 3366 | O GLN C 82 | -14.006 -4.011 6.956 1.00 32.01 | O |
| ATOM | 97 | CB ASN A 50 | -16.424 -16.526 59.488 1.00 23.81 | C | ATOM | 3367 | CB GLN C 82 | -14.800 -1.306 5.895 1.00 36.08 | C |
| ATOM | 98 | CG ASN A 50 | -17.402 -17.156 58.527 1.00 25.18 | C | ATOM | 3368 | CG GLN C 82 | -15.919 -0.667 5.103 1.00 39.05 | C |
| ATOM | 99 | OD1 ASN A 50 | -17.334 -16.923 57.321 1.00 27.07 | O | ATOM | 3369 | CD GLN C 82 | -17.065 -0.202 5.974 1.00 39.35 | C |
| ATOM | 100 | ND2 ASN A 50 | -18.325 -17.950 59.053 1.00 27.29 | N | ATOM | 3370 | OE1 GLN C 82 | -16.945 0.776 6.705 1.00 38.33 | O |
| ATOM | 101 | N PHE A 51 | -13.732 -15.775 60.889 1.00 18.54 | N | ATOM | 3371 | NE2 GLN C 82 | -18.193 -0.915 5.895 1.00 38.01 | N |
| ATOM | 102 | CA PHE A 51 | -12.919 -14.774 61.621 1.00 17.24 | C | ATOM | 3372 | N VAL C 83 | -12.051 -3.407 6.044 1.00 32.72 | N |
| ATOM | 103 | C PHE A 51 | -11.605 -14.495 60.889 1.00 18.07 | C | ATOM | 3373 | CA VAL C 83 | -11.286 -4.253 6.949 1.00 30.36 | C |
| ATOM | 104 | O PHE A 51 | -11.316 -13.356 60.505 1.00 18.63 | O | ATOM | 3374 | C VAL C 83 | -9.987 -3.593 7.363 1.00 29.84 | C |
| ATOM | 105 | CB PHE A 51 | -12.620 -15.226 63.043 1.00 15.20 | C | ATOM | 3375 | O VAL C 83 | -9.245 -3.080 6.529 1.00 30.66 | O |
| ATOM | 106 | CG PHE A 51 | -11.610 -14.376 63.741 1.00 14.28 | C | ATOM | 3376 | CB VAL C 83 | -10.952 -5.598 6.302 1.00 29.89 | C |
| ATOM | 107 | CD1 PHE A 51 | -11.955 -13.119 64.211 1.00 13.22 | C | ATOM | 3377 | CG1 VAL C 83 | -10.226 -6.468 7.292 1.00 28.24 | C |
| ATOM | 108 | CD2 PHE A 51 | -10.299 -14.814 63.882 1.00 12.20 | C | ATOM | 3378 | CG2 VAL C 83 | -12.213 -6.273 5.823 1.00 28.89 | C |
| ATOM | 109 | CE1 PHE A 51 | -11.010 -12.307 64.807 1.00 13.49 | C | ATOM | 3379 | N GLN C 84 | -9.709 -3.617 8.658 1.00 28.36 | N |

FIG. 6 (con't)

| | | | | | | | |
|---|---|---|---|---|---|---|---|
| ATOM | 110 | CE2 PHE A 51 | -9.345 -14.009 64.475 1.00 12.16 | C | ATOM | 3380 | CA GLN C 84 | -8.494 -3.023 9.201 1.00 26.62 | C |
| ATOM | 111 | CZ PHE A 51 | -9.700 -12.750 64.939 1.00 13.88 | C | ATOM | 3381 | C GLN C 84 | -7.902 -3.982 10.213 1.00 26.25 | C |
| ATOM | 112 | N PHE A 52 | -10.806 -15.546 60.706 1.00 18.74 | N | ATOM | 3382 | O GLN C 84 | -8.591 -4.382 11.132 1.00 26.54 | O |
| ATOM | 113 | CA PHE A 52 | -9.517 -15.431 60.040 1.00 19.25 | C | ATOM | 3383 | CB GLN C 84 | -8.836 -1.724 9.902 1.00 25.11 | C |
| ATOM | 114 | C PHE A 52 | -9.583 -15.020 58.579 1.00 21.22 | C | ATOM | 3384 | CG GLN C 84 | -9.514 -0.735 9.011 1.00 26.91 | C |
| ATOM | 115 | O PHE A 52 | -8.592 -14.543 58.039 1.00 21.77 | O | ATOM | 3385 | CD GLN C 84 | -9.998 0.451 9.783 1.00 27.76 | C |
| ATOM | 116 | CB PHE A 52 | -8.721 -16.730 60.158 1.00 17.63 | C | ATOM | 3386 | OE1 GLN C 84 | -9.507 0.734 10.874 1.00 29.17 | O |
| ATOM | 117 | CG PHE A 52 | -8.288 -17.036 61.549 1.00 16.54 | C | ATOM | 3387 | NE2 GLN C 84 | -10.972 1.160 9.228 1.00 28.98 | N |
| ATOM | 118 | CD1 PHE A 52 | -9.031 -17.901 62.332 1.00 15.12 | C | ATOM | 3388 | N ALA C 85 | -6.632 -4.350 10.049 1.00 26.44 | N |
| ATOM | 119 | CD2 PHE A 52 | -7.175 -16.400 62.099 1.00 15.65 | C | ATOM | 3389 | CA ALA C 85 | -5.992 -5.262 10.997 1.00 25.64 | C |
| ATOM | 120 | CE1 PHE A 52 | -8.678 -18.127 63.644 1.00 17.35 | C | ATOM | 3390 | C ALA C 85 | -4.538 -4.855 11.230 1.00 25.02 | C |
| ATOM | 121 | CE2 PHE A 52 | -6.820 -16.622 63.420 1.00 17.05 | C | ATOM | 3391 | O ALA C 85 | -3.679 -5.105 10.385 1.00 26.20 | O |
| ATOM | 122 | CZ PHE A 52 | -7.570 -17.487 64.199 1.00 15.92 | C | ATOM | 3392 | CB ALA C 85 | -6.056 -6.708 10.483 1.00 24.28 | C |
| ATOM | 123 | N LYS A 53 | -10.732 -15.209 57.933 1.00 22.58 | N | ATOM | 3393 | N SER C 86 | -4.270 -4.222 12.361 1.00 23.53 | N |
| ATOM | 124 | CA LYS A 53 | -10.860 -14.826 56.530 1.00 24.42 | C | ATOM | 3394 | CA SER C 86 | -2.922 -3.808 12.683 1.00 23.26 | C |
| ATOM | 125 | C LYS A 53 | -11.376 -13.414 56.300 1.00 23.52 | C | ATOM | 3395 | C SER C 86 | -2.397 -4.598 13.875 1.00 23.15 | C |
| ATOM | 126 | O LYS A 53 | -11.255 -12.905 55.191 1.00 24.47 | O | ATOM | 3396 | O SER C 86 | -3.144 -5.319 14.541 1.00 23.40 | O |
| ATOM | 127 | CB LYS A 53 | -11.777 -15.798 55.763 1.00 26.77 | C | ATOM | 3397 | CB SER C 86 | -2.876 -2.313 13.020 1.00 22.77 | C |
| ATOM | 128 | CG LYS A 53 | -11.058 -16.979 55.079 1.00 31.52 | C | ATOM | 3398 | OG SER C 86 | -3.466 -2.071 14.267 1.00 19.73 | O |
| ATOM | 129 | CD LYS A 53 | -10.402 -17.973 56.080 1.00 32.24 | C | ATOM | 3399 | N ARG C 87 | -1.104 -4.461 14.142 1.00 22.60 | N |
| ATOM | 130 | CE LYS A 53 | -8.853 -18.053 55.976 1.00 34.63 | C | ATOM | 3400 | CA ARG C 87 | -0.486 -5.171 15.249 1.00 20.20 | C |
| ATOM | 131 | NZ LYS A 53 | -8.352 -18.705 54.728 1.00 34.84 | N | ATOM | 3401 | C ARG C 87 | 0.758 -4.423 15.717 1.00 17.91 | C |
| ATOM | 132 | N PHE A 54 | -11.957 -12.794 57.324 1.00 22.89 | N | ATOM | 3402 | O ARG C 87 | 1.555 -3.952 14.909 1.00 17.13 | O |
| ATOM | 133 | CA PHE A 54 | -12.509 -11.441 57.205 1.00 22.84 | C | ATOM | 3403 | CB ARG C 87 | -0.138 -6.590 14.794 1.00 21.11 | C |
| ATOM | 134 | C PHE A 54 | -12.018 -10.471 58.294 1.00 23.16 | C | ATOM | 3404 | CG ARG C 87 | 0.405 -7.464 15.895 1.00 24.50 | C |
| ATOM | 135 | O PHE A 54 | -11.243 -9.546 58.019 1.00 24.84 | O | ATOM | 3405 | CD ARG C 87 | 0.564 -8.879 15.402 1.00 27.17 | C |
| ATOM | 136 | CB PHE A 54 | -14.051 -11.491 57.229 1.00 23.62 | C | ATOM | 3406 | NE ARG C 87 | 1.759 -9.033 14.593 1.00 30.42 | N |
| ATOM | 137 | CG PHE A 54 | -14.656 -12.322 56.114 1.00 24.14 | C | ATOM | 3407 | CZ ARG C 87 | 1.853 -9.849 13.552 1.00 33.09 | C |
| ATOM | 138 | CD1 PHE A 54 | -15.247 -13.556 56.380 1.00 23.43 | C | ATOM | 3408 | NH1 ARG C 87 | 0.805 -10.588 13.185 1.00 34.29 | N |
| ATOM | 139 | CD2 PHE A 54 | -14.599 -11.879 54.796 1.00 23.29 | C | ATOM | 3409 | NH2 ARG C 87 | 2.990 -9.022 12.879 1.00 31.58 | N |
| ATOM | 140 | CE1 PHE A 54 | -15.768 -14.337 55.347 1.00 24.86 | C | ATOM | 3410 | N GLY C 88 | 0.919 -4.300 17.022 1.00 16.85 | N |
| ATOM | 141 | CE2 PHE A 54 | -15.116 -12.652 53.760 1.00 23.63 | C | ATOM | 3411 | CA GLY C 88 | 2.080 -3.593 17.533 1.00 17.23 | C |
| ATOM | 142 | CZ PHE A 54 | -15.702 -13.884 54.034 1.00 24.34 | C | ATOM | 3412 | C GLY C 88 | 2.300 -3.764 19.020 1.00 17.46 | C |
| ATOM | 143 | N GLN A 55 | -12.461 -10.682 59.527 1.00 21.78 | N | ATOM | 3413 | O GLY C 88 | 1.827 -4.735 19.616 1.00 19.20 | O |
| ATOM | 144 | CA GLN A 55 | -12.076 -9.814 60.622 1.00 22.32 | C | ATOM | 3414 | N TYR C 89 | 3.010 -2.827 19.631 1.00 16.81 | N |
| ATOM | 145 | C GLN A 55 | -10.579 -9.792 60.881 1.00 20.63 | C | ATOM | 3415 | CA TYR C 89 | 3.290 -2.900 21.049 1.00 17.24 | C |
| ATOM | 146 | O GLN A 55 | -10.023 -8.786 61.313 1.00 19.51 | O | ATOM | 3416 | C TYR C 89 | 3.652 -1.535 21.573 1.00 17.77 | C |
| ATOM | 147 | CB GLN A 55 | -12.821 -10.215 61.913 1.00 25.16 | C | ATOM | 3417 | O TYR C 89 | 3.901 -0.609 20.801 1.00 19.05 | O |
| ATOM | 148 | CG GLN A 55 | -14.342 -9.942 61.871 1.00 28.79 | C | ATOM | 3418 | CB TYR C 89 | 4.435 -3.877 21.329 1.00 18.06 | C |
| ATOM | 149 | CD GLN A 55 | -15.119 -11.002 61.093 1.00 31.13 | C | ATOM | 3419 | CG TYR C 89 | 5.800 -3.242 21.491 1.00 17.48 | C |
| ATOM | 150 | OE1 GLN A 55 | -16.228 -10.750 60.600 1.00 31.80 | O | ATOM | 3420 | CD1 TYR C 89 | 6.361 -3.072 22.756 1.00 17.90 | C |
| ATOM | 151 | NE2 GLN A 55 | -14.546 -12.193 60.993 1.00 30.90 | N | ATOM | 3421 | CD2 TYR C 89 | 6.540 -2.846 20.380 1.00 16.92 | C |
| ATOM | 152 | N PHE A 56 | -9.918 -10.902 60.581 1.00 19.44 | N | ATOM | 3422 | CE1 TYR C 89 | 7.623 -2.535 22.914 1.00 18.30 | C |
| ATOM | 153 | CA PHE A 56 | -8.491 -10.997 60.820 1.00 17.34 | C | ATOM | 3423 | CE2 TYR C 89 | 7.803 -2.306 20.524 1.00 18.33 | C |
| ATOM | 154 | C PHE A 56 | -7.653 -10.372 59.721 1.00 17.95 | C | ATOM | 3424 | CZ TYR C 89 | 8.340 -2.152 21.788 1.00 19.42 | C |
| ATOM | 155 | O PHE A 56 | -6.437 -10.332 59.828 1.00 16.43 | O | ATOM | 3425 | OH TYR C 89 | 9.583 -1.599 21.933 1.00 18.43 | O |
| ATOM | 156 | CB PHE A 56 | -8.103 -12.459 60.984 1.00 17.88 | C | ATOM | 3426 | N LEU C 90 | 3.719 -1.419 22.891 1.00 19.32 | N |
| ATOM | 157 | CG PHE A 56 | -6.681 -12.673 61.412 1.00 18.04 | C | ATOM | 3427 | CA LEU C 90 | 4.015 -0.159 23.530 1.00 20.51 | C |
| ATOM | 158 | CD1 PHE A 56 | 6.242 -12.256 62.662 1.00 18.72 | C | ATOM | 3428 | C LEU C 90 | 4.760 -0.398 24.838 1.00 20.15 | C |
| ATOM | 159 | CD2 PHE A 56 | -5.785 -13.321 60.569 1.00 17.81 | C | ATOM | 3429 | O LEU C 90 | 4.428 -1.334 25.556 1.00 21.17 | O |
| ATOM | 160 | CE1 PHE A 56 | -4.935 -12.484 63.075 1.00 19.14 | C | ATOM | 3430 | CB LEU C 90 | 2.707 0.541 23.801 1.00 22.92 | C |
| ATOM | 161 | CE2 PHE A 56 | -4.474 -13.557 60.971 1.00 18.70 | C | ATOM | 3431 | CG LEU C 90 | 2.758 1.644 24.835 1.00 27.85 | C |
| ATOM | 162 | CZ PHE A 56 | -4.052 -13.138 62.229 1.00 18.69 | C | ATOM | 3432 | CD1 LEU C 90 | 3.686 2.795 24.341 1.00 30.48 | C |
| ATOM | 163 | N ARG A 57 | -8.291 -9.863 58.667 1.00 19.86 | N | ATOM | 3433 | CD2 LEU C 90 | 1.309 2.082 25.087 1.00 28.85 | C |
| ATOM | 164 | CA ARG A 57 | -7.539 -9.291 57.553 1.00 19.81 | C | ATOM | 3434 | N GLU C 91 | 5.748 0.441 25.151 1.00 21.49 | N |
| ATOM | 165 | C ARG A 57 | -6.789 -8.007 57.847 1.00 20.16 | C | ATOM | 3435 | CA GLU C 91 | 6.510 0.303 26.400 1.00 25.02 | C |
| ATOM | 166 | O ARG A 57 | -7.309 -7.082 58.467 1.00 19.37 | O | ATOM | 3436 | C GLU C 91 | 7.054 1.628 26.914 1.00 26.87 | C |
| ATOM | 167 | CB ARG A 57 | -8.448 -9.062 56.358 1.00 20.23 | C | ATOM | 3437 | O GLU C 91 | 7.198 2.587 26.157 1.00 26.81 | O |
| ATOM | 168 | CG ARG A 57 | -7.708 -8.585 55.121 1.00 20.97 | C | ATOM | 3438 | CB GLU C 91 | 7.696 -0.665 26.233 1.00 24.94 | C |
| ATOM | 169 | CD ARG A 57 | -8.483 -8.899 53.849 1.00 21.79 | C | ATOM | 3439 | CG GLU C 91 | 8.943 -0.069 25.572 1.00 25.40 | C |
| ATOM | 170 | NE ARG A 57 | -7.750 -8.497 52.656 1.00 26.71 | N | ATOM | 3440 | CD GLU C 91 | 10.149 -1.015 25.597 1.00 26.52 | C |
| ATOM | 171 | CZ ARG A 57 | -7.982 -7.378 51.970 1.00 28.62 | C | ATOM | 3441 | OE1 GLU C 91 | 10.599 -1.398 26.698 1.00 28.92 | O |
| ATOM | 172 | NH1 ARG A 57 | -8.940 -6.555 52.352 1.00 29.91 | N | ATOM | 3442 | OE2 GLU C 91 | 10.657 -1.380 24.524 1.00 25.21 | O |
| ATOM | 173 | NH2 ARG A 57 | -7.234 -7.067 50.914 1.00 28.18 | N | ATOM | 3443 | N ASP C 92 | 7.378 1.671 28.198 1.00 29.94 | N |
| ATOM | 174 | N ASN A 58 | -5.558 -7.945 57.363 1.00 21.19 | N | ATOM | 3444 | CA ASP C 92 | 7.913 2.888 28.797 1.00 35.29 | C |
| ATOM | 175 | CA ASN A 58 | -4.723 -6.779 57.556 1.00 22.52 | C | ATOM | 3445 | C ASP C 92 | 8.712 2.537 30.048 1.00 35.57 | C |
| ATOM | 176 | C ASN A 58 | -4.239 -6.319 56.187 1.00 24.20 | C | ATOM | 3446 | O ASP C 92 | 8.352 1.619 30.779 1.00 35.92 | O |
| ATOM | 177 | O ASN A 58 | -3.344 -6.919 55.606 1.00 22.98 | O | ATOM | 3447 | CB ASP C 92 | 6.769 3.838 29.182 1.00 35.67 | C |
| ATOM | 178 | CB ASN A 58 | -3.532 -7.123 58.437 1.00 20.93 | C | ATOM | 3448 | CG ASP C 92 | 7.226 5.285 29.334 1.00 38.10 | C |
| ATOM | 179 | CG ASN A 58 | -2.642 -5.925 58.700 1.00 19.59 | C | ATOM | 3449 | OD1 ASP C 92 | 8.415 5.518 29.661 1.00 38.70 | O |
| ATOM | 180 | OD1 ASN A 58 | -3.043 -4.980 59.372 1.00 17.63 | O | ATOM | 3450 | OD2 ASP C 92 | 6.384 6.193 29.145 1.00 38.87 | O |
| ATOM | 181 | ND2 ASN A 58 | -1.425 -5.959 58.158 1.00 16.30 | N | ATOM | 3451 | N GLU C 93 | 9.797 3.266 30.288 1.00 37.50 | N |
| ATOM | 182 | N VAL A 59 | -4.842 -5.240 55.690 1.00 27.67 | N | ATOM | 3452 | CA GLU C 93 | 10.625 3.017 31.455 1.00 38.93 | C |
| ATOM | 183 | CA VAL A 59 | -4.504 -4.691 54.383 1.00 29.73 | C | ATOM | 3453 | C GLU C 93 | 9.946 3.537 32.712 1.00 39.28 | C |
| ATOM | 184 | C VAL A 59 | -3.124 -4.054 54.377 1.00 31.35 | C | ATOM | 3454 | O GLU C 93 | 9.931 2.871 33.744 1.00 37.32 | O |
| ATOM | 185 | O VAL A 59 | -2.786 -3.290 55.277 1.00 33.05 | O | ATOM | 3455 | CB GLU C 93 | 11.987 3.691 31.309 1.00 40.74 | C |
| ATOM | 186 | CB VAL A 59 | -5.545 -3.634 53.953 1.00 28.58 | C | ATOM | 3456 | CG GLU C 93 | 13.014 2.888 30.522 1.00 44.39 | C |
| ATOM | 187 | CG1 VAL A 59 | -5.318 -3.221 52.501 1.00 27.60 | C | ATOM | 3457 | CD GLU C 93 | 14.411 3.489 30.600 1.00 46.43 | C |
| ATOM | 188 | CG2 VAL A 59 | -6.948 -4.193 54.143 1.00 29.31 | C | ATOM | 3458 | OE1 GLU C 93 | 14.895 3.716 31.731 1.00 47.52 | O |
| ATOM | 189 | N GLU A 60 | -2.339 -4.370 53.348 1.00 33.94 | N | ATOM | 3459 | OE2 GLU C 93 | 15.030 3.729 29.537 1.00 48.38 | O |
| ATOM | 190 | CA GLU A 60 | -0.983 -3.844 53.179 1.00 35.88 | C | ATOM | 3460 | N HIS C 94 | 9.385 4.738 32.612 1.00 40.70 | N |
| ATOM | 191 | C GLU A 60 | -0.848 -3.086 51.856 1.00 37.65 | C | ATOM | 3461 | CA HIS C 94 | 8.712 5.369 33.738 1.00 42.45 | C |
| ATOM | 192 | O GLU A 60 | 0.258 -2.886 51.348 1.00 38.68 | O | ATOM | 3462 | C HIS C 94 | 7.507 6.139 33.217 1.00 42.74 | C |
| ATOM | 193 | CB GLU A 60 | 0.020 -5.005 53.214 1.00 35.18 | C | ATOM | 3463 | O HIS C 94 | 7.509 7.371 33.223 1.00 44.30 | O |
| ATOM | 194 | CG GLU A 60 | 0.181 -5.650 54.584 1.00 36.90 | C | ATOM | 3464 | CB HIS C 94 | 9.677 6.321 34.461 1.00 44.98 | C |
| ATOM | 195 | CD GLU A 60 | 0.980 -4.773 55.518 1.00 36.90 | C | ATOM | 3465 | CG HIS C 94 | 10.463 5.668 35.556 1.00 47.40 | C |

FIG. 6 (con't)

```
ATOM 196 OE1 GLU A 60    2.100 -4.412 55.106 1.00 37.75   O
ATOM 197 OE2 GLU A 60    0.511 -4.451 56.635 1.00 35.89   O
ATOM 198 N   TYR A 61   -1.973 -2.663 51.293 1.00 39.37   N
ATOM 199 CA  TYR A 61   -1.953 -1.941 50.027 1.00 41.81   C
ATOM 200 C   TYR A 61   -0.999 -0.753 50.059 1.00 43.72   C
ATOM 201 O   TYR A 61   -1.111  0.129 50.910 1.00 43.48   O
ATOM 202 CB  TYR A 61   -3.360 -1.474 49.654 1.00 41.53   C
ATOM 203 CG  TYR A 61   -4.253 -2.571 49.098 1.00 41.89   C
ATOM 204 CD1 TYR A 61   -5.647 -2.455 49.142 1.00 41.24   C
ATOM 205 CD2 TYR A 61   -3.707 -3.717 48.510 1.00 41.74   C
ATOM 206 CE1 TYR A 61   -6.472 -3.456 48.612 1.00 41.75   C
ATOM 207 CE2 TYR A 61   -4.522 -4.719 47.978 1.00 41.34   C
ATOM 208 CZ  TYR A 61   -5.900 -4.584 48.031 1.00 41.37   C
ATOM 209 OH  TYR A 61   -6.695 -5.566 47.491 1.00 41.05   O
ATOM 210 N   SER A 62   -0.064 -0.752 49.113 1.00 46.36   N
ATOM 211 CA  SER A 62    0.930  0.300 48.978 1.00 48.19   C
ATOM 212 C   SER A 62    0.378  1.729 49.082 1.00 49.20   C
ATOM 213 O   SER A 62    1.119  2.661 49.397 1.00 49.70   O
ATOM 214 CB  SER A 62    1.696  0.119 47.648 1.00 49.01   C
ATOM 215 OG  SER A 62    0.839 -0.197 46.558 1.00 48.98   O
ATOM 216 N   SER A 63   -0.919  1.908 48.835 1.00 49.37   N
ATOM 217 CA  SER A 63   -1.521  3.236 48.895 1.00 49.02   C
ATOM 218 C   SER A 63   -2.820  3.248 49.694 1.00 49.71   C
ATOM 219 O   SER A 63   -3.379  2.196 50.011 1.00 49.73   O
ATOM 220 CB  SER A 63   -1.795  3.760 47.481 1.00 49.63   C
ATOM 221 OG  SER A 63   -2.844  3.037 46.854 1.00 50.54   O
ATOM 222 N   GLY A 64   -3.295  4.450 50.016 1.00 49.23   N
ATOM 223 CA  GLY A 64   -4.521  4.591 50.769 1.00 48.21   C
ATOM 224 C   GLY A 64   -4.366  4.295 52.245 1.00 48.41   C
ATOM 225 O   GLY A 64   -3.271  4.004 52.733 1.00 48.61   O
ATOM 226 N   ARG A 65   -5.479  4.371 52.965 1.00 47.82   N
ATOM 227 CA  ARG A 65   -5.480  4.111 54.393 1.00 47.49   C
ATOM 228 C   ARG A 65   -6.564  3.086 54.676 1.00 45.38   C
ATOM 229 O   ARG A 65   -7.634  3.441 55.142 1.00 44.85   O
ATOM 230 CB  ARG A 65   -5.797  5.395 55.153 1.00 50.26   C
ATOM 231 CG  ARG A 65   -5.415  6.655 54.397 1.00 54.10   C
ATOM 232 CD  ARG A 65   -5.595  7.920 55.242 1.00 56.61   C
ATOM 233 NE  ARG A 65   -6.914  8.021 55.870 1.00 58.58   N
ATOM 234 CZ  ARG A 65   -7.194  7.597 57.102 1.00 60.03   C
ATOM 235 NH1 ARG A 65   -6.247  7.045 57.848 1.00 60.37   N
ATOM 236 NH2 ARG A 65   -8.425  7.719 57.590 1.00 59.58   N
ATOM 237 N   ASN A 66   -6.273  1.820 54.387 1.00 43.47   N
ATOM 238 CA  ASN A 66   -7.229  0.741 54.589 1.00 40.09   C
ATOM 239 C   ASN A 66   -7.260  0.287 56.044 1.00 38.08   C
ATOM 240 O   ASN A 66   -6.776  0.990 56.937 1.00 35.03   O
ATOM 241 CB  ASN A 66   -6.875 -0.442 53.698 1.00 41.22   C
ATOM 242 CG  ASN A 66   -6.352 -0.005 52.336 1.00 42.59   C
ATOM 243 OD1 ASN A 66   -5.217  0.467 52.209 1.00 41.35   O
ATOM 244 ND2 ASN A 66   -7.180 -0.155 51.311 1.00 44.16   N
ATOM 245 N   LYS A 67   -7.812 -0.901 56.279 1.00 34.15   N
ATOM 246 CA  LYS A 67   -7.915 -1.428 57.618 1.00 30.52   C
ATOM 247 C   LYS A 67   -6.671 -2.187 58.037 1.00 29.04   C
ATOM 248 O   LYS A 67   -5.863 -2.604 57.208 1.00 28.64   O
ATOM 249 CB  LYS A 67   -9.129 -2.360 57.756 1.00 30.06   C
ATOM 250 CG  LYS A 67   -8.969 -3.694 57.062 1.00 28.54   C
ATOM 251 CD  LYS A 67  -10.015 -4.695 57.511 1.00 27.36   C
ATOM 252 CE  LYS A 67    9.788 -5.110 58.953 1.00 29.78   C
ATOM 253 NZ  LYS A 67  -10.707 -6.204 59.367 1.00 28.57   N
ATOM 254 N   THR A 68   -6.507 -2.357 59.344 1.00 26.40   N
ATOM 255 CA  THR A 68   -5.357 -3.065 59.854 1.00 23.50   C
ATOM 256 C   THR A 68   -5.749 -3.981 61.004 1.00 20.98   C
ATOM 257 O   THR A 68   -6.721 -3.721 61.708 1.00 20.99   O
ATOM 258 CB  THR A 68   -4.244 -2.080 60.339 1.00 23.83   C
ATOM 259 OG1 THR A 68   -4.820 -1.286 61.394 1.00 26.02   O
ATOM 260 CG2 THR A 68   -3.862 -1.161 59.216 1.00 24.72   C
ATOM 261 N   PHE A 69   -5.000 -5.061 61.187 1.00 18.62   N
ATOM 262 CA  PHE A 69   -5.275 -6.001 62.274 1.00 16.84   C
ATOM 263 C   PHE A 69   -3.961 -6.696 62.627 1.00 16.13   C
ATOM 264 O   PHE A 69   -3.172 -6.995 61.741 1.00 14.51   O
ATOM 265 CB  PHE A 69   -6.306 -7.042 61.838 1.00 14.21   C
ATOM 266 CG  PHE A 69   -6.970 -7.756 62.983 1.00 12.89   C
ATOM 267 CD1 PHE A 69   -8.220 -7.362 63.434 1.00 11.28   C
ATOM 268 CD2 PHE A 69   -6.324 -8.819 63.619 1.00 13.47   C
ATOM 269 CE1 PHE A 69   -8.833 -8.002 64.493 1.00 10.96   C
ATOM 270 CE2 PHE A 69   -6.930 -9.473 64.685 1.00 12.99   C
ATOM 271 CZ  PHE A 69   -8.185 -9.065 65.119 1.00 13.34   C
ATOM 272 N   LEU A 70   -3.727 -6.950 63.916 1.00 15.36   N
ATOM 273 CA  LEU A 70   -2.485 -7.604 64.327 1.00 14.51   C
ATOM 274 C   LEU A 70   -2.484 -8.078 65.768 1.00 14.76   C
ATOM 275 O   LEU A 70   -2.736 -7.301 66.686 1.00 15.16   O
ATOM 276 CB  LEU A 70   -1.306 -6.665 64.115 1.00 12.51   C
ATOM 277 CG  LEU A 70    0.095 -7.134 64.525 1.00 12.29   C
ATOM 278 CD1 LEU A 70    1.121 -6.381 63.741 1.00 11.90   C
ATOM 279 CD2 LEU A 70    0.318 -6.871 65.970 1.00 12.92   C
ATOM 280 N   CYS A 71   -2.185 -9.360 65.968 1.00 14.57   N
ATOM 281 CA  CYS A 71   -2.082 -9.923 67.313 1.00 13.24   C

ATOM 3466 ND1 HIS C 94    9.910  5.361 36.786 1.00 49.28   N
ATOM 3467 CD2 HIS C 94   11.748  5.236 35.597 1.00 48.01   C
ATOM 3468 CE1 HIS C 94   10.823  4.769 37.538 1.00 49.79   C
ATOM 3469 NE2 HIS C 94   11.945  4.678 36.843 1.00 49.83   N
ATOM 3470 N   ALA C 95    6.471  5.410 32.854 1.00 42.94   N
ATOM 3471 CA  ALA C 95    5.252  6.032 32.343 1.00 42.61   C
ATOM 3472 C   ALA C 95    4.355  6.538 33.466 1.00 41.63   C
ATOM 3473 O   ALA C 95    4.235  5.912 34.513 1.00 41.54   O
ATOM 3474 CB  ALA C 95    4.489  5.044 31.457 1.00 42.49   C
ATOM 3475 N   ALA C 96    3.725  7.678 33.229 1.00 41.27   N
ATOM 3476 CA  ALA C 96    2.829  8.263 34.213 1.00 40.08   C
ATOM 3477 C   ALA C 96    1.541  7.449 34.282 1.00 38.90   C
ATOM 3478 O   ALA C 96    0.972  7.236 35.359 1.00 38.90   O
ATOM 3479 CB  ALA C 96    2.513  9.692 33.819 1.00 42.28   C
ATOM 3480 N   ALA C 97    1.082  6.994 33.120 1.00 36.67   N
ATOM 3481 CA  ALA C 97   -0.129  6.186 33.035 1.00 34.87   C
ATOM 3482 C   ALA C 97    0.227  4.728 32.777 1.00 33.50   C
ATOM 3483 O   ALA C 97    1.274  4.429 32.211 1.00 32.56   O
ATOM 3484 CB  ALA C 97   -1.032  6.701 31.909 1.00 34.61   C
ATOM 3485 N   HIS C 98   -0.657  3.825 33.186 1.00 33.59   N
ATOM 3486 CA  HIS C 98   -0.444  2.399 32.976 1.00 33.11   C
ATOM 3487 C   HIS C 98   -0.758  1.996 31.525 1.00 32.60   C
ATOM 3488 O   HIS C 98   -1.466  2.709 30.808 1.00 33.08   O
ATOM 3489 CB  HIS C 98   -1.322  1.598 33.949 1.00 33.43   C
ATOM 3490 CG  HIS C 98   -1.047  1.880 35.392 1.00 32.29   C
ATOM 3491 ND1 HIS C 98   -1.492  1.066 36.406 1.00 32.76   N
ATOM 3492 CD2 HIS C 98   -0.372  2.890 35.997 1.00 32.70   C
ATOM 3493 CE1 HIS C 98   -1.107  1.548 37.573 1.00 31.64   C
ATOM 3494 NE2 HIS C 98   -0.425  2.657 37.349 1.00 33.10   N
ATOM 3495 N   ALA C 99   -0.227  0.851 31.097 1.00 32.39   N
ATOM 3496 CA  ALA C 99   -0.426  0.357 29.737 1.00 31.58   C
ATOM 3497 C   ALA C 99   -1.886  0.465 29.305 1.00 32.37   C
ATOM 3498 O   ALA C 99   -2.187  0.904 28.194 1.00 30.86   O
ATOM 3499 CB  ALA C 99    0.051 -1.085 29.641 1.00 30.66   C
ATOM 3500 N   GLU C 100  -2.795  0.078 30.199 1.00 34.01   N
ATOM 3501 CA  GLU C 100  -4.221  0.126 29.900 1.00 35.46   C
ATOM 3502 C   GLU C 100  -4.665  1.522 29.479 1.00 35.48   C
ATOM 3503 O   GLU C 100  -5.462  1.674 28.557 1.00 35.00   O
ATOM 3504 CB  GLU C 100  -5.047 -0.313 31.113 1.00 37.57   C
ATOM 3505 CG  GLU C 100  -4.879 -1.781 31.558 1.00 39.07   C
ATOM 3506 CD  GLU C 100  -3.497 -2.128 32.140 1.00 40.24   C
ATOM 3507 OE1 GLU C 100  -2.789 -1.229 32.655 1.00 41.09   O
ATOM 3508 OE2 GLU C 100  -3.128 -3.324 32.098 1.00 39.78   O
ATOM 3509 N   GLU C 101  -4.156  2.537 30.168 1.00 35.64   N
ATOM 3510 CA  GLU C 101  -4.509  3.914 29.869 1.00 35.03   C
ATOM 3511 C   GLU C 101  -3.919  4.370 28.539 1.00 33.66   C
ATOM 3512 O   GLU C 101  -4.645  4.814 27.651 1.00 32.43   O
ATOM 3513 CB  GLU C 101  -4.010  4.835 30.987 1.00 37.81   C
ATOM 3514 CG  GLU C 101  -4.589  4.523 32.369 1.00 41.93   C
ATOM 3515 CD  GLU C 101  -4.134  5.507 33.447 1.00 43.61   C
ATOM 3516 OE1 GLU C 101  -3.234  5.172 34.257 1.00 43.04   O
ATOM 3517 OE2 GLU C 101  -4.693  6.627 33.474 1.00 44.32   O
ATOM 3518 N   ALA C 102  -2.601  4.248 28.411 1.00 30.72   N
ATOM 3519 CA  ALA C 102  -1.912  4.681 27.203 1.00 29.29   C
ATOM 3520 C   ALA C 102  -2.559  4.156 25.940 1.00 28.88   C
ATOM 3521 O   ALA C 102  -2.638  4.856 24.929 1.00 30.12   O
ATOM 3522 CB  ALA C 102  -0.442  4.249 27.249 1.00 27.17   C
ATOM 3523 N   PHE C 103  -3.035  2.918 25.998 1.00 27.66   N
ATOM 3524 CA  PHE C 103  -3.650  2.299 24.840 1.00 25.55   C
ATOM 3525 C   PHE C 103  -4.853  3.061 24.322 1.00 25.70   C
ATOM 3526 O   PHE C 103  -4.954  3.337 23.127 1.00 25.59   O
ATOM 3527 CB  PHE C 103  -4.070  0.874 25.156 1.00 24.51   C
ATOM 3528 CG  PHE C 103  -4.544  0.112 23.953 1.00 23.33   C
ATOM 3529 CD1 PHE C 103  -3.637 -0.338 23.008 1.00 21.98   C
ATOM 3530 CD2 PHE C 103  -5.893 -0.158 23.769 1.00 22.79   C
ATOM 3531 CE1 PHE C 103  -4.070 -1.053 21.897 1.00 22.02   C
ATOM 3532 CE2 PHE C 103  -6.335 -0.869 22.654 1.00 21.01   C
ATOM 3533 CZ  PHE C 103  -5.422 -1.315 21.721 1.00 21.09   C
ATOM 3534 N   PHE C 104  -5.777  3.383 25.218 1.00 26.23   N
ATOM 3535 CA  PHE C 104  -6.979  4.109 24.821 1.00 26.71   C
ATOM 3536 C   PHE C 104  -6.792  5.620 24.740 1.00 29.12   C
ATOM 3537 O   PHE C 104  -7.764  6.343 24.524 1.00 30.18   O
ATOM 3538 CB  PHE C 104  -8.127  3.813 25.785 1.00 23.18   C
ATOM 3539 CG  PHE C 104  -8.570  2.385 25.781 1.00 19.94   C
ATOM 3540 CD1 PHE C 104  -8.428  1.587 26.917 1.00 19.06   C
ATOM 3541 CD2 PHE C 104  -9.140  1.833 24.648 1.00 20.82   C
ATOM 3542 CE1 PHE C 104  -8.852  0.260 26.922 1.00 17.05   C
ATOM 3543 CE2 PHE C 104  -9.566  0.513 24.638 1.00 20.16   C
ATOM 3544 CZ  PHE C 104  -9.420 -0.274 25.782 1.00 18.33   C
ATOM 3545 N   ASN C 105  -5.566  6.109 24.912 1.00 30.62   N
ATOM 3546 CA  ASN C 105  -5.328  7.540 24.863 1.00 31.85   C
ATOM 3547 C   ASN C 105  -4.513  7.963 23.656 1.00 33.26   C
ATOM 3548 O   ASN C 105  -4.547  9.131 23.271 1.00 33.56   O
ATOM 3549 CB  ASN C 105  -4.620  8.024 26.132 1.00 32.77   C
ATOM 3550 CG  ASN C 105  -5.526  8.004 27.349 1.00 34.60   C
ATOM 3551 OD1 ASN C 105  -6.720  8.295 27.257 1.00 35.07   O
```

FIG. 6 (con't)

```
ATOM  282  C   CYS A  71    -0.621 -10.058  67.600  1.00 14.34    C
ATOM  283  O   CYS A  71     0.164 -10.323  66.688  1.00 14.18    O
ATOM  284  CB  CYS A  71    -2.659 -11.317  67.371  1.00 13.28    C
ATOM  285  SG  CYS A  71    -4.380 -11.421  66.933  1.00 11.98    S
ATOM  286  N   TYR A  72    -0.240  -9.942  68.870  1.00 15.75    N
ATOM  287  CA  TYR A  72     1.184 -10.060  69.234  1.00 13.62    C
ATOM  288  C   TYR A  72     1.445 -10.705  70.581  1.00 13.66    C
ATOM  289  O   TYR A  72     0.538 -10.934  71.401  1.00 13.43    O
ATOM  290  CB  TYR A  72     1.846  -8.682  69.181  1.00 11.98    C
ATOM  291  CG  TYR A  72     1.307  -7.690  70.187  1.00 14.01    C
ATOM  292  CD1 TYR A  72     1.694  -7.746  71.532  1.00 14.85    C
ATOM  293  CD2 TYR A  72     0.370  -6.725  69.817  1.00 14.44    C
ATOM  294  CE1 TYR A  72     1.164  -6.874  72.470  1.00 15.52    C
ATOM  295  CE2 TYR A  72    -0.172  -5.849  70.750  1.00 15.43    C
ATOM  296  CZ  TYR A  72     0.233  -5.931  72.077  1.00 16.16    C
ATOM  297  OH  TYR A  72    -0.287  -5.083  73.027  1.00 18.77    O
ATOM  298  N   VAL A  73     2.713 -10.997  70.810  1.00 13.41    N
ATOM  299  CA  VAL A  73     3.168 -11.590  72.065  1.00 14.19    C
ATOM  300  C   VAL A  73     4.544 -11.042  72.374  1.00 13.66    C
ATOM  301  O   VAL A  73     5.429 -11.079  71.526  1.00 14.27    O
ATOM  302  CB  VAL A  73     3.259 -13.136  71.973  1.00 13.10    C
ATOM  303  CG1 VAL A  73     3.946 -13.688  73.209  1.00 11.85    C
ATOM  304  CG2 VAL A  73     1.883 -13.732  71.898  1.00 13.20    C
ATOM  305  N   VAL A  74     4.723 -10.528  73.584  1.00 15.31    N
ATOM  306  CA  VAL A  74     6.021  -9.994  73.988  1.00 16.34    C
ATOM  307  C   VAL A  74     6.554 -10.683  75.239  1.00 17.68    C
ATOM  308  O   VAL A  74     5.816 -10.899  76.200  1.00 18.39    O
ATOM  309  CB  VAL A  74     5.935  -8.489  74.240  1.00 14.55    C
ATOM  310  CG1 VAL A  74     7.279  -7.959  74.708  1.00 13.50    C
ATOM  311  CG2 VAL A  74     5.510  -7.792  72.977  1.00 13.44    C
ATOM  312  N   GLU A  75     7.829 -11.029  75.214  1.00 20.54    N
ATOM  313  CA  GLU A  75     8.476 -11.676  76.350  1.00 24.00    C
ATOM  314  C   GLU A  75     9.895 -11.151  76.484  1.00 25.05    C
ATOM  315  O   GLU A  75    10.723 -11.363  75.601  1.00 24.19    O
ATOM  316  CB  GLU A  75     8.499 -13.187  76.153  1.00 26.10    C
ATOM  317  CG  GLU A  75     7.120 -13.784  76.018  1.00 31.35    C
ATOM  318  CD  GLU A  75     7.135 -15.291  76.085  1.00 35.63    C
ATOM  319  OE1 GLU A  75     7.964 -15.912  75.374  1.00 37.54    O
ATOM  320  OE2 GLU A  75     6.321 -15.866  76.842  1.00 38.67    O
ATOM  321  N   ALA A  76    10.173 -10.459  77.585  1.00 26.87    N
ATOM  322  CA  ALA A  76    11.496  -9.891  77.825  1.00 28.77    C
ATOM  323  C   ALA A  76    12.165 -10.557  79.019  1.00 30.78    C
ATOM  324  O   ALA A  76    11.543 -10.751  80.061  1.00 31.11    O
ATOM  325  CB  ALA A  76    11.374  -8.406  78.053  1.00 27.76    C
ATOM  326  N   GLN A  77    13.434 -10.908  78.853  1.00 34.96    N
ATOM  327  CA  GLN A  77    14.225 -11.564  79.899  1.00 38.74    C
ATOM  328  C   GLN A  77    15.412 -10.672  80.259  1.00 39.88    C
ATOM  329  O   GLN A  77    16.013 -10.051  79.385  1.00 40.01    O
ATOM  330  CB  GLN A  77    14.725 -12.927  79.386  1.00 41.39    C
ATOM  331  CG  GLN A  77    16.074 -13.383  79.973  1.00 46.84    C
ATOM  332  CD  GLN A  77    16.960 -14.119  78.958  1.00 49.73    C
ATOM  333  OE1 GLN A  77    18.133 -14.416  79.228  1.00 51.56    O
ATOM  334  NE2 GLN A  77    16.400 -14.416  77.789  1.00 50.92    N
ATOM  335  N   GLY A  78    15.741 -10.606  81.544  1.00 40.74    N
ATOM  336  CA  GLY A  78    16.865  -9.797  81.981  1.00 41.57    C
ATOM  337  C   GLY A  78    17.694 -10.533  83.015  1.00 43.22    C
ATOM  338  O   GLY A  78    17.158 -11.072  83.987  1.00 43.14    O
ATOM  339  N   LYS A  79    19.003 -10.562  82.802  1.00 44.77    N
ATOM  340  CA  LYS A  79    19.907 -11.246  83.718  1.00 46.43    C
ATOM  341  C   LYS A  79    19.885 -10.529  85.066  1.00 46.17    C
ATOM  342  O   LYS A  79    20.693  -9.638  85.306  1.00 47.25    O
ATOM  343  CB  LYS A  79    21.334 -11.261  83.145  1.00 47.07    C
ATOM  344  CG  LYS A  79    22.268 -12.307  83.763  1.00 48.81    C
ATOM  345  CD  LYS A  79    23.073 -13.019  82.677  1.00 51.68    C
ATOM  346  CE  LYS A  79    23.911 -14.171  83.226  1.00 52.59    C
ATOM  347  NZ  LYS A  79    24.647 -14.889  82.136  1.00 52.97    N
ATOM  348  N   GLY A  80    18.946 -10.916  85.929  1.00 45.59    N
ATOM  349  CA  GLY A  80    18.833 -10.307  87.244  1.00 44.46    C
ATOM  350  C   GLY A  80    17.492 -10.592  87.901  1.00 44.04    C
ATOM  351  O   GLY A  80    17.178 -10.068  88.976  1.00 43.95    O
ATOM  352  N   GLY A  81    16.698 -11.435  87.243  1.00 42.18    N
ATOM  353  CA  GLY A  81    15.386 -11.780  87.753  1.00 39.56    C
ATOM  354  C   GLY A  81    14.273 -10.915  87.178  1.00 37.50    C
ATOM  355  O   GLY A  81    13.125 -11.016  87.607  1.00 36.38    O
ATOM  356  N   GLN A  82    14.614 -10.058  86.216  1.00 36.01    N
ATOM  357  CA  GLN A  82    13.637  -9.176  85.576  1.00 34.06    C
ATOM  358  C   GLN A  82    12.914  -9.936  84.459  1.00 31.83    C
ATOM  359  O   GLN A  82    13.543 -10.467  83.543  1.00 30.92    O
ATOM  360  CB  GLN A  82    14.347  -7.954  84.988  1.00 34.17    C
ATOM  361  CG  GLN A  82    15.445  -7.422  85.880  1.00 37.64    C
ATOM  362  CD  GLN A  82    16.589  -6.827  85.093  1.00 37.58    C
ATOM  363  OE1 GLN A  82    16.474  -5.742  84.533  1.00 36.42    O
ATOM  364  NE2 GLN A  82    17.710  -7.552  85.044  1.00 38.46    N
ATOM  365  N   VAL A  83    11.594 -10.010  84.542  1.00 29.61    N
ATOM  366  CA  VAL A  83    10.839 -10.710  83.514  1.00 28.42    C
ATOM  367  C   VAL A  83     9.544  -9.992  83.170  1.00 27.22    C

ATOM 3552  ND2 ASN C 105    -4.957  7.675  28.508  1.00 35.93    N
ATOM 3553  N   THR C 106    -3.780  7.025  23.062  1.00 33.37    N
ATOM 3554  CA  THR C 106    -2.959  7.347  21.900  1.00 34.88    C
ATOM 3555  C   THR C 106    -2.963  6.298  20.800  1.00 34.27    C
ATOM 3556  O   THR C 106    -2.773  6.629  19.629  1.00 35.26    O
ATOM 3557  CB  THR C 106    -1.495  7.606  22.294  1.00 35.72    C
ATOM 3558  OG1 THR C 106    -1.061  6.591  23.203  1.00 36.06    O
ATOM 3559  CG2 THR C 106    -1.345  9.005  22.919  1.00 37.14    C
ATOM 3560  N   ILE C 107    -3.168  5.040  21.165  1.00 33.30    N
ATOM 3561  CA  ILE C 107    -3.191  3.970  20.174  1.00 32.56    C
ATOM 3562  C   ILE C 107    -4.578  3.780  19.537  1.00 32.05    C
ATOM 3563  O   ILE C 107    -4.711  3.654  18.315  1.00 32.19    O
ATOM 3564  CB  ILE C 107    -2.734  2.644  20.804  1.00 32.57    C
ATOM 3565  CG1 ILE C 107    -1.374  2.853  21.475  1.00 33.49    C
ATOM 3566  CG2 ILE C 107    -2.605  1.570  19.737  1.00 31.44    C
ATOM 3567  CD1 ILE C 107    -0.912  1.667  22.241  1.00 36.01    C
ATOM 3568  N   LEU C 108    -5.613  3.782  20.355  1.00 30.89    N
ATOM 3569  CA  LEU C 108    -6.952  3.196  19.842  1.00 30.69    C
ATOM 3570  C   LEU C 108    -7.861  4.638  20.460  1.00 31.75    C
ATOM 3571  O   LEU C 108    -8.731  4.314  21.261  1.00 31.24    O
ATOM 3572  CB  LEU C 108    -7.418  2.188  20.217  1.00 29.55    C
ATOM 3573  CG  LEU C 108    -8.486  1.551  19.346  1.00 31.15    C
ATOM 3574  CD1 LEU C 108    -8.052  1.564  17.892  1.00 29.84    C
ATOM 3575  CD2 LEU C 108    -8.718  0.132  19.813  1.00 30.09    C
ATOM 3576  N   PRO C 109    -7.657  5.923  20.102  1.00 32.99    N
ATOM 3577  CA  PRO C 109    -8.430  7.071  20.598  1.00 33.01    C
ATOM 3578  C   PRO C 109    -9.925  6.987  20.317  1.00 32.74    C
ATOM 3579  O   PRO C 109   -10.722  7.125  21.232  1.00 33.42    O
ATOM 3580  CB  PRO C 109    -7.781  8.261  19.888  1.00 33.39    C
ATOM 3581  CG  PRO C 109    -6.384  7.810  19.672  1.00 34.18    C
ATOM 3582  CD  PRO C 109    -6.558  6.381  19.232  1.00 32.72    C
ATOM 3583  N   ALA C 110   -10.303  6.769  19.063  1.00 33.03    N
ATOM 3584  CA  ALA C 110   -11.719  6.692  18.726  1.00 34.44    C
ATOM 3585  C   ALA C 110   -12.062  5.509  17.821  1.00 35.26    C
ATOM 3586  O   ALA C 110   -11.197  4.949  17.152  1.00 35.46    O
ATOM 3587  CB  ALA C 110   -12.173  7.992  18.059  1.00 34.35    C
ATOM 3588  N   PHE C 111   -13.338  5.134  17.805  1.00 35.26    N
ATOM 3589  CA  PHE C 111   -13.787  4.020  16.984  1.00 35.38    C
ATOM 3590  C   PHE C 111   -14.944  4.489  16.118  1.00 36.80    C
ATOM 3591  O   PHE C 111   -15.793  5.242  16.593  1.00 37.52    O
ATOM 3592  CB  PHE C 111   -14.283  2.872  17.863  1.00 33.27    C
ATOM 3593  CG  PHE C 111   -13.395  2.560  19.028  1.00 29.72    C
ATOM 3594  CD1 PHE C 111   -13.291  3.438  20.100  1.00 29.28    C
ATOM 3595  CD2 PHE C 111   -12.673  1.377  19.060  1.00 28.01    C
ATOM 3596  CE1 PHE C 111   -12.476  3.141  21.188  1.00 28.16    C
ATOM 3597  CE2 PHE C 111   -11.858  1.071  20.142  1.00 27.32    C
ATOM 3598  CZ  PHE C 111   -11.760  1.955  21.207  1.00 28.11    C
ATOM 3599  N   ASP C 112   -14.991  4.053  14.860  1.00 36.95    N
ATOM 3600  CA  ASP C 112   -16.103  4.439  13.991  1.00 38.22    C
ATOM 3601  C   ASP C 112   -17.212  3.393  14.111  1.00 37.71    C
ATOM 3602  O   ASP C 112   -16.986  2.195  13.923  1.00 36.80    O
ATOM 3603  CB  ASP C 112   -15.642  4.571  12.532  1.00 41.47    C
ATOM 3604  CG  ASP C 112   -15.483  3.238  11.845  1.00 44.30    C
ATOM 3605  OD1 ASP C 112   -14.828  2.340  12.422  1.00 47.48    O
ATOM 3606  OD2 ASP C 112   -16.005  3.092  10.724  1.00 45.06    O
ATOM 3607  N   PRO C 113   -18.435  3.838  14.436  1.00 37.08    N
ATOM 3608  CA  PRO C 113   -19.612  2.976  14.598  1.00 35.48    C
ATOM 3609  C   PRO C 113   -19.796  1.912  13.527  1.00 34.40    C
ATOM 3610  O   PRO C 113   -20.241  0.802  13.820  1.00 34.36    O
ATOM 3611  CB  PRO C 113   -20.756  3.978  14.615  1.00 36.36    C
ATOM 3612  CG  PRO C 113   -20.140  5.144  15.309  1.00 36.35    C
ATOM 3613  CD  PRO C 113   -18.802  5.253  14.616  1.00 36.20    C
ATOM 3614  N   ALA C 114   -19.452  2.255  12.292  1.00 33.34    N
ATOM 3615  CA  ALA C 114   -19.607  1.335  11.175  1.00 32.43    C
ATOM 3616  C   ALA C 114   -18.708  0.118  11.249  1.00 31.65    C
ATOM 3617  O   ALA C 114   -18.842 -0.803  10.445  1.00 33.96    O
ATOM 3618  CB  ALA C 114   -19.356  2.072   9.860  1.00 33.35    C
ATOM 3619  N   LEU C 115   -17.792  0.095  12.201  1.00 30.07    N
ATOM 3620  CA  LEU C 115   -16.906 -1.051  12.332  1.00 27.27    C
ATOM 3621  C   LEU C 115   -17.053 -1.765  13.678  1.00 26.12    C
ATOM 3622  O   LEU C 115   -17.559 -1.206  14.653  1.00 23.11    O
ATOM 3623  CB  LEU C 115   -15.457 -0.613  12.136  1.00 26.25    C
ATOM 3624  CG  LEU C 115   -14.993 -0.294  10.718  1.00 27.53    C
ATOM 3625  CD1 LEU C 115   -13.557  0.187  10.748  1.00 24.67    C
ATOM 3626  CD2 LEU C 115   -15.106 -1.537   9.859  1.00 27.56    C
ATOM 3627  N   ARG C 116   -16.608 -3.015  13.704  1.00 25.79    N
ATOM 3628  CA  ARG C 116   -16.631 -3.813  14.914  1.00 26.14    C
ATOM 3629  C   ARG C 116   -15.189 -4.236  15.214  1.00 25.44    C
ATOM 3630  O   ARG C 116   -14.582 -4.981  14.451  1.00 25.35    O
ATOM 3631  CB  ARG C 116   -17.521 -5.039  14.740  1.00 27.81    C
ATOM 3632  CG  ARG C 116   -18.980 -4.693  14.487  1.00 32.22    C
ATOM 3633  CD  ARG C 116   -19.894 -5.724  15.128  1.00 36.51    C
ATOM 3634  NE  ARG C 116   -19.585 -5.850  16.556  1.00 42.07    N
ATOM 3635  CZ  ARG C 116   -20.206 -6.672  17.400  1.00 41.93    C
ATOM 3636  NH1 ARG C 116   -21.189 -7.454  16.972  1.00 41.80    N
ATOM 3637  NH2 ARG C 116   -19.824 -6.717  18.668  1.00 42.65    N
```

FIG. 6 (con't)

```
ATOM  368  O   VAL A 83     8.797  -9.590 84.056 1.00 27.49   O
ATOM  369  CB  VAL A 83    10.500 -12.148 83.959 1.00 28.55   C
ATOM  370  CG1 VAL A 83     9.763 -12.873 82.842 1.00 26.97   C
ATOM  371  CG2 VAL A 83    11.771 -12.891 84.340 1.00 26.81   C
ATOM  372  N   GLN A 84     9.289  -9.819 81.879 1.00 26.91   N
ATOM  373  CA  GLN A 84     8.056  -9.176 81.425 1.00 26.48   C
ATOM  374  C   GLN A 84     7.473  -9.964 80.266 1.00 26.36   C
ATOM  375  O   GLN A 84     8.163 -10.194 79.284 1.00 27.52   O
ATOM  376  CB  GLN A 84     8.332  -7.763 80.960 1.00 25.82   C
ATOM  377  CG  GLN A 84     9.002  -6.933 81.994 1.00 27.92   C
ATOM  378  CD  GLN A 84     9.488  -5.648 81.414 1.00 28.14   C
ATOM  379  OE1 GLN A 84     8.984  -5.198 80.385 1.00 29.64   O
ATOM  380  NE2 GLN A 84    10.470  -5.040 82.060 1.00 29.61   N
ATOM  381  N   ALA A 85     6.211 -10.383 80.372 1.00 26.56   N
ATOM  382  CA  ALA A 85     5.563 -11.124 79.289 1.00 25.59   C
ATOM  383  C   ALA A 85     4.106 -10.680 79.131 1.00 25.48   C
ATOM  384  O   ALA A 85     3.255 -11.027 79.942 1.00 26.61   O
ATOM  385  CB  ALA A 85     5.619 -12.622 79.554 1.00 24.51   C
ATOM  386  N   SER A 86     3.822  -9.912 78.091 1.00 24.49   N
ATOM  387  CA  SER A 86     2.463  -9.453 77.881 1.00 23.75   C
ATOM  388  C   SER A 86     1.939 -10.044 76.588 1.00 23.67   C
ATOM  389  O   SER A 86     2.695 -10.656 75.838 1.00 25.50   O
ATOM  390  CB  SER A 86     2.431  -7.933 77.785 1.00 23.36   C
ATOM  391  OG  SER A 86     3.031  -7.527 76.577 1.00 21.66   O
ATOM  392  N   ARG A 87     0.652  -9.856 76.325 1.00 22.22   N
ATOM  393  CA  ARG A 87     0.046 -10.385 75.113 1.00 20.45   C
ATOM  394  C   ARG A 87    -1.204  -9.597 74.767 1.00 18.82   C
ATOM  395  O   ARG A 87    -1.997  -9.256 75.645 1.00 18.95   O
ATOM  396  CB  ARG A 87    -0.308 -11.861 75.336 1.00 22.14   C
ATOM  397  CG  ARG A 87    -0.837 -12.553 74.110 1.00 23.90   C
ATOM  398  CD  ARG A 87    -0.979 -14.024 74.392 1.00 27.83   C
ATOM  399  NE  ARG A 87    -2.177 -14.318 75.165 1.00 29.95   N
ATOM  400  CZ  ARG A 87    -2.262 -15.290 76.062 1.00 31.20   C
ATOM  401  NH1 ARG A 87    -1.204 -16.064 76.311 1.00 31.83   N
ATOM  402  NH2 ARG A 87    -3.403 -15.490 76.702 1.00 30.33   N
ATOM  403  N   GLY A 88    -1.384  -9.295 73.496 1.00 17.26   N
ATOM  404  CA  GLY A 88    -2.550  -8.535 73.107 1.00 15.71   C
ATOM  405  C   GLY A 88    -2.742  -8.447 71.609 1.00 16.65   C
ATOM  406  O   GLY A 88    -2.199  -9.258 70.863 1.00 15.58   O
ATOM  407  N   TYR A 89    -3.500  -7.446 71.161 1.00 16.10   N
ATOM  408  CA  TYR A 89    -3.769  -7.281 69.747 1.00 15.92   C
ATOM  409  C   TYR A 89    -4.153  -5.840 69.420 1.00 15.73   C
ATOM  410  O   TYR A 89    -4.422  -5.046 70.317 1.00 15.36   O
ATOM  411  CB  TYR A 89    -4.896  -8.218 69.325 1.00 15.20   C
ATOM  412  CG  TYR A 89    -6.246  -7.564 69.254 1.00 14.21   C
ATOM  413  CD1 TYR A 89    -6.793  -7.197 68.032 1.00 14.43   C
ATOM  414  CD2 TYR A 89    -6.991  -7.339 70.407 1.00 14.75   C
ATOM  415  CE1 TYR A 89    -8.048  -6.633 67.956 1.00 15.39   C
ATOM  416  CE2 TYR A 89    -8.247  -6.776 70.345 1.00 13.17   C
ATOM  417  CZ  TYR A 89    -8.771  -6.431 69.119 1.00 14.99   C
ATOM  418  OH  TYR A 89   -10.032  -5.893 69.054 1.00 14.53   O
ATOM  419  N   LEU A 90    -4.212  -5.531 68.134 1.00 16.33   N
ATOM  420  CA  LEU A 90    -4.512  -4.191 67.689 1.00 19.09   C
ATOM  421  C   LEU A 90    -5.234  -4.225 66.350 1.00 20.18   C
ATOM  422  O   LEU A 90    -4.891  -5.034 65.486 1.00 19.77   O
ATOM  423  CB  LEU A 90    -3.210  -3.420 67.546 1.00 22.45   C
ATOM  424  CG  LEU A 90    -3.251  -2.151 66.724 1.00 26.97   C
ATOM  425  CD1 LEU A 90    -4.163  -1.092 67.399 1.00 28.71   C
ATOM  426  CD2 LEU A 90    -1.811  -1.659 66.549 1.00 27.47   C
ATOM  427  N   GLU A 91    -6.230  -3.360 66.173 1.00 20.86   N
ATOM  428  CA  GLU A 91    -6.979  -3.300 64.924 1.00 23.59   C
ATOM  429  C   GLU A 91    -7.515  -1.906 64.634 1.00 25.15   C
ATOM  430  O   GLU A 91    -7.628  -1.073 65.533 1.00 26.09   O
ATOM  431  CB  GLU A 91    -8.157  -4.288 64.942 1.00 23.40   C
ATOM  432  CG  GLU A 91    -9.400  -3.797 65.674 1.00 23.71   C
ATOM  433  CD  GLU A 91   -10.604  -4.727 65.504 1.00 25.29   C
ATOM  434  OE1 GLU A 91   -11.062  -4.945 64.365 1.00 25.45   O
ATOM  435  OE2 GLU A 91   -11.112  -5.246 66.520 1.00 27.19   O
ATOM  436  N   ASP A 92    -7.849  -1.651 63.377 1.00 27.65   N
ATOM  437  CA  ASP A 92    -8.386  -0.348 62.979 1.00 31.86   C
ATOM  438  C   ASP A 92    -9.185  -0.509 61.692 1.00 32.85   C
ATOM  439  O   ASP A 92    -8.824  -1.309 60.837 1.00 32.71   O
ATOM  440  CB  ASP A 92    -7.245   0.656 62.733 1.00 34.56   C
ATOM  441  CG  ASP A 92    -7.705   2.120 62.793 1.00 38.54   C
ATOM  442  OD1 ASP A 92    -8.902   2.414 62.523 1.00 39.55   O
ATOM  443  OD2 ASP A 92    -6.858   2.991 63.099 1.00 38.84   O
ATOM  444  N   GLU A 93   -10.267   0.252 61.558 1.00 35.55   N
ATOM  445  CA  GLU A 93   -11.098   0.175 60.360 1.00 37.34   C
ATOM  446  C   GLU A 93   -10.422   0.899 59.216 1.00 37.68   C
ATOM  447  O   GLU A 93   -10.396   0.413 58.088 1.00 36.49   O
ATOM  448  CB  GLU A 93   -12.478   0.794 60.596 1.00 39.79   C
ATOM  449  CG  GLU A 93   -13.497  -0.128 61.271 1.00 43.84   C
ATOM  450  CD  GLU A 93   -14.909   0.456 61.285 1.00 45.13   C
ATOM  451  OE1 GLU A 93   -15.389   0.844 60.199 1.00 46.73   O
ATOM  452  OE2 GLU A 93   -15.539   0.520 62.367 1.00 45.51   O
ATOM  453  N   HIS A 94    -9.876   2.071 59.509 1.00 39.10   N

ATOM 3638  N   TYR C 117  -14.648  -3.748 16.326 1.00 23.88   N
ATOM 3639  CA  TYR C 117  -13.284  -4.042 16.712 1.00 23.76   C
ATOM 3640  C   TYR C 117  -13.102  -5.296 17.579 1.00 24.22   C
ATOM 3641  O   TYR C 117  -13.917  -5.601 18.446 1.00 23.68   O
ATOM 3642  CB  TYR C 117  -12.686  -2.837 17.436 1.00 24.47   C
ATOM 3643  CG  TYR C 117  -12.691  -1.561 16.617 1.00 25.35   C
ATOM 3644  CD1 TYR C 117  -13.885  -0.880 16.359 1.00 25.91   C
ATOM 3645  CD2 TYR C 117  -11.505  -1.027 16.115 1.00 24.50   C
ATOM 3646  CE1 TYR C 117  -13.892   0.302 15.625 1.00 26.22   C
ATOM 3647  CE2 TYR C 117  -11.504   0.156 15.380 1.00 26.16   C
ATOM 3648  CZ  TYR C 117  -12.697   0.814 15.139 1.00 26.29   C
ATOM 3649  OH  TYR C 117  -12.692   1.969 14.402 1.00 27.48   O
ATOM 3650  N   ASN C 118  -12.006  -6.014 17.331 1.00 25.04   N
ATOM 3651  CA  ASN C 118  -11.667  -7.220 18.069 1.00 23.72   C
ATOM 3652  C   ASN C 118  -10.256  -7.038 18.559 1.00 22.70   C
ATOM 3653  O   ASN C 118   -9.312  -7.513 17.920 1.00 23.84   O
ATOM 3654  CB  ASN C 118  -11.709  -8.422 17.159 1.00 25.85   C
ATOM 3655  CG  ASN C 118  -12.670  -9.442 17.634 1.00 30.20   C
ATOM 3656  OD1 ASN C 118  -13.882  -9.235 17.588 1.00 33.03   O
ATOM 3657  ND2 ASN C 118  -12.152 -10.559 18.119 1.00 33.09   N
ATOM 3658  N   VAL C 119  -10.109  -6.351 19.686 1.00 20.29   N
ATOM 3659  CA  VAL C 119   -8.796  -6.068 20.259 1.00 19.30   C
ATOM 3660  C   VAL C 119   -8.315  -7.212 21.132 1.00 17.98   C
ATOM 3661  O   VAL C 119   -9.104  -7.830 21.833 1.00 18.73   O
ATOM 3662  CB  VAL C 119   -8.831  -4.777 21.120 1.00 19.04   C
ATOM 3663  CG1 VAL C 119   -7.448  -4.510 21.700 1.00 17.53   C
ATOM 3664  CG2 VAL C 119   -9.303  -3.582 20.279 1.00 18.62   C
ATOM 3665  N   THR C 120   -7.019  -7.489 21.091 1.00 15.57   N
ATOM 3666  CA  THR C 120   -6.449  -8.551 21.905 1.00 14.21   C
ATOM 3667  C   THR C 120   -5.155  -8.047 22.567 1.00 13.40   C
ATOM 3668  O   THR C 120   -4.267  -7.598 21.862 1.00 13.31   O
ATOM 3669  CB  THR C 120   -6.136  -9.769 21.051 1.00 14.67   C
ATOM 3670  OG1 THR C 120   -7.358 -10.301 20.531 1.00 18.80   O
ATOM 3671  CG2 THR C 120   -5.452 -10.832 21.857 1.00 13.20   C
ATOM 3672  N   TRP C 121   -5.074  -8.110 23.903 1.00 11.82   N
ATOM 3673  CA  TRP C 121   -3.879  -7.668 24.635 1.00 12.81   C
ATOM 3674  C   TRP C 121   -3.029  -8.832 25.145 1.00 13.59   C
ATOM 3675  O   TRP C 121   -3.529  -9.929 25.388 1.00 14.81   O
ATOM 3676  CB  TRP C 121   -4.220  -6.809 25.857 1.00 11.93   C
ATOM 3677  CG  TRP C 121   -4.818  -5.477 25.574 1.00 12.03   C
ATOM 3678  CD1 TRP C 121   -4.859  -4.824 24.373 1.00 12.50   C
ATOM 3679  CD2 TRP C 121   -5.454  -4.613 26.524 1.00 11.60   C
ATOM 3680  NE1 TRP C 121   -5.487  -3.606 24.520 1.00 11.12   N
ATOM 3681  CE2 TRP C 121   -5.868  -3.460 25.823 1.00 11.43   C
ATOM 3682  CE3 TRP C 121   -5.726  -4.710 27.895 1.00 12.70   C
ATOM 3683  CZ2 TRP C 121   -6.534  -2.401 26.454 1.00 12.72   C
ATOM 3684  CZ3 TRP C 121   -6.386  -3.657 28.530 1.00 15.00   C
ATOM 3685  CH2 TRP C 121   -6.789  -2.513 27.802 1.00 16.00   C
ATOM 3686  N   TYR C 122   -1.738  -8.571 25.330 1.00 14.66   N
ATOM 3687  CA  TYR C 122   -0.792  -9.562 25.816 1.00 14.20   C
ATOM 3688  C   TYR C 122    0.097  -8.847 26.819 1.00 14.86   C
ATOM 3689  O   TYR C 122    1.061  -8.197 26.428 1.00 14.01   O
ATOM 3690  CB  TYR C 122    0.071 -10.085 24.687 1.00 14.72   C
ATOM 3691  CG  TYR C 122   -0.642 -10.974 23.700 1.00 14.09   C
ATOM 3692  CD1 TYR C 122   -1.143 -10.475 22.503 1.00 15.08   C
ATOM 3693  CD2 TYR C 122   -0.775 -12.340 23.947 1.00 14.96   C
ATOM 3694  CE1 TYR C 122   -1.756 -11.316 21.569 1.00 15.73   C
ATOM 3695  CE2 TYR C 122   -1.385 -13.190 23.026 1.00 15.44   C
ATOM 3696  CZ  TYR C 122   -1.873 -12.671 21.837 1.00 15.74   C
ATOM 3697  OH  TYR C 122   -2.476 -13.500 20.914 1.00 16.49   O
ATOM 3698  N   VAL C 123   -0.243  -8.973 28.104 1.00 15.53   N
ATOM 3699  CA  VAL C 123    0.481  -8.344 29.185 1.00 15.63   C
ATOM 3700  C   VAL C 123    0.969  -9.362 30.199 1.00 16.00   C
ATOM 3701  O   VAL C 123    0.428 -10.477 30.290 1.00 14.93   O
ATOM 3702  CB  VAL C 123   -0.393  -7.311 29.936 1.00 15.60   C
ATOM 3703  CG1 VAL C 123   -0.501  -6.058 29.116 1.00 18.53   C
ATOM 3704  CG2 VAL C 123   -1.783  -7.879 30.172 1.00 16.13   C
ATOM 3705  N   SER C 124    1.971  -8.951 30.980 1.00 14.23   N
ATOM 3706  CA  SER C 124    2.587  -9.798 31.967 1.00 14.50   C
ATOM 3707  C   SER C 124    1.653 -10.216 33.074 1.00 15.45   C
ATOM 3708  O   SER C 124    1.707 -11.355 33.525 1.00 16.35   O
ATOM 3709  CB  SER C 124    3.840  -9.111 32.573 1.00 14.83   C
ATOM 3710  OG  SER C 124    3.527  -8.011 33.404 1.00 13.74   O
ATOM 3711  N   SER C 125    0.774  -9.316 33.499 1.00 16.04   N
ATOM 3712  CA  SER C 125   -0.165  -9.653 34.563 1.00 17.76   C
ATOM 3713  C   SER C 125   -1.498  -8.951 34.404 1.00 17.22   C
ATOM 3714  O   SER C 125   -1.623  -8.015 33.622 1.00 17.01   O
ATOM 3715  CB  SER C 125    0.423  -9.282 35.929 1.00 20.15   C
ATOM 3716  OG  SER C 125    0.202  -7.904 36.232 1.00 23.07   O
ATOM 3717  N   SER C 126   -2.495  -9.404 35.161 1.00 16.68   N
ATOM 3718  CA  SER C 126   -3.824  -8.801 35.122 1.00 16.35   C
ATOM 3719  C   SER C 126   -3.771  -7.347 35.616 1.00 16.04   C
ATOM 3720  O   SER C 126   -2.899  -6.962 36.393 1.00 15.76   O
ATOM 3721  CB  SER C 126   -4.794  -9.610 35.965 1.00 16.05   C
ATOM 3722  OG  SER C 126   -4.184  -9.964 37.190 1.00 21.12   O
ATOM 3723  N   PRO C 127   -4.723  -6.528 35.165 1.00 16.47   N
```

FIG. 6 (con't)

| | | | | | | | | | | | | | | | |
|---|---|---|---|---|---|---|---|---|---|---|---|---|---|---|---|
| ATOM | 454 | CA | HIS A 94 | -9.205 | 2.868 | 58.494 | 1.00 40.87 | C | ATOM | 3724 | CA | PRO C 127 | -4.788 -5.117 35.540 | 1.00 17.34 | C |
| ATOM | 455 | C | HIS A 94 | -8.008 | 3.552 | 59.110 | 1.00 41.00 | C | ATOM | 3725 | C | PRO C 127 | -5.103 -4.836 37.001 | 1.00 19.13 | C |
| ATOM | 456 | O | HIS A 94 | -8.024 | 4.758 | 59.337 | 1.00 41.86 | O | ATOM | 3726 | O | PRO C 127 | -5.620 -5.694 37.722 | 1.00 19.58 | O |
| ATOM | 457 | CB | HIS A 94 | -10.164 | 3.915 | 57.927 | 1.00 42.66 | C | ATOM | 3727 | CB | PRO C 127 | -5.853 -4.568 34.605 | 1.00 16.63 | C |
| ATOM | 458 | CG | HIS A 94 | -10.944 | 3.438 | 56.743 | 1.00 45.89 | C | ATOM | 3728 | CG | PRO C 127 | -6.791 -5.714 34.480 | 1.00 16.89 | C |
| ATOM | 459 | ND1 | HIS A 94 | -10.400 | 3.335 | 55.482 | 1.00 47.73 | N | ATOM | 3729 | CD | PRO C 127 | -5.862 -6.892 34.300 | 1.00 16.34 | C |
| ATOM | 460 | CD2 | HIS A 94 | -12.232 | 3.013 | 56.632 | 1.00 46.71 | C | ATOM | 3730 | N | CYS C 128 | -4.783 -3.625 37.438 | 1.00 19.76 | N |
| ATOM | 461 | CE1 | HIS A 94 | -11.311 | 2.872 | 54.641 | 1.00 48.84 | C | ATOM | 3731 | CA | CYS C 128 | -5.048 -3.211 38.805 | 1.00 19.47 | C |
| ATOM | 462 | NE2 | HIS A 94 | -12.429 | 2.670 | 55.320 | 1.00 48.36 | N | ATOM | 3732 | C | CYS C 128 | -6.526 -2.814 38.919 | 1.00 20.97 | C |
| ATOM | 463 | N | ALA A 95 | -6.968 | 2.774 | 59.375 | 1.00 41.11 | N | ATOM | 3733 | O | CYS C 128 | -7.216 -2.670 37.911 | 1.00 19.57 | O |
| ATOM | 464 | CA | ALA A 95 | -5.757 | 3.302 | 59.983 | 1.00 41.64 | C | ATOM | 3734 | CB | CYS C 128 | -4.162 -2.011 39.174 | 1.00 18.90 | C |
| ATOM | 465 | C | ALA A 95 | -4.867 | 3.992 | 58.961 | 1.00 41.21 | C | ATOM | 3735 | SG | CYS C 128 | -4.525 -0.423 38.316 | 1.00 18.18 | S |
| ATOM | 466 | O | ALA A 95 | -4.741 | 3.543 | 57.831 | 1.00 41.52 | O | ATOM | 3736 | N | ALA C 129 | -6.993 -2.631 40.153 | 1.00 22.79 | N |
| ATOM | 467 | CB | ALA A 95 | -4.983 | 2.190 | 60.663 | 1.00 41.38 | C | ATOM | 3737 | CA | ALA C 129 | -8.378 -2.251 40.399 | 1.00 23.96 | C |
| ATOM | 468 | N | ALA A 96 | -4.238 | 5.083 | 59.381 | 1.00 40.46 | N | ATOM | 3738 | C | ALA C 129 | -8.772 -1.004 39.602 | 1.00 24.97 | C |
| ATOM | 469 | CA | ALA A 96 | -3.354 | 5.828 | 58.508 | 1.00 39.29 | C | ATOM | 3739 | O | ALA C 129 | -9.794 -1.008 38.925 | 1.00 24.58 | O |
| ATOM | 470 | C | ALA A 96 | -2.059 | 5.044 | 58.308 | 1.00 37.94 | C | ATOM | 3740 | CB | ALA C 129 | -8.604 -2.001 41.887 | 1.00 24.58 | C |
| ATOM | 471 | O | ALA A 96 | -1.487 | 5.008 | 57.213 | 1.00 37.83 | O | ATOM | 3741 | N | ALA C 130 | -7.962 0.051 39.680 | 1.00 25.33 | N |
| ATOM | 472 | CB | ALA A 96 | -3.055 | 7.169 | 59.123 | 1.00 40.86 | C | ATOM | 3742 | CA | ALA C 130 | -8.232 1.289 38.947 | 1.00 26.59 | C |
| ATOM | 473 | N | ALA A 97 | -1.600 | 4.415 | 59.380 | 1.00 34.87 | N | ATOM | 3743 | C | ALA C 130 | -8.323 1.058 37.443 | 1.00 27.88 | C |
| ATOM | 474 | CA | ALA A 97 | -0.386 | 3.620 | 59.323 | 1.00 33.04 | C | ATOM | 3744 | O | ALA C 130 | -9.288 1.474 36.795 | 1.00 28.64 | O |
| ATOM | 475 | C | ALA A 97 | -0.726 | 2.132 | 59.354 | 1.00 31.16 | C | ATOM | 3745 | CB | ALA C 130 | -7.157 2.319 39.228 | 1.00 26.59 | C |
| ATOM | 476 | O | ALA A 97 | -1.761 | 1.735 | 59.870 | 1.00 29.76 | O | ATOM | 3746 | N | CYS C 131 | -7.303 0.432 36.878 | 1.00 28.73 | N |
| ATOM | 477 | CB | ALA A 97 | 0.523 | 3.960 | 60.499 | 1.00 33.02 | C | ATOM | 3747 | CA | CYS C 131 | -7.294 0.146 35.442 | 1.00 31.34 | C |
| ATOM | 478 | N | HIS A 98 | 0.163 | 1.317 | 58.798 | 1.00 30.47 | N | ATOM | 3748 | C | CYS C 131 | -8.543 -0.647 35.008 | 1.00 31.41 | C |
| ATOM | 479 | CA | HIS A 98 | -0.029 | -0.122 | 58.791 | 1.00 29.55 | C | ATOM | 3749 | O | CYS C 131 | -9.116 -0.403 33.935 | 1.00 31.62 | O |
| ATOM | 480 | C | HIS A 98 | 0.287 | -0.752 | 60.164 | 1.00 29.61 | C | ATOM | 3750 | CB | CYS C 131 | -6.030 -0.647 35.075 | 1.00 31.27 | C |
| ATOM | 481 | O | HIS A 98 | 1.007 | -0.177 | 60.989 | 1.00 27.88 | O | ATOM | 3751 | SG | CYS C 131 | -4.573 0.348 34.736 | 1.00 34.25 | S |
| ATOM | 482 | CB | HIS A 98 | 0.843 | -0.757 | 57.712 | 1.00 29.13 | C | ATOM | 3752 | N | ALA C 132 | -8.953 -1.601 35.842 | 1.00 30.77 | N |
| ATOM | 483 | CG | HIS A 98 | 0.572 | -0.240 | 56.331 | 1.00 30.25 | C | ATOM | 3753 | CA | ALA C 132 | -10.130 -2.403 35.535 | 1.00 30.66 | C |
| ATOM | 484 | ND1 | HIS A 98 | 1.027 | -0.888 | 55.203 | 1.00 31.62 | N | ATOM | 3754 | C | ALA C 132 | -11.304 -1.480 35.288 | 1.00 31.06 | C |
| ATOM | 485 | CD2 | HIS A 98 | -0.108 | 0.845 | 55.898 | 1.00 30.54 | C | ATOM | 3755 | O | ALA C 132 | -11.963 -1.591 34.260 | 1.00 31.22 | O |
| ATOM | 486 | CE1 | HIS A 98 | 0.636 | -0.218 | 54.131 | 1.00 31.59 | C | ATOM | 3756 | CB | ALA C 132 | -10.445 -3.352 36.679 | 1.00 28.53 | C |
| ATOM | 487 | NE2 | HIS A 98 | -0.054 | 0.836 | 54.520 | 1.00 30.92 | N | ATOM | 3757 | N | ASP C 133 | -11.555 -0.561 36.227 | 1.00 31.49 | N |
| ATOM | 488 | N | ALA A 99 | -0.250 | -1.947 | 60.392 | 1.00 29.60 | N | ATOM | 3758 | CA | ASP C 133 | -12.663 0.383 36.098 | 1.00 31.61 | C |
| ATOM | 489 | CA | ALA A 99 | -0.052 | -2.656 | 61.644 | 1.00 30.33 | C | ATOM | 3759 | C | ASP C 133 | -12.556 1.173 34.815 | 1.00 31.03 | C |
| ATOM | 490 | C | ALA A 99 | 1.398 | -2.605 | 62.093 | 1.00 31.77 | C | ATOM | 3760 | O | ASP C 133 | -13.549 1.385 34.125 | 1.00 31.83 | O |
| ATOM | 491 | O | ALA A 99 | 1.682 | -2.344 | 63.262 | 1.00 31.22 | O | ATOM | 3761 | CB | ASP C 133 | -12.709 1.350 37.287 | 1.00 35.13 | C |
| ATOM | 492 | CB | ALA A 99 | -0.504 | -4.092 | 61.500 | 1.00 29.64 | C | ATOM | 3762 | CG | ASP C 133 | -13.486 0.790 38.467 | 1.00 37.09 | C |
| ATOM | 493 | N | GLU A 100 | 2.316 | -2.839 | 61.163 | 1.00 33.41 | N | ATOM | 3763 | OD1 | ASP C 133 | -12.991 -0.131 39.134 | 1.00 37.59 | O |
| ATOM | 494 | CA | GLU A 100 | 3.743 | -2.820 | 61.476 | 1.00 35.26 | C | ATOM | 3764 | OD2 | ASP C 133 | -14.622 1.265 38.707 | 1.00 40.69 | O |
| ATOM | 495 | C | GLU A 100 | 4.174 | -1.498 | 62.107 | 1.00 35.17 | C | ATOM | 3765 | N | ARG C 134 | -11.347 1.610 34.486 | 1.00 29.69 | N |
| ATOM | 496 | O | GLU A 100 | 4.966 | -1.473 | 63.046 | 1.00 34.71 | O | ATOM | 3766 | CA | ARG C 134 | -11.144 2.360 33.267 | 1.00 30.05 | C |
| ATOM | 497 | CB | GLU A 100 | 4.574 | -3.064 | 60.212 | 1.00 37.51 | C | ATOM | 3767 | C | ARG C 134 | -11.551 1.542 32.048 | 1.00 29.45 | C |
| ATOM | 498 | CG | GLU A 100 | 4.406 | -4.445 | 59.539 | 1.00 39.79 | C | ATOM | 3768 | O | ARG C 134 | -12.147 2.081 31.100 | 1.00 29.30 | O |
| ATOM | 499 | CD | GLU A 100 | 3.025 | -4.708 | 58.914 | 1.00 41.46 | C | ATOM | 3769 | CB | ARG C 134 | -9.689 2.803 33.152 | 1.00 32.08 | C |
| ATOM | 500 | OE1 | GLU A 100 | 2.307 | -3.745 | 58.537 | 1.00 42.28 | O | ATOM | 3770 | CG | ARG C 134 | -9.349 4.020 34.000 | 1.00 35.43 | C |
| ATOM | 501 | OE2 | GLU A 100 | 2.662 | -5.896 | 58.780 | 1.00 41.23 | O | ATOM | 3771 | CD | ARG C 134 | -8.003 4.609 33.601 | 1.00 39.31 | C |
| ATOM | 502 | N | GLU A 101 | 3.654 | -0.396 | 61.581 | 1.00 35.32 | N | ATOM | 3772 | NE | ARG C 134 | -6.877 3.920 34.236 | 1.00 44.13 | N |
| ATOM | 503 | CA | GLU A 101 | 4.020 | 0.912 | 62.099 | 1.00 34.70 | C | ATOM | 3773 | CZ | ARG C 134 | -6.576 4.022 35.529 | 1.00 44.03 | C |
| ATOM | 504 | C | GLU A 101 | 3.433 | 1.153 | 63.471 | 1.00 33.76 | C | ATOM | 3774 | NH1 | ARG C 134 | -7.318 4.788 36.318 | 1.00 44.35 | N |
| ATOM | 505 | O | GLU A 101 | 4.165 | 1.454 | 64.417 | 1.00 34.89 | O | ATOM | 3775 | NH2 | ARG C 134 | -5.544 3.357 36.036 | 1.00 43.34 | N |
| ATOM | 506 | CB | GLU A 101 | 3.546 | 2.005 | 61.144 | 1.00 37.37 | C | ATOM | 3776 | N | ILE C 135 | -11.244 0.252 32.078 | 1.00 29.37 | N |
| ATOM | 507 | CG | GLU A 101 | 4.112 | 1.899 | 59.729 | 1.00 41.75 | C | ATOM | 3777 | CA | ILE C 135 | -11.572 -0.636 30.957 | 1.00 29.01 | C |
| ATOM | 508 | CD | GLU A 101 | 3.635 | 3.024 | 58.806 | 1.00 43.89 | C | ATOM | 3778 | C | ILE C 135 | -13.069 -0.841 30.870 | 1.00 28.30 | C |
| ATOM | 509 | OE1 | GLU A 101 | 2.728 | 2.798 | 57.968 | 1.00 44.04 | O | ATOM | 3779 | O | ILE C 135 | -13.630 -0.923 29.781 | 1.00 27.25 | O |
| ATOM | 510 | OE2 | GLU A 101 | 4.174 | 4.146 | 58.928 | 1.00 44.93 | O | ATOM | 3780 | CB | ILE C 135 | -10.889 -2.017 31.111 | 1.00 28.68 | C |
| ATOM | 511 | N | ALA A 102 | 2.113 | 1.023 | 63.587 | 1.00 30.60 | N | ATOM | 3781 | CG1 | ILE C 135 | -9.366 -1.849 31.066 | 1.00 27.17 | C |
| ATOM | 512 | CA | ALA A 102 | 1.425 | 1.245 | 64.854 | 1.00 28.41 | C | ATOM | 3782 | CG2 | ILE C 135 | -11.382 -2.968 30.009 | 1.00 28.58 | C |
| ATOM | 513 | C | ALA A 102 | 2.069 | 0.511 | 66.021 | 1.00 28.14 | C | ATOM | 3783 | CD1 | ILE C 135 | -8.624 -3.112 31.418 | 1.00 26.17 | C |
| ATOM | 514 | O | ALA A 102 | 2.104 | 1.024 | 67.146 | 1.00 29.70 | O | ATOM | 3784 | N | ILE C 136 | -13.711 -0.922 32.029 | 1.00 27.94 | N |
| ATOM | 515 | CB | ALA A 102 | -0.055 | 0.826 | 64.740 | 1.00 25.71 | C | ATOM | 3785 | CA | ILE C 136 | -15.150 -1.120 32.097 | 1.00 27.53 | C |
| ATOM | 516 | N | PHE A 103 | 2.574 | -0.692 | 65.762 | 1.00 26.55 | N | ATOM | 3786 | C | ILE C 136 | -15.905 0.096 31.560 | 1.00 28.15 | C |
| ATOM | 517 | CA | PHE A 103 | 3.180 | -1.501 | 66.810 | 1.00 25.13 | C | ATOM | 3787 | O | ILE C 136 | -16.914 -0.043 30.862 | 1.00 26.47 | O |
| ATOM | 518 | C | PHE A 103 | 4.383 | -0.817 | 67.442 | 1.00 24.36 | C | ATOM | 3788 | CB | ILE C 136 | -15.570 -1.397 33.544 | 1.00 27.38 | C |
| ATOM | 519 | O | PHE A 103 | 4.473 | -0.709 | 68.665 | 1.00 23.47 | O | ATOM | 3789 | CG1 | ILE C 136 | -14.938 -2.713 34.015 | 1.00 27.83 | C |
| ATOM | 520 | CB | PHE A 103 | 3.605 | -2.864 | 66.256 | 1.00 23.54 | C | ATOM | 3790 | CG2 | ILE C 136 | -17.077 -1.459 33.647 | 1.00 26.65 | C |
| ATOM | 521 | CG | PHE A 103 | 4.077 | -3.813 | 67.315 | 1.00 21.94 | C | ATOM | 3791 | CD1 | ILE C 136 | -15.187 -3.032 35.484 | 1.00 27.73 | C |
| ATOM | 522 | CD1 | PHE A 103 | 3.169 | -4.415 | 68.177 | 1.00 22.73 | C | ATOM | 3792 | N | LYS C 137 | -15.415 1.287 31.882 | 1.00 29.86 | N |
| ATOM | 523 | CD2 | PHE A 103 | 5.426 | -4.085 | 67.476 | 1.00 21.49 | C | ATOM | 3793 | CA | LYS C 137 | -16.075 2.497 31.411 | 1.00 32.08 | C |
| ATOM | 524 | CE1 | PHE A 103 | 3.602 | -5.277 | 69.185 | 1.00 22.49 | C | ATOM | 3794 | C | LYS C 137 | -15.877 2.710 29.927 | 1.00 31.96 | C |
| ATOM | 525 | CE2 | PHE A 103 | 5.873 | -4.945 | 68.484 | 1.00 21.79 | C | ATOM | 3795 | O | LYS C 137 | -16.689 3.369 29.290 | 1.00 33.15 | O |
| ATOM | 526 | CZ | PHE A 103 | 4.958 | -5.542 | 69.336 | 1.00 21.63 | C | ATOM | 3796 | CB | LYS C 137 | -15.573 3.728 32.165 | 1.00 35.47 | C |
| ATOM | 527 | N | PHE A 104 | 5.298 | -0.357 | 66.600 | 1.00 24.45 | N | ATOM | 3797 | CG | LYS C 137 | -16.168 3.880 33.556 | 1.00 39.92 | C |
| ATOM | 528 | CA | PHE A 104 | 6.498 | 0.319 | 67.090 | 1.00 25.83 | C | ATOM | 3798 | CD | LYS C 137 | -15.890 5.268 34.129 | 1.00 43.11 | C |
| ATOM | 529 | C | PHE A 104 | 6.297 | 1.806 | 67.412 | 1.00 26.83 | C | ATOM | 3799 | CE | LYS C 137 | -16.498 5.454 35.518 | 1.00 44.26 | C |
| ATOM | 530 | O | PHE A 104 | 7.257 | 2.492 | 67.749 | 1.00 27.82 | O | ATOM | 3800 | NZ | LYS C 137 | -16.296 6.842 36.043 | 1.00 45.84 | N |
| ATOM | 531 | CB | PHE A 104 | 7.631 | 0.182 | 66.070 | 1.00 21.81 | C | ATOM | 3801 | N | THR C 138 | -14.795 2.159 29.377 | 1.00 31.36 | N |
| ATOM | 532 | CG | PHE A 104 | 8.097 | -1.222 | 65.871 | 1.00 17.73 | C | ATOM | 3802 | CA | THR C 138 | -14.493 2.284 27.958 | 1.00 30.58 | C |
| ATOM | 533 | CD1 | PHE A 104 | 7.961 | -1.843 | 64.641 | 1.00 16.65 | C | ATOM | 3803 | C | THR C 138 | -15.375 1.315 27.153 | 1.00 30.13 | C |
| ATOM | 534 | CD2 | PHE A 104 | 8.673 | -1.930 | 66.915 | 1.00 17.77 | C | ATOM | 3804 | O | THR C 138 | -15.987 1.687 26.148 | 1.00 30.57 | O |
| ATOM | 535 | CE1 | PHE A 104 | 8.391 | -3.138 | 64.442 | 1.00 14.86 | C | ATOM | 3805 | CB | THR C 138 | -12.976 1.959 27.668 | 1.00 31.56 | C |
| ATOM | 536 | CE2 | PHE A 104 | 9.102 | -3.231 | 66.726 | 1.00 16.29 | C | ATOM | 3806 | OG1 | THR C 138 | -12.127 2.845 28.421 | 1.00 31.89 | O |
| ATOM | 537 | CZ | PHE A 104 | 8.960 | -3.833 | 65.484 | 1.00 15.13 | C | ATOM | 3807 | CG2 | THR C 138 | -12.649 2.101 26.181 | 1.00 28.98 | C |
| ATOM | 538 | N | ASN A 105 | 5.064 | 2.293 | 67.325 | 1.00 28.02 | N | ATOM | 3808 | N | LEU C 139 | -15.445 0.071 27.602 | 1.00 29.97 | N |
| ATOM | 539 | CA | ASN A 105 | 4.805 | 3.684 | 67.614 | 1.00 30.45 | C | ATOM | 3809 | CA | LEU C 139 | -16.230 -0.941 26.910 | 1.00 29.82 | C |

FIG. 6 (con't)

| | | | | | | | | | | |
|---|---|---|---|---|---|---|---|---|---|---|
| ATOM | 540 | C   ASN A 105 | 4.001  3.903 68.871 1.00 31.79 | C | ATOM | 3810 | C   LEU C 139 | -17.698 -0.570 26.931 1.00 31.23 | C |
| ATOM | 541 | O   ASN A 105 | 4.047  4.985 69.447 1.00 34.01 | O | ATOM | 3811 | O   LEU C 139 | -18.460 -0.909 26.014 1.00 30.53 | O |
| ATOM | 542 | CB  ASN A 105 | 4.093  4.373 66.442 1.00 31.94 | C | ATOM | 3812 | CB  LEU C 139 | -16.026 -2.311 27.569 1.00 27.58 | C |
| ATOM | 543 | CG  ASN A 105 | 4.997  4.561 65.240 1.00 33.98 | C | ATOM | 3813 | CG  LEU C 139 | -14.652 -2.990 27.375 1.00 24.92 | C |
| ATOM | 544 | OD1 ASN A 105 | 6.189  4.855 65.388 1.00 35.96 | O | ATOM | 3814 | CD1 LEU C 139 | -14.559 -4.221 28.245 1.00 22.79 | C |
| ATOM | 545 | ND2 ASN A 105 | 4.439  4.413 64.049 1.00 33.43 | N | ATOM | 3815 | CD2 LEU C 139 | -14.471 -3.379 25.921 1.00 23.75 | C |
| ATOM | 546 | N   THR A 106 | 3.270  2.890 69.316 1.00 32.65 | N | ATOM | 3816 | N   SER C 140 | -18.081  0.151 27.976 1.00 32.11 | N |
| ATOM | 547 | CA  THR A 106 | 2.457  3.040 70.522 1.00 33.94 | C | ATOM | 3817 | CA  SER C 140 | -19.465  0.575 28.147 1.00 33.53 | C |
| ATOM | 548 | C   THR A 106 | 2.464  1.841 71.447 1.00 33.85 | C | ATOM | 3818 | C   SER C 140 | -19.847  1.714 27.226 1.00 33.33 | C |
| ATOM | 549 | O   THR A 106 | 2.267  1.985 72.655 1.00 34.59 | O | ATOM | 3819 | O   SER C 140 | -21.027  1.918 26.948 1.00 34.34 | O |
| ATOM | 550 | CB  THR A 106 | 1.018  3.359 70.169 1.00 34.54 | C | ATOM | 3820 | CB  SER C 140 | -19.700  0.992 29.603 1.00 35.15 | C |
| ATOM | 551 | OG1 THR A 106 | 0.611  2.531 69.067 1.00 36.21 | O | ATOM | 3821 | OG  SER C 140 | -21.091  1.072 29.866 1.00 38.15 | O |
| ATOM | 552 | CG2 THR A 106 | 0.880  4.826 69.801 1.00 35.14 | C | ATOM | 3822 | N   LYS C 141 | -18.855  2.461 26.758 1.00 34.61 | N |
| ATOM | 553 | N   ILE A 107 | 2.678  0.657 70.884 1.00 33.30 | N | ATOM | 3823 | CA  LYS C 141 | -19.094  3.577 25.857 1.00 34.86 | C |
| ATOM | 554 | CA  ILE A 107 | 2.705 -0.562 71.681 1.00 32.40 | C | ATOM | 3824 | C   LYS C 141 | -18.936  3.093 24.416 1.00 33.86 | C |
| ATOM | 555 | C   ILE A 107 | 4.080 -0.848 72.288 1.00 31.75 | C | ATOM | 3825 | O   LYS C 141 | -19.489  3.685 23.498 1.00 35.19 | O |
| ATOM | 556 | O   ILE A 107 | 4.194 -1.179 73.467 1.00 31.71 | O | ATOM | 3826 | CB  LYS C 141 | -18.095  4.707 26.135 1.00 37.93 | C |
| ATOM | 557 | CB  ILE A 107 | 2.272 -1.765 70.843 1.00 32.26 | C | ATOM | 3827 | CG  LYS C 141 | -18.153  5.254 27.549 1.00 39.43 | C |
| ATOM | 558 | CG1 ILE A 107 | 0.919 -1.476 70.214 1.00 32.28 | C | ATOM | 3828 | CD  LYS C 141 | -19.516  5.886 27.834 1.00 44.91 | C |
| ATOM | 559 | CG2 ILE A 107 | 2.151 -3.007 71.719 1.00 31.74 | C | ATOM | 3829 | CE  LYS C 141 | -19.742  7.225 27.092 1.00 46.58 | C |
| ATOM | 560 | CD1 ILE A 107 | 0.487 -2.531 69.277 1.00 34.74 | C | ATOM | 3830 | NZ  LYS C 141 | -21.021  7.920 27.498 1.00 46.23 | N |
| ATOM | 561 | N   LEU A 108 | 5.124 -0.706 71.485 1.00 30.92 | N | ATOM | 3831 | N   THR C 142 | -18.185  2.019 24.216 1.00 32.20 | N |
| ATOM | 562 | CA  LEU A 108 | 6.464 -0.975 71.964 1.00 30.03 | C | ATOM | 3832 | CA  THR C 142 | -17.985  1.487 22.876 1.00 31.09 | C |
| ATOM | 563 | C   LEU A 108 | 7.365  0.166 71.515 1.00 30.38 | C | ATOM | 3833 | C   THR C 142 | -18.516  0.058 22.777 1.00 29.81 | C |
| ATOM | 564 | O   LEU A 108 | 8.233 -0.018 70.668 1.00 31.35 | O | ATOM | 3834 | O   THR C 142 | -17.810 -0.906 23.085 1.00 28.74 | O |
| ATOM | 565 | CB  LEU A 108 | 6.935 -2.298 71.377 1.00 29.78 | C | ATOM | 3835 | CB  THR C 142 | -16.488  1.512 22.483 1.00 31.21 | C |
| ATOM | 566 | CG  LEU A 108 | 8.019 -3.058 72.126 1.00 31.17 | C | ATOM | 3836 | OG1 THR C 142 | -15.695  1.216 23.639 1.00 32.49 | O |
| ATOM | 567 | CD1 LEU A 108 | 7.601 -3.299 73.559 1.00 30.95 | C | ATOM | 3837 | CG2 THR C 142 | -16.094  2.871 21.963 1.00 30.75 | C |
| ATOM | 568 | CD2 LEU A 108 | 8.250 -4.373 71.431 1.00 31.92 | C | ATOM | 3838 | N   LYS C 143 | -19.771 -0.058 22.348 1.00 29.27 | N |
| ATOM | 569 | N   PRO A 109 | 7.160  1.372 72.075 1.00 31.40 | N | ATOM | 3839 | CA  LYS C 143 | -20.445 -1.351 22.219 1.00 27.92 | C |
| ATOM | 570 | CA  PRO A 109 | 7.921  2.589 71.764 1.00 31.13 | C | ATOM | 3840 | C   LYS C 143 | -19.851 -2.170 21.082 1.00 26.21 | C |
| ATOM | 571 | C   PRO A 109 | 9.409  2.478 72.022 1.00 31.04 | C | ATOM | 3841 | O   LYS C 143 | -19.908 -3.400 21.101 1.00 26.43 | O |
| ATOM | 572 | O   PRO A 109 | 10.212  2.779 71.144 1.00 31.29 | O | ATOM | 3842 | CB  LYS C 143 | -21.942 -1.137 21.935 1.00 29.76 | C |
| ATOM | 573 | CB  PRO A 109 | 7.271  3.640 72.657 1.00 31.39 | C | ATOM | 3843 | CG  LYS C 143 | -22.686 -0.260 22.935 1.00 29.72 | C |
| ATOM | 574 | CG  PRO A 109 | 5.883  3.161 72.781 1.00 32.99 | C | ATOM | 3844 | CD  LYS C 143 | -22.764 -0.909 24.308 1.00 32.22 | C |
| ATOM | 575 | CD  PRO A 109 | 6.077  1.685 73.024 1.00 32.10 | C | ATOM | 3845 | CE  LYS C 143 | -23.620 -0.099 25.275 1.00 31.36 | C |
| ATOM | 576 | N   ALA A 110 | 9.782  2.063 73.225 1.00 31.49 | N | ATOM | 3846 | NZ  LYS C 143 | -23.772  0.799 26.590 1.00 31.14 | N |
| ATOM | 577 | CA  ALA A 110 | 11.204  1.940 73.552 1.00 33.30 | C | ATOM | 3847 | N   ASN C 144 | -19.289 -1.480 20.097 1.00 22.91 | N |
| ATOM | 578 | C   ALA A 110 | 11.562  0.627 74.247 1.00 33.23 | C | ATOM | 3848 | CA  ASN C 144 | -18.703 -2.142 18.941 1.00 21.98 | C |
| ATOM | 579 | O   ALA A 110 | 10.705 -0.044 74.820 1.00 33.66 | O | ATOM | 3849 | C   ASN C 144 | -17.248 -2.519 19.158 1.00 20.80 | C |
| ATOM | 580 | CB  ALA A 110 | 11.630  3.134 74.424 1.00 33.91 | C | ATOM | 3850 | O   ASN C 144 | -16.490 -2.694 18.199 1.00 19.55 | O |
| ATOM | 581 | N   PHE A 111 | 12.839  0.263 74.191 1.00 33.53 | N | ATOM | 3851 | CB  ASN C 144 | -18.821 -1.239 17.707 1.00 21.74 | C |
| ATOM | 582 | CA  PHE A 111 | 13.313 -0.969 74.832 1.00 34.05 | C | ATOM | 3852 | CG  ASN C 144 | -18.183  0.109 17.921 1.00 22.28 | C |
| ATOM | 583 | C   PHE A 111 | 14.467 -0.636 75.774 1.00 35.38 | C | ATOM | 3853 | OD1 ASN C 144 | -18.145  0.609 19.046 1.00 24.50 | O |
| ATOM | 584 | O   PHE A 111 | 15.323  0.173 75.424 1.00 36.35 | O | ATOM | 3854 | ND2 ASN C 144 | -17.690  0.716 16.850 1.00 22.13 | N |
| ATOM | 585 | CB  PHE A 111 | 13.833 -1.964 73.789 1.00 30.80 | C | ATOM | 3855 | N   LEU C 145 | -16.877 -2.656 20.422 1.00 19.61 | N |
| ATOM | 586 | CG  PHE A 111 | 12.958 -2.100 72.581 1.00 28.52 | C | ATOM | 3856 | CA  LEU C 145 | -15.519 -3.019 20.811 1.00 18.68 | C |
| ATOM | 587 | CD1 PHE A 111 | 12.847 -1.064 71.662 1.00 28.58 | C | ATOM | 3857 | C   LEU C 145 | -15.509 -4.273 21.687 1.00 18.67 | C |
| ATOM | 588 | CD2 PHE A 111 | 12.225 -3.258 72.369 1.00 26.83 | C | ATOM | 3858 | O   LEU C 145 | -16.107 -4.278 22.762 1.00 19.59 | O |
| ATOM | 589 | CE1 PHE A 111 | 12.014 -1.181 70.548 1.00 27.64 | C | ATOM | 3859 | CB  LEU C 145 | -14.881 -1.860 21.592 1.00 17.22 | C |
| ATOM | 590 | CE2 PHE A 111 | 11.391 -3.385 71.260 1.00 26.13 | C | ATOM | 3860 | CG  LEU C 145 | -13.633 -2.212 22.424 1.00 17.47 | C |
| ATOM | 591 | CZ  PHE A 111 | 11.286 -2.345 70.350 1.00 26.71 | C | ATOM | 3861 | CD1 LEU C 145 | -12.480 -2.721 21.539 1.00 15.40 | C |
| ATOM | 592 | N   ASP A 112 | 14.504 -1.253 76.953 1.00 35.63 | N | ATOM | 3862 | CD2 LEU C 145 | -13.209 -0.976 23.200 1.00 16.87 | C |
| ATOM | 593 | CA  ASP A 112 | 15.606 -0.999 77.878 1.00 37.37 | C | ATOM | 3863 | N   ARG C 146 | -14.850 -5.327 21.222 1.00 18.05 | N |
| ATOM | 594 | C   ASP A 112 | 16.730 -2.012 77.597 1.00 36.28 | C | ATOM | 3864 | CA  ARG C 146 | -14.735 -6.568 22.002 1.00 16.88 | C |
| ATOM | 595 | O   ASP A 112 | 16.506 -3.223 77.576 1.00 35.18 | O | ATOM | 3865 | C   ARG C 146 | -13.272 -6.657 22.465 1.00 14.37 | C |
| ATOM | 596 | CB  ASP A 112 | 15.131 -1.098 79.336 1.00 40.34 | C | ATOM | 3866 | O   ARG C 146 | -12.357 -6.455 21.668 1.00 15.73 | O |
| ATOM | 597 | CG  ASP A 112 | 15.006 -2.521 79.810 1.00 42.74 | C | ATOM | 3867 | CB  ARG C 146 | -15.091 -7.768 21.124 1.00 18.45 | C |
| ATOM | 598 | OD1 ASP A 112 | 14.360 -3.328 79.106 1.00 45.41 | O | ATOM | 3868 | CG  ARG C 146 | -14.996 -9.086 21.848 1.00 23.11 | C |
| ATOM | 599 | OD2 ASP A 112 | 15.549 -2.823 80.886 1.00 42.72 | O | ATOM | 3869 | CD  ARG C 146 | -15.290 -10.266 20.924 1.00 28.44 | C |
| ATOM | 600 | N   PRO A 113 | 17.950 -1.512 77.360 1.00 35.36 | N | ATOM | 3870 | NE  ARG C 146 | -15.610 -11.482 21.682 1.00 31.85 | N |
| ATOM | 601 | CA  PRO A 113 | 19.132 -2.327 77.066 1.00 33.92 | C | ATOM | 3871 | CZ  ARG C 146 | -14.778 -12.143 22.497 1.00 33.30 | C |
| ATOM | 602 | C   PRO A 113 | 19.319 -3.551 77.944 1.00 32.23 | C | ATOM | 3872 | NH1 ARG C 146 | -13.530 -11.740 22.687 1.00 31.13 | N |
| ATOM | 603 | O   PRO A 113 | 19.763 -4.597 77.475 1.00 31.02 | O | ATOM | 3873 | NH2 ARG C 146 | -15.227 -13.205 23.158 1.00 34.28 | N |
| ATOM | 604 | CB  PRO A 113 | 20.271 -1.327 77.225 1.00 34.30 | C | ATOM | 3874 | N   LEU C 147 | -13.058 -6.953 23.743 1.00 12.23 | N |
| ATOM | 605 | CG  PRO A 113 | 19.656 -0.082 76.700 1.00 35.20 | C | ATOM | 3875 | CA  LEU C 147 | -11.700 -7.026 24.290 1.00 9.94 | C |
| ATOM | 606 | CD  PRO A 113 | 18.302 -0.081 77.378 1.00 34.86 | C | ATOM | 3876 | C   LEU C 147 | -11.312 -8.375 24.901 1.00 10.03 | C |
| ATOM | 607 | N   ALA A 114 | 18.963 -3.410 79.212 1.00 31.30 | N | ATOM | 3877 | O   LEU C 147 | -12.044 -8.940 25.705 1.00 6.22 | O |
| ATOM | 608 | CA  ALA A 114 | 19.127 -4.487 80.173 1.00 30.48 | C | ATOM | 3878 | CB  LEU C 147 | -11.500 -5.926 25.348 1.00 8.39 | C |
| ATOM | 609 | C   ALA A 114 | 18.255 -5.696 79.905 1.00 29.74 | C | ATOM | 3879 | CG  LEU C 147 | -10.109 -5.820 25.979 1.00 7.27 | C |
| ATOM | 610 | O   ALA A 114 | 18.401 -6.726 80.559 1.00 30.20 | O | ATOM | 3880 | CD1 LEU C 147 | -9.105 -5.488 24.902 1.00 7.96 | C |
| ATOM | 611 | CB  ALA A 114 | 18.861 -3.965 81.578 1.00 30.69 | C | ATOM | 3881 | CD2 LEU C 147 | -10.071 -4.759 27.063 1.00 6.90 | C |
| ATOM | 612 | N   LEU A 115 | 17.354 -5.588 78.943 1.00 28.59 | N | ATOM | 3882 | N   LEU C 148 | -10.138 -8.878 24.514 1.00 10.47 | N |
| ATOM | 613 | CA  LEU A 115 | 16.477 -6.702 78.639 1.00 26.74 | C | ATOM | 3883 | CA  LEU C 148 | -9.631 -10.142 25.040 1.00 9.36 | C |
| ATOM | 614 | C   LEU A 115 | 16.606 -7.184 77.211 1.00 26.21 | C | ATOM | 3884 | C   LEU C 148 | -8.288 -9.863 25.673 1.00 9.38 | C |
| ATOM | 615 | O   LEU A 115 | 17.075 -6.463 76.325 1.00 25.99 | O | ATOM | 3885 | O   LEU C 148 | -7.346 -9.448 24.987 1.00 9.83 | O |
| ATOM | 616 | CB  LEU A 115 | 15.020 -6.317 78.909 1.00 25.62 | C | ATOM | 3886 | CB  LEU C 148 | -9.470 -11.152 23.916 1.00 9.27 | C |
| ATOM | 617 | CG  LEU A 115 | 14.537 -6.198 80.349 1.00 25.20 | C | ATOM | 3887 | CG  LEU C 148 | -8.627 -12.400 24.242 1.00 9.84 | C |
| ATOM | 618 | CD1 LEU A 115 | 13.091 -5.725 80.379 1.00 24.76 | C | ATOM | 3888 | CD1 LEU C 148 | -9.228 -13.162 25.395 1.00 10.23 | C |
| ATOM | 619 | CD2 LEU A 115 | 14.664 -7.545 81.029 1.00 25.97 | C | ATOM | 3889 | CD2 LEU C 148 | -8.602 -13.288 23.031 1.00 10.90 | C |
| ATOM | 620 | N   ARG A 116 | 16.178 -8.419 76.998 1.00 25.26 | N | ATOM | 3890 | N   ILE C 149 | -8.171 -10.079 26.976 1.00 7.85 | N |
| ATOM | 621 | CA  ARG A 116 | 16.194 -9.010 75.679 1.00 25.16 | C | ATOM | 3891 | CA  ILE C 149 | -6.895 -9.818 27.632 1.00 8.26 | C |
| ATOM | 622 | C   ARG A 116 | 14.753 -9.378 75.322 1.00 23.32 | C | ATOM | 3892 | C   ILE C 149 | -6.236 -11.113 28.070 1.00 8.79 | C |
| ATOM | 623 | O   ARG A 116 | 14.142 -10.222 75.967 1.00 22.07 | O | ATOM | 3893 | O   ILE C 149 | -6.780 -11.829 28.909 1.00 11.23 | O |
| ATOM | 624 | CB  ARG A 116 | 17.096 -10.239 75.673 1.00 27.53 | C | ATOM | 3894 | CB  ILE C 149 | -7.065 -8.898 28.886 1.00 8.69 | C |
| ATOM | 625 | CG  ARG A 116 | 18.555 -9.909 75.966 1.00 31.30 | C | ATOM | 3895 | CG1 ILE C 149 | -7.824 -7.612 28.537 1.00 10.12 | C |

FIG. 6 (con't)

```
ATOM  626  CD  ARG A 116   19.485 -10.803  75.152  1.00 36.39   C
ATOM  627  NE  ARG A 116   19.176 -10.717  73.720  1.00 39.38   N
ATOM  628  CZ  ARG A 116   19.794 -11.406  72.762  1.00 39.62   C
ATOM  629  NH1 ARG A 116   20.775 -12.246  73.063  1.00 39.78   N
ATOM  630  NH2 ARG A 116   19.417 -11.257  71.497  1.00 39.62   N
ATOM  631  N   TYR A 117   14.215  -8.729  74.294  1.00 22.29   N
ATOM  632  CA  TYR A 117   12.843  -8.961  73.861  1.00 22.17   C
ATOM  633  C   TYR A 117   12.675 -10.063  72.810  1.00 22.68   C
ATOM  634  O   TYR A 117   13.499 -10.215  71.903  1.00 23.33   O
ATOM  635  CB  TYR A 117   12.241  -7.662  73.332  1.00 22.44   C
ATOM  636  CG  TYR A 117   12.235  -6.524  74.332  1.00 24.66   C
ATOM  637  CD1 TYR A 117   13.421  -5.889  74.702  1.00 25.81   C
ATOM  638  CD2 TYR A 117   11.048  -6.080  74.912  1.00 25.52   C
ATOM  639  CE1 TYR A 117   13.426  -4.849  75.620  1.00 26.80   C
ATOM  640  CE2 TYR A 117   11.038  -5.037  75.831  1.00 26.04   C
ATOM  641  CZ  TYR A 117   12.226  -4.431  76.179  1.00 27.59   C
ATOM  642  OH  TYR A 117   12.215  -3.417  77.108  1.00 29.37   O
ATOM  643  N   ASN A 118   11.592 -10.823  72.937  1.00 23.61   N
ATOM  644  CA  ASN A 118   11.255 -11.900  72.009  1.00 23.56   C
ATOM  645  C   ASN A 118    9.843 -11.643  71.538  1.00 22.14   C
ATOM  646  O   ASN A 118    8.895 -12.204  72.086  1.00 22.31   O
ATOM  647  CB  ASN A 118   11.291 -13.239  72.725  1.00 26.22   C
ATOM  648  CG  ASN A 118   12.268 -14.180  72.110  1.00 30.40   C
ATOM  649  OD1 ASN A 118   13.483 -14.005  72.246  1.00 34.07   O
ATOM  650  ND2 ASN A 118   11.764 -15.181  71.406  1.00 32.12   N
ATOM  651  N   VAL A 119    9.702 -10.804  70.519  1.00 20.48   N
ATOM  652  CA  VAL A 119    8.382 -10.442  70.009  1.00 17.96   C
ATOM  653  C   VAL A 119    7.909 -11.427  68.988  1.00 16.86   C
ATOM  654  O   VAL A 119    8.702 -11.928  68.205  1.00 18.02   O
ATOM  655  CB  VAL A 119    8.415  -9.044  69.366  1.00 17.77   C
ATOM  656  CG1 VAL A 119    7.032  -8.702  68.832  1.00 18.50   C
ATOM  657  CG2 VAL A 119    8.895  -7.997  70.382  1.00 18.24   C
ATOM  658  N   THR A 120    6.616 -11.712  68.989  1.00 16.23   N
ATOM  659  CA  THR A 120    6.046 -12.637  68.018  1.00 15.49   C
ATOM  660  C   THR A 120    4.757 -12.046  67.439  1.00 15.95   C
ATOM  661  O   THR A 120    3.865 -11.725  68.205  1.00 16.29   O
ATOM  662  CB  THR A 120    5.746 -13.952  68.672  1.00 14.15   C
ATOM  663  OG1 THR A 120    6.970 -14.531  69.104  1.00 14.89   O
ATOM  664  CG2 THR A 120    5.043 -14.881  67.706  1.00 14.01   C
ATOM  665  N   TRP A 121    4.670 -11.904  66.105  1.00 15.04   N
ATOM  666  CA  TRP A 121    3.474 -11.351  65.451  1.00 14.59   C
ATOM  667  C   TRP A 121    2.629 -12.417  64.762  1.00 14.80   C
ATOM  668  O   TRP A 121    3.140 -13.450  64.357  1.00 14.85   O
ATOM  669  CB  TRP A 121    3.828 -10.321  64.372  1.00 13.65   C
ATOM  670  CG  TRP A 121    4.371  -9.027  64.860  1.00 12.34   C
ATOM  671  CD1 TRP A 121    4.413  -8.581  66.151  1.00 10.88   C
ATOM  672  CD2 TRP A 121    5.008  -8.026  64.060  1.00 11.77   C
ATOM  673  NE1 TRP A 121    5.047  -7.359  66.206  1.00  9.27   N
ATOM  674  CE2 TRP A 121    5.423  -6.994  64.935  1.00 11.56   C
ATOM  675  CE3 TRP A 121    5.273  -7.899  62.687  1.00 11.99   C
ATOM  676  CZ2 TRP A 121    6.096  -5.845  64.482  1.00 11.62   C
ATOM  677  CZ3 TRP A 121    5.948  -6.749  62.236  1.00 15.58   C
ATOM  678  CH2 TRP A 121    6.346  -5.741  63.130  1.00 12.25   C
ATOM  679  N   TYR A 122    1.335 -12.133  64.614  1.00 15.12   N
ATOM  680  CA  TYR A 122    0.399 -13.048  63.969  1.00 14.52   C
ATOM  681  C   TYR A 122   -0.485 -12.199  63.081  1.00 14.18   C
ATOM  682  O   TYR A 122   -1.467 -11.628  63.554  1.00 15.95   O
ATOM  683  CB  TYR A 122   -0.466 -13.758  65.008  1.00 15.40   C
ATOM  684  CG  TYR A 122    0.257 -14.791  65.846  1.00 15.65   C
ATOM  685  CD1 TYR A 122    0.770 -14.475  67.101  1.00 16.26   C
ATOM  686  CD2 TYR A 122    0.386 -16.108  65.400  1.00 16.74   C
ATOM  687  CE1 TYR A 122    1.388 -15.453  67.902  1.00 17.44   C
ATOM  688  CE2 TYR A 122    0.999 -17.095  66.188  1.00 14.89   C
ATOM  689  CZ  TYR A 122    1.491 -16.760  67.439  1.00 16.76   C
ATOM  690  OH  TYR A 122    2.055 -17.721  68.248  1.00 15.81   O
ATOM  691  N   VAL A 123   -0.139 -12.104  61.807  1.00 14.48   N
ATOM  692  CA  VAL A 123   -0.893 -11.304  60.854  1.00 16.35   C
ATOM  693  C   VAL A 123   -1.402 -12.152  59.701  1.00 16.04   C
ATOM  694  O   VAL A 123   -0.873 -13.232  59.458  1.00 18.44   O
ATOM  695  CB  VAL A 123   -0.031 -10.177  60.256  1.00 17.58   C
ATOM  696  CG1 VAL A 123    0.060  -9.039  61.233  1.00 18.57   C
ATOM  697  CG2 VAL A 123    1.365 -10.710  59.928  1.00 19.50   C
ATOM  698  N   SER A 124   -2.394 -11.636  58.982  1.00 15.27   N
ATOM  699  CA  SER A 124   -2.992 -12.358  57.860  1.00 15.80   C
ATOM  700  C   SER A 124   -2.039 -12.583  56.693  1.00 15.80   C
ATOM  701  O   SER A 124   -2.115 -13.615  56.034  1.00 18.18   O
ATOM  702  CB  SER A 124   -4.234 -11.623  57.334  1.00 13.04   C
ATOM  703  OG  SER A 124   -3.910 -10.400  56.695  1.00 12.72   O
ATOM  704  N   SER A 125   -1.159 -11.631  56.427  1.00 14.87   N
ATOM  705  CA  SER A 125   -0.246 -11.783  55.327  1.00 16.64   C
ATOM  706  C   SER A 125    1.087 -11.084  55.593  1.00 16.05   C
ATOM  707  O   SER A 125    1.182 -10.263  56.498  1.00 16.72   O
ATOM  708  CB  SER A 125   -0.843 -11.213  54.050  1.00 19.25   C
ATOM  709  OG  SER A 125   -0.613  -9.817  53.997  1.00 24.71   O
ATOM  710  N   SER A 126    2.106 -11.414  54.795  1.00 15.34   N
ATOM  711  CA  SER A 126    3.430 -10.816  54.922  1.00 15.00   C

ATOM 3896  CG2 ILE C 149   -5.690  -8.464  29.396  1.00  8.11   C
ATOM 3897  CD1 ILE C 149   -8.074  -6.696  29.749  1.00  6.04   C
ATOM 3898  N   LEU C 150   -5.082 -11.423  27.495  1.00  8.72   N
ATOM 3899  CA  LEU C 150   -4.333 -12.625  27.873  1.00 11.00   C
ATOM 3900  C   LEU C 150   -3.148 -12.224  28.761  1.00 10.97   C
ATOM 3901  O   LEU C 150   -2.241 -11.516  28.312  1.00 11.47   O
ATOM 3902  CB  LEU C 150   -3.815 -13.356  26.626  1.00 10.84   C
ATOM 3903  CG  LEU C 150   -4.884 -13.981  25.726  1.00 10.32   C
ATOM 3904  CD1 LEU C 150   -4.241 -14.683  24.575  1.00 11.92   C
ATOM 3905  CD2 LEU C 150   -5.664 -14.978  26.499  1.00 10.13   C
ATOM 3906  N   VAL C 151   -3.165 -12.685  30.006  1.00 11.21   N
ATOM 3907  CA  VAL C 151   -2.128 -12.347  30.987  1.00 10.68   C
ATOM 3908  C   VAL C 151   -1.164 -13.502  31.307  1.00 10.73   C
ATOM 3909  O   VAL C 151   -1.558 -14.662  31.290  1.00  9.63   O
ATOM 3910  CB  VAL C 151   -2.774 -11.877  32.348  1.00 12.07   C
ATOM 3911  CG1 VAL C 151   -3.776 -10.730  32.108  1.00 10.76   C
ATOM 3912  CG2 VAL C 151   -3.464 -13.044  33.041  1.00  9.03   C
ATOM 3913  N   GLY C 152    0.091 -13.167  31.587  1.00 10.69   N
ATOM 3914  CA  GLY C 152    1.070 -14.190  31.919  1.00 12.10   C
ATOM 3915  C   GLY C 152    0.771 -14.792  33.286  1.00 12.94   C
ATOM 3916  O   GLY C 152    1.008 -15.970  33.519  1.00 11.25   O
ATOM 3917  N   ARG C 153    0.275 -13.962  34.201  1.00 14.33   N
ATOM 3918  CA  ARG C 153   -0.104 -14.424  35.530  1.00 16.13   C
ATOM 3919  C   ARG C 153   -1.046 -13.411  36.155  1.00 17.80   C
ATOM 3920  O   ARG C 153   -1.302 -12.351  35.574  1.00 20.77   O
ATOM 3921  CB  ARG C 153    1.119 -14.603  36.439  1.00 16.61   C
ATOM 3922  CG  ARG C 153    1.894 -13.334  36.717  1.00 16.48   C
ATOM 3923  CD  ARG C 153    2.768 -13.553  37.932  1.00 19.75   C
ATOM 3924  NE  ARG C 153    3.722 -12.474  38.159  1.00 23.09   N
ATOM 3925  CZ  ARG C 153    3.412 -11.270  38.633  1.00 22.97   C
ATOM 3926  NH1 ARG C 153    2.158 -10.970  38.945  1.00 22.31   N
ATOM 3927  NH2 ARG C 153    4.368 -10.364  38.782  1.00 22.27   N
ATOM 3928  N   LEU C 154   -1.573 -13.728  37.328  1.00 17.83   N
ATOM 3929  CA  LEU C 154   -2.481 -12.836  38.032  1.00 18.32   C
ATOM 3930  C   LEU C 154   -1.736 -11.847  38.942  1.00 19.65   C
ATOM 3931  O   LEU C 154   -0.656 -12.144  39.458  1.00 20.77   O
ATOM 3932  CB  LEU C 154   -3.476 -13.670  38.847  1.00 17.71   C
ATOM 3933  CG  LEU C 154   -4.870 -13.902  38.243  1.00 18.68   C
ATOM 3934  CD1 LEU C 154   -4.826 -13.972  36.725  1.00 18.30   C
ATOM 3935  CD2 LEU C 154   -5.445 -15.170  38.827  1.00 18.64   C
ATOM 3936  N   PHE C 155   -2.317 -10.669  39.127  1.00 19.94   N
ATOM 3937  CA  PHE C 155   -1.725  -9.636  39.968  1.00 21.13   C
ATOM 3938  C   PHE C 155   -2.572  -9.426  41.231  1.00 22.49   C
ATOM 3939  O   PHE C 155   -3.752  -9.086  41.132  1.00 22.33   O
ATOM 3940  CB  PHE C 155   -1.639  -8.333  39.174  1.00 21.78   C
ATOM 3941  CG  PHE C 155   -1.159  -7.170  39.977  1.00 21.10   C
ATOM 3942  CD1 PHE C 155    0.115  -7.163  40.507  1.00 19.62   C
ATOM 3943  CD2 PHE C 155   -1.995  -6.074  40.197  1.00 20.60   C
ATOM 3944  CE1 PHE C 155    0.565  -6.081  41.250  1.00 19.18   C
ATOM 3945  CE2 PHE C 155   -1.550  -4.985  40.945  1.00 19.35   C
ATOM 3946  CZ  PHE C 155   -0.273  -4.988  41.469  1.00 18.16   C
ATOM 3947  N   MET C 156   -1.972  -9.616  42.404  1.00 23.17   N
ATOM 3948  CA  MET C 156   -2.678  -9.479  43.680  1.00 24.43   C
ATOM 3949  C   MET C 156   -4.012 -10.222  43.641  1.00 26.24   C
ATOM 3950  O   MET C 156   -5.019  -9.754  44.184  1.00 26.28   O
ATOM 3951  CB  MET C 156   -2.936  -8.014  44.011  1.00 25.35   C
ATOM 3952  CG  MET C 156   -1.692  -7.185  44.183  1.00 27.61   C
ATOM 3953  SD  MET C 156   -2.079  -5.675  45.099  1.00 33.60   S
ATOM 3954  CE  MET C 156   -3.053  -4.761  43.934  1.00 30.88   C
ATOM 3955  N   TRP C 157   -4.028 -11.389  42.999  1.00 26.89   N
ATOM 3956  CA  TRP C 157   -5.268 -12.161  42.882  1.00 28.67   C
ATOM 3957  C   TRP C 157   -5.955 -12.490  44.208  1.00 29.90   C
ATOM 3958  O   TRP C 157   -7.184 -12.569  44.272  1.00 32.06   O
ATOM 3959  CB  TRP C 157   -5.026 -13.459  42.125  1.00 27.67   C
ATOM 3960  CG  TRP C 157   -4.186 -14.421  42.853  1.00 27.96   C
ATOM 3961  CD1 TRP C 157   -2.830 -14.475  42.854  1.00 28.36   C
ATOM 3962  CD2 TRP C 157   -4.640 -15.489  43.686  1.00 28.05   C
ATOM 3963  NE1 TRP C 157   -2.405 -15.523  43.632  1.00 29.31   N
ATOM 3964  CE2 TRP C 157   -3.495 -16.168  44.148  1.00 27.66   C
ATOM 3965  CE3 TRP C 157   -5.904 -15.951  44.071  1.00 29.72   C
ATOM 3966  CZ2 TRP C 157   -3.573 -17.273  44.995  1.00 27.74   C
ATOM 3967  CZ3 TRP C 157   -5.985 -17.054  44.915  1.00 29.20   C
ATOM 3968  CH2 TRP C 157   -4.822 -17.706  45.359  1.00 28.61   C
ATOM 3969  N   GLU C 158   -5.170 -12.690  45.254  1.00 31.07   N
ATOM 3970  CA  GLU C 158   -5.726 -13.032  46.552  1.00 31.91   C
ATOM 3971  C   GLU C 158   -6.515 -11.893  47.210  1.00 29.97   C
ATOM 3972  O   GLU C 158   -7.387 -12.144  48.032  1.00 28.36   O
ATOM 3973  CB  GLU C 158   -4.604 -13.502  47.487  1.00 35.12   C
ATOM 3974  CG  GLU C 158   -3.370 -12.599  47.503  1.00 39.63   C
ATOM 3975  CD  GLU C 158   -2.303 -13.065  46.550  1.00 40.94   C
ATOM 3976  OE1 GLU C 158   -2.200 -12.533  45.418  1.00 42.73   O
ATOM 3977  OE2 GLU C 158   -1.572 -13.999  46.959  1.00 41.66   O
ATOM 3978  N   GLU C 159   -6.218 -10.648  46.840  1.00 29.01   N
ATOM 3979  CA  GLU C 159   -6.923  -9.507  47.418  1.00 26.96   C
ATOM 3980  C   GLU C 159   -8.371  -9.398  46.947  1.00 27.22   C
ATOM 3981  O   GLU C 159   -8.676  -9.514  45.757  1.00 27.11   O
```

FIG. 6 (con't)

```
ATOM    712  C   SER A 126       3.368  -9.311 54.658  1.00 14.82           C
ATOM    713  O   SER A 126       2.517  -8.825 53.928  1.00 14.74           O
ATOM    714  CB  SER A 126       4.395 -11.471 53.950  1.00 15.19           C
ATOM    715  OG  SER A 126       3.776 -11.601 52.683  1.00 17.28           O
ATOM    716  N   PRO A 127       4.300  -8.560 55.243  1.00 16.07           N
ATOM    717  CA  PRO A 127       4.353  -7.105 55.092  1.00 17.03           C
ATOM    718  C   PRO A 127       4.677  -6.581 53.688  1.00 19.08           C
ATOM    719  O   PRO A 127       5.199  -7.307 52.834  1.00 18.40           O
ATOM    720  CB  PRO A 127       5.405  -6.704 56.113  1.00 17.23           C
ATOM    721  CG  PRO A 127       6.367  -7.845 56.044  1.00 16.41           C
ATOM    722  CD  PRO A 127       5.461  -9.054 56.014  1.00 17.60           C
ATOM    723  N   CYS A 128       4.352  -5.315 53.455  1.00 19.18           N
ATOM    724  CA  CYS A 128       4.613  -4.691 52.171  1.00 20.22           C
ATOM    725  C   CYS A 128       6.074  -4.286 52.122  1.00 21.46           C
ATOM    726  O   CYS A 128       6.763  -4.328 53.146  1.00 21.23           O
ATOM    727  CB  CYS A 128       3.729  -3.441 52.002  1.00 19.67           C
ATOM    728  SG  CYS A 128       4.103  -2.059 53.134  1.00 19.62           S
ATOM    729  N   ALA A 129       6.548  -3.893 50.938  1.00 22.22           N
ATOM    730  CA  ALA A 129       7.941  -3.477 50.754  1.00 22.51           C
ATOM    731  C   ALA A 129       8.317  -2.378 51.741  1.00 23.45           C
ATOM    732  O   ALA A 129       9.341  -2.475 52.420  1.00 23.51           O
ATOM    733  CB  ALA A 129       8.162  -2.997 49.313  1.00 22.20           C
ATOM    734  N   ALA A 130       7.498  -1.333 51.830  1.00 24.79           N
ATOM    735  CA  ALA A 130       7.770  -0.219 52.749  1.00 25.79           C
ATOM    736  C   ALA A 130       7.877  -0.691 54.195  1.00 27.57           C
ATOM    737  O   ALA A 130       8.851  -0.392 54.885  1.00 27.60           O
ATOM    738  CB  ALA A 130       6.681   0.837 52.640  1.00 23.96           C
ATOM    739  N   CYS A 131       6.853  -1.399 54.664  1.00 28.78           N
ATOM    740  CA  CYS A 131       6.839  -1.916 56.027  1.00 29.65           C
ATOM    741  C   CYS A 131       8.092  -2.765 56.323  1.00 29.09           C
ATOM    742  O   CYS A 131       8.683  -2.684 57.409  1.00 28.45           O
ATOM    743  CB  CYS A 131       5.572  -2.752 56.254  1.00 30.64           C
ATOM    744  SG  CYS A 131       4.096  -1.825 56.740  1.00 33.86           S
ATOM    745  N   ALA A 132       8.492  -3.582 55.358  1.00 28.98           N
ATOM    746  CA  ALA A 132       9.674  -4.400 55.539  1.00 29.57           C
ATOM    747  C   ALA A 132      10.839  -3.502 55.922  1.00 30.73           C
ATOM    748  O   ALA A 132      11.499  -3.755 56.924  1.00 31.49           O
ATOM    749  CB  ALA A 132      10.003  -5.156 54.278  1.00 27.72           C
ATOM    750  N   ASP A 133      11.081  -2.446 55.136  1.00 31.97           N
ATOM    751  CA  ASP A 133      12.180  -1.516 55.405  1.00 32.50           C
ATOM    752  C   ASP A 133      12.073  -0.945 56.798  1.00 31.96           C
ATOM    753  O   ASP A 133      13.068  -0.847 57.512  1.00 32.73           O
ATOM    754  CB  ASP A 133      12.219  -0.379 54.376  1.00 34.69           C
ATOM    755  CG  ASP A 133      13.003  -0.755 53.122  1.00 37.68           C
ATOM    756  OD1 ASP A 133      12.507  -1.574 52.314  1.00 37.51           O
ATOM    757  OD2 ASP A 133      14.129  -0.237 52.954  1.00 40.18           O
ATOM    758  N   ARG A 134      10.865  -0.569 57.195  1.00 31.15           N
ATOM    759  CA  ARG A 134      10.669  -0.030 58.528  1.00 30.86           C
ATOM    760  C   ARG A 134      11.077  -1.033 59.599  1.00 30.17           C
ATOM    761  O   ARG A 134      11.688  -0.659 60.598  1.00 29.88           O
ATOM    762  CB  ARG A 134       9.214   0.379 58.727  1.00 32.61           C
ATOM    763  CG  ARG A 134       8.863   1.708 58.085  1.00 36.85           C
ATOM    764  CD  ARG A 134       7.496   2.210 58.563  1.00 39.90           C
ATOM    765  NE  ARG A 134       6.377   1.630 57.825  1.00 42.27           N
ATOM    766  CZ  ARG A 134       6.079   1.937 56.564  1.00 43.86           C
ATOM    767  NH1 ARG A 134       6.820   2.820 55.913  1.00 44.43           N
ATOM    768  NH2 ARG A 134       5.057   1.346 55.948  1.00 43.80           N
ATOM    769  N   ILE A 135      10.744  -2.304 59.392  1.00 29.88           N
ATOM    770  CA  ILE A 135      11.091  -3.351 60.356  1.00 28.44           C
ATOM    771  C   ILE A 135      12.592  -3.547 60.382  1.00 28.03           C
ATOM    772  O   ILE A 135      13.170  -3.786 61.442  1.00 28.10           O
ATOM    773  CB  ILE A 135      10.431  -4.699 59.983  1.00 28.64           C
ATOM    774  CG1 ILE A 135       8.912  -4.565 60.045  1.00 27.00           C
ATOM    775  CG2 ILE A 135      10.915  -5.809 60.924  1.00 27.75           C
ATOM    776  CD1 ILE A 135       8.199  -5.761 59.448  1.00 27.14           C
ATOM    777  N   ILE A 136      13.227  -3.451 59.215  1.00 27.77           N
ATOM    778  CA  ILE A 136      14.674  -3.627 59.110  1.00 27.53           C
ATOM    779  C   ILE A 136      15.442  -2.518 59.830  1.00 28.11           C
ATOM    780  O   ILE A 136      16.451  -2.771 60.488  1.00 26.28           O
ATOM    781  CB  ILE A 136      15.117  -3.680 57.629  1.00 26.65           C
ATOM    782  CG1 ILE A 136      14.520  -4.915 56.961  1.00 26.41           C
ATOM    783  CG2 ILE A 136      16.641  -3.749 57.536  1.00 25.54           C
ATOM    784  CD1 ILE A 136      14.764  -4.984 55.472  1.00 25.91           C
ATOM    785  N   LYS A 137      14.952  -1.290 59.701  1.00 29.45           N
ATOM    786  CA  LYS A 137      15.596  -0.170 60.361  1.00 31.31           C
ATOM    787  C   LYS A 137      15.402  -0.218 61.868  1.00 31.05           C
ATOM    788  O   LYS A 137      16.213   0.321 62.605  1.00 31.84           O
ATOM    789  CB  LYS A 137      15.071   1.156 59.818  1.00 33.70           C
ATOM    790  CG  LYS A 137      15.645   1.532 58.462  1.00 39.43           C
ATOM    791  CD  LYS A 137      15.388   2.999 58.136  1.00 43.11           C
ATOM    792  CE  LYS A 137      16.000   3.406 56.799  1.00 45.83           C
ATOM    793  NZ  LYS A 137      15.793   4.861 56.510  1.00 48.23           N
ATOM    794  N   THR A 138      14.328  -0.860 62.322  1.00 30.57           N
ATOM    795  CA  THR A 138      14.032  -0.951 63.754  1.00 30.73           C
ATOM    796  C   THR A 138      14.922  -2.020 64.403  1.00 30.12           C
ATOM    797  O   THR A 138      15.541  -1.795 65.450  1.00 30.61           O

ATOM   3982  CB  GLU C 159      -6.180  -8.217 47.109  1.00 25.28           C
ATOM   3983  CG  GLU C 159      -4.734  -8.241 47.580  1.00 28.47           C
ATOM   3984  CD  GLU C 159      -4.563  -8.677 49.050  1.00 28.91           C
ATOM   3985  OE1 GLU C 159      -5.150  -8.044 49.958  1.00 29.00           O
ATOM   3986  OE2 GLU C 159      -3.822  -9.648 49.300  1.00 27.98           O
ATOM   3987  N   PRO C 160      -9.292  -9.175 47.886  1.00 26.96           N
ATOM   3988  CA  PRO C 160     -10.706  -9.049 47.538  1.00 26.69           C
ATOM   3989  C   PRO C 160     -11.017  -7.869 46.618  1.00 26.22           C
ATOM   3990  O   PRO C 160     -11.973  -7.930 45.846  1.00 26.59           O
ATOM   3991  CB  PRO C 160     -11.379  -8.928 48.902  1.00 27.50           C
ATOM   3992  CG  PRO C 160     -10.319  -8.228 49.726  1.00 27.59           C
ATOM   3993  CD  PRO C 160      -9.086  -8.987 49.333  1.00 27.44           C
ATOM   3994  N   GLU C 161     -10.235  -6.799 46.696  1.00 25.41           N
ATOM   3995  CA  GLU C 161     -10.480  -5.640 45.829  1.00 25.75           C
ATOM   3996  C   GLU C 161     -10.239  -6.053 44.374  1.00 25.09           C
ATOM   3997  O   GLU C 161     -11.017  -5.730 43.476  1.00 24.64           O
ATOM   3998  CB  GLU C 161      -9.525  -4.480 46.164  1.00 28.02           C
ATOM   3999  CG  GLU C 161      -9.838  -3.646 47.413  1.00 30.74           C
ATOM   4000  CD  GLU C 161      -9.902  -4.447 48.694  1.00 32.76           C
ATOM   4001  OE1 GLU C 161      -9.106  -5.403 48.861  1.00 32.26           O
ATOM   4002  OE2 GLU C 161     -10.754  -4.101 49.550  1.00 36.09           O
ATOM   4003  N   ILE C 162      -9.147  -6.773 44.147  1.00 23.92           N
ATOM   4004  CA  ILE C 162      -8.814  -7.204 42.808  1.00 22.37           C
ATOM   4005  C   ILE C 162      -9.850  -8.177 42.261  1.00 22.31           C
ATOM   4006  O   ILE C 162     -10.264  -8.081 41.100  1.00 22.41           O
ATOM   4007  CB  ILE C 162      -7.409  -7.852 42.781  1.00 19.47           C
ATOM   4008  CG1 ILE C 162      -6.352  -6.832 43.203  1.00 18.24           C
ATOM   4009  CG2 ILE C 162      -7.084  -8.324 41.388  1.00 19.96           C
ATOM   4010  CD1 ILE C 162      -6.238  -5.589 42.289  1.00 17.16           C
ATOM   4011  N   GLN C 163     -10.280  -9.101 43.107  1.00 22.89           N
ATOM   4012  CA  GLN C 163     -11.280 -10.098 42.706  1.00 21.96           C
ATOM   4013  C   GLN C 163     -12.603  -9.468 42.325  1.00 20.73           C
ATOM   4014  O   GLN C 163     -13.297  -9.948 41.428  1.00 20.50           O
ATOM   4015  CB  GLN C 163     -11.492 -11.104 43.834  1.00 22.20           C
ATOM   4016  CG  GLN C 163     -10.336 -12.066 43.999  1.00 24.01           C
ATOM   4017  CD  GLN C 163     -10.621 -13.142 45.015  1.00 23.76           C
ATOM   4018  OE1 GLN C 163     -11.751 -13.615 45.135  1.00 26.16           O
ATOM   4019  NE2 GLN C 163      -9.594 -13.554 45.740  1.00 23.78           N
ATOM   4020  N   ALA C 164     -12.972  -8.397 43.009  1.00 20.07           N
ATOM   4021  CA  ALA C 164     -14.233  -7.745 42.692  1.00 18.40           C
ATOM   4022  C   ALA C 164     -14.103  -7.054 41.343  1.00 17.99           C
ATOM   4023  O   ALA C 164     -15.039  -7.023 40.545  1.00 18.38           O
ATOM   4024  CB  ALA C 164     -14.571  -6.742 43.761  1.00 16.92           C
ATOM   4025  N   ALA C 165     -12.931  -6.494 41.096  1.00 17.28           N
ATOM   4026  CA  ALA C 165     -12.696  -5.793 39.854  1.00 17.05           C
ATOM   4027  C   ALA C 165     -12.705  -6.748 38.649  1.00 17.75           C
ATOM   4028  O   ALA C 165     -13.215  -6.413 37.570  1.00 15.90           O
ATOM   4029  CB  ALA C 165     -11.370  -5.046 39.946  1.00 16.35           C
ATOM   4030  N   LEU C 166     -12.157  -7.947 38.842  1.00 17.15           N
ATOM   4031  CA  LEU C 166     -12.104  -8.934 37.773  1.00 17.68           C
ATOM   4032  C   LEU C 166     -13.481  -9.433 37.403  1.00 19.12           C
ATOM   4033  O   LEU C 166     -13.743  -9.725 36.239  1.00 19.32           O
ATOM   4034  CB  LEU C 166     -11.216 -10.122 38.160  1.00 17.08           C
ATOM   4035  CG  LEU C 166      -9.721  -9.800 38.304  1.00 17.22           C
ATOM   4036  CD1 LEU C 166      -8.924 -11.038 38.633  1.00 16.65           C
ATOM   4037  CD2 LEU C 166      -9.218  -9.228 37.016  1.00 14.61           C
ATOM   4038  N   LYS C 167     -14.363  -9.539 38.393  1.00 22.09           N
ATOM   4039  CA  LYS C 167     -15.725 -10.003 38.154  1.00 23.95           C
ATOM   4040  C   LYS C 167     -16.476  -8.958 37.346  1.00 24.21           C
ATOM   4041  O   LYS C 167     -17.090  -9.271 36.327  1.00 24.50           O
ATOM   4042  CB  LYS C 167     -16.452 -10.240 39.482  1.00 26.06           C
ATOM   4043  CG  LYS C 167     -15.810 -11.290 40.376  1.00 28.69           C
ATOM   4044  CD  LYS C 167     -16.521 -11.402 41.722  1.00 29.81           C
ATOM   4045  CE  LYS C 167     -15.646 -12.128 42.748  1.00 30.10           C
ATOM   4046  NZ  LYS C 167     -16.162 -11.968 44.140  1.00 30.51           N
ATOM   4047  N   LYS C 168     -16.425  -7.710 37.812  1.00 25.21           N
ATOM   4048  CA  LYS C 168     -17.100  -6.602 37.140  1.00 25.53           C
ATOM   4049  C   LYS C 168     -16.576  -6.513 35.722  1.00 25.04           C
ATOM   4050  O   LYS C 168     -17.307  -6.182 34.778  1.00 25.47           O
ATOM   4051  CB  LYS C 168     -16.840  -5.293 37.884  1.00 25.17           C
ATOM   4052  CG  LYS C 168     -17.449  -5.249 39.273  1.00 29.29           C
ATOM   4053  CD  LYS C 168     -17.221  -3.896 39.928  1.00 33.27           C
ATOM   4054  CE  LYS C 168     -17.895  -3.791 41.301  1.00 36.03           C
ATOM   4055  NZ  LYS C 168     -17.646  -2.466 41.966  1.00 36.58           N
ATOM   4056  N   LEU C 169     -15.296  -6.828 35.580  1.00 23.97           N
ATOM   4057  CA  LEU C 169     -14.642  -6.796 34.286  1.00 22.37           C
ATOM   4058  C   LEU C 169     -15.227  -7.875 33.400  1.00 21.77           C
ATOM   4059  O   LEU C 169     -15.507  -7.620 32.236  1.00 22.48           O
ATOM   4060  CB  LEU C 169     -13.135  -7.017 34.448  1.00 22.96           C
ATOM   4061  CG  LEU C 169     -12.251  -6.784 33.221  1.00 23.16           C
ATOM   4062  CD1 LEU C 169     -12.278  -5.328 32.835  1.00 23.34           C
ATOM   4063  CD2 LEU C 169     -10.835  -7.190 33.541  1.00 24.44           C
ATOM   4064  N   LYS C 170     -15.417  -9.074 33.937  1.00 21.59           N
ATOM   4065  CA  LYS C 170     -15.979 -10.166 33.154  1.00 22.60           C
ATOM   4066  C   LYS C 170     -17.440  -9.852 32.842  1.00 22.54           C
ATOM   4067  O   LYS C 170     -17.972 -10.228 31.794  1.00 24.78           O
```

FIG. 6 (con't)

```
ATOM  798  CB  THR A 138   12.515  -1.302 64.008 1.00 30.33   C
ATOM  799  OG1 THR A 138   11.669  -0.289 63.449 1.00 30.91   O
ATOM  800  CG2 THR A 138   12.218  -1.380 65.479 1.00 28.73   C
ATOM  801  N   LEU A 139   14.991  -3.184 63.773 1.00 29.17   N
ATOM  802  CA  LEU A 139   15.783  -4.281 64.295 1.00 28.33   C
ATOM  803  C   LEU A 139   17.247  -3.894 64.327 1.00 30.34   C
ATOM  804  O   LEU A 139   18.014  -4.361 65.176 1.00 31.18   O
ATOM  805  CB  LEU A 139   15.595  -5.532 63.429 1.00 25.69   C
ATOM  806  CG  LEU A 139   14.240  -6.248 63.490 1.00 24.30   C
ATOM  807  CD1 LEU A 139   14.165  -7.334 62.421 1.00 21.25   C
ATOM  808  CD2 LEU A 139   14.045  -6.845 64.875 1.00 22.30   C
ATOM  809  N   SER A 140   17.627  -3.023 63.404 1.00 31.22   N
ATOM  810  CA  SER A 140   18.998  -2.570 63.293 1.00 32.30   C
ATOM  811  C   SER A 140   19.363  -1.595 64.404 1.00 33.09   C
ATOM  812  O   SER A 140   20.539  -1.456 64.751 1.00 32.74   O
ATOM  813  CB  SER A 140   19.214  -1.910 61.933 1.00 32.90   C
ATOM  814  OG  SER A 140   20.591  -1.753 61.665 1.00 36.45   O
ATOM  815  N   LYS A 141   18.355  -0.925 64.958 1.00 33.24   N
ATOM  816  CA  LYS A 141   18.571   0.028 66.033 1.00 34.11   C
ATOM  817  C   LYS A 141   18.419  -0.661 67.377 1.00 32.46   C
ATOM  818  O   LYS A 141   18.945   0.193 68.371 1.00 33.08   O
ATOM  819  CB  LYS A 141   17.575   1.188 65.945 1.00 36.83   C
ATOM  820  CG  LYS A 141   17.646   1.960 64.639 1.00 40.47   C
ATOM  821  CD  LYS A 141   19.006   2.652 64.442 1.00 44.25   C
ATOM  822  CE  LYS A 141   19.230   3.861 65.378 1.00 45.65   C
ATOM  823  NZ  LYS A 141   20.507   4.615 65.089 1.00 45.95   N
ATOM  824  N   THR A 142   17.699  -1.772 67.408 1.00 31.67   N
ATOM  825  CA  THR A 142   17.512  -2.493 68.659 1.00 30.34   C
ATOM  826  C   THR A 142   18.053  -3.906 68.519 1.00 28.69   C
ATOM  827  O   THR A 142   17.358  -4.801 68.036 1.00 28.84   O
ATOM  828  CB  THR A 142   16.028  -2.553 69.046 1.00 31.00   C
ATOM  829  OG1 THR A 142   15.244  -2.703 67.864 1.00 32.61   O
ATOM  830  CG2 THR A 142   15.610  -1.292 69.747 1.00 31.79   C
ATOM  831  N   LYS A 143   19.295  -4.091 68.946 1.00 27.28   N
ATOM  832  CA  LYS A 143   19.968  -5.379 68.862 1.00 26.57   C
ATOM  833  C   LYS A 143   19.382  -6.377 69.844 1.00 24.70   C
ATOM  834  O   LYS A 143   19.449  -7.589 69.626 1.00 24.78   O
ATOM  835  CB  LYS A 143   21.461  -5.214 69.156 1.00 27.13   C
ATOM  836  CG  LYS A 143   22.188  -4.191 68.298 1.00 27.80   C
ATOM  837  CD  LYS A 143   22.277  -4.625 66.851 1.00 28.75   C
ATOM  838  CE  LYS A 143   23.135  -3.656 66.055 1.00 28.49   C
ATOM  839  NZ  LYS A 143   23.275  -4.094 64.642 1.00 29.43   N
ATOM  840  N   ASN A 144   18.813  -5.862 70.926 1.00 21.82   N
ATOM  841  CA  ASN A 144   18.236  -6.702 71.967 1.00 20.08   C
ATOM  842  C   ASN A 144   16.789  -7.046 71.672 1.00 18.62   C
ATOM  843  O   ASN A 144   16.017  -7.368 72.574 1.00 16.24   O
ATOM  844  CB  ASN A 144   18.352  -5.999 73.321 1.00 20.53   C
ATOM  845  CG  ASN A 144   17.702  -4.627 73.326 1.00 22.83   C
ATOM  846  OD1 ASN A 144   17.656  -3.942 72.302 1.00 23.33   O
ATOM  847  ND2 ASN A 144   17.210  -4.208 74.490 1.00 23.75   N
ATOM  848  N   LEU A 145   16.430  -6.990 70.396 1.00 17.97   N
ATOM  849  CA  LEU A 145   15.070  -7.296 69.974 1.00 17.00   C
ATOM  850  C   LEU A 145   15.061  -8.408 68.934 1.00 16.69   C
ATOM  851  O   LEU A 145   15.667  -8.253 67.882 1.00 16.00   O
ATOM  852  CB  LEU A 145   14.431  -6.039 69.364 1.00 16.89   C
ATOM  853  CG  LEU A 145   13.170  -6.234 68.495 1.00 15.84   C
ATOM  854  CD1 LEU A 145   12.052  -6.880 69.294 1.00 14.43   C
ATOM  855  CD2 LEU A 145   12.722  -4.880 67.968 1.00 16.07   C
ATOM  856  N   ARG A 146   14.394  -9.515 69.235 1.00 16.48   N
ATOM  857  CA  ARG A 146   14.273 -10.622 68.272 1.00 17.03   C
ATOM  858  C   ARG A 146   12.813 -10.646 67.799 1.00 15.61   C
ATOM  859  O   ARG A 146   11.889 -10.581 68.622 1.00 15.69   O
ATOM  860  CB  ARG A 146   14.627 -11.952 68.935 1.00 19.21   C
ATOM  861  CG  ARG A 146   14.568 -13.132 67.997 1.00 24.03   C
ATOM  862  CD  ARG A 146   14.865 -14.443 68.721 1.00 28.94   C
ATOM  863  NE  ARG A 146   15.194 -15.531 67.791 1.00 32.64   N
ATOM  864  CZ  ARG A 146   14.373 -16.051 66.872 1.00 34.91   C
ATOM  865  NH1 ARG A 146   13.127 -15.612 66.725 1.00 32.12   N
ATOM  866  NH2 ARG A 146   14.824 -17.005 66.063 1.00 34.18   N
ATOM  867  N   LEU A 147   12.599 -10.736 66.491 1.00 12.70   N
ATOM  868  CA  LEU A 147   11.247 -10.717 65.943 1.00 10.85   C
ATOM  869  C   LEU A 147   10.882 -11.969 65.120 1.00  9.49   C
ATOM  870  O   LEU A 147   11.653 -12.438 64.300 1.00  7.48   O
ATOM  871  CB  LEU A 147   11.044  -9.447 65.091 1.00  9.95   C
ATOM  872  CG  LEU A 147    9.647  -9.236 64.447 1.00  9.67   C
ATOM  873  CD1 LEU A 147    8.635  -9.077 65.544 1.00  8.41   C
ATOM  874  CD2 LEU A 147    9.593  -8.016 63.552 1.00  5.99   C
ATOM  875  N   LEU A 148    9.692 -12.504 65.373 1.00  9.19   N
ATOM  876  CA  LEU A 148    9.230 -13.675 64.662 1.00  9.00   C
ATOM  877  C   LEU A 148    7.878 -13.326 64.104 1.00  9.20   C
ATOM  878  O   LEU A 148    6.950 -13.078 64.873 1.00 11.01   O
ATOM  879  CB  LEU A 148    9.077 -14.860 65.604 1.00 10.33   C
ATOM  880  CG  LEU A 148    8.230 -16.050 65.088 1.00 10.56   C
ATOM  881  CD1 LEU A 148    8.841 -16.613 63.825 1.00  9.10   C
ATOM  882  CD2 LEU A 148    8.187 -17.133 66.143 1.00 11.52   C
ATOM  883  N   ILE A 149    7.753 -13.301 62.785 1.00  8.64   N

ATOM 4068  CB  LYS C 170  -15.876 -11.489 33.918 1.00 22.87   C
ATOM 4069  CG  LYS C 170  -16.635 -12.628 33.267 1.00 21.42   C
ATOM 4070  CD  LYS C 170  -17.081 -13.647 34.294 1.00 22.19   C
ATOM 4071  CE  LYS C 170  -17.822 -14.794 33.637 1.00 22.95   C
ATOM 4072  NZ  LYS C 170  -18.481 -15.652 34.651 1.00 23.77   N
ATOM 4073  N   GLU C 171  -18.089  -9.147 33.748 1.00 21.70   N
ATOM 4074  CA  GLU C 171  -19.484  -8.785 33.544 1.00 22.62   C
ATOM 4075  C   GLU C 171  -19.644  -7.693 32.483 1.00 22.29   C
ATOM 4076  O   GLU C 171  -20.708  -7.547 31.883 1.00 21.71   O
ATOM 4077  CB  GLU C 171  -20.089  -8.315 34.865 1.00 24.95   C
ATOM 4078  CG  GLU C 171  -20.034  -9.352 35.986 1.00 27.58   C
ATOM 4079  CD  GLU C 171  -20.704  -8.876 37.267 1.00 29.47   C
ATOM 4080  OE1 GLU C 171  -21.307  -7.776 37.246 1.00 28.22   O
ATOM 4081  OE2 GLU C 171  -20.630  -9.610 38.284 1.00 30.10   O
ATOM 4082  N   ALA C 172  -18.588  -6.914 32.261 1.00 21.76   N
ATOM 4083  CA  ALA C 172  -18.646  -5.852 31.270 1.00 20.80   C
ATOM 4084  C   ALA C 172  -18.469  -6.433 29.874 1.00 21.23   C
ATOM 4085  O   ALA C 172  -18.497  -5.702 28.888 1.00 20.40   O
ATOM 4086  CB  ALA C 172  -17.558  -4.818 31.539 1.00 22.26   C
ATOM 4087  N   GLY C 173  -18.269  -7.756 29.807 1.00 20.97   N
ATOM 4088  CA  GLY C 173  -18.083  -8.442 28.530 1.00 19.13   C
ATOM 4089  C   GLY C 173  -16.632  -8.704 28.160 1.00 18.34   C
ATOM 4090  O   GLY C 173  -16.341  -9.330 27.131 1.00 17.46   O
ATOM 4091  N   CYS C 174  -15.715  -8.216 28.990 1.00 16.93   N
ATOM 4092  CA  CYS C 174  -14.290  -8.405 28.740 1.00 16.60   C
ATOM 4093  C   CYS C 174  -13.847  -9.819 29.095 1.00 16.64   C
ATOM 4094  O   CYS C 174  -13.925 -10.243 30.246 1.00 17.62   O
ATOM 4095  CB  CYS C 174  -13.472  -7.397 29.548 1.00 15.39   C
ATOM 4096  SG  CYS C 174  -11.711  -7.770 29.468 1.00 17.17   S
ATOM 4097  N   LYS C 175  -13.372 -10.550 28.110 1.00 18.71   N
ATOM 4098  CA  LYS C 175  -12.956 -11.925 28.335 1.00 21.28   C
ATOM 4099  C   LYS C 175  -11.522 -11.937 28.821 1.00 21.95   C
ATOM 4100  O   LYS C 175  -10.641 -11.462 28.123 1.00 23.50   O
ATOM 4101  CB  LYS C 175  -13.080 -12.706 27.038 1.00 20.25   C
ATOM 4102  CG  LYS C 175  -12.876 -14.197 27.187 1.00 25.17   C
ATOM 4103  CD  LYS C 175  -12.826 -14.883 25.822 1.00 29.62   C
ATOM 4104  CE  LYS C 175  -12.776 -16.407 25.910 1.00 30.06   C
ATOM 4105  NZ  LYS C 175  -12.682 -16.993 24.536 1.00 31.68   N
ATOM 4106  N   LEU C 176  -11.284 -12.488 30.009 1.00 23.48   N
ATOM 4107  CA  LEU C 176   -9.931 -12.533 30.564 1.00 25.13   C
ATOM 4108  C   LEU C 176   -9.445 -13.978 30.703 1.00 22.49   C
ATOM 4109  O   LEU C 176  -10.151 -14.800 31.268 1.00 23.07   O
ATOM 4110  CB  LEU C 176   -9.935 -11.861 31.932 1.00 24.31   C
ATOM 4111  CG  LEU C 176   -8.694 -11.028 32.263 1.00 26.92   C
ATOM 4112  CD1 LEU C 176   -8.899 -10.377 33.606 1.00 26.44   C
ATOM 4113  CD2 LEU C 176   -7.446 -11.893 32.280 1.00 25.73   C
ATOM 4114  N   ARG C 177   -8.248 -14.280 30.204 1.00 22.40   N
ATOM 4115  CA  ARG C 177   -7.703 -15.636 30.286 1.00 23.40   C
ATOM 4116  C   ARG C 177   -6.201 -15.646 30.593 1.00 22.50   C
ATOM 4117  O   ARG C 177   -5.516 -14.641 30.422 1.00 22.30   O
ATOM 4118  CB  ARG C 177   -7.944 -16.390 28.974 1.00 25.59   C
ATOM 4119  CG  ARG C 177   -9.416 -16.667 28.654 1.00 30.52   C
ATOM 4120  CD  ARG C 177  -10.032 -17.695 29.616 1.00 34.55   C
ATOM 4121  NE  ARG C 177  -11.436 -17.991 29.314 1.00 38.19   N
ATOM 4122  CZ  ARG C 177  -12.475 -17.244 29.688 1.00 40.35   C
ATOM 4123  NH1 ARG C 177  -12.298 -16.138 30.399 1.00 40.06   N
ATOM 4124  NH2 ARG C 177  -13.707 -17.599 29.327 1.00 41.84   N
ATOM 4125  N   ILE C 178   -5.697 -16.791 31.048 1.00 20.59   N
ATOM 4126  CA  ILE C 178   -4.286 -16.871 31.352 1.00 19.53   C
ATOM 4127  C   ILE C 178   -3.504 -17.409 30.128 1.00 20.12   C
ATOM 4128  O   ILE C 178   -3.973 -18.256 29.368 1.00 19.36   O
ATOM 4129  CB  ILE C 178   -4.062 -17.925 32.490 1.00 19.01   C
ATOM 4130  CG1 ILE C 178   -4.874 -17.505 33.712 1.00 19.12   C
ATOM 4131  CG2 ILE C 178   -2.586 -18.009 32.828 1.00 17.89   C
ATOM 4132  CD1 ILE C 178   -4.561 -16.123 34.207 1.00 17.48   C
ATOM 4133  N   MET C 179   -2.306 -16.868 29.951 1.00 21.09   N
ATOM 4134  CA  MET C 179   -1.464 -17.239 28.818 1.00 21.46   C
ATOM 4135  C   MET C 179   -0.893 -18.635 28.954 1.00 21.65   C
ATOM 4136  O   MET C 179    0.260 -18.965 29.955 1.00 22.44   O
ATOM 4137  CB  MET C 179   -0.318 -16.247 28.673 1.00 21.12   C
ATOM 4138  CG  MET C 179   -0.503 -15.193 27.600 1.00 21.66   C
ATOM 4139  SD  MET C 179    0.986 -14.167 27.466 1.00 24.09   S
ATOM 4140  CE  MET C 179    0.594 -12.974 28.614 1.00 21.29   C
ATOM 4141  N   LYS C 180   -1.099 -19.451 27.934 1.00 21.21   N
ATOM 4142  CA  LYS C 180   -0.581 -20.801 27.962 1.00 22.23   C
ATOM 4143  C   LYS C 180    0.699 -20.839 27.136 1.00 22.19   C
ATOM 4144  O   LYS C 180    1.017 -19.876 26.448 1.00 22.62   O
ATOM 4145  CB  LYS C 180   -1.632 -21.762 27.409 1.00 22.04   C
ATOM 4146  CG  LYS C 180   -2.191 -21.348 26.084 1.00 21.19   C
ATOM 4147  CD  LYS C 180   -3.262 -22.321 25.642 1.00 22.34   C
ATOM 4148  CE  LYS C 180   -4.449 -22.325 26.592 1.00 22.51   C
ATOM 4149  NZ  LYS C 180   -5.520 -23.254 26.135 1.00 22.39   N
ATOM 4150  N   PRO C 181    1.463 -21.943 27.215 1.00 22.11   N
ATOM 4151  CA  PRO C 181    2.714 -22.058 26.456 1.00 21.44   C
ATOM 4152  C   PRO C 181    2.623 -21.594 25.003 1.00 20.80   C
ATOM 4153  O   PRO C 181    3.517 -20.903 24.508 1.00 20.37   O
```

FIG. 6 (con't)

| | | | | | |
|---|---|---|---|---|---|
| ATOM | 884 CA ILE A 149 | 6.489 -12.963 62.165 1.00 9.20 | | | C |
| ATOM | 885 C ILE A 149 | 5.856 -14.200 61.520 1.00 9.56 | | | C |
| ATOM | 886 O ILE A 149 | 6.428 -14.776 60.597 1.00 9.65 | | | O |
| ATOM | 887 CB ILE A 149 | 6.651 -11.875 61.058 1.00 8.35 | | | C |
| ATOM | 888 CG1 ILE A 149 | 7.413 -10.661 61.600 1.00 10.66 | | | C |
| ATOM | 889 CG2 ILE A 149 | 5.296 -11.378 60.619 1.00 7.82 | | | C |
| ATOM | 890 CD1 ILE A 149 | 7.611 -9.529 60.579 1.00 5.95 | | | C |
| ATOM | 891 N LEU A 150 | 4.687 -14.605 62.024 1.00 10.12 | | | N |
| ATOM | 892 CA LEU A 150 | 3.933 -15.744 61.483 1.00 10.54 | | | C |
| ATOM | 893 C LEU A 150 | 2.753 -15.206 60.656 1.00 11.69 | | | C |
| ATOM | 894 O LEU A 150 | 1.836 -14.576 61.197 1.00 12.15 | | | O |
| ATOM | 895 CB LEU A 150 | 3.432 -16.649 62.607 1.00 8.05 | | | C |
| ATOM | 896 CG LEU A 150 | 4.502 -17.414 63.395 1.00 10.15 | | | C |
| ATOM | 897 CD1 LEU A 150 | 3.850 -18.297 64.421 1.00 14.11 | | | C |
| ATOM | 898 CD2 LEU A 150 | 5.324 -18.279 62.481 1.00 10.62 | | | C |
| ATOM | 899 N VAL A 151 | 2.765 -15.466 59.347 1.00 11.63 | | | N |
| ATOM | 900 CA VAL A 151 | 1.717 -14.974 58.446 1.00 11.45 | | | C |
| ATOM | 901 C VAL A 151 | 0.764 -16.051 57.953 1.00 11.20 | | | C |
| ATOM | 902 O VAL A 151 | 1.159 -17.198 57.796 1.00 11.78 | | | O |
| ATOM | 903 CB VAL A 151 | 2.349 -14.282 57.177 1.00 12.48 | | | C |
| ATOM | 904 CG1 VAL A 151 | 3.324 -13.180 57.607 1.00 10.25 | | | C |
| ATOM | 905 CG2 VAL A 151 | 3.047 -15.326 56.280 1.00 10.68 | | | C |
| ATOM | 906 N GLY A 152 | -0.492 -15.677 57.703 1.00 11.01 | | | N |
| ATOM | 907 CA GLY A 152 | -1.477 -16.638 57.219 1.00 12.05 | | | C |
| ATOM | 908 C GLY A 152 | -1.152 -17.036 55.794 1.00 13.47 | | | C |
| ATOM | 909 O GLY A 152 | -1.331 -18.190 55.392 1.00 13.66 | | | O |
| ATOM | 910 N ARG A 153 | -0.688 -16.061 55.020 1.00 14.21 | | | N |
| ATOM | 911 CA ARG A 153 | -0.282 -16.303 53.644 1.00 16.23 | | | C |
| ATOM | 912 C ARG A 153 | 0.666 -15.197 53.178 1.00 17.21 | | | C |
| ATOM | 913 O ARG A 153 | 0.937 -14.247 53.909 1.00 18.17 | | | O |
| ATOM | 914 CB ARG A 153 | -1.508 -16.371 52.725 1.00 18.09 | | | C |
| ATOM | 915 CG ARG A 153 | -2.280 -15.073 52.616 1.00 18.56 | | | C |
| ATOM | 916 CD ARG A 153 | -3.178 -15.123 51.407 1.00 20.48 | | | C |
| ATOM | 917 NE ARG A 153 | -4.129 -14.020 51.345 1.00 23.75 | | | N |
| ATOM | 918 CZ ARG A 153 | -3.825 -12.756 51.064 1.00 23.54 | | | C |
| ATOM | 919 NH1 ARG A 153 | -2.573 -12.397 50.807 1.00 24.38 | | | N |
| ATOM | 920 NH2 ARG A 153 | -4.792 -11.849 51.022 1.00 24.43 | | | N |
| ATOM | 921 N LEU A 154 | 1.192 -15.333 51.971 1.00 18.41 | | | N |
| ATOM | 922 CA LEU A 154 | 2.103 -14.337 51.424 1.00 18.83 | | | C |
| ATOM | 923 C LEU A 154 | 1.341 -13.247 50.674 1.00 19.96 | | | C |
| ATOM | 924 O LEU A 154 | 0.268 -13.492 50.118 1.00 20.86 | | | O |
| ATOM | 925 CB LEU A 154 | 3.105 -15.011 50.489 1.00 18.36 | | | C |
| ATOM | 926 CG LEU A 154 | 4.491 -15.351 51.036 1.00 17.98 | | | C |
| ATOM | 927 CD1 LEU A 154 | 4.422 -15.661 52.518 1.00 17.77 | | | C |
| ATOM | 928 CD2 LEU A 154 | 5.068 -16.508 50.231 1.00 18.19 | | | C |
| ATOM | 929 N PHE A 155 | 1.910 -12.046 50.665 1.00 20.98 | | | N |
| ATOM | 930 CA PHE A 155 | 1.320 -10.887 49.998 1.00 20.88 | | | C |
| ATOM | 931 C PHE A 155 | 2.172 -10.479 48.793 1.00 21.47 | | | C |
| ATOM | 932 O PHE A 155 | 3.349 -10.151 48.946 1.00 21.49 | | | O |
| ATOM | 933 CB PHE A 155 | 1.240 -9.733 50.985 1.00 19.60 | | | C |
| ATOM | 934 CG PHE A 155 | 0.755 -8.464 50.376 1.00 19.16 | | | C |
| ATOM | 935 CD1 PHE A 155 | -0.521 -8.380 49.862 1.00 16.14 | | | C |
| ATOM | 936 CD2 PHE A 155 | 1.581 -7.339 50.325 1.00 18.69 | | | C |
| ATOM | 937 CE1 PHE A 155 | -0.984 -7.203 49.305 1.00 14.95 | | | C |
| ATOM | 938 CE2 PHE A 155 | 1.121 -6.150 49.765 1.00 17.26 | | | C |
| ATOM | 939 CZ PHE A 155 | -0.163 -6.085 49.256 1.00 16.12 | | | C |
| ATOM | 940 N MET A 156 | 1.562 -10.476 47.609 1.00 22.57 | | | N |
| ATOM | 941 CA MET A 156 | 2.263 -10.143 46.366 1.00 23.38 | | | C |
| ATOM | 942 C MET A 156 | 3.595 -10.870 46.309 1.00 23.86 | | | C |
| ATOM | 943 O MET A 156 | 4.602 -10.301 45.889 1.00 23.59 | | | O |
| ATOM | 944 CB MET A 156 | 2.525 -8.648 46.267 1.00 23.99 | | | C |
| ATOM | 945 CG MET A 156 | 1.297 -7.796 46.275 1.00 26.95 | | | C |
| ATOM | 946 SD MET A 156 | 1.682 -6.167 45.590 1.00 29.35 | | | S |
| ATOM | 947 CE MET A 156 | 2.577 -5.461 46.847 1.00 28.03 | | | C |
| ATOM | 948 N TRP A 157 | 3.610 -12.132 46.730 1.00 24.70 | | | N |
| ATOM | 949 CA TRP A 157 | 4.856 -12.899 46.741 1.00 27.04 | | | C |
| ATOM | 950 C TRP A 157 | 5.566 -13.003 45.389 1.00 28.65 | | | C |
| ATOM | 951 O TRP A 157 | 6.796 -13.024 45.330 1.00 30.30 | | | O |
| ATOM | 952 CB TRP A 157 | 4.609 -14.299 47.272 1.00 25.35 | | | C |
| ATOM | 953 CG TRP A 157 | 3.794 -15.107 46.387 1.00 25.33 | | | C |
| ATOM | 954 CD1 TRP A 157 | 2.440 -15.175 46.370 1.00 25.36 | | | C |
| ATOM | 955 CD2 TRP A 157 | 4.262 -16.038 45.405 1.00 25.45 | | | C |
| ATOM | 956 NE1 TRP A 157 | 2.027 -16.097 45.441 1.00 26.01 | | | N |
| ATOM | 957 CE2 TRP A 157 | 3.124 -16.637 44.831 1.00 26.09 | | | C |
| ATOM | 958 CE3 TRP A 157 | 5.532 -16.413 44.951 1.00 26.55 | | | C |
| ATOM | 959 CZ2 TRP A 157 | 3.213 -17.613 43.840 1.00 26.76 | | | C |
| ATOM | 960 CZ3 TRP A 157 | 5.626 -17.384 43.956 1.00 26.18 | | | C |
| ATOM | 961 CH2 TRP A 157 | 4.469 -17.965 43.410 1.00 27.75 | | | C |
| ATOM | 962 N GLU A 158 | 4.788 -13.072 44.312 1.00 31.14 | | | N |
| ATOM | 963 CA GLU A 158 | 5.336 -13.183 42.968 1.00 30.86 | | | C |
| ATOM | 964 C GLU A 158 | 6.114 -11.944 42.519 1.00 29.33 | | | C |
| ATOM | 965 O GLU A 158 | 7.014 -12.040 41.682 1.00 29.42 | | | O |
| ATOM | 966 CB GLU A 158 | 4.212 -13.496 41.963 1.00 32.67 | | | C |
| ATOM | 967 CG GLU A 158 | 2.972 -12.617 42.094 1.00 36.58 | | | C |
| ATOM | 968 CD GLU A 158 | 1.913 -13.237 42.955 1.00 36.70 | | | C |
| ATOM | 969 OE1 GLU A 158 | 1.829 -12.911 44.165 1.00 37.61 | | | O |
| ATOM | 4154 CB PRO C 181 | 3.055 -23.534 26.593 1.00 21.57 | | | C |
| ATOM | 4155 CG PRO C 181 | 2.601 -23.826 27.986 1.00 21.37 | | | C |
| ATOM | 4156 CD PRO C 181 | 1.241 -23.147 28.036 1.00 21.07 | | | C |
| ATOM | 4157 N GLN C 182 | 1.550 -21.961 24.321 1.00 21.82 | | | N |
| ATOM | 4158 CA GLN C 182 | 1.392 -21.561 22.924 1.00 21.69 | | | C |
| ATOM | 4159 C GLN C 182 | 1.337 -20.045 22.792 1.00 20.67 | | | C |
| ATOM | 4160 O GLN C 182 | 1.804 -19.484 21.803 1.00 19.32 | | | O |
| ATOM | 4161 CB GLN C 182 | 0.132 -22.193 22.333 1.00 23.96 | | | C |
| ATOM | 4162 CG GLN C 182 | 0.142 -23.719 22.409 1.00 29.33 | | | C |
| ATOM | 4163 CD GLN C 182 | -0.443 -24.276 23.710 1.00 32.38 | | | C |
| ATOM | 4164 OE1 GLN C 182 | -1.656 -24.444 23.824 1.00 36.57 | | | O |
| ATOM | 4165 NE2 GLN C 182 | 0.416 -24.563 24.693 1.00 32.77 | | | N |
| ATOM | 4166 N ASP C 183 | 0.780 -19.382 23.800 1.00 19.26 | | | N |
| ATOM | 4167 CA ASP C 183 | 0.656 -17.937 23.750 1.00 18.25 | | | C |
| ATOM | 4168 C ASP C 183 | 2.012 -17.258 23.790 1.00 17.57 | | | C |
| ATOM | 4169 O ASP C 183 | 2.261 -16.338 23.018 1.00 16.38 | | | O |
| ATOM | 4170 CB ASP C 183 | -0.216 -17.419 24.890 1.00 17.94 | | | C |
| ATOM | 4171 CG ASP C 183 | -1.657 -17.890 24.785 1.00 19.13 | | | C |
| ATOM | 4172 OD1 ASP C 183 | -2.258 -17.816 23.690 1.00 16.53 | | | O |
| ATOM | 4173 OD2 ASP C 183 | -2.205 -18.327 25.816 1.00 22.63 | | | O |
| ATOM | 4174 N PHE C 184 | 2.887 -17.715 24.681 1.00 16.21 | | | N |
| ATOM | 4175 CA PHE C 184 | 4.207 -17.122 24.799 1.00 16.93 | | | C |
| ATOM | 4176 C PHE C 184 | 4.967 -17.299 23.511 1.00 18.75 | | | C |
| ATOM | 4177 O PHE C 184 | 5.604 -16.366 23.013 1.00 19.73 | | | O |
| ATOM | 4178 CB PHE C 184 | 4.982 -17.745 25.956 1.00 14.40 | | | C |
| ATOM | 4179 CG PHE C 184 | 4.467 -17.346 27.306 1.00 11.68 | | | C |
| ATOM | 4180 CD1 PHE C 184 | 3.598 -18.174 28.000 1.00 10.41 | | | C |
| ATOM | 4181 CD2 PHE C 184 | 4.866 -16.146 27.891 1.00 10.89 | | | C |
| ATOM | 4182 CE1 PHE C 184 | 3.131 -17.821 29.267 1.00 10.64 | | | C |
| ATOM | 4183 CE2 PHE C 184 | 4.405 -15.781 29.162 1.00 11.47 | | | C |
| ATOM | 4184 CZ PHE C 184 | 3.537 -16.625 29.850 1.00 10.92 | | | C |
| ATOM | 4185 N GLU C 185 | 4.901 -18.499 22.962 1.00 20.50 | | | N |
| ATOM | 4186 CA GLU C 185 | 5.558 -18.773 21.699 1.00 23.19 | | | C |
| ATOM | 4187 C GLU C 185 | 5.006 -17.839 20.595 1.00 22.79 | | | C |
| ATOM | 4188 O GLU C 185 | 5.758 -17.304 19.789 1.00 23.86 | | | O |
| ATOM | 4189 CB GLU C 185 | 5.345 -20.239 21.325 1.00 24.01 | | | C |
| ATOM | 4190 CG GLU C 185 | 5.825 -20.582 19.938 1.00 27.98 | | | C |
| ATOM | 4191 CD GLU C 185 | 5.640 -22.054 19.599 1.00 31.55 | | | C |
| ATOM | 4192 OE1 GLU C 185 | 4.532 -22.598 19.817 1.00 33.23 | | | O |
| ATOM | 4193 OE2 GLU C 185 | 6.600 -22.666 19.100 1.00 33.92 | | | O |
| ATOM | 4194 N TYR C 186 | 3.693 -17.650 20.572 1.00 22.38 | | | N |
| ATOM | 4195 CA TYR C 186 | 3.068 -16.781 19.589 1.00 21.42 | | | C |
| ATOM | 4196 C TYR C 186 | 3.637 -15.354 19.676 1.00 21.59 | | | C |
| ATOM | 4197 O TYR C 186 | 4.110 -14.783 18.682 1.00 21.49 | | | O |
| ATOM | 4198 CB TYR C 186 | 1.566 -16.740 19.828 1.00 21.53 | | | C |
| ATOM | 4199 CG TYR C 186 | 0.829 -15.860 18.861 1.00 23.12 | | | C |
| ATOM | 4200 CD1 TYR C 186 | 0.629 -16.261 17.547 1.00 23.17 | | | C |
| ATOM | 4201 CD2 TYR C 186 | 0.363 -14.603 19.251 1.00 23.51 | | | C |
| ATOM | 4202 CE1 TYR C 186 | -0.019 -15.440 16.636 1.00 24.95 | | | C |
| ATOM | 4203 CE2 TYR C 186 | -0.286 -13.768 18.349 1.00 24.30 | | | C |
| ATOM | 4204 CZ TYR C 186 | -0.478 -14.196 17.044 1.00 24.69 | | | C |
| ATOM | 4205 OH TYR C 186 | -1.165 -13.406 16.151 1.00 27.20 | | | O |
| ATOM | 4206 N VAL C 187 | 3.594 -14.793 20.879 1.00 20.60 | | | N |
| ATOM | 4207 CA VAL C 187 | 4.065 -13.435 21.122 1.00 20.32 | | | C |
| ATOM | 4208 C VAL C 187 | 5.521 -13.275 20.747 1.00 22.02 | | | C |
| ATOM | 4209 O VAL C 187 | 5.923 -12.271 20.156 1.00 22.75 | | | O |
| ATOM | 4210 CB VAL C 187 | 3.895 -13.031 22.613 1.00 18.84 | | | C |
| ATOM | 4211 CG1 VAL C 187 | 4.307 -11.589 22.802 1.00 18.48 | | | C |
| ATOM | 4212 CG2 VAL C 187 | 2.455 -13.205 23.049 1.00 15.10 | | | C |
| ATOM | 4213 N TRP C 188 | 6.313 -14.280 21.091 1.00 23.28 | | | N |
| ATOM | 4214 CA TRP C 188 | 7.738 -14.269 20.806 1.00 24.39 | | | C |
| ATOM | 4215 C TRP C 188 | 8.038 -14.219 19.326 1.00 26.86 | | | C |
| ATOM | 4216 O TRP C 188 | 8.822 -13.380 18.885 1.00 29.62 | | | O |
| ATOM | 4217 CB TRP C 188 | 8.392 -15.508 21.411 1.00 23.40 | | | C |
| ATOM | 4218 CG TRP C 188 | 9.872 -15.595 21.152 1.00 22.36 | | | C |
| ATOM | 4219 CD1 TRP C 188 | 10.502 -16.439 20.274 1.00 21.00 | | | C |
| ATOM | 4220 CD2 TRP C 188 | 10.903 -14.803 21.762 1.00 20.20 | | | C |
| ATOM | 4221 NE1 TRP C 188 | 11.860 -16.218 20.307 1.00 20.86 | | | N |
| ATOM | 4222 CE2 TRP C 188 | 12.134 -15.218 21.205 1.00 20.42 | | | C |
| ATOM | 4223 CE3 TRP C 188 | 10.903 -13.779 22.716 1.00 20.17 | | | C |
| ATOM | 4224 CZ2 TRP C 188 | 13.361 -14.648 21.579 1.00 19.75 | | | C |
| ATOM | 4225 CZ3 TRP C 188 | 12.134 -13.205 23.094 1.00 19.20 | | | C |
| ATOM | 4226 CH2 TRP C 188 | 13.338 -13.646 22.521 1.00 19.07 | | | C |
| ATOM | 4227 N GLN C 189 | 7.426 -15.114 18.557 1.00 27.86 | | | N |
| ATOM | 4228 CA GLN C 189 | 7.672 -15.187 17.117 1.00 30.23 | | | C |
| ATOM | 4229 C GLN C 189 | 6.935 -14.149 16.273 1.00 30.21 | | | C |
| ATOM | 4230 O GLN C 189 | 7.253 -13.966 15.101 1.00 29.95 | | | O |
| ATOM | 4231 CB GLN C 189 | 7.319 -16.584 16.595 1.00 31.40 | | | C |
| ATOM | 4232 CG GLN C 189 | 7.766 -17.702 17.500 1.00 33.31 | | | C |
| ATOM | 4233 CD GLN C 189 | 7.434 -17.670 16.943 1.00 36.57 | | | C |
| ATOM | 4234 OE1 GLN C 189 | 6.371 -19.280 16.342 1.00 37.36 | | | O |
| ATOM | 4235 NE2 GLN C 189 | 8.336 -20.026 17.154 1.00 36.65 | | | N |
| ATOM | 4236 N ASN C 190 | 5.967 -13.465 16.872 1.00 30.87 | | | N |
| ATOM | 4237 CA ASN C 190 | 5.192 -12.471 16.143 1.00 30.84 | | | C |
| ATOM | 4238 C ASN C 190 | 5.368 -11.026 16.589 1.00 30.20 | | | C |
| ATOM | 4239 O ASN C 190 | 5.132 -10.110 15.805 1.00 29.38 | | | O |

FIG. 6 (con't)

| | | | | | |
|---|---|---|---|---|---|
| ATOM | 970 OE2 GLU A 158 | 1.178 -14.081 42.393 1.00 37.46 | O |
| ATOM | 971 N GLU A 159 | 5.795 -10.779 43.072 1.00 28.03 | N |
| ATOM | 972 CA GLU A 159 | 6.492 -9.557 42.679 1.00 26.60 | C |
| ATOM | 973 C GLU A 159 | 7.945 -9.507 43.155 1.00 26.46 | C |
| ATOM | 974 O GLU A 159 | 8.253 -9.801 44.309 1.00 26.25 | O |
| ATOM | 975 CB GLU A 159 | 5.739 -8.330 43.190 1.00 25.49 | C |
| ATOM | 976 CG GLU A 159 | 4.291 -8.265 42.719 1.00 24.92 | C |
| ATOM | 977 CD GLU A 159 | 4.126 -8.441 41.214 1.00 25.00 | C |
| ATOM | 978 OE1 GLU A 159 | 4.706 -7.652 40.435 1.00 24.10 | O |
| ATOM | 979 OE2 GLU A 159 | 3.398 -9.380 40.807 1.00 26.07 | O |
| ATOM | 980 N PRO A 160 | 8.866 -9.130 42.258 1.00 26.09 | N |
| ATOM | 981 CA PRO A 160 | 10.281 -9.051 42.624 1.00 25.59 | C |
| ATOM | 982 C PRO A 160 | 10.586 -8.029 43.713 1.00 24.98 | C |
| ATOM | 983 O PRO A 160 | 11.552 -8.189 44.471 1.00 25.95 | O |
| ATOM | 984 CB PRO A 160 | 10.956 -8.715 41.296 1.00 25.48 | C |
| ATOM | 985 CG PRO A 160 | 9.900 -7.934 40.577 1.00 25.14 | C |
| ATOM | 986 CD PRO A 160 | 8.666 -8.746 40.847 1.00 24.60 | C |
| ATOM | 987 N GLU A 161 | 9.785 -6.982 43.802 1.00 23.99 | N |
| ATOM | 988 CA GLU A 161 | 10.022 -5.972 44.830 1.00 23.98 | C |
| ATOM | 989 C GLU A 161 | 9.806 -6.580 46.205 1.00 22.39 | C |
| ATOM | 990 O GLU A 161 | 10.596 -6.363 47.118 1.00 22.10 | O |
| ATOM | 991 CB GLU A 161 | 9.065 -4.788 44.675 1.00 25.40 | C |
| ATOM | 992 CG GLU A 161 | 9.422 -3.777 43.602 1.00 26.04 | C |
| ATOM | 993 CD GLU A 161 | 9.464 -4.357 42.202 1.00 27.64 | C |
| ATOM | 994 OE1 GLU A 161 | 8.656 -5.257 41.885 1.00 28.55 | O |
| ATOM | 995 OE2 GLU A 161 | 10.305 -3.888 41.409 1.00 30.68 | O |
| ATOM | 996 N ILE A 162 | 8.721 -7.333 46.346 1.00 20.89 | N |
| ATOM | 997 CA ILE A 162 | 8.388 -7.968 47.609 1.00 19.10 | C |
| ATOM | 998 C ILE A 162 | 9.440 -9.014 47.982 1.00 19.76 | C |
| ATOM | 999 O ILE A 162 | 9.856 -9.110 49.144 1.00 19.28 | O |
| ATOM | 1000 CB ILE A 162 | 6.982 -8.624 47.528 1.00 17.30 | C |
| ATOM | 1001 CG1 ILE A 162 | 5.934 -7.545 47.240 1.00 17.11 | C |
| ATOM | 1002 CG2 ILE A 162 | 6.621 -9.323 48.825 1.00 14.85 | C |
| ATOM | 1003 CD1 ILE A 162 | 5.804 -6.510 48.348 1.00 15.95 | C |
| ATOM | 1004 N GLN A 163 | 9.883 -9.779 46.989 1.00 18.99 | N |
| ATOM | 1005 CA GLN A 163 | 10.870 -10.823 47.220 1.00 19.77 | C |
| ATOM | 1006 C GLN A 163 | 12.178 -10.262 47.714 1.00 19.64 | C |
| ATOM | 1007 O GLN A 163 | 12.851 -10.857 48.556 1.00 20.89 | O |
| ATOM | 1008 CB GLN A 163 | 11.099 -11.651 45.949 1.00 19.69 | C |
| ATOM | 1009 CG GLN A 163 | 9.959 -12.608 45.651 1.00 20.76 | C |
| ATOM | 1010 CD GLN A 163 | 10.224 -13.518 44.477 1.00 20.36 | C |
| ATOM | 1011 OE1 GLN A 163 | 11.353 -13.973 44.272 1.00 23.17 | O |
| ATOM | 1012 NE2 GLN A 163 | 9.189 -13.810 43.711 1.00 21.56 | N |
| ATOM | 1013 N ALA A 164 | 12.550 -9.105 47.199 1.00 20.11 | N |
| ATOM | 1014 CA ALA A 164 | 13.793 -8.488 47.617 1.00 18.05 | C |
| ATOM | 1015 C ALA A 164 | 13.653 -8.024 49.055 1.00 18.24 | C |
| ATOM | 1016 O ALA A 164 | 14.574 -8.142 49.873 1.00 19.10 | O |
| ATOM | 1017 CB ALA A 164 | 14.107 -7.325 46.716 1.00 16.51 | C |
| ATOM | 1018 N ALA A 165 | 12.483 -7.502 49.379 1.00 16.67 | N |
| ATOM | 1019 CA ALA A 165 | 12.254 -7.012 50.724 1.00 16.07 | C |
| ATOM | 1020 C ALA A 165 | 12.256 -8.145 51.770 1.00 16.35 | C |
| ATOM | 1021 O ALA A 165 | 12.763 -7.969 52.879 1.00 15.23 | O |
| ATOM | 1022 CB ALA A 165 | 10.961 -6.240 50.746 1.00 13.13 | C |
| ATOM | 1023 N LEU A 166 | 11.707 -9.304 51.398 1.00 17.26 | N |
| ATOM | 1024 CA LEU A 166 | 11.666 -10.459 52.296 1.00 18.54 | C |
| ATOM | 1025 C LEU A 166 | 13.067 -11.003 52.576 1.00 19.58 | C |
| ATOM | 1026 O LEU A 166 | 13.351 -11.447 53.683 1.00 18.09 | O |
| ATOM | 1027 CB LEU A 166 | 10.794 -11.578 51.713 1.00 18.23 | C |
| ATOM | 1028 CG LEU A 166 | 9.287 -11.252 51.607 1.00 19.45 | C |
| ATOM | 1029 CD1 LEU A 166 | 8.534 -12.452 51.116 1.00 19.88 | C |
| ATOM | 1030 CD2 LEU A 166 | 8.741 -10.876 52.953 1.00 18.88 | C |
| ATOM | 1031 N LYS A 167 | 13.943 -10.968 51.569 1.00 20.96 | N |
| ATOM | 1032 CA LYS A 167 | 15.310 -11.450 51.743 1.00 22.76 | C |
| ATOM | 1033 C LYS A 167 | 16.064 -10.528 52.715 1.00 23.03 | C |
| ATOM | 1034 O LYS A 167 | 16.680 -10.994 53.675 1.00 22.49 | O |
| ATOM | 1035 CB LYS A 167 | 16.041 -11.496 50.402 1.00 23.99 | C |
| ATOM | 1036 CG LYS A 167 | 15.381 -12.381 49.352 1.00 27.53 | C |
| ATOM | 1037 CD LYS A 167 | 16.089 -12.261 48.007 1.00 30.15 | C |
| ATOM | 1038 CE LYS A 167 | 15.226 -12.800 46.872 1.00 32.48 | C |
| ATOM | 1039 NZ LYS A 167 | 15.755 -12.464 45.512 1.00 33.18 | N |
| ATOM | 1040 N LYS A 168 | 15.998 -9.221 52.459 1.00 22.85 | N |
| ATOM | 1041 CA LYS A 168 | 16.670 -8.230 53.280 1.00 22.23 | C |
| ATOM | 1042 C LYS A 168 | 16.155 -8.347 54.691 1.00 21.82 | C |
| ATOM | 1043 O LYS A 168 | 16.884 -8.126 55.666 1.00 20.73 | O |
| ATOM | 1044 CB LYS A 168 | 16.408 -6.827 52.748 1.00 23.31 | C |
| ATOM | 1045 CG LYS A 168 | 17.026 -6.567 51.396 1.00 27.42 | C |
| ATOM | 1046 CD LYS A 168 | 16.788 -5.124 50.973 1.00 32.41 | C |
| ATOM | 1047 CE LYS A 168 | 17.440 -4.789 49.628 1.00 35.51 | C |
| ATOM | 1048 NZ LYS A 168 | 17.186 -3.377 49.177 1.00 35.22 | N |
| ATOM | 1049 N LEU A 169 | 14.882 -8.707 54.785 1.00 21.82 | N |
| ATOM | 1050 CA LEU A 169 | 14.221 -8.875 56.071 1.00 21.28 | C |
| ATOM | 1051 C LEU A 169 | 14.805 -10.086 56.794 1.00 19.82 | C |
| ATOM | 1052 O LEU A 169 | 15.084 -9.996 57.978 1.00 20.17 | O |
| ATOM | 1053 CB LEU A 169 | 12.712 -9.059 55.874 1.00 22.53 | C |
| ATOM | 1054 CG LEU A 169 | 11.818 -9.066 57.128 1.00 22.31 | C |
| ATOM | 1055 CD1 LEU A 169 | 11.822 -7.695 57.754 1.00 22.18 | C |
| ATOM | 4240 CB ASN C 190 | 3.718 -12.834 16.200 1.00 33.75 | C |
| ATOM | 4241 CG ASN C 190 | 3.376 -14.014 15.331 1.00 36.87 | C |
| ATOM | 4242 OD1 ASN C 190 | 3.309 -13.892 14.112 1.00 40.50 | O |
| ATOM | 4243 ND2 ASN C 190 | 3.174 -15.177 15.950 1.00 38.74 | N |
| ATOM | 4244 N PHE C 191 | 5.777 -10.815 17.838 1.00 29.78 | N |
| ATOM | 4245 CA PHE C 191 | 5.953 -9.460 18.356 1.00 28.96 | C |
| ATOM | 4246 C PHE C 191 | 7.423 -9.121 18.570 1.00 29.25 | C |
| ATOM | 4247 O PHE C 191 | 7.828 -7.956 18.515 1.00 28.96 | O |
| ATOM | 4248 CB PHE C 191 | 5.168 -9.303 19.661 1.00 28.63 | C |
| ATOM | 4249 CG PHE C 191 | 3.682 -9.120 19.463 1.00 28.76 | C |
| ATOM | 4250 CD1 PHE C 191 | 3.149 -7.855 19.242 1.00 27.45 | C |
| ATOM | 4251 CD2 PHE C 191 | 2.820 -10.214 19.494 1.00 28.14 | C |
| ATOM | 4252 CE1 PHE C 191 | 1.784 -7.681 19.057 1.00 27.75 | C |
| ATOM | 4253 CE2 PHE C 191 | 1.453 -10.045 19.306 1.00 27.34 | C |
| ATOM | 4254 CZ PHE C 191 | 0.934 -8.776 19.087 1.00 27.56 | C |
| ATOM | 4255 N VAL C 192 | 8.229 -10.145 18.802 1.00 30.72 | N |
| ATOM | 4256 CA VAL C 192 | 9.646 -9.937 19.022 1.00 33.07 | C |
| ATOM | 4257 C VAL C 192 | 10.383 -10.030 17.708 1.00 35.15 | C |
| ATOM | 4258 O VAL C 192 | 10.377 -11.074 17.059 1.00 34.87 | O |
| ATOM | 4259 CB VAL C 192 | 10.225 -10.987 19.978 1.00 33.27 | C |
| ATOM | 4260 CG1 VAL C 192 | 11.747 -10.793 20.108 1.00 32.56 | C |
| ATOM | 4261 CG2 VAL C 192 | 9.529 -10.884 21.332 1.00 33.24 | C |
| ATOM | 4262 N GLU C 193 | 11.017 -8.931 17.324 1.00 38.47 | N |
| ATOM | 4263 CA GLU C 193 | 11.766 -8.876 16.080 1.00 42.37 | C |
| ATOM | 4264 C GLU C 193 | 12.927 -9.855 16.143 1.00 44.45 | C |
| ATOM | 4265 O GLU C 193 | 13.788 -9.770 17.012 1.00 44.48 | O |
| ATOM | 4266 CB GLU C 193 | 12.279 -7.458 15.833 1.00 42.27 | C |
| ATOM | 4267 CG GLU C 193 | 13.261 -7.356 14.676 1.00 44.64 | C |
| ATOM | 4268 CD GLU C 193 | 13.807 -5.948 14.474 1.00 45.83 | C |
| ATOM | 4269 OE1 GLU C 193 | 13.067 -5.090 13.949 1.00 46.14 | O |
| ATOM | 4270 OE2 GLU C 193 | 14.981 -5.700 14.842 1.00 45.62 | O |
| ATOM | 4271 N GLN C 194 | 12.923 -10.806 15.227 1.00 48.92 | N |
| ATOM | 4272 CA GLN C 194 | 13.965 -11.805 15.217 1.00 53.71 | C |
| ATOM | 4273 C GLN C 194 | 15.359 -11.262 14.913 1.00 57.11 | C |
| ATOM | 4274 O GLN C 194 | 15.597 -10.631 13.877 1.00 57.03 | O |
| ATOM | 4275 CB GLN C 194 | 13.589 -12.926 14.250 1.00 53.64 | C |
| ATOM | 4276 CG GLN C 194 | 13.603 -14.283 14.922 1.00 54.54 | C |
| ATOM | 4277 CD GLN C 194 | 13.023 -14.238 16.325 1.00 53.86 | C |
| ATOM | 4278 OE1 GLN C 194 | 11.820 -14.063 16.510 1.00 54.51 | O |
| ATOM | 4279 NE2 GLN C 194 | 13.888 -14.380 17.324 1.00 53.75 | N |
| ATOM | 4280 N GLU C 195 | 16.265 -11.515 15.859 1.00 60.85 | N |
| ATOM | 4281 CA GLU C 195 | 17.663 -11.095 15.790 1.00 64.50 | C |
| ATOM | 4282 C GLU C 195 | 18.148 -11.081 14.337 1.00 65.78 | C |
| ATOM | 4283 O GLU C 195 | 18.850 -10.164 13.907 1.00 66.15 | O |
| ATOM | 4284 CB GLU C 195 | 18.533 -12.067 16.612 1.00 65.98 | C |
| ATOM | 4285 CG GLU C 195 | 18.025 -12.386 18.039 1.00 67.65 | C |
| ATOM | 4286 CD GLU C 195 | 18.325 -11.294 19.073 1.00 69.60 | C |
| ATOM | 4287 OE1 GLU C 195 | 19.493 -10.857 19.175 1.00 70.24 | O |
| ATOM | 4288 OE2 GLU C 195 | 17.394 -10.883 19.802 1.00 70.17 | O |
| ATOM | 4289 N GLU C 196 | 17.753 -12.108 13.589 1.00 66.84 | N |
| ATOM | 4290 CA GLU C 196 | 18.123 -12.240 12.187 1.00 67.79 | C |
| ATOM | 4291 C GLU C 196 | 16.989 -12.951 11.452 1.00 68.33 | C |
| ATOM | 4292 O GLU C 196 | 16.679 -14.101 11.758 1.00 67.57 | O |
| ATOM | 4293 CB GLU C 196 | 19.417 -13.048 12.060 1.00 68.19 | C |
| ATOM | 4294 N GLY C 197 | 16.379 -12.261 10.488 1.00 69.46 | N |
| ATOM | 4295 CA GLY C 197 | 15.269 -12.813 9.704 1.00 71.09 | C |
| ATOM | 4296 C GLY C 197 | 15.515 -14.269 9.297 1.00 72.07 | C |
| ATOM | 4297 O GLY C 197 | 16.360 -14.549 8.446 1.00 72.21 | O |
| ATOM | 4298 N GLU C 198 | 14.757 -15.178 9.916 1.00 73.13 | N |
| ATOM | 4299 CA GLU C 198 | 14.844 -16.626 9.672 1.00 73.20 | C |
| ATOM | 4300 C GLU C 198 | 16.055 -17.289 10.351 1.00 72.95 | C |
| ATOM | 4301 O GLU C 198 | 16.748 -18.093 9.729 1.00 72.49 | O |
| ATOM | 4302 CB GLU C 198 | 14.857 -16.920 8.157 1.00 73.01 | C |
| ATOM | 4303 N SER C 199 | 16.299 -16.951 11.625 1.00 72.53 | N |
| ATOM | 4304 CA SER C 199 | 17.424 -17.511 12.397 1.00 71.21 | C |
| ATOM | 4305 C SER C 199 | 17.178 -17.448 13.910 1.00 69.97 | C |
| ATOM | 4306 O SER C 199 | 17.905 -16.768 14.642 1.00 69.70 | O |
| ATOM | 4307 CB SER C 199 | 18.732 -16.771 12.048 1.00 71.38 | C |
| ATOM | 4308 N LYS C 200 | 16.157 -18.174 14.366 1.00 68.49 | N |
| ATOM | 4309 CA LYS C 200 | 15.794 -18.217 15.781 1.00 66.53 | C |
| ATOM | 4310 C LYS C 200 | 14.721 -19.279 16.082 1.00 65.27 | C |
| ATOM | 4311 O LYS C 200 | 14.153 -19.892 15.172 1.00 65.06 | O |
| ATOM | 4312 CB LYS C 200 | 15.315 -16.839 16.231 1.00 66.58 | C |
| ATOM | 4313 N ALA C 201 | 14.453 -19.489 17.369 1.00 62.54 | N |
| ATOM | 4314 CA ALA C 201 | 13.465 -20.472 17.802 1.00 59.76 | C |
| ATOM | 4315 C ALA C 201 | 13.016 -20.200 19.230 1.00 57.59 | C |
| ATOM | 4316 O ALA C 201 | 13.728 -19.571 20.012 1.00 58.89 | O |
| ATOM | 4317 CB ALA C 201 | 14.045 -21.877 17.703 1.00 59.76 | C |
| ATOM | 4318 N PHE C 202 | 11.833 -20.688 19.573 1.00 53.52 | N |
| ATOM | 4319 CA PHE C 202 | 11.291 -20.488 20.909 1.00 49.15 | C |
| ATOM | 4320 C PHE C 202 | 11.702 -21.627 21.842 1.00 47.27 | C |
| ATOM | 4321 O PHE C 202 | 11.609 -22.791 21.466 1.00 46.65 | O |
| ATOM | 4322 CB PHE C 202 | 9.766 -20.415 20.840 1.00 46.98 | C |
| ATOM | 4323 CG PHE C 202 | 9.102 -20.369 22.181 1.00 44.69 | C |
| ATOM | 4324 CD1 PHE C 202 | 9.112 -19.208 22.940 1.00 42.42 | C |
| ATOM | 4325 CD2 PHE C 202 | 8.474 -21.501 22.695 1.00 43.49 | C |

FIG. 6 (con't)

| | | | | |
|---|---|---|---|---|
| ATOM 1056 CD2 LEU A 169 | 10.400 -9.453 56.747 1.00 24.04 | C | ATOM 4326 CE1 PHE C 202 | 8.507 -19.175 24.186 1.00 40.03 | C |
| ATOM 1057 N LYS A 170 | 14.976 -11.199 56.088 1.00 19.32 | N | ATOM 4327 CE2 PHE C 202 | 7.870 -21.476 23.941 1.00 40.35 | C |
| ATOM 1058 CA LYS A 170 | 15.546 -12.397 56.674 1.00 20.07 | C | ATOM 4328 CZ PHE C 202 | 7.884 -20.314 24.687 1.00 40.63 | C |
| ATOM 1059 C LYS A 170 | 17.015 -12.115 57.057 1.00 21.35 | C | ATOM 4329 N GLN C 203 | 12.147 -21.288 23.053 1.00 44.47 | N |
| ATOM 1060 O LYS A 170 | 17.527 -12.623 58.055 1.00 20.49 | O | ATOM 4330 CA GLN C 203 | 12.559 -22.292 24.033 1.00 41.56 | C |
| ATOM 1061 CB LYS A 170 | 15.495 -13.555 55.671 1.00 20.11 | C | ATOM 4331 C GLN C 203 | 11.754 -22.172 25.328 1.00 39.00 | C |
| ATOM 1062 CG LYS A 170 | 16.239 -14.788 56.122 1.00 21.04 | C | ATOM 4332 O GLN C 203 | 11.842 -21.171 26.050 1.00 38.17 | O |
| ATOM 1063 CD LYS A 170 | 16.704 -15.633 54.954 1.00 21.57 | C | ATOM 4333 CB GLN C 203 | 14.046 -22.166 24.346 1.00 42.30 | C |
| ATOM 1064 CE LYS A 170 | 17.460 -16.841 55.461 1.00 21.76 | C | ATOM 4334 CG GLN C 203 | 14.567 -23.290 25.207 1.00 45.64 | C |
| ATOM 1065 NZ LYS A 170 | 18.099 -17.565 54.346 1.00 23.42 | N | ATOM 4335 CD GLN C 203 | 15.922 -22.987 25.795 1.00 48.43 | C |
| ATOM 1066 N GLU A 171 | 17.673 -11.285 56.256 1.00 20.61 | N | ATOM 4336 OE1 GLN C 203 | 16.905 -22.822 25.070 1.00 49.30 | O |
| ATOM 1067 CA GLU A 171 | 19.062 -10.915 56.496 1.00 20.40 | C | ATOM 4337 NE2 GLN C 203 | 15.985 -22.901 27.120 1.00 49.38 | N |
| ATOM 1068 C GLU A 171 | 19.214 -10.001 57.712 1.00 19.22 | C | ATOM 4338 N PRO C 204 | 10.964 -23.207 25.641 1.00 36.29 | N |
| ATOM 1069 O GLU A 171 | 20.280 -9.925 58.330 1.00 16.62 | O | ATOM 4339 CA PRO C 204 | 10.141 -23.211 26.845 1.00 35.80 | C |
| ATOM 1070 CB GLU A 171 | 19.634 -10.227 55.259 1.00 21.63 | C | ATOM 4340 C PRO C 204 | 10.966 -23.245 28.103 1.00 35.16 | C |
| ATOM 1071 CG GLU A 171 | 19.617 -11.101 54.010 1.00 26.74 | C | ATOM 4341 O PRO C 204 | 12.099 -23.719 28.085 1.00 36.14 | O |
| ATOM 1072 CD GLU A 171 | 20.277 -10.429 52.830 1.00 30.58 | C | ATOM 4342 CB PRO C 204 | 9.293 -24.469 26.679 1.00 36.43 | C |
| ATOM 1073 OE1 GLU A 171 | 20.883 -9.355 53.041 1.00 29.90 | O | ATOM 4343 CG PRO C 204 | 10.196 -25.383 25.953 1.00 35.00 | C |
| ATOM 1074 OE2 GLU A 171 | 20.197 -10.981 51.696 1.00 30.64 | O | ATOM 4344 CD PRO C 204 | 10.846 -24.487 24.922 1.00 34.77 | C |
| ATOM 1075 N ALA A 172 | 18.141 -9.301 58.049 1.00 18.37 | N | ATOM 4345 N TRP C 205 | 10.403 -22.736 29.191 1.00 34.11 | N |
| ATOM 1076 CA ALA A 172 | 18.190 -8.413 59.192 1.00 17.49 | C | ATOM 4346 CA TRP C 205 | 11.111 -22.712 30.455 1.00 34.69 | C |
| ATOM 1077 C ALA A 172 | 18.045 -9.205 60.480 1.00 17.60 | C | ATOM 4347 C TRP C 205 | 10.470 -23.586 31.546 1.00 36.25 | C |
| ATOM 1078 O ALA A 172 | 18.132 -8.634 61.557 1.00 16.96 | O | ATOM 4348 O TRP C 205 | 9.251 -23.766 31.605 1.00 35.88 | O |
| ATOM 1079 CB ALA A 172 | 17.094 -7.367 59.098 1.00 17.02 | C | ATOM 4349 CB TRP C 205 | 11.284 -21.265 30.943 1.00 31.32 | C |
| ATOM 1080 N GLY A 173 | 17.814 -10.520 60.349 1.00 18.65 | N | ATOM 4350 CG TRP C 205 | 10.003 -20.473 31.024 1.00 29.84 | C |
| ATOM 1081 CA GLY A 173 | 17.657 -11.400 61.505 1.00 17.60 | C | ATOM 4351 CD1 TRP C 205 | 9.045 -20.540 32.004 1.00 28.41 | C |
| ATOM 1082 C GLY A 173 | 16.200 -11.720 61.840 1.00 18.07 | C | ATOM 4352 CD2 TRP C 205 | 9.515 -19.535 30.058 1.00 27.19 | C |
| ATOM 1083 O GLY A 173 | 15.911 -12.487 62.763 1.00 17.73 | O | ATOM 4353 NE1 TRP C 205 | 7.998 -19.710 31.704 1.00 25.93 | N |
| ATOM 1084 N CYS A 174 | 15.281 -11.121 61.092 1.00 16.33 | N | ATOM 4354 CE2 TRP C 205 | 8.255 -19.079 30.513 1.00 26.56 | C |
| ATOM 1085 CA CYS A 174 | 13.863 -11.346 61.313 1.00 16.16 | C | ATOM 4355 CE3 TRP C 205 | 10.017 -19.038 28.847 1.00 25.51 | C |
| ATOM 1086 C CYS A 174 | 13.444 -12.696 60.733 1.00 16.33 | C | ATOM 4356 CZ2 TRP C 205 | 7.489 -18.144 29.797 1.00 24.50 | C |
| ATOM 1087 O CYS A 174 | 13.542 -12.929 59.534 1.00 15.43 | O | ATOM 4357 CZ3 TRP C 205 | 9.259 -18.112 28.137 1.00 25.08 | C |
| ATOM 1088 CB CYS A 174 | 13.037 -10.241 60.674 1.00 15.16 | C | ATOM 4358 CH2 TRP C 205 | 8.009 -17.678 28.613 1.00 24.11 | C |
| ATOM 1089 SG CYS A 174 | 11.279 -10.569 60.787 1.00 17.07 | S | ATOM 4359 N GLU C 206 | 11.328 -24.134 32.393 1.00 37.99 | N |
| ATOM 1090 N LYS A 175 | 12.965 -13.584 61.596 1.00 17.50 | N | ATOM 4360 CA GLU C 206 | 10.944 -25.013 33.482 1.00 40.84 | C |
| ATOM 1091 CA LYS A 175 | 12.562 -14.905 61.163 1.00 19.73 | C | ATOM 4361 C GLU C 206 | 9.471 -25.028 33.920 1.00 40.15 | C |
| ATOM 1092 C LYS A 175 | 11.126 -14.846 60.677 1.00 20.26 | C | ATOM 4362 O GLU C 206 | 8.799 -26.047 33.784 1.00 40.61 | O |
| ATOM 1093 O LYS A 175 | 10.240 -14.472 61.434 1.00 20.74 | O | ATOM 4363 CB GLU C 206 | 11.828 -24.716 34.703 1.00 44.40 | C |
| ATOM 1094 CB LYS A 175 | 12.691 -15.874 62.323 1.00 19.81 | C | ATOM 4364 CG GLU C 206 | 13.323 -24.589 34.374 1.00 50.13 | C |
| ATOM 1095 CG LYS A 175 | 12.463 -17.322 61.953 1.00 24.58 | C | ATOM 4365 CD GLU C 206 | 14.147 -23.996 35.518 1.00 53.41 | C |
| ATOM 1096 CD LYS A 175 | 12.440 -18.213 63.188 1.00 27.49 | C | ATOM 4366 OE1 GLU C 206 | 14.266 -24.651 36.583 1.00 53.81 | O |
| ATOM 1097 CE LYS A 175 | 12.425 -19.693 62.839 1.00 29.10 | C | ATOM 4367 OE2 GLU C 206 | 14.677 -22.869 35.350 1.00 55.20 | O |
| ATOM 1098 NZ LYS A 175 | 12.336 -20.492 64.092 1.00 32.01 | N | ATOM 4368 N ASP C 207 | 8.972 -23.910 34.428 1.00 39.44 | N |
| ATOM 1099 N LEU A 176 | 10.892 -15.217 59.419 1.00 21.18 | N | ATOM 4369 CA ASP C 207 | 7.602 -23.848 34.915 1.00 39.67 | C |
| ATOM 1100 CA LEU A 176 | 9.540 -15.182 58.866 1.00 22.24 | C | ATOM 4370 C ASP C 207 | 6.637 -23.052 34.028 1.00 37.38 | C |
| ATOM 1101 C LEU A 176 | 9.067 -16.586 58.499 1.00 21.94 | C | ATOM 4371 O ASP C 207 | 5.852 -22.251 34.526 1.00 36.35 | O |
| ATOM 1102 O LEU A 176 | 9.784 -17.311 57.819 1.00 22.52 | O | ATOM 4372 CB ASP C 207 | 7.610 -23.249 36.327 1.00 43.95 | C |
| ATOM 1103 CB LEU A 176 | 9.522 -14.298 57.615 1.00 23.01 | C | ATOM 4373 CG ASP C 207 | 8.011 -21.773 36.340 1.00 48.01 | C |
| ATOM 1104 CG LEU A 176 | 8.270 -13.438 57.397 1.00 25.46 | C | ATOM 4374 OD1 ASP C 207 | 8.872 -21.366 35.520 1.00 48.96 | O |
| ATOM 1105 CD1 LEU A 176 | 8.463 -12.617 56.140 1.00 27.46 | C | ATOM 4375 OD2 ASP C 207 | 7.469 -21.018 37.184 1.00 50.39 | O |
| ATOM 1106 CD2 LEU A 176 | 7.024 -14.296 57.279 1.00 24.28 | C | ATOM 4376 N ILE C 208 | 6.690 -23.280 32.724 1.00 35.30 | N |
| ATOM 1107 N ARG A 177 | 7.866 -16.967 58.932 1.00 21.87 | N | ATOM 4377 CA ILE C 208 | 5.820 -22.547 31.821 1.00 34.13 | C |
| ATOM 1108 CA ARG A 177 | 7.317 -18.291 58.638 1.00 22.85 | C | ATOM 4378 C ILE C 208 | 4.419 -23.132 31.888 1.00 33.46 | C |
| ATOM 1109 C ARG A 177 | 5.819 -18.255 58.322 1.00 22.84 | C | ATOM 4379 O ILE C 208 | 3.430 -22.423 31.770 1.00 32.99 | O |
| ATOM 1110 O ARG A 177 | 5.128 -17.284 58.638 1.00 22.66 | O | ATOM 4380 CB ILE C 208 | 6.347 -22.599 30.349 1.00 33.37 | C |
| ATOM 1111 CB ARG A 177 | 7.560 -19.237 59.825 1.00 25.46 | C | ATOM 4381 CG1 ILE C 208 | 5.579 -21.608 29.480 1.00 32.02 | C |
| ATOM 1112 CG ARG A 177 | 9.038 -19.554 60.090 1.00 29.18 | C | ATOM 4382 CG2 ILE C 208 | 6.229 -24.024 29.788 1.00 31.68 | C |
| ATOM 1113 CD ARG A 177 | 9.666 -20.394 58.968 1.00 33.66 | C | ATOM 4383 CD1 ILE C 208 | 6.021 -21.591 28.043 1.00 33.66 | C |
| ATOM 1114 NE ARG A 177 | 11.076 -20.735 59.231 1.00 38.67 | N | ATOM 4384 N GLN C 209 | 4.346 -24.432 32.127 1.00 33.29 | N |
| ATOM 1115 CZ ARG A 177 | 12.117 -19.936 58.987 1.00 39.65 | C | ATOM 4385 CA GLN C 209 | 3.061 -25.108 32.178 1.00 32.42 | C |
| ATOM 1116 NH1 ARG A 177 | 11.940 -18.733 58.457 1.00 39.33 | N | ATOM 4386 C GLN C 209 | 2.437 -25.053 33.578 1.00 31.14 | C |
| ATOM 1117 NH2 ARG A 177 | 13.342 -20.341 59.293 1.00 40.65 | N | ATOM 4387 O GLN C 209 | 1.246 -24.749 33.746 1.00 31.42 | O |
| ATOM 1118 N ILE A 178 | 5.311 -19.310 57.681 1.00 22.35 | N | ATOM 4388 CB GLN C 209 | 3.256 -26.556 31.715 1.00 32.69 | C |
| ATOM 1119 CA ILE A 178 | 3.894 -19.400 57.349 1.00 20.34 | C | ATOM 4389 CG GLN C 209 | 2.073 -27.175 30.972 1.00 34.85 | C |
| ATOM 1120 C ILE A 178 | 3.126 -20.056 58.494 1.00 21.15 | C | ATOM 4390 CD GLN C 209 | 2.483 -27.806 29.649 1.00 35.35 | C |
| ATOM 1121 O ILE A 178 | 3.629 -20.974 59.137 1.00 21.86 | O | ATOM 4391 OE1 GLN C 209 | 3.455 -28.558 29.589 1.00 36.11 | O |
| ATOM 1122 CB ILE A 178 | 3.686 -20.223 56.084 1.00 19.73 | C | ATOM 4392 NE2 GLN C 209 | 1.744 -27.501 28.585 1.00 36.08 | N |
| ATOM 1123 CG1 ILE A 178 | 4.491 -19.615 54.939 1.00 19.71 | C | ATOM 4393 N GLU C 210 | 3.251 -25.332 34.586 1.00 28.90 | N |
| ATOM 1124 CG2 ILE A 178 | 2.217 -20.261 53.733 1.00 18.35 | C | ATOM 4394 CA GLU C 210 | 2.791 -25.329 35.960 1.00 27.74 | C |
| ATOM 1125 CD1 ILE A 178 | 4.197 -18.140 54.691 1.00 17.93 | C | ATOM 4395 C GLU C 210 | 2.270 -23.960 36.393 1.00 26.42 | C |
| ATOM 1126 N MET A 179 | 1.908 -19.587 58.749 1.00 21.52 | N | ATOM 4396 O GLU C 210 | 1.324 -23.865 37.182 1.00 25.86 | O |
| ATOM 1127 CA MET A 179 | 1.086 -20.127 59.836 1.00 21.73 | C | ATOM 4397 CB GLU C 210 | 3.912 -25.807 36.903 1.00 27.95 | C |
| ATOM 1128 C MET A 179 | 0.525 -21.491 59.469 1.00 21.63 | C | ATOM 4398 CG GLU C 210 | 5.347 -25.810 36.305 1.00 32.21 | C |
| ATOM 1129 O MET A 179 | -0.090 -21.648 58.415 1.00 21.49 | O | ATOM 4399 CD GLU C 210 | 5.591 -26.833 35.160 1.00 32.33 | C |
| ATOM 1130 CB MET A 179 | -0.073 -19.181 60.132 1.00 21.14 | C | ATOM 4400 OE1 GLU C 210 | 5.528 -28.062 35.401 1.00 30.31 | O |
| ATOM 1131 CG MET A 179 | 0.043 -18.312 61.379 1.00 21.98 | C | ATOM 4401 OE2 GLU C 210 | 5.857 -26.407 34.012 1.00 31.93 | O |
| ATOM 1132 SD MET A 179 | -1.463 -17.320 61.574 1.00 20.07 | S | ATOM 4402 N ASN C 211 | 2.881 -22.903 35.874 1.00 25.33 | N |
| ATOM 1133 CE MET A 179 | -1.024 -16.022 60.719 1.00 19.83 | C | ATOM 4403 CA ASN C 211 | 2.480 -21.542 36.202 1.00 23.63 | C |
| ATOM 1134 N LYS A 180 | 0.729 -22.462 60.346 1.00 20.59 | N | ATOM 4404 C ASN C 211 | 1.126 -21.230 35.579 1.00 22.66 | C |
| ATOM 1135 CA LYS A 180 | 0.212 -23.802 60.108 1.00 21.79 | C | ATOM 4405 O ASN C 211 | 0.263 -20.635 36.213 1.00 21.05 | O |
| ATOM 1136 C LYS A 180 | -1.073 -23.983 60.906 1.00 21.48 | C | ATOM 4406 CB ASN C 211 | 3.525 -20.546 35.696 1.00 25.47 | C |
| ATOM 1137 O LYS A 180 | -1.427 -23.127 61.719 1.00 21.37 | O | ATOM 4407 CG ASN C 211 | 4.615 -20.277 36.714 1.00 29.70 | C |
| ATOM 1138 CB LYS A 180 | 1.272 -24.843 60.505 1.00 22.90 | C | ATOM 4408 OD1 ASN C 211 | 4.679 -20.926 37.767 1.00 32.72 | O |
| ATOM 1139 CG LYS A 180 | 1.847 -24.646 61.875 1.00 23.11 | C | ATOM 4409 ND2 ASN C 211 | 5.491 -19.323 36.411 1.00 29.51 | N |
| ATOM 1140 CD LYS A 180 | 2.929 -25.666 62.152 1.00 23.25 | C | ATOM 4410 N PHE C 212 | 0.943 -21.635 34.328 1.00 21.23 | N |
| ATOM 1141 CE LYS A 180 | 4.112 -25.505 61.215 1.00 24.25 | C | ATOM 4411 CA PHE C 212 | -0.312 -21.412 33.648 1.00 22.12 | C |

FIG. 6 (con't)

```
ATOM  1142  NZ  LYS A 180    5.208 -26.468 61.539 1.00 24.93   N
ATOM  1143  N   PRO A 181   -1.816 -25.075 60.657 1.00 21.00   N
ATOM  1144  CA  PRO A 181   -3.060 -25.315 61.382 1.00 20.19   C
ATOM  1145  C   PRO A 181   -2.969 -25.075 62.882 1.00 19.75   C
ATOM  1146  O   PRO A 181   -3.862 -24.461 63.464 1.00 18.22   O
ATOM  1147  CB  PRO A 181   -3.385 -26.751 61.016 1.00 20.40   C
ATOM  1148  CG  PRO A 181   -2.975 -26.788 59.595 1.00 20.15   C
ATOM  1149  CD  PRO A 181   -1.606 -26.120 59.645 1.00 21.32   C
ATOM  1150  N   GLN A 182   -1.890 -25.543 63.507 1.00 21.37   N
ATOM  1151  CA  GLN A 182   -1.722 -25.357 64.957 1.00 21.62   C
ATOM  1152  C   GLN A 182   -1.689 -23.887 65.346 1.00 20.06   C
ATOM  1153  O   GLN A 182   -2.182 -23.515 66.412 1.00 19.52   O
ATOM  1154  CB  GLN A 182   -0.462 -26.067 65.455 1.00 22.77   C
ATOM  1155  CG  GLN A 182   -0.466 -27.554 65.139 1.00 28.65   C
ATOM  1156  CD  GLN A 182    0.125 -27.868 63.767 1.00 31.78   C
ATOM  1157  OE1 GLN A 182    1.343 -27.985 63.635 1.00 34.11   O
ATOM  1158  NE2 GLN A 182   -0.726 -28.000 62.750 1.00 30.20   N
ATOM  1159  N   ASP A 183   -1.123 -23.057 64.472 1.00 19.76   N
ATOM  1160  CA  ASP A 183   -1.025 -21.623 64.724 1.00 18.68   C
ATOM  1161  C   ASP A 183   -2.383 -20.959 64.777 1.00 18.25   C
ATOM  1162  O   ASP A 183   -2.651 -20.181 65.685 1.00 16.97   O
ATOM  1163  CB  ASP A 183   -0.172 -20.942 63.669 1.00 19.59   C
ATOM  1164  CG  ASP A 183    1.273 -21.414 63.705 1.00 18.01   C
ATOM  1165  OD1 ASP A 183    1.867 -21.456 64.790 1.00 17.51   O
ATOM  1166  OD2 ASP A 183    1.807 -21.737 62.630 1.00 22.87   O
ATOM  1167  N   PHE A 184   -3.238 -21.248 63.797 1.00 17.75   N
ATOM  1168  CA  PHE A 184   -4.571 -20.665 63.782 1.00 17.68   C
ATOM  1169  C   PHE A 184   -5.315 -21.064 65.046 1.00 19.64   C
ATOM  1170  O   PHE A 184   -5.949 -20.232 65.685 1.00 19.95   O
ATOM  1171  CB  PHE A 184   -5.356 -21.111 62.565 1.00 15.70   C
ATOM  1172  CG  PHE A 184   -4.855 -20.525 61.295 1.00 14.98   C
ATOM  1173  CD1 PHE A 184   -3.972 -21.232 60.488 1.00 14.41   C
ATOM  1174  CD2 PHE A 184   -5.258 -19.261 60.900 1.00 13.40   C
ATOM  1175  CE1 PHE A 184   -3.503 -20.683 59.305 1.00 13.56   C
ATOM  1176  CE2 PHE A 184   -4.798 -18.708 59.721 1.00 12.12   C
ATOM  1177  CZ  PHE A 184   -3.917 -19.419 58.921 1.00 12.15   C
ATOM  1178  N   GLU A 185   -5.247 -22.343 65.407 1.00 20.76   N
ATOM  1179  CA  GLU A 185   -5.910 -22.820 66.611 1.00 22.07   C
ATOM  1180  C   GLU A 185   -5.384 -22.066 67.853 1.00 22.23   C
ATOM  1181  O   GLU A 185   -6.151 -21.662 68.736 1.00 22.55   O
ATOM  1182  CB  GLU A 185   -5.688 -24.320 66.766 1.00 23.80   C
ATOM  1183  CG  GLU A 185   -6.165 -24.892 68.086 1.00 29.28   C
ATOM  1184  CD  GLU A 185   -5.965 -26.402 68.195 1.00 33.31   C
ATOM  1185  OE1 GLU A 185   -4.847 -26.895 67.926 1.00 34.86   O
ATOM  1186  OE2 GLU A 185   -6.928 -27.106 68.564 1.00 36.20   O
ATOM  1187  N   TYR A 186   -4.073 -21.881 67.912 1.00 20.95   N
ATOM  1188  CA  TYR A 186   -3.445 -21.172 69.011 1.00 20.20   C
ATOM  1189  C   TYR A 186   -4.031 -19.752 69.151 1.00 20.26   C
ATOM  1190  O   TYR A 186   -4.536 -19.361 70.220 1.00 19.28   O
ATOM  1191  CB  TYR A 186   -1.938 -21.085 68.764 1.00 21.30   C
ATOM  1192  CG  TYR A 186   -1.192 -20.365 69.858 1.00 23.68   C
ATOM  1193  CD1 TYR A 186   -0.987 -20.969 71.099 1.00 23.12   C
ATOM  1194  CD2 TYR A 186   -0.747 -19.051 69.683 1.00 22.52   C
ATOM  1195  CE1 TYR A 186   -0.362 -20.284 72.141 1.00 22.83   C
ATOM  1196  CE2 TYR A 186   -0.123 -18.354 70.721 1.00 22.50   C
ATOM  1197  CZ  TYR A 186    0.066 -18.982 71.950 1.00 23.41   C
ATOM  1198  OH  TYR A 186    0.700 -18.331 72.987 1.00 24.95   O
ATOM  1199  N   VAL A 187   -3.966 -18.988 68.065 1.00 18.99   N
ATOM  1200  CA  VAL A 187   -4.450 -17.617 68.033 1.00 19.66   C
ATOM  1201  C   VAL A 187   -5.924 -17.528 68.422 1.00 21.19   C
ATOM  1202  O   VAL A 187   -6.343 -16.627 69.156 1.00 20.67   O
ATOM  1203  CB  VAL A 187   -4.285 -16.989 66.606 1.00 20.33   C
ATOM  1204  CG1 VAL A 187   -4.710 -15.541 66.623 1.00 18.54   C
ATOM  1205  CG2 VAL A 187   -2.836 -17.079 66.154 1.00 17.62   C
ATOM  1206  N   TRP A 188   -6.704 -18.481 67.933 1.00 21.81   N
ATOM  1207  CA  TRP A 188   -8.117 -18.527 68.212 1.00 23.01   C
ATOM  1208  C   TRP A 188   -8.424 -18.740 69.675 1.00 26.07   C
ATOM  1209  O   TRP A 188   -9.231 -18.020 70.259 1.00 28.04   O
ATOM  1210  CB  TRP A 188   -8.783 -19.645 67.410 1.00 22.14   C
ATOM  1211  CG  TRP A 188  -10.266 -19.784 67.664 1.00 21.24   C
ATOM  1212  CD1 TRP A 188  -10.895 -20.759 68.396 1.00 19.15   C
ATOM  1213  CD2 TRP A 188  -11.301 -18.918 67.184 1.00 18.71   C
ATOM  1214  NE1 TRP A 188  -12.252 -20.555 68.387 1.00 17.30   N
ATOM  1215  CE2 TRP A 188  -12.531 -19.431 67.650 1.00 18.92   C
ATOM  1216  CE3 TRP A 188  -11.312 -17.756 66.399 1.00 18.39   C
ATOM  1217  CZ2 TRP A 188  -13.762 -18.823 67.362 1.00 19.31   C
ATOM  1218  CZ3 TRP A 188  -12.534 -17.149 66.109 1.00 17.90   C
ATOM  1219  CH2 TRP A 188  -13.740 -17.686 66.585 1.00 18.35   C
ATOM  1220  N   GLN A 189   -7.786 -19.731 70.282 1.00 28.68   N
ATOM  1221  CA  GLN A 189   -8.053 -20.026 71.683 1.00 30.60   C
ATOM  1222  C   GLN A 189   -7.348 -19.117 72.679 1.00 31.17   C
ATOM  1223  O   GLN A 189   -7.698 -19.102 73.857 1.00 30.63   O
ATOM  1224  CB  GLN A 189   -7.685 -21.476 71.982 1.00 32.34   C
ATOM  1225  CG  GLN A 189   -8.116 -22.445 70.909 1.00 34.32   C
ATOM  1226  CD  GLN A 189   -7.782 -23.881 71.259 1.00 36.97   C
ATOM  1227  OE1 GLN A 189   -6.727 -24.168 71.838 1.00 35.41   O
ATOM  4412  C   PHE C 212   -1.472 -22.156 34.327 1.00 22.88   C
ATOM  4413  O   PHE C 212   -2.523 -21.580 34.656 1.00 21.60   O
ATOM  4414  CB  PHE C 212   -0.206 -21.883 32.206 1.00 22.27   C
ATOM  4415  CG  PHE C 212   -1.523 -22.032 31.524 1.00 23.88   C
ATOM  4416  CD1 PHE C 212   -2.297 -20.911 31.218 1.00 25.95   C
ATOM  4417  CD2 PHE C 212   -2.016 -23.297 31.219 1.00 23.87   C
ATOM  4418  CE1 PHE C 212   -3.563 -21.042 30.618 1.00 25.65   C
ATOM  4419  CE2 PHE C 212   -3.274 -23.452 30.622 1.00 26.02   C
ATOM  4420  CZ  PHE C 212   -4.053 -22.320 30.322 1.00 26.19   C
ATOM  4421  N   LEU C 213   -1.277 -23.452 34.529 1.00 23.16   N
ATOM  4422  CA  LEU C 213   -2.304 -24.281 35.156 1.00 23.22   C
ATOM  4423  C   LEU C 213   -2.692 -23.760 36.531 1.00 23.08   C
ATOM  4424  O   LEU C 213   -3.818 -23.973 36.977 1.00 24.55   O
ATOM  4425  CB  LEU C 213   -1.822 -25.732 35.265 1.00 21.66   C
ATOM  4426  CG  LEU C 213   -1.624 -26.447 33.922 1.00 21.56   C
ATOM  4427  CD1 LEU C 213   -0.816 -27.722 34.129 1.00 20.65   C
ATOM  4428  CD2 LEU C 213   -2.985 -26.735 33.282 1.00 20.02   C
ATOM  4429  N   TYR C 214   -1.774 -23.082 37.204 1.00 22.91   N
ATOM  4430  CA  TYR C 214   -2.060 -22.545 38.526 1.00 23.01   C
ATOM  4431  C   TYR C 214   -3.003 -21.347 38.461 1.00 22.49   C
ATOM  4432  O   TYR C 214   -4.044 -21.329 39.109 1.00 21.95   O
ATOM  4433  CB  TYR C 214   -0.756 -22.109 39.216 1.00 25.82   C
ATOM  4434  CG  TYR C 214   -0.965 -21.478 40.576 1.00 28.16   C
ATOM  4435  CD1 TYR C 214   -1.264 -22.260 41.687 1.00 27.93   C
ATOM  4436  CD2 TYR C 214   -0.933 -20.089 40.735 1.00 28.36   C
ATOM  4437  CE1 TYR C 214   -1.533 -21.681 42.924 1.00 28.57   C
ATOM  4438  CE2 TYR C 214   -1.200 -19.498 41.967 1.00 27.59   C
ATOM  4439  CZ  TYR C 214   -1.498 -20.294 43.051 1.00 29.43   C
ATOM  4440  OH  TYR C 214   -1.757 -19.688 44.262 1.00 29.20   O
ATOM  4441  N   TYR C 215   -2.644 -20.342 37.674 1.00 22.26   N
ATOM  4442  CA  TYR C 215   -3.477 -19.163 37.569 1.00 21.51   C
ATOM  4443  C   TYR C 215   -4.759 -19.392 36.775 1.00 20.34   C
ATOM  4444  O   TYR C 215   -5.765 -18.699 36.980 1.00 19.32   O
ATOM  4445  CB  TYR C 215   -2.661 -18.009 36.982 1.00 22.05   C
ATOM  4446  CG  TYR C 215   -1.606 -17.504 37.937 1.00 22.14   C
ATOM  4447  CD1 TYR C 215   -0.264 -17.834 37.778 1.00 21.52   C
ATOM  4448  CD2 TYR C 215   -1.963 -16.712 39.033 1.00 23.10   C
ATOM  4449  CE1 TYR C 215    0.703 -17.391 38.686 1.00 22.55   C
ATOM  4450  CE2 TYR C 215   -1.012 -16.262 39.947 1.00 21.77   C
ATOM  4451  CZ  TYR C 215    0.312 -16.602 39.769 1.00 23.34   C
ATOM  4452  OH  TYR C 215    1.250 -16.131 40.674 1.00 25.13   O
ATOM  4453  N   GLU C 216   -4.736 -20.356 35.874 1.00 20.03   N
ATOM  4454  CA  GLU C 216   -5.948 -20.644 35.113 1.00 20.61   C
ATOM  4455  C   GLU C 216   -6.993 -21.090 36.112 1.00 20.91   C
ATOM  4456  O   GLU C 216   -8.114 -20.613 36.074 1.00 22.02   O
ATOM  4457  CB  GLU C 216   -5.710 -21.745 34.072 1.00 19.47   C
ATOM  4458  CG  GLU C 216   -6.983 -22.470 33.633 1.00 21.25   C
ATOM  4459  CD  GLU C 216   -6.796 -23.331 32.378 1.00 21.33   C
ATOM  4460  OE1 GLU C 216   -6.046 -24.329 32.400 1.00 22.03   O
ATOM  4461  OE2 GLU C 216   -7.418 -22.991 31.352 1.00 21.88   O
ATOM  4462  N   GLU C 217   -6.611 -21.992 37.019 1.00 22.58   N
ATOM  4463  CA  GLU C 217   -7.524 -22.517 38.044 1.00 23.96   C
ATOM  4464  C   GLU C 217   -7.980 -21.420 39.004 1.00 23.79   C
ATOM  4465  O   GLU C 217   -9.120 -21.398 39.469 1.00 22.58   O
ATOM  4466  CB  GLU C 217   -6.834 -23.609 38.846 1.00 25.51   C
ATOM  4467  CG  GLU C 217   -7.773 -24.439 39.695 1.00 32.35   C
ATOM  4468  CD  GLU C 217   -7.041 -25.287 40.708 1.00 33.93   C
ATOM  4469  OE1 GLU C 217   -6.820 -24.783 41.831 1.00 35.47   O
ATOM  4470  OE2 GLU C 217   -6.683 -26.442 40.372 1.00 35.88   O
ATOM  4471  N   LYS C 218   -7.058 -20.518 39.309 1.00 23.75   N
ATOM  4472  CA  LYS C 218   -7.353 -19.436 40.213 1.00 23.49   C
ATOM  4473  C   LYS C 218   -8.313 -18.436 39.598 1.00 23.15   C
ATOM  4474  O   LYS C 218   -9.324 -18.096 40.204 1.00 22.80   O
ATOM  4475  CB  LYS C 218   -6.063 -18.726 40.620 1.00 24.12   C
ATOM  4476  CG  LYS C 218   -5.144 -19.583 41.468 1.00 23.76   C
ATOM  4477  CD  LYS C 218   -5.860 -20.125 42.704 1.00 24.03   C
ATOM  4478  CE  LYS C 218   -5.004 -21.138 43.469 1.00 23.40   C
ATOM  4479  NZ  LYS C 218   -5.767 -21.754 44.595 1.00 22.56   N
ATOM  4480  N   LEU C 219   -7.995 -17.974 38.393 1.00 22.76   N
ATOM  4481  CA  LEU C 219   -8.826 -17.001 37.698 1.00 21.64   C
ATOM  4482  C   LEU C 219  -10.241 -17.516 37.559 1.00 22.42   C
ATOM  4483  O   LEU C 219  -11.211 -16.773 37.722 1.00 21.66   O
ATOM  4484  CB  LEU C 219   -8.257 -16.719 36.308 1.00 21.22   C
ATOM  4485  CG  LEU C 219   -8.999 -15.693 35.459 1.00 18.52   C
ATOM  4486  CD1 LEU C 219   -8.987 -14.347 36.167 1.00 16.33   C
ATOM  4487  CD2 LEU C 219   -8.334 -15.608 34.091 1.00 19.99   C
ATOM  4488  N   ALA C 220  -10.361 -18.798 37.258 1.00 23.29   N
ATOM  4489  CA  ALA C 220  -11.662 -19.420 37.090 1.00 25.13   C
ATOM  4490  C   ALA C 220  -12.463 -19.380 38.389 1.00 27.54   C
ATOM  4491  O   ALA C 220  -13.612 -18.930 38.420 1.00 28.01   O
ATOM  4492  CB  ALA C 220  -11.479 -20.843 36.634 1.00 22.89   C
ATOM  4493  N   ASP C 221  -11.849 -19.841 39.463 1.00 30.55   N
ATOM  4494  CA  ASP C 221  -12.508 -19.864 40.749 1.00 34.75   C
ATOM  4495  C   ASP C 221  -13.152 -18.534 41.070 1.00 35.74   C
ATOM  4496  O   ASP C 221  -14.329 -18.459 41.429 1.00 36.58   O
ATOM  4497  CB  ASP C 221  -11.494 -20.209 41.826 1.00 37.95   C
```

FIG. 6 (con't)

```
ATOM   1228  NE2 GLN A 189    -8.673 -24.798 70.895  1.00 36.12     N
ATOM   1229  N   ASN A 190    -6.371 -18.349 72.203  1.00 31.77     N
ATOM   1230  CA  ASN A 190    -5.614 -17.463 73.090  1.00 31.59     C
ATOM   1231  C   ASN A 190    -5.810 -15.973 72.877  1.00 29.99     C
ATOM   1232  O   ASN A 190    -5.622 -15.192 73.801  1.00 28.93     O
ATOM   1233  CB  ASN A 190    -4.129 -17.800 72.979  1.00 34.39     C
ATOM   1234  CG  ASN A 190    -3.774 -19.108 73.648  1.00 36.68     C
ATOM   1235  OD1 ASN A 190    -3.706 -19.184 74.871  1.00 38.40     O
ATOM   1236  ND2 ASN A 190    -3.552 -20.150 72.847  1.00 38.16     N
ATOM   1237  N   PHE A 191    -6.187 -15.577 71.666  1.00 29.38     N
ATOM   1238  CA  PHE A 191    -6.378 -14.162 71.374  1.00 28.28     C
ATOM   1239  C   PHE A 191    -7.856 -13.812 71.218  1.00 28.17     C
ATOM   1240  O   PHE A 191    -8.272 -12.680 71.455  1.00 27.98     O
ATOM   1241  CB  PHE A 191    -5.605 -13.798 70.107  1.00 27.26     C
ATOM   1242  CG  PHE A 191    -4.127 -13.640 70.325  1.00 28.00     C
ATOM   1243  CD1 PHE A 191    -3.599 -12.420 70.731  1.00 26.92     C
ATOM   1244  CD2 PHE A 191    -3.255 -14.718 70.140  1.00 28.21     C
ATOM   1245  CE1 PHE A 191    -2.233 -12.266 70.949  1.00 28.38     C
ATOM   1246  CE2 PHE A 191    -1.881 -14.573 70.360  1.00 27.03     C
ATOM   1247  CZ  PHE A 191    -1.370 -13.346 70.763  1.00 27.77     C
ATOM   1248  N   VAL A 192    -8.649 -14.793 70.820  1.00 28.18     N
ATOM   1249  CA  VAL A 192   -10.059 -14.559 70.639  1.00 30.52     C
ATOM   1250  C   VAL A 192   -10.803 -14.871 71.925  1.00 32.74     C
ATOM   1251  O   VAL A 192   -10.789 -16.007 72.393  1.00 31.06     O
ATOM   1252  CB  VAL A 192   -10.642 -15.431 69.525  1.00 29.42     C
ATOM   1253  CG1 VAL A 192   -12.146 -15.227 69.425  1.00 27.45     C
ATOM   1254  CG2 VAL A 192    -9.956 -15.105 68.209  1.00 27.82     C
ATOM   1255  N   GLU A 193   -11.448 -13.849 72.485  1.00 34.96     N
ATOM   1256  CA  GLU A 193   -12.209 -13.989 73.714  1.00 38.93     C
ATOM   1257  C   GLU A 193   -13.417 -14.905 73.563  1.00 41.77     C
ATOM   1258  O   GLU A 193   -14.224 -14.741 72.647  1.00 41.55     O
ATOM   1259  CB  GLU A 193   -12.696 -12.622 74.196  1.00 39.47     C
ATOM   1260  CG  GLU A 193   -13.705 -12.706 75.339  1.00 41.69     C
ATOM   1261  CD  GLU A 193   -14.272 -11.357 75.780  1.00 42.68     C
ATOM   1262  OE1 GLU A 193   -13.550 -10.590 76.451  1.00 43.65     O
ATOM   1263  OE2 GLU A 193   -15.440 -11.059 75.452  1.00 42.03     O
ATOM   1264  N   GLN A 194   -13.562 -15.837 74.499  1.00 46.22     N
ATOM   1265  CA  GLN A 194   -14.673 -16.783 74.522  1.00 50.57     C
ATOM   1266  C   GLN A 194   -15.498 -16.435 75.763  1.00 53.36     C
ATOM   1267  O   GLN A 194   -15.106 -15.571 76.546  1.00 54.46     O
ATOM   1268  CB  GLN A 194   -14.140 -18.208 74.660  1.00 51.86     C
ATOM   1269  CG  GLN A 194   -12.820 -18.487 73.926  1.00 53.59     C
ATOM   1270  CD  GLN A 194   -12.985 -18.653 72.420  1.00 54.54     C
ATOM   1271  OE1 GLN A 194   -13.627 -19.595 71.955  1.00 54.99     O
ATOM   1272  NE2 GLN A 194   -12.399 -17.738 71.651  1.00 55.33     N
ATOM   1273  N   GLU A 195   -16.617 -17.121 75.968  1.00 56.13     N
ATOM   1274  CA  GLU A 195   -17.447 -16.851 77.141  1.00 59.03     C
ATOM   1275  C   GLU A 195   -17.857 -18.134 77.879  1.00 59.59     C
ATOM   1276  O   GLU A 195   -17.995 -18.142 79.107  1.00 59.77     O
ATOM   1277  CB  GLU A 195   -18.696 -16.077 76.716  1.00 60.67     C
ATOM   1278  CG  GLU A 195   -18.415 -14.833 75.884  1.00 63.08     C
ATOM   1279  CD  GLU A 195   -19.430 -14.654 74.763  1.00 64.67     C
ATOM   1280  OE1 GLU A 195   -20.637 -14.507 75.054  1.00 66.01     O
ATOM   1281  OE2 GLU A 195   -19.015 -14.663 73.586  1.00 65.30     O
ATOM   1282  N   GLU A 196   -18.042 -19.213 77.121  1.00 59.97     N
ATOM   1283  CA  GLU A 196   -18.453 -20.499 77.692  1.00 59.86     C
ATOM   1284  C   GLU A 196   -17.401 -21.032 78.668  1.00 59.57     C
ATOM   1285  O   GLU A 196   -17.669 -21.936 79.464  1.00 58.23     O
ATOM   1286  CB  GLU A 196   -18.716 -21.526 76.555  1.00 58.96     C
ATOM   1287  N   ALA A 201   -14.693 -25.334 70.791  1.00 41.42     N
ATOM   1288  CA  ALA A 201   -13.676 -26.193 70.198  1.00 41.96     C
ATOM   1289  C   ALA A 201   -13.301 -25.743 68.780  1.00 42.33     C
ATOM   1290  O   ALA A 201   -14.155 -25.673 67.893  1.00 42.50     O
ATOM   1291  CB  ALA A 201   -14.169 -27.643 70.181  1.00 42.56     C
ATOM   1292  N   PHE A 202   -12.019 -25.436 68.575  1.00 41.90     N
ATOM   1293  CA  PHE A 202   -11.517 -24.990 67.275  1.00 40.32     C
ATOM   1294  C   PHE A 202   -11.889 -25.978 66.181  1.00 40.67     C
ATOM   1295  O   PHE A 202   -12.007 -27.178 66.432  1.00 41.39     O
ATOM   1296  CB  PHE A 202    -9.991 -24.846 67.314  1.00 37.36     C
ATOM   1297  CG  PHE A 202    -9.394 -24.381 66.015  1.00 34.24     C
ATOM   1298  CD1 PHE A 202    -9.677 -23.114 65.516  1.00 32.73     C
ATOM   1299  CD2 PHE A 202    -8.554 -25.206 65.277  1.00 33.86     C
ATOM   1300  CE1 PHE A 202    -9.137 -22.681 64.301  1.00 29.90     C
ATOM   1301  CE2 PHE A 202    -8.008 -24.780 64.062  1.00 30.90     C
ATOM   1302  CZ  PHE A 202    -8.305 -23.515 63.576  1.00 29.55     C
ATOM   1303  N   GLN A 203   -12.067 -25.475 64.967  1.00 40.74     N
ATOM   1304  CA  GLN A 203   -12.414 -26.339 63.848  1.00 41.28     C
ATOM   1305  C   GLN A 203   -11.728 -25.880 62.564  1.00 39.69     C
ATOM   1306  O   GLN A 203   -11.906 -24.746 62.128  1.00 38.68     O
ATOM   1307  CB  GLN A 203   -13.930 -26.343 63.656  1.00 44.69     C
ATOM   1308  CG  GLN A 203   -14.706 -26.687 64.924  1.00 50.11     C
ATOM   1309  CD  GLN A 203   -16.200 -26.415 64.796  1.00 53.41     C
ATOM   1310  OE1 GLN A 203   -16.634 -25.259 64.730  1.00 55.20     O
ATOM   1311  NE2 GLN A 203   -16.994 -27.481 64.756  1.00 54.06     N
ATOM   1312  N   PRO A 204   -10.928 -26.762 61.946  1.00 38.73     N
ATOM   1313  CA  PRO A 204   -10.236 -26.399 60.709  1.00 37.82     C
ATOM   4498  CG  ASP C 221   -11.142 -21.682 41.848  1.00 41.53     C
ATOM   4499  OD1 ASP C 221   -11.106 -22.338 40.773  1.00 44.09     O
ATOM   4500  OD2 ASP C 221   -10.887 -22.185 42.955  1.00 43.35     O
ATOM   4501  N   ILE C 222   -12.379 -17.473 40.931  1.00 36.75     N
ATOM   4502  CA  ILE C 222   -12.893 -16.157 41.235  1.00 38.28     C
ATOM   4503  C   ILE C 222   -13.929 -15.678 40.236  1.00 39.07     C
ATOM   4504  O   ILE C 222   -15.016 -15.261 40.619  1.00 38.44     O
ATOM   4505  CB  ILE C 222   -11.744 -15.140 41.295  1.00 38.66     C
ATOM   4506  CG1 ILE C 222   -12.292 -13.727 41.063  1.00 39.31     C
ATOM   4507  CG2 ILE C 222   -10.685 -15.517 40.312  1.00 37.09     C
ATOM   4508  CD1 ILE C 222   -11.269 -12.732 40.566  1.00 41.39     C
ATOM   4509  N   LEU C 223   -13.582 -15.759 38.958  1.00 40.08     N
ATOM   4510  CA  LEU C 223   -14.455 -15.285 37.889  1.00 41.41     C
ATOM   4511  C   LEU C 223   -15.871 -15.834 37.925  1.00 43.61     C
ATOM   4512  O   LEU C 223   -16.769 -15.252 38.543  1.00 45.14     O
ATOM   4513  CB  LEU C 223   -13.801 -15.582 36.541  1.00 39.04     C
ATOM   4514  CG  LEU C 223   -13.488 -14.384 35.651  1.00 37.12     C
ATOM   4515  CD1 LEU C 223   -12.974 -13.215 36.478  1.00 35.29     C
ATOM   4516  CD2 LEU C 223   -12.478 -14.805 34.601  1.00 37.82     C
ATOM   4517  N   LYS C 224   -16.084 -16.943 37.240  1.00 46.22     N
ATOM   4518  CA  LYS C 224   -17.393 -17.556 37.212  1.00 48.21     C
ATOM   4519  C   LYS C 224   -17.779 -17.998 38.609  1.00 49.23     C
ATOM   4520  O   LYS C 224   -18.700 -17.369 39.180  1.00 49.97     O
ATOM   4521  CB  LYS C 224   -17.383 -18.766 36.289  1.00 50.23     C
ATOM   4522  CG  LYS C 224   -17.248 -18.424 34.811  1.00 52.06     C
ATOM   4523  CD  LYS C 224   -17.076 -19.682 33.960  1.00 53.47     C
ATOM   4524  CE  LYS C 224   -18.220 -20.671 34.160  1.00 54.25     C
ATOM   4525  NZ  LYS C 224   -18.008 -21.934 33.394  1.00 55.49     N
ATOM   4526  OXT LYS C 224   -17.151 -18.960 39.108  1.00 48.43     O
TER    4527      LYS C 224
ATOM   4528  N   MET D 40    -1.158 -11.060  9.204  1.00 41.85     N
ATOM   4529  CA  MET D 40    -2.471 -10.432  9.541  1.00 41.90     C
ATOM   4530  C   MET D 40    -3.432 -10.414  8.347  1.00 41.11     C
ATOM   4531  O   MET D 40    -4.624 -10.628  8.517  1.00 42.25     O
ATOM   4532  CB  MET D 40    -2.249  -9.015 10.040  1.00 42.13     C
ATOM   4533  CG  MET D 40    -1.478  -8.194  9.050  1.00 43.74     C
ATOM   4534  SD  MET D 40    -0.905  -6.690  9.798  1.00 46.02     S
ATOM   4535  CE  MET D 40     0.804  -7.077 10.150  1.00 44.02     C
ATOM   4536  N   ILE D 41    -2.924 -10.145  7.152  1.00 40.04     N
ATOM   4537  CA  ILE D 41    -3.770 -10.136  5.959  1.00 39.39     C
ATOM   4538  C   ILE D 41    -4.081 -11.578  5.542  1.00 39.71     C
ATOM   4539  O   ILE D 41    -3.183 -12.420  5.490  1.00 39.40     O
ATOM   4540  CB  ILE D 41    -3.067  -9.442  4.786  1.00 38.28     C
ATOM   4541  CG1 ILE D 41    -2.629  -8.046  5.194  1.00 38.20     C
ATOM   4542  CG2 ILE D 41    -4.008  -9.325  3.615  1.00 38.24     C
ATOM   4543  CD1 ILE D 41    -1.807  -7.360  4.135  1.00 37.41     C
ATOM   4544  N   VAL D 42    -5.343 -11.858  5.237  1.00 40.03     N
ATOM   4545  CA  VAL D 42    -5.748 -13.200  4.838  1.00 41.05     C
ATOM   4546  C   VAL D 42    -6.405 -13.214  3.464  1.00 42.31     C
ATOM   4547  O   VAL D 42    -7.413 -12.543  3.239  1.00 41.86     O
ATOM   4548  CB  VAL D 42    -6.749 -13.794  5.844  1.00 41.51     C
ATOM   4549  CG1 VAL D 42    -7.076 -15.220  5.451  1.00 40.75     C
ATOM   4550  CG2 VAL D 42    -6.176 -13.724  7.255  1.00 40.15     C
ATOM   4551  N   THR D 43    -5.823 -13.987  2.555  1.00 44.18     N
ATOM   4552  CA  THR D 43    -6.335 -14.112  1.195  1.00 46.53     C
ATOM   4553  C   THR D 43    -6.199 -15.544  0.710  1.00 46.87     C
ATOM   4554  O   THR D 43    -5.350 -16.300  1.187  1.00 46.38     O
ATOM   4555  CB  THR D 43    -5.572 -13.193  0.200  1.00 47.90     C
ATOM   4556  OG1 THR D 43    -4.194 -13.101  0.586  1.00 47.53     O
ATOM   4557  CG2 THR D 43    -6.217 -11.801  0.145  1.00 49.09     C
ATOM   4558  N   GLY D 44    -7.047 -15.911 -0.240  1.00 47.36     N
ATOM   4559  CA  GLY D 44    -7.007 -17.255 -0.774  1.00 48.64     C
ATOM   4560  C   GLY D 44    -5.975 -17.377 -1.872  1.00 49.54     C
ATOM   4561  O   GLY D 44    -5.839 -18.435 -2.487  1.00 50.03     O
ATOM   4562  N   GLU D 45    -5.244 -16.294 -2.116  1.00 49.70     N
ATOM   4563  CA  GLU D 45    -4.223 -16.284 -3.157  1.00 49.82     C
ATOM   4564  C   GLU D 45    -2.904 -16.831 -2.618  1.00 49.81     C
ATOM   4565  O   GLU D 45    -2.353 -16.317 -1.642  1.00 49.05     O
ATOM   4566  CB  GLU D 45    -4.021 -14.867 -3.685  1.00 49.31     C
ATOM   4567  CG  GLU D 45    -3.376 -14.843 -5.042  1.00 50.05     C
ATOM   4568  CD  GLU D 45    -4.278 -15.418 -6.106  1.00 51.84     C
ATOM   4569  OE1 GLU D 45    -5.245 -14.729 -6.508  1.00 52.27     O
ATOM   4570  OE2 GLU D 45    -4.021 -16.564 -6.534  1.00 52.80     O
ATOM   4571  N   ARG D 46    -2.406 -17.875 -3.265  1.00 49.86     N
ATOM   4572  CA  ARG D 46    -1.167 -18.507 -2.839  1.00 50.90     C
ATOM   4573  C   ARG D 46     0.047 -17.911 -3.558  1.00 49.26     C
ATOM   4574  O   ARG D 46     1.177 -18.043 -3.093  1.00 48.86     O
ATOM   4575  CB  ARG D 46    -1.249 -20.025 -3.099  1.00 53.69     C
ATOM   4576  CG  ARG D 46    -0.817 -20.920 -1.920  1.00 57.26     C
ATOM   4577  CD  ARG D 46     0.633 -20.651 -1.482  1.00 61.59     C
ATOM   4578  NE  ARG D 46     1.060 -21.488 -0.353  1.00 64.24     N
ATOM   4579  CZ  ARG D 46     2.247 -21.403  0.249  1.00 65.24     C
ATOM   4580  NH1 ARG D 46     3.148 -20.515 -0.157  1.00 65.04     N
ATOM   4581  NH2 ARG D 46     2.531 -22.209  1.265  1.00 65.87     N
ATOM   4582  N   LEU D 47    -0.194 -17.247 -4.683  1.00 47.32     N
ATOM   4583  CA  LEU D 47     0.897 -16.644 -5.440  1.00 45.64     C
```

FIG. 6 (con't)

```
ATOM 1314 C   PRO A 204   -11.225 -26.151 59.575 1.00 36.81   C
ATOM 1315 O   PRO A 204   -12.416 -26.410 59.715 1.00 36.26   O
ATOM 1316 CB  PRO A 204    -9.332 -27.603 60.454 1.00 38.41   C
ATOM 1317 CG  PRO A 204   -10.123 -28.733 61.024 1.00 37.88   C
ATOM 1318 CD  PRO A 204   -10.604 -28.152 62.326 1.00 38.35   C
ATOM 1319 N   TRP A 205   -10.733 -25.647 58.452 1.00 35.50   N
ATOM 1320 CA  TRP A 205   -11.616 -25.370 57.336 1.00 34.59   C
ATOM 1321 C   TRP A 205   -11.099 -25.925 56.024 1.00 36.17   C
ATOM 1322 O   TRP A 205   -10.033 -26.530 55.973 1.00 34.54   O
ATOM 1323 CB  TRP A 205   -11.846 -23.857 57.209 1.00 30.52   C
ATOM 1324 CG  TRP A 205   -10.581 -23.051 57.196 1.00 25.07   C
ATOM 1325 CD1 TRP A 205    -9.735 -22.859 56.140 1.00 22.63   C
ATOM 1326 CD2 TRP A 205    -9.998 -22.360 58.309 1.00 22.48   C
ATOM 1327 NE1 TRP A 205    -8.661 -22.098 56.527 1.00 21.07   N
ATOM 1328 CE2 TRP A 205    -8.793 -21.777 57.855 1.00 21.49   C
ATOM 1329 CE3 TRP A 205   -10.373 -22.182 59.651 1.00 19.62   C
ATOM 1330 CZ2 TRP A 205    -7.956 -21.021 58.698 1.00 20.40   C
ATOM 1331 CZ3 TRP A 205    -9.537 -21.428 60.488 1.00 20.31   C
ATOM 1332 CH2 TRP A 205    -8.343 -20.862 60.006 1.00 17.57   C
ATOM 1333 N   GLU A 206   -11.897 -25.696 54.979 1.00 39.70   N
ATOM 1334 CA  GLU A 206   -11.678 -26.130 53.607 1.00 42.71   C
ATOM 1335 C   GLU A 206   -10.214 -26.646 53.394 1.00 42.39   C
ATOM 1336 O   GLU A 206    -9.956 -27.843 53.509 1.00 43.48   O
ATOM 1337 CB  GLU A 206   -11.874 -24.977 52.615 1.00 46.46   C
ATOM 1338 CG  GLU A 206   -12.635 -23.748 53.145 1.00 50.39   C
ATOM 1339 CD  GLU A 206   -14.141 -23.849 53.000 1.00 53.17   C
ATOM 1340 OE1 GLU A 206   -14.807 -24.469 53.867 1.00 54.75   O
ATOM 1341 OE2 GLU A 206   -14.658 -23.303 51.999 1.00 55.04   O
ATOM 1342 N   ASP A 207    -9.312 -25.720 53.076 1.00 41.36   N
ATOM 1343 CA  ASP A 207    -7.912 -26.033 52.804 1.00 40.79   C
ATOM 1344 C   ASP A 207    -6.924 -25.334 53.757 1.00 38.08   C
ATOM 1345 O   ASP A 207    -6.011 -24.629 53.332 1.00 36.62   O
ATOM 1346 CB  ASP A 207    -7.593 -25.684 51.333 1.00 44.46   C
ATOM 1347 CG  ASP A 207    -8.330 -24.439 50.841 1.00 47.83   C
ATOM 1348 OD1 ASP A 207    -8.214 -23.379 51.499 1.00 49.50   O
ATOM 1349 OD2 ASP A 207    -9.017 -24.517 49.788 1.00 49.24   O
ATOM 1350 N   ILE A 208    -7.110 -25.542 55.054 1.00 34.07   N
ATOM 1351 CA  ILE A 208    -6.229 -24.926 56.016 1.00 31.01   C
ATOM 1352 C   ILE A 208    -4.824 -25.520 55.928 1.00 30.50   C
ATOM 1353 O   ILE A 208    -3.844 -24.819 56.148 1.00 29.03   O
ATOM 1354 CB  ILE A 208    -6.754 -25.105 57.431 1.00 29.12   C
ATOM 1355 CG1 ILE A 208    -5.871 -24.349 58.408 1.00 27.44   C
ATOM 1356 CG2 ILE A 208    -6.794 -26.577 57.777 1.00 28.10   C
ATOM 1357 CD1 ILE A 208    -6.366 -24.410 59.822 1.00 27.40   C
ATOM 1358 N   GLN A 209    -4.736 -26.805 55.582 1.00 31.26   N
ATOM 1359 CA  GLN A 209    -3.449 -27.497 55.477 1.00 31.70   C
ATOM 1360 C   GLN A 209    -2.759 -27.307 54.131 1.00 30.36   C
ATOM 1361 O   GLN A 209    -1.538 -27.201 54.078 1.00 31.41   O
ATOM 1362 CB  GLN A 209    -3.625 -28.994 55.753 1.00 33.07   C
ATOM 1363 CG  GLN A 209    -2.325 -29.796 55.835 1.00 35.17   C
ATOM 1364 CD  GLN A 209    -1.337 -29.226 56.840 1.00 37.16   C
ATOM 1365 OE1 GLN A 209    -1.644 -29.077 58.028 1.00 37.31   O
ATOM 1366 NE2 GLN A 209    -0.142 -28.908 56.369 1.00 37.65   N
ATOM 1367 N   GLU A 210    -3.529 -27.272 53.056 1.00 30.28   N
ATOM 1368 CA  GLU A 210    -2.945 -27.103 51.740 1.00 32.33   C
ATOM 1369 C   GLU A 210    -2.429 -25.687 51.528 1.00 31.79   C
ATOM 1370 O   GLU A 210    -1.398 -25.508 50.896 1.00 32.58   O
ATOM 1371 CB  GLU A 210    -3.946 -27.458 50.632 1.00 34.07   C
ATOM 1372 CG  GLU A 210    -5.334 -27.893 51.114 1.00 39.54   C
ATOM 1373 CD  GLU A 210    -5.314 -29.147 51.959 1.00 41.45   C
ATOM 1374 OE1 GLU A 210    -4.656 -30.118 51.514 1.00 44.53   O
ATOM 1375 OE2 GLU A 210    -5.952 -29.160 53.049 1.00 40.18   O
ATOM 1376 N   ASN A 211    -3.139 -24.685 52.049 1.00 31.96   N
ATOM 1377 CA  ASN A 211    -2.716 -23.287 51.908 1.00 31.08   C
ATOM 1378 C   ASN A 211    -1.359 -23.115 52.609 1.00 29.91   C
ATOM 1379 O   ASN A 211    -0.442 -22.466 52.110 1.00 27.63   O
ATOM 1380 CB  ASN A 211    -3.742 -22.314 52.524 1.00 33.88   C
ATOM 1381 CG  ASN A 211    -5.116 -22.368 51.831 1.00 38.73   C
ATOM 1382 OD1 ASN A 211    -5.264 -22.966 50.762 1.00 41.62   O
ATOM 1383 ND2 ASN A 211    -6.130 -21.737 52.443 1.00 38.00   N
ATOM 1384 N   PHE A 212    -1.256 -23.695 53.794 1.00 28.77   N
ATOM 1385 CA  PHE A 212    -0.027 -23.634 54.558 1.00 26.34   C
ATOM 1386 C   PHE A 212     1.144 -24.194 53.731 1.00 25.80   C
ATOM 1387 O   PHE A 212     2.110 -23.488 53.420 1.00 23.73   O
ATOM 1388 CB  PHE A 212    -0.206 -24.440 55.835 1.00 26.16   C
ATOM 1389 CG  PHE A 212     1.075 -24.843 56.489 1.00 25.80   C
ATOM 1390 CD1 PHE A 212     1.938 -23.883 56.998 1.00 26.05   C
ATOM 1391 CD2 PHE A 212     1.411 -26.184 56.612 1.00 25.22   C
ATOM 1392 CE1 PHE A 212     3.116 -24.248 57.626 1.00 25.73   C
ATOM 1393 CE2 PHE A 212     2.588 -26.559 57.232 1.00 26.75   C
ATOM 1394 CZ  PHE A 212     3.444 -25.586 57.743 1.00 27.21   C
ATOM 1395 N   LEU A 213     1.045 -25.469 53.372 1.00 23.96   N
ATOM 1396 CA  LEU A 213     2.115 -26.102 52.626 1.00 22.98   C
ATOM 1397 C   LEU A 213     2.486 -25.338 51.364 1.00 21.49   C
ATOM 1398 O   LEU A 213     3.659 -25.226 51.032 1.00 22.36   O
ATOM 1399 CB  LEU A 213     1.753 -27.550 52.282 1.00 23.27   C

ATOM 4584 C   LEU D 47    0.923 -15.142 -5.224 1.00 44.04   C
ATOM 4585 O   LEU D 47   -0.084 -14.461 -5.426 1.00 43.88   O
ATOM 4586 CB  LEU D 47    0.740 -16.937 -6.934 1.00 45.42   C
ATOM 4587 CG  LEU D 47    1.945 -16.607 -7.828 1.00 45.44   C
ATOM 4588 CD1 LEU D 47    3.085 -17.594 -7.576 1.00 43.74   C
ATOM 4589 CD2 LEU D 47    1.512 -16.677 -9.284 1.00 44.99   C
ATOM 4590 N   PRO D 48    2.082 -14.606 -4.821 1.00 42.50   N
ATOM 4591 CA  PRO D 48    2.220 -13.169 -4.577 1.00 41.08   C
ATOM 4592 C   PRO D 48    2.022 -12.342 -5.829 1.00 39.45   C
ATOM 4593 O   PRO D 48    1.615 -11.185 -5.761 1.00 39.44   O
ATOM 4594 CB  PRO D 48    3.634 -13.052 -4.015 1.00 41.79   C
ATOM 4595 CG  PRO D 48    4.358 -14.156 -4.696 1.00 42.67   C
ATOM 4596 CD  PRO D 48    3.366 -15.295 -4.598 1.00 42.50   C
ATOM 4597 N   ALA D 49    2.303 -12.946 -6.974 1.00 38.02   N
ATOM 4598 CA  ALA D 49    2.157 -12.254 -8.236 1.00 37.17   C
ATOM 4599 C   ALA D 49    0.702 -11.863 -8.448 1.00 37.31   C
ATOM 4600 O   ALA D 49    0.416 -10.831 -9.060 1.00 38.17   O
ATOM 4601 CB  ALA D 49    2.637 -13.137 -9.363 1.00 36.82   C
ATOM 4602 N   ASN D 50   -0.215 -12.681 -7.932 1.00 30.77   N
ATOM 4603 CA  ASN D 50   -1.648 -12.410 -8.075 1.00 36.41   C
ATOM 4604 C   ASN D 50   -2.156 -11.494 -6.974 1.00 35.09   C
ATOM 4605 O   ASN D 50   -2.989 -10.619 -7.218 1.00 34.80   O
ATOM 4606 CB  ASN D 50   -2.445 -13.717 -8.060 1.00 37.40   C
ATOM 4607 CG  ASN D 50   -2.058 -14.641 -9.193 1.00 38.55   C
ATOM 4608 OD1 ASN D 50   -2.184 -14.294 -10.372 1.00 38.31   O
ATOM 4609 ND2 ASN D 50   -1.580 -15.822 -8.843 1.00 38.61   N
ATOM 4610 N   PHE D 51   -1.641 -11.704 -5.768 1.00 32.53   N
ATOM 4611 CA  PHE D 51   -2.013 -10.896 -4.627 1.00 31.18   C
ATOM 4612 C   PHE D 51   -1.686  -9.423 -4.873 1.00 31.15   C
ATOM 4613 O   PHE D 51   -2.491  -8.547 -4.557 1.00 32.17   O
ATOM 4614 CB  PHE D 51   -1.266 -11.375 -3.382 1.00 29.20   C
ATOM 4615 CG  PHE D 51   -1.461 -10.492 -2.186 1.00 27.55   C
ATOM 4616 CD1 PHE D 51   -2.683 -10.468 -1.517 1.00 26.47   C
ATOM 4617 CD2 PHE D 51   -0.444  -9.649 -1.753 1.00 27.69   C
ATOM 4618 CE1 PHE D 51   -2.892  -9.606 -0.430 1.00 26.43   C
ATOM 4619 CE2 PHE D 51   -0.643  -8.782 -0.665 1.00 29.02   C
ATOM 4620 CZ  PHE D 51   -1.874  -8.760 -0.002 1.00 26.84   C
ATOM 4621 N   PHE D 52    0.512  -9.151 -5.443 1.00 30.71   N
ATOM 4622 CA  PHE D 52   -0.089  -7.776 -5.718 1.00 31.07   C
ATOM 4623 C   PHE D 52   -0.655  -7.216 -7.012 1.00 33.44   C
ATOM 4624 O   PHE D 52   -0.460   6.039 -7.339 1.00 34.89   O
ATOM 4625 CB  PHE D 52    1.443  -7.663 -5.755 1.00 27.35   C
ATOM 4626 CG  PHE D 52    2.091  -7.763 -4.402 1.00 24.31   C
ATOM 4627 CD1 PHE D 52    2.780  -8.912 -4.035 1.00 23.47   C
ATOM 4628 CD2 PHE D 52    1.979  -6.726 -3.478 1.00 21.34   C
ATOM 4629 CE1 PHE D 52    3.346  -9.035 -2.780 1.00 21.37   C
ATOM 4630 CE2 PHE D 52    2.545  -6.845 -2.216 1.00 20.04   C
ATOM 4631 CZ  PHE D 52    3.231  -8.005 -1.869 1.00 19.72   C
ATOM 4632 N   LYS D 53   -1.355  -8.065 -7.757 1.00 35.32   N
ATOM 4633 CA  LYS D 53   -1.964  -7.656 -9.019 1.00 35.97   C
ATOM 4634 C   LYS D 53   -3.425  -7.275 -8.793 1.00 36.01   C
ATOM 4635 O   LYS D 53   -3.914  -6.327 -9.401 1.00 37.49   O
ATOM 4636 CB  LYS D 53   -1.863  -8.792 -10.041 1.00 37.42   C
ATOM 4637 CG  LYS D 53    2.377  -8.462 -11.444 1.00 38.08   C
ATOM 4638 CD  LYS D 53   -1.513  -7.406 -12.110 1.00 39.59   C
ATOM 4639 CE  LYS D 53   -1.917  -7.179 -13.561 1.00 40.50   C
ATOM 4640 NZ  LYS D 53   -1.079  -6.143 -14.245 1.00 40.83   N
ATOM 4641 N   PHE D 54   -4.113  -7.999 -7.912 1.00 35.26   N
ATOM 4642 CA  PHE D 54   -5.533  -7.742 -7.657 1.00 34.88   C
ATOM 4643 C   PHE D 54   -5.815  -7.167 -6.281 1.00 34.51   C
ATOM 4644 O   PHE D 54   -6.201  -6.000 -6.137 1.00 35.62   O
ATOM 4645 CB  PHE D 54    6.343  -9.035 -7.824 1.00 35.95   C
ATOM 4646 CG  PHE D 54   -6.129  -9.732 -9.147 1.00 37.59   C
ATOM 4647 CD1 PHE D 54   -5.551 -11.000 -9.189 1.00 38.55   C
ATOM 4648 CD2 PHE D 54   -6.485  -9.118 -10.345 1.00 38.63   C
ATOM 4649 CE1 PHE D 54   -5.324 -11.648 -10.410 1.00 39.87   C
ATOM 4650 CE2 PHE D 54   -6.265  -9.756 -11.577 1.00 40.29   C
ATOM 4651 CZ  PHE D 54   -5.680 -11.024 -11.605 1.00 40.95   C
ATOM 4652 N   GLN D 55   -5.634  -7.994 -5.261 1.00 32.84   N
ATOM 4653 CA  GLN D 55   -5.888  -7.563 -3.899 1.00 32.41   C
ATOM 4654 C   GLN D 55   -5.160  -6.306 -3.488 1.00 31.42   C
ATOM 4655 O   GLN D 55   -5.777  -5.399 -2.929 1.00 33.08   O
ATOM 4656 CB  GLN D 55   -5.552  -8.672  2.910 1.00 33.65   C
ATOM 4657 CG  GLN D 55   -6.665  -9.684 -2.725 1.00 37.95   C
ATOM 4658 CD  GLN D 55   -6.724 -10.710 -3.844 1.00 40.53   C
ATOM 4659 OE1 GLN D 55   -7.733 -11.409 -4.008 1.00 42.71   O
ATOM 4660 NE2 GLN D 55   -5.645 -10.821 -4.610 1.00 41.19   N
ATOM 4661 N   PHE D 56   -3.857  -6.245 -3.756 1.00 29.46   N
ATOM 4662 CA  PHE D 56   -3.032  -5.090 -3.371 1.00 28.75   C
ATOM 4663 C   PHE D 56   -3.379  -3.815 -4.145 1.00 28.34   C
ATOM 4664 O   PHE D 56   -3.045  -2.707 -3.729 1.00 27.43   O
ATOM 4665 CB  PHE D 56   -1.540  -5.426 -3.564 1.00 26.53   C
ATOM 4666 CG  PHE D 56   -0.601  -4.521 -2.798 1.00 24.55   C
ATOM 4667 CD1 PHE D 56   -0.553  -4.558 -1.412 1.00 23.26   C
ATOM 4668 CD2 PHE D 56    0.236  -3.631 -3.477 1.00 23.77   C
ATOM 4669 CE1 PHE D 56    0.311   3.726 -0.706 1.00 23.44   C
```

*FIG. 6 (con't)*

```
ATOM  1400  CG  LEU A 213    1.717 -28.519  53.466  1.00 24.09   C
ATOM  1401  CD1 LEU A 213    1.033 -29.798  53.037  1.00 24.67   C
ATOM  1402  CD2 LEU A 213    3.116 -28.805  53.967  1.00 22.04   C
ATOM  1403  N   TYR A 214    1.498 -24.797  50.673  1.00 19.45   N
ATOM  1404  CA  TYR A 214    1.762 -24.053  49.467  1.00 18.74   C
ATOM  1405  C   TYR A 214    2.675 -22.850  49.715  1.00 19.90   C
ATOM  1406  O   TYR A 214    3.726 -22.704  49.078  1.00 21.76   O
ATOM  1407  CB  TYR A 214    0.472 -23.571  48.848  1.00 19.08   C
ATOM  1408  CG  TYR A 214    0.682 -22.727  47.621  1.00 19.97   C
ATOM  1409  CD1 TYR A 214    0.880 -23.302  46.374  1.00 19.30   C
ATOM  1410  CD2 TYR A 214    0.719 -21.337  47.717  1.00 22.30   C
ATOM  1411  CE1 TYR A 214    1.116 -22.505  45.232  1.00 21.38   C
ATOM  1412  CE2 TYR A 214    0.952 -20.536  46.597  1.00 23.24   C
ATOM  1413  CZ  TYR A 214    1.152 -21.114  45.359  1.00 22.72   C
ATOM  1414  OH  TYR A 214    1.396 -20.265  44.291  1.00 22.46   O
ATOM  1415  N   TYR A 215    2.277 -21.981  50.635  1.00 18.41   N
ATOM  1416  CA  TYR A 215    3.044 -20.788  50.942  1.00 18.24   C
ATOM  1417  C   TYR A 215    4.356 -21.048  51.674  1.00 18.83   C
ATOM  1418  O   TYR A 215    5.262 -20.204  51.671  1.00 18.60   O
ATOM  1419  CB  TYR A 215    2.198 -19.787  51.737  1.00 16.51   C
ATOM  1420  CG  TYR A 215    1.214 -19.016  50.885  1.00 17.10   C
ATOM  1421  CD1 TYR A 215   -0.135 -19.354  50.853  1.00 14.46   C
ATOM  1422  CD2 TYR A 215    1.644 -17.965  50.063  1.00 16.80   C
ATOM  1423  CE1 TYR A 215   -1.035 -18.679  50.029  1.00 16.00   C
ATOM  1424  CE2 TYR A 215    0.755 -17.279  49.232  1.00 16.39   C
ATOM  1425  CZ  TYR A 215   -0.579 -17.646  49.215  1.00 18.26   C
ATOM  1426  OH  TYR A 215   -1.447 -17.026  48.323  1.00 21.26   O
ATOM  1427  N   GLU A 216    4.469 -22.206  52.300  1.00 19.52   N
ATOM  1428  CA  GLU A 216    5.681 -22.541  53.003  1.00 20.54   C
ATOM  1429  C   GLU A 216    6.709 -22.785  51.931  1.00 22.53   C
ATOM  1430  O   GLU A 216    7.861 -22.372  52.059  1.00 24.00   O
ATOM  1431  CB  GLU A 216    5.499 -23.802  53.846  1.00 20.92   C
ATOM  1432  CG  GLU A 216    6.771 -24.259  54.531  1.00 24.55   C
ATOM  1433  CD  GLU A 216    6.586 -25.490  55.382  1.00 26.85   C
ATOM  1434  OE1 GLU A 216    6.191 -26.556  54.836  1.00 26.59   O
ATOM  1435  OE2 GLU A 216    6.842 -25.386  56.605  1.00 27.10   O
ATOM  1436  N   GLU A 217    6.286 -23.440  50.848  1.00 24.09   N
ATOM  1437  CA  GLU A 217    7.187 -23.755  49.728  1.00 25.51   C
ATOM  1438  C   GLU A 217    7.688 -22.500  49.042  1.00 24.63   C
ATOM  1439  O   GLU A 217    8.881 -22.340  48.816  1.00 22.91   O
ATOM  1440  CB  GLU A 217    6.473 -24.662  48.710  1.00 28.86   C
ATOM  1441  CG  GLU A 217    7.077 -24.635  47.290  1.00 33.24   C
ATOM  1442  CD  GLU A 217    6.045 -24.280  46.222  1.00 38.07   C
ATOM  1443  OE1 GLU A 217    5.161 -23.433  46.499  1.00 39.02   O
ATOM  1444  OE2 GLU A 217    6.114 -24.829  45.097  1.00 40.85   O
ATOM  1445  N   LYS A 218    6.750 -21.622  48.702  1.00 25.71   N
ATOM  1446  CA  LYS A 218    7.071 -20.362  48.044  1.00 26.11   C
ATOM  1447  C   LYS A 218    7.968 -19.475  48.904  1.00 24.92   C
ATOM  1448  O   LYS A 218    8.900 -18.864  48.393  1.00 24.92   O
ATOM  1449  CB  LYS A 218    5.786 -19.607  47.731  1.00 27.40   C
ATOM  1450  CG  LYS A 218    4.887 -20.318  46.753  1.00 29.84   C
ATOM  1451  CD  LYS A 218    5.530 -20.433  45.379  1.00 28.91   C
ATOM  1452  CE  LYS A 218    4.641 -21.240  44.443  1.00 30.13   C
ATOM  1453  NZ  LYS A 218    5.200 -21.333  43.070  1.00 30.40   N
ATOM  1454  N   LEU A 219    7.669 -19.387  50.199  1.00 23.72   N
ATOM  1455  CA  LEU A 219    8.467 -18.567  51.092  1.00 23.67   C
ATOM  1456  C   LEU A 219    9.863 -19.150  51.212  1.00 25.66   C
ATOM  1457  O   LEU A 219   10.830 -18.410  51.375  1.00 27.47   O
ATOM  1458  CB  LEU A 219    7.830 -18.475  52.484  1.00 22.58   C
ATOM  1459  CG  LEU A 219    8.601 -17.721  53.582  1.00 20.97   C
ATOM  1460  CD1 LEU A 219    8.705 -16.262  53.212  1.00 20.14   C
ATOM  1461  CD2 LEU A 219    7.891 -17.853  54.920  1.00 21.69   C
ATOM  1462  N   ALA A 220    9.985 -20.473  51.135  1.00 26.23   N
ATOM  1463  CA  ALA A 220   11.296 -21.122  51.238  1.00 27.57   C
ATOM  1464  C   ALA A 220   12.142 -20.913  49.974  1.00 29.46   C
ATOM  1465  O   ALA A 220   13.355 -20.709  50.054  1.00 29.16   O
ATOM  1466  CB  ALA A 220   11.133 -22.605  51.515  1.00 24.98   C
ATOM  1467  N   ASP A 221   11.500 -20.969  48.811  1.00 30.65   N
ATOM  1468  CA  ASP A 221   12.197 -20.770  47.549  1.00 32.42   C
ATOM  1469  C   ASP A 221   12.841 -19.395  47.468  1.00 32.14   C
ATOM  1470  O   ASP A 221   14.002 -19.252  47.079  1.00 31.87   O
ATOM  1471  CB  ASP A 221   11.244 -20.933  46.368  1.00 34.87   C
ATOM  1472  CG  ASP A 221   11.065 -22.375  45.966  1.00 38.82   C
ATOM  1473  OD1 ASP A 221   11.883 -23.215  46.396  1.00 40.17   O
ATOM  1474  OD2 ASP A 221   10.113 -22.667  45.208  1.00 42.34   O
ATOM  1475  N   ILE A 222   12.079 -18.376  47.838  1.00 31.44   N
ATOM  1476  CA  ILE A 222   12.571 -17.015  47.790  1.00 32.16   C
ATOM  1477  C   ILE A 222   13.616 -16.736  48.867  1.00 31.34   C
ATOM  1478  O   ILE A 222   14.640 -16.107  48.597  1.00 30.55   O
ATOM  1479  CB  ILE A 222   11.411 -16.007  47.934  1.00 31.93   C
ATOM  1480  CG1 ILE A 222   11.973 -14.617  48.225  1.00 31.99   C
ATOM  1481  CG2 ILE A 222   10.468 -16.472  48.999  1.00 33.78   C
ATOM  1482  CD1 ILE A 222   11.014 -13.677  48.846  1.00 32.26   C
ATOM  1483  N   LEU A 223   13.360 -17.211  50.074  1.00 32.73   N
ATOM  1484  CA  LEU A 223   14.280 -16.977  51.178  1.00 35.39   C
ATOM  1485  C   LEU A 223   15.564 -17.790  51.105  1.00 37.03   C

ATOM  4670  CE2 PHE D 56     1.107 -2.796 -2.783  1.00 21.76    C
ATOM  4671  CZ  PHE D 56     1.145 -2.841 -1.400  1.00 22.86    C
ATOM  4672  N   ARG D 57    -4.082 -3.989 -5.257  1.00 29.43    N
ATOM  4673  CA  ARG D 57    -4.449 -2.873 -6.120  1.00 29.95    C
ATOM  4674  C   ARG D 57    -5.431 -1.874 -5.513  1.00 27.16    C
ATOM  4675  O   ARG D 57    -6.179 -2.206 -4.601  1.00 27.33    O
ATOM  4676  CB  ARG D 57    -5.035 -3.415 -7.431  1.00 32.32    C
ATOM  4677  CG  ARG D 57    -4.539 -2.706 -8.695  1.00 37.08    C
ATOM  4678  CD  ARG D 57    -3.151 -3.195 -9.125  1.00 39.70    C
ATOM  4679  NE  ARG D 57    -2.797 -2.741 -10.465 1.00 43.59    N
ATOM  4680  CZ  ARG D 57    -1.829 -3.274 -11.210 1.00 47.08    C
ATOM  4681  NH1 ARG D 57    -1.110 -4.290 -10.746 1.00 48.37    N
ATOM  4682  NH2 ARG D 57    -1.583 -2.796 -12.427 1.00 48.26    N
ATOM  4683  N   ASN D 58    -5.394 -0.648 -6.022  1.00 26.38    N
ATOM  4684  CA  ASN D 58    -6.296  0.430 -5.606  1.00 25.11    C
ATOM  4685  C   ASN D 58    -6.986  0.928 -6.873  1.00 25.10    C
ATOM  4686  O   ASN D 58    -6.324  1.328 -7.834  1.00 23.57    O
ATOM  4687  CB  ASN D 58    -5.539  1.615 -4.995  1.00 22.16    C
ATOM  4688  CG  ASN D 58    -5.239  1.438 -3.523  1.00 20.82    C
ATOM  4689  OD1 ASN D 58    -4.312  0.720 -3.147  1.00 20.48    O
ATOM  4690  ND2 ASN D 58    -6.013  2.105 -2.682  1.00 18.89    N
ATOM  4691  N   VAL D 59    -8.316  0.918 -6.862  1.00 25.88    N
ATOM  4692  CA  VAL D 59    -9.098  1.348 -8.018  1.00 25.62    C
ATOM  4693  C   VAL D 59   -10.295  2.212 -7.632  1.00 25.96    C
ATOM  4694  O   VAL D 59   -11.014  1.928 -6.667  1.00 26.18    O
ATOM  4695  CB  VAL D 59    -9.620  0.121 -8.815  1.00 25.26    C
ATOM  4696  CG1 VAL D 59   -10.369  0.582 -10.041 1.00 25.63    C
ATOM  4697  CG2 VAL D 59    -8.467 -0.782 -9.219  1.00 28.05    C
ATOM  4698  N   GLU D 60   -10.517  3.269 -8.391  1.00 26.25    N
ATOM  4699  CA  GLU D 60   -11.650  4.130 -8.134  1.00 27.64    C
ATOM  4700  C   GLU D 60   -12.713  3.901 -9.215  1.00 27.00    C
ATOM  4701  O   GLU D 60   -12.614  4.462 -10.301 1.00 26.23    O
ATOM  4702  CB  GLU D 60   -11.211  5.586 -8.147  1.00 29.54    C
ATOM  4703  CG  GLU D 60   -12.355  6.553 -7.989  1.00 33.46    C
ATOM  4704  CD  GLU D 60   -11.916  7.993 -8.142  1.00 35.37    C
ATOM  4705  OE1 GLU D 60   -10.939  8.394 -7.470  1.00 38.01    O
ATOM  4706  OE2 GLU D 60   -12.543  8.730 -8.923  1.00 36.78    O
ATOM  4707  N   TYR D 61   -13.716  3.077 -8.903  1.00 26.03    N
ATOM  4708  CA  TYR D 61   -14.789  2.781 -9.849  1.00 26.07    C
ATOM  4709  C   TYR D 61   -15.636  4.026 -10.080 1.00 27.24    C
ATOM  4710  O   TYR D 61   -15.833  4.437 -11.216 1.00 27.42    O
ATOM  4711  CB  TYR D 61   -15.675  1.639 -9.347  1.00 22.35    C
ATOM  4712  CG  TYR D 61   -14.907  0.433 -8.873  1.00 21.12    C
ATOM  4713  CD1 TYR D 61   -14.744  0.183 -7.510  1.00 20.80    C
ATOM  4714  CD2 TYR D 61   -14.331 -0.459 -9.774  1.00 19.27    C
ATOM  4715  CE1 TYR D 61   -14.036 -0.915 -7.058  1.00 19.52    C
ATOM  4716  CE2 TYR D 61   -13.619 -1.565 -9.334  1.00 18.16    C
ATOM  4717  CZ  TYR D 61   -13.479 -1.790 -7.975  1.00 19.06    C
ATOM  4718  OH  TYR D 61   -12.821 -2.909 -7.523  1.00 16.82    O
ATOM  4719  N   SER D 62   -16.121  4.631 -8.998  1.00 29.63    N
ATOM  4720  CA  SER D 62   -16.949  5.834 -9.090  1.00 30.90    C
ATOM  4721  C   SER D 62   -16.468  6.846 -8.068  1.00 31.68    C
ATOM  4722  O   SER D 62   -15.613  6.539 -7.240  1.00 32.91    O
ATOM  4723  CB  SER D 62   -18.419  5.498 -8.820  1.00 33.46    C
ATOM  4724  OG  SER D 62   -19.235  5.750 -9.954  1.00 32.43    O
ATOM  4725  N   SER D 63   -17.036  8.046 -8.113  1.00 32.13    N
ATOM  4726  CA  SER D 63   -16.648  9.123 -7.216  1.00 32.27    C
ATOM  4727  C   SER D 63   -16.546  8.685 -5.750  1.00 32.49    C
ATOM  4728  O   SER D 63   -15.507  8.861 -5.106  1.00 33.42    O
ATOM  4729  CB  SER D 63   -17.619 10.288 -7.345  1.00 33.59    C
ATOM  4730  OG  SER D 63   -18.906  9.930 -6.856  1.00 37.22    O
ATOM  4731  N   GLY D 64   -17.608  8.109 -5.217  1.00 29.38    N
ATOM  4732  CA  GLY D 64   -17.541  7.709 -3.830  1.00 27.25    C
ATOM  4733  C   GLY D 64   -17.575  6.214 -3.612  1.00 25.97    C
ATOM  4734  O   GLY D 64   -18.087  5.749 -2.597  1.00 25.95    O
ATOM  4735  N   ARG D 65   -17.037  5.467 -4.571  1.00 24.32    N
ATOM  4736  CA  ARG D 65   -17.005  4.014 -4.490  1.00 23.53    C
ATOM  4737  C   ARG D 65   -15.701  3.526 -5.102  1.00 24.29    C
ATOM  4738  O   ARG D 65   -15.564  3.405 -6.321  1.00 24.58    O
ATOM  4739  CB  ARG D 65   -18.200  3.400 -5.229  1.00 22.40    C
ATOM  4740  CG  ARG D 65   -18.232  1.866 -5.254  1.00 21.05    C
ATOM  4741  CD  ARG D 65   -19.456  1.332 -6.000  1.00 19.39    C
ATOM  4742  NE  ARG D 65   -19.371  1.549 -7.441  1.00 19.03    N
ATOM  4743  CZ  ARG D 65   -18.774  0.727 -8.290  1.00 17.79    C
ATOM  4744  NH1 ARG D 65   -18.204 -0.386 -7.855  1.00 20.01    N
ATOM  4745  NH2 ARG D 65   -18.739  1.021 -9.581  1.00 21.76    N
ATOM  4746  N   ASN D 66   -14.719  3.260 -4.253  1.00 23.59    N
ATOM  4747  CA  ASN D 66   -13.466  2.779 -4.777  1.00 23.49    C
ATOM  4748  C   ASN D 66   -12.837  1.718 -3.895  1.00 21.64    C
ATOM  4749  O   ASN D 66   -13.012  1.724 -2.686  1.00 23.04    O
ATOM  4750  CB  ASN D 66   -12.506  3.951 -4.981  1.00 25.04    C
ATOM  4751  CG  ASN D 66   -12.562  4.927 -3.867  1.00 22.76    C
ATOM  4752  OD1 ASN D 66   -13.577  5.571 -3.643  1.00 24.38    O
ATOM  4753  ND2 ASN D 66   -11.468  5.044 -3.144  1.00 26.57    N
ATOM  4754  N   LYS D 67   -12.135  0.784 -4.528  1.00 20.98    N
ATOM  4755  CA  LYS D 67   -11.468 -0.308 -3.829  1.00 20.23    C
```

FIG. 6 (con't)

```
ATOM   1486  O   LEU A 223    16.499 -17.536  51.856 1.00 37.69    O
ATOM   1487  CB  LEU A 223    13.588 -17.235  52.518 1.00 33.88    C
ATOM   1488  CG  LEU A 223    12.968 -16.033  53.224 1.00 32.85    C
ATOM   1489  CD1 LEU A 223    12.038 -15.275  52.278 1.00 32.57    C
ATOM   1490  CD2 LEU A 223    12.227 -16.529  54.461 1.00 32.42    C
ATOM   1491  N   LYS A 224    15.618 -18.759  50.203 1.00 39.82    N
ATOM   1492  CA  LYS A 224    16.808 -19.582  50.077 1.00 42.13    C
ATOM   1493  C   LYS A 224    16.886 -20.133  48.674 1.00 43.06    C
ATOM   1494  O   LYS A 224    17.537 -19.471  47.839 1.00 43.58    O
ATOM   1495  CB  LYS A 224    16.758 -20.741  51.087 1.00 44.93    C
ATOM   1496  CG  LYS A 224    16.896 -20.320  52.549 1.00 46.58    C
ATOM   1497  CD  LYS A 224    16.737 -21.505  53.504 1.00 47.58    C
ATOM   1498  CE  LYS A 224    17.818 -22.569  53.300 1.00 48.37    C
ATOM   1499  NZ  LYS A 224    17.606 -23.755  54.190 1.00 50.33    N
ATOM   1500  OXT LYS A 224    16.278 -21.200  48.427 1.00 43.78    O
TER    1501      LYS A 224
ATOM   1502  N   GLY B  35   -10.627 -21.550  77.712 1.00 65.95    N
ATOM   1503  CA  GLY B  35   -11.789 -20.604  77.728 1.00 65.74    C
ATOM   1504  C   GLY B  35   -11.777 -19.666  78.924 1.00 65.88    C
ATOM   1505  O   GLY B  35   -12.113 -18.482  78.804 1.00 65.82    O
ATOM   1506  N   SER B  36   -11.391 -20.196  80.084 1.00 65.25    N
ATOM   1507  CA  SER B  36   -11.332 -19.406  81.316 1.00 64.34    C
ATOM   1508  C   SER B  36   -10.181 -18.403  81.291 1.00 63.25    C
ATOM   1509  O   SER B  36   -10.320 -17.280  81.782 1.00 63.83    O
ATOM   1510  CB  SER B  36   -11.194 -20.325  82.537 1.00 64.89    C
ATOM   1511  OG  SER B  36   -12.357 -21.122  82.705 1.00 65.58    O
ATOM   1512  N   GLY B  37    -9.048 -18.815  80.719 1.00 61.08    N
ATOM   1513  CA  GLY B  37    -7.889 -17.940  80.622 1.00 58.37    C
ATOM   1514  C   GLY B  37    -6.627 -18.655  80.176 1.00 56.48    C
ATOM   1515  O   GLY B  37    -6.508 -19.870  80.341 1.00 56.22    O
ATOM   1516  N   GLY B  38    -5.683 -17.898  79.613 1.00 54.16    N
ATOM   1517  CA  GLY B  38    -4.428 -18.478  79.157 1.00 52.32    C
ATOM   1518  C   GLY B  38    -3.368 -18.471  80.239 1.00 51.43    C
ATOM   1519  O   GLY B  38    -3.421 -19.244  81.203 1.00 52.20    O
ATOM   1520  N   GLY B  39    -2.385 -17.596  80.084 1.00 49.18    N
ATOM   1521  CA  GLY B  39    -1.340 -17.519  81.085 1.00 47.03    C
ATOM   1522  C   GLY B  39    -0.017 -17.121  80.494 1.00 45.63    C
ATOM   1523  O   GLY B  39     0.391 -17.656  79.462 1.00 46.65    O
ATOM   1524  N   MET B  40     0.648 -16.177  81.152 1.00 43.33    N
ATOM   1525  CA  MET B  40     1.952 -15.681  80.718 1.00 41.32    C
ATOM   1526  C   MET B  40     2.954 -15.760  81.860 1.00 39.92    C
ATOM   1527  O   MET B  40     4.154 -15.656  81.634 1.00 40.36    O
ATOM   1528  CB  MET B  40     1.831 -14.231  80.240 1.00 41.10    C
ATOM   1529  CG  MET B  40     1.284 -13.293  81.296 1.00 41.23    C
ATOM   1530  SD  MET B  40    -0.175 -12.424  80.751 1.00 41.22    S
ATOM   1531  CE  MET B  40    -1.319 -13.808  80.575 1.00 42.14    C
ATOM   1532  N   ILE B  41     2.455 -15.944  83.084 1.00 39.53    N
ATOM   1533  CA  ILE B  41     3.303 -16.047  84.270 1.00 38.14    C
ATOM   1534  C   ILE B  41     3.596 -17.508  84.578 1.00 38.77    C
ATOM   1535  O   ILE B  41     2.689 -18.340  84.581 1.00 38.59    O
ATOM   1536  CB  ILE B  41     2.617 -15.434  85.495 1.00 37.33    C
ATOM   1537  CG1 ILE B  41     2.187 -14.002  85.180 1.00 36.78    C
ATOM   1538  CG2 ILE B  41     3.563 -15.426  86.666 1.00 35.32    C
ATOM   1539  CD1 ILE B  41     1.348 -13.360  86.250 1.00 36.32    C
ATOM   1540  N   VAL B  42     4.860 -17.818  84.843 1.00 39.95    N
ATOM   1541  CA  VAL B  42     5.255 -19.186  85.154 1.00 41.19    C
ATOM   1542  C   VAL B  42     5.923 -19.284  86.521 1.00 42.18    C
ATOM   1543  O   VAL B  42     6.912 -18.603  86.788 1.00 41.93    O
ATOM   1544  CB  VAL B  42     6.231 -19.731  84.101 1.00 41.11    C
ATOM   1545  CG1 VAL B  42     6.532 -21.189  84.389 1.00 40.37    C
ATOM   1546  CG2 VAL B  42     5.637 -19.566  82.711 1.00 41.56    C
ATOM   1547  N   THR B  43     5.367 -20.136  87.379 1.00 43.82    N
ATOM   1548  CA  THR B  43     5.887 -20.353  88.723 1.00 45.39    C
ATOM   1549  C   THR B  43     5.739 -21.815  89.095 1.00 46.40    C
ATOM   1550  O   THR B  43     4.884 -22.525  88.557 1.00 45.59    O
ATOM   1551  CB  THR B  43     5.136 -19.517  89.778 1.00 45.76    C
ATOM   1552  OG1 THR B  43     3.761 -19.394  89.392 1.00 45.90    O
ATOM   1553  CG2 THR B  43     5.779 -18.136  89.940 1.00 47.70    C
ATOM   1554  N   GLY B  44     6.583 -22.261  90.021 1.00 46.95    N
ATOM   1555  CA  GLY B  44     6.533 -23.641  90.465 1.00 47.63    C
ATOM   1556  C   GLY B  44     5.504 -23.824  91.561 1.00 47.94    C
ATOM   1557  O   GLY B  44     5.351 -24.919  92.100 1.00 48.43    O
ATOM   1558  N   GLU B  45     4.786 -22.753  91.884 1.00 47.48    N
ATOM   1559  CA  GLU B  45     3.782 -22.811  92.927 1.00 47.90    C
ATOM   1560  C   GLU B  45     2.454 -23.313  92.373 1.00 47.93    C
ATOM   1561  O   GLU B  45     1.889 -22.740  91.443 1.00 45.94    O
ATOM   1562  CB  GLU B  45     3.601 -21.438  93.561 1.00 48.53    C
ATOM   1563  CG  GLU B  45     2.969 -21.498  94.929 1.00 50.43    C
ATOM   1564  CD  GLU B  45     3.864 -22.151  95.957 1.00 51.36    C
ATOM   1565  OE1 GLU B  45     4.830 -21.492  96.414 1.00 51.15    O
ATOM   1566  OE2 GLU B  45     3.598 -23.324  96.303 1.00 51.55    O
ATOM   1567  N   ARG B  46     1.958 -24.393  92.962 1.00 49.04    N
ATOM   1568  CA  ARG B  46     0.718 -24.985  92.509 1.00 49.97    C
ATOM   1569  C   ARG B  46    -0.484 -24.439  93.281 1.00 48.13    C
ATOM   1570  O   ARG B  46    -1.617 -24.540  92.821 1.00 47.87    O
ATOM   1571  CB  ARG B  46     0.797 -26.510  92.658 1.00 53.46    C
ATOM   4756  C   LYS D  67   -10.199  0.265  -3.223 1.00 20.41    C
ATOM   4757  O   LYS D  67    -9.339  0.762  -3.948 1.00 19.19    O
ATOM   4758  CB  LYS D  67   -11.107 -1.423  -4.807 1.00 18.30    C
ATOM   4759  CG  LYS D  67   -10.464 -2.654  -4.185 1.00 17.85    C
ATOM   4760  CD  LYS D  67    -9.156 -3.027  -4.877 1.00 16.58    C
ATOM   4761  CE  LYS D  67    -8.681  4.396  -4.430 1.00 17.35    C
ATOM   4762  NZ  LYS D  67    -9.708 -5.420  -4.760 1.00 16.14    N
ATOM   4763  N   THR D  68   -10.091  0.188  -1.899 1.00 20.48    N
ATOM   4764  CA  THR D  68    -8.938  0.695  -1.171 1.00 19.45    C
ATOM   4765  C   THR D  68    -8.094 -0.408  -0.560 1.00 18.89    C
ATOM   4766  O   THR D  68    -8.597 -1.487  -0.241 1.00 20.69    O
ATOM   4767  CB  THR D  68    -9.403  1.650  -0.077 1.00 20.95    C
ATOM   4768  OG1 THR D  68    -9.212  2.999  -0.523 1.00 22.83    O
ATOM   4769  CG2 THR D  68    -8.644  1.428   1.215 1.00 23.70    C
ATOM   4770  N   PHE D  69    -6.802 -0.150  -0.410 1.00 18.50    N
ATOM   4771  CA  PHE D  69    -5.895 -1.116   0.200 1.00 18.56    C
ATOM   4772  C   PHE D  69    -4.577 -0.431   0.537 1.00 18.27    C
ATOM   4773  O   PHE D  69    -3.926  0.109  -0.341 1.00 17.87    O
ATOM   4774  CB  PHE D  69    -5.611 -2.293  -0.723 1.00 18.98    C
ATOM   4775  CG  PHE D  69    -4.993 -3.481  -0.020 1.00 20.68    C
ATOM   4776  CD1 PHE D  69    -5.793 -4.522   0.465 1.00 20.29    C
ATOM   4777  CD2 PHE D  69    -3.613 -3.545   0.183 1.00 20.65    C
ATOM   4778  CE1 PHE D  69    -5.233 -5.612   1.152 1.00 21.01    C
ATOM   4779  CE2 PHE D  69    -3.040 -4.628   0.870 1.00 22.02    C
ATOM   4780  CZ  PHE D  69    -3.853 -5.665   1.361 1.00 22.14    C
ATOM   4781  N   LEU D  70    -4.172 -0.479   1.809 1.00 17.70    N
ATOM   4782  CA  LEU D  70    -2.927  0.166   2.204 1.00 16.05    C
ATOM   4783  C   LEU D  70    -2.227 -0.556   3.355 1.00 15.86    C
ATOM   4784  O   LEU D  70    -2.872 -0.929   4.337 1.00 16.43    O
ATOM   4785  CB  LEU D  70    -3.213  1.616   2.602 1.00 14.97    C
ATOM   4786  CG  LEU D  70    -2.027  2.536   2.877 1.00 16.12    C
ATOM   4787  CD1 LEU D  70    -2.434  3.979   2.622 1.00 18.82    C
ATOM   4788  CD2 LEU D  70    -1.557  2.367   4.312 1.00 16.25    C
ATOM   4789  N   CYS D  71    -0.922  0.365   3.228 1.00 15.55    N
ATOM   4790  CA  CYS D  71    -0.132 -1.388   4.280 1.00 17.49    C
ATOM   4791  C   CYS D  71     0.725 -0.315   4.951 1.00 18.37    C
ATOM   4792  O   CYS D  71     1.254  0.574   4.276 1.00 20.35    O
ATOM   4793  CB  CYS D  71     0.782 -2.482   3.721 1.00 17.63    C
ATOM   4794  SG  CYS D  71    -0.060 -4.007   3.238 1.00 22.44    S
ATOM   4795  N   TYR D  72     0.894 -0.394   6.268 1.00 17.53    N
ATOM   4796  CA  TYR D  72     1.668  0.624   6.950 1.00 18.63    C
ATOM   4797  C   TYR D  72     2.475  0.107   8.132 1.00 19.44    C
ATOM   4798  O   TYR D  72     2.304 -1.028   8.578 1.00 19.68    O
ATOM   4799  CB  TYR D  72     0.728  1.747   7.422 1.00 17.05    C
ATOM   4800  CG  TYR D  72    -0.256  1.311   8.487 1.00 14.71    C
ATOM   4801  CD1 TYR D  72     0.121  1.243   9.827 1.00 15.38    C
ATOM   4802  CD2 TYR D  72    -1.545  0.936   8.151 1.00 13.17    C
ATOM   4803  CE1 TYR D  72    -0.772  0.811  10.807 1.00 14.44    C
ATOM   4804  CE2 TYR D  72    -2.442  0.504   9.120 1.00 15.44    C
ATOM   4805  CZ  TYR D  72    -2.042  0.452  10.453 1.00 15.29    C
ATOM   4806  OH  TYR D  72    -2.926  0.080  11.438 1.00 18.51    O
ATOM   4807  N   VAL D  73     3.360  0.964   8.630 1.00 19.84    N
ATOM   4808  CA  VAL D  73     4.208  0.652   9.762 1.00 20.09    C
ATOM   4809  C   VAL D  73     4.380  1.947  10.536 1.00 21.37    C
ATOM   4810  O   VAL D  73     4.647  2.990   9.940 1.00 20.47    O
ATOM   4811  CB  VAL D  73     5.592  0.139   9.301 1.00 19.30    C
ATOM   4812  CG1 VAL D  73     6.526 -0.002  10.479 1.00 18.84    C
ATOM   4813  CG2 VAL D  73     5.444 -1.211   8.632 1.00 20.49    C
ATOM   4814  N   VAL D  74     4.201  1.889  11.857 1.00 23.48    N
ATOM   4815  CA  VAL D  74     4.353  3.067  12.712 1.00 25.17    C
ATOM   4816  C   VAL D  74     5.424  2.860  13.778 1.00 27.23    C
ATOM   4817  O   VAL D  74     5.419  1.846  14.472 1.00 28.23    O
ATOM   4818  CB  VAL D  74     3.037  3.412  13.428 1.00 24.98    C
ATOM   4819  CG1 VAL D  74     3.222  4.675  14.251 1.00 25.10    C
ATOM   4820  CG2 VAL D  74     1.935  3.615  12.425 1.00 22.68    C
ATOM   4821  N   GLU D  75     6.330  3.834  13.899 1.00 29.61    N
ATOM   4822  CA  GLU D  75     7.438  3.813  14.873 1.00 31.25    C
ATOM   4823  C   GLU D  75     7.486  5.180  15.561 1.00 31.84    C
ATOM   4824  O   GLU D  75     7.814  6.185  14.927 1.00 32.51    O
ATOM   4825  CB  GLU D  75     8.774  3.581  14.157 1.00 32.68    C
ATOM   4826  CG  GLU D  75     8.814  2.391  13.200 1.00 36.25    C
ATOM   4827  CD  GLU D  75     9.303  1.119  13.864 1.00 39.50    C
ATOM   4828  OE1 GLU D  75    10.319  1.194  14.587 1.00 41.33    O
ATOM   4829  OE2 GLU D  75     8.687  0.044  13.665 1.00 41.30    O
ATOM   4830  N   ALA D  76     7.176  5.222  16.851 1.00 33.13    N
ATOM   4831  CA  ALA D  76     7.172  6.483  17.585 1.00 34.51    C
ATOM   4832  C   ALA D  76     8.131  6.455  18.763 1.00 35.51    C
ATOM   4833  O   ALA D  76     8.052  5.577  19.620 1.00 34.35    O
ATOM   4834  CB  ALA D  76     5.761  6.795  18.069 1.00 33.85    C
ATOM   4835  N   GLN D  77     9.034  7.424  18.789 1.00 37.76    N
ATOM   4836  CA  GLN D  77     9.998  7.529  19.868 1.00 41.13    C
ATOM   4837  C   GLN D  77     9.822  8.862  20.571 1.00 42.62    C
ATOM   4838  O   GLN D  77     9.893  9.917  19.945 1.00 43.01    O
ATOM   4839  CB  GLN D  77    11.421  7.409  19.321 1.00 42.70    C
ATOM   4840  CG  GLN D  77    11.703  6.046  18.710 1.00 46.15    C
ATOM   4841  CD  GLN D  77    13.161  5.627  18.814 1.00 47.70    C
```

FIG. 6 (con't)

```
ATOM  1572  CG   ARG B  46    0.328 -27.308  91.427  1.00 58.32    C
ATOM  1573  CD   ARG B  46   -1.136 -26.997  91.023  1.00 61.93    C
ATOM  1574  NE   ARG B  46   -1.577 -27.757  89.841  1.00 64.77    N
ATOM  1575  CZ   ARG B  46   -2.772 -27.640  89.260  1.00 65.91    C
ATOM  1576  NH1  ARG B  46   -3.676 -26.789  89.737  1.00 66.29    N
ATOM  1577  NH2  ARG B  46   -3.066 -28.376  88.193  1.00 65.31    N
ATOM  1578  N    LEU B  47   -0.236 -23.853  94.444  1.00 46.05    N
ATOM  1579  CA   LEU B  47   -1.330 -23.313  95.246  1.00 44.88    C
ATOM  1580  C    LEU B  47   -1.357 -21.803  95.130  1.00 43.20    C
ATOM  1581  O    LEU B  47   -0.346 -21.147  95.360  1.00 44.01    O
ATOM  1582  CB   LEU B  47   -1.153 -23.700  96.714  1.00 44.69    C
ATOM  1583  CG   LEU B  47   -2.332 -23.410  97.648  1.00 45.22    C
ATOM  1584  CD1  LEU B  47   -3.494 -24.345  97.335  1.00 43.81    C
ATOM  1585  CD2  LEU B  47   -1.884 -23.601  99.087  1.00 44.57    C
ATOM  1586  N    PRO B  48   -2.518 -21.228  94.784  1.00 41.40    N
ATOM  1587  CA   PRO B  48   -2.646 -19.775  94.643  1.00 39.91    C
ATOM  1588  C    PRO B  48   -2.418 -19.024  95.943  1.00 38.63    C
ATOM  1589  O    PRO B  48   -1.992 -17.866  95.945  1.00 37.68    O
ATOM  1590  CB   PRO B  48   -4.064 -19.609  94.110  1.00 40.40    C
ATOM  1591  CG   PRO B  48   -4.780 -20.757  94.701  1.00 40.22    C
ATOM  1592  CD   PRO B  48   -3.803 -21.884  94.498  1.00 41.21    C
ATOM  1593  N    ALA B  49   -2.695 -19.699  97.051  1.00 37.40    N
ATOM  1594  CA   ALA B  49   -2.531 -19.103  98.361  1.00 36.74    C
ATOM  1595  C    ALA B  49   -1.077 -18.727  98.588  1.00 37.22    C
ATOM  1596  O    ALA B  49   -0.784 -17.745  99.272  1.00 37.92    O
ATOM  1597  CB   ALA B  49   -2.999 -20.072  99.425  1.00 35.73    C
ATOM  1598  N    ASN B  50   -0.164 -19.506  97.999  1.00 36.86    N
ATOM  1599  CA   ASN B  50    1.274 -19.261  98.148  1.00 35.55    C
ATOM  1600  C    ASN B  50    1.783 -18.268  97.115  1.00 34.57    C
ATOM  1601  O    ASN B  50    2.632 -17.425  97.412  1.00 34.74    O
ATOM  1602  CB   ASN B  50    2.054 -20.573  98.031  1.00 36.48    C
ATOM  1603  CG   ASN B  50    1.685 -21.572  99.111  1.00 37.81    C
ATOM  1604  OD1  ASN B  50    1.836 -21.304 100.305  1.00 38.68    O
ATOM  1605  ND2  ASN B  50    1.193 -22.730  98.695  1.00 38.96    N
ATOM  1606  N    PHE B  51    1.258 -18.377  95.901  1.00 32.25    N
ATOM  1607  CA   PHE B  51    1.634 -17.496  94.819  1.00 30.10    C
ATOM  1608  C    PHE B  51    1.309 -16.045  95.164  1.00 29.79    C
ATOM  1609  O    PHE B  51    2.101 -15.146  94.889  1.00 31.28    O
ATOM  1610  CB   PHE B  51    0.876 -17.882  93.548  1.00 29.23    C
ATOM  1611  CG   PHE B  51    1.063 -16.920  92.415  1.00 26.10    C
ATOM  1612  CD1  PHE B  51    2.274 -16.857  91.737  1.00 26.15    C
ATOM  1613  CD2  PHE B  51    0.042 -16.055  92.043  1.00 26.87    C
ATOM  1614  CE1  PHE B  51    2.471 -15.942  90.698  1.00 25.67    C
ATOM  1615  CE2  PHE B  51    0.229 -15.130  91.005  1.00 26.81    C
ATOM  1616  CZ   PHE B  51    1.448 -15.078  90.334  1.00 25.60    C
ATOM  1617  N    PHE B  52    0.150 -15.819  95.773  1.00 28.87    N
ATOM  1618  CA   PHE B  52   -0.267 -14.469  96.135  1.00 29.04    C
ATOM  1619  C    PHE B  52    0.308 -14.002  97.460  1.00 30.61    C
ATOM  1620  O    PHE B  52    0.124 -12.850  97.865  1.00 31.07    O
ATOM  1621  CB   PHE B  52   -1.801 -14.369  96.190  1.00 27.06    C
ATOM  1622  CG   PHE B  52   -2.459 -14.378  94.833  1.00 24.65    C
ATOM  1623  CD1  PHE B  52   -3.158 -15.493  94.397  1.00 22.56    C
ATOM  1624  CD2  PHE B  52   -2.351 -13.276  93.980  1.00 23.11    C
ATOM  1625  CE1  PHE B  52   -3.745 -15.528  93.138  1.00 20.90    C
ATOM  1626  CE2  PHE B  52   -2.937 -13.301  92.713  1.00 22.18    C
ATOM  1627  CZ   PHE B  52   -3.635 -14.432  92.295  1.00 21.66    C
ATOM  1628  N    LYS B  53    1.002 -14.902  98.138  1.00 32.05    N
ATOM  1629  CA   LYS B  53    1.613 -14.581  99.411  1.00 33.59    C
ATOM  1630  C    LYS B  53    3.082 -14.190  99.201  1.00 34.05    C
ATOM  1631  O    LYS B  53    3.578 -13.270  99.852  1.00 33.80    O
ATOM  1632  CB   LYS B  53    1.510 -15.785 100.354  1.00 35.16    C
ATOM  1633  CG   LYS B  53    2.068 -15.563 101.751  1.00 37.21    C
ATOM  1634  CD   LYS B  53    1.228 -14.553 102.520  1.00 40.42    C
ATOM  1635  CE   LYS B  53    1.651 -14.439 103.985  1.00 40.80    C
ATOM  1636  NZ   LYS B  53    0.818 -13.452 104.755  1.00 41.58    N
ATOM  1637  N    PHE B  54    3.759 -14.872  98.272  1.00 33.63    N
ATOM  1638  CA   PHE B  54    5.175 -14.609  98.004  1.00 33.84    C
ATOM  1639  C    PHE B  54    5.435 -13.950  96.655  1.00 32.83    C
ATOM  1640  O    PHE B  54    5.823 -12.781  96.580  1.00 34.43    O
ATOM  1641  CB   PHE B  54    5.985 -15.908  98.083  1.00 34.77    C
ATOM  1642  CG   PHE B  54    5.766 -16.690  99.353  1.00 37.23    C
ATOM  1643  CD1  PHE B  54    5.179 -17.956  99.315  1.00 37.86    C
ATOM  1644  CD2  PHE B  54    6.124 -16.158 100.589  1.00 37.44    C
ATOM  1645  CE1  PHE B  54    4.949 -18.674 100.495  1.00 39.19    C
ATOM  1646  CE2  PHE B  54    5.899 -16.868 101.777  1.00 38.15    C
ATOM  1647  CZ   PHE B  54    5.307 -18.128 101.729  1.00 38.53    C
ATOM  1648  N    GLN B  55    5.226 -14.698  95.590  1.00 30.82    N
ATOM  1649  CA   GLN B  55    5.484 -14.173  94.272  1.00 30.73    C
ATOM  1650  C    GLN B  55    4.766 -12.886  93.950  1.00 29.59    C
ATOM  1651  O    GLN B  55    5.377 -11.952  93.432  1.00 30.41    O
ATOM  1652  CB   GLN B  55    5.147 -15.203  93.203  1.00 32.98    C
ATOM  1653  CG   GLN B  55    6.262 -16.211  92.945  1.00 37.44    C
ATOM  1654  CD   GLN B  55    6.344 -17.313  93.997  1.00 39.61    C
ATOM  1655  OE1  GLN B  55    7.340 -18.039  94.079  1.00 40.35    O
ATOM  1656  NE2  GLN B  55    5.288 -17.452  94.794  1.00 40.46    N
ATOM  1657  N    PHE B  56    3.474 -12.826  94.258  1.00 27.72    N

ATOM  4842  OE1  GLN D  77   14.011   6.091  18.047  1.00 49.86    O
ATOM  4843  NE2  GLN D  77   13.462   4.748  19.770  1.00 47.53    N
ATOM  4844  N    GLY D  78    9.584   8.810  21.872  1.00 44.59    N
ATOM  4845  CA   GLY D  78    9.384  10.032  22.617  1.00 47.64    C
ATOM  4846  C    GLY D  78   10.486  10.383  23.598  1.00 49.82    C
ATOM  4847  O    GLY D  78   10.205  10.749  24.738  1.00 50.25    O
ATOM  4848  N    LYS D  79   11.738  10.260  23.167  1.00 51.66    N
ATOM  4849  CA   LYS D  79   12.879  10.603  24.012  1.00 52.54    C
ATOM  4850  C    LYS D  79   12.580  10.515  25.522  1.00 52.64    C
ATOM  4851  O    LYS D  79   12.212  11.510  26.154  1.00 52.91    O
ATOM  4852  CB   LYS D  79   13.369  12.023  23.669  1.00 53.89    C
ATOM  4853  CG   LYS D  79   12.553  12.767  22.594  1.00 55.07    C
ATOM  4854  CD   LYS D  79   12.861  12.242  21.191  1.00 55.34    C
ATOM  4855  CE   LYS D  79   11.708  12.472  20.211  1.00 54.94    C
ATOM  4856  NZ   LYS D  79   11.290  13.899  20.073  1.00 54.67    N
ATOM  4857  N    GLY D  80   12.742   9.327  26.095  1.00 51.63    N
ATOM  4858  CA   GLY D  80   12.488   9.159  27.515  1.00 48.99    C
ATOM  4859  C    GLY D  80   12.071   7.743  27.853  1.00 47.47    C
ATOM  4860  O    GLY D  80   11.373   7.502  28.837  1.00 47.30    O
ATOM  4861  N    GLY D  81   12.510   6.794  27.034  1.00 45.99    N
ATOM  4862  CA   GLY D  81   12.152   5.411  27.269  1.00 42.62    C
ATOM  4863  C    GLY D  81   10.868   5.023  26.557  1.00 40.35    C
ATOM  4864  O    GLY D  81   10.616   3.843  26.328  1.00 40.69    O
ATOM  4865  N    GLN D  82   10.059   6.012  26.198  1.00 38.48    N
ATOM  4866  CA   GLN D  82    8.798   5.757  25.518  1.00 36.71    C
ATOM  4867  C    GLN D  82    8.982   5.431  24.042  1.00 34.16    C
ATOM  4868  O    GLN D  82    9.378   6.276  23.235  1.00 33.03    O
ATOM  4869  CB   GLN D  82    7.858   6.945  25.704  1.00 38.61    C
ATOM  4870  CG   GLN D  82    8.531   8.286  25.543  1.00 43.65    C
ATOM  4871  CD   GLN D  82    7.774   9.400  26.239  1.00 46.79    C
ATOM  4872  OE1  GLN D  82    6.548   9.503  26.109  1.00 48.92    O
ATOM  4873  NE2  GLN D  82    8.494  10.236  26.978  1.00 48.70    N
ATOM  4874  N    VAL D  83    8.701   4.173  23.713  1.00 31.87    N
ATOM  4875  CA   VAL D  83    8.816   3.667  22.357  1.00 29.21    C
ATOM  4876  C    VAL D  83    7.476   3.109  21.882  1.00 27.93    C
ATOM  4877  O    VAL D  83    6.707   2.556  22.670  1.00 26.55    O
ATOM  4878  CB   VAL D  83    9.874   2.563  22.278  1.00 29.08    C
ATOM  4879  CG1  VAL D  83   10.015   2.093  20.852  1.00 30.03    C
ATOM  4880  CG2  VAL D  83   11.206   3.077  22.807  1.00 30.30    C
ATOM  4881  N    GLN D  84    7.198   3.250  20.593  1.00 27.02    N
ATOM  4882  CA   GLN D  84    5.942   2.754  20.035  1.00 25.73    C
ATOM  4883  C    GLN D  84    6.168   2.141  18.649  1.00 25.11    C
ATOM  4884  O    GLN D  84    6.837   2.728  17.802  1.00 25.13    O
ATOM  4885  CB   GLN D  84    4.956   3.905  19.954  1.00 25.81    C
ATOM  4886  CG   GLN D  84    3.575   3.580  20.397  1.00 24.19    C
ATOM  4887  CD   GLN D  84    2.843   4.830  20.765  1.00 25.69    C
ATOM  4888  OE1  GLN D  84    3.187   5.493  21.738  1.00 25.49    O
ATOM  4889  NE2  GLN D  84    1.836   5.185  19.971  1.00 28.23    N
ATOM  4890  N    ALA D  85    5.627   0.957  18.419  1.00 23.00    N
ATOM  4891  CA   ALA D  85    5.808   0.334  17.121  1.00 22.96    C
ATOM  4892  C    ALA D  85    4.613  -0.538  16.746  1.00 24.13    C
ATOM  4893  O    ALA D  85    4.025  -1.191  17.603  1.00 25.01    O
ATOM  4894  CB   ALA D  85    7.083  -0.497  17.105  1.00 23.30    C
ATOM  4895  N    SER D  86    4.244  -0.528  15.472  1.00 23.78    N
ATOM  4896  CA   SER D  86    3.130  -1.332  15.011  1.00 23.27    C
ATOM  4897  C    SER D  86    3.129  -1.452  13.497  1.00 23.53    C
ATOM  4898  O    SER D  86    3.857  -0.738  12.804  1.00 23.77    O
ATOM  4899  CB   SER D  86    1.796  -0.720  15.459  1.00 23.28    C
ATOM  4900  OG   SER D  86    1.640   0.586  14.947  1.00 23.95    O
ATOM  4901  N    ARG D  87    2.327  -2.370  12.987  1.00 24.11    N
ATOM  4902  CA   ARG D  87    2.203  -2.539  11.554  1.00 25.25    C
ATOM  4903  C    ARG D  87    0.851  -3.172  11.224  1.00 24.61    C
ATOM  4904  O    ARG D  87    0.474  -4.199  11.792  1.00 25.27    O
ATOM  4905  CB   ARG D  87    3.363  -3.385  11.016  1.00 27.95    C
ATOM  4906  CG   ARG D  87    3.301  -4.843  11.392  1.00 30.62    C
ATOM  4907  CD   ARG D  87    4.636  -5.524  11.124  1.00 34.75    C
ATOM  4908  NE   ARG D  87    4.472  -6.950  10.837  1.00 37.85    N
ATOM  4909  CZ   ARG D  87    5.354  -7.891  11.172  1.00 40.61    C
ATOM  4910  NH1  ARG D  87    6.471  -7.574  11.815  1.00 39.20    N
ATOM  4911  NH2  ARG D  87    5.116  -9.156  10.853  1.00 41.97    N
ATOM  4912  N    GLY D  88    0.103  -2.542  10.327  1.00 23.93    N
ATOM  4913  CA   GLY D  88   -1.203  -3.070   9.954  1.00 23.06    C
ATOM  4914  C    GLY D  88   -1.551  -2.760   8.510  1.00 22.36    C
ATOM  4915  O    GLY D  88    0.664  -2.475   7.708  1.00 23.05    O
ATOM  4916  N    TYR D  89   -2.835  -2.813   8.170  1.00 21.66    N
ATOM  4917  CA   TYR D  89   -3.266  -2.527   6.816  1.00 21.72    C
ATOM  4918  C    TYR D  89   -4.759  -2.183   6.769  1.00 22.02    C
ATOM  4919  O    TYR D  89   -5.488  -2.424   7.728  1.00 21.39    O
ATOM  4920  CB   TYR D  89   -2.980  -3.722   5.903  1.00 21.82    C
ATOM  4921  CG   TYR D  89   -4.080  -4.745   5.916  1.00 22.99    C
ATOM  4922  CD1  TYR D  89   -4.834  -4.998   4.769  1.00 22.91    C
ATOM  4923  CD2  TYR D  89   -4.370  -5.468   7.065  1.00 22.32    C
ATOM  4924  CE1  TYR D  89   -5.849  -5.937   4.764  1.00 23.99    C
ATOM  4925  CE2  TYR D  89   -5.385  -6.420   7.076  1.00 23.57    C
ATOM  4926  CZ   TYR D  89   -6.116  -6.651   5.917  1.00 25.35    C
ATOM  4927  OH   TYR D  89   -7.104  -7.622   5.887  1.00 27.95    O
```

FIG. 6 (con't)

```
ATOM  1658  CA  PHE B 56    2.664 -11.650 93.944 1.00 26.73   C
ATOM  1659  C   PHE B 56    3.033 -10.434 94.797 1.00 27.37   C
ATOM  1660  O   PHE B 56    2.701  -9.295 94.461 1.00 27.11   O
ATOM  1661  CB  PHE B 56    1.175 -11.992 94.115 1.00 23.65   C
ATOM  1662  CG  PHE B 56    0.238 -11.028 93.426 1.00 22.80   C
ATOM  1663  CD1 PHE B 56    0.158 -10.983 92.036 1.00 21.59   C
ATOM  1664  CD2 PHE B 56   -0.580 -10.178 94.168 1.00 22.28   C
ATOM  1665  CE1 PHE B 56   -0.722 -10.107 91.397 1.00 20.82   C
ATOM  1666  CE2 PHE B 56   -1.463  -9.297 93.539 1.00 21.92   C
ATOM  1667  CZ  PHE B 56   -1.533  -9.263 92.150 1.00 21.01   C
ATOM  1668  N   ARG B 57    3.756 -10.689 95.882 1.00 27.57   N
ATOM  1669  CA  ARG B 57    4.135  -9.644 96.815 1.00 28.14   C
ATOM  1670  C   ARG B 57    5.111  -8.601 96.266 1.00 25.87   C
ATOM  1671  O   ARG B 57    5.841  -8.861 95.318 1.00 24.30   O
ATOM  1672  CB  ARG B 57    4.731 -10.273 98.075 1.00 31.68   C
ATOM  1673  CG  ARG B 57    4.248  -9.645 99.385 1.00 37.55   C
ATOM  1674  CD  ARG B 57    2.853 -10.146 99.793 1.00 40.52   C
ATOM  1675  NE  ARG B 57    2.504  -9.769 101.161 1.00 43.37  N
ATOM  1676  CZ  ARG B 57    1.543 -10.343 101.879 1.00 46.49  C
ATOM  1677  NH1 ARG B 57    0.822 -11.331 101.362 1.00 48.70  N
ATOM  1678  NH2 ARG B 57    1.310  -9.941 103.125 1.00 47.88  N
ATOM  1679  N   ASN B 58    5.079  -7.412 96.860 1.00 24.69   N
ATOM  1680  CA  ASN B 58    5.970  -6.319 96.500 1.00 23.73   C
ATOM  1681  C   ASN B 58    6.692  -5.909 97.787 1.00 24.86   C
ATOM  1682  O   ASN B 58    6.048  -5.567 98.777 1.00 24.08   O
ATOM  1683  CB  ASN B 58    5.214  -5.097 95.975 1.00 22.38   C
ATOM  1684  CG  ASN B 58    4.900  -5.183 94.498 1.00 22.23   C
ATOM  1685  OD1 ASN B 58    3.965  -5.862 94.089 1.00 20.24   O
ATOM  1686  ND2 ASN B 58    5.692  -4.484 93.685 1.00 19.40   N
ATOM  1687  N   VAL B 59    8.025  -5.938 97.765 1.00 25.46   N
ATOM  1688  CA  VAL B 59    8.808  -5.586 98.943 1.00 25.97   C
ATOM  1689  C   VAL B 59   10.020  -4.718 98.620 1.00 26.99   C
ATOM  1690  O   VAL B 59   10.746  -4.968 97.656 1.00 26.55   O
ATOM  1691  CB  VAL B 59    9.322  -6.847 99.654 1.00 25.65   C
ATOM  1692  CG1 VAL B 59   10.098  -6.457 100.887 1.00 26.97  C
ATOM  1693  CG2 VAL B 59    8.168  -7.760 100.010 1.00 27.12  C
ATOM  1694  N   GLU B 60   10.245  -3.706 99.441 1.00 27.82   N
ATOM  1695  CA  GLU B 60   11.388  -2.829 99.247 1.00 29.19   C
ATOM  1696  C   GLU B 60   12.450  -3.149 100.300 1.00 28.80  C
ATOM  1697  O   GLU B 60   12.357  -2.674 101.431 1.00 28.69  O
ATOM  1698  CB  GLU B 60   10.956  -1.377 99.375 1.00 30.04   C
ATOM  1699  CG  GLU B 60   12.096  -0.400 99.244 1.00 33.08   C
ATOM  1700  CD  GLU B 60   11.666   1.026 99.505 1.00 35.77   C
ATOM  1701  OE1 GLU B 60   10.703   1.487 98.861 1.00 37.27   O
ATOM  1702  OE2 GLU B 60   12.291   1.691 100.357 1.00 37.28  O
ATOM  1703  N   TYR B 61   13.445  -3.955 99.925 1.00 27.51   N
ATOM  1704  CA  TYR B 61   14.523  -4.321 100.845 1.00 26.91  C
ATOM  1705  C   TYR B 61   15.384  -3.093 101.157 1.00 27.18  C
ATOM  1706  O   TYR B 61   15.601  -2.770 102.317 1.00 24.54  O
ATOM  1707  CB  TYR B 61   15.409  -5.424 100.241 1.00 25.34  C
ATOM  1708  CG  TYR B 61   14.644  -6.599 99.686 1.00 23.96   C
ATOM  1709  CD1 TYR B 61   14.470  -6.753 98.310 1.00 23.62   C
ATOM  1710  CD2 TYR B 61   14.059  -7.540 100.532 1.00 23.24  C
ATOM  1711  CE1 TYR B 61   13.737  -7.814 97.791 1.00 22.83   C
ATOM  1712  CE2 TYR B 61   13.321  -8.601 100.024 1.00 23.69  C
ATOM  1713  CZ  TYR B 61   13.167  -8.734 98.658 1.00 23.37   C
ATOM  1714  OH  TYR B 61   12.452  -9.808 98.175 1.00 23.82   O
ATOM  1715  N   SER B 62   15.854  -2.419 100.105 1.00 29.35  N
ATOM  1716  CA  SER B 62   16.691  -1.227 100.240 1.00 31.06  C
ATOM  1717  C   SER B 62   16.212  -0.133 99.296 1.00 31.66   C
ATOM  1718  O   SER B 62   15.354  -0.366 98.454 1.00 31.17   O
ATOM  1719  CB  SER B 62   18.153  -1.550 99.914 1.00 32.00   C
ATOM  1720  OG  SER B 62   18.978  -1.392 101.050 1.00 31.84  O
ATOM  1721  N   SER B 63   16.797   1.055 99.424 1.00 32.00   N
ATOM  1722  CA  SER B 63   16.409   2.187 98.596 1.00 32.39   C
ATOM  1723  C   SER B 63   16.284   1.847 97.102 1.00 31.21   C
ATOM  1724  O   SER B 63   15.239   2.082 96.482 1.00 33.08   O
ATOM  1725  CB  SER B 63   17.391   3.333 98.790 1.00 33.46   C
ATOM  1726  OG  SER B 63   18.667   2.991 98.266 1.00 37.88   O
ATOM  1727  N   GLY B 64   17.333   1.299 96.521 1.00 28.40   N
ATOM  1728  CA  GLY B 64   17.263   0.985 95.109 1.00 26.47   C
ATOM  1729  C   GLY B 64   17.292  -0.498 94.813 1.00 24.74   C
ATOM  1730  O   GLY B 64   17.810  -0.917 93.781 1.00 24.90   O
ATOM  1731  N   ARG B 65   16.747  -1.290 95.726 1.00 22.73   N
ATOM  1732  CA  ARG B 65   16.708  -2.730 95.556 1.00 22.68   C
ATOM  1733  C   ARG B 65   15.415  -3.266 96.138 1.00 22.62   C
ATOM  1734  O   ARG B 65   15.298  -3.484 97.342 1.00 22.28   O
ATOM  1735  CB  ARG B 65   17.905  -3.395 96.252 1.00 22.67   C
ATOM  1736  CG  ARG B 65   17.930  -4.927 96.171 1.00 21.91   C
ATOM  1737  CD  ARG B 65   19.177  -5.516 96.852 1.00 19.71   C
ATOM  1738  NE  ARG B 65   19.125  -5.420 98.303 1.00 21.30   N
ATOM  1739  CZ  ARG B 65   18.501  -6.289 99.095 1.00 22.37   C
ATOM  1740  NH1 ARG B 65   17.872  -7.338 98.580 1.00 23.22   N
ATOM  1741  NH2 ARG B 65   18.491  -6.101 100.409 1.00 23.11  N
ATOM  1742  N   ASN B 66   14.430  -3.473 95.282 1.00 23.50   N
ATOM  1743  CA  ASN B 66   13.170  -3.978 95.780 1.00 24.38   C

ATOM  4928  N   LEU D 90   -5.196 -1.625  5.640 1.00 23.01   N
ATOM  4929  CA  LEU D 90   -6.576 -1.201  5.438 1.00 24.23   C
ATOM  4930  C   LEU D 90   -7.030 -1.713  4.100 1.00 24.86   C
ATOM  4931  O   LEU D 90   -6.228 -1.826  3.171 1.00 26.68   O
ATOM  4932  CB  LEU D 90   -6.663  0.331  5.398 1.00 24.72   C
ATOM  4933  CG  LEU D 90   -6.040  1.111  6.544 1.00 27.77   C
ATOM  4934  CD1 LEU D 90   -6.350  2.609  6.426 1.00 27.38   C
ATOM  4935  CD2 LEU D 90   -6.585  0.539  7.856 1.00 28.43   C
ATOM  4936  N   GLU D 91   -8.312 -2.003  3.992 1.00 24.69   N
ATOM  4937  CA  GLU D 91   -8.868 -2.467  2.739 1.00 24.64   C
ATOM  4938  C   GLU D 91  -10.377 -2.298  2.752 1.00 24.73   C
ATOM  4939  O   GLU D 91  -11.036 -2.552  3.762 1.00 23.58   O
ATOM  4940  CB  GLU D 91   -8.496 -3.927  2.495 1.00 24.28   C
ATOM  4941  CG  GLU D 91   -9.217 -4.919  3.365 1.00 27.37   C
ATOM  4942  CD  GLU D 91   -9.147 -6.320  2.798 1.00 30.51   C
ATOM  4943  OE1 GLU D 91   -9.684 -6.558  1.691 1.00 30.18   O
ATOM  4944  OE2 GLU D 91   -8.542 -7.196  3.466 1.00 32.94   O
ATOM  4945  N   ASP D 92  -10.912 -1.846  1.626 1.00 25.02   N
ATOM  4946  CA  ASP D 92  -12.345 -1.646  1.465 1.00 26.21   C
ATOM  4947  C   ASP D 92  -12.654 -1.864 -0.011 1.00 28.21   C
ATOM  4948  O   ASP D 92  -11.786 -1.680 -0.869 1.00 27.74   O
ATOM  4949  CB  ASP D 92  -12.724 -0.220  1.877 1.00 24.31   C
ATOM  4950  CG  ASP D 92  -14.184 -0.078  2.178 1.00 23.69   C
ATOM  4951  OD1 ASP D 92  -14.987 -0.889  1.652 1.00 25.18   O
ATOM  4952  OD2 ASP D 92  -14.538  0.855  2.933 1.00 22.42   O
ATOM  4953  N   GLU D 93  -13.888 -2.264 -0.313 1.00 30.66   N
ATOM  4954  CA  GLU D 93  -14.317 -2.500 -1.687 1.00 31.01   C
ATOM  4955  C   GLU D 93  -15.321 -1.418 -2.108 1.00 31.20   C
ATOM  4956  O   GLU D 93  -15.588 -1.224 -3.297 1.00 31.70   O
ATOM  4957  CB  GLU D 93  -14.944 -3.894 -1.784 1.00 31.95   C
ATOM  4958  CG  GLU D 93  -15.135 -4.403 -3.201 1.00 35.86   C
ATOM  4959  CD  GLU D 93  -13.830 -4.480 -3.991 1.00 37.24   C
ATOM  4960  OE1 GLU D 93  -12.832 -5.005 -3.452 1.00 36.32   O
ATOM  4961  OE2 GLU D 93  -13.817 -4.027 -5.161 1.00 37.84   O
ATOM  4962  N   HIS D 94  -15.867 -0.708 -1.123 1.00 31.61   N
ATOM  4963  CA  HIS D 94  -16.845  0.355 -1.384 1.00 32.25   C
ATOM  4964  C   HIS D 94  -16.499  1.613 -0.565 1.00 31.19   C
ATOM  4965  O   HIS D 94  -17.380  2.314 -0.059 1.00 31.14   O
ATOM  4966  CB  HIS D 94  -18.259 -0.135 -1.041 1.00 32.07   C
ATOM  4967  CG  HIS D 94  -18.619 -1.440 -1.685 1.00 34.60   C
ATOM  4968  ND1 HIS D 94  -18.767 -1.595 -3.046 1.00 37.26   N
ATOM  4969  CD2 HIS D 94  -18.854 -2.661 -1.147 1.00 35.69   C
ATOM  4970  CE1 HIS D 94  -19.075 -2.851 -3.321 1.00 37.02   C
ATOM  4971  NE2 HIS D 94  -19.132 -3.523 -2.184 1.00 36.28   N
ATOM  4972  N   ALA D 95  -15.208  1.891 -0.455 1.00 30.02   N
ATOM  4973  CA  ALA D 95  -14.752  3.055  0.295 1.00 29.72   C
ATOM  4974  C   ALA D 95  -15.146  4.368 -0.384 1.00 28.99   C
ATOM  4975  O   ALA D 95  -15.059  4.508 -1.606 1.00 29.53   O
ATOM  4976  CB  ALA D 95  -13.228  2.989  0.477 1.00 28.30   C
ATOM  4977  N   ALA D 96  -15.581  5.326  0.413 1.00 28.18   N
ATOM  4978  CA  ALA D 96  -15.975  6.620 -0.106 1.00 28.95   C
ATOM  4979  C   ALA D 96  -14.742  7.491 -0.342 1.00 30.04   C
ATOM  4980  O   ALA D 96  -14.801  8.516 -1.025 1.00 30.87   O
ATOM  4981  CB  ALA D 96  -16.905  7.307  0.870 1.00 26.08   C
ATOM  4982  N   ALA D 97  -13.615  7.084  0.225 1.00 30.90   N
ATOM  4983  CA  ALA D 97  -12.381  7.841  0.067 1.00 31.82   C
ATOM  4984  C   ALA D 97  -11.215  6.910 -0.270 1.00 31.92   C
ATOM  4985  O   ALA D 97  -11.344  5.692 -0.167 1.00 32.61   O
ATOM  4986  CB  ALA D 97  -12.095  8.617  1.347 1.00 31.30   C
ATOM  4987  N   HIS D 98  -10.085  7.483 -0.686 1.00 32.37   N
ATOM  4988  CA  HIS D 98   -8.905  6.681 -1.012 1.00 31.34   C
ATOM  4989  C   HIS D 98   -8.157  6.281  0.246 1.00 29.98   C
ATOM  4990  O   HIS D 98   -8.282  6.936  1.282 1.00 28.69   O
ATOM  4991  CB  HIS D 98   -7.967  7.445 -1.932 1.00 32.17   C
ATOM  4992  CG  HIS D 98   -8.582  7.796 -3.246 1.00 34.57   C
ATOM  4993  ND1 HIS D 98   -7.834  8.167 -4.344 1.00 35.45   N
ATOM  4994  CD2 HIS D 98   -9.877  7.836 -3.638 1.00 35.43   C
ATOM  4995  CE1 HIS D 98   -8.648  8.416 -5.358 1.00 35.00   C
ATOM  4996  NE2 HIS D 98   -9.892  8.222 -4.958 1.00 34.24   N
ATOM  4997  N   ALA D 99   -7.381  5.207  0.130 1.00 29.29   N
ATOM  4998  CA  ALA D 99   -6.600  4.667  1.243 1.00 30.18   C
ATOM  4999  C   ALA D 99   -5.827  5.738  2.005 1.00 30.52   C
ATOM  5000  O   ALA D 99   -5.724  5.680  3.229 1.00 30.28   O
ATOM  5001  CB  ALA D 99   -5.635  3.589  0.722 1.00 29.20   C
ATOM  5002  N   GLU D 100  -5.294  6.715  1.277 1.00 31.39   N
ATOM  5003  CA  GLU D 100  -4.518  7.790  1.888 1.00 33.27   C
ATOM  5004  C   GLU D 100  -5.348  8.627  2.856 1.00 34.66   C
ATOM  5005  O   GLU D 100  -4.874  9.045  3.918 1.00 34.48   O
ATOM  5006  CB  GLU D 100  -3.906  8.681  0.796 1.00 33.32   C
ATOM  5007  CG  GLU D 100  -2.776  7.996 -0.008 1.00 33.33   C
ATOM  5008  CD  GLU D 100  -3.242  7.372 -1.322 1.00 33.29   C
ATOM  5009  OE1 GLU D 100  -4.453  7.128 -1.470 1.00 31.47   O
ATOM  5010  OE2 GLU D 100  -2.383  7.117 -2.207 1.00 34.27   O
ATOM  5011  N   GLU D 101  -6.601  8.859  2.490 1.00 35.73   N
ATOM  5012  CA  GLU D 101  -7.487  9.641  3.325 1.00 35.60   C
ATOM  5013  C   GLU D 101  -7.905  8.812  4.513 1.00 33.98   C
```

FIG. 6 (con't)

| | | | | | |
|---|---|---|---|---|---|
| ATOM 1744 C ASN B 66 | 12.524 -4.973 94.840 1.00 22.48 | C | ATOM 5014 O GLU D 101 | -7.891 9.289 5.645 1.00 36.03 | O |
| ATOM 1745 O ASN B 66 | 12.683 -4.876 93.632 1.00 23.32 | O | ATOM 5015 CB GLU D 101 | -8.729 10.051 2.528 1.00 38.48 | C |
| ATOM 1746 CB ASN B 66 | 12.225 -2.808 96.057 1.00 25.89 | C | ATOM 5016 CG GLU D 101 | -8.428 10.771 1.203 1.00 42.71 | C |
| ATOM 1747 CG ASN B 66 | 12.275 -1.763 94.983 1.00 25.63 | C | ATOM 5017 CD GLU D 101 | -9.666 10.954 0.325 1.00 46.09 | C |
| ATOM 1748 OD1 ASN B 66 | 13.293 -1.102 94.782 1.00 27.35 | O | ATOM 5018 OE1 GLU D 101 | -10.671 11.471 0.863 1.00 47.74 | O |
| ATOM 1749 ND2 ASN B 66 | 11.170 -1.595 94.284 1.00 29.96 | N | ATOM 5019 OE2 GLU D 101 | -9.643 10.600 -0.890 1.00 43.74 | O |
| ATOM 1750 N LYS B 67 | 11.817 -5.939 95.419 1.00 22.30 | N | ATOM 5020 N ALA D 102 | -8.267 7.564 4.256 1.00 32.47 | N |
| ATOM 1751 CA LYS B 67 | 11.117 -6.974 94.666 1.00 21.90 | C | ATOM 5021 CA ALA D 102 | -8.736 6.667 5.316 1.00 31.36 | C |
| ATOM 1752 C LYS B 67 | 9.845 -6.372 94.096 1.00 22.07 | C | ATOM 5022 C ALA D 102 | -7.753 6.478 6.445 1.00 29.80 | C |
| ATOM 1753 O LYS B 67 | 8.972 -5.947 94.852 1.00 22.80 | O | ATOM 5023 O ALA D 102 | -8.152 6.310 7.593 1.00 28.93 | O |
| ATOM 1754 CB LYS B 67 | 10.730 -8.129 95.586 1.00 21.10 | C | ATOM 5024 CB ALA D 102 | -9.095 5.302 4.725 1.00 32.44 | C |
| ATOM 1755 CG LYS B 67 | 10.081 -9.302 94.875 1.00 21.44 | C | ATOM 5025 N PHE D 103 | -6.466 6.496 6.111 1.00 28.82 | N |
| ATOM 1756 CD LYS B 67 | 8.796 -9.734 95.563 1.00 20.82 | C | ATOM 5026 CA PHE D 103 | -5.420 6.299 7.098 1.00 27.79 | C |
| ATOM 1757 CE LYS B 67 | 8.316 -11.064 95.016 1.00 23.26 | C | ATOM 5027 C PHE D 103 | -5.390 7.399 8.154 1.00 28.31 | C |
| ATOM 1758 NZ LYS B 67 | 9.352 -12.091 95.303 1.00 23.48 | N | ATOM 5028 O PHE D 103 | -5.544 7.136 9.344 1.00 28.69 | O |
| ATOM 1759 N THR B 68 | 9.741 -6.352 92.775 1.00 21.38 | N | ATOM 5029 CB PHE D 103 | -4.057 6.215 6.401 1.00 26.08 | C |
| ATOM 1760 CA THR B 68 | 8.581 -5.792 92.092 1.00 21.28 | C | ATOM 5030 CG PHE D 103 | -2.917 5.963 7.338 1.00 25.06 | C |
| ATOM 1761 C THR B 68 | 7.728 -6.843 91.413 1.00 19.26 | C | ATOM 5031 CD1 PHE D 103 | -2.685 4.687 7.845 1.00 24.78 | C |
| ATOM 1762 O THR B 68 | 8.221 -7.894 91.008 1.00 18.73 | O | ATOM 5032 CD2 PHE D 103 | -2.115 7.017 7.780 1.00 24.84 | C |
| ATOM 1763 CB THR B 68 | 9.043 -4.750 91.044 1.00 23.67 | C | ATOM 5033 CE1 PHE D 103 | -1.678 4.461 8.780 1.00 23.45 | C |
| ATOM 1764 OG1 THR B 68 | 8.885 -3.436 91.599 1.00 27.35 | O | ATOM 5034 CE2 PHE D 103 | -1.105 6.809 8.717 1.00 24.39 | C |
| ATOM 1765 CG2 THR B 68 | 8.248 -4.851 89.756 1.00 24.64 | C | ATOM 5035 CZ PHE D 103 | -0.886 5.528 9.218 1.00 25.36 | C |
| ATOM 1766 N PHE B 69 | 6.433 -6.563 91.313 1.00 19.46 | N | ATOM 5036 N PHE D 104 | -5.195 8.633 7.712 1.00 29.33 | N |
| ATOM 1767 CA PHE B 69 | 5.505 -7.474 90.645 1.00 18.31 | C | ATOM 5037 CA PHE D 104 | -5.122 9.769 8.610 1.00 30.61 | C |
| ATOM 1768 C PHE B 69 | 4.191 -6.736 90.357 1.00 16.79 | C | ATOM 5038 C PHE D 104 | -6.435 10.152 9.279 1.00 33.04 | C |
| ATOM 1769 O PHE B 69 | 3.571 -6.205 91.260 1.00 16.15 | O | ATOM 5039 O PHE D 104 | -6.468 11.064 10.109 1.00 33.27 | O |
| ATOM 1770 CB PHE B 69 | 5.241 -8.716 91.493 1.00 17.28 | C | ATOM 5040 CB PHE D 104 | -4.555 10.976 7.866 1.00 29.86 | C |
| ATOM 1771 CG PHE B 69 | 4.606 -9.849 90.723 1.00 17.46 | C | ATOM 5041 CG PHE D 104 | -3.088 10.868 7.570 1.00 26.80 | C |
| ATOM 1772 CD1 PHE B 69 | 5.388 -10.852 90.146 1.00 19.90 | C | ATOM 5042 CD1 PHE D 104 | -2.605 11.142 6.297 1.00 25.55 | C |
| ATOM 1773 CD2 PHE B 69 | 3.231 -9.883 90.527 1.00 18.31 | C | ATOM 5043 CD2 PHE D 104 | -2.183 10.522 8.574 1.00 26.17 | C |
| ATOM 1774 CE1 PHE B 69 | 4.805 -11.879 89.369 1.00 22.06 | C | ATOM 5044 CE1 PHE D 104 | -1.246 11.077 6.019 1.00 25.26 | C |
| ATOM 1775 CE2 PHE B 69 | 2.634 -10.898 89.757 1.00 21.88 | C | ATOM 5045 CE2 PHE D 104 | -0.817 10.452 8.308 1.00 24.60 | C |
| ATOM 1776 CZ PHE B 69 | 3.427 -11.897 89.175 1.00 22.21 | C | ATOM 5046 CZ PHE D 104 | -0.349 10.730 7.025 1.00 25.67 | C |
| ATOM 1777 N LEU B 70 | 3.767 -6.718 89.088 1.00 16.55 | N | ATOM 5047 N ASN D 105 | -7.513 9.463 8.928 1.00 35.83 | N |
| ATOM 1778 CA LEU B 70 | 2.538 -6.036 88.733 1.00 15.10 | C | ATOM 5048 CA ASN D 105 | -8.810 9.772 9.524 1.00 39.11 | C |
| ATOM 1779 C LEU B 70 | 1.833 -6.652 87.532 1.00 16.49 | C | ATOM 5049 C ASN D 105 | -9.295 8.750 10.541 1.00 39.75 | C |
| ATOM 1780 O LEU B 70 | 2.472 -6.932 86.508 1.00 15.21 | O | ATOM 5050 O ASN D 105 | -10.215 9.035 11.304 1.00 41.66 | O |
| ATOM 1781 CB LEU B 70 | 2.831 -4.563 88.451 1.00 15.47 | C | ATOM 5051 CB ASN D 105 | -9.871 9.938 8.427 1.00 40.66 | C |
| ATOM 1782 CG LEU B 70 | 1.660 -3.602 88.247 1.00 17.39 | C | ATOM 5052 CG ASN D 105 | -9.664 11.198 7.599 1.00 42.76 | C |
| ATOM 1783 CD1 LEU B 70 | 2.093 -2.184 88.562 1.00 19.71 | C | ATOM 5053 OD1 ASN D 105 | -8.765 12.001 7.875 1.00 43.46 | O |
| ATOM 1784 CD2 LEU B 70 | 1.181 -3.688 86.818 1.00 16.56 | C | ATOM 5054 ND2 ASN D 105 | -10.506 11.385 6.587 1.00 41.71 | N |
| ATOM 1785 N CYS B 71 | 0.521 -6.886 87.661 1.00 16.69 | N | ATOM 5055 N THR D 106 | -8.683 7.573 10.566 1.00 40.22 | N |
| ATOM 1786 CA CYS B 71 | -0.301 -7.417 86.567 1.00 17.53 | C | ATOM 5056 CA THR D 106 | -9.099 6.540 11.509 1.00 40.81 | C |
| ATOM 1787 C CYS B 71 | -1.159 -6.278 85.981 1.00 18.34 | C | ATOM 5057 C THR D 106 | -7.936 5.791 12.142 1.00 40.87 | C |
| ATOM 1788 O CYS B 71 | -1.671 -5.415 86.704 1.00 18.50 | O | ATOM 5058 O THR D 106 | -7.995 5.446 13.315 1.00 40.74 | O |
| ATOM 1789 CB CYS B 71 | -1.224 -8.543 87.047 1.00 18.69 | C | ATOM 5059 CB THR D 106 | -10.047 5.511 10.835 1.00 41.86 | C |
| ATOM 1790 SG CYS B 71 | -0.411 -10.128 87.416 1.00 20.26 | S | ATOM 5060 OG1 THR D 106 | -9.513 5.123 9.566 1.00 41.48 | O |
| ATOM 1791 N TYR B 72 | -1.350 -6.283 84.671 1.00 18.23 | N | ATOM 5061 CG2 THR D 106 | -11.442 6.103 10.638 1.00 42.28 | C |
| ATOM 1792 CA TYR B 72 | -2.113 -5.213 84.073 1.00 18.50 | C | ATOM 5062 N ILE D 107 | -6.877 5.543 11.364 1.00 41.67 | N |
| ATOM 1793 C TYR B 72 | -2.944 -5.650 82.883 1.00 19.73 | C | ATOM 5063 CA ILE D 107 | -5.698 4.826 11.856 1.00 40.54 | C |
| ATOM 1794 O TYR B 72 | -2.817 -6.772 82.388 1.00 20.04 | O | ATOM 5064 C ILE D 107 | -4.843 5.715 12.770 1.00 41.10 | C |
| ATOM 1795 CB TYR B 72 | -1.176 -4.073 83.665 1.00 15.86 | C | ATOM 5065 O ILE D 107 | -4.570 5.356 13.915 1.00 41.26 | O |
| ATOM 1796 CG TYR B 72 | -0.206 -4.440 82.567 1.00 15.74 | C | ATOM 5066 CB ILE D 107 | -4.840 4.303 10.685 1.00 39.64 | C |
| ATOM 1797 CD1 TYR B 72 | -0.592 -4.407 81.223 1.00 17.04 | C | ATOM 5067 CG1 ILE D 107 | -5.732 3.590 9.665 1.00 39.72 | C |
| ATOM 1798 CD2 TYR B 72 | 1.086 -4.850 82.861 1.00 12.50 | C | ATOM 5068 CG2 ILE D 107 | -3.779 3.338 11.196 1.00 39.06 | C |
| ATOM 1799 CE1 TYR B 72 | 0.298 -4.776 80.212 1.00 15.53 | C | ATOM 5069 CD1 ILE D 107 | -6.719 2.634 10.284 1.00 39.09 | C |
| ATOM 1800 CE2 TYR B 72 | 1.969 -5.216 81.866 1.00 12.74 | C | ATOM 5070 N LEU D 108 | -4.423 6.872 12.269 1.00 41.03 | N |
| ATOM 1801 CZ TYR B 72 | 1.573 -5.174 80.547 1.00 13.77 | C | ATOM 5071 CA LEU D 108 | -3.618 7.794 13.055 1.00 41.53 | C |
| ATOM 1802 OH TYR B 72 | 2.490 -5.498 79.572 1.00 16.57 | O | ATOM 5072 C LEU D 108 | -4.276 9.163 13.122 1.00 43.06 | C |
| ATOM 1803 N VAL B 73 | -3.798 -4.739 82.432 1.00 19.50 | N | ATOM 5073 O LEU D 108 | -3.741 10.154 12.615 1.00 42.79 | O |
| ATOM 1804 CA VAL B 73 | -4.666 -4.967 81.300 1.00 19.35 | C | ATOM 5074 CB LEU D 108 | -2.224 7.941 12.454 1.00 41.75 | C |
| ATOM 1805 C VAL B 73 | -4.850 -3.616 80.628 1.00 20.74 | C | ATOM 5075 CG LEU D 108 | -1.106 7.075 13.025 1.00 41.12 | C |
| ATOM 1806 O VAL B 73 | -5.144 -2.627 81.294 1.00 20.41 | O | ATOM 5076 CD1 LEU D 108 | 0.229 7.486 12.413 1.00 40.73 | C |
| ATOM 1807 CB VAL B 73 | -6.056 -5.510 81.731 1.00 19.58 | C | ATOM 5077 CD2 LEU D 108 | -1.060 7.267 14.523 1.00 41.36 | C |
| ATOM 1808 CG1 VAL B 73 | -7.004 -5.562 80.545 1.00 17.68 | C | ATOM 5078 N PRO D 109 | -5.462 9.239 13.741 1.00 44.82 | N |
| ATOM 1809 CG2 VAL B 73 | -5.919 -6.906 82.305 1.00 19.65 | C | ATOM 5079 CA PRO D 109 | -6.183 10.506 13.865 1.00 45.65 | C |
| ATOM 1810 N VAL B 74 | -4.657 -3.578 79.310 1.00 21.21 | N | ATOM 5080 C PRO D 109 | -5.446 11.428 14.794 1.00 46.23 | C |
| ATOM 1811 CA VAL B 74 | -4.824 -2.352 78.542 1.00 22.37 | C | ATOM 5081 O PRO D 109 | -5.317 12.610 14.512 1.00 47.04 | O |
| ATOM 1812 C VAL B 74 | -5.949 -2.488 77.491 1.00 24.19 | C | ATOM 5082 CB PRO D 109 | -7.527 10.088 14.438 1.00 44.96 | C |
| ATOM 1813 O VAL B 74 | -6.021 -3.481 76.770 1.00 24.68 | O | ATOM 5083 CG PRO D 109 | -7.695 8.709 13.919 1.00 46.29 | C |
| ATOM 1814 CB VAL B 74 | -3.515 -1.963 77.827 1.00 21.61 | C | ATOM 5084 CD PRO D 109 | -6.327 8.126 14.154 1.00 44.99 | C |
| ATOM 1815 CG1 VAL B 74 | -3.688 -0.666 77.105 1.00 20.37 | C | ATOM 5085 N ALA D 110 | -4.961 10.876 15.900 1.00 47.13 | N |
| ATOM 1816 CG2 VAL B 74 | -2.399 -1.820 78.823 1.00 20.61 | C | ATOM 5086 CA ALA D 110 | -4.245 11.662 16.900 1.00 47.85 | C |
| ATOM 1817 N GLU B 75 | -6.823 -1.483 77.428 1.00 26.60 | N | ATOM 5087 C ALA D 110 | -2.742 11.395 16.908 1.00 47.54 | C |
| ATOM 1818 CA GLU B 75 | -7.941 -1.449 76.477 1.00 29.66 | C | ATOM 5088 O ALA D 110 | -2.292 10.312 16.537 1.00 47.39 | O |
| ATOM 1819 C GLU B 75 | -7.975 -0.038 75.876 1.00 30.33 | C | ATOM 5089 CB ALA D 110 | -4.826 11.375 18.282 1.00 48.34 | C |
| ATOM 1820 O GLU B 75 | -8.263 0.917 76.586 1.00 32.01 | O | ATOM 5090 N PHE D 111 | -1.977 12.394 17.343 1.00 47.67 | N |
| ATOM 1821 CB GLU B 75 | -9.260 -1.722 77.185 1.00 30.43 | C | ATOM 5091 CA PHE D 111 | -0.523 12.285 17.421 1.00 47.91 | C |
| ATOM 1822 CG GLU B 75 | -9.271 -2.982 78.045 1.00 35.94 | C | ATOM 5092 C PHE D 111 | -0.031 12.816 18.763 1.00 48.30 | C |
| ATOM 1823 CD GLU B 75 | -9.778 -4.207 77.313 1.00 39.42 | C | ATOM 5093 O PHE D 111 | -0.426 13.899 19.194 1.00 49.07 | O |
| ATOM 1824 OE1 GLU B 75 | -10.808 -4.085 76.601 1.00 43.71 | O | ATOM 5094 CB PHE D 111 | 0.148 13.080 16.300 1.00 47.50 | C |
| ATOM 1825 OE2 GLU B 75 | -9.177 -5.298 77.444 1.00 39.81 | O | ATOM 5095 CG PHE D 111 | -0.154 12.560 14.921 1.00 47.00 | C |
| ATOM 1826 N ALA B 76 | -7.698 0.091 74.583 1.00 30.93 | N | ATOM 5096 CD1 PHE D 111 | -1.154 13.145 14.147 1.00 46.49 | C |
| ATOM 1827 CA ALA B 76 | -7.680 1.392 73.946 1.00 33.80 | C | ATOM 5097 CD2 PHE D 111 | 0.556 11.477 14.401 1.00 46.33 | C |
| ATOM 1828 C ALA B 76 | -8.639 1.461 72.771 1.00 36.71 | C | ATOM 5098 CE1 PHE D 111 | -1.445 12.658 12.867 1.00 46.89 | C |
| ATOM 1829 O ALA B 76 | -8.558 0.654 71.844 1.00 37.57 | O | ATOM 5099 CE2 PHE D 111 | 0.277 10.979 13.122 1.00 47.24 | C |

FIG. 6 (con't)

```
ATOM 1830  CB  ALA B 76   -6.266   1.745  73.481  1.00 33.29  C
ATOM 1831  N   GLN B 77   -9.548   2.428  72.816  1.00 39.33  N
ATOM 1832  CA  GLN B 77  -10.516   2.628  71.762  1.00 41.16  C
ATOM 1833  C   GLN B 77  -10.319   4.010  71.166  1.00 42.83  C
ATOM 1834  O   GLN B 77  -10.333   5.015  71.875  1.00 41.75  O
ATOM 1835  CB  GLN B 77  -11.925   2.478  72.316  1.00 42.02  C
ATOM 1836  CG  GLN B 77  -12.197   1.082  72.832  1.00 45.11  C
ATOM 1837  CD  GLN B 77  -13.652   0.683  72.699  1.00 47.38  C
ATOM 1838  OE1 GLN B 77  -14.497   1.104  73.491  1.00 49.70  O
ATOM 1839  NE2 GLN B 77  -13.959  -0.123  71.681  1.00 46.60  N
ATOM 1840  N   GLY B 78  -10.133   4.051  69.851  1.00 45.23  N
ATOM 1841  CA  GLY B 78   -9.908   5.313  69.178  1.00 47.78  C
ATOM 1842  C   GLY B 78  -10.999   5.738  68.221  1.00 49.77  C
ATOM 1843  O   GLY B 78  -10.715   6.192  67.110  1.00 51.48  O
ATOM 1844  N   LYS B 79  -12.246   5.582  68.640  1.00 50.31  N
ATOM 1845  CA  LYS B 79  -13.388   5.987  67.829  1.00 50.85  C
ATOM 1846  C   LYS B 79  -13.117   6.011  66.320  1.00 49.98  C
ATOM 1847  O   LYS B 79  -12.771   7.050  65.754  1.00 49.90  O
ATOM 1848  CB  LYS B 79  -13.867   7.382  68.279  1.00 52.65  C
ATOM 1849  CG  LYS B 79  -13.036   8.044  69.399  1.00 53.98  C
ATOM 1850  CD  LYS B 79  -13.355   7.452  70.773  1.00 54.06  C
ATOM 1851  CE  LYS B 79  -12.190   7.595  71.752  1.00 54.11  C
ATOM 1852  NZ  LYS B 79  -11.762   9.005  71.973  1.00 53.73  N
ATOM 1853  N   GLY B 80  -13.277   4.868  65.666  1.00 49.05  N
ATOM 1854  CA  GLY B 80  -13.056   4.812  64.231  1.00 45.78  C
ATOM 1855  C   GLY B 80  -12.654   3.417  63.804  1.00 44.57  C
ATOM 1856  O   GLY B 80  -11.958   3.248  62.808  1.00 43.84  O
ATOM 1857  N   GLY B 81  -13.109   2.419  64.557  1.00 43.43  N
ATOM 1858  CA  GLY B 81  -12.767   1.044  64.257  1.00 41.67  C
ATOM 1859  C   GLY B 81  -11.477   0.587  64.939  1.00 40.48  C
ATOM 1860  O   GLY B 81  -11.248  -0.612  65.102  1.00 40.35  O
ATOM 1861  N   GLN B 82  -10.643   1.545  65.343  1.00 38.32  N
ATOM 1862  CA  GLN B 82   -9.369   1.247  65.988  1.00 37.07  C
ATOM 1863  C   GLN B 82   -9.536   0.827  67.442  1.00 34.54  C
ATOM 1864  O   GLN B 82   -9.903   1.626  68.299  1.00 32.52  O
ATOM 1865  CB  GLN B 82   -8.425   2.440  65.884  1.00 38.26  C
ATOM 1866  CG  GLN B 82   -9.085   3.770  66.137  1.00 42.25  C
ATOM 1867  CD  GLN B 82   -8.311   4.913  65.518  1.00 45.54  C
ATOM 1868  OE1 GLN B 82   -7.092   5.010  65.674  1.00 46.80  O
ATOM 1869  NE2 GLN B 82   -9.018   5.792  64.812  1.00 47.43  N
ATOM 1870  N   VAL B 83   -9.271  -0.453  67.691  1.00 31.57  N
ATOM 1871  CA  VAL B 83   -9.386  -1.036  69.010  1.00 29.10  C
ATOM 1872  C   VAL B 83   -8.035  -1.629  69.423  1.00 27.71  C
ATOM 1873  O   VAL B 83   -7.285  -2.104  68.580  1.00 26.66  O
ATOM 1874  CB  VAL B 83  -10.441  -2.146  69.021  1.00 28.90  C
ATOM 1875  CG1 VAL B 83  -10.574  -2.726  70.407  1.00 28.59  C
ATOM 1876  CG2 VAL B 83  -11.773  -1.597  68.539  1.00 30.37  C
ATOM 1877  N   GLN B 84   -7.730  -1.605  70.718  1.00 26.59  N
ATOM 1878  CA  GLN B 84   -6.462  -2.137  71.198  1.00 24.94  C
ATOM 1879  C   GLN B 84   -6.683  -2.831  72.526  1.00 24.72  C
ATOM 1880  O   GLN B 84   -7.332  -2.278  73.410  1.00 25.50  O
ATOM 1881  CB  GLN B 84   -5.483  -0.997  71.371  1.00 25.06  C
ATOM 1882  CG  GLN B 84   -4.109  -1.289  70.897  1.00 25.16  C
ATOM 1883  CD  GLN B 84   -3.364  -0.019  70.592  1.00 26.22  C
ATOM 1884  OE1 GLN B 84   -3.681   0.686  69.632  1.00 25.01  O
ATOM 1885  NE2 GLN B 84   -2.374   0.296  71.416  1.00 28.41  N
ATOM 1886  N   ALA B 85   -6.151  -4.036  72.689  1.00 23.24  N
ATOM 1887  CA  ALA B 85   -6.335  -4.756  73.950  1.00 22.14  C
ATOM 1888  C   ALA B 85   -5.139  -5.649  74.246  1.00 21.37  C
ATOM 1889  O   ALA B 85   -4.564  -6.239  73.338  1.00 22.65  O
ATOM 1890  CB  ALA B 85   -7.631  -5.583  73.896  1.00 20.00  C
ATOM 1891  N   SER B 86   -4.758  -5.749  75.512  1.00 21.18  N
ATOM 1892  CA  SER B 86   -3.630  -6.595  75.902  1.00 21.56  C
ATOM 1893  C   SER B 86   -3.618  -6.820  77.395  1.00 21.44  C
ATOM 1894  O   SER B 86   -4.322  -6.136  78.134  1.00 21.89  O
ATOM 1895  CB  SER B 86   -2.291  -5.958  75.488  1.00 21.65  C
ATOM 1896  OG  SER B 86   -2.095  -4.675  76.077  1.00 21.09  O
ATOM 1897  N   ARG B 87   -2.822  -7.786  77.835  1.00 22.70  N
ATOM 1898  CA  ARG B 87   -2.679  -8.053  79.264  1.00 24.84  C
ATOM 1899  C   ARG B 87   -1.325  -8.730  79.562  1.00 24.05  C
ATOM 1900  O   ARG B 87   -0.981  -9.742  78.959  1.00 24.65  O
ATOM 1901  CB  ARG B 87   -3.844  -8.908  79.761  1.00 26.91  C
ATOM 1902  CG  ARG B 87   -3.808 -10.333  79.289  1.00 30.39  C
ATOM 1903  CD  ARG B 87   -5.146 -11.015  79.496  1.00 35.17  C
ATOM 1904  NE  ARG B 87   -4.979 -12.451  79.694  1.00 38.13  N
ATOM 1905  CZ  ARG B 87   -5.863 -13.368  79.319  1.00 39.59  C
ATOM 1906  NH1 ARG B 87   -6.984 -13.004  78.714  1.00 40.31  N
ATOM 1907  NH2 ARG B 87   -5.628 -14.657  79.556  1.00 40.28  N
ATOM 1908  N   GLY B 88   -0.550  -8.151  80.473  1.00 22.82  N
ATOM 1909  CA  GLY B 88    0.730  -8.740  80.813  1.00 20.92  C
ATOM 1910  C   GLY B 88    1.085  -8.528  82.273  1.00 20.97  C
ATOM 1911  O   GLY B 88    0.209  -8.293  83.111  1.00 19.06  O
ATOM 1912  N   TYR B 89    2.373  -8.608  82.586  1.00 20.84  N
ATOM 1913  CA  TYR B 89    2.820  -8.397  83.953  1.00 21.58  C
ATOM 1914  C   TYR B 89    4.312  -8.055  83.996  1.00 21.11  C
ATOM 1915  O   TYR B 89    5.009  -8.215  83.004  1.00 19.77  O
ATOM 5100  CZ  PHE D 111  -0.727  11.571  12.351  1.00 47.42  C
ATOM 5101  N   ASP D 112   0.832  12.050  19.418  1.00 47.39  N
ATOM 5102  CA  ASP D 112   1.381  12.454  20.700  1.00 47.10  C
ATOM 5103  C   ASP D 112   2.499  13.461  20.434  1.00 46.65  C
ATOM 5104  O   ASP D 112   3.582  13.085  19.990  1.00 47.01  O
ATOM 5105  CB  ASP D 112   1.946  11.239  21.432  1.00 48.41  C
ATOM 5106  CG  ASP D 112   2.281  11.532  22.872  1.00 49.97  C
ATOM 5107  OD1 ASP D 112   2.815  12.633  23.149  1.00 51.38  O
ATOM 5108  OD2 ASP D 112   2.022  10.655  23.728  1.00 49.99  O
ATOM 5109  N   PRO D 113   2.251  14.755  20.707  1.00 46.07  N
ATOM 5110  CA  PRO D 113   3.218  15.841  20.502  1.00 44.56  C
ATOM 5111  C   PRO D 113   4.601  15.579  21.082  1.00 43.42  C
ATOM 5112  O   PRO D 113   5.569  16.251  20.722  1.00 42.30  O
ATOM 5113  CB  PRO D 113   2.531  17.033  21.159  1.00 45.28  C
ATOM 5114  CG  PRO D 113   1.075  16.752  20.884  1.00 46.11  C
ATOM 5115  CD  PRO D 113   0.988  15.284  21.252  1.00 46.00  C
ATOM 5116  N   ALA D 114   4.691  14.605  21.981  1.00 42.27  N
ATOM 5117  CA  ALA D 114   5.963  14.263  22.606  1.00 41.29  C
ATOM 5118  C   ALA D 114   6.758  13.283  21.764  1.00 40.46  C
ATOM 5119  O   ALA D 114   7.964  13.448  21.563  1.00 41.86  O
ATOM 5120  CB  ALA D 114   5.716  13.660  23.970  1.00 41.62  C
ATOM 5121  N   LEU D 115   6.078  12.253  21.281  1.00 38.75  N
ATOM 5122  CA  LEU D 115   6.712  11.226  20.471  1.00 36.71  C
ATOM 5123  C   LEU D 115   7.000  11.718  19.051  1.00 35.50  C
ATOM 5124  O   LEU D 115   6.284  12.556  18.508  1.00 35.06  O
ATOM 5125  CB  LEU D 115   5.801  10.001  20.404  1.00 36.65  C
ATOM 5126  CG  LEU D 115   5.216   9.479  21.717  1.00 34.16  C
ATOM 5127  CD1 LEU D 115   4.129   8.456  21.441  1.00 35.29  C
ATOM 5128  CD2 LEU D 115   6.321   8.878  22.530  1.00 34.35  C
ATOM 5129  N   ARG D 116   8.064  11.190  18.456  1.00 34.33  N
ATOM 5130  CA  ARG D 116   8.441  11.544  17.099  1.00 32.53  C
ATOM 5131  C   ARG D 116   7.966  10.380  16.238  1.00 30.98  C
ATOM 5132  O   ARG D 116   8.440   9.255  16.383  1.00 31.39  O
ATOM 5133  CB  ARG D 116   9.953  11.683  17.004  1.00 34.62  C
ATOM 5134  CG  ARG D 116  10.434  12.892  16.230  1.00 39.65  C
ATOM 5135  CD  ARG D 116   9.852  12.978  14.821  1.00 40.71  C
ATOM 5136  NE  ARG D 116  10.680  13.807  13.948  1.00 44.15  N
ATOM 5137  CZ  ARG D 116  11.867  13.438  13.468  1.00 45.54  C
ATOM 5138  NH1 ARG D 116  12.366  12.248  13.772  1.00 46.64  N
ATOM 5139  NH2 ARG D 116  12.558  14.255  12.681  1.00 46.93  N
ATOM 5140  N   TYR D 117   7.026  10.638  15.342  1.00 28.69  N
ATOM 5141  CA  TYR D 117   6.486   9.579  14.510  1.00 26.80  C
ATOM 5142  C   TYR D 117   7.199   9.351  13.189  1.00 27.00  C
ATOM 5143  O   TYR D 117   7.545  10.301  12.495  1.00 28.83  O
ATOM 5144  CB  TYR D 117   5.015   9.846  14.224  1.00 25.52  C
ATOM 5145  CG  TYR D 117   4.110   9.722  15.426  1.00 25.62  C
ATOM 5146  CD1 TYR D 117   4.002  10.749  16.369  1.00 25.59  C
ATOM 5147  CD2 TYR D 117   3.377   8.566  15.637  1.00 25.73  C
ATOM 5148  CE1 TYR D 117   3.177  10.613  17.498  1.00 25.34  C
ATOM 5149  CE2 TYR D 117   2.561   8.419  16.750  1.00 26.79  C
ATOM 5150  CZ  TYR D 117   2.464   9.437  17.678  1.00 26.04  C
ATOM 5151  OH  TYR D 117   1.677   9.243  18.795  1.00 27.27  O
ATOM 5152  N   ASN D 118   7.397   8.080  12.844  1.00 25.70  N
ATOM 5153  CA  ASN D 118   8.026   7.677  11.586  1.00 23.81  C
ATOM 5154  C   ASN D 118   7.089   6.810  10.900  1.00 22.97  C
ATOM 5155  O   ASN D 118   7.074   5.482  11.238  1.00 21.43  O
ATOM 5156  CB  ASN D 118   9.368   7.053  11.862  1.00 24.22  C
ATOM 5157  CG  ASN D 118  10.493   7.984  11.550  1.00 26.43  C
ATOM 5158  OD1 ASN D 118  11.131   7.839  10.518  1.00 30.15  O
ATOM 5159  ND2 ASN D 118  10.743   8.956  12.420  1.00 26.04  N
ATOM 5160  N   VAL D 119   6.312   7.138   9.929  1.00 20.36  N
ATOM 5161  CA  VAL D 119   5.364   6.296   9.244  1.00 18.63  C
ATOM 5162  C   VAL D 119   5.874   5.847   7.895  1.00 18.99  C
ATOM 5163  O   VAL D 119   6.528   6.612   7.193  1.00 19.17  O
ATOM 5164  CB  VAL D 119   4.026   7.030   9.040  1.00 18.53  C
ATOM 5165  CG1 VAL D 119   3.008   6.127   8.389  1.00 17.83  C
ATOM 5166  CG2 VAL D 119   3.502   7.511  10.368  1.00 17.97  C
ATOM 5167  N   THR D 120   5.574   4.597   7.536  1.00 18.75  N
ATOM 5168  CA  THR D 120   5.983   4.036   6.260  1.00 18.77  C
ATOM 5169  C   THR D 120   4.790   3.354   5.594  1.00 18.56  C
ATOM 5170  O   THR D 120   4.161   2.480   6.186  1.00 19.25  O
ATOM 5171  CB  THR D 120   7.101   3.005   6.448  1.00 19.04  C
ATOM 5172  OG1 THR D 120   8.230   3.628   7.070  1.00 20.70  O
ATOM 5173  CG2 THR D 120   7.537   2.455   5.119  1.00 18.68  C
ATOM 5174  N   TRP D 121   4.473   3.754   4.369  1.00 17.95  N
ATOM 5175  CA  TRP D 121   3.353   3.146   3.658  1.00 18.14  C
ATOM 5176  C   TRP D 121   3.801   2.229   2.523  1.00 18.31  C
ATOM 5177  O   TRP D 121   4.882   2.392   1.960  1.00 17.34  O
ATOM 5178  CB  TRP D 121   2.432   4.218   3.060  1.00 16.81  C
ATOM 5179  CG  TRP D 121   1.649   5.037   4.044  1.00 17.61  C
ATOM 5180  CD1 TRP D 121   1.508   4.811   5.385  1.00 19.04  C
ATOM 5181  CD2 TRP D 121   0.835   6.184   3.745  1.00 17.07  C
ATOM 5182  NE1 TRP D 121   0.650   5.738   5.939  1.00 15.46  N
ATOM 5183  CE2 TRP D 121   0.217   6.581   4.953  1.00 16.89  C
ATOM 5184  CE3 TRP D 121   0.549   6.896   2.569  1.00 16.39  C
ATOM 5185  CZ2 TRP D 121  -0.651   7.679   5.021  1.00 16.08  C
```

FIG. 6 (con't)

```
ATOM   1916  CB  TYR B  89      2.543  -9.652 84.786 1.00 21.43           C
ATOM   1917  CG  TYR B  89      3.631 -10.680 84.696 1.00 21.53           C
ATOM   1918  CD1 TYR B  89      4.393 -11.007 85.816 1.00 22.29           C
ATOM   1919  CD2 TYR B  89      3.917 -11.315 83.494 1.00 21.95           C
ATOM   1920  CE1 TYR B  89      5.417 -11.945 85.747 1.00 22.65           C
ATOM   1921  CE2 TYR B  89      4.940 -12.257 83.407 1.00 23.15           C
ATOM   1922  CZ  TYR B  89      5.688 -12.571 84.545 1.00 23.51           C
ATOM   1923  OH  TYR B  89      6.683 -13.528 84.504 1.00 22.15           O
ATOM   1924  N   LEU B  90      4.772  -7.583 85.153 1.00 22.66           N
ATOM   1925  CA  LEU B  90      6.165  -7.179 85.362 1.00 23.09           C
ATOM   1926  C   LEU B  90      6.627  -7.794 86.648 1.00 23.80           C
ATOM   1927  O   LEU B  90      5.830  -7.987 87.571 1.00 23.38           O
ATOM   1928  CB  LEU B  90      6.265  -5.655 85.528 1.00 24.70           C
ATOM   1929  CG  LEU B  90      5.642  -4.797 84.436 1.00 28.23           C
ATOM   1930  CD1 LEU B  90      5.962  -3.301 84.666 1.00 27.79           C
ATOM   1931  CD2 LEU B  90      6.174  -5.305 83.074 1.00 29.19           C
ATOM   1932  N   GLU B  91      7.917  -8.083 86.723 1.00 23.69           N
ATOM   1933  CA  GLU B  91      8.488  -8.646 87.927 1.00 23.61           C
ATOM   1934  C   GLU B  91     10.015  -8.494 87.922 1.00 23.57           C
ATOM   1935  O   GLU B  91     10.676  -8.689 86.900 1.00 21.44           O
ATOM   1936  CB  GLU B  91      8.088 -10.112 88.068 1.00 22.96           C
ATOM   1937  CG  GLU B  91      8.812 -11.055 87.143 1.00 26.61           C
ATOM   1938  CD  GLU B  91      8.754 -12.507 87.621 1.00 29.63           C
ATOM   1939  OE1 GLU B  91      9.308 -12.815 88.698 1.00 30.15           O
ATOM   1940  OE2 GLU B  91      8.151 -13.350 86.921 1.00 30.07           O
ATOM   1941  N   ASP B  92     10.554  -8.113 89.073 1.00 23.55           N
ATOM   1942  CA  ASP B  92     11.984  -7.930 89.225 1.00 25.71           C
ATOM   1943  C   ASP B  92     12.314  -8.240 90.680 1.00 27.32           C
ATOM   1944  O   ASP B  92     11.456  -8.098 91.556 1.00 27.13           O
ATOM   1945  CB  ASP B  92     12.373  -6.486 88.892 1.00 24.87           C
ATOM   1946  CG  ASP B  92     13.839  -6.333 88.612 1.00 24.80           C
ATOM   1947  OD1 ASP B  92     14.615  -7.194 89.085 1.00 27.35           O
ATOM   1948  OD2 ASP B  92     14.225  -5.356 87.928 1.00 23.80           O
ATOM   1949  N   GLU B  93     13.545  -8.673 90.934 1.00 29.32           N
ATOM   1950  CA  GLU B  93     13.983  -9.002 92.292 1.00 31.14           C
ATOM   1951  C   GLU B  93     15.003  -7.962 92.783 1.00 31.81           C
ATOM   1952  O   GLU B  93     15.283  -7.862 93.980 1.00 32.87           O
ATOM   1953  CB  GLU B  93     14.593 -10.404 92.304 1.00 32.68           C
ATOM   1954  CG  GLU B  93     14.796 -10.987 93.695 1.00 35.81           C
ATOM   1955  CD  GLU B  93     13.495 -11.115 94.463 1.00 37.16           C
ATOM   1956  OE1 GLU B  93     12.509 -11.587 93.861 1.00 37.11           O
ATOM   1957  OE2 GLU B  93     13.468 -10.757 95.666 1.00 36.62           O
ATOM   1958  N   HIS B  94     15.545  -7.183 91.852 1.00 31.80           N
ATOM   1959  CA  HIS B  94     16.513  -6.160 92.191 1.00 32.24           C
ATOM   1960  C   HIS B  94     16.165  -4.858 91.476 1.00 31.69           C
ATOM   1961  O   HIS B  94     17.043  -4.132 91.021 1.00 32.87           O
ATOM   1962  CB  HIS B  94     17.916  -6.628 91.795 1.00 32.09           C
ATOM   1963  CG  HIS B  94     18.269  -7.978 92.335 1.00 33.63           C
ATOM   1964  ND1 HIS B  94     18.398  -8.229 93.686 1.00 34.75           N
ATOM   1965  CD2 HIS B  94     18.506  -9.152 91.708 1.00 34.17           C
ATOM   1966  CE1 HIS B  94     18.704  -9.501 93.865 1.00 34.41           C
ATOM   1967  NE2 HIS B  94     18.776 -10.088 92.684 1.00 33.98           N
ATOM   1968  N   ALA B  95     14.879  -4.568 91.374 1.00 31.25           N
ATOM   1969  CA  ALA B  95     14.448  -3.344 90.702 1.00 30.66           C
ATOM   1970  C   ALA B  95     14.876  -2.081 91.465 1.00 29.97           C
ATOM   1971  O   ALA B  95     14.831  -2.022 92.696 1.00 30.16           O
ATOM   1972  CB  ALA B  95     12.927  -3.362 90.500 1.00 29.25           C
ATOM   1973  N   ALA B  96     15.299  -1.067 90.728 1.00 28.62           N
ATOM   1974  CA  ALA B  96     15.702   0.178 91.340 1.00 28.40           C
ATOM   1975  C   ALA B  96     14.472   1.043 91.654 1.00 29.99           C
ATOM   1976  O   ALA B  96     14.553   2.002 92.419 1.00 30.71           O
ATOM   1977  CB  ALA B  96     16.621   0.919 90.416 1.00 27.25           C
ATOM   1978  N   ALA B  97     13.331   0.692 91.065 1.00 30.19           N
ATOM   1979  CA  ALA B  97     12.094   1.440 91.273 1.00 30.32           C
ATOM   1980  C   ALA B  97     10.928   0.493 91.544 1.00 30.58           C
ATOM   1981  O   ALA B  97     11.045  -0.710 91.322 1.00 30.16           O
ATOM   1982  CB  ALA B  97     11.799   2.285 90.047 1.00 29.28           C
ATOM   1983  N   HIS B  98      9.804   1.037 92.024 1.00 31.20           N
ATOM   1984  CA  HIS B  98      8.615   0.228 92.307 1.00 30.17           C
ATOM   1985  C   HIS B  98      7.869  -0.086 91.026 1.00 29.50           C
ATOM   1986  O   HIS B  98      8.022   0.614 90.021 1.00 28.00           O
ATOM   1987  CB  HIS B  98      7.689   0.940 93.283 1.00 30.91           C
ATOM   1988  CG  HIS B  98      8.319   1.196 94.617 1.00 33.22           C
ATOM   1989  ND1 HIS B  98      7.587   1.489 95.749 1.00 32.52           N
ATOM   1990  CD2 HIS B  98      9.620   1.206 94.999 1.00 32.97           C
ATOM   1991  CE1 HIS B  98      8.408   1.665 96.767 1.00 32.55           C
ATOM   1992  NE2 HIS B  98      9.649   1.499 96.337 1.00 32.87           N
ATOM   1993  N   ALA B  99      7.061  -1.145 91.080 1.00 29.92           N
ATOM   1994  CA  ALA B  99      6.272  -1.613 89.941 1.00 29.60           C
ATOM   1995  C   ALA B  99      5.508  -0.490 89.272 1.00 29.58           C
ATOM   1996  O   ALA B  99      5.412  -0.449 88.043 1.00 30.39           O
ATOM   1997  CB  ALA B  99      5.311  -2.728 90.386 1.00 29.03           C
ATOM   1998  N   GLU B 100      4.968   0.425 90.069 1.00 30.76           N
ATOM   1999  CA  GLU B 100      4.199   1.556 89.536 1.00 32.10           C
ATOM   2000  C   GLU B 100      5.035   2.453 88.615 1.00 32.56           C
ATOM   2001  O   GLU B 100      4.548   2.941 87.593 1.00 31.67           O

ATOM   5186  CZ3 TRP D 121     -0.318   7.989  2.638 1.00 16.10           C
ATOM   5187  CH2 TRP D 121     -0.917   8.361  3.863 1.00 15.93           C
ATOM   5188  N   TYR D 122      2.944   1.263  2.207 1.00 18.79           N
ATOM   5189  CA  TYR D 122      3.182   0.332  1.108 1.00 17.67           C
ATOM   5190  C   TYR D 122      1.884   0.315  0.299 1.00 18.40           C
ATOM   5191  O   TYR D 122      0.924  -0.371  0.665 1.00 17.92           O
ATOM   5192  CB  TYR D 122      3.484  -1.068  1.620 1.00 18.25           C
ATOM   5193  CG  TYR D 122      4.826  -1.208  2.291 1.00 17.52           C
ATOM   5194  CD1 TYR D 122      4.973  -1.024  3.665 1.00 17.72           C
ATOM   5195  CD2 TYR D 122      5.948  -1.562  1.546 1.00 18.58           C
ATOM   5196  CE1 TYR D 122      6.210  -1.201  4.283 1.00 18.83           C
ATOM   5197  CE2 TYR D 122      7.182  -1.739  2.147 1.00 17.95           C
ATOM   5198  CZ  TYR D 122      7.310  -1.558  3.517 1.00 18.61           C
ATOM   5199  OH  TYR D 122      8.531  -1.738  4.118 1.00 19.82           O
ATOM   5200  N   VAL D 123      1.859   1.082 -0.784 1.00 16.86           N
ATOM   5201  CA  VAL D 123      0.690   1.170 -1.632 1.00 17.29           C
ATOM   5202  C   VAL D 123      1.021   0.697 -3.026 1.00 17.54           C
ATOM   5203  O   VAL D 123      2.187   0.638 -3.393 1.00 18.89           O
ATOM   5204  CB  VAL D 123      0.162   2.628 -1.778 1.00 16.51           C
ATOM   5205  CG1 VAL D 123     -1.157   2.752 -1.079 1.00 15.79           C
ATOM   5206  CG2 VAL D 123      1.156   3.621 -1.220 1.00 13.60           C
ATOM   5207  N   SER D 124     -0.010   0.383 -3.808 1.00 17.70           N
ATOM   5208  CA  SER D 124      0.166  -0.108 -5.172 1.00 18.25           C
ATOM   5209  C   SER D 124      0.535   1.020 -6.142 1.00 18.01           C
ATOM   5210  O   SER D 124      1.234   0.799 -7.129 1.00 18.83           O
ATOM   5211  CB  SER D 124     -1.118  -0.781 -5.638 1.00 15.66           C
ATOM   5212  OG  SER D 124     -2.162   0.165 -5.687 1.00 14.32           O
ATOM   5213  N   SER D 125      0.057   2.221 -5.867 1.00 17.80           N
ATOM   5214  CA  SER D 125      0.369   3.338 -6.731 1.00 18.16           C
ATOM   5215  C   SER D 125      0.495   4.623 -5.928 1.00 17.89           C
ATOM   5216  O   SER D 125     -0.056   4.734 -4.835 1.00 18.45           O
ATOM   5217  CB  SER D 125     -0.718   3.508 -7.790 1.00 19.02           C
ATOM   5218  OG  SER D 125     -1.945   3.847 -7.173 1.00 22.16           O
ATOM   5219  N   SER D 126      1.224   5.585 -6.480 1.00 18.08           N
ATOM   5220  CA  SER D 126      1.423   6.880 -5.838 1.00 17.96           C
ATOM   5221  C   SER D 126      0.082   7.582 -5.679 1.00 17.77           C
ATOM   5222  O   SER D 126     -0.866   7.299 -6.410 1.00 16.28           O
ATOM   5223  CB  SER D 126      2.360   7.754 -6.682 1.00 17.50           C
ATOM   5224  OG  SER D 126      1.783   8.121 -7.930 1.00 18.71           O
ATOM   5225  N   PRO D 127     -0.006   8.517 -4.731 1.00 18.97           N
ATOM   5226  CA  PRO D 127     -1.251   9.258 -4.482 1.00 21.04           C
ATOM   5227  C   PRO D 127     -1.658  10.157 -5.651 1.00 22.09           C
ATOM   5228  O   PRO D 127     -0.827  10.522 -6.483 1.00 22.72           O
ATOM   5229  CB  PRO D 127     -0.930  10.054 -3.222 1.00 19.80           C
ATOM   5230  CG  PRO D 127      0.545  10.324 -3.371 1.00 19.40           C
ATOM   5231  CD  PRO D 127      1.074   8.997  3.851 1.00 19.12           C
ATOM   5232  N   CYS D 128     -2.939  10.499 -5.714 1.00 24.44           N
ATOM   5233  CA  CYS D 128     -3.447  11.369 -6.770 1.00 26.25           C
ATOM   5234  C   CYS D 128     -3.228  12.811 -6.367 1.00 27.49           C
ATOM   5235  O   CYS D 128     -2.742  13.102 -5.267 1.00 29.40           O
ATOM   5236  CB  CYS D 128     -4.941  11.138 -6.999 1.00 26.21           C
ATOM   5237  SG  CYS D 128     -6.010  11.597 -5.604 1.00 30.68           S
ATOM   5238  N   ALA D 129     -3.606  13.723 -7.248 1.00 28.04           N
ATOM   5239  CA  ALA D 129     -3.442  15.143 -6.968 1.00 27.71           C
ATOM   5240  C   ALA D 129     -4.114  15.534 -5.654 1.00 27.47           C
ATOM   5241  O   ALA D 129     -3.513  16.212 -4.824 1.00 27.07           O
ATOM   5242  CB  ALA D 129     -4.018  15.945 -8.109 1.00 27.09           C
ATOM   5243  N   ALA D 130     -5.358  15.097  5.469 1.00 27.55           N
ATOM   5244  CA  ALA D 130     -6.099  15.432 -4.257 1.00 28.95           C
ATOM   5245  C   ALA D 130     -5.504  14.817 -3.004 1.00 29.95           C
ATOM   5246  O   ALA D 130     -5.365  15.490 -1.987 1.00 31.59           O
ATOM   5247  CB  ALA D 130     -7.553  15.018 -4.394 1.00 28.45           C
ATOM   5248  N   CYS D 131     -5.173  13.535 -3.072 1.00 30.68           N
ATOM   5249  CA  CYS D 131     -4.604  12.847 -1.927 1.00 31.25           C
ATOM   5250  C   CYS D 131     -3.264  13.455 -1.506 1.00 31.32           C
ATOM   5251  O   CYS D 131     -2.975  13.562 -0.315 1.00 31.10           O
ATOM   5252  CB  CYS D 131     -4.467  11.356 -2.240 1.00 31.99           C
ATOM   5253  SG  CYS D 131     -6.063  10.493 -2.209 1.00 33.06           S
ATOM   5254  N   ALA D 132     -2.465  13.872 -2.481 1.00 31.97           N
ATOM   5255  CA  ALA D 132     -1.176  14.480 -2.197 1.00 33.19           C
ATOM   5256  C   ALA D 132     -1.374  15.729 -1.340 1.00 33.96           C
ATOM   5257  O   ALA D 132     -0.610  15.974 -0.402 1.00 35.10           O
ATOM   5258  CB  ALA D 132     -0.478  14.841 -3.493 1.00 33.02           C
ATOM   5259  N   ASP D 133     -2.397  16.514 -1.653 1.00 35.08           N
ATOM   5260  CA  ASP D 133     -2.674  17.719 -0.881 1.00 37.23           C
ATOM   5261  C   ASP D 133     -3.024  17.378  0.555 1.00 37.69           C
ATOM   5262  O   ASP D 133     -2.487  17.978  1.487 1.00 38.69           O
ATOM   5263  CB  ASP D 133     -3.820  18.529 -1.500 1.00 38.65           C
ATOM   5264  CG  ASP D 133     -3.388  19.295 -2.731 1.00 40.65           C
ATOM   5265  OD1 ASP D 133     -2.212  19.720 -2.781 1.00 42.17           O
ATOM   5266  OD2 ASP D 133     -4.218  19.491 -3.643 1.00 42.68           O
ATOM   5267  N   ARG D 134     -3.933  16.434  0.745 1.00 38.43           N
ATOM   5268  CA  ARG D 134     -4.319  16.023  2.097 1.00 38.76           C
ATOM   5269  C   ARG D 134     -3.052  15.671  2.860 1.00 37.25           C
ATOM   5270  O   ARG D 134     -2.846  16.104  3.998 1.00 36.85           O
ATOM   5271  CB  ARG D 134     -5.216  14.787  2.031 1.00 41.17           C
```

FIG. 6 (con't)

| | | | | | | | | | | | | |
|---|---|---|---|---|---|---|---|---|---|---|---|---|
| ATOM | 2002 | CB  | GLU | B 100 |  3.606 |  2.380 | 90.691 | 1.00 32.94 | C | | | |
| ATOM | 2003 | CG  | GLU | B 100 |  2.484 |  1.657 | 91.470 | 1.00 33.25 | C | | | |
| ATOM | 2004 | CD  | GLU | B 100 |  2.967 |  0.946 | 92.732 | 1.00 32.63 | C | | | |
| ATOM | 2005 | OE1 | GLU | B 100 |  4.173 |  0.655 | 92.836 | 1.00 30.43 | O | | | |
| ATOM | 2006 | OE2 | GLU | B 100 |  2.121 |  0.668 | 93.623 | 1.00 34.00 | O | | | |
| ATOM | 2007 | N   | GLU | B 101 |  6.296 |  2.656 | 88.973 | 1.00 33.19 | N | | | |
| ATOM | 2008 | CA  | GLU | B 101 |  7.181 |  3.493 | 88.186 | 1.00 33.91 | C | | | |
| ATOM | 2009 | C   | GLU | B 101 |  7.598 |  2.744 | 86.931 | 1.00 33.21 | C | | | |
| ATOM | 2010 | O   | GLU | B 101 |  7.593 |  3.294 | 85.826 | 1.00 34.04 | O | | | |
| ATOM | 2011 | CB  | GLU | B 101 |  8.427 |  3.859 | 88.999 | 1.00 35.98 | C | | | |
| ATOM | 2012 | CG  | GLU | B 101 |  8.149 |  4.490 | 90.380 | 1.00 40.27 | C | | | |
| ATOM | 2013 | CD  | GLU | B 101 |  9.406 |  4.590 | 91.262 | 1.00 43.83 | C | | | |
| ATOM | 2014 | OE1 | GLU | B 101 | 10.412 |  5.139 | 90.760 | 1.00 46.44 | O | | | |
| ATOM | 2015 | OE2 | GLU | B 101 |  9.399 |  4.139 | 92.439 | 1.00 42.52 | O | | | |
| ATOM | 2016 | N   | ALA | B 102 |  7.955 |  1.478 | 87.106 | 1.00 31.56 | N | | | |
| ATOM | 2017 | CA  | ALA | B 102 |  8.406 |  0.652 | 85.993 | 1.00 29.65 | C | | | |
| ATOM | 2018 | C   | ALA | B 102 |  7.385 |  0.551 | 84.881 | 1.00 28.86 | C | | | |
| ATOM | 2019 | O   | ALA | B 102 |  7.747 |  0.467 | 83.710 | 1.00 28.47 | O | | | |
| ATOM | 2020 | CB  | ALA | B 102 |  8.758 | -0.750 | 86.494 | 1.00 30.14 | C | | | |
| ATOM | 2021 | N   | PHE | B 103 |  6.105 |  0.552 | 85.240 | 1.00 27.81 | N | | | |
| ATOM | 2022 | CA  | PHE | B 103 |  5.059 |  0.430 | 84.245 | 1.00 27.36 | C | | | |
| ATOM | 2023 | C   | PHE | B 103 |  5.030 |  1.591 | 83.266 | 1.00 28.18 | C | | | |
| ATOM | 2024 | O   | PHE | B 103 |  5.189 |  1.398 | 82.064 | 1.00 28.86 | O | | | |
| ATOM | 2025 | CB  | PHE | B 103 |  3.695 |  0.306 | 84.923 | 1.00 26.13 | C | | | |
| ATOM | 2026 | CG  | PHE | B 103 |  2.559 |  0.132 | 83.959 | 1.00 25.25 | C | | | |
| ATOM | 2027 | CD1 | PHE | B 103 |  2.296 | -1.108 | 83.386 | 1.00 23.58 | C | | | |
| ATOM | 2028 | CD2 | PHE | B 103 |  1.755 |  1.217 | 83.608 | 1.00 25.36 | C | | | |
| ATOM | 2029 | CE1 | PHE | B 103 |  1.256 | -1.272 | 82.482 | 1.00 22.52 | C | | | |
| ATOM | 2030 | CE2 | PHE | B 103 |  0.706 |  1.068 | 82.706 | 1.00 23.78 | C | | | |
| ATOM | 2031 | CZ  | PHE | B 103 |  0.457 | -0.181 | 82.142 | 1.00 24.57 | C | | | |
| ATOM | 2032 | N   | PHE | B 104 |  4.825 |  2.798 | 83.786 | 1.00 29.24 | N | | | |
| ATOM | 2033 | CA  | PHE | B 104 |  4.757 |  3.998 | 82.956 | 1.00 29.26 | C | | | |
| ATOM | 2034 | C   | PHE | B 104 |  6.073 |  4.406 | 82.308 | 1.00 31.16 | C | | | |
| ATOM | 2035 | O   | PHE | B 104 |  6.114 |  5.365 | 81.533 | 1.00 31.26 | O | | | |
| ATOM | 2036 | CB  | PHE | B 104 |  4.202 |  5.160 | 83.771 | 1.00 26.65 | C | | | |
| ATOM | 2037 | CG  | PHE | B 104 |  2.738 |  5.037 | 84.082 | 1.00 25.20 | C | | | |
| ATOM | 2038 | CD1 | PHE | B 104 |  2.274 |  5.216 | 85.381 | 1.00 22.70 | C | | | |
| ATOM | 2039 | CD2 | PHE | B 104 |  1.819 |  4.778 | 83.072 | 1.00 24.69 | C | | | |
| ATOM | 2040 | CE1 | PHE | B 104 |  0.917 |  5.138 | 85.669 | 1.00 23.29 | C | | | |
| ATOM | 2041 | CE2 | PHE | B 104 |  0.458 |  4.701 | 83.354 | 1.00 24.22 | C | | | |
| ATOM | 2042 | CZ  | PHE | B 104 |  0.007 |  4.880 | 84.658 | 1.00 22.70 | C | | | |
| ATOM | 2043 | N   | ASN | B 105 |  7.151 |  3.689 | 82.611 | 1.00 33.67 | N | | | |
| ATOM | 2044 | CA  | ASN | B 105 |  8.446 |  4.025 | 82.020 | 1.00 35.86 | C | | | |
| ATOM | 2045 | C   | ASN | B 105 |  8.912 |  3.075 | 80.926 | 1.00 36.14 | C | | | |
| ATOM | 2046 | O   | ASN | B 105 |  9.816 |  3.411 | 80.168 | 1.00 35.61 | O | | | |
| ATOM | 2047 | CB  | ASN | B 105 |  9.515 |  4.122 | 83.104 | 1.00 38.40 | C | | | |
| ATOM | 2048 | CG  | ASN | B 105 |  9.315 |  5.321 | 84.009 | 1.00 41.32 | C | | | |
| ATOM | 2049 | OD1 | ASN | B 105 |  8.419 |  6.141 | 83.788 | 1.00 42.54 | O | | | |
| ATOM | 2050 | ND2 | ASN | B 105 | 10.152 |  5.438 | 85.032 | 1.00 41.83 | N | | | |
| ATOM | 2051 | N   | THR | B 106 |  8.299 |  1.901 | 80.833 | 1.00 37.38 | N | | | |
| ATOM | 2052 | CA  | THR | B 106 |  8.690 |  0.943 | 79.809 | 1.00 39.06 | C | | | |
| ATOM | 2053 | C   | THR | B 106 |  7.518 |  0.239 | 79.144 | 1.00 39.10 | C | | | |
| ATOM | 2054 | O   | THR | B 106 |  7.571 | -0.049 | 77.952 | 1.00 39.32 | O | | | |
| ATOM | 2055 | CB  | THR | B 106 |  9.624 | -0.131 | 80.384 | 1.00 40.61 | C | | | |
| ATOM | 2056 | OG1 | THR | B 106 |  9.098 | -0.605 | 81.624 | 1.00 41.74 | O | | | |
| ATOM | 2057 | CG2 | THR | B 106 | 11.013 |  0.437 | 80.608 | 1.00 41.42 | C | | | |
| ATOM | 2058 | N   | ILE | B 107 |  6.465 | -0.039 | 79.912 | 1.00 38.64 | N | | | |
| ATOM | 2059 | CA  | ILE | B 107 |  5.287 | -0.711 | 79.376 | 1.00 39.05 | C | | | |
| ATOM | 2060 | C   | ILE | B 107 |  4.437 |  0.240 | 78.528 | 1.00 39.47 | C | | | |
| ATOM | 2061 | O   | ILE | B 107 |  4.186 | -0.032 | 77.359 | 1.00 39.91 | O | | | |
| ATOM | 2062 | CB  | ILE | B 107 |  4.424 | -1.314 | 80.507 | 1.00 39.08 | C | | | |
| ATOM | 2063 | CG1 | ILE | B 107 |  5.316 | -2.095 | 81.473 | 1.00 38.43 | C | | | |
| ATOM | 2064 | CG2 | ILE | B 107 |  3.334 | -2.222 | 79.920 | 1.00 37.59 | C | | | |
| ATOM | 2065 | CD1 | ILE | B 107 |  6.278 | -3.037 | 80.793 | 1.00 38.27 | C | | | |
| ATOM | 2066 | N   | LEU | B 108 |  4.008 |  1.355 | 79.112 | 1.00 39.98 | N | | | |
| ATOM | 2067 | CA  | LEU | B 108 |  3.203 |  2.336 | 78.391 | 1.00 40.78 | C | | | |
| ATOM | 2068 | C   | LEU | B 108 |  3.876 |  3.697 | 78.412 | 1.00 42.16 | C | | | |
| ATOM | 2069 | O   | LEU | B 108 |  3.363 |  4.654 | 79.001 | 1.00 41.46 | O | | | |
| ATOM | 2070 | CB  | LEU | B 108 |  1.819 |  2.453 | 79.023 | 1.00 41.19 | C | | | |
| ATOM | 2071 | CG  | LEU | B 108 |  0.689 |  1.639 | 78.418 | 1.00 40.26 | C | | | |
| ATOM | 2072 | CD1 | LEU | B 108 | -0.632 |  2.021 | 79.073 | 1.00 39.76 | C | | | |
| ATOM | 2073 | CD2 | LEU | B 108 |  0.635 |  1.925 | 76.937 | 1.00 41.10 | C | | | |
| ATOM | 2074 | N   | PRO | B 109 |  5.049 |  3.799 | 77.784 | 1.00 43.67 | N | | | |
| ATOM | 2075 | CA  | PRO | B 109 |  5.765 |  5.072 | 77.757 | 1.00 44.76 | C | | | |
| ATOM | 2076 | C   | PRO | B 109 |  5.033 |  6.063 | 76.891 | 1.00 45.07 | C | | | |
| ATOM | 2077 | O   | PRO | B 109 |  4.930 |  7.231 | 77.237 | 1.00 45.84 | O | | | |
| ATOM | 2078 | CB  | PRO | B 109 |  7.118 |  4.698 | 77.159 | 1.00 45.21 | C | | | |
| ATOM | 2079 | CG  | PRO | B 109 |  7.277 |  3.265 | 77.544 | 1.00 46.15 | C | | | |
| ATOM | 2080 | CD  | PRO | B 109 |  5.903 |  2.716 | 77.274 | 1.00 44.82 | C | | | |
| ATOM | 2081 | N   | ALA | B 110 |  4.518 |  5.587 | 75.763 | 1.00 45.59 | N | | | |
| ATOM | 2082 | CA  | ALA | B 110 |  3.813 |  6.453 | 74.832 | 1.00 46.09 | C | | | |
| ATOM | 2083 | C   | ALA | B 110 |  2.304 |  6.203 | 74.817 | 1.00 45.65 | C | | | |
| ATOM | 2084 | O   | ALA | B 110 |  1.846 |  5.108 | 75.129 | 1.00 45.08 | O | | | |
| ATOM | 2085 | CB  | ALA | B 110 |  4.386 |  6.269 | 73.431 | 1.00 46.57 | C | | | |
| ATOM | 2086 | N   | PHE | B 111 |  1.544 |  7.233 | 74.452 | 1.00 44.98 | N | | | |
| ATOM | 2087 | CA  | PHE | B 111 |  0.097 |  7.130 | 74.376 | 1.00 44.99 | C | | | |
| ATOM | 5272 | CG  | ARG | D 134 | -6.450 | 14.946 |  1.149 | 1.00 45.85 | C | | | |
| ATOM | 5273 | CD  | ARG | D 134 | -6.867 | 13.617 |  0.499 | 1.00 48.09 | C | | | |
| ATOM | 5274 | NE  | ARG | D 134 | -8.103 | 13.723 | -0.274 | 1.00 48.48 | N | | | |
| ATOM | 5275 | CZ  | ARG | D 134 | -9.301 | 13.914 |  0.267 | 1.00 49.30 | C | | | |
| ATOM | 5276 | NH1 | ARG | D 134 | -9.417 | 14.016 |  1.586 | 1.00 49.52 | N | | | |
| ATOM | 5277 | NH2 | ARG | D 134 | -10.379 | 14.000 | -0.503 | 1.00 48.92 | N | | | |
| ATOM | 5278 | N   | ILE | D 135 | -2.203 | 14.870 |  2.219 | 1.00 34.95 | N | | | |
| ATOM | 5279 | CA  | ILE | D 135 | -0.954 | 14.431 |  2.829 | 1.00 33.29 | C | | | |
| ATOM | 5280 | C   | ILE | D 135 | -0.104 | 15.635 |  3.213 | 1.00 33.00 | C | | | |
| ATOM | 5281 | O   | ILE | D 135 |  0.439 | 15.712 |  4.317 | 1.00 33.44 | O | | | |
| ATOM | 5282 | CB  | ILE | D 135 | -0.162 | 13.504 |  1.866 | 1.00 31.37 | C | | | |
| ATOM | 5283 | CG1 | ILE | D 135 | -0.973 | 12.231 |  1.573 | 1.00 30.03 | C | | | |
| ATOM | 5284 | CG2 | ILE | D 135 |  1.192 | 13.148 |  2.481 | 1.00 30.53 | C | | | |
| ATOM | 5285 | CD1 | ILE | D 135 | -0.381 | 11.358 |  0.486 | 1.00 29.38 | C | | | |
| ATOM | 5286 | N   | ILE | D 136 | -0.003 | 16.587 |  2.302 | 1.00 32.47 | N | | | |
| ATOM | 5287 | CA  | ILE | D 136 |  0.779 | 17.782 |  2.558 | 1.00 32.24 | C | | | |
| ATOM | 5288 | C   | ILE | D 136 |  0.194 | 18.605 |  3.705 | 1.00 32.90 | C | | | |
| ATOM | 5289 | O   | ILE | D 136 |  0.921 | 19.064 |  4.593 | 1.00 33.08 | O | | | |
| ATOM | 5290 | CB  | ILE | D 136 |  0.855 | 18.625 |  1.286 | 1.00 30.67 | C | | | |
| ATOM | 5291 | CG1 | ILE | D 136 |  1.700 | 17.891 |  0.244 | 1.00 29.16 | C | | | |
| ATOM | 5292 | CG2 | ILE | D 136 |  1.444 | 19.972 |  1.600 | 1.00 30.56 | C | | | |
| ATOM | 5293 | CD1 | ILE | D 136 |  1.656 | 18.495 | -1.139 | 1.00 28.41 | C | | | |
| ATOM | 5294 | N   | LYS | D 137 | -1.119 | 18.785 |  3.693 | 1.00 34.20 | N | | | |
| ATOM | 5295 | CA  | LYS | D 137 | -1.767 | 19.560 |  4.740 | 1.00 36.70 | C | | | |
| ATOM | 5296 | C   | LYS | D 137 | -1.587 | 18.916 |  6.106 | 1.00 37.71 | C | | | |
| ATOM | 5297 | O   | LYS | D 137 | -1.416 | 19.612 |  7.103 | 1.00 38.94 | O | | | |
| ATOM | 5298 | CB  | LYS | D 137 | -3.252 | 19.738 |  4.436 | 1.00 38.06 | C | | | |
| ATOM | 5299 | CG  | LYS | D 137 | -3.504 | 20.419 |  3.097 | 1.00 41.49 | C | | | |
| ATOM | 5300 | CD  | LYS | D 137 | -4.919 | 20.987 |  2.983 | 1.00 43.04 | C | | | |
| ATOM | 5301 | CE  | LYS | D 137 | -5.111 | 21.742 |  1.663 | 1.00 44.69 | C | | | |
| ATOM | 5302 | NZ  | LYS | D 137 | -6.395 | 22.500 |  1.593 | 1.00 45.35 | N | | | |
| ATOM | 5303 | N   | THR | D 138 | -1.631 | 17.587 |  6.160 | 1.00 37.76 | N | | | |
| ATOM | 5304 | CA  | THR | D 138 | -1.438 | 16.884 |  7.417 | 1.00 37.04 | C | | | |
| ATOM | 5305 | C   | THR | D 138 |  0.027 | 17.001 |  7.839 | 1.00 36.86 | C | | | |
| ATOM | 5306 | O   | THR | D 138 |  0.328 | 17.285 |  9.003 | 1.00 36.30 | O | | | |
| ATOM | 5307 | CB  | THR | D 138 | -1.823 | 15.403 |  7.279 | 1.00 37.98 | C | | | |
| ATOM | 5308 | OG1 | THR | D 138 | -3.212 | 15.312 |  6.923 | 1.00 38.32 | O | | | |
| ATOM | 5309 | CG2 | THR | D 138 | -1.580 | 14.645 |  8.587 | 1.00 36.81 | C | | | |
| ATOM | 5310 | N   | LEU | D 139 |  0.940 | 16.788 |  6.891 | 1.00 36.95 | N | | | |
| ATOM | 5311 | CA  | LEU | D 139 |  2.375 | 16.888 |  7.170 | 1.00 37.66 | C | | | |
| ATOM | 5312 | C   | LEU | D 139 |  2.704 | 18.293 |  7.626 | 1.00 39.08 | C | | | |
| ATOM | 5313 | O   | LEU | D 139 |  3.652 | 18.503 |  8.382 | 1.00 39.67 | O | | | |
| ATOM | 5314 | CB  | LEU | D 139 |  3.196 | 16.565 |  5.923 | 1.00 36.53 | C | | | |
| ATOM | 5315 | CG  | LEU | D 139 |  3.462 | 15.094 |  5.629 | 1.00 35.68 | C | | | |
| ATOM | 5316 | CD1 | LEU | D 139 |  4.138 | 14.952 |  4.269 | 1.00 34.44 | C | | | |
| ATOM | 5317 | CD2 | LEU | D 139 |  4.328 | 14.523 |  6.738 | 1.00 35.12 | C | | | |
| ATOM | 5318 | N   | SER | D 140 |  1.919 | 19.254 |  7.150 | 1.00 40.21 | N | | | |
| ATOM | 5319 | CA  | SER | D 140 |  2.091 | 20.653 |  7.510 | 1.00 41.11 | C | | | |
| ATOM | 5320 | C   | SER | D 140 |  1.666 | 20.908 |  8.961 | 1.00 42.19 | C | | | |
| ATOM | 5321 | O   | SER | D 140 |  2.335 | 21.640 |  9.696 | 1.00 42.08 | O | | | |
| ATOM | 5322 | CB  | SER | D 140 |  1.257 | 21.523 |  6.577 | 1.00 41.64 | C | | | |
| ATOM | 5323 | OG  | SER | D 140 |  1.223 | 22.856 |  7.045 | 1.00 42.29 | O | | | |
| ATOM | 5324 | N   | LYS | D 141 |  0.546 | 20.310 |  9.363 | 1.00 43.44 | N | | | |
| ATOM | 5325 | CA  | LYS | D 141 |  0.038 | 20.463 | 10.726 | 1.00 44.58 | C | | | |
| ATOM | 5326 | C   | LYS | D 141 |  0.972 | 19.831 | 11.749 | 1.00 44.37 | C | | | |
| ATOM | 5327 | O   | LYS | D 141 |  1.520 | 20.530 | 12.591 | 1.00 45.26 | O | | | |
| ATOM | 5328 | CB  | LYS | D 141 | -1.352 | 19.832 | 10.877 | 1.00 46.66 | C | | | |
| ATOM | 5329 | CG  | LYS | D 141 | -2.478 | 20.575 | 10.168 | 1.00 49.25 | C | | | |
| ATOM | 5330 | CD  | LYS | D 141 | -3.810 | 19.827 | 10.292 | 1.00 51.58 | C | | | |
| ATOM | 5331 | CE  | LYS | D 141 | -4.958 | 20.563 |  9.590 | 1.00 52.78 | C | | | |
| ATOM | 5332 | NZ  | LYS | D 141 | -5.308 | 21.866 | 10.238 | 1.00 53.98 | N | | | |
| ATOM | 5333 | N   | THR | D 142 |  1.156 | 18.514 | 11.684 | 1.00 43.82 | N | | | |
| ATOM | 5334 | CA  | THR | D 142 |  2.019 | 17.828 | 12.644 | 1.00 43.49 | C | | | |
| ATOM | 5335 | C   | THR | D 142 |  3.480 | 17.846 | 12.193 | 1.00 43.04 | C | | | |
| ATOM | 5336 | O   | THR | D 142 |  3.846 | 17.225 | 11.194 | 1.00 44.26 | O | | | |
| ATOM | 5337 | CB  | THR | D 142 |  1.585 | 16.369 | 12.839 | 1.00 43.27 | C | | | |
| ATOM | 5338 | OG1 | THR | D 142 |  1.958 | 15.615 | 11.689 | 1.00 46.27 | O | | | |
| ATOM | 5339 | CG2 | THR | D 142 |  0.074 | 16.275 | 13.005 | 1.00 43.26 | C | | | |
| ATOM | 5340 | N   | LYS | D 143 |  4.320 | 18.556 | 12.938 | 1.00 41.61 | N | | | |
| ATOM | 5341 | CA  | LYS | D 143 |  5.721 | 18.649 | 12.586 | 1.00 39.98 | C | | | |
| ATOM | 5342 | C   | LYS | D 143 |  6.498 | 17.484 | 13.154 | 1.00 37.87 | C | | | |
| ATOM | 5343 | O   | LYS | D 143 |  7.640 | 17.244 | 12.769 | 1.00 38.09 | O | | | |
| ATOM | 5344 | CB  | LYS | D 143 |  6.326 | 19.962 | 13.101 | 1.00 41.71 | C | | | |
| ATOM | 5345 | CG  | LYS | D 143 |  5.672 | 21.238 | 12.573 | 1.00 44.29 | C | | | |
| ATOM | 5346 | CD  | LYS | D 143 |  4.568 | 21.731 | 13.501 | 1.00 45.93 | C | | | |
| ATOM | 5347 | CE  | LYS | D 143 |  3.997 | 23.068 | 13.036 | 1.00 47.84 | C | | | |
| ATOM | 5348 | NZ  | LYS | D 143 |  5.054 | 24.108 | 12.847 | 1.00 49.64 | N | | | |
| ATOM | 5349 | N   | ASN | D 144 |  5.889 | 16.757 | 14.077 | 1.00 35.77 | N | | | |
| ATOM | 5350 | CA  | ASN | D 144 |  6.555 | 15.621 | 14.692 | 1.00 34.11 | C | | | |
| ATOM | 5351 | C   | ASN | D 144 |  6.318 | 14.326 | 13.904 | 1.00 33.69 | C | | | |
| ATOM | 5352 | O   | ASN | D 144 |  6.664 | 13.238 | 14.358 | 1.00 33.62 | O | | | |
| ATOM | 5353 | CB  | ASN | D 144 |  6.076 | 15.454 | 16.135 | 1.00 33.16 | C | | | |
| ATOM | 5354 | CG  | ASN | D 144 |  4.586 | 15.200 | 16.237 | 1.00 33.60 | C | | | |
| ATOM | 5355 | OD1 | ASN | D 144 |  4.094 | 14.772 | 17.279 | 1.00 33.28 | O | | | |
| ATOM | 5356 | ND2 | ASN | D 144 |  3.856 | 15.468 | 15.159 | 1.00 34.11 | N | | | |
| ATOM | 5357 | N   | LEU | D 145 |  5.741 | 14.464 | 12.711 | 1.00 32.36 | N | | | |

FIG. 6 (con't)

```
ATOM  2088  C    PHE B 111    -0.409   7.738  73.073  1.00 45.71   C
ATOM  2089  O    PHE B 111    -0.007   8.840  72.694  1.00 47.07   O
ATOM  2090  CB   PHE B 111    -0.574   7.854  75.556  1.00 43.75   C
ATOM  2091  CG   PHE B 111    -0.272   7.249  76.904  1.00 43.28   C
ATOM  2092  CD1  PHE B 111     0.734   7.775  77.710  1.00 42.73   C
ATOM  2093  CD2  PHE B 111    -0.986   6.140  77.365  1.00 43.11   C
ATOM  2094  CE1  PHE B 111     1.027   7.205  78.955  1.00 42.47   C
ATOM  2095  CE2  PHE B 111    -0.702   5.562  78.613  1.00 42.95   C
ATOM  2096  CZ   PHE B 111     0.306   6.097  79.407  1.00 42.32   C
ATOM  2097  N    ASP B 112    -1.283   7.022  72.379  1.00 45.74   N
ATOM  2098  CA   ASP B 112    -1.846   7.523  71.138  1.00 45.60   C
ATOM  2099  C    ASP B 112    -2.956   8.523  71.479  1.00 45.20   C
ATOM  2100  O    ASP B 112    -4.040   8.135  71.903  1.00 43.83   O
ATOM  2101  CB   ASP B 112    -2.438   6.369  70.332  1.00 47.51   C
ATOM  2102  CG   ASP B 112    -2.799   6.771  68.918  1.00 48.52   C
ATOM  2103  OD1  ASP B 112    -3.347   7.878  68.735  1.00 49.31   O
ATOM  2104  OD2  ASP B 112    -2.538   5.970  67.996  1.00 49.15   O
ATOM  2105  N    PRO B 113    -2.696   9.829  71.289  1.00 45.48   N
ATOM  2106  CA   PRO B 113    -3.659  10.906  71.576  1.00 44.02   C
ATOM  2107  C    PRO B 113    -5.046  10.679  71.006  1.00 42.57   C
ATOM  2108  O    PRO B 113    -6.010  11.309  71.438  1.00 43.23   O
ATOM  2109  CB   PRO B 113    -2.976  12.134  70.982  1.00 44.42   C
ATOM  2110  CG   PRO B 113    -1.513  11.833  71.236  1.00 46.02   C
ATOM  2111  CD   PRO B 113    -1.425  10.390  70.786  1.00 45.45   C
ATOM  2112  N    ALA B 114    -5.152   9.774  70.043  1.00 41.43   N
ATOM  2113  CA   ALA B 114    -6.438   9.486  69.416  1.00 39.56   C
ATOM  2114  C    ALA B 114    -7.229   8.456  70.195  1.00 38.00   C
ATOM  2115  O    ALA B 114    -8.424   8.611  70.414  1.00 38.59   O
ATOM  2116  CB   ALA B 114    -6.217   8.998  68.014  1.00 38.88   C
ATOM  2117  N    LEU B 115    -6.554   7.390  70.598  1.00 36.47   N
ATOM  2118  CA   LEU B 115    -7.194   6.322  71.343  1.00 34.00   C
ATOM  2119  C    LEU B 115    -7.471   6.720  72.796  1.00 31.90   C
ATOM  2120  O    LEU B 115    -6.732   7.497  73.394  1.00 31.23   O
ATOM  2121  CB   LEU B 115    -6.294   5.096  71.333  1.00 34.26   C
ATOM  2122  CG   LEU B 115    -5.716   4.669  69.992  1.00 34.14   C
ATOM  2123  CD1  LEU B 115    -4.615   3.622  70.185  1.00 33.90   C
ATOM  2124  CD2  LEU B 115    -6.846   4.143  69.144  1.00 34.56   C
ATOM  2125  N    ARG B 116    -8.538   6.173  73.368  1.00 31.01   N
ATOM  2126  CA   ARG B 116    -8.884   6.437  74.758  1.00 28.60   C
ATOM  2127  C    ARG B 116    -8.410   5.220  75.548  1.00 26.76   C
ATOM  2128  O    ARG B 116    -8.929   4.122  75.363  1.00 25.42   O
ATOM  2129  CB   ARG B 116   -10.382   6.563  74.898  1.00 32.04   C
ATOM  2130  CG   ARG B 116   -10.825   7.721  75.738  1.00 37.33   C
ATOM  2131  CD   ARG B 116   -10.236   7.705  77.139  1.00 38.69   C
ATOM  2132  NE   ARG B 116   -11.059   8.488  78.062  1.00 41.96   N
ATOM  2133  CZ   ARG B 116   -12.246   8.096  78.523  1.00 43.72   C
ATOM  2134  NH1  ARG B 116   -12.753   6.926  78.154  1.00 45.48   N
ATOM  2135  NH2  ARG B 116   -12.927   8.869  79.357  1.00 45.09   N
ATOM  2136  N    TYR B 117    -7.450   5.409  76.439  1.00 24.66   N
ATOM  2137  CA   TYR B 117    -6.914   4.290  77.195  1.00 24.15   C
ATOM  2138  C    TYR B 117    -7.606   3.969  78.504  1.00 23.87   C
ATOM  2139  O    TYR B 117    -7.944   4.865  79.270  1.00 25.73   O
ATOM  2140  CB   TYR B 117    -5.421   4.511  77.476  1.00 22.85   C
ATOM  2141  CG   TYR B 117    -4.537   4.460  76.246  1.00 21.61   C
ATOM  2142  CD1  TYR B 117    -4.443   5.542  75.370  1.00 21.30   C
ATOM  2143  CD2  TYR B 117    -3.814   3.315  75.949  1.00 22.98   C
ATOM  2144  CE1  TYR B 117    -3.641   5.475  74.217  1.00 22.30   C
ATOM  2145  CE2  TYR B 117    -3.016   3.237  74.810  1.00 24.43   C
ATOM  2146  CZ   TYR B 117    -2.934   4.321  73.951  1.00 23.77   C
ATOM  2147  OH   TYR B 117    -2.139   4.228  72.823  1.00 26.97   O
ATOM  2148  N    ASN B 118    -7.805   2.681  78.756  1.00 23.52   N
ATOM  2149  CA   ASN B 118    -8.420   2.194  79.986  1.00 23.33   C
ATOM  2150  C    ASN B 118    -7.495   1.133  80.601  1.00 22.78   C
ATOM  2151  O    ASN B 118    -7.534  -0.037  80.217  1.00 23.03   O
ATOM  2152  CB   ASN B 118    -9.770   1.582  79.673  1.00 24.96   C
ATOM  2153  CG   ASN B 118   -10.905   2.489  80.033  1.00 26.13   C
ATOM  2154  OD1  ASN B 118   -11.543   2.293  81.058  1.00 29.62   O
ATOM  2155  ND2  ASN B 118   -11.167   3.496  79.203  1.00 27.07   N
ATOM  2156  N    VAL B 119    -6.667   1.541  81.556  1.00 20.63   N
ATOM  2157  CA   VAL B 119    -5.735   0.632  82.192  1.00 18.93   C
ATOM  2158  C    VAL B 119    -6.242   0.102  83.520  1.00 19.43   C
ATOM  2159  O    VAL B 119    -6.872   0.828  84.291  1.00 20.90   O
ATOM  2160  CB   VAL B 119    -4.384   1.305  82.427  1.00 17.41   C
ATOM  2161  CG1  VAL B 119    -3.398   0.335  83.011  1.00 15.86   C
ATOM  2162  CG2  VAL B 119    -3.852   1.843  81.132  1.00 17.10   C
ATOM  2163  N    THR B 120    -5.956  -1.172  83.783  1.00 18.85   N
ATOM  2164  CA   THR B 120    -6.353  -1.825  85.021  1.00 18.06   C
ATOM  2165  C    THR B 120    -5.153  -2.547  85.643  1.00 18.23   C
ATOM  2166  O    THR B 120    -4.524  -3.382  85.006  1.00 18.08   O
ATOM  2167  CB   THR B 120    -7.451  -2.846  84.765  1.00 18.34   C
ATOM  2168  OG1  THR B 120    -8.562  -2.203  84.127  1.00 20.38   O
ATOM  2169  CG2  THR B 120    -7.903  -3.456  86.067  1.00 18.11   C
ATOM  2170  N    TRP B 121    -4.829  -2.237  86.890  1.00 17.12   N
ATOM  2171  CA   TRP B 121    -3.703  -2.903  87.515  1.00 15.87   C
ATOM  2172  C    TRP B 121    -4.143  -3.908  88.568  1.00 16.14   C
ATOM  2173  O    TRP B 121    -5.226  -3.796  89.140  1.00 15.96   O

ATOM  5358  CA   LEU D 145     5.439  13.327  11.843  1.00 29.82   C
ATOM  5359  C    LEU D 145     6.315  13.305  10.601  1.00 29.60   C
ATOM  5360  O    LEU D 145     6.505  14.332   9.948  1.00 29.81   O
ATOM  5361  CB   LEU D 145     3.973  13.392  11.415  1.00 28.82   C
ATOM  5362  CG   LEU D 145     3.519  12.422  10.325  1.00 28.72   C
ATOM  5363  CD1  LEU D 145     3.378  11.032  10.892  1.00 29.12   C
ATOM  5364  CD2  LEU D 145     2.192  12.871   9.779  1.00 27.17   C
ATOM  5365  N    ARG D 146     6.834  12.130  10.262  1.00 28.91   N
ATOM  5366  CA   ARG D 146     7.687  11.970   9.088  1.00 27.88   C
ATOM  5367  C    ARG D 146     7.115  10.793   8.302  1.00 27.87   C
ATOM  5368  O    ARG D 146     6.985   9.691   8.839  1.00 29.02   O
ATOM  5369  CB   ARG D 146     9.117  11.673   9.517  1.00 29.52   C
ATOM  5370  CG   ARG D 146    10.182  12.378   8.695  1.00 32.17   C
ATOM  5371  CD   ARG D 146    10.777  13.571   9.440  1.00 31.73   C
ATOM  5372  NE   ARG D 146     9.760  14.573   9.773  1.00 33.45   N
ATOM  5373  CZ   ARG D 146    10.020  15.715  10.407  1.00 32.70   C
ATOM  5374  NH1  ARG D 146    11.265  16.007  10.776  1.00 32.58   N
ATOM  5375  NH2  ARG D 146     9.035  16.551  10.690  1.00 30.97   N
ATOM  5376  N    LEU D 147     6.782  11.022   7.030  1.00 25.00   N
ATOM  5377  CA   LEU D 147     6.183   9.996   6.182  1.00 21.59   C
ATOM  5378  C    LEU D 147     7.059   9.498   5.044  1.00 21.23   C
ATOM  5379  O    LEU D 147     7.796  10.261   4.424  1.00 20.68   O
ATOM  5380  CB   LEU D 147     4.862  10.517   5.598  1.00 20.40   C
ATOM  5381  CG   LEU D 147     4.058   9.554   4.734  1.00 20.40   C
ATOM  5382  CD1  LEU D 147     3.668   8.341   5.559  1.00 21.70   C
ATOM  5383  CD2  LEU D 147     2.810  10.234   4.183  1.00 19.03   C
ATOM  5384  N    LEU D 148     6.950   8.196   4.774  1.00 20.81   N
ATOM  5385  CA   LEU D 148     7.688   7.511   3.723  1.00 17.18   C
ATOM  5386  C    LEU D 148     6.713   6.648   2.930  1.00 17.85   C
ATOM  5387  O    LEU D 148     6.144   5.687   3.455  1.00 18.10   O
ATOM  5388  CB   LEU D 148     8.766   6.634   4.339  1.00 17.70   C
ATOM  5389  CG   LEU D 148     9.341   5.529   3.455  1.00 18.31   C
ATOM  5390  CD1  LEU D 148     9.971   6.138   2.209  1.00 18.21   C
ATOM  5391  CD2  LEU D 148    10.363   4.739   4.261  1.00 17.59   C
ATOM  5392  N    ILE D 149     6.524   6.985   1.664  1.00 15.49   N
ATOM  5393  CA   ILE D 149     5.620   6.239   0.836  1.00 14.23   C
ATOM  5394  C    ILE D 149     6.372   5.397  -0.166  1.00 16.16   C
ATOM  5395  O    ILE D 149     7.158   5.913  -0.970  1.00 16.11   O
ATOM  5396  CB   ILE D 149     4.679   7.179   0.075  1.00 14.76   C
ATOM  5397  CG1  ILE D 149     4.054   8.186   1.049  1.00 16.74   C
ATOM  5398  CG2  ILE D 149     3.574   6.394  -0.555  1.00 12.78   C
ATOM  5399  CD1  ILE D 149     3.071   9.169   0.413  1.00 16.08   C
ATOM  5400  N    LEU D 150     6.150   4.085  -0.109  1.00 16.37   N
ATOM  5401  CA   LEU D 150     6.777   3.134  -1.019  1.00 15.78   C
ATOM  5402  C    LEU D 150     5.731   2.617  -2.017  1.00 16.06   C
ATOM  5403  O    LEU D 150     5.030   1.649  -1.733  1.00 18.43   O
ATOM  5404  CB   LEU D 150     7.348   1.967  -0.222  1.00 15.91   C
ATOM  5405  CG   LEU D 150     8.574   2.331   0.615  1.00 18.04   C
ATOM  5406  CD1  LEU D 150     8.992   1.115   1.454  1.00 17.79   C
ATOM  5407  CD2  LEU D 150     9.701   2.710  -0.317  1.00 18.36   C
ATOM  5408  N    VAL D 151     5.638   3.237  -3.192  1.00 15.76   N
ATOM  5409  CA   VAL D 151     4.652   2.842  -4.206  1.00 13.81   C
ATOM  5410  C    VAL D 151     5.120   1.738  -5.154  1.00 14.84   C
ATOM  5411  O    VAL D 151     6.307   1.655  -5.479  1.00 16.79   O
ATOM  5412  CB   VAL D 151     4.262   4.060  -5.046  1.00 12.78   C
ATOM  5413  CG1  VAL D 151     3.969   5.220  -4.140  1.00 12.04   C
ATOM  5414  CG2  VAL D 151     5.385   4.443  -5.983  1.00 11.76   C
ATOM  5415  N    GLY D 152     4.201   0.894  -5.610  1.00 15.27   N
ATOM  5416  CA   GLY D 152     4.551  -0.171  -6.532  1.00 16.08   C
ATOM  5417  C    GLY D 152     4.718   0.360  -7.941  1.00 17.68   C
ATOM  5418  O    GLY D 152     5.418  -0.214  -8.785  1.00 16.74   O
ATOM  5419  N    ARG D 153     4.051   1.465  -8.214  1.00 19.71   N
ATOM  5420  CA   ARG D 153     4.161   2.092  -9.527  1.00 22.17   C
ATOM  5421  C    ARG D 153     3.728   3.534  -9.413  1.00 21.60   C
ATOM  5422  O    ARG D 153     3.158   3.949  -8.402  1.00 20.53   O
ATOM  5423  CB   ARG D 153     3.289   1.368 -10.541  1.00 24.13   C
ATOM  5424  CG   ARG D 153     1.822   1.522 -10.267  1.00 29.08   C
ATOM  5425  CD   ARG D 153     0.979   0.783 -11.289  1.00 33.84   C
ATOM  5426  NE   ARG D 153    -0.437   1.126 -11.150  1.00 40.15   N
ATOM  5427  CZ   ARG D 153    -1.259   1.369 -12.172  1.00 40.75   C
ATOM  5428  NH1  ARG D 153    -0.811   1.302 -13.416  1.00 41.69   N
ATOM  5429  NH2  ARG D 153    -2.523   1.712 -11.944  1.00 42.08   N
ATOM  5430  N    LEU D 154     4.006   4.302 -10.447  1.00 20.16   N
ATOM  5431  CA   LEU D 154     3.626   5.702 -10.455  1.00 20.73   C
ATOM  5432  C    LEU D 154     2.232   5.879 -11.068  1.00 21.16   C
ATOM  5433  O    LEU D 154     2.002   5.516 -12.220  1.00 19.91   O
ATOM  5434  CB   LEU D 154     4.663   6.506 -11.242  1.00 18.97   C
ATOM  5435  CG   LEU D 154     5.334   7.624 -10.483  1.00 17.55   C
ATOM  5436  CD1  LEU D 154     5.621   7.167  -9.079  1.00 17.29   C
ATOM  5437  CD2  LEU D 154     6.606   8.038 -11.191  1.00 15.32   C
ATOM  5438  N    PHE D 155     1.315   6.429 -10.271  1.00 22.23   N
ATOM  5439  CA   PHE D 155     -0.064   6.668 -10.700  1.00 24.37   C
ATOM  5440  C    PHE D 155     -0.168   7.841 -11.688  1.00 24.95   C
ATOM  5441  O    PHE D 155     -0.104   9.008 -11.292  1.00 25.66   O
ATOM  5442  CB   PHE D 155     -0.955   6.950  -9.462  1.00 25.90   C
ATOM  5443  CG   PHE D 155     -2.439   7.067  -9.771  1.00 25.09   C
```

FIG. 6 (con't)

| | | | | | |
|---|---|---|---|---|---|
| ATOM | 2174 | CB  TRP B 121 | -2.763 -1.897 88.183 1.00 13.51 | C |
| ATOM | 2175 | CG  TRP B 121 | -2.022 -0.999 87.255 1.00 14.95 | C |
| ATOM | 2176 | CD1 TRP B 121 | -1.879 -1.139 85.907 1.00 15.66 | C |
| ATOM | 2177 | CD2 TRP B 121 | -1.183 0.106 87.626 1.00 15.87 | C |
| ATOM | 2178 | NE1 TRP B 121 | -1.013 -0.198 85.414 1.00 13.06 | N |
| ATOM | 2179 | CE2 TRP B 121 | -0.574 0.589 86.444 1.00 13.64 | C |
| ATOM | 2180 | CE3 TRP B 121 | -0.896 0.756 88.846 1.00 15.19 | C |
| ATOM | 2181 | CZ2 TRP B 121 | 0.319 1.658 86.439 1.00 13.41 | C |
| ATOM | 2182 | CZ3 TRP B 121 | -0.003 1.828 88.838 1.00 12.86 | C |
| ATOM | 2183 | CH2 TRP B 121 | 0.580 2.273 87.640 1.00 13.34 | C |
| ATOM | 2184 | N   TYR B 122 | -3.286 -4.900 88.804 1.00 15.44 | N |
| ATOM | 2185 | CA  TYR B 122 | -3.519 -5.892 89.851 1.00 15.97 | C |
| ATOM | 2186 | C   TYR B 122 | -2.222 -5.959 90.660 1.00 16.17 | C |
| ATOM | 2187 | O   TYR B 122 | -1.266 -6.613 90.250 1.00 16.08 | O |
| ATOM | 2188 | CB  TYR B 122 | -3.837 -7.256 89.263 1.00 16.33 | C |
| ATOM | 2189 | CG  TYR B 122 | -5.192 -7.342 88.608 1.00 16.18 | C |
| ATOM | 2190 | CD1 TYR B 122 | -5.356 -7.073 87.250 1.00 16.99 | C |
| ATOM | 2191 | CD2 TYR B 122 | -6.307 -7.724 89.342 1.00 16.95 | C |
| ATOM | 2192 | CE1 TYR B 122 | -6.611 -7.193 86.638 1.00 18.46 | C |
| ATOM | 2193 | CE2 TYR B 122 | -7.560 -7.845 88.754 1.00 16.77 | C |
| ATOM | 2194 | CZ  TYR B 122 | -7.711 -7.581 87.403 1.00 19.17 | C |
| ATOM | 2195 | OH  TYR B 122 | -8.962 -7.703 86.837 1.00 18.02 | O |
| ATOM | 2196 | N   VAL B 123 | -2.190 -5.276 91.799 1.00 16.34 | N |
| ATOM | 2197 | CA  VAL B 123 | -1.012 -5.252 92.647 1.00 16.27 | C |
| ATOM | 2198 | C   VAL B 123 | -1.342 -5.837 93.997 1.00 17.21 | C |
| ATOM | 2199 | O   VAL B 123 | -2.515 -5.954 94.351 1.00 17.42 | O |
| ATOM | 2200 | CB  VAL B 123 | -0.468 -3.818 92.883 1.00 14.39 | C |
| ATOM | 2201 | CG1 VAL B 123 | 0.824 -3.634 92.155 1.00 13.34 | C |
| ATOM | 2202 | CG2 VAL B 123 | -1.460 -2.789 92.414 1.00 13.79 | C |
| ATOM | 2203 | N   SER B 124 | -0.299 -6.179 94.755 1.00 17.17 | N |
| ATOM | 2204 | CA  SER B 124 | -0.451 -6.765 96.086 1.00 17.43 | C |
| ATOM | 2205 | C   SER B 124 | -0.827 -5.711 97.119 1.00 17.04 | C |
| ATOM | 2206 | O   SER B 124 | -1.564 -5.991 98.065 1.00 18.00 | O |
| ATOM | 2207 | CB  SER B 124 | 0.850 -7.469 96.498 1.00 16.15 | C |
| ATOM | 2208 | OG  SER B 124 | 1.941 -6.563 96.576 1.00 14.06 | O |
| ATOM | 2209 | N   SER B 125 | -0.334 -4.499 96.931 1.00 17.34 | N |
| ATOM | 2210 | CA  SER B 125 | -0.632 -3.436 97.873 1.00 17.65 | C |
| ATOM | 2211 | C   SER B 125 | 0.738 -2.103 97.160 1.00 16.78 | C |
| ATOM | 2212 | O   SER B 125 | -0.131 -1.909 96.107 1.00 17.41 | O |
| ATOM | 2213 | CB  SER B 125 | 0.465 -3.347 98.921 1.00 19.10 | C |
| ATOM | 2214 | OG  SER B 125 | 1.689 -2.970 98.303 1.00 23.89 | O |
| ATOM | 2215 | N   SER B 126 | -1.495 -1.189 97.753 1.00 16.73 | N |
| ATOM | 2216 | CA  SER B 126 | -1.676 0.156 97.218 1.00 16.16 | C |
| ATOM | 2217 | C   SER B 126 | -0.321 0.846 97.102 1.00 15.14 | C |
| ATOM | 2218 | O   SER B 126 | 0.621 0.482 97.784 1.00 14.33 | O |
| ATOM | 2219 | CB  SER B 126 | -2.580 0.982 98.146 1.00 16.63 | C |
| ATOM | 2220 | OG  SER B 126 | -1.949 1.285 99.393 1.00 18.88 | O |
| ATOM | 2221 | N   PRO B 127 | -0.226 1.866 96.243 1.00 16.79 | N |
| ATOM | 2222 | CA  PRO B 127 | 1.024 2.613 96.033 1.00 18.72 | C |
| ATOM | 2223 | C   PRO B 127 | 1.465 3.449 97.249 1.00 19.06 | C |
| ATOM | 2224 | O   PRO B 127 | 0.657 3.785 98.121 1.00 18.57 | O |
| ATOM | 2225 | CB  PRO B 127 | 0.708 3.471 94.807 1.00 18.56 | C |
| ATOM | 2226 | CG  PRO B 127 | -0.770 3.751 94.973 1.00 19.12 | C |
| ATOM | 2227 | CD  PRO B 127 | -1.315 2.408 95.402 1.00 18.60 | C |
| ATOM | 2228 | N   CYS B 128 | 2.752 3.759 97.309 1.00 20.85 | N |
| ATOM | 2229 | CA  CYS B 128 | 3.280 4.540 98.403 1.00 22.90 | C |
| ATOM | 2230 | C   CYS B 128 | 3.070 6.012 98.085 1.00 23.71 | C |
| ATOM | 2231 | O   CYS B 128 | 2.570 6.354 97.011 1.00 23.05 | O |
| ATOM | 2232 | CB  CYS B 128 | 4.774 4.246 98.622 1.00 23.04 | C |
| ATOM | 2233 | SG  CYS B 128 | 5.891 4.647 97.240 1.00 24.18 | S |
| ATOM | 2234 | N   ALA B 129 | 3.453 6.867 99.024 1.00 24.79 | N |
| ATOM | 2235 | CA  ALA B 129 | 3.289 8.299 98.861 1.00 25.62 | C |
| ATOM | 2236 | C   ALA B 129 | 3.940 8.779 97.589 1.00 25.75 | C |
| ATOM | 2237 | O   ALA B 129 | 3.333 9.515 96.813 1.00 26.64 | O |
| ATOM | 2238 | CB  ALA B 129 | 3.898 9.017 100.050 1.00 27.15 | C |
| ATOM | 2239 | N   ALA B 130 | 5.177 8.359 97.368 1.00 26.43 | N |
| ATOM | 2240 | CA  ALA B 130 | 5.914 8.763 96.178 1.00 27.45 | C |
| ATOM | 2241 | C   ALA B 130 | 5.293 8.216 94.891 1.00 28.53 | C |
| ATOM | 2242 | O   ALA B 130 | 5.138 8.947 93.915 1.00 29.62 | O |
| ATOM | 2243 | CB  ALA B 130 | 7.358 8.322 96.293 1.00 25.77 | C |
| ATOM | 2244 | N   CYS B 131 | 4.954 6.932 94.881 1.00 28.75 | N |
| ATOM | 2245 | CA  CYS B 131 | 4.354 6.333 93.701 1.00 29.91 | C |
| ATOM | 2246 | C   CYS B 131 | 3.021 6.987 93.328 1.00 29.50 | C |
| ATOM | 2247 | O   CYS B 131 | 2.719 7.184 92.152 1.00 28.24 | O |
| ATOM | 2248 | CB  CYS B 131 | 4.159 4.832 93.920 1.00 30.09 | C |
| ATOM | 2249 | SG  CYS B 131 | 5.693 3.919 93.746 1.00 32.76 | S |
| ATOM | 2250 | N   ALA B 132 | 2.237 7.332 94.339 1.00 29.93 | N |
| ATOM | 2251 | CA  ALA B 132 | 0.959 7.975 94.110 1.00 31.40 | C |
| ATOM | 2252 | C   ALA B 132 | 1.163 9.281 93.332 1.00 31.89 | C |
| ATOM | 2253 | O   ALA B 132 | 0.409 9.583 92.410 1.00 32.31 | O |
| ATOM | 2254 | CB  ALA B 132 | 0.286 8.251 95.427 1.00 30.62 | C |
| ATOM | 2255 | N   ASP B 133 | 2.187 10.044 93.695 1.00 32.98 | N |
| ATOM | 2256 | CA  ASP B 133 | 2.459 11.292 93.005 1.00 35.62 | C |
| ATOM | 2257 | C   ASP B 133 | 2.791 11.055 91.545 1.00 36.66 | C |
| ATOM | 2258 | O   ASP B 133 | 2.246 11.722 90.663 1.00 37.83 | O |
| ATOM | 2259 | CB  ASP B 133 | 3.612 12.054 93.662 1.00 37.11 | C |
| ATOM | 5444 | CD1 PHE D 155 | -3.164 5.960 -10.211 1.00 26.79 | C |
| ATOM | 5445 | CD2 PHE D 155 | -3.112 8.286 -9.608 1.00 27.59 | C |
| ATOM | 5446 | CE1 PHE D 155 | -4.546 6.041 -10.491 1.00 26.16 | C |
| ATOM | 5447 | CE2 PHE D 155 | -4.501 8.390 -9.884 1.00 28.29 | C |
| ATOM | 5448 | CZ  PHE D 155 | -5.214 7.255 -10.326 1.00 26.96 | C |
| ATOM | 5449 | N   MET D 156 | -0.315 7.528 -12.977 1.00 25.83 | N |
| ATOM | 5450 | CA  MET D 156 | -0.433 8.546 -14.022 1.00 25.13 | C |
| ATOM | 5451 | C   MET D 156 | 0.675 9.595 -13.964 1.00 24.88 | C |
| ATOM | 5452 | O   MET D 156 | 0.413 10.793 -13.821 1.00 23.61 | O |
| ATOM | 5453 | CB  MET D 156 | -1.798 9.231 -13.912 1.00 27.00 | C |
| ATOM | 5454 | CG  MET D 156 | -2.960 8.298 -14.194 1.00 28.62 | C |
| ATOM | 5455 | SD  MET D 156 | -4.570 9.089 -13.980 1.00 33.79 | S |
| ATOM | 5456 | CE  MET D 156 | -5.630 7.950 -14.825 1.00 30.99 | C |
| ATOM | 5457 | N   TRP D 157 | 1.911 9.131 -14.085 1.00 25.17 | N |
| ATOM | 5458 | CA  TRP D 157 | 3.072 10.006 -14.023 1.00 26.18 | C |
| ATOM | 5459 | C   TRP D 157 | 3.137 10.940 -15.215 1.00 27.55 | C |
| ATOM | 5460 | O   TRP D 157 | 3.863 11.932 -15.196 1.00 28.62 | O |
| ATOM | 5461 | CB  TRP D 157 | 4.355 9.179 -13.963 1.00 23.93 | C |
| ATOM | 5462 | CG  TRP D 157 | 4.529 8.280 -15.133 1.00 23.26 | C |
| ATOM | 5463 | CD1 TRP D 157 | 3.975 7.049 -15.313 1.00 24.19 | C |
| ATOM | 5464 | CD2 TRP D 157 | 5.329 8.531 -16.296 1.00 23.00 | C |
| ATOM | 5465 | NE1 TRP D 157 | 4.387 6.510 -16.515 1.00 23.02 | N |
| ATOM | 5466 | CE2 TRP D 157 | 5.220 7.401 -17.135 1.00 21.97 | C |
| ATOM | 5467 | CE3 TRP D 157 | 6.135 9.602 -16.710 1.00 22.23 | C |
| ATOM | 5468 | CZ2 TRP D 157 | 5.878 7.305 -18.360 1.00 23.49 | C |
| ATOM | 5469 | CZ3 TRP D 157 | 6.795 9.512 -17.934 1.00 20.65 | C |
| ATOM | 5470 | CH2 TRP D 157 | 6.663 8.370 -18.743 1.00 22.08 | C |
| ATOM | 5471 | N   GLU D 158 | 2.383 10.621 -16.256 1.00 28.11 | N |
| ATOM | 5472 | CA  GLU D 158 | 2.375 11.460 -17.447 1.00 29.13 | C |
| ATOM | 5473 | C   GLU D 158 | 1.638 12.778 -17.232 1.00 31.49 | C |
| ATOM | 5474 | O   GLU D 158 | 1.935 13.760 -17.907 1.00 30.72 | O |
| ATOM | 5475 | CB  GLU D 158 | 1.742 10.728 -18.623 1.00 27.52 | C |
| ATOM | 5476 | CG  GLU D 158 | 2.565 9.573 -19.171 1.00 25.86 | C |
| ATOM | 5477 | CD  GLU D 158 | 1.844 8.789 -20.273 1.00 26.01 | C |
| ATOM | 5478 | OE1 GLU D 158 | 1.515 9.365 -21.330 1.00 24.64 | O |
| ATOM | 5479 | OE2 GLU D 158 | 1.609 7.574 -20.078 1.00 25.82 | O |
| ATOM | 5480 | N   GLU D 159 | 0.664 12.794 -16.320 1.00 33.84 | N |
| ATOM | 5481 | CA  GLU D 159 | -0.091 14.016 -16.040 1.00 37.18 | C |
| ATOM | 5482 | C   GLU D 159 | 0.787 15.067 -15.395 1.00 37.99 | C |
| ATOM | 5483 | O   GLU D 159 | 1.436 14.806 -14.380 1.00 39.09 | O |
| ATOM | 5484 | CB  GLU D 159 | -1.258 13.751 -15.087 1.00 38.87 | C |
| ATOM | 5485 | CG  GLU D 159 | -2.526 13.261 -15.732 1.00 43.03 | C |
| ATOM | 5486 | CD  GLU D 159 | -3.653 13.114 -14.732 1.00 46.79 | C |
| ATOM | 5487 | OE1 GLU D 159 | -4.173 14.152 -14.256 1.00 47.75 | O |
| ATOM | 5488 | OE2 GLU D 159 | -4.013 11.955 -14.411 1.00 48.46 | O |
| ATOM | 5489 | N   PRO D 160 | 0.810 16.280 -15.963 1.00 39.05 | N |
| ATOM | 5490 | CA  PRO D 160 | 1.622 17.361 -15.405 1.00 39.86 | C |
| ATOM | 5491 | C   PRO D 160 | 1.104 17.744 -14.021 1.00 39.91 | C |
| ATOM | 5492 | O   PRO D 160 | 1.850 18.254 -13.183 1.00 40.40 | O |
| ATOM | 5493 | CB  PRO D 160 | 1.456 18.472 -16.436 1.00 39.97 | C |
| ATOM | 5494 | CG  PRO D 160 | 0.072 18.241 -16.937 1.00 40.79 | C |
| ATOM | 5495 | CD  PRO D 160 | 0.077 16.747 -17.147 1.00 39.62 | C |
| ATOM | 5496 | N   GLU D 161 | -0.179 17.480 -13.790 1.00 39.72 | N |
| ATOM | 5497 | CA  GLU D 161 | -0.794 17.789 -12.503 1.00 39.81 | C |
| ATOM | 5498 | C   GLU D 161 | -0.250 16.834 -11.466 1.00 38.81 | C |
| ATOM | 5499 | O   GLU D 161 | -0.049 17.209 -10.315 1.00 39.71 | O |
| ATOM | 5500 | CB  GLU D 161 | -2.316 17.658 -12.568 1.00 40.77 | C |
| ATOM | 5501 | CG  GLU D 161 | -2.992 18.596 -13.572 1.00 44.12 | C |
| ATOM | 5502 | CD  GLU D 161 | -3.053 18.021 -14.986 1.00 46.51 | C |
| ATOM | 5503 | OE1 GLU D 161 | -2.473 16.938 -15.214 1.00 48.37 | O |
| ATOM | 5504 | OE2 GLU D 161 | -3.676 18.649 -15.877 1.00 47.13 | O |
| ATOM | 5505 | N   ILE D 162 | -0.018 15.593 -11.878 1.00 36.91 | N |
| ATOM | 5506 | CA  ILE D 162 | 0.510 14.578 -10.980 1.00 35.16 | C |
| ATOM | 5507 | C   ILE D 162 | 1.977 14.852 -10.657 1.00 34.48 | C |
| ATOM | 5508 | O   ILE D 162 | 2.424 14.672 -9.521 1.00 34.33 | O |
| ATOM | 5509 | CB  ILE D 162 | 0.379 13.190 -11.611 1.00 34.31 | C |
| ATOM | 5510 | CG1 ILE D 162 | -1.098 12.821 -11.735 1.00 34.00 | C |
| ATOM | 5511 | CG2 ILE D 162 | 1.139 12.167 -10.792 1.00 34.93 | C |
| ATOM | 5512 | CD1 ILE D 162 | -1.796 12.661 -10.404 1.00 32.72 | C |
| ATOM | 5513 | N   GLN D 163 | 2.728 15.287 -11.660 1.00 33.54 | N |
| ATOM | 5514 | CA  GLN D 163 | 4.140 15.567 -11.443 1.00 32.88 | C |
| ATOM | 5515 | C   GLN D 163 | 4.291 16.726 -10.484 1.00 32.46 | C |
| ATOM | 5516 | O   GLN D 163 | 5.300 16.833 -9.790 1.00 34.04 | O |
| ATOM | 5517 | CB  GLN D 163 | 4.837 15.913 -12.749 1.00 31.98 | C |
| ATOM | 5518 | CG  GLN D 163 | 4.625 14.910 -13.849 1.00 31.39 | C |
| ATOM | 5519 | CD  GLN D 163 | 5.613 15.071 -14.991 1.00 32.96 | C |
| ATOM | 5520 | OE1 GLN D 163 | 5.403 14.553 -16.082 1.00 31.92 | O |
| ATOM | 5521 | NE2 GLN D 163 | 6.714 15.786 -14.736 1.00 35.20 | N |
| ATOM | 5522 | N   ALA D 164 | 3.292 17.598 -10.459 1.00 31.78 | N |
| ATOM | 5523 | CA  ALA D 164 | 3.306 18.751 -9.572 1.00 31.71 | C |
| ATOM | 5524 | C   ALA D 164 | 3.071 18.313 -8.139 1.00 31.32 | C |
| ATOM | 5525 | O   ALA D 164 | 3.689 18.845 -7.218 1.00 32.25 | O |
| ATOM | 5526 | CB  ALA D 164 | 2.244 19.728 -9.986 1.00 31.06 | C |
| ATOM | 5527 | N   ALA D 165 | 2.166 17.356 -7.957 1.00 32.18 | N |
| ATOM | 5528 | CA  ALA D 165 | 1.842 16.843 -6.627 1.00 32.93 | C |
| ATOM | 5529 | C   ALA D 165 | 3.054 16.142 -6.034 1.00 33.64 | C |

FIG. 6 (con't)

```
ATOM   2260  CG  ASP B 133      3.202  12.736 94.947  1.00 38.64      C
ATOM   2261  OD1 ASP B 133      2.028  13.170 95.052  1.00 39.37      O
ATOM   2262  OD2 ASP B 133      4.050  12.858 95.849  1.00 40.21      O
ATOM   2263  N   ARG B 134      3.691  10.117 91.282  1.00 37.48      N
ATOM   2264  CA  ARG B 134      4.064   9.783 89.908  1.00 38.09      C
ATOM   2265  C   ARG B 134      2.794   9.472 89.135  1.00 36.52      C
ATOM   2266  O   ARG B 134      2.585   9.976 88.034  1.00 37.99      O
ATOM   2267  CB  ARG B 134      4.963   8.549 89.883  1.00 41.14      C
ATOM   2268  CG  ARG B 134      6.206   8.649 90.748  1.00 44.82      C
ATOM   2269  CD  ARG B 134      6.614   7.270 91.281  1.00 47.86      C
ATOM   2270  NE  ARG B 134      7.848   7.315 92.062  1.00 48.00      N
ATOM   2271  CZ  ARG B 134      9.037   7.537 91.525  1.00 47.68      C
ATOM   2272  NH1 ARG B 134      9.125   7.722 90.215  1.00 48.22      N
ATOM   2273  NH2 ARG B 134     10.125   7.578 92.283  1.00 47.56      N
ATOM   2274  N   ILE B 135      1.952   8.622 89.712  1.00 33.49      N
ATOM   2275  CA  ILE B 135      0.698   8.245 89.076  1.00 31.24      C
ATOM   2276  C   ILE B 135     -0.140   9.495 88.769  1.00 30.81      C
ATOM   2277  O   ILE B 135     -0.653   9.657 87.666  1.00 30.33      O
ATOM   2278  CB  ILE B 135     -0.109   7.282 89.988  1.00 29.47      C
ATOM   2279  CG1 ILE B 135      0.680   5.983 90.187  1.00 27.46      C
ATOM   2280  CG2 ILE B 135     -1.474   6.987 89.376  1.00 27.90      C
ATOM   2281  CD1 ILE B 135      0.092   5.059 91.228  1.00 26.02      C
ATOM   2282  N   ILE B 136     -0.253  10.382 89.752  1.00 30.45      N
ATOM   2283  CA  ILE B 136     -1.022  11.610 89.603  1.00 30.68      C
ATOM   2284  C   ILE B 136     -0.440  12.518 88.510  1.00 32.06      C
ATOM   2285  O   ILE B 136     -1.170  13.070 87.674  1.00 31.72      O
ATOM   2286  CB  ILE B 136     -1.072  12.369 90.950  1.00 28.90      C
ATOM   2287  CG1 ILE B 136     -1.927  11.589 91.948  1.00 27.80      C
ATOM   2288  CG2 ILE B 136     -1.638  13.753 90.764  1.00 29.12      C
ATOM   2289  CD1 ILE B 136     -1.834  12.103 93.356  1.00 26.90      C
ATOM   2290  N   LYS B 137      0.874  12.659 88.506  1.00 32.68      N
ATOM   2291  CA  LYS B 137      1.507  13.508 87.517  1.00 35.72      C
ATOM   2292  C   LYS B 137      1.298  12.973 86.105  1.00 35.76      C
ATOM   2293  O   LYS B 137      1.099  13.745 85.164  1.00 35.63      O
ATOM   2294  CB  LYS B 137      3.007  13.657 87.822  1.00 37.87      C
ATOM   2295  CG  LYS B 137      3.293  14.233 89.218  1.00 41.24      C
ATOM   2296  CD  LYS B 137      4.701  14.825 89.350  1.00 42.17      C
ATOM   2297  CE  LYS B 137      4.902  15.483 90.717  1.00 43.82      C
ATOM   2298  NZ  LYS B 137      6.179  16.245 90.796  1.00 45.43      N
ATOM   2299  N   THR B 138      1.335  11.651 85.962  1.00 35.39      N
ATOM   2300  CA  THR B 138      1.129  11.019 84.666  1.00 35.04      C
ATOM   2301  C   THR B 138     -0.340  11.174 84.266  1.00 33.96      C
ATOM   2302  O   THR B 138     -0.642  11.537 83.138  1.00 32.49      O
ATOM   2303  CB  THR B 138      1.494   9.523 84.710  1.00 34.86      C
ATOM   2304  OG1 THR B 138      2.878   9.380 85.029  1.00 34.79      O
ATOM   2305  CG2 THR B 138      1.236   8.877 83.361  1.00 34.43      C
ATOM   2306  N   LEU B 139     -1.237  10.892 85.205  1.00 34.40      N
ATOM   2307  CA  LEU B 139     -2.662  11.026 84.952  1.00 35.51      C
ATOM   2308  C   LEU B 139     -2.976  12.474 84.590  1.00 36.91      C
ATOM   2309  O   LEU B 139     -3.926  12.746 83.862  1.00 37.56      O
ATOM   2310  CB  LEU B 139     -3.470  10.624 86.185  1.00 34.03      C
ATOM   2311  CG  LEU B 139     -3.743   9.139 86.390  1.00 33.41      C
ATOM   2312  CD1 LEU B 139     -4.416   8.898 87.737  1.00 32.54      C
ATOM   2313  CD2 LEU B 139     -4.627   8.659 85.263  1.00 33.87      C
ATOM   2314  N   SER B 140     -2.170  13.397 85.108  1.00 38.70      N
ATOM   2315  CA  SER B 140     -2.345  14.823 84.850  1.00 40.17      C
ATOM   2316  C   SER B 140     -1.921  15.192 83.421  1.00 40.74      C
ATOM   2317  O   SER B 140     -2.573  15.999 82.749  1.00 39.59      O
ATOM   2318  CB  SER B 140     -1.538  15.628 85.859  1.00 41.74      C
ATOM   2319  OG  SER B 140     -1.453  16.987 85.466  1.00 43.64      O
ATOM   2320  N   LYS B 141     -0.822  14.602 82.970  1.00 42.10      N
ATOM   2321  CA  LYS B 141     -0.324  14.843 81.622  1.00 43.45      C
ATOM   2322  C   LYS B 141     -1.271  14.301 80.559  1.00 43.29      C
ATOM   2323  O   LYS B 141     -1.801  15.066 79.763  1.00 44.45      O
ATOM   2324  CB  LYS B 141      1.048  14.195 81.423  1.00 44.76      C
ATOM   2325  CG  LYS B 141      2.173  14.873 82.168  1.00 47.52      C
ATOM   2326  CD  LYS B 141      3.488  14.131 81.968  1.00 50.79      C
ATOM   2327  CE  LYS B 141      4.652  14.809 82.706  1.00 52.67      C
ATOM   2328  NZ  LYS B 141      5.036  16.149 82.151  1.00 54.39      N
ATOM   2329  N   THR B 142     -1.482  12.983 80.538  1.00 42.75      N
ATOM   2330  CA  THR B 142     -2.359  12.355 79.544  1.00 42.17      C
ATOM   2331  C   THR B 142     -3.813  12.336 80.008  1.00 41.50      C
ATOM   2332  O   THR B 142     -4.161  11.627 80.952  1.00 42.71      O
ATOM   2333  CB  THR B 142     -1.927  10.903 79.258  1.00 41.90      C
ATOM   2334  OG1 THR B 142     -2.305  10.076 80.358  1.00 44.46      O
ATOM   2335  CG2 THR B 142     -0.421  10.816 79.098  1.00 42.21      C
ATOM   2336  N   LYS B 143     -4.660  13.109 79.338  1.00 40.08      N
ATOM   2337  CA  LYS B 143     -6.070  13.189 79.701  1.00 38.21      C
ATOM   2338  C   LYS B 143     -6.869  12.077 79.060  1.00 35.50      C
ATOM   2339  O   LYS B 143     -8.017  11.833 79.421  1.00 33.75      O
ATOM   2340  CB  LYS B 143     -6.661  14.540 79.265  1.00 40.79      C
ATOM   2341  CG  LYS B 143     -5.993  15.776 79.869  1.00 43.12      C
ATOM   2342  CD  LYS B 143     -4.890  16.331 78.970  1.00 46.16      C
ATOM   2343  CE  LYS B 143     -4.301  17.631 79.528  1.00 48.14      C
ATOM   2344  NZ  LYS B 143     -5.343  18.665 79.813  1.00 48.76      N
ATOM   2345  N   ASN B 144     -6.257  11.400 78.097  1.00 34.11      N

ATOM   5530  O   ALA D 165      3.436  16.432 -4.901  1.00 35.68      O
ATOM   5531  CB  ALA D 165      0.657  15.879 -6.703  1.00 32.57      C
ATOM   5532  N   LEU D 166      3.667  15.229 -6.791  1.00 33.46      N
ATOM   5533  CA  LEU D 166      4.844  14.508 -6.306  1.00 34.33      C
ATOM   5534  C   LEU D 166      5.917  15.475 -5.837  1.00 35.03      C
ATOM   5535  O   LEU D 166      6.508  15.287 -4.772  1.00 35.48      O
ATOM   5536  CB  LEU D 166      5.436  13.612 -7.398  1.00 34.02      C
ATOM   5537  CG  LEU D 166      4.594  12.392 -7.791  1.00 35.27      C
ATOM   5538  CD1 LEU D 166      5.288  11.593 -8.891  1.00 34.87      C
ATOM   5539  CD2 LEU D 166      4.379  11.556 -6.559  1.00 34.02      C
ATOM   5540  N   LYS D 167      6.171  16.515 -6.633  1.00 35.34      N
ATOM   5541  CA  LYS D 167      7.191  17.501 -6.286  1.00 35.27      C
ATOM   5542  C   LYS D 167      6.797  18.250 -5.028  1.00 34.80      C
ATOM   5543  O   LYS D 167      7.617  18.427 -4.134  1.00 35.43      O
ATOM   5544  CB  LYS D 167      7.412  18.484 -7.425  1.00 36.10      C
ATOM   5545  CG  LYS D 167      7.989  17.860 -8.669  1.00 37.03      C
ATOM   5546  CD  LYS D 167      8.217  18.913 -9.732  1.00 38.35      C
ATOM   5547  CE  LYS D 167      7.972  18.341 -11.114 1.00 40.23      C
ATOM   5548  NZ  LYS D 167      8.082  19.358 -12.191 1.00 41.62      N
ATOM   5549  N   LYS D 168      5.556  18.705 -4.948  1.00 33.35      N
ATOM   5550  CA  LYS D 168      5.111  19.413 -3.758  1.00 34.68      C
ATOM   5551  C   LYS D 168      5.117  18.493 -2.529  1.00 34.16      C
ATOM   5552  O   LYS D 168      5.281  18.951 -1.393  1.00 34.81      O
ATOM   5553  CB  LYS D 168      3.700  19.954 -3.978  1.00 36.13      C
ATOM   5554  CG  LYS D 168      3.662  21.161 -4.884  1.00 39.03      C
ATOM   5555  CD  LYS D 168      2.246  21.515 -5.291  1.00 40.86      C
ATOM   5556  CE  LYS D 168      2.248  22.690 -6.257  1.00 41.95      C
ATOM   5557  NZ  LYS D 168      0.907  22.888 -6.869  1.00 44.63      N
ATOM   5558  N   LEU D 169      4.934  17.196 -2.768  1.00 32.86      N
ATOM   5559  CA  LEU D 169      4.917  16.206 -1.705  1.00 30.83      C
ATOM   5560  C   LEU D 169      6.317  16.132 -1.095  1.00 29.22      C
ATOM   5561  O   LEU D 169      6.470  16.032  0.124  1.00 29.21      O
ATOM   5562  CB  LEU D 169      4.487  14.841 -2.263  1.00 31.15      C
ATOM   5563  CG  LEU D 169      3.602  13.991 -1.335  1.00 31.69      C
ATOM   5564  CD1 LEU D 169      2.288  14.697 -1.057  1.00 32.01      C
ATOM   5565  CD2 LEU D 169      3.326  12.661 -1.984  1.00 31.26      C
ATOM   5566  N   LYS D 170      7.333  16.201 -1.944  1.00 27.24      N
ATOM   5567  CA  LYS D 170      8.722  16.182 -1.497  1.00 26.98      C
ATOM   5568  C   LYS D 170      9.047  17.488 -0.774  1.00 27.67      C
ATOM   5569  O   LYS D 170      9.888  17.528  0.129  1.00 28.74      O
ATOM   5570  CB  LYS D 170      9.652  16.024 -2.695  1.00 25.11      C
ATOM   5571  CG  LYS D 170     11.103  16.266 -2.366  1.00 24.17      C
ATOM   5572  CD  LYS D 170     11.985  16.079 -3.583  1.00 24.78      C
ATOM   5573  CE  LYS D 170     13.432  16.414 -3.249  1.00 25.18      C
ATOM   5574  NZ  LYS D 170     14.384  15.871 -4.256  1.00 27.96      N
ATOM   5575  N   GLU D 171      8.389  18.560 -1.200  1.00 29.38      N
ATOM   5576  CA  GLU D 171      8.565  19.875 -0.604  1.00 29.70      C
ATOM   5577  C   GLU D 171      8.096  19.815  0.838  1.00 29.21      C
ATOM   5578  O   GLU D 171      8.739  20.360  1.735  1.00 30.68      O
ATOM   5579  CB  GLU D 171      7.724  20.923 -1.338  1.00 31.99      C
ATOM   5580  CG  GLU D 171      8.008  21.077 -2.830  1.00 37.48      C
ATOM   5581  CD  GLU D 171      9.441  21.455 -3.128  1.00 41.09      C
ATOM   5582  OE1 GLU D 171     10.087  22.067 -2.246  1.00 43.93      O
ATOM   5583  OE2 GLU D 171      9.923  21.152 -4.248  1.00 43.50      O
ATOM   5584  N   ALA D 172      6.961  19.161  1.063  1.00 26.87      N
ATOM   5585  CA  ALA D 172      6.396  19.044  2.406  1.00 25.99      C
ATOM   5586  C   ALA D 172      7.257  18.156  3.316  1.00 25.51      C
ATOM   5587  O   ALA D 172      6.948  17.992  4.498  1.00 26.12      O
ATOM   5588  CB  ALA D 172      4.970  18.505  2.323  1.00 23.74      C
ATOM   5589  N   GLY D 173      8.330  17.601  2.751  1.00 24.51      N
ATOM   5590  CA  GLY D 173      9.229  16.741  3.499  1.00 23.82      C
ATOM   5591  C   GLY D 173      8.906  15.252  3.433  1.00 22.94      C
ATOM   5592  O   GLY D 173      9.454  14.448  4.192  1.00 22.76      O
ATOM   5593  N   CYS D 174      8.012  14.886  2.530  1.00 22.30      N
ATOM   5594  CA  CYS D 174      7.610  13.505  2.353  1.00 22.59      C
ATOM   5595  C   CYS D 174      8.613  12.754  1.475  1.00 22.97      C
ATOM   5596  O   CYS D 174      9.058  13.269  0.447  1.00 23.61      O
ATOM   5597  CB  CYS D 174      6.223  13.460  1.717  1.00 22.38      C
ATOM   5598  SG  CYS D 174      5.527  11.816  1.522  1.00 24.98      S
ATOM   5599  N   LYS D 175      8.980  11.547  1.885  1.00 23.23      N
ATOM   5600  CA  LYS D 175      9.928  10.740  1.139  1.00 23.92      C
ATOM   5601  C   LYS D 175      9.183   9.732  0.271  1.00 24.67      C
ATOM   5602  O   LYS D 175      8.413   8.916  0.773  1.00 24.42      O
ATOM   5603  CB  LYS D 175     10.863   9.992  2.091  1.00 27.00      C
ATOM   5604  CG  LYS D 175     11.878  10.866  2.834  1.00 31.91      C
ATOM   5605  CD  LYS D 175     12.905  11.460  1.876  1.00 35.00      C
ATOM   5606  CE  LYS D 175     14.035  12.169  2.609  1.00 36.67      C
ATOM   5607  NZ  LYS D 175     15.066  12.664  1.649  1.00 39.70      N
ATOM   5608  N   LEU D 176      9.419   9.787 -1.038  1.00 23.40      N
ATOM   5609  CA  LEU D 176      8.766   8.877 -1.963  1.00 22.77      C
ATOM   5610  C   LEU D 176      9.775   7.950 -2.609  1.00 22.88      C
ATOM   5611  O   LEU D 176     10.852   8.388 -2.999  1.00 23.26      O
ATOM   5612  CB  LEU D 176      8.055   9.661 -3.058  1.00 22.13      C
ATOM   5613  CG  LEU D 176      6.981  10.632 -2.580  1.00 24.29      C
ATOM   5614  CD1 LEU D 176      6.611  11.584 -3.708  1.00 24.25      C
ATOM   5615  CD2 LEU D 176      5.779   9.846 -2.088  1.00 23.16      C
```

FIG. 6 (con't)

```
ATOM   2346  CA  ASN B 144     -6.936  10.314  77.405  1.00 31.65     C
ATOM   2347  C   ASN B 144     -6.702   8.979  78.094  1.00 30.66     C
ATOM   2348  O   ASN B 144     -7.057   7.938  77.552  1.00 30.15     O
ATOM   2349  CB  ASN B 144     -6.468  10.230  75.965  1.00 31.74     C
ATOM   2350  CG  ASN B 144     -4.977   9.983  75.844  1.00 31.40     C
ATOM   2351  OD1 ASN B 144     -4.496   9.617  74.773  1.00 31.14     O
ATOM   2352  ND2 ASN B 144     -4.241  10.185  76.930  1.00 29.98     N
ATOM   2353  N   LEU B 145     -6.102   9.027  79.285  1.00 29.02     N
ATOM   2354  CA  LEU B 145     -5.794   7.839  80.075  1.00 27.76     C
ATOM   2355  C   LEU B 145     -6.658   7.733  81.334  1.00 27.57     C
ATOM   2356  O   LEU B 145     -6.814   8.705  82.072  1.00 27.04     O
ATOM   2357  CB  LEU B 145     -4.326   7.861  80.497  1.00 28.45     C
ATOM   2358  CG  LEU B 145     -3.873   6.822  81.534  1.00 28.94     C
ATOM   2359  CD1 LEU B 145     -3.750   5.460  80.890  1.00 29.85     C
ATOM   2360  CD2 LEU B 145     -2.532   7.231  82.100  1.00 28.94     C
ATOM   2361  N   ARG B 146     -7.196   6.541  81.588  1.00 26.96     N
ATOM   2362  CA  ARG B 146     -8.031   6.290  82.760  1.00 26.21     C
ATOM   2363  C   ARG B 146     -7.457   5.065  83.464  1.00 25.46     C
ATOM   2364  O   ARG B 146     -7.346   4.002  82.862  1.00 25.45     O
ATOM   2365  CB  ARG B 146     -9.474   6.019  82.337  1.00 27.96     C
ATOM   2366  CG  ARG B 146    -10.521   6.703  83.214  1.00 29.77     C
ATOM   2367  CD  ARG B 146    -11.108   7.951  82.562  1.00 29.46     C
ATOM   2368  NE  ARG B 146    -10.091   8.955  82.261  1.00 30.14     N
ATOM   2369  CZ  ARG B 146    -10.346  10.135  81.702  1.00 28.29     C
ATOM   2370  NH1 ARG B 146    -11.586  10.455  81.384  1.00 27.95     N
ATOM   2371  NH2 ARG B 146     -9.360  10.980  81.453  1.00 28.19     N
ATOM   2372  N   LEU B 147     -7.104   5.210  84.744  1.00 24.29     N
ATOM   2373  CA  LEU B 147     -6.496   4.127  85.505  1.00 21.79     C
ATOM   2374  C   LEU B 147     -7.366   3.543  86.617  1.00 20.79     C
ATOM   2375  O   LEU B 147     -8.088   4.261  87.299  1.00 20.53     O
ATOM   2376  CB  LEU B 147     -5.168   4.601  86.098  1.00 21.66     C
ATOM   2377  CG  LEU B 147     -4.371   3.566  86.901  1.00 21.65     C
ATOM   2378  CD1 LEU B 147     -4.022   2.396  85.997  1.00 21.64     C
ATOM   2379  CD2 LEU B 147     -3.110   4.195  87.472  1.00 19.04     C
ATOM   2380  N   LEU B 148     -7.261   2.221  86.783  1.00 19.06     N
ATOM   2381  CA  LEU B 148     -7.996   1.465  87.788  1.00 15.72     C
ATOM   2382  C   LEU B 148     -7.025   0.553  88.525  1.00 16.09     C
ATOM   2383  O   LEU B 148     -6.465  -0.382  87.946  1.00 15.26     O
ATOM   2384  CB  LEU B 148     -9.078   0.616  87.127  1.00 14.89     C
ATOM   2385  CG  LEU B 148     -9.660  -0.531  87.972  1.00 14.68     C
ATOM   2386  CD1 LEU B 148    -10.299   0.000  89.246  1.00 14.36     C
ATOM   2387  CD2 LEU B 148    -10.688  -1.282  87.151  1.00 13.45     C
ATOM   2388  N   ILE B 149     -6.826   0.818  89.806  1.00 14.70     N
ATOM   2389  CA  ILE B 149     -5.917   0.005  90.581  1.00 14.28     C
ATOM   2390  C   ILE B 149     -6.664  -0.922  91.534  1.00 15.06     C
ATOM   2391  O   ILE B 149     -7.431  -0.475  92.382  1.00 15.28     O
ATOM   2392  CB  ILE B 149     -4.968   0.888  91.390  1.00 14.06     C
ATOM   2393  CG1 ILE B 149     -4.332   1.936  90.471  1.00 14.16     C
ATOM   2394  CG2 ILE B 149     -3.868   0.058  91.981  1.00 12.52     C
ATOM   2395  CD1 ILE B 149     -3.366   2.818  91.182  1.00 12.01     C
ATOM   2396  N   LEU B 150     -6.446  -2.223  91.377  1.00 15.28     N
ATOM   2397  CA  LEU B 150     -7.071  -3.215  92.239  1.00 15.89     C
ATOM   2398  C   LEU B 150     -6.003  -3.785  93.202  1.00 16.63     C
ATOM   2399  O   LEU B 150     -5.248  -4.680  92.840  1.00 19.24     O
ATOM   2400  CB  LEU B 150     -7.675  -4.325  91.378  1.00 15.36     C
ATOM   2401  CG  LEU B 150     -8.906  -3.901  90.569  1.00 18.61     C
ATOM   2402  CD1 LEU B 150     -9.327  -5.019  89.629  1.00 18.25     C
ATOM   2403  CD2 LEU B 150    -10.044  -3.567  91.530  1.00 18.95     C
ATOM   2404  N   VAL B 151     -5.937  -3.270  94.420  1.00 16.49     N
ATOM   2405  CA  VAL B 151     -4.928  -3.735  95.371  1.00 15.56     C
ATOM   2406  C   VAL B 151     -5.398  -4.909  96.231  1.00 16.31     C
ATOM   2407  O   VAL B 151     -6.591  -5.039  96.511  1.00 16.59     O
ATOM   2408  CB  VAL B 151     -4.524  -2.589  96.280  1.00 12.13     C
ATOM   2409  CG1 VAL B 151     -4.213  -1.380  95.432  1.00  9.75     C
ATOM   2410  CG2 VAL B 151     -5.663  -2.259  97.228  1.00 11.08     C
ATOM   2411  N   GLY B 152     -4.462  -5.759  96.648  1.00 17.30     N
ATOM   2412  CA  GLY B 152     -4.800  -6.903  97.488  1.00 17.76     C
ATOM   2413  C   GLY B 152     -4.986  -6.472  98.932  1.00 19.59     C
ATOM   2414  O   GLY B 152     -5.694  -7.100  99.725  1.00 16.62     O
ATOM   2415  N   ARG B 153     -4.327  -5.371  99.275  1.00 20.99     N
ATOM   2416  CA  ARG B 153     -4.417  -4.835 100.616  1.00 22.11     C
ATOM   2417  C   ARG B 153     -3.953  -3.389 100.692  1.00 20.94     C
ATOM   2418  O   ARG B 153     -3.360  -2.928  99.633  1.00 19.83     O
ATOM   2419  CB  ARG B 153     -3.542  -5.639 101.565  1.00 25.36     C
ATOM   2420  CG  ARG B 153     -2.065  -5.461 101.287  1.00 31.57     C
ATOM   2421  CD  ARG B 153     -1.213  -6.276 102.253  1.00 36.23     C
ATOM   2422  NE  ARG B 153      0.210  -5.945 102.117  1.00 41.06     N
ATOM   2423  CZ  ARG B 153      1.042  -5.788 103.146  1.00 42.13     C
ATOM   2424  NH1 ARG B 153      0.602  -5.942 104.389  1.00 40.06     N
ATOM   2425  NH2 ARG B 153      2.306  -5.436 102.927  1.00 42.40     N
ATOM   2426  N   LEU B 154     -4.221  -2.678 101.690  1.00 20.33     N
ATOM   2427  CA  LEU B 154     -3.814  -1.286 101.795  1.00 20.87     C
ATOM   2428  C   LEU B 154     -2.421  -1.166 102.402  1.00 21.95     C
ATOM   2429  O   LEU B 154     -2.180  -1.604 103.528  1.00 20.15     O
ATOM   2430  CB  LEU B 154     -4.820  -0.519 102.637  1.00 20.32     C
ATOM   2431  CG  LEU B 154     -5.528   0.630 101.934  1.00 20.10     C
ATOM   5616  N   ARG D 177      9.424   6.669  -2.721  1.00 23.53     N
ATOM   5617  CA  ARG D 177     10.298   5.680  -3.363  1.00 23.84     C
ATOM   5618  C   ARG D 177      9.506   4.574  -4.041  1.00 23.21     C
ATOM   5619  O   ARG D 177      8.387   4.247  -3.638  1.00 24.47     O
ATOM   5620  CB  ARG D 177     11.257   5.045  -2.356  1.00 25.89     C
ATOM   5621  CG  ARG D 177     12.369   5.942  -1.859  1.00 30.35     C
ATOM   5622  CD  ARG D 177     13.460   5.109  -1.157  1.00 35.54     C
ATOM   5623  NE  ARG D 177     12.958   4.316  -0.023  1.00 37.62     N
ATOM   5624  CZ  ARG D 177     13.699   3.471   0.699  1.00 38.84     C
ATOM   5625  NH1 ARG D 177     14.984   3.291   0.415  1.00 38.72     N
ATOM   5626  NH2 ARG D 177     13.161   2.814   1.723  1.00 38.25     N
ATOM   5627  N   ILE D 178     10.089   3.997  -5.073  1.00 21.10     N
ATOM   5628  CA  ILE D 178      9.429   2.924  -5.784  1.00 21.02     C
ATOM   5629  C   ILE D 178      9.779   1.606  -5.089  1.00 21.25     C
ATOM   5630  O   ILE D 178     10.934   1.353  -4.756  1.00 21.51     O
ATOM   5631  CB  ILE D 178      9.890   2.871  -7.260  1.00 19.82     C
ATOM   5632  CG1 ILE D 178      9.804   4.272  -7.890  1.00 21.53     C
ATOM   5633  CG2 ILE D 178      9.032   1.908  -8.029  1.00 16.15     C
ATOM   5634  CD1 ILE D 178      8.421   4.867  -7.921  1.00 21.27     C
ATOM   5635  N   MET D 179      8.773   0.781  -4.843  1.00 21.67     N
ATOM   5636  CA  MET D 179      9.007  -0.492  -4.185  1.00 22.08     C
ATOM   5637  C   MET D 179      9.987  -1.359  -4.960  1.00 21.68     C
ATOM   5638  O   MET D 179      9.783  -1.633  -6.144  1.00 21.78     O
ATOM   5639  CB  MET D 179      7.682  -1.232  -4.013  1.00 21.86     C
ATOM   5640  CG  MET D 179      6.741  -0.564  -3.031  1.00 22.71     C
ATOM   5641  SD  MET D 179      5.190  -1.477  -2.857  1.00 24.40     S
ATOM   5642  CE  MET D 179      5.762  -2.929  -2.024  1.00 21.76     C
ATOM   5643  N   LYS D 180     11.053  -1.780  -4.294  1.00 22.13     N
ATOM   5644  CA  LYS D 180     12.051  -2.648  -4.913  1.00 23.16     C
ATOM   5645  C   LYS D 180     11.574  -4.097  -4.779  1.00 23.26     C
ATOM   5646  O   LYS D 180     10.714  -4.403  -3.952  1.00 23.42     O
ATOM   5647  CB  LYS D 180     13.405  -2.486  -4.211  1.00 24.84     C
ATOM   5648  CG  LYS D 180     13.794  -1.040  -3.939  1.00 27.39     C
ATOM   5649  CD  LYS D 180     15.266  -0.905  -3.571  1.00 28.99     C
ATOM   5650  CE  LYS D 180     15.575  -1.510  -2.216  1.00 28.82     C
ATOM   5651  NZ  LYS D 180     15.015  -0.684  -1.114  1.00 29.02     N
ATOM   5652  N   PRO D 181     12.111  -5.009  -5.600  1.00 24.03     N
ATOM   5653  CA  PRO D 181     11.691   6.412  -5.509  1.00 23.97     C
ATOM   5654  C   PRO D 181     11.731  -6.905  -4.051  1.00 24.50     C
ATOM   5655  O   PRO D 181     10.867  -7.672  -3.616  1.00 24.96     O
ATOM   5656  CB  PRO D 181     12.711  -7.122  -6.400  1.00 24.35     C
ATOM   5657  CG  PRO D 181     12.959   6.103  -7.478  1.00 23.58     C
ATOM   5658  CD  PRO D 181     13.097  -4.816  -6.688  1.00 24.26     C
ATOM   5659  N   GLN D 182     12.728  -6.450  -3.293  1.00 24.31     N
ATOM   5660  CA  GLN D 182     12.871  -6.830  -1.891  1.00 24.80     C
ATOM   5661  C   GLN D 182     11.656  -6.365  -1.065  1.00 24.74     C
ATOM   5662  O   GLN D 182     11.230  -7.033  -0.111  1.00 25.89     O
ATOM   5663  CB  GLN D 182     14.158  -6.226  -1.308  1.00 25.75     C
ATOM   5664  CG  GLN D 182     15.484  -6.753  -1.896  1.00 31.14     C
ATOM   5665  CD  GLN D 182     15.670  -6.504  -3.403  1.00 33.45     C
ATOM   5666  OE1 GLN D 182     15.567  -5.372  -3.888  1.00 33.48     O
ATOM   5667  NE2 GLN D 182     15.967  -7.572  -4.141  1.00 33.96     N
ATOM   5668  N   ASP D 183     11.105  -5.219  -1.438  1.00 22.80     N
ATOM   5669  CA  ASP D 183      9.944  -4.634  -0.757  1.00 21.76     C
ATOM   5670  C   ASP D 183      8.683  -5.520  -0.881  1.00 21.83     C
ATOM   5671  O   ASP D 183      7.960  -5.730   0.097  1.00 21.35     O
ATOM   5672  CB  ASP D 183      9.672  -3.230  -1.326  1.00 20.25     C
ATOM   5673  CG  ASP D 183     10.785  -2.221  -0.984  1.00 19.69     C
ATOM   5674  OD1 ASP D 183     11.236  -1.464  -1.876  1.00 17.19     O
ATOM   5675  OD2 ASP D 183     11.200  -2.168   0.192  1.00 18.62     O
ATOM   5676  N   PHE D 184      8.412  -6.027  -2.079  1.00 21.66     N
ATOM   5677  CA  PHE D 184      7.254  -6.885  -2.268  1.00 22.28     C
ATOM   5678  C   PHE D 184      7.397  -8.133  -1.401  1.00 23.59     C
ATOM   5679  O   PHE D 184      6.423  -8.624  -0.828  1.00 23.30     O
ATOM   5680  CB  PHE D 184      7.102  -7.290  -3.734  1.00 19.48     C
ATOM   5681  CG  PHE D 184      6.667  -6.171  -4.621  1.00 19.69     C
ATOM   5682  CD1 PHE D 184      7.605  -5.291  -5.170  1.00 17.96     C
ATOM   5683  CD2 PHE D 184      5.308  -5.974  -4.900  1.00 18.57     C
ATOM   5684  CE1 PHE D 184      7.212  -4.247  -5.972  1.00 16.51     C
ATOM   5685  CE2 PHE D 184      4.902  -4.931  -5.703  1.00 19.01     C
ATOM   5686  CZ  PHE D 184      5.856  -4.055  -6.248  1.00 18.68     C
ATOM   5687  N   GLU D 185      8.619  -8.642  -1.311  1.00 24.47     N
ATOM   5688  CA  GLU D 185      8.884  -9.824  -0.503  1.00 25.74     C
ATOM   5689  C   GLU D 185      8.714  -9.477   0.971  1.00 25.34     C
ATOM   5690  O   GLU D 185      8.276 -10.300   1.763  1.00 26.74     O
ATOM   5691  CB  GLU D 185     10.305 -10.322  -0.752  1.00 26.65     C
ATOM   5692  CG  GLU D 185     10.673 -11.550   0.055  1.00 30.50     C
ATOM   5693  CD  GLU D 185     12.142 -11.908  -0.065  1.00 33.56     C
ATOM   5694  OE1 GLU D 185     12.985 -11.043   0.254  1.00 35.77     O
ATOM   5695  OE2 GLU D 185     12.469 -13.045  -0.474  1.00 34.96     O
ATOM   5696  N   TYR D 186      9.064  -8.252   1.340  1.00 24.91     N
ATOM   5697  CA  TYR D 186      8.943  -7.829   2.724  1.00 24.18     C
ATOM   5698  C   TYR D 186      7.468  -7.747   3.149  1.00 23.20     C
ATOM   5699  O   TYR D 186      7.084  -8.200   4.228  1.00 21.30     O
ATOM   5700  CB  TYR D 186      9.615  -6.477   2.911  1.00 25.46     C
ATOM   5701  CG  TYR D 186      9.477  -5.924   4.306  1.00 28.77     C
```

FIG. 6 (con't)

```
ATOM  2432  CD1 LEU B 154   -5.810  0.220 100.515 1.00 17.57   C
ATOM  2433  CD2 LEU B 154   -6.815  0.985 102.669 1.00 19.17   C
ATOM  2434  N   PHE B 155   -1.517 -0.561 101.637 1.00 23.13   N
ATOM  2435  CA  PHE B 155   -0.134 -0.375 102.064 1.00 24.44   C
ATOM  2436  C   PHE B 155   -0.026  0.732 103.090 1.00 24.13   C
ATOM  2437  O   PHE B 155   -0.103  1.918 102.748 1.00 24.25   O
ATOM  2438  CB  PHE B 155    0.745 -0.026 100.851 1.00 26.25   C
ATOM  2439  CG  PHE B 155    2.224  0.065 101.170 1.00 25.81   C
ATOM  2440  CD1 PHE B 155    2.942 -1.075 101.510 1.00 26.50   C
ATOM  2441  CD2 PHE B 155    2.902  1.285 101.094 1.00 27.32   C
ATOM  2442  CE1 PHE B 155    4.322 -1.019 101.762 1.00 25.85   C
ATOM  2443  CE2 PHE B 155    4.291  1.358 101.350 1.00 26.84   C
ATOM  2444  CZ  PHE B 155    4.996  0.200 101.679 1.00 26.33   C
ATOM  2445  N   MET B 156    0.149  0.342 104.343 1.00 25.15   N
ATOM  2446  CA  MET B 156    0.279  1.281 105.448 1.00 25.67   C
ATOM  2447  C   MET B 156   -0.818  2.343 105.487 1.00 25.77   C
ATOM  2448  O   MET B 156   -0.538  3.545 105.470 1.00 24.32   O
ATOM  2449  CB  MET B 156    1.647  1.961 105.385 1.00 26.82   C
ATOM  2450  CG  MET B 156    2.817  1.075 105.629 1.00 28.39   C
ATOM  2451  SD  MET B 156    4.430  1.843 105.481 1.00 32.72   S
ATOM  2452  CE  MET B 156    5.482  0.656 106.223 1.00 30.63   C
ATOM  2453  N   TRP B 157   -2.064  1.881 105.550 1.00 25.51   N
ATOM  2454  CA  TRP B 157   -3.226  2.756 105.595 1.00 25.32   C
ATOM  2455  C   TRP B 157   -3.266  3.612 106.857 1.00 26.75   C
ATOM  2456  O   TRP B 157   -3.969  4.615 106.897 1.00 26.48   O
ATOM  2457  CB  TRP B 157   -4.509  1.928 105.526 1.00 24.55   C
ATOM  2458  CG  TRP B 157   -4.661  0.949 106.659 1.00 23.68   C
ATOM  2459  CD1 TRP B 157   -4.102 -0.301 106.753 1.00 22.81   C
ATOM  2460  CD2 TRP B 157   -5.454  1.124 107.840 1.00 23.50   C
ATOM  2461  NE1 TRP B 157   -4.504 -0.910 107.917 1.00 23.45   N
ATOM  2462  CE2 TRP B 157   -5.326 -0.060 108.607 1.00 22.56   C
ATOM  2463  CE3 TRP B 157   -6.244  2.169 108.328 1.00 23.04   C
ATOM  2464  CZ2 TRP B 157   -5.981 -0.231 109.825 1.00 22.23   C
ATOM  2465  CZ3 TRP B 157   -6.897  1.998 109.545 1.00 22.69   C
ATOM  2466  CH2 TRP B 157   -6.753  0.806 110.282 1.00 23.45   C
ATOM  2467  N   GLU B 158   -2.527  3.208 107.890 1.00 28.38   N
ATOM  2468  CA  GLU B 158   -2.495  3.964 109.140 1.00 28.90   C
ATOM  2469  C   GLU B 158   -1.742  5.296 109.002 1.00 30.21   C
ATOM  2470  O   GLU B 158   -2.019  6.249 109.731 1.00 29.61   O
ATOM  2471  CB  GLU B 158   -1.844  3.138 110.252 1.00 28.21   C
ATOM  2472  CG  GLU B 158   -2.660  1.967 110.739 1.00 26.97   C
ATOM  2473  CD  GLU B 158   -1.913  1.129 111.762 1.00 27.15   C
ATOM  2474  OE1 GLU B 158   -1.570  1.647 112.847 1.00 26.39   O
ATOM  2475  OE2 GLU B 158   -1.670 -0.059 111.469 1.00 27.94   O
ATOM  2476  N   GLU B 159   -0.785  5.356 108.084 1.00 31.94   N
ATOM  2477  CA  GLU B 159   -0.026  6.587 107.881 1.00 35.28   C
ATOM  2478  C   GLU B 159   -0.906  7.689 107.330 1.00 36.39   C
ATOM  2479  O   GLU B 159   -1.585  7.505 106.321 1.00 36.78   O
ATOM  2480  CB  GLU B 159    1.124  6.387 106.895 1.00 36.81   C
ATOM  2481  CG  GLU B 159    2.395  5.837 107.489 1.00 41.62   C
ATOM  2482  CD  GLU B 159    3.523  5.751 106.476 1.00 45.62   C
ATOM  2483  OE1 GLU B 159    4.046  6.811 106.049 1.00 46.78   O
ATOM  2484  OE2 GLU B 159    3.885  4.615 106.095 1.00 47.98   O
ATOM  2485  N   PRO B 160   -0.904  8.860 107.980 1.00 37.22   N
ATOM  2486  CA  PRO B 160   -1.722  9.978 107.504 1.00 37.55   C
ATOM  2487  C   PRO B 160   -1.232 10.455 106.136 1.00 37.63   C
ATOM  2488  O   PRO B 160   -2.003 11.000 105.344 1.00 37.49   O
ATOM  2489  CB  PRO B 160   -1.544 11.022 108.610 1.00 37.77   C
ATOM  2490  CG  PRO B 160   -0.177 10.733 109.125 1.00 38.32   C
ATOM  2491  CD  PRO B 160   -0.165  9.231 109.198 1.00 37.29   C
ATOM  2492  N   GLU B 161    0.055 10.225 105.865 1.00 38.14   N
ATOM  2493  CA  GLU B 161    0.661 10.604 104.590 1.00 37.35   C
ATOM  2494  C   GLU B 161    0.106  9.710 103.491 1.00 35.52   C
ATOM  2495  O   GLU B 161   -0.111 10.158 102.375 1.00 35.44   O
ATOM  2496  CB  GLU B 161    2.188 10.468 104.645 1.00 39.10   C
ATOM  2497  CG  GLU B 161    2.863 11.330 105.709 1.00 42.24   C
ATOM  2498  CD  GLU B 161    2.934 10.651 107.068 1.00 45.01   C
ATOM  2499  OE1 GLU B 161    2.352  9.554 107.221 1.00 46.39   O
ATOM  2500  OE2 GLU B 161    3.571 11.215 107.990 1.00 47.20   O
ATOM  2501  N   ILE B 162   -0.116  8.443 103.812 1.00 34.28   N
ATOM  2502  CA  ILE B 162   -0.659  7.491 102.860 1.00 33.22   C
ATOM  2503  C   ILE B 162   -2.136  7.803 102.578 1.00 32.21   C
ATOM  2504  O   ILE B 162   -2.602  7.734 101.439 1.00 31.82   O
ATOM  2505  CB  ILE B 162   -0.543  6.054 103.409 1.00 33.32   C
ATOM  2506  CG1 ILE B 162    0.927  5.654 103.502 1.00 33.19   C
ATOM  2507  CG2 ILE B 162   -1.310  5.089 102.535 1.00 33.61   C
ATOM  2508  CD1 ILE B 162    1.615  5.598 102.168 1.00 32.61   C
ATOM  2509  N   GLN B 163   -2.877  8.149 103.621 1.00 31.22   N
ATOM  2510  CA  GLN B 163   -4.282  8.457 103.445 1.00 30.19   C
ATOM  2511  C   GLN B 163   -4.427  9.673 102.537 1.00 30.24   C
ATOM  2512  O   GLN B 163   -5.408  9.797 101.805 1.00 29.02   O
ATOM  2513  CB  GLN B 163   -4.965  8.735 104.782 1.00 28.72   C
ATOM  2514  CG  GLN B 163   -4.764  7.652 105.830 1.00 29.23   C
ATOM  2515  CD  GLN B 163   -5.767  7.735 106.978 1.00 30.35   C
ATOM  2516  OE1 GLN B 163   -5.583  7.108 108.020 1.00 29.29   O
ATOM  2517  NE2 GLN B 163   -6.843  8.501 106.782 1.00 30.60   N

ATOM  5702  CD1 TYR D 186   10.234 -6.428  5.355 1.00 29.27   C
ATOM  5703  CD2 TYR D 186    8.553 -4.907  4.584 1.00 30.82   C
ATOM  5704  CE1 TYR D 186   10.084 -5.943  6.657 1.00 30.90   C
ATOM  5705  CE2 TYR D 186    8.392 -4.411  5.884 1.00 31.01   C
ATOM  5706  CZ  TYR D 186    9.164 -4.934  6.913 1.00 31.16   C
ATOM  5707  OH  TYR D 186    9.018 -4.446  8.195 1.00 33.17   O
ATOM  5708  N   VAL D 187    6.652 -7.153  2.290 1.00 22.87   N
ATOM  5709  CA  VAL D 187    5.231 -7.016  2.563 1.00 22.37   C
ATOM  5710  C   VAL D 187    4.542 -8.375  2.550 1.00 24.15   C
ATOM  5711  O   VAL D 187    3.572 -8.606  3.272 1.00 25.07   O
ATOM  5712  CB  VAL D 187    4.551 -6.097  1.541 1.00 20.50   C
ATOM  5713  CG1 VAL D 187    3.045 -6.105  1.732 1.00 18.15   C
ATOM  5714  CG2 VAL D 187    5.085 -4.689  1.690 1.00 19.85   C
ATOM  5715  N   TRP D 188    5.051 -9.287  1.733 1.00 25.26   N
ATOM  5716  CA  TRP D 188    4.450 -10.605 1.621 1.00 25.52   C
ATOM  5717  C   TRP D 188    4.708 -11.484 2.834 1.00 27.72   C
ATOM  5718  O   TRP D 188    3.842 -12.255 3.254 1.00 28.30   O
ATOM  5719  CB  TRP D 188    4.949 -11.285 0.350 1.00 24.30   C
ATOM  5720  CG  TRP D 188    4.472 -12.684 0.179 1.00 23.84   C
ATOM  5721  CD1 TRP D 188    5.119 -13.819 0.559 1.00 23.41   C
ATOM  5722  CD2 TRP D 188    3.212 -13.104 -0.364 1.00 23.30   C
ATOM  5723  NE1 TRP D 188    4.347 -14.918 0.287 1.00 23.85   N
ATOM  5724  CE2 TRP D 188    3.176 -14.512 -0.286 1.00 23.11   C
ATOM  5725  CE3 TRP D 188    2.121 -12.428 -0.924 1.00 23.55   C
ATOM  5726  CZ2 TRP D 188    2.079 -15.260 -0.722 1.00 22.52   C
ATOM  5727  CZ3 TRP D 188    1.025 -13.172 -1.361 1.00 22.68   C
ATOM  5728  CH2 TRP D 188    1.020 -14.572 -1.264 1.00 23.53   C
ATOM  5729  N   GLN D 189    5.892 -11.356 3.411 1.00 28.73   N
ATOM  5730  CA  GLN D 189    6.245 -12.184 4.543 1.00 30.06   C
ATOM  5731  C   GLN D 189    6.044 -11.516 5.897 1.00 28.91   C
ATOM  5732  O   GLN D 189    6.363 -12.103 6.924 1.00 29.47   O
ATOM  5733  CB  GLN D 189    7.704 -12.643 4.393 1.00 32.74   C
ATOM  5734  CG  GLN D 189    7.955 -13.557 3.181 1.00 38.12   C
ATOM  5735  CD  GLN D 189    9.425 -13.957 3.013 1.00 41.54   C
ATOM  5736  OE1 GLN D 189    9.753 -14.858 2.227 1.00 43.40   O
ATOM  5737  NE2 GLN D 189   10.313 -13.285 3.740 1.00 42.36   N
ATOM  5738  N   ASN D 190    5.502 -10.306 5.914 1.00 26.81   N
ATOM  5739  CA  ASN D 190    5.306 -9.616  7.181 1.00 25.50   C
ATOM  5740  C   ASN D 190    3.899 -9.070  7.347 1.00 25.76   C
ATOM  5741  O   ASN D 190    3.537 -8.560  8.416 1.00 25.45   O
ATOM  5742  CB  ASN D 190    6.308 -8.470  7.316 1.00 24.20   C
ATOM  5743  CG  ASN D 190    7.719 -8.959  7.604 1.00 24.54   C
ATOM  5744  OD1 ASN D 190    8.021 -9.406  8.711 1.00 24.20   O
ATOM  5745  ND2 ASN D 190    8.593 -8.869  6.605 1.00 24.32   N
ATOM  5746  N   PHE D 191    3.110 -9.157  6.283 1.00 24.92   N
ATOM  5747  CA  PHE D 191    1.741 -8.681  6.311 1.00 25.52   C
ATOM  5748  C   PHE D 191    0.767 -9.770  5.879 1.00 27.02   C
ATOM  5749  O   PHE D 191   -0.308 -9.908  6.457 1.00 28.90   O
ATOM  5750  CB  PHE D 191    1.569 -7.446  5.415 1.00 23.01   C
ATOM  5751  CG  PHE D 191    2.244 -6.203  5.939 1.00 20.65   C
ATOM  5752  CD1 PHE D 191    3.624 -6.039  5.846 1.00 19.27   C
ATOM  5753  CD2 PHE D 191    1.490 -5.185  6.529 1.00 18.97   C
ATOM  5754  CE1 PHE D 191    4.249 -4.885  6.330 1.00 17.44   C
ATOM  5755  CE2 PHE D 191    2.104 -4.032  7.019 1.00 17.80   C
ATOM  5756  CZ  PHE D 191    3.487 -3.879  6.920 1.00 17.53   C
ATOM  5757  N   VAL D 192    1.137 -10.550 4.879 1.00 29.42   N
ATOM  5758  CA  VAL D 192    0.251 -11.591 4.404 1.00 33.86   C
ATOM  5759  C   VAL D 192    0.404 -12.841 5.249 1.00 37.59   C
ATOM  5760  O   VAL D 192    1.495 -13.398 5.355 1.00 37.82   O
ATOM  5761  CB  VAL D 192    0.539 -11.936 2.927 1.00 32.60   C
ATOM  5762  CG1 VAL D 192   -0.353 -13.069 2.482 1.00 31.89   C
ATOM  5763  CG2 VAL D 192    0.308 -10.706 2.051 1.00 30.32   C
ATOM  5764  N   GLU D 193   -0.691 -13.271 5.865 1.00 42.93   N
ATOM  5765  CA  GLU D 193   -0.669 -14.457 6.710 1.00 47.97   C
ATOM  5766  C   GLU D 193   -0.479 -15.656 5.785 1.00 50.64   C
ATOM  5767  O   GLU D 193   -1.436 -16.178 5.210 1.00 50.50   O
ATOM  5768  CB  GLU D 193   -1.988 -14.564 7.493 1.00 48.86   C
ATOM  5769  CG  GLU D 193   -1.805 -14.955 8.964 1.00 51.19   C
ATOM  5770  CD  GLU D 193   -3.123 -15.180 9.699 1.00 52.38   C
ATOM  5771  OE1 GLU D 193   -3.879 -16.091 9.296 1.00 52.46   O
ATOM  5772  OE2 GLU D 193   -3.398 -14.454 10.683 1.00 52.71   O
ATOM  5773  N   GLN D 194    0.770 -16.062 5.605 1.00 53.90   N
ATOM  5774  CA  GLN D 194    1.099 -17.165 4.700 1.00 56.41   C
ATOM  5775  C   GLN D 194    0.863 -18.556 5.277 1.00 58.05   C
ATOM  5776  O   GLN D 194    0.734 -18.731 6.492 1.00 58.43   O
ATOM  5777  CB  GLN D 194    2.562 -17.017 4.239 1.00 57.37   C
ATOM  5778  CG  GLN D 194    2.966 -17.892 3.042 1.00 59.23   C
ATOM  5779  CD  GLN D 194    4.408 -17.649 2.573 1.00 59.62   C
ATOM  5780  OE1 GLN D 194    4.877 -18.271 1.613 1.00 58.85   O
ATOM  5781  NE2 GLN D 194    5.110 -16.743 3.251 1.00 59.36   N
ATOM  5782  N   GLU D 195    0.793 -19.541 4.381 1.00 59.86   N
ATOM  5783  CA  GLU D 195    0.580 -20.946 4.736 1.00 60.26   C
ATOM  5784  C   GLU D 195   -0.772 -21.149 5.415 1.00 59.93   C
ATOM  5785  O   GLU D 195   -1.517 -22.071 5.082 1.00 59.04   O
ATOM  5786  CB  GLU D 195    1.715 -21.429 5.654 1.00 61.42   C
ATOM  5787  CG  GLU D 195    1.737 -22.939 5.898 1.00 63.15   C
```

FIG. 6 (con't)

```
ATOM   2518  N   ALA B 164      -3.442  10.564 102.594  1.00 30.02           N
ATOM   2519  CA  ALA B 164      -3.442  11.772 101.777  1.00 29.62           C
ATOM   2520  C   ALA B 164      -3.206  11.430 100.315  1.00 29.76           C
ATOM   2521  O   ALA B 164      -3.779  12.049  99.422  1.00 29.19           O
ATOM   2522  CB  ALA B 164      -2.366  12.711 102.246  1.00 29.66           C
ATOM   2523  N   ALA B 165      -2.344  10.451 100.076  1.00 30.25           N
ATOM   2524  CA  ALA B 165      -2.041  10.045  98.715  1.00 30.76           C
ATOM   2525  C   ALA B 165      -3.265   9.401  98.080  1.00 30.90           C
ATOM   2526  O   ALA B 165      -3.663   9.768  96.981  1.00 30.01           O
ATOM   2527  CB  ALA B 165      -0.876   9.074  98.708  1.00 30.96           C
ATOM   2528  N   LEU B 166      -3.861   8.442  98.783  1.00 31.51           N
ATOM   2529  CA  LEU B 166      -5.041   7.767  98.270  1.00 33.05           C
ATOM   2530  C   LEU B 166      -6.121   8.768  97.861  1.00 34.58           C
ATOM   2531  O   LEU B 166      -6.714   8.648  96.789  1.00 34.70           O
ATOM   2532  CB  LEU B 166      -5.606   6.804  99.312  1.00 32.37           C
ATOM   2533  CG  LEU B 166      -4.771   5.555  99.598  1.00 32.84           C
ATOM   2534  CD1 LEU B 166      -5.451   4.689 100.640  1.00 33.14           C
ATOM   2535  CD2 LEU B 166      -4.602   4.785  98.316  1.00 32.37           C
ATOM   2536  N   LYS B 167      -6.369   9.760  98.719  1.00 35.76           N
ATOM   2537  CA  LYS B 167      -7.384  10.775  98.449  1.00 34.98           C
ATOM   2538  C   LYS B 167      -6.980  11.603  97.244  1.00 34.26           C
ATOM   2539  O   LYS B 167      -7.795  11.859  96.365  1.00 34.25           O
ATOM   2540  CB  LYS B 167      -7.593  11.688  99.654  1.00 35.97           C
ATOM   2541  CG  LYS B 167      -8.142  10.985 100.880  1.00 38.58           C
ATOM   2542  CD  LYS B 167      -8.372  11.955 102.030  1.00 39.92           C
ATOM   2543  CE  LYS B 167      -8.142  11.268 103.367  1.00 41.16           C
ATOM   2544  NZ  LYS B 167      -8.204  12.216 104.506  1.00 43.44           N
ATOM   2545  N   LYS B 168      -5.732  12.035  97.189  1.00 33.17           N
ATOM   2546  CA  LYS B 168      -5.300  12.825  96.049  1.00 33.56           C
ATOM   2547  C   LYS B 168      -5.328  11.995  94.761  1.00 32.49           C
ATOM   2548  O   LYS B 168      -5.523  12.533  93.666  1.00 32.99           O
ATOM   2549  CB  LYS B 168      -3.890  13.371  96.280  1.00 34.72           C
ATOM   2550  CG  LYS B 168      -3.836  14.529  97.258  1.00 36.85           C
ATOM   2551  CD  LYS B 168      -2.406  14.848  97.678  1.00 39.47           C
ATOM   2552  CE  LYS B 168      -2.391  15.952  98.731  1.00 40.85           C
ATOM   2553  NZ  LYS B 168      -1.052  16.123  99.360  1.00 42.89           N
ATOM   2554  N   LEU B 169      -5.134  10.687  94.899  1.00 30.29           N
ATOM   2555  CA  LEU B 169      -5.143   9.780  93.763  1.00 27.74           C
ATOM   2556  C   LEU B 169      -6.557   9.771  93.183  1.00 26.16           C
ATOM   2557  O   LEU B 169      -6.730   9.781  91.969  1.00 25.12           O
ATOM   2558  CB  LEU B 169      -4.735   8.372  94.198  1.00 28.13           C
ATOM   2559  CG  LEU B 169      -3.870   7.573  93.222  1.00 27.91           C
ATOM   2560  CD1 LEU B 169      -2.564   8.286  92.987  1.00 28.10           C
ATOM   2561  CD2 LEU B 169      -3.594   6.203  93.794  1.00 28.49           C
ATOM   2562  N   LYS B 170      -7.557   9.756  94.058  1.00 24.78           N
ATOM   2563  CA  LYS B 170      -8.947   9.784  93.630  1.00 24.87           C
ATOM   2564  C   LYS B 170      -9.275  11.138  93.005  1.00 26.04           C
ATOM   2565  O   LYS B 170     -10.122  11.232  92.122  1.00 25.01           O
ATOM   2566  CB  LYS B 170      -9.884   9.548  94.805  1.00 24.63           C
ATOM   2567  CG  LYS B 170     -11.340   9.808  94.494  1.00 22.59           C
ATOM   2568  CD  LYS B 170     -12.205   9.556  95.717  1.00 21.73           C
ATOM   2569  CE  LYS B 170     -13.649   9.955  95.456  1.00 22.54           C
ATOM   2570  NZ  LYS B 170     -14.600   9.349  96.430  1.00 25.72           N
ATOM   2571  N   GLU B 171      -8.618  12.188  93.505  1.00 27.99           N
ATOM   2572  CA  GLU B 171      -8.786  13.548  92.993  1.00 27.48           C
ATOM   2573  C   GLU B 171      -8.338  13.582  91.529  1.00 26.08           C
ATOM   2574  O   GLU B 171      -8.991  14.192  90.686  1.00 24.94           O
ATOM   2575  CB  GLU B 171      -7.927  14.536  93.785  1.00 30.21           C
ATOM   2576  CG  GLU B 171      -8.189  14.592  95.286  1.00 34.50           C
ATOM   2577  CD  GLU B 171      -9.619  14.957  95.622  1.00 38.27           C
ATOM   2578  OE1 GLU B 171     -10.282  15.601  94.772  1.00 38.88           O
ATOM   2579  OE2 GLU B 171     -10.074  14.612  96.740  1.00 38.33           O
ATOM   2580  N   ALA B 172      -7.207  12.934  91.244  1.00 24.56           N
ATOM   2581  CA  ALA B 172      -6.653  12.889  89.890  1.00 23.01           C
ATOM   2582  C   ALA B 172      -7.522  12.075  88.933  1.00 22.36           C
ATOM   2583  O   ALA B 172      -7.236  11.996  87.737  1.00 22.84           O
ATOM   2584  CB  ALA B 172      -5.245  12.325  89.922  1.00 21.63           C
ATOM   2585  N   GLY B 173      -8.576  11.466  89.470  1.00 21.96           N
ATOM   2586  CA  GLY B 173      -9.486  10.680  88.660  1.00 22.00           C
ATOM   2587  C   GLY B 173      -9.176   9.197  88.624  1.00 22.85           C
ATOM   2588  O   GLY B 173      -9.741   8.452  87.818  1.00 24.08           O
ATOM   2589  N   CYS B 174      -8.280   8.760  89.501  1.00 21.81           N
ATOM   2590  CA  CYS B 174      -7.887   7.364  89.566  1.00 20.51           C
ATOM   2591  C   CYS B 174      -8.872   6.566  90.396  1.00 20.55           C
ATOM   2592  O   CYS B 174      -9.296   7.006  91.467  1.00 20.68           O
ATOM   2593  CB  CYS B 174      -6.486   7.246  90.168  1.00 19.92           C
ATOM   2594  SG  CYS B 174      -5.858   5.557  90.295  1.00 18.22           S
ATOM   2595  N   LYS B 175      -9.243   5.394  89.904  1.00 20.69           N
ATOM   2596  CA  LYS B 175     -10.186   4.550  90.627  1.00 22.91           C
ATOM   2597  C   LYS B 175      -9.448   3.489  91.420  1.00 22.03           C
ATOM   2598  O   LYS B 175      -8.685   2.704  90.861  1.00 23.44           O
ATOM   2599  CB  LYS B 175     -11.158   3.877  89.646  1.00 25.46           C
ATOM   2600  CG  LYS B 175     -12.175   4.811  88.973  1.00 30.51           C
ATOM   2601  CD  LYS B 175     -13.176   5.364  89.978  1.00 33.81           C
ATOM   2602  CE  LYS B 175     -14.317   6.106  89.302  1.00 36.20           C
ATOM   2603  NZ  LYS B 175     -15.331   6.520  90.317  1.00 38.39           N
ATOM   5788  CD  GLU D 195       2.958 -23.397   6.686  1.00 63.19           C
ATOM   5789  OE1 GLU D 195       4.092 -23.131   6.230  1.00 63.27           O
ATOM   5790  OE2 GLU D 195       2.783 -24.028   7.751  1.00 62.81           O
ATOM   5791  N   PHE D 202       9.470 -16.877  -1.220  1.00 42.41           N
ATOM   5792  CA  PHE D 202       8.837 -15.862  -2.051  1.00 41.74           C
ATOM   5793  C   PHE D 202       8.755 -16.417  -3.459  1.00 43.03           C
ATOM   5794  O   PHE D 202       9.150 -17.556  -3.695  1.00 45.02           O
ATOM   5795  CB  PHE D 202       9.657 -14.574  -2.048  1.00 39.98           C
ATOM   5796  CG  PHE D 202       8.915 -13.381  -2.580  1.00 37.50           C
ATOM   5797  CD1 PHE D 202       7.708 -12.987  -2.018  1.00 37.32           C
ATOM   5798  CD2 PHE D 202       9.426 -12.646  -3.643  1.00 35.88           C
ATOM   5799  CE1 PHE D 202       7.024 -11.878  -2.512  1.00 35.77           C
ATOM   5800  CE2 PHE D 202       8.751 -11.539  -4.142  1.00 33.99           C
ATOM   5801  CZ  PHE D 202       7.551 -11.154  -3.578  1.00 34.47           C
ATOM   5802  N   GLN D 203       8.262 -15.619  -4.398  1.00 42.66           N
ATOM   5803  CA  GLN D 203       8.118 -16.074  -5.772  1.00 42.47           C
ATOM   5804  C   GLN D 203       7.879 -14.853  -6.646  1.00 41.32           C
ATOM   5805  O   GLN D 203       6.735 -14.551  -7.005  1.00 42.19           O
ATOM   5806  CB  GLN D 203       6.924 -17.030  -5.867  1.00 44.76           C
ATOM   5807  CG  GLN D 203       6.996 -18.055  -6.996  1.00 48.47           C
ATOM   5808  CD  GLN D 203       6.804 -17.461  -8.390  1.00 50.70           C
ATOM   5809  OE1 GLN D 203       7.536 -16.562  -8.809  1.00 51.36           O
ATOM   5810  NE2 GLN D 203       5.817 -17.980  -9.121  1.00 51.54           N
ATOM   5811  N   PRO D 204       8.959 -14.130  -6.997  1.00 40.13           N
ATOM   5812  CA  PRO D 204       8.913 -12.924  -7.830  1.00 38.18           C
ATOM   5813  C   PRO D 204       8.523 -13.210  -9.265  1.00 36.50           C
ATOM   5814  O   PRO D 204       8.673 -14.331  -9.734  1.00 36.07           O
ATOM   5815  CB  PRO D 204      10.331 -12.378  -7.720  1.00 37.93           C
ATOM   5816  CG  PRO D 204      11.148 -13.621  -7.608  1.00 37.73           C
ATOM   5817  CD  PRO D 204      10.350 -14.438  -6.617  1.00 39.29           C
ATOM   5818  N   TRP D 205       8.028 -12.182  -9.953  1.00 35.12           N
ATOM   5819  CA  TRP D 205       7.615 -12.290 -11.341  1.00 34.30           C
ATOM   5820  C   TRP D 205       8.651 -11.663 -12.271  1.00 35.78           C
ATOM   5821  O   TRP D 205       9.291 -10.656 -11.942  1.00 35.38           O
ATOM   5822  CB  TRP D 205       6.226 -11.659 -11.531  1.00 32.85           C
ATOM   5823  CG  TRP D 205       6.013 -10.737 -10.765  1.00 30.73           C
ATOM   5824  CD1 TRP D 205       6.101  -9.102 -11.246  1.00 30.22           C
ATOM   5825  CD2 TRP D 205       5.751 -10.256  -9.360  1.00 29.38           C
ATOM   5826  NE1 TRP D 205       5.909  -8.198 -10.227  1.00 29.35           N
ATOM   5827  CE2 TRP D 205       5.695  -8.877  -9.059  1.00 27.87           C
ATOM   5828  CE3 TRP D 205       5.561 -11.181  -8.325  1.00 28.41           C
ATOM   5829  CZ2 TRP D 205       5.460  -8.399  -7.766  1.00 26.69           C
ATOM   5830  CZ3 TRP D 205       5.325 -10.707  -7.040  1.00 27.09           C
ATOM   5831  CH2 TRP D 205       5.275  -9.334  -6.772  1.00 26.32           C
ATOM   5832  N   GLU D 206       8.818 -12.279 -13.434  1.00 36.92           N
ATOM   5833  CA  GLU D 206       9.797 -11.849 -14.418  1.00 38.36           C
ATOM   5834  C   GLU D 206      10.050 -10.347 -14.537  1.00 37.13           C
ATOM   5835  O   GLU D 206      11.196  -9.923 -14.715  1.00 37.61           O
ATOM   5836  CB  GLU D 206       9.425 -12.402 -15.803  1.00 41.33           C
ATOM   5837  CG  GLU D 206      10.547 -12.254 -16.837  1.00 45.79           C
ATOM   5838  CD  GLU D 206      10.108 -11.568 -18.118  1.00 50.06           C
ATOM   5839  OE1 GLU D 206       9.362 -12.192 -18.915  1.00 51.85           O
ATOM   5840  OE2 GLU D 206      10.509 -10.397 -18.329  1.00 51.31           O
ATOM   5841  N   ASP D 207       9.000  -9.541 -14.428  1.00 33.71           N
ATOM   5842  CA  ASP D 207       9.161  -8.098 -14.558  1.00 31.70           C
ATOM   5843  C   ASP D 207       9.218  -7.347 -13.240  1.00 29.68           C
ATOM   5844  O   ASP D 207       9.084  -6.126 -13.214  1.00 30.50           O
ATOM   5845  CB  ASP D 207       8.040  -7.533 -15.429  1.00 33.04           C
ATOM   5846  CG  ASP D 207       6.672  -7.827 -14.863  1.00 35.25           C
ATOM   5847  OD1 ASP D 207       6.409  -9.008 -14.528  1.00 36.50           O
ATOM   5848  OD2 ASP D 207       5.864  -6.885 -14.761  1.00 35.78           O
ATOM   5849  N   ILE D 208       9.432  -8.054 -12.142  1.00 26.83           N
ATOM   5850  CA  ILE D 208       9.487  -7.387 -10.851  1.00 25.07           C
ATOM   5851  C   ILE D 208      10.633  -6.379 -10.778  1.00 23.76           C
ATOM   5852  O   ILE D 208      10.473  -5.284 -10.243  1.00 23.57           O
ATOM   5853  CB  ILE D 208       9.628  -8.411  -9.688  1.00 25.24           C
ATOM   5854  CG1 ILE D 208       9.221  -7.773  -8.362  1.00 23.77           C
ATOM   5855  CG2 ILE D 208      11.075  -8.944  -9.611  1.00 23.56           C
ATOM   5856  CD1 ILE D 208       9.069  -8.801  -7.221  1.00 26.29           C
ATOM   5857  N   GLN D 209      11.785  -6.731 -11.325  1.00 22.53           N
ATOM   5858  CA  GLN D 209      12.917  -5.820 -11.242  1.00 23.19           C
ATOM   5859  C   GLN D 209      12.820  -4.721 -12.285  1.00 24.18           C
ATOM   5860  O   GLN D 209      13.086  -3.539 -12.015  1.00 24.01           O
ATOM   5861  CB  GLN D 209      14.218  -6.589 -11.402  1.00 19.24           C
ATOM   5862  CG  GLN D 209      15.428  -5.694 -11.421  1.00 19.08           C
ATOM   5863  CD  GLN D 209      16.695  -6.449 -11.712  1.00 19.06           C
ATOM   5864  OE1 GLN D 209      16.761  -7.216 -12.672  1.00 18.53           O
ATOM   5865  NE2 GLN D 209      17.715  -6.241 -10.886  1.00 19.06           N
ATOM   5866  N   GLU D 210      12.419  -5.131 -13.476  1.00 25.29           N
ATOM   5867  CA  GLU D 210      12.255  -4.229 -14.597  1.00 27.39           C
ATOM   5868  C   GLU D 210      11.286  -3.089 -14.273  1.00 26.54           C
ATOM   5869  O   GLU D 210      11.517  -1.963 -14.690  1.00 26.39           O
ATOM   5870  CB  GLU D 210      11.757  -5.014 -15.813  1.00 30.60           C
ATOM   5871  CG  GLU D 210      11.885  -4.288 -17.160  1.00 36.35           C
ATOM   5872  CD  GLU D 210      11.566  -5.196 -18.363  1.00 40.31           C
ATOM   5873  OE1 GLU D 210      10.428  -5.721 -18.451  1.00 39.06           O
```

FIG. 6 (con't)

```
ATOM   2604  N   LEU B 176      -9.669   3.463  92.724  1.00 21.01           N
ATOM   2605  CA  LEU B 176      -9.018   2.469  93.575  1.00 20.17           C
ATOM   2606  C   LEU B 176     -10.038   1.497  94.162  1.00 20.32           C
ATOM   2607  O   LEU B 176     -11.115   1.919  94.579  1.00 20.75           O
ATOM   2608  CB  LEU B 176      -8.282   3.172  94.710  1.00 19.98           C
ATOM   2609  CG  LEU B 176      -7.216   4.171  94.305  1.00 21.46           C
ATOM   2610  CD1 LEU B 176      -6.848   5.022  95.507  1.00 23.30           C
ATOM   2611  CD2 LEU B 176      -6.008   3.439  93.754  1.00 21.32           C
ATOM   2612  N   ARG B 177      -9.702   0.211  94.184  1.00 19.61           N
ATOM   2613  CA  ARG B 177     -10.576  -0.824  94.759  1.00 21.31           C
ATOM   2614  C   ARG B 177      -9.799  -1.997  95.348  1.00 21.44           C
ATOM   2615  O   ARG B 177      -8.702  -2.344  94.898  1.00 21.85           O
ATOM   2616  CB  ARG B 177     -11.567  -1.368  93.732  1.00 23.36           C
ATOM   2617  CG  ARG B 177     -12.673  -0.420  93.330  1.00 26.92           C
ATOM   2618  CD  ARG B 177     -13.772  -1.189  92.581  1.00 32.18           C
ATOM   2619  NE  ARG B 177     -13.281  -1.911  91.402  1.00 36.46           N
ATOM   2620  CZ  ARG B 177     -14.028  -2.692  90.615  1.00 37.62           C
ATOM   2621  NH1 ARG B 177     -15.319  -2.867  90.871  1.00 39.00           N
ATOM   2622  NH2 ARG B 177     -13.486  -3.300  89.566  1.00 36.59           N
ATOM   2623  N   ILE B 178     -10.372  -2.618  96.362  1.00 21.30           N
ATOM   2624  CA  ILE B 178      -9.715  -3.740  96.992  1.00 20.29           C
ATOM   2625  C   ILE B 178     -10.089  -5.000  96.219  1.00 21.29           C
ATOM   2626  O   ILE B 178     -11.259  -5.242  95.935  1.00 21.66           O
ATOM   2627  CB  ILE B 178     -10.160  -3.878  98.459  1.00 18.23           C
ATOM   2628  CG1 ILE B 178     -10.068  -2.518  99.172  1.00 18.67           C
ATOM   2629  CG2 ILE B 178      -9.306  -4.899  99.150  1.00 16.05           C
ATOM   2630  CD1 ILE B 178      -8.685  -1.924  99.237  1.00 17.16           C
ATOM   2631  N   MET B 179      -9.086  -5.787  95.850  1.00 21.50           N
ATOM   2632  CA  MET B 179      -9.326  -7.020  95.133  1.00 20.80           C
ATOM   2633  C   MET B 179     -10.294  -7.916  95.897  1.00 22.36           C
ATOM   2634  O   MET B 179     -10.061  -8.252  97.061  1.00 22.01           O
ATOM   2635  CB  MET B 179      -8.008  -7.763  94.913  1.00 20.69           C
ATOM   2636  CG  MET B 179      -7.030  -7.034  94.001  1.00 20.79           C
ATOM   2637  SD  MET B 179      -5.491  -7.940  93.683  1.00 18.03           S
ATOM   2638  CE  MET B 179      -6.095  -9.300  92.817  1.00 20.76           C
ATOM   2639  N   LYS B 180     -11.392  -8.291  95.237  1.00 23.05           N
ATOM   2640  CA  LYS B 180     -12.392  -9.188  95.818  1.00 23.33           C
ATOM   2641  C   LYS B 180     -11.916 -10.629  95.575  1.00 22.45           C
ATOM   2642  O   LYS B 180     -11.054 -10.871  94.735  1.00 22.97           O
ATOM   2643  CB  LYS B 180     -13.743  -8.973  95.130  1.00 25.72           C
ATOM   2644  CG  LYS B 180     -14.116  -7.509  94.934  1.00 28.31           C
ATOM   2645  CD  LYS B 180     -15.589  -7.338  94.600  1.00 26.92           C
ATOM   2646  CE  LYS B 180     -15.918  -7.864  93.214  1.00 28.09           C
ATOM   2647  NZ  LYS B 180     -15.387  -6.995  92.122  1.00 28.03           N
ATOM   2648  N   PRO B 181     -12.464 -11.599  96.310  1.00 22.63           N
ATOM   2649  CA  PRO B 181     -12.048 -12.997  96.112  1.00 22.85           C
ATOM   2650  C   PRO B 181     -12.092 -13.411  94.630  1.00 23.80           C
ATOM   2651  O   PRO B 181     -11.226 -14.155  94.139  1.00 23.89           O
ATOM   2652  CB  PRO B 181     -13.037 -13.762  96.985  1.00 23.10           C
ATOM   2653  CG  PRO B 181     -13.225 -12.798  98.159  1.00 21.37           C
ATOM   2654  CD  PRO B 181     -13.377 -11.464  97.463  1.00 21.27           C
ATOM   2655  N   GLN B 182     -13.092 -12.913  93.909  1.00 24.02           N
ATOM   2656  CA  GLN B 182     -13.245 -13.201  92.485  1.00 23.93           C
ATOM   2657  C   GLN B 182     -12.048 -12.671  91.681  1.00 23.19           C
ATOM   2658  O   GLN B 182     -11.661 -13.250  90.660  1.00 24.42           O
ATOM   2659  CB  GLN B 182     -14.536 -12.561  91.953  1.00 26.36           C
ATOM   2660  CG  GLN B 182     -15.850 -13.123  92.516  1.00 30.15           C
ATOM   2661  CD  GLN B 182     -16.011 -12.948  94.029  1.00 33.78           C
ATOM   2662  OE1 GLN B 182     -15.879 -11.842  94.566  1.00 35.01           O
ATOM   2663  NE2 GLN B 182     -16.318 -14.043  94.719  1.00 35.02           N
ATOM   2664  N   ASP B 183     -11.468 -11.566  92.138  1.00 20.73           N
ATOM   2665  CA  ASP B 183     -10.324 -10.946  91.477  1.00 19.23           C
ATOM   2666  C   ASP B 183      -9.083 -11.845  91.517  1.00 19.89           C
ATOM   2667  O   ASP B 183      -8.400 -12.028  90.504  1.00 18.48           O
ATOM   2668  CB  ASP B 183     -10.028  -9.589  92.137  1.00 18.49           C
ATOM   2669  CG  ASP B 183     -11.128  -8.566  91.880  1.00 17.42           C
ATOM   2670  OD1 ASP B 183     -11.559  -7.868  92.831  1.00 15.93           O
ATOM   2671  OD2 ASP B 183     -11.559  -8.463  90.716  1.00 15.46           O
ATOM   2672  N   PHE B 184      -8.792 -12.413  92.679  1.00 20.46           N
ATOM   2673  CA  PHE B 184      -7.637 -13.291  92.794  1.00 23.62           C
ATOM   2674  C   PHE B 184      -7.782 -14.488  91.848  1.00 24.67           C
ATOM   2675  O   PHE B 184      -6.808 -14.945  91.251  1.00 24.85           O
ATOM   2676  CB  PHE B 184      -7.469 -13.796  94.242  1.00 23.00           C
ATOM   2677  CG  PHE B 184      -7.009 -12.730  95.210  1.00 22.04           C
ATOM   2678  CD1 PHE B 184      -7.937 -11.890  95.835  1.00 20.18           C
ATOM   2679  CD2 PHE B 184      -5.643 -12.549  95.479  1.00 21.35           C
ATOM   2680  CE1 PHE B 184      -7.525 -10.886  96.714  1.00 19.54           C
ATOM   2681  CE2 PHE B 184      -5.210 -11.546  96.361  1.00 20.02           C
ATOM   2682  CZ  PHE B 184      -6.156 -10.710  96.983  1.00 20.43           C
ATOM   2683  N   GLU B 185      -9.007 -14.981  91.719  1.00 25.70           N
ATOM   2684  CA  GLU B 185      -9.287 -16.099  90.847  1.00 25.87           C
ATOM   2685  C   GLU B 185      -9.147 -15.646  89.406  1.00 24.28           C
ATOM   2686  O   GLU B 185      -8.745 -16.411  88.542  1.00 24.15           O
ATOM   2687  CB  GLU B 185     -10.717 -16.599  91.081  1.00 28.62           C
ATOM   2688  CG  GLU B 185     -11.116 -17.762  90.193  1.00 32.44           C
ATOM   2689  CD  GLU B 185     -12.590 -18.114  90.312  1.00 35.88           C
ATOM   5874  OE2 GLU D 210      12.462  -5.381 -19.227  1.00 41.65           O
ATOM   5875  N   ASN D 211      10.197  -3.380 -13.556  1.00 25.06           N
ATOM   5876  CA  ASN D 211       9.227  -2.344 -13.192  1.00 23.59           C
ATOM   5877  C   ASN D 211       9.837  -1.324 -12.224  1.00 20.98           C
ATOM   5878  O   ASN D 211       9.710  -0.117 -12.422  1.00 18.90           O
ATOM   5879  CB  ASN D 211       7.997  -2.961 -12.537  1.00 26.66           C
ATOM   5880  CG  ASN D 211       7.188  -3.787 -13.497  1.00 31.54           C
ATOM   5881  OD1 ASN D 211       7.509  -3.885 -14.688  1.00 34.14           O
ATOM   5882  ND2 ASN D 211       6.117  -4.385 -12.998  1.00 35.03           N
ATOM   5883  N   PHE D 212      10.471  -1.815 -11.162  1.00 17.66           N
ATOM   5884  CA  PHE D 212      11.125  -0.946 -10.199  1.00 16.63           C
ATOM   5885  C   PHE D 212      12.040   0.075 -10.931  1.00 16.89           C
ATOM   5886  O   PHE D 212      11.892   1.291 -10.786  1.00 16.45           O
ATOM   5887  CB  PHE D 212      11.983  -1.790  -9.243  1.00 16.81           C
ATOM   5888  CG  PHE D 212      12.994  -0.989  -8.459  1.00 15.39           C
ATOM   5889  CD1 PHE D 212      12.558  -0.021  -7.560  1.00 13.74           C
ATOM   5890  CD2 PHE D 212      14.379  -1.171  -8.652  1.00 16.41           C
ATOM   5891  CE1 PHE D 212      13.473   0.779  -6.850  1.00 13.17           C
ATOM   5892  CE2 PHE D 212      15.333  -0.375  -7.945  1.00 14.63           C
ATOM   5893  CZ  PHE D 212      14.873   0.605  -7.042  1.00 14.49           C
ATOM   5894  N   LEU D 213      12.973  -0.445 -11.724  1.00 15.32           N
ATOM   5895  CA  LEU D 213      13.903   0.401 -12.465  1.00 15.87           C
ATOM   5896  C   LEU D 213      13.170   1.413 -13.328  1.00 15.82           C
ATOM   5897  O   LEU D 213      13.531   2.590 -13.375  1.00 15.75           O
ATOM   5898  CB  LEU D 213      14.812  -0.449 -13.344  1.00 12.78           C
ATOM   5899  CG  LEU D 213      15.736  -1.397 -12.582  1.00 12.37           C
ATOM   5900  CD1 LEU D 213      16.290  -2.422 -13.524  1.00 11.13           C
ATOM   5901  CD2 LEU D 213      16.866  -0.633 -11.934  1.00 13.04           C
ATOM   5902  N   TYR D 214      12.149   0.934  14.023  1.00 16.49           N
ATOM   5903  CA  TYR D 214      11.346   1.771 -14.888  1.00 16.71           C
ATOM   5904  C   TYR D 214      10.775   2.976 -14.113  1.00 17.61           C
ATOM   5905  O   TYR D 214      11.094   4.120 -14.429  1.00 17.07           O
ATOM   5906  CB  TYR D 214      10.188   0.949 -15.480  1.00 18.00           C
ATOM   5907  CG  TYR D 214       9.277   1.714 -16.429  1.00 17.95           C
ATOM   5908  CD1 TYR D 214       9.654   1.927 -17.763  1.00 17.82           C
ATOM   5909  CD2 TYR D 214       8.066   2.246 -15.989  1.00 16.89           C
ATOM   5910  CE1 TYR D 214       8.847   2.652 -18.635  1.00 16.94           C
ATOM   5911  CE2 TYR D 214       7.249   2.955 -16.859  1.00 21.00           C
ATOM   5912  CZ  TYR D 214       7.651   3.168 -18.188  1.00 20.25           C
ATOM   5913  OH  TYR D 214       6.837   3.835 -19.074  1.00 22.72           O
ATOM   5914  N   TYR D 215       9.960   2.706 -13.089  1.00 17.19           N
ATOM   5915  CA  TYR D 215       9.338   3.771 -12.325  1.00 17.96           C
ATOM   5916  C   TYR D 215      10.313   4.524 -11.446  1.00 18.75           C
ATOM   5917  O   TYR D 215      10.040   5.643 -11.009  1.00 20.30           O
ATOM   5918  CB  TYR D 215       8.163   3.250 -11.477  1.00 17.37           C
ATOM   5919  CG  TYR D 215       6.952   2.818 -12.286  1.00 17.83           C
ATOM   5920  CD1 TYR D 215       6.709   1.472 -12.554  1.00 19.09           C
ATOM   5921  CD2 TYR D 215       6.055   3.754 -12.794  1.00 17.44           C
ATOM   5922  CE1 TYR D 215       5.602   1.068 -13.311  1.00 17.12           C
ATOM   5923  CE2 TYR D 215       4.948   3.364 -13.551  1.00 17.41           C
ATOM   5924  CZ  TYR D 215       4.734   2.021 -13.806  1.00 18.51           C
ATOM   5925  OH  TYR D 215       3.664   1.630 -14.596  1.00 19.34           O
ATOM   5926  N   GLU D 216      11.456   3.927 -11.174  1.00 18.94           N
ATOM   5927  CA  GLU D 216      12.448   4.621 -10.380  1.00 20.06           C
ATOM   5928  C   GLU D 216      13.011   5.816 -11.188  1.00 21.60           C
ATOM   5929  O   GLU D 216      13.234   6.907 -10.655  1.00 21.62           O
ATOM   5930  CB  GLU D 216      13.587   3.675 -10.015  1.00 17.31           C
ATOM   5931  CG  GLU D 216      14.700   4.374  -9.270  1.00 17.81           C
ATOM   5932  CD  GLU D 216      15.968   3.532  -9.138  1.00 22.14           C
ATOM   5933  OE1 GLU D 216      16.504   3.082 -10.171  1.00 23.42           O
ATOM   5934  OE2 GLU D 216      16.445   3.307  -7.995  1.00 21.14           O
ATOM   5935  N   GLU D 217      13.231   5.602 -12.481  1.00 21.79           N
ATOM   5936  CA  GLU D 217      13.767   6.639 -13.325  1.00 25.27           C
ATOM   5937  C   GLU D 217      12.737   7.726 -13.544  1.00 26.94           C
ATOM   5938  O   GLU D 217      13.055   8.918 -13.515  1.00 28.50           O
ATOM   5939  CB  GLU D 217      14.185   6.083 -14.676  1.00 27.27           C
ATOM   5940  CG  GLU D 217      14.821   7.127 -15.566  1.00 33.13           C
ATOM   5941  CD  GLU D 217      14.627   6.845 -17.049  1.00 38.05           C
ATOM   5942  OE1 GLU D 217      13.478   6.530 -17.450  1.00 39.38           O
ATOM   5943  OE2 GLU D 217      15.605   6.951 -17.818  1.00 38.56           O
ATOM   5944  N   LYS D 218      11.499   7.323 -13.776  1.00 25.26           N
ATOM   5945  CA  LYS D 218      10.447   8.288 -13.967  1.00 26.36           C
ATOM   5946  C   LYS D 218      10.347   9.213 -12.750  1.00 25.95           C
ATOM   5947  O   LYS D 218      10.353  10.433 -12.881  1.00 26.01           O
ATOM   5948  CB  LYS D 218       9.095   7.577 -14.144  1.00 29.13           C
ATOM   5949  CG  LYS D 218       9.086   6.471 -15.187  1.00 30.49           C
ATOM   5950  CD  LYS D 218       9.468   6.960 -16.577  1.00 29.62           C
ATOM   5951  CE  LYS D 218       9.659   5.774 -17.518  1.00 32.07           C
ATOM   5952  NZ  LYS D 218      10.167   6.183 -18.855  1.00 31.30           N
ATOM   5953  N   LEU D 219      10.280   8.627 -11.558  1.00 25.40           N
ATOM   5954  CA  LEU D 219      10.140   9.410 -10.328  1.00 25.36           C
ATOM   5955  C   LEU D 219      11.280  10.384 -10.088  1.00 26.75           C
ATOM   5956  O   LEU D 219      11.078  11.514  -9.624  1.00 27.32           O
ATOM   5957  CB  LEU D 219      10.009   8.471  -9.128  1.00 22.20           C
ATOM   5958  CG  LEU D 219       9.836   9.095  -7.747  1.00 19.08           C
ATOM   5959  CD1 LEU D 219       8.548   9.908  -7.690  1.00 19.06           C
```

FIG. 6 (con't)

```
ATOM  2690  OE1 GLU B 185   -13.433 -17.210 90.113 1.00 38.50   O
ATOM  2691  OE2 GLU B 185   -12.921 -19.288 90.588 1.00 37.99   O
ATOM  2692  N   TYR B 186    -9.483 -14.397 89.142 1.00 23.63   N
ATOM  2693  CA  TYR B 186    -9.366 -13.888 87.786 1.00 23.72   C
ATOM  2694  C   TYR B 186    -7.883 -13.796 87.365 1.00 22.46   C
ATOM  2695  O   TYR B 186    -7.495 -14.217 86.272 1.00 21.29   O
ATOM  2696  CB  TYR B 186   -10.031 -12.513 87.689 1.00 25.73   C
ATOM  2697  CG  TYR B 186    -9.904 -11.866 86.330 1.00 29.26   C
ATOM  2698  CD1 TYR B 186   -10.689 -12.290 85.251 1.00 29.67   C
ATOM  2699  CD2 TYR B 186    -8.963 -10.855 86.105 1.00 29.80   C
ATOM  2700  CE1 TYR B 186   -10.534 -11.716 83.974 1.00 31.05   C
ATOM  2701  CE2 TYR B 186    -8.800 -10.280 84.840 1.00 31.40   C
ATOM  2702  CZ  TYR B 186    -9.584 -10.707 83.788 1.00 32.24   C
ATOM  2703  OH  TYR B 186    -9.416 -10.080 82.567 1.00 35.03   O
ATOM  2704  N   VAL B 187    -7.063 -13.246 88.246 1.00 21.12   N
ATOM  2705  CA  VAL B 187    -5.651 -13.103 87.968 1.00 20.71   C
ATOM  2706  C   VAL B 187    -4.990 -14.476 87.865 1.00 22.47   C
ATOM  2707  O   VAL B 187    -4.059 -14.698 87.075 1.00 23.30   O
ATOM  2708  CB  VAL B 187    -4.961 -12.282 89.071 1.00 18.25   C
ATOM  2709  CG1 VAL B 187    -3.466 -12.300 88.888 1.00 17.39   C
ATOM  2710  CG2 VAL B 187    -5.458 -10.850 89.029 1.00 16.85   C
ATOM  2711  N   TRP B 188    -5.488 -15.419 88.640 1.00 22.99   N
ATOM  2712  CA  TRP B 188    -4.913 -16.743 88.641 1.00 24.97   C
ATOM  2713  C   TRP B 188    -5.180 -17.541 87.382 1.00 27.24   C
ATOM  2714  O   TRP B 188    -4.318 -18.291 86.914 1.00 29.11   O
ATOM  2715  CB  TRP B 188    -5.398 -17.515 89.867 1.00 23.34   C
ATOM  2716  CG  TRP B 188    -4.918 -18.934 89.929 1.00 23.16   C
ATOM  2717  CD1 TRP B 188    -5.587 -20.042 89.501 1.00 22.79   C
ATOM  2718  CD2 TRP B 188    -3.662 -19.397 90.437 1.00 22.35   C
ATOM  2719  NE1 TRP B 188    -4.829 -21.167 89.707 1.00 22.57   N
ATOM  2720  CE2 TRP B 188    -3.637 -20.798 90.272 1.00 22.63   C
ATOM  2721  CE3 TRP B 188    -2.543 -18.764 90.997 1.00 22.96   C
ATOM  2722  CZ2 TRP B 188    -2.549 -21.583 90.670 1.00 21.99   C
ATOM  2723  CZ3 TRP B 188    -1.463 -19.541 91.392 1.00 23.43   C
ATOM  2724  CH2 TRP B 188    -1.472 -20.940 91.215 1.00 23.30   C
ATOM  2725  N   GLN B 189    -6.361 -17.370 86.815 1.00 28.12   N
ATOM  2726  CA  GLN B 189    -6.724 -18.116 85.628 1.00 29.70   C
ATOM  2727  C   GLN B 189    -6.514 -17.353 84.328 1.00 28.64   C
ATOM  2728  O   GLN B 189    -6.815 -17.862 83.254 1.00 31.14   O
ATOM  2729  CB  GLN B 189    -8.187 -18.580 85.753 1.00 32.03   C
ATOM  2730  CG  GLN B 189    -8.430 -19.579 86.903 1.00 37.20   C
ATOM  2731  CD  GLN B 189    -9.898 -19.988 87.063 1.00 40.80   C
ATOM  2732  OE1 GLN B 189   -10.208 -20.963 87.760 1.00 42.46   O
ATOM  2733  NE2 GLN B 189   -10.805 -19.242 86.433 1.00 41.54   N
ATOM  2734  N   ASN B 190    -5.980 -16.148 84.396 1.00 26.37   N
ATOM  2735  CA  ASN B 190    -5.790 -15.399 83.172 1.00 24.53   C
ATOM  2736  C   ASN B 190    -4.388 -14.859 83.035 1.00 25.67   C
ATOM  2737  O   ASN B 190    -4.043 -14.293 82.003 1.00 26.47   O
ATOM  2738  CB  ASN B 190    -6.776 -14.244 83.102 1.00 23.33   C
ATOM  2739  CG  ASN B 190    -8.186 -14.705 82.821 1.00 23.10   C
ATOM  2740  OD1 ASN B 190    -8.510 -15.102 81.703 1.00 21.83   O
ATOM  2741  ND2 ASN B 190    -9.038 -14.658 83.837 1.00 22.66   N
ATOM  2742  N   PHE B 191    -3.585 -15.012 84.084 1.00 25.47   N
ATOM  2743  CA  PHE B 191    -2.216 -14.537 84.062 1.00 25.85   C
ATOM  2744  C   PHE B 191    -1.238 -15.656 84.410 1.00 28.13   C
ATOM  2745  O   PHE B 191    -0.171 -15.767 83.816 1.00 29.21   O
ATOM  2746  CB  PHE B 191    -2.014 -13.363 85.037 1.00 22.38   C
ATOM  2747  CG  PHE B 191    -2.680 -12.085 84.612 1.00 19.64   C
ATOM  2748  CD1 PHE B 191    -4.058 -11.920 84.733 1.00 18.87   C
ATOM  2749  CD2 PHE B 191    -1.928 -11.041 84.081 1.00 18.00   C
ATOM  2750  CE1 PHE B 191    -4.673 -10.740 84.332 1.00 16.26   C
ATOM  2751  CE2 PHE B 191    -2.531  -9.861 83.680 1.00 16.59   C
ATOM  2752  CZ  PHE B 191    -3.908  -9.708 83.807 1.00 16.38   C
ATOM  2753  N   VAL B 192    -1.599 -16.495 85.368 1.00 31.82   N
ATOM  2754  CA  VAL B 192    -0.714 -17.577 85.764 1.00 34.59   C
ATOM  2755  C   VAL B 192    -0.885 -18.757 84.829 1.00 38.26   C
ATOM  2756  O   VAL B 192    -1.983 -19.297 84.684 1.00 39.28   O
ATOM  2757  CB  VAL B 192    -0.991 -18.013 87.197 1.00 33.12   C
ATOM  2758  CG1 VAL B 192    -0.116 -19.185 87.554 1.00 33.15   C
ATOM  2759  CG2 VAL B 192    -0.742 -16.847 88.143 1.00 32.22   C
ATOM  2760  N   GLU B 193     0.208 -19.162 84.201 1.00 41.91   N
ATOM  2761  CA  GLU B 193     0.164 -20.262 83.267 1.00 46.74   C
ATOM  2762  C   GLU B 193    -0.029 -21.592 83.957 1.00 50.07   C
ATOM  2763  O   GLU B 193     0.848 -22.055 84.686 1.00 50.30   O
ATOM  2764  CB  GLU B 193     1.459 -20.315 82.447 1.00 47.59   C
ATOM  2765  CG  GLU B 193     1.254 -20.636 80.965 1.00 49.55   C
ATOM  2766  CD  GLU B 193     2.563 -20.817 80.214 1.00 50.50   C
ATOM  2767  OE1 GLU B 193     3.306 -21.761 80.559 1.00 50.73   O
ATOM  2768  OE2 GLU B 193     2.853 -20.022 79.283 1.00 50.94   O
ATOM  2769  N   GLN B 194    -1.173 -22.216 83.680 1.00 54.47   N
ATOM  2770  CA  GLN B 194    -1.508 -23.541 84.208 1.00 58.83   C
ATOM  2771  C   GLN B 194    -0.657 -24.577 83.447 1.00 62.10   C
ATOM  2772  O   GLN B 194    -0.624 -24.573 82.211 1.00 61.64   O
ATOM  2773  CB  GLN B 194    -2.994 -23.852 83.979 1.00 58.57   C
ATOM  2774  CG  GLN B 194    -3.970 -22.932 84.686 1.00 57.78   C
ATOM  2775  CD  GLN B 194    -3.898 -23.058 86.191 1.00 57.30   C
ATOM  5960  CD2 LEU D 219     9.815   7.993  -6.697 1.00 19.40   C
ATOM  5961  N   ALA D 220    12.483   9.932 -10.403 1.00 28.40   N
ATOM  5962  CA  ALA D 220    13.674  10.730 -10.215 1.00 30.22   C
ATOM  5963  C   ALA D 220    13.603  12.015 -11.040 1.00 31.85   C
ATOM  5964  O   ALA D 220    13.737  13.116 -10.503 1.00 31.51   O
ATOM  5965  CB  ALA D 220    14.910   9.912 -10.603 1.00 30.23   C
ATOM  5966  N   ASP D 221    13.374  11.870 -12.341 1.00 32.72   N
ATOM  5967  CA  ASP D 221    13.285  13.011 -13.243 1.00 34.45   C
ATOM  5968  C   ASP D 221    12.239  14.042 -12.794 1.00 34.97   C
ATOM  5969  O   ASP D 221    12.360  15.236 -13.080 1.00 34.30   O
ATOM  5970  CB  ASP D 221    12.944  12.531 -14.660 1.00 36.09   C
ATOM  5971  CG  ASP D 221    13.933  11.509 -15.186 1.00 38.95   C
ATOM  5972  OD1 ASP D 221    15.157  11.784 -15.149 1.00 40.42   O
ATOM  5973  OD2 ASP D 221    13.491  10.429 -15.644 1.00 40.43   O
ATOM  5974  N   ILE D 222    11.215  13.569 -12.088 1.00 35.09   N
ATOM  5975  CA  ILE D 222    10.136  14.424 -11.614 1.00 35.46   C
ATOM  5976  C   ILE D 222    10.517  15.249 -10.396 1.00 38.02   C
ATOM  5977  O   ILE D 222    10.087  16.389 -10.264 1.00 37.81   O
ATOM  5978  CB  ILE D 222     8.884  13.594 -11.282 1.00 33.55   C
ATOM  5979  CG1 ILE D 222     8.335  12.968 -12.563 1.00 32.17   C
ATOM  5980  CG2 ILE D 222     7.822  14.467 -10.648 1.00 32.47   C
ATOM  5981  CD1 ILE D 222     7.193  12.009 -12.350 1.00 29.60   C
ATOM  5982  N   LEU D 223    11.323  14.678  -9.504 1.00 41.13   N
ATOM  5983  CA  LEU D 223    11.735  15.384  -8.297 1.00 44.28   C
ATOM  5984  C   LEU D 223    13.002  16.220  -8.477 1.00 46.95   C
ATOM  5985  O   LEU D 223    12.942  17.445  -8.397 1.00 48.87   O
ATOM  5986  CB  LEU D 223    11.912  14.405  -7.139 1.00 43.51   C
ATOM  5987  CG  LEU D 223    10.615  13.981  -6.449 1.00 43.25   C
ATOM  5988  CD1 LEU D 223     9.745  13.264  -7.437 1.00 42.48   C
ATOM  5989  CD2 LEU D 223    10.915  13.088  -5.268 1.00 43.45   C
ATOM  5990  N   LYS D 224    14.143  15.576  -8.713 1.00 48.75   N
ATOM  5991  CA  LYS D 224    15.387  16.316  -8.906 1.00 50.91   C
ATOM  5992  C   LYS D 224    15.959  16.145 -10.316 1.00 50.85   C
ATOM  5993  O   LYS D 224    17.165  15.832 -10.460 1.00 51.26   O
ATOM  5994  CB  LYS D 224    16.434  15.903  -7.852 1.00 53.20   C
ATOM  5995  CG  LYS D 224    16.512  14.411  -7.540 1.00 55.40   C
ATOM  5996  CD  LYS D 224    15.780  14.087  -6.240 1.00 57.40   C
ATOM  5997  CE  LYS D 224    16.144  12.706  -5.686 1.00 58.63   C
ATOM  5998  NZ  LYS D 224    17.594  12.599  -5.328 1.00 58.95   N
ATOM  5999  OXT LYS D 224    15.194  16.343 -11.276 1.00 51.00   O
TER   6000      LYS D 224
HETATM 6001 ZN   ZN A2000     2.813  -2.216  55.075 1.00 25.47  ZN
HETATM 6002 ZN   ZN B2001     5.759   2.763  95.567 1.00 31.22  ZN
HETATM 6003 ZN   ZN C2002    -3.331  -0.531  36.423 1.00 28.56  ZN
HETATM 6004 ZN   ZN D2003    -5.927   9.449  -4.332 1.00 52.16  ZN
HETATM 6005 O   HOH 1001   -11.777  -6.097  70.798 1.00 19.62   O
HETATM 6006 O   HOH 1002   -17.627  -7.783  65.904 1.00 32.47   O
HETATM 6007 O   HOH 1003    -3.890  -9.893  61.065 1.00 11.98   O
HETATM 6008 O   HOH 1004     1.841  -2.707  49.108 1.00 28.65   O
HETATM 6009 O   HOH 1005    -8.960  -1.856  51.060 1.00 23.23   O
HETATM 6010 O   HOH 1006    12.956 -13.505  88.105 1.00 56.31   O
HETATM 6011 O   HOH 1007    16.123  -2.548  83.814 1.00 28.11   O
HETATM 6012 O   HOH 1008     3.455  -8.196  58.101 1.00 36.87   O
HETATM 6013 O   HOH 1009    10.142   0.777  68.703 1.00 45.99   O
HETATM 6014 O   HOH 1010    16.365 -10.197  71.968 1.00  8.86   O
HETATM 6015 O   HOH 1011     6.945 -13.880  71.347 1.00  6.51   O
HETATM 6016 O   HOH 1012     6.445 -16.948  69.427 1.00 38.80   O
HETATM 6017 O   HOH 1013    -4.552 -10.891  54.369 1.00 10.11   O
HETATM 6018 O   HOH 1014     5.291  -9.676  51.731 1.00  9.79   O
HETATM 6019 O   HOH 1015    -1.525 -20.768  56.188 1.00  8.54   O
HETATM 6020 O   HOH 1016    -6.284 -20.957  55.197 1.00 12.17   O
HETATM 6021 O   HOH 1017    -8.003 -11.786  52.206 1.00 10.63   O
HETATM 6022 O   HOH 1018     4.530  -6.992  37.998 1.00 12.80   O
HETATM 6023 O   HOH 1019    11.541 -12.316  55.627 1.00 36.42   O
HETATM 6024 O   HOH 1020    19.416 -19.808  54.337 1.00 65.07   O
HETATM 6025 O   HOH 1021    15.684 -14.311  59.922 1.00 27.29   O
HETATM 6026 O   HOH 1022    19.678 -13.830  51.005 1.00 41.08   O
HETATM 6027 O   HOH 1023    21.543  -6.808  53.769 1.00 17.37   O
HETATM 6028 O   HOH 1024   -10.496 -22.306  49.612 1.00 39.03   O
HETATM 6029 O   HOH 1025    -3.988 -22.193  55.969 1.00 20.76   O
HETATM 6030 O   HOH 1026     1.422  -7.774  92.992 1.00 14.27   O
HETATM 6031 O   HOH 1027    11.924   3.665  98.538 1.00 28.04   O
HETATM 6032 O   HOH 1028    10.214  -2.920  88.773 1.00 14.35   O
HETATM 6033 O   HOH 1029    -8.528 -10.718  79.067 1.00 46.57   O
HETATM 6034 O   HOH 1030    12.682  -3.505  87.179 1.00 19.02   O
HETATM 6035 O   HOH 1031     7.117   7.292  85.665 1.00 18.35   O
HETATM 6036 O   HOH 1032    -6.281   4.011  80.879 1.00 52.79   O
HETATM 6037 O   HOH 1033    -8.382  -2.194  81.833 1.00 10.41   O
HETATM 6038 O   HOH 1034    -9.730  -6.414  84.717 1.00 28.96   O
HETATM 6039 O   HOH 1035     2.611  -6.584  99.210 1.00  3.75   O
HETATM 6040 O   HOH 1036    -7.897   7.673  85.922 1.00 12.80   O
HETATM 6041 O   HOH 1037    -8.575  -8.347  99.272 1.00  8.60   O
HETATM 6042 O   HOH 1038    -0.920   0.319 108.353 1.00 22.12   O
HETATM 6043 O   HOH 1039    -7.628  10.465  85.628 1.00 19.32   O
HETATM 6044 O   HOH 1040   -12.953  -1.477  96.944 1.00 16.75   O
HETATM 6045 O   HOH 1041   -11.987 -21.807  89.283 1.00 36.76   O
```

FIG. 6 (con't)

```
HETATM 6046  O  HOH 1042    -12.409 -15.443 104.704 1.00 30.22      O
HETATM 6047  O  HOH 1043     -8.246 -11.180 100.300 1.00 16.20      O
HETATM 6048  O  HOH 1044    -17.930 -10.177 100.461 1.00 17.15      O
HETATM 6049  O  HOH 1045     10.963  -2.295  14.615 1.00 11.89      O
HETATM 6050  O  HOH 1046     17.275  -4.112  24.295 1.00 50.49      O
HETATM 6051  O  HOH 1047     11.850  -4.212  27.311 1.00 19.66      O
HETATM 6052  O  HOH 1048      0.767  -6.077  33.753 1.00 14.62      O
HETATM 6053  O  HOH 1049      0.976  -0.569  33.439 1.00 21.79      O
HETATM 6054  O  HOH 1050      6.615  -4.050  46.289 1.00 15.33      O
HETATM 6055  O  HOH 1051    -19.101  -7.251   4.365 1.00 31.40      O
HETATM 6056  O  HOH 1052    -16.724  -5.850  18.439 1.00  7.67      O
HETATM 6057  O  HOH 1053     -2.878 -16.069  20.667 1.00 77.81      O
HETATM 6058  O  HOH 1054      3.812  -8.859  35.730 1.00 11.57      O
HETATM 6059  O  HOH 1055     -5.747  -8.167  38.683 1.00 10.71      O
HETATM 6060  O  HOH 1056    -16.512 -11.479  29.974 1.00 25.65      O
HETATM 6061  O  HOH 1057      0.957 -18.402  32.186 1.00 15.46      O
HETATM 6062  O  HOH 1058      8.348 -26.557  30.363 1.00 39.89      O
HETATM 6063  O  HOH 1059      3.427 -19.847  32.444 1.00 15.58      O
HETATM 6064  O  HOH 1060      3.179 -20.414  41.262 1.00 19.89      O
HETATM 6065  O  HOH 1061     -7.821   3.945  -3.114 1.00 25.42      O
HETATM 6066  O  HOH 1062     10.154   2.643  17.469 1.00 21.06      O
HETATM 6067  O  HOH 1063     10.284   9.910  29.334 1.00 63.69      O
HETATM 6068  O  HOH 1064     11.438   1.044  27.258 1.00 28.44      O
HETATM 6069  O  HOH 1065     12.502   7.368  22.138 1.00 32.72      O
HETATM 6070  O  HOH 1066    -10.899  -0.533   5.442 1.00 33.70      O
HETATM 6071  O  HOH 1067     -4.794   6.725  -6.283 1.00 50.84      O
HETATM 6072  O  HOH 1068     -2.952   0.760  -7.979 1.00  1.71      O
HETATM 6073  O  HOH 1069     13.653  18.825  -0.835 1.00 20.28      O
HETATM 6074  O  HOH 1070      7.624  13.221   5.964 1.00 29.61      O
HETATM 6075  O  HOH 1071     16.522   1.178   0.375 1.00 43.24      O
HETATM 6076  O  HOH 1072     17.936  -3.425  -9.514 1.00 16.49      O
HETATM 6077  O  HOH 1073     13.339   0.007 103.676 1.00 24.31      O
HETATM 6078  O  HOH 1074    -14.714  10.254  82.026 1.00 10.07      O
HETATM 6079  O  HOH 1075     10.996 -19.630  66.078 1.00 28.97      O
HETATM 6080  O  HOH 1076      0.707  -4.035  75.981 1.00 23.93      O
HETATM 6081  O  HOH 1077      6.411 -29.729  54.638 1.00 27.52      O
HETATM 6082  O  HOH 1078     15.872 -20.639  60.507 1.00 65.85      O
HETATM 6083  O  HOH 1079      7.888 -21.619  43.932 1.00 72.00      O
HETATM 6084  O  HOH 1080     20.077  -5.693  64.171 1.00 24.35      O
HETATM 6085  O  HOH 1081      7.006 -21.645  56.920 1.00 15.94      O
HETATM 6086  O  HOH 1082     -5.696  -0.806  45.536 1.00 40.68      O
HETATM 6087  O  HOH 1083     -5.517  -1.414  42.400 1.00 31.80      O
HETATM 6088  O  HOH 1084     -9.334   5.557  30.424 1.00 26.46      O
HETATM 6089  O  HOH 1085      2.994   6.933  25.853 1.00 23.43      O
HETATM 6090  O  HOH 1086     -1.902   4.254 -13.502 1.00 40.79      O
HETATM 6091  O  HOH 1087     -1.936  19.666  -9.076 1.00 24.16      O
HETATM 6092  O  HOH 1088     -8.254   5.995  62.122 1.00 47.36      O
MASTER     290    0    4   24   36    0    0 6 6088    4    0   60
END
```

FIG. 7

| ATOM | 1 | N | SER A 36 | -3.298 -22.445 78.217 1.00 60.22 | N |
|---|---|---|---|---|---|
| ATOM | 2 | CA | SER A 36 | -4.662 -22.689 77.656 1.00 60.60 | C |
| ATOM | 3 | C | SER A 36 | -5.074 -21.622 76.656 1.00 60.33 | C |
| ATOM | 4 | O | SER A 36 | -4.865 -21.775 75.449 1.00 61.84 | O |
| ATOM | 5 | CB | SER A 36 | -5.695 -22.747 78.783 1.00 61.34 | C |
| ATOM | 6 | OG | SER A 36 | -7.013 -22.646 78.257 1.00 62.46 | O |
| ATOM | 7 | N | GLY A 37 | -5.677 -20.544 77.157 1.00 59.14 | N |
| ATOM | 8 | CA | GLY A 37 | -6.113 -19.448 76.300 1.00 56.40 | C |
| ATOM | 9 | C | GLY A 37 | -7.178 -18.571 76.925 1.00 54.50 | C |
| ATOM | 10 | O | GLY A 37 | -8.252 -19.053 77.281 1.00 54.69 | O |
| ATOM | 11 | N | GLY A 38 | -6.893 -17.275 77.041 1.00 53.40 | N |
| ATOM | 12 | CA | GLY A 38 | -7.845 -16.351 77.645 1.00 51.22 | C |
| ATOM | 13 | C | GLY A 38 | -8.510 -15.399 76.676 1.00 49.73 | C |
| ATOM | 14 | O | GLY A 38 | -8.236 -15.399 75.478 1.00 48.90 | O |
| ATOM | 15 | N | GLY A 39 | -9.397 -14.563 77.192 1.00 48.94 | N |
| ATOM | 16 | CA | GLY A 39 | -10.073 -13.635 76.305 1.00 46.33 | C |
| ATOM | 17 | C | GLY A 39 | -9.193 -12.455 75.954 1.00 44.17 | C |
| ATOM | 18 | O | GLY A 39 | -8.110 -12.307 76.510 1.00 46.03 | O |
| ATOM | 19 | N | MET A 40 | -9.659 -11.617 75.034 1.00 40.58 | N |
| ATOM | 20 | CA | MET A 40 | -8.912 -10.424 74.636 1.00 35.27 | C |
| ATOM | 21 | C | MET A 40 | -9.651 -9.680 73.524 1.00 32.75 | C |
| ATOM | 22 | O | MET A 40 | -10.150 -8.570 73.712 1.00 31.53 | O |
| ATOM | 23 | CB | MET A 40 | -7.544 -10.843 74.153 1.00 36.46 | C |
| ATOM | 24 | CG | MET A 40 | -6.560 -9.748 74.122 1.00 34.33 | C |
| ATOM | 25 | SD | MET A 40 | -5.122 -10.626 73.644 1.00 35.10 | S |
| ATOM | 26 | CE | MET A 40 | -4.743 -11.654 75.256 1.00 35.47 | C |
| ATOM | 27 | N | ILE A 41 | -9.716 -10.323 72.366 1.00 27.95 | N |
| ATOM | 28 | CA | ILE A 41 | -10.388 -9.766 71.211 1.00 25.80 | C |
| ATOM | 29 | C | ILE A 41 | -11.877 -10.047 71.277 1.00 24.30 | C |
| ATOM | 30 | O | ILE A 41 | -12.276 -11.209 71.304 1.00 23.96 | O |
| ATOM | 31 | CB | ILE A 41 | -9.867 -10.404 69.915 1.00 24.92 | C |
| ATOM | 32 | CG1 | ILE A 41 | -8.355 -10.185 69.796 1.00 25.08 | C |
| ATOM | 33 | CG2 | ILE A 41 | -10.568 -9.804 68.725 1.00 23.59 | C |
| ATOM | 34 | CD1 | ILE A 41 | -7.707 -10.772 68.525 1.00 20.84 | C |
| ATOM | 35 | N | VAL A 42 | -12.691 -8.994 71.305 1.00 23.41 | N |
| ATOM | 36 | CA | VAL A 42 | -14.155 -9.137 71.343 1.00 22.08 | C |
| ATOM | 37 | C | VAL A 42 | -14.679 -9.043 69.905 1.00 22.86 | C |
| ATOM | 38 | O | VAL A 42 | -14.486 -8.024 69.241 1.00 23.94 | O |
| ATOM | 39 | CB | VAL A 42 | -14.794 -8.024 72.217 1.00 20.15 | C |
| ATOM | 40 | CG1 | VAL A 42 | -16.297 -8.251 72.370 1.00 18.38 | C |
| ATOM | 41 | CG2 | VAL A 42 | -14.135 -8.000 73.579 1.00 18.94 | C |
| ATOM | 42 | N | THR A 43 | -15.322 -10.105 69.424 1.00 22.77 | N |
| ATOM | 43 | CA | THR A 43 | -15.881 -10.141 68.073 1.00 22.69 | C |
| ATOM | 44 | C | THR A 43 | -17.234 -10.827 68.032 1.00 23.62 | C |
| ATOM | 45 | O | THR A 43 | -17.581 -11.575 68.939 1.00 23.01 | O |
| ATOM | 46 | CB | THR A 43 | -14.996 -10.906 67.129 1.00 22.17 | C |
| ATOM | 47 | OG1 | THR A 43 | -13.646 -10.544 67.406 1.00 28.17 | O |
| ATOM | 48 | CG2 | THR A 43 | -15.309 -10.568 65.685 1.00 20.20 | C |
| ATOM | 49 | N | GLY A 44 | -17.978 -10.575 66.960 1.00 23.82 | N |
| ATOM | 50 | CA | GLY A 44 | -19.275 -11.182 66.813 1.00 24.08 | C |
| ATOM | 51 | C | GLY A 44 | -19.191 -12.501 66.067 1.00 25.62 | C |
| ATOM | 52 | O | GLY A 44 | -20.002 -13.398 66.283 1.00 25.79 | O |
| ATOM | 53 | N | GLU A 45 | -18.203 -12.625 65.190 1.00 25.75 | N |
| ATOM | 54 | CA | GLU A 45 | -18.038 -13.845 64.429 1.00 27.88 | C |
| ATOM | 55 | C | GLU A 45 | -17.896 -15.039 65.376 1.00 28.91 | C |
| ATOM | 56 | O | GLU A 45 | -17.236 -14.942 66.403 1.00 29.04 | O |
| ATOM | 57 | CB | GLU A 45 | -16.821 -13.735 63.520 1.00 28.04 | C |
| ATOM | 58 | CG | GLU A 45 | -16.651 -14.917 62.609 1.00 30.62 | C |
| ATOM | 59 | CD | GLU A 45 | -17.947 -15.312 61.937 1.00 31.52 | C |
| ATOM | 60 | OE1 | GLU A 45 | -18.569 -14.448 61.284 1.00 32.36 | O |
| ATOM | 61 | OE2 | GLU A 45 | -18.342 -16.497 62.066 1.00 32.94 | O |
| ATOM | 62 | N | ARG A 46 | -18.520 -16.159 65.028 1.00 30.75 | N |
| ATOM | 63 | CA | ARG A 46 | -18.474 -17.341 65.871 1.00 32.60 | C |
| ATOM | 64 | C | ARG A 46 | -17.531 -18.414 65.311 1.00 32.42 | C |
| ATOM | 65 | O | ARG A 46 | -16.793 -19.051 66.063 1.00 32.40 | O |
| ATOM | 66 | CB | ARG A 46 | -19.882 -17.923 65.998 1.00 36.08 | C |
| ATOM | 67 | CG | ARG A 46 | -20.144 -18.681 67.276 1.00 40.89 | C |
| ATOM | 68 | CD | ARG A 46 | -20.455 -17.716 68.408 1.00 45.55 | C |
| ATOM | 69 | NE | ARG A 46 | -20.654 -18.398 69.686 1.00 49.81 | N |
| ATOM | 70 | CZ | ARG A 46 | -21.637 -19.254 69.955 1.00 52.19 | C |
| ATOM | 71 | NH1 | ARG A 46 | -22.554 -19.555 69.037 1.00 52.84 | N |
| ATOM | 72 | NH2 | ARG A 46 | -21.689 -19.825 71.151 1.00 53.17 | N |
| ATOM | 73 | N | LEU A 47 | -17.567 -18.605 63.989 1.00 31.06 | N |
| ATOM | 74 | CA | LEU A 47 | -16.740 -19.604 63.308 1.00 30.16 | C |
| ATOM | 75 | C | LEU A 47 | -15.319 -19.108 63.042 1.00 28.29 | C |
| ATOM | 76 | O | LEU A 47 | -15.127 -17.987 62.571 1.00 27.10 | O |
| ATOM | 77 | CB | LEU A 47 | -17.388 -20.006 61.970 1.00 33.05 | C |
| ATOM | 78 | CG | LEU A 47 | -16.509 -20.838 61.010 1.00 37.28 | C |
| ATOM | 79 | CD1 | LEU A 47 | -16.346 -22.281 61.551 1.00 36.15 | C |
| ATOM | 80 | CD2 | LEU A 47 | -17.125 -20.806 59.591 1.00 35.68 | C |
| ATOM | 81 | N | PRO A 48 | -14.306 -19.941 63.349 1.00 26.74 | N |
| ATOM | 82 | CA | PRO A 48 | -12.898 -19.586 63.136 1.00 25.76 | C |
| ATOM | 83 | C | PRO A 48 | -12.624 -19.188 61.692 1.00 25.17 | C |
| ATOM | 84 | O | PRO A 48 | -12.045 -18.134 61.430 1.00 25.26 | O |
| ATOM | 85 | CB | PRO A 48 | -12.161 -20.861 63.521 1.00 23.74 | C |
| ATOM | 86 | CG | PRO A 48 | -13.012 -21.405 64.605 1.00 22.93 | C |
| ATOM | 1513 | CA | GLY B 37 | -7.889 -17.940 80.622 1.00 58.37 | C |
| ATOM | 1514 | C | GLY B 37 | -6.627 -18.655 80.176 1.00 56.48 | C |
| ATOM | 1515 | O | GLY B 37 | -6.508 -19.870 80.341 1.00 56.22 | O |
| ATOM | 1516 | N | GLY B 38 | -5.683 -17.898 79.613 1.00 54.16 | N |
| ATOM | 1517 | CA | GLY B 38 | -4.428 -18.478 79.157 1.00 52.32 | C |
| ATOM | 1518 | C | GLY B 38 | -3.368 -18.471 80.239 1.00 51.43 | C |
| ATOM | 1519 | O | GLY B 38 | -3.421 -19.244 81.203 1.00 52.20 | O |
| ATOM | 1520 | N | GLY B 39 | -2.385 -17.596 80.084 1.00 49.18 | N |
| ATOM | 1521 | CA | GLY B 39 | -1.340 -17.519 81.085 1.00 47.03 | C |
| ATOM | 1522 | C | GLY B 39 | -0.017 -17.121 80.494 1.00 45.63 | C |
| ATOM | 1523 | O | GLY B 39 | 0.391 -17.656 79.462 1.00 46.65 | O |
| ATOM | 1524 | N | MET B 40 | 0.648 -16.177 81.152 1.00 43.33 | N |
| ATOM | 1525 | CA | MET B 40 | 1.952 -15.681 80.718 1.00 41.32 | C |
| ATOM | 1526 | C | MET B 40 | 2.954 -15.760 81.860 1.00 39.92 | C |
| ATOM | 1527 | O | MET B 40 | 4.154 -15.656 81.634 1.00 40.36 | O |
| ATOM | 1528 | CB | MET B 40 | 1.831 -14.231 80.240 1.00 41.10 | C |
| ATOM | 1529 | CG | MET B 40 | 1.284 -13.293 81.296 1.00 41.23 | C |
| ATOM | 1530 | SD | MET B 40 | -0.175 -12.424 80.751 1.00 41.22 | S |
| ATOM | 1531 | CE | MET B 40 | -1.319 -13.808 80.575 1.00 42.14 | C |
| ATOM | 1532 | N | ILE B 41 | 2.455 -15.944 83.084 1.00 39.53 | N |
| ATOM | 1533 | CA | ILE B 41 | 3.303 -16.047 84.270 1.00 38.14 | C |
| ATOM | 1534 | C | ILE B 41 | 3.596 -17.508 84.578 1.00 38.77 | C |
| ATOM | 1535 | O | ILE B 41 | 2.689 -18.340 84.581 1.00 38.59 | O |
| ATOM | 1536 | CB | ILE B 41 | 2.617 -15.434 85.495 1.00 37.33 | C |
| ATOM | 1537 | CG1 | ILE B 41 | 2.187 -14.002 85.180 1.00 36.78 | C |
| ATOM | 1538 | CG2 | ILE B 41 | 3.563 -15.426 86.666 1.00 35.32 | C |
| ATOM | 1539 | CD1 | ILE B 41 | 1.348 -13.360 86.250 1.00 36.32 | C |
| ATOM | 1540 | N | VAL B 42 | 4.860 -17.818 84.843 1.00 39.95 | N |
| ATOM | 1541 | CA | VAL B 42 | 5.255 -19.186 85.154 1.00 41.19 | C |
| ATOM | 1542 | C | VAL B 42 | 5.923 -19.284 86.521 1.00 42.18 | C |
| ATOM | 1543 | O | VAL B 42 | 6.912 -18.603 86.788 1.00 41.93 | O |
| ATOM | 1544 | CB | VAL B 42 | 6.231 -19.731 84.101 1.00 41.11 | C |
| ATOM | 1545 | CG1 | VAL B 42 | 6.532 -21.189 84.389 1.00 40.37 | C |
| ATOM | 1546 | CG2 | VAL B 42 | 5.637 -19.566 82.711 1.00 41.56 | C |
| ATOM | 1547 | N | THR B 43 | 5.367 -20.136 87.379 1.00 43.82 | N |
| ATOM | 1548 | CA | THR B 43 | 5.887 -20.353 88.723 1.00 45.23 | C |
| ATOM | 1549 | C | THR B 43 | 5.739 -21.815 89.095 1.00 46.40 | C |
| ATOM | 1550 | O | THR B 43 | 4.884 -22.525 88.557 1.00 45.59 | O |
| ATOM | 1551 | CB | THR B 43 | 5.136 -19.517 89.778 1.00 45.76 | C |
| ATOM | 1552 | OG1 | THR B 43 | 3.761 -19.394 89.392 1.00 45.90 | O |
| ATOM | 1553 | CG2 | THR B 43 | 5.779 -18.136 89.940 1.00 47.70 | C |
| ATOM | 1554 | N | GLY B 44 | 6.583 -22.261 90.021 1.00 46.95 | N |
| ATOM | 1555 | CA | GLY B 44 | 6.533 -23.641 90.465 1.00 47.63 | C |
| ATOM | 1556 | C | GLY B 44 | 5.504 -23.824 91.561 1.00 47.94 | C |
| ATOM | 1557 | O | GLY B 44 | 5.351 -24.919 92.100 1.00 48.43 | O |
| ATOM | 1558 | N | GLU B 45 | 4.786 -22.753 91.884 1.00 47.48 | N |
| ATOM | 1559 | CA | GLU B 45 | 3.782 -22.811 92.927 1.00 47.90 | C |
| ATOM | 1560 | C | GLU B 45 | 2.454 -23.313 92.373 1.00 47.93 | C |
| ATOM | 1561 | O | GLU B 45 | 1.889 -22.740 91.443 1.00 45.94 | O |
| ATOM | 1562 | CB | GLU B 45 | 3.601 -21.438 93.561 1.00 48.53 | C |
| ATOM | 1563 | CG | GLU B 45 | 2.969 -21.498 94.929 1.00 50.43 | C |
| ATOM | 1564 | CD | GLU B 45 | 3.864 -22.151 95.957 1.00 51.36 | C |
| ATOM | 1565 | OE1 | GLU B 45 | 4.830 -21.492 96.414 1.00 51.15 | O |
| ATOM | 1566 | OE2 | GLU B 45 | 3.598 -23.324 96.303 1.00 51.55 | O |
| ATOM | 1567 | N | ARG B 46 | 1.958 -24.393 92.962 1.00 49.04 | N |
| ATOM | 1568 | CA | ARG B 46 | 0.718 -24.985 92.509 1.00 49.97 | C |
| ATOM | 1569 | C | ARG B 46 | -0.484 -24.439 93.281 1.00 48.13 | C |
| ATOM | 1570 | O | ARG B 46 | -1.617 -24.540 92.821 1.00 47.87 | O |
| ATOM | 1571 | CB | ARG B 46 | 0.797 -26.510 92.658 1.00 53.46 | C |
| ATOM | 1572 | CG | ARG B 46 | 0.328 -27.308 91.427 1.00 58.32 | C |
| ATOM | 1573 | CD | ARG B 46 | -1.136 -26.997 91.023 1.00 61.93 | C |
| ATOM | 1574 | NE | ARG B 46 | -1.577 -27.757 89.841 1.00 64.77 | N |
| ATOM | 1575 | CZ | ARG B 46 | -2.772 -27.640 89.260 1.00 65.91 | C |
| ATOM | 1576 | NH1 | ARG B 46 | -3.676 -26.789 89.737 1.00 66.29 | N |
| ATOM | 1577 | NH2 | ARG B 46 | -3.066 -28.376 88.193 1.00 65.31 | N |
| ATOM | 1578 | N | LEU B 47 | -0.236 -23.853 94.444 1.00 46.05 | N |
| ATOM | 1579 | CA | LEU B 47 | -1.330 -23.313 95.246 1.00 44.88 | C |
| ATOM | 1580 | C | LEU B 47 | -1.357 -21.803 95.130 1.00 43.20 | C |
| ATOM | 1581 | O | LEU B 47 | -0.346 -21.147 95.360 1.00 44.51 | O |
| ATOM | 1582 | CB | LEU B 47 | -1.153 -23.700 96.714 1.00 44.69 | C |
| ATOM | 1583 | CG | LEU B 47 | -2.332 -23.410 97.648 1.00 45.22 | C |
| ATOM | 1584 | CD1 | LEU B 47 | -3.494 -24.345 97.335 1.00 43.81 | C |
| ATOM | 1585 | CD2 | LEU B 47 | -1.884 -23.601 99.087 1.00 44.57 | C |
| ATOM | 1586 | N | PRO B 48 | -2.518 -21.228 94.784 1.00 41.40 | N |
| ATOM | 1587 | CA | PRO B 48 | -2.646 -19.775 94.643 1.00 39.91 | C |
| ATOM | 1588 | C | PRO B 48 | -2.418 -19.024 95.943 1.00 38.63 | C |
| ATOM | 1589 | O | PRO B 48 | -1.992 -17.866 95.945 1.00 37.68 | O |
| ATOM | 1590 | CB | PRO B 48 | -4.064 -19.609 94.110 1.00 40.40 | C |
| ATOM | 1591 | CG | PRO B 48 | -4.780 -20.757 94.701 1.00 40.22 | C |
| ATOM | 1592 | CD | PRO B 48 | -3.803 -21.884 94.498 1.00 41.21 | C |
| ATOM | 1593 | N | ALA B 49 | -2.695 -19.699 97.051 1.00 37.40 | N |
| ATOM | 1594 | CA | ALA B 49 | -2.531 -19.103 98.361 1.00 36.74 | C |
| ATOM | 1595 | C | ALA B 49 | -1.077 -18.727 98.588 1.00 37.22 | C |
| ATOM | 1596 | O | ALA B 49 | -0.784 -17.745 99.272 1.00 37.92 | O |
| ATOM | 1597 | CB | ALA B 49 | -2.999 -20.072 99.425 1.00 35.73 | C |
| ATOM | 1598 | N | ASN B 50 | -0.164 -19.506 97.999 1.00 36.86 | N |

FIG. 7 (con't)

| | | | | | | |
|---|---|---|---|---|---|---|
| ATOM | 87 | CD PRO A 48 | -14.399 -21.241 64.034 1.00 26.04 | | | C |
| ATOM | 88 | N ALA A 49 | -13.050 -20.041 60.766 1.00 25.16 | | | N |
| ATOM | 89 | CA ALA A 49 | -12.845 -19.805 59.340 1.00 24.41 | | | C |
| ATOM | 90 | C ALA A 49 | -13.306 -18.437 58.904 1.00 23.89 | | | C |
| ATOM | 91 | O ALA A 49 | -12.634 -17.782 58.119 1.00 24.84 | | | O |
| ATOM | 92 | CB ALA A 49 | -13.552 -20.854 58.528 1.00 24.69 | | | C |
| ATOM | 93 | N ASN A 50 | -14.469 -18.012 59.389 1.00 23.87 | | | N |
| ATOM | 94 | CA ASN A 50 | -14.977 -16.689 59.039 1.00 21.61 | | | C |
| ATOM | 95 | C ASN A 50 | -14.119 -15.593 59.677 1.00 20.06 | | | C |
| ATOM | 96 | O ASN A 50 | -13.817 -14.589 59.044 1.00 19.10 | | | O |
| ATOM | 97 | CB ASN A 50 | -16.434 -16.526 59.488 1.00 23.81 | | | C |
| ATOM | 98 | CG ASN A 50 | -17.402 -17.156 58.527 1.00 25.17 | | | C |
| ATOM | 99 | OD1 ASN A 50 | -17.334 -16.923 57.321 1.00 27.07 | | | O |
| ATOM | 100 | ND2 ASN A 50 | -18.325 -17.950 59.053 1.00 27.29 | | | N |
| ATOM | 101 | N PHE A 51 | -13.732 -15.775 60.936 1.00 18.54 | | | N |
| ATOM | 102 | CA PHE A 51 | -12.919 -14.774 61.621 1.00 17.24 | | | C |
| ATOM | 103 | C PHE A 51 | -11.605 -14.495 60.889 1.00 18.07 | | | C |
| ATOM | 104 | O PHE A 51 | -11.316 -13.356 60.505 1.00 18.63 | | | O |
| ATOM | 105 | CB PHE A 51 | -12.620 -15.226 63.043 1.00 15.20 | | | C |
| ATOM | 106 | CG PHE A 51 | -11.610 -14.376 63.741 1.00 14.28 | | | C |
| ATOM | 107 | CD1 PHE A 51 | -11.955 -13.119 64.211 1.00 13.22 | | | C |
| ATOM | 108 | CD2 PHE A 51 | -10.299 -14.814 63.882 1.00 12.20 | | | C |
| ATOM | 109 | CE1 PHE A 51 | -11.010 -12.307 64.807 1.00 13.49 | | | C |
| ATOM | 110 | CE2 PHE A 51 | -9.345 -14.009 64.475 1.00 12.16 | | | C |
| ATOM | 111 | CZ PHE A 51 | -9.700 -12.750 64.939 1.00 13.88 | | | C |
| ATOM | 112 | N PHE A 52 | -10.806 -15.546 60.706 1.00 18.74 | | | N |
| ATOM | 113 | CA PHE A 52 | -9.517 -15.431 60.040 1.00 19.25 | | | C |
| ATOM | 114 | C PHE A 52 | -9.583 -15.020 58.579 1.00 21.22 | | | C |
| ATOM | 115 | O PHE A 52 | -8.592 -14.543 58.039 1.00 21.77 | | | O |
| ATOM | 116 | CB PHE A 52 | -8.721 -16.730 60.158 1.00 17.63 | | | C |
| ATOM | 117 | CG PHE A 52 | -8.288 -17.036 61.549 1.00 16.54 | | | C |
| ATOM | 118 | CD1 PHE A 52 | -9.031 -17.901 62.332 1.00 15.12 | | | C |
| ATOM | 119 | CD2 PHE A 52 | -7.175 -16.400 62.099 1.00 15.65 | | | C |
| ATOM | 120 | CE1 PHE A 52 | -8.678 -18.127 63.644 1.00 17.35 | | | C |
| ATOM | 121 | CE2 PHE A 52 | -6.820 -16.622 63.420 1.00 17.05 | | | C |
| ATOM | 122 | CZ PHE A 52 | -7.570 -17.487 64.199 1.00 15.92 | | | C |
| ATOM | 123 | N LYS A 53 | -10.732 -15.209 57.933 1.00 22.58 | | | N |
| ATOM | 124 | CA LYS A 53 | -10.860 -14.826 56.530 1.00 24.42 | | | C |
| ATOM | 125 | C LYS A 53 | -11.376 -13.414 56.300 1.00 23.62 | | | C |
| ATOM | 126 | O LYS A 53 | -11.255 -12.905 55.191 1.00 24.47 | | | O |
| ATOM | 127 | CB LYS A 53 | -11.777 -15.798 55.763 1.00 26.77 | | | C |
| ATOM | 128 | CG LYS A 53 | -11.058 -16.979 55.079 1.00 31.52 | | | C |
| ATOM | 129 | CD LYS A 53 | -10.402 -17.973 56.080 1.00 32.24 | | | C |
| ATOM | 130 | CE LYS A 53 | -8.853 -18.053 55.976 1.00 34.63 | | | C |
| ATOM | 131 | NZ LYS A 53 | -8.352 -18.705 54.728 1.00 34.84 | | | N |
| ATOM | 132 | N PHE A 54 | -11.957 -12.794 57.324 1.00 22.89 | | | N |
| ATOM | 133 | CA PHE A 54 | -12.509 -11.441 57.205 1.00 22.84 | | | C |
| ATOM | 134 | C PHE A 54 | -12.018 -10.471 58.294 1.00 23.16 | | | C |
| ATOM | 135 | O PHE A 54 | -11.243 -9.546 58.019 1.00 24.84 | | | O |
| ATOM | 136 | CB PHE A 54 | -14.051 -11.491 57.229 1.00 23.62 | | | C |
| ATOM | 137 | CG PHE A 54 | -14.656 -12.322 56.114 1.00 24.14 | | | C |
| ATOM | 138 | CD1 PHE A 54 | -15.247 -13.556 56.380 1.00 23.43 | | | C |
| ATOM | 139 | CD2 PHE A 54 | -14.599 -11.879 54.796 1.00 23.29 | | | C |
| ATOM | 140 | CE1 PHE A 54 | -15.768 -14.337 55.347 1.00 24.86 | | | C |
| ATOM | 141 | CE2 PHE A 54 | -15.116 -12.652 53.760 1.00 23.63 | | | C |
| ATOM | 142 | CZ PHE A 54 | -15.702 -13.884 54.034 1.00 24.34 | | | C |
| ATOM | 143 | N GLN A 55 | -12.461 -10.682 59.527 1.00 21.78 | | | N |
| ATOM | 144 | CA GLN A 55 | -12.076 -9.814 60.622 1.00 22.32 | | | C |
| ATOM | 145 | C GLN A 55 | -10.579 -9.792 60.881 1.00 20.60 | | | C |
| ATOM | 146 | O GLN A 55 | -10.023 -8.786 61.313 1.00 19.51 | | | O |
| ATOM | 147 | CB GLN A 55 | -12.821 -10.215 61.913 1.00 25.16 | | | C |
| ATOM | 148 | CG GLN A 55 | -14.342 -9.942 61.871 1.00 28.79 | | | C |
| ATOM | 149 | CD GLN A 55 | -15.119 -11.002 61.093 1.00 31.13 | | | C |
| ATOM | 150 | OE1 GLN A 55 | -16.228 -10.750 60.600 1.00 31.89 | | | O |
| ATOM | 151 | NE2 GLN A 55 | -14.546 -12.193 60.993 1.00 30.90 | | | N |
| ATOM | 152 | N PHE A 56 | -9.918 -10.902 60.581 1.00 19.44 | | | N |
| ATOM | 153 | CA PHE A 56 | -8.491 -10.997 60.820 1.00 17.34 | | | C |
| ATOM | 154 | C PHE A 56 | -7.653 -10.372 59.721 1.00 17.95 | | | C |
| ATOM | 155 | O PHE A 56 | -6.437 -10.332 59.828 1.00 16.43 | | | O |
| ATOM | 156 | CB PHE A 56 | -8.103 -12.459 60.984 1.00 17.88 | | | C |
| ATOM | 157 | CG PHE A 56 | -6.681 -12.673 61.412 1.00 18.04 | | | C |
| ATOM | 158 | CD1 PHE A 56 | -6.242 -12.256 62.662 1.00 18.72 | | | C |
| ATOM | 159 | CD2 PHE A 56 | -5.785 -13.321 60.569 1.00 17.81 | | | C |
| ATOM | 160 | CE1 PHE A 56 | -4.935 -12.484 63.075 1.00 19.14 | | | C |
| ATOM | 161 | CE2 PHE A 56 | -4.474 -13.557 60.971 1.00 18.70 | | | C |
| ATOM | 162 | CZ PHE A 56 | -4.052 -13.138 62.229 1.00 18.69 | | | C |
| ATOM | 163 | N ARG A 57 | -8.291 -9.863 58.667 1.00 19.86 | | | N |
| ATOM | 164 | CA ARG A 57 | -7.539 -9.291 57.553 1.00 19.81 | | | C |
| ATOM | 165 | C ARG A 57 | -6.789 -8.007 57.817 1.00 20.16 | | | C |
| ATOM | 166 | O ARG A 57 | -7.309 -7.082 58.467 1.00 19.37 | | | O |
| ATOM | 167 | CB ARG A 57 | -8.448 -9.062 56.358 1.00 20.23 | | | C |
| ATOM | 168 | CG ARG A 57 | -7.708 -8.585 55.121 1.00 20.97 | | | C |
| ATOM | 169 | CD ARG A 57 | -8.483 -8.899 53.849 1.00 21.79 | | | C |
| ATOM | 170 | NE ARG A 57 | -7.750 -8.497 52.656 1.00 26.71 | | | N |
| ATOM | 171 | CZ ARG A 57 | -7.982 -7.378 51.970 1.00 28.62 | | | C |
| ATOM | 172 | NH1 ARG A 57 | -8.940 -6.555 52.352 1.00 29.91 | | | N |
| ATOM | 1599 | CA ASN B 50 | 1.274 -19.261 98.148 1.00 35.55 | | | C |
| ATOM | 1600 | C ASN B 50 | 1.783 -18.268 97.115 1.00 34.57 | | | C |
| ATOM | 1601 | O ASN B 50 | 2.632 -17.425 97.412 1.00 34.74 | | | O |
| ATOM | 1602 | CB ASN B 50 | 2.054 -20.573 98.031 1.00 36.48 | | | C |
| ATOM | 1603 | CG ASN B 50 | 1.685 -21.572 99.111 1.00 37.81 | | | C |
| ATOM | 1604 | OD1 ASN B 50 | 1.836 -21.304 100.305 1.00 38.68 | | | O |
| ATOM | 1605 | ND2 ASN B 50 | 1.193 -22.730 98.695 1.00 38.96 | | | N |
| ATOM | 1606 | N PHE B 51 | 1.258 -18.377 95.901 1.00 32.25 | | | N |
| ATOM | 1607 | CA PHE B 51 | 1.634 -17.496 94.819 1.00 30.10 | | | C |
| ATOM | 1608 | C PHE B 51 | 1.309 -16.045 95.164 1.00 29.79 | | | C |
| ATOM | 1609 | O PHE B 51 | 2.101 -15.146 94.889 1.00 31.28 | | | O |
| ATOM | 1610 | CB PHE B 51 | 0.876 -17.882 93.548 1.00 29.23 | | | C |
| ATOM | 1611 | CG PHE B 51 | 1.063 -16.920 92.415 1.00 26.10 | | | C |
| ATOM | 1612 | CD1 PHE B 51 | 2.274 -16.857 91.737 1.00 26.15 | | | C |
| ATOM | 1613 | CD2 PHE B 51 | 0.042 -16.055 92.043 1.00 26.87 | | | C |
| ATOM | 1614 | CE1 PHE B 51 | 2.471 -15.942 90.698 1.00 25.67 | | | C |
| ATOM | 1615 | CE2 PHE B 51 | 0.229 -15.130 91.005 1.00 26.81 | | | C |
| ATOM | 1616 | CZ PHE B 51 | 1.448 -15.078 90.334 1.00 25.60 | | | C |
| ATOM | 1617 | N PHE B 52 | 0.150 -15.819 95.773 1.00 28.87 | | | N |
| ATOM | 1618 | CA PHE B 52 | -0.267 -14.469 96.135 1.00 29.04 | | | C |
| ATOM | 1619 | C PHE B 52 | 0.308 -14.002 97.460 1.00 30.61 | | | C |
| ATOM | 1620 | O PHE B 52 | 0.124 -12.850 97.865 1.00 31.07 | | | O |
| ATOM | 1621 | CB PHE B 52 | -1.801 -14.369 96.190 1.00 27.06 | | | C |
| ATOM | 1622 | CG PHE B 52 | -2.459 -14.378 94.833 1.00 24.65 | | | C |
| ATOM | 1623 | CD1 PHE B 52 | -3.158 -15.493 94.397 1.00 22.56 | | | C |
| ATOM | 1624 | CD2 PHE B 52 | -2.351 -13.276 93.980 1.00 23.11 | | | C |
| ATOM | 1625 | CE1 PHE B 52 | -3.745 -15.528 93.138 1.00 20.90 | | | C |
| ATOM | 1626 | CE2 PHE B 52 | -2.937 -13.301 92.713 1.00 22.18 | | | C |
| ATOM | 1627 | CZ PHE B 52 | -3.635 -14.432 92.295 1.00 21.66 | | | C |
| ATOM | 1628 | N LYS B 53 | 1.003 -14.902 98.138 1.00 32.05 | | | N |
| ATOM | 1629 | CA LYS B 53 | 1.613 -14.581 99.411 1.00 33.59 | | | C |
| ATOM | 1630 | C LYS B 53 | 3.082 -14.190 99.201 1.00 34.05 | | | C |
| ATOM | 1631 | O LYS B 53 | 3.578 -13.270 99.852 1.00 33.80 | | | O |
| ATOM | 1632 | CB LYS B 53 | 1.510 -15.785 100.354 1.00 35.16 | | | C |
| ATOM | 1633 | CG LYS B 53 | 2.068 -15.563 101.751 1.00 37.21 | | | C |
| ATOM | 1634 | CD LYS B 53 | 1.228 -14.553 102.520 1.00 40.42 | | | C |
| ATOM | 1635 | CE LYS B 53 | 1.651 -14.439 103.985 1.00 40.80 | | | C |
| ATOM | 1636 | NZ LYS B 53 | 0.818 -13.452 104.755 1.00 41.58 | | | N |
| ATOM | 1637 | N PHE B 54 | 3.759 -14.872 98.272 1.00 33.63 | | | N |
| ATOM | 1638 | CA PHE B 54 | 5.175 -14.609 98.004 1.00 33.84 | | | C |
| ATOM | 1639 | C PHE B 54 | 5.435 -13.950 96.655 1.00 32.83 | | | C |
| ATOM | 1640 | O PHE B 54 | 5.823 -12.781 96.580 1.00 34.43 | | | O |
| ATOM | 1641 | CB PHE B 54 | 5.985 -15.908 98.083 1.00 34.77 | | | C |
| ATOM | 1642 | CG PHE B 54 | 5.766 -16.690 99.353 1.00 37.23 | | | C |
| ATOM | 1643 | CD1 PHE B 54 | 5.179 -17.956 99.315 1.00 37.86 | | | C |
| ATOM | 1644 | CD2 PHE B 54 | 6.124 -16.158 100.589 1.00 37.44 | | | C |
| ATOM | 1645 | CE1 PHE B 54 | 4.949 -18.674 100.495 1.00 39.19 | | | C |
| ATOM | 1646 | CE2 PHE B 54 | 5.899 -16.868 101.777 1.00 38.15 | | | C |
| ATOM | 1647 | CZ PHE B 54 | 5.307 -18.128 101.729 1.00 38.53 | | | C |
| ATOM | 1648 | N GLN B 55 | 5.226 -14.608 95.590 1.00 30.82 | | | N |
| ATOM | 1649 | CA GLN B 55 | 5.484 -14.173 94.272 1.00 30.73 | | | C |
| ATOM | 1650 | C GLN B 55 | 4.766 -12.886 93.950 1.00 29.59 | | | C |
| ATOM | 1651 | O GLN B 55 | 5.377 -11.952 93.432 1.00 30.41 | | | O |
| ATOM | 1652 | CB GLN B 55 | 5.147 -15.203 93.203 1.00 32.98 | | | C |
| ATOM | 1653 | CG GLN B 55 | 6.262 -16.211 92.945 1.00 37.44 | | | C |
| ATOM | 1654 | CD GLN B 55 | 6.344 -17.313 93.997 1.00 39.61 | | | C |
| ATOM | 1655 | OE1 GLN B 55 | 7.340 -18.039 94.079 1.00 40.35 | | | O |
| ATOM | 1656 | NE2 GLN B 55 | 5.288 -17.452 94.794 1.00 40.46 | | | N |
| ATOM | 1657 | N PHE B 56 | 3.474 -12.826 94.258 1.00 27.72 | | | N |
| ATOM | 1658 | CA PHE B 56 | 2.664 -11.650 93.944 1.00 26.73 | | | C |
| ATOM | 1659 | C PHE B 56 | 3.033 -10.434 94.797 1.00 27.37 | | | C |
| ATOM | 1660 | O PHE B 56 | 2.701 -9.295 94.461 1.00 27.11 | | | O |
| ATOM | 1661 | CB PHE B 56 | 1.175 -11.992 94.115 1.00 23.65 | | | C |
| ATOM | 1662 | CG PHE B 56 | 0.238 -11.028 93.426 1.00 22.80 | | | C |
| ATOM | 1663 | CD1 PHE B 56 | 0.158 -10.983 92.036 1.00 21.59 | | | C |
| ATOM | 1664 | CD2 PHE B 56 | -0.580 -10.178 94.168 1.00 22.28 | | | C |
| ATOM | 1665 | CE1 PHE B 56 | -0.722 -10.107 91.397 1.00 20.82 | | | C |
| ATOM | 1666 | CE2 PHE B 56 | -1.463 -9.297 93.539 1.00 21.92 | | | C |
| ATOM | 1667 | CZ PHE B 56 | -1.533 -9.263 92.150 1.00 21.01 | | | C |
| ATOM | 1668 | N ARG B 57 | 3.756 -10.689 95.882 1.00 27.57 | | | N |
| ATOM | 1669 | CA ARG B 57 | 4.135 -9.614 96.815 1.00 28.14 | | | C |
| ATOM | 1670 | C ARG B 57 | 5.111 -8.601 96.266 1.00 25.87 | | | C |
| ATOM | 1671 | O ARG B 57 | 5.841 -8.861 95.318 1.00 24.30 | | | O |
| ATOM | 1672 | CB ARG B 57 | 4.731 -10.273 98.075 1.00 31.68 | | | C |
| ATOM | 1673 | CG ARG B 57 | 4.248 -9.645 99.385 1.00 37.55 | | | C |
| ATOM | 1674 | CD ARG B 57 | 2.853 -10.146 99.793 1.00 40.52 | | | C |
| ATOM | 1675 | NE ARG B 57 | 2.504 -9.769 101.161 1.00 43.37 | | | N |
| ATOM | 1676 | CZ ARG B 57 | 1.543 -10.343 101.879 1.00 46.49 | | | C |
| ATOM | 1677 | NH1 ARG B 57 | 0.822 -11.331 101.362 1.00 48.70 | | | N |
| ATOM | 1678 | NH2 ARG B 57 | 1.310 -9.941 103.125 1.00 47.88 | | | N |
| ATOM | 1679 | N ASN B 58 | 5.079 -7.412 96.860 1.00 24.69 | | | N |
| ATOM | 1680 | CA ASN B 58 | 5.970 -6.319 96.500 1.00 23.73 | | | C |
| ATOM | 1681 | C ASN B 58 | 6.692 -5.909 97.787 1.00 24.86 | | | C |
| ATOM | 1682 | O ASN B 58 | 6.048 -5.567 98.777 1.00 24.08 | | | O |
| ATOM | 1683 | CB ASN B 58 | 5.214 -5.097 95.975 1.00 22.38 | | | C |
| ATOM | 1684 | CG ASN B 58 | 4.900 -5.183 94.498 1.00 22.23 | | | C |

FIG. 7 (con't)

| | | | | | |
|---|---|---|---|---|---|
| ATOM | 173 | NH2 ARG A 57 | 7.234 -7.067 50.914 1.00 28.18 | N |
| ATOM | 174 | N ASN A 58 | -5.558 7.945 57.363 1.00 21.19 | N |
| ATOM | 175 | CA ASN A 58 | -4.723 -6.779 57.556 1.00 22.52 | C |
| ATOM | 176 | C ASN A 58 | -4.239 -6.319 56.187 1.00 24.20 | C |
| ATOM | 177 | O ASN A 58 | -3.344 -6.919 55.606 1.00 22.98 | O |
| ATOM | 178 | CB ASN A 58 | -3.532 -7.123 58.437 1.00 20.93 | C |
| ATOM | 179 | CG ASN A 58 | -2.642 -5.925 58.700 1.00 19.59 | C |
| ATOM | 180 | OD1 ASN A 58 | -3.043 -4.980 59.372 1.00 17.63 | O |
| ATOM | 181 | ND2 ASN A 58 | -1.425 -5.959 58.158 1.00 16.30 | N |
| ATOM | 182 | N VAL A 59 | -4.842 -5.240 55.690 1.00 27.67 | N |
| ATOM | 183 | CA VAL A 59 | -4.504 -4.691 54.383 1.00 29.73 | C |
| ATOM | 184 | C VAL A 59 | -3.124 -4.054 54.377 1.00 31.35 | C |
| ATOM | 185 | O VAL A 59 | -2.786 -3.290 55.277 1.00 33.05 | O |
| ATOM | 186 | CB VAL A 59 | -5.545 -3.634 53.953 1.00 28.58 | C |
| ATOM | 187 | CG1 VAL A 59 | -5.318 -3.221 52.501 1.00 27.60 | C |
| ATOM | 188 | CG2 VAL A 59 | -6.948 -4.193 54.143 1.00 29.31 | C |
| ATOM | 189 | N GLU A 60 | -2.339 -4.370 53.348 1.00 33.94 | N |
| ATOM | 190 | CA GLU A 60 | -0.983 -3.844 53.179 1.00 35.88 | C |
| ATOM | 191 | C GLU A 60 | -0.848 -3.086 51.856 1.00 37.65 | C |
| ATOM | 192 | O GLU A 60 | 0.258 -2.886 51.348 1.00 38.68 | O |
| ATOM | 193 | CB GLU A 60 | 0.020 -5.005 53.214 1.00 35.18 | C |
| ATOM | 194 | CG GLU A 60 | 0.181 5.650 54.584 1.00 36.90 | C |
| ATOM | 195 | CD GLU A 60 | 0.980 -4.773 55.518 1.00 36.90 | C |
| ATOM | 196 | OE1 GLU A 60 | 2.100 -4.412 55.106 1.00 37.75 | O |
| ATOM | 197 | OE2 GLU A 60 | 0.511 -4.451 56.635 1.00 35.89 | O |
| ATOM | 198 | N TYR A 61 | -1.973 -2.663 51.293 1.00 39.37 | N |
| ATOM | 199 | CA TYR A 61 | -1.953 -1.941 50.027 1.00 41.81 | C |
| ATOM | 200 | C TYR A 61 | -0.999 -0.753 50.059 1.00 43.72 | C |
| ATOM | 201 | O TYR A 61 | -1.111 0.129 50.910 1.00 43.48 | O |
| ATOM | 202 | CB TYR A 61 | -3.360 -1.474 49.654 1.00 41.53 | C |
| ATOM | 203 | CG TYR A 61 | -4.253 -2.571 49.098 1.00 41.89 | C |
| ATOM | 204 | CD1 TYR A 61 | -5.647 -2.455 49.142 1.00 41.24 | C |
| ATOM | 205 | CD2 TYR A 61 | -3.707 -3.717 48.510 1.00 41.74 | C |
| ATOM | 206 | CE1 TYR A 61 | -6.472 -3.456 48.612 1.00 41.75 | C |
| ATOM | 207 | CE2 TYR A 61 | -4.522 -4.719 47.978 1.00 41.34 | C |
| ATOM | 208 | CZ TYR A 61 | -5.900 -4.584 48.031 1.00 41.37 | C |
| ATOM | 209 | OH TYR A 61 | -6.695 -5.566 47.491 1.00 41.05 | O |
| ATOM | 210 | N SER A 62 | -0.064 -0.752 49.113 1.00 46.36 | N |
| ATOM | 211 | CA SER A 62 | 0.930 0.300 48.978 1.00 48.19 | C |
| ATOM | 212 | C SER A 62 | 0.378 1.729 49.082 1.00 49.20 | C |
| ATOM | 213 | O SER A 62 | 1.119 2.661 49.397 1.00 49.70 | O |
| ATOM | 214 | CB SER A 62 | 1.696 0.119 47.648 1.00 49.01 | C |
| ATOM | 215 | OG SER A 62 | 0.839 -0.197 46.558 1.00 48.98 | O |
| ATOM | 216 | N SER A 63 | -0.919 1.908 48.835 1.00 49.37 | N |
| ATOM | 217 | CA SER A 63 | -1.521 3.236 48.895 1.00 49.02 | C |
| ATOM | 218 | C SER A 63 | -2.820 3.248 49.694 1.00 49.71 | C |
| ATOM | 219 | O SER A 63 | -3.379 2.196 50.011 1.00 49.73 | O |
| ATOM | 220 | CB SER A 63 | -1.795 3.760 47.481 1.00 49.63 | C |
| ATOM | 221 | OG SER A 63 | -2.844 3.037 46.854 1.00 50.54 | O |
| ATOM | 222 | N GLY A 64 | -3.295 4.450 50.016 1.00 49.23 | N |
| ATOM | 223 | CA GLY A 64 | -1.521 4.591 50.769 1.00 48.21 | C |
| ATOM | 224 | C GLY A 64 | -4.366 4.295 52.245 1.00 48.41 | C |
| ATOM | 225 | O GLY A 64 | -3.271 4.004 52.733 1.00 48.61 | O |
| ATOM | 226 | N ARG A 65 | -5.479 4.371 52.965 1.00 47.82 | N |
| ATOM | 227 | CA ARG A 65 | -5.480 4.111 54.393 1.00 47.49 | C |
| ATOM | 228 | C ARG A 65 | -6.564 3.086 54.676 1.00 45.38 | C |
| ATOM | 229 | O ARG A 65 | -7.634 3.441 55.142 1.00 44.85 | O |
| ATOM | 230 | CB ARG A 65 | -5.797 5.395 55.153 1.00 50.26 | C |
| ATOM | 231 | CG ARG A 65 | -5.415 6.655 54.397 1.00 54.10 | C |
| ATOM | 232 | CD ARG A 65 | -5.595 7.920 55.242 1.00 56.61 | C |
| ATOM | 233 | NE ARG A 65 | -6.914 8.021 55.870 1.00 58.58 | N |
| ATOM | 234 | CZ ARG A 65 | -7.194 7.597 57.102 1.00 60.03 | C |
| ATOM | 235 | NH1 ARG A 65 | -6.247 7.015 57.848 1.00 60.37 | N |
| ATOM | 236 | NH2 ARG A 65 | -8.425 7.719 57.590 1.00 59.58 | N |
| ATOM | 237 | N ASN A 66 | -6.273 1.820 54.387 1.00 43.47 | N |
| ATOM | 238 | CA ASN A 66 | -7.229 0.741 54.589 1.00 40.09 | C |
| ATOM | 239 | C ASN A 66 | -7.260 0.287 56.044 1.00 38.08 | C |
| ATOM | 240 | O ASN A 66 | -6.776 0.990 56.937 1.00 38.39 | O |
| ATOM | 241 | CB ASN A 66 | -6.875 -0.442 53.698 1.00 41.22 | C |
| ATOM | 242 | CG ASN A 66 | -6.352 -0.005 52.336 1.00 42.59 | C |
| ATOM | 243 | OD1 ASN A 66 | -5.217 0.467 52.209 1.00 41.35 | O |
| ATOM | 244 | ND2 ASN A 66 | -7.180 -0.155 51.311 1.00 44.16 | N |
| ATOM | 245 | N LYS A 67 | -7.812 -0.901 56.279 1.00 34.15 | N |
| ATOM | 246 | CA LYS A 67 | -7.915 -1.428 57.618 1.00 30.52 | C |
| ATOM | 247 | C LYS A 67 | -6.671 -2.187 58.037 1.00 29.04 | C |
| ATOM | 248 | O LYS A 67 | -5.863 -2.604 57.208 1.00 28.64 | O |
| ATOM | 249 | CB LYS A 67 | -9.129 -2.360 57.756 1.00 30.06 | C |
| ATOM | 250 | CG LYS A 67 | -8.969 -3.694 57.062 1.00 28.54 | C |
| ATOM | 251 | CD LYS A 67 | -10.015 -4.695 57.511 1.00 27.36 | C |
| ATOM | 252 | CE LYS A 67 | -9.788 -5.110 58.953 1.00 29.78 | C |
| ATOM | 253 | NZ LYS A 67 | -10.707 -6.204 59.367 1.00 28.57 | N |
| ATOM | 254 | N THR A 68 | -6.507 -2.357 59.344 1.00 26.40 | N |
| ATOM | 255 | CA THR A 68 | -5.357 -3.065 59.854 1.00 23.50 | C |
| ATOM | 256 | C THR A 68 | -5.749 -3.981 61.004 1.00 20.98 | C |
| ATOM | 257 | O THR A 68 | -6.721 -3.721 61.708 1.00 20.99 | O |
| ATOM | 258 | CB THR A 68 | -4.285 -2.080 60.339 1.00 23.83 | C |
| ATOM | 1685 | OD1 ASN B 58 | 3.965 -5.862 94.089 1.00 20.24 | O |
| ATOM | 1686 | ND2 ASN B 58 | 5.692 -4.484 93.685 1.00 19.40 | N |
| ATOM | 1687 | N VAL B 59 | 8.025 -5.938 97.765 1.00 25.46 | N |
| ATOM | 1688 | CA VAL B 59 | 8.808 -5.586 98.943 1.00 25.97 | C |
| ATOM | 1689 | C VAL B 59 | 10.020 -4.718 98.620 1.00 26.99 | C |
| ATOM | 1690 | O VAL B 59 | 10.746 -4.968 97.656 1.00 26.55 | O |
| ATOM | 1691 | CB VAL B 59 | 9.322 -6.847 99.654 1.00 25.65 | C |
| ATOM | 1692 | CG1 VAL B 59 | 10.098 -6.457 100.887 1.00 26.97 | C |
| ATOM | 1693 | CG2 VAL B 59 | 8.168 -7.760 100.010 1.00 27.12 | C |
| ATOM | 1694 | N GLU B 60 | 10.245 -3.706 99.441 1.00 27.82 | N |
| ATOM | 1695 | CA GLU B 60 | 11.388 -2.829 99.247 1.00 29.19 | C |
| ATOM | 1696 | C GLU B 60 | 12.450 -3.149 100.300 1.00 28.80 | C |
| ATOM | 1697 | O GLU B 60 | 12.357 -2.674 101.431 1.00 28.69 | O |
| ATOM | 1698 | CB GLU B 60 | 10.956 -1.377 99.375 1.00 30.04 | C |
| ATOM | 1699 | CG GLU B 60 | 12.096 -0.400 99.244 1.00 33.08 | C |
| ATOM | 1700 | CD GLU B 60 | 11.666 1.026 99.505 1.00 35.77 | C |
| ATOM | 1701 | OE1 GLU B 60 | 10.703 1.487 98.861 1.00 37.27 | O |
| ATOM | 1702 | OE2 GLU B 60 | 12.291 1.691 100.357 1.00 37.28 | O |
| ATOM | 1703 | N TYR B 61 | 13.445 -3.955 99.925 1.00 27.51 | N |
| ATOM | 1704 | CA TYR B 61 | 14.523 -4.321 100.845 1.00 26.91 | C |
| ATOM | 1705 | C TYR B 61 | 15.384 -3.093 101.157 1.00 27.18 | C |
| ATOM | 1706 | O TYR B 61 | 15.601 -2.770 102.317 1.00 24.54 | O |
| ATOM | 1707 | CB TYR B 61 | 15.409 -5.424 100.241 1.00 25.34 | C |
| ATOM | 1708 | CG TYR B 61 | 14.644 -6.599 99.686 1.00 23.96 | C |
| ATOM | 1709 | CD1 TYR B 61 | 14.470 -6.753 98.310 1.00 23.62 | C |
| ATOM | 1710 | CD2 TYR B 61 | 14.059 7.540 100.532 1.00 23.24 | C |
| ATOM | 1711 | CE1 TYR B 61 | 13.737 -7.814 97.791 1.00 22.83 | C |
| ATOM | 1712 | CE2 TYR B 61 | 13.321 -8.601 100.024 1.00 23.69 | C |
| ATOM | 1713 | CZ TYR B 61 | 13.167 -8.734 98.658 1.00 23.37 | C |
| ATOM | 1714 | OH TYR B 61 | 12.452 -9.808 98.175 1.00 23.82 | O |
| ATOM | 1715 | N SER B 62 | 15.854 -2.419 100.105 1.00 29.35 | N |
| ATOM | 1716 | CA SER B 62 | 16.691 -1.227 100.240 1.00 31.06 | C |
| ATOM | 1717 | C SER B 62 | 16.212 -0.133 99.296 1.00 31.66 | C |
| ATOM | 1718 | O SER B 62 | 15.354 -0.366 98.454 1.00 31.17 | O |
| ATOM | 1719 | CB SER B 62 | 18.153 -1.550 99.914 1.00 32.00 | C |
| ATOM | 1720 | OG SER B 62 | 18.978 -1.392 101.050 1.00 31.84 | O |
| ATOM | 1721 | N SER B 63 | 16.797 1.055 99.424 1.00 32.00 | N |
| ATOM | 1722 | CA SER B 63 | 16.409 2.187 98.596 1.00 32.39 | C |
| ATOM | 1723 | C SER B 63 | 16.284 1.847 97.102 1.00 31.21 | C |
| ATOM | 1724 | O SER B 63 | 15.239 2.082 96.482 1.00 33.08 | O |
| ATOM | 1725 | CB SER B 63 | 17.391 3.333 98.790 1.00 33.46 | C |
| ATOM | 1726 | OG SER B 63 | 18.667 2.991 98.266 1.00 37.88 | O |
| ATOM | 1727 | N GLY B 64 | 17.333 1.299 96.521 1.00 28.40 | N |
| ATOM | 1728 | CA GLY B 64 | 17.263 0.985 95.109 1.00 26.47 | C |
| ATOM | 1729 | C GLY B 64 | 17.292 -0.498 94.813 1.00 24.74 | C |
| ATOM | 1730 | O GLY B 64 | 17.810 0.917 93.781 1.00 24.90 | O |
| ATOM | 1731 | N ARG B 65 | 16.747 -1.290 95.726 1.00 22.73 | N |
| ATOM | 1732 | CA ARG B 65 | 16.708 -2.730 95.556 1.00 22.68 | C |
| ATOM | 1733 | C ARG B 65 | 15.415 -3.266 96.138 1.00 23.62 | C |
| ATOM | 1734 | O ARG B 65 | 15.298 -3.484 97.347 1.00 22.28 | O |
| ATOM | 1735 | CB ARG B 65 | 17.905 -3.395 96.252 1.00 22.67 | C |
| ATOM | 1736 | CG ARG B 65 | 17.930 -4.927 96.171 1.00 21.91 | C |
| ATOM | 1737 | CD ARG B 65 | 19.177 -5.516 96.852 1.00 19.71 | C |
| ATOM | 1738 | NE ARG B 65 | 19.125 -5.420 98.303 1.00 21.30 | N |
| ATOM | 1739 | CZ ARG B 65 | 18.501 -6.289 99.095 1.00 22.37 | C |
| ATOM | 1740 | NH1 ARG B 65 | 17.872 -7.338 98.580 1.00 23.22 | N |
| ATOM | 1741 | NH2 ARG B 65 | 18.491 -6.101 100.409 1.00 23.11 | N |
| ATOM | 1742 | N ASN B 66 | 14.434 -3.473 95.282 1.00 23.50 | N |
| ATOM | 1743 | CA ASN B 66 | 13.170 -3.978 95.780 1.00 24.38 | C |
| ATOM | 1744 | C ASN B 66 | 12.524 -4.973 94.840 1.00 22.48 | C |
| ATOM | 1745 | O ASN B 66 | 12.683 -4.876 93.632 1.00 23.32 | O |
| ATOM | 1746 | CB ASN B 66 | 12.225 -2.808 96.057 1.00 25.89 | C |
| ATOM | 1747 | CG ASN B 66 | 12.275 -1.763 94.983 1.00 25.63 | C |
| ATOM | 1748 | OD1 ASN B 66 | 13.293 -1.102 94.782 1.00 27.35 | O |
| ATOM | 1749 | ND2 ASN B 66 | 11.170 -1.595 94.284 1.00 29.96 | N |
| ATOM | 1750 | N LYS B 67 | 11.817 5.939 95.419 1.00 22.30 | N |
| ATOM | 1751 | CA LYS B 67 | 11.117 -6.974 94.666 1.00 21.90 | C |
| ATOM | 1752 | C LYS B 67 | 9.845 -6.372 94.096 1.00 22.07 | C |
| ATOM | 1753 | O LYS B 67 | 8.972 -5.947 94.852 1.00 22.80 | O |
| ATOM | 1754 | CB LYS B 67 | 10.730 -8.129 95.586 1.00 21.10 | C |
| ATOM | 1755 | CG LYS B 67 | 10.081 -9.302 94.875 1.00 21.44 | C |
| ATOM | 1756 | CD LYS B 67 | 8.796 -9.734 95.563 1.00 20.82 | C |
| ATOM | 1757 | CE LYS B 67 | 8.316 -11.064 95.016 1.00 23.26 | C |
| ATOM | 1758 | NZ LYS B 67 | 9.352 -12.091 95.303 1.00 23.48 | N |
| ATOM | 1759 | N THR B 68 | 9.741 -6.352 92.775 1.00 21.38 | N |
| ATOM | 1760 | CA THR B 68 | 8.581 -5.792 92.092 1.00 21.28 | C |
| ATOM | 1761 | C THR B 68 | 7.728 -6.843 91.413 1.00 19.26 | C |
| ATOM | 1762 | O THR B 68 | 8.221 -7.894 91.008 1.00 18.73 | O |
| ATOM | 1763 | CB THR B 68 | 9.043 -4.750 91.044 1.00 23.67 | C |
| ATOM | 1764 | OG1 THR B 68 | 8.885 -3.436 91.599 1.00 27.35 | O |
| ATOM | 1765 | CG2 THR B 68 | 8.248 -4.851 89.756 1.00 25.25 | C |
| ATOM | 1766 | N PHE B 69 | 6.433 -6.563 91.313 1.00 19.46 | N |
| ATOM | 1767 | CA PHE B 69 | 5.505 -7.474 90.645 1.00 18.31 | C |
| ATOM | 1768 | C PHE B 69 | 4.191 -6.736 90.357 1.00 16.79 | C |
| ATOM | 1769 | O PHE B 69 | 3.571 -6.205 91.260 1.00 16.15 | O |
| ATOM | 1770 | CB PHE B 69 | 5.241 -8.716 91.493 1.00 17.28 | C |

FIG. 7 (con't)

```
ATOM    259  OG1 THR A  68      -4.820  -1.286  61.394  1.00 26.02        O
ATOM    260  CG2 THR A  68      -3.862  -1.161  59.216  1.00 24.72        C
ATOM    261  N   PHE A  69      -5.000  -5.061  61.187  1.00 18.62        N
ATOM    262  CA  PHE A  69      -5.275  -6.001  62.274  1.00 16.84        C
ATOM    263  C   PHE A  69      -3.961  -6.696  62.627  1.00 16.13        C
ATOM    264  O   PHE A  69      -3.172  -6.995  61.741  1.00 14.51        O
ATOM    265  CB  PHE A  69      -6.306  -7.042  61.838  1.00 14.21        C
ATOM    266  CG  PHE A  69      -6.970  -7.756  62.983  1.00 12.89        C
ATOM    267  CD1 PHE A  69      -8.220  -7.362  63.434  1.00 11.28        C
ATOM    268  CD2 PHE A  69      -6.324  -8.819  63.619  1.00 13.47        C
ATOM    269  CE1 PHE A  69      -8.833  -8.002  64.493  1.00 10.96        C
ATOM    270  CE2 PHE A  69      -6.930  -9.473  64.685  1.00 12.99        C
ATOM    271  CZ  PHE A  69      -8.185  -9.065  65.119  1.00 13.34        C
ATOM    272  N   LEU A  70      -3.727  -6.950  63.916  1.00 15.36        N
ATOM    273  CA  LEU A  70      -2.485  -7.604  64.327  1.00 14.51        C
ATOM    274  C   LEU A  70      -2.484  -8.078  65.768  1.00 14.76        C
ATOM    275  O   LEU A  70      -2.736  -7.301  66.686  1.00 15.16        O
ATOM    276  CB  LEU A  70      -1.306  -6.665  64.115  1.00 12.51        C
ATOM    277  CG  LEU A  70       0.095  -7.134  64.525  1.00 12.29        C
ATOM    278  CD1 LEU A  70       1.121  -6.381  63.741  1.00 11.90        C
ATOM    279  CD2 LEU A  70       0.318  -6.871  65.970  1.00 12.92        C
ATOM    280  N   CYS A  71      -2.185  -9.360  65.968  1.00 14.57        N
ATOM    281  CA  CYS A  71      -2.082  -9.923  67.313  1.00 13.24        C
ATOM    282  C   CYS A  71      -0.621 -10.058  67.600  1.00 14.34        C
ATOM    283  O   CYS A  71       0.164 -10.323  66.688  1.00 14.18        O
ATOM    284  CB  CYS A  71      -2.659 -11.317  67.371  1.00 13.28        C
ATOM    285  SG  CYS A  71      -4.380 -11.421  66.933  1.00 11.98        S
ATOM    286  N   TYR A  72      -0.240  -9.942  68.870  1.00 15.75        N
ATOM    287  CA  TYR A  72       1.184 -10.060  69.234  1.00 13.62        C
ATOM    288  C   TYR A  72       1.445 -10.705  70.581  1.00 13.66        C
ATOM    289  O   TYR A  72       0.538 -10.934  71.401  1.00 13.43        O
ATOM    290  CB  TYR A  72       1.846  -8.682  69.181  1.00 11.98        C
ATOM    291  CG  TYR A  72       1.307  -7.690  70.187  1.00 14.01        C
ATOM    292  CD1 TYR A  72       1.694  -7.746  71.532  1.00 14.85        C
ATOM    293  CD2 TYR A  72       0.370  -6.725  69.817  1.00 14.44        C
ATOM    294  CE1 TYR A  72       1.164  -6.874  72.470  1.00 15.52        C
ATOM    295  CE2 TYR A  72      -0.172  -5.849  70.750  1.00 15.43        C
ATOM    296  CZ  TYR A  72       0.233  -5.931  72.077  1.00 16.16        C
ATOM    297  OH  TYR A  72      -0.287  -5.083  73.027  1.00 18.77        O
ATOM    298  N   VAL A  73       2.713 -10.997  70.810  1.00 13.41        N
ATOM    299  CA  VAL A  73       3.168 -11.590  72.065  1.00 14.19        C
ATOM    300  C   VAL A  73       4.544 -11.042  72.374  1.00 13.66        C
ATOM    301  O   VAL A  73       5.429 -11.079  71.526  1.00 14.27        O
ATOM    302  CB  VAL A  73       3.259 -13.136  71.973  1.00 13.10        C
ATOM    303  CG1 VAL A  73       3.946 -13.688  73.209  1.00 11.85        C
ATOM    304  CG2 VAL A  73       1.883 -13.732  71.898  1.00 13.20        C
ATOM    305  N   VAL A  74       4.723 -10.528  73.584  1.00 15.31        N
ATOM    306  CA  VAL A  74       6.021  -9.994  73.988  1.00 16.34        C
ATOM    307  C   VAL A  74       6.554 -10.683  75.239  1.00 17.68        C
ATOM    308  O   VAL A  74       5.816 -10.899  76.200  1.00 18.39        O
ATOM    309  CB  VAL A  74       5.935  -8.489  74.240  1.00 14.55        C
ATOM    310  CG1 VAL A  74       7.279  -7.959  74.708  1.00 13.50        C
ATOM    311  CG2 VAL A  74       5.510  -7.792  72.977  1.00 13.44        C
ATOM    312  N   GLU A  75       7.829 -11.029  75.214  1.00 20.54        N
ATOM    313  CA  GLU A  75       8.476 -11.676  76.350  1.00 24.00        C
ATOM    314  C   GLU A  75       9.895 -11.151  76.484  1.00 25.05        C
ATOM    315  O   GLU A  75      10.723 -11.363  75.601  1.00 24.19        O
ATOM    316  CB  GLU A  75       8.499 -13.187  76.153  1.00 26.10        C
ATOM    317  CG  GLU A  75       7.120 -13.784  76.018  1.00 31.35        C
ATOM    318  CD  GLU A  75       7.135 -15.291  76.085  1.00 35.63        C
ATOM    319  OE1 GLU A  75       7.964 -15.912  75.374  1.00 37.54        O
ATOM    320  OE2 GLU A  75       6.321 -15.866  76.842  1.00 38.67        O
ATOM    321  N   ALA A  76      10.173 -10.459  77.585  1.00 26.87        N
ATOM    322  CA  ALA A  76      11.496  -9.891  77.825  1.00 28.77        C
ATOM    323  C   ALA A  76      12.165 -10.557  79.019  1.00 30.78        C
ATOM    324  O   ALA A  76      11.543 -10.751  80.061  1.00 31.11        O
ATOM    325  CB  ALA A  76      11.374  -8.406  78.053  1.00 27.76        C
ATOM    326  N   GLN A  77      13.434 -10.908  78.853  1.00 34.96        N
ATOM    327  CA  GLN A  77      14.225 -11.564  79.899  1.00 38.74        C
ATOM    328  C   GLN A  77      15.412 -10.672  80.259  1.00 39.88        C
ATOM    329  O   GLN A  77      16.013 -10.051  79.385  1.00 40.01        O
ATOM    330  CB  GLN A  77      14.725 -12.927  79.386  1.00 41.39        C
ATOM    331  CG  GLN A  77      16.074 -13.383  79.973  1.00 46.84        C
ATOM    332  CD  GLN A  77      16.960 -14.119  78.958  1.00 49.73        C
ATOM    333  OE1 GLN A  77      18.133 -14.416  79.228  1.00 51.56        O
ATOM    334  NE2 GLN A  77      16.400 -14.416  77.789  1.00 50.92        N
ATOM    335  N   GLY A  78      15.741 -10.606  81.544  1.00 40.74        N
ATOM    336  CA  GLY A  78      16.865  -9.797  81.981  1.00 41.57        C
ATOM    337  C   GLY A  78      17.694 -10.533  83.015  1.00 43.22        C
ATOM    338  O   GLY A  78      17.158 -11.072  83.987  1.00 43.14        O
ATOM    339  N   LYS A  79      19.003 -10.562  82.802  1.00 44.77        N
ATOM    340  CA  LYS A  79      19.907 -11.246  83.718  1.00 46.43        C
ATOM    341  C   LYS A  79      19.885 -10.529  85.066  1.00 46.17        C
ATOM    342  O   LYS A  79      20.693  -9.638  85.306  1.00 47.25        O
ATOM    343  CB  LYS A  79      21.334 -11.261  83.145  1.00 47.07        C
ATOM    344  CG  LYS A  79      22.268 -12.307  83.763  1.00 48.81        C
ATOM   1771  CG  PHE B  69       4.606  -9.849  90.723  1.00 17.46        C
ATOM   1772  CD1 PHE B  69       5.388 -10.852  90.146  1.00 19.90        C
ATOM   1773  CD2 PHE B  69       3.231  -9.883  90.527  1.00 18.31        C
ATOM   1774  CE1 PHE B  69       4.805 -11.879  89.369  1.00 22.06        C
ATOM   1775  CE2 PHE B  69       2.634 -10.898  89.757  1.00 21.88        C
ATOM   1776  CZ  PHE B  69       3.427 -11.897  89.175  1.00 22.21        C
ATOM   1777  N   LEU B  70       3.767  -6.718  89.088  1.00 16.55        N
ATOM   1778  CA  LEU B  70       2.538  -6.036  88.733  1.00 15.10        C
ATOM   1779  C   LEU B  70       1.833  -6.652  87.532  1.00 16.49        C
ATOM   1780  O   LEU B  70       2.472  -6.932  86.508  1.00 15.21        O
ATOM   1781  CB  LEU B  70       2.831  -4.563  88.451  1.00 15.47        C
ATOM   1782  CG  LEU B  70       1.660  -3.602  88.247  1.00 17.39        C
ATOM   1783  CD1 LEU B  70       2.093  -2.184  88.562  1.00 19.71        C
ATOM   1784  CD2 LEU B  70       1.181  -3.688  86.818  1.00 16.56        C
ATOM   1785  N   CYS B  71       0.521  -6.886  87.661  1.00 16.69        N
ATOM   1786  CA  CYS B  71      -0.301  -7.417  86.567  1.00 17.53        C
ATOM   1787  C   CYS B  71      -1.159  -6.278  85.981  1.00 18.34        C
ATOM   1788  O   CYS B  71      -1.671  -5.415  86.704  1.00 18.50        O
ATOM   1789  CB  CYS B  71      -1.224  -8.543  87.047  1.00 18.69        C
ATOM   1790  SG  CYS B  71      -0.411 -10.128  87.416  1.00 20.26        S
ATOM   1791  N   TYR B  72      -1.350  -6.283  84.671  1.00 18.23        N
ATOM   1792  CA  TYR B  72      -2.113  -5.213  84.073  1.00 18.50        C
ATOM   1793  C   TYR B  72      -2.944  -5.650  82.883  1.00 19.73        C
ATOM   1794  O   TYR B  72      -2.817  -6.772  82.388  1.00 20.04        O
ATOM   1795  CB  TYR B  72      -1.176  -4.073  83.665  1.00 15.86        C
ATOM   1796  CG  TYR B  72      -0.206  -4.440  82.567  1.00 15.74        C
ATOM   1797  CD1 TYR B  72      -0.592  -4.407  81.223  1.00 17.04        C
ATOM   1798  CD2 TYR B  72       1.086  -4.850  82.861  1.00 12.50        C
ATOM   1799  CE1 TYR B  72       0.298  -4.776  80.212  1.00 15.53        C
ATOM   1800  CE2 TYR B  72       1.969  -5.216  81.866  1.00 12.74        C
ATOM   1801  CZ  TYR B  72       1.573  -5.174  80.547  1.00 13.77        C
ATOM   1802  OH  TYR B  72       2.490  -5.498  79.572  1.00 16.57        O
ATOM   1803  N   VAL B  73      -3.798  -4.739  82.432  1.00 19.50        N
ATOM   1804  CA  VAL B  73      -4.666  -4.967  81.300  1.00 19.35        C
ATOM   1805  C   VAL B  73      -4.850  -3.616  80.628  1.00 20.74        C
ATOM   1806  O   VAL B  73      -5.144  -2.627  81.294  1.00 20.41        O
ATOM   1807  CB  VAL B  73      -6.056  -5.510  81.731  1.00 19.58        C
ATOM   1808  CG1 VAL B  73      -7.004  -5.562  80.545  1.00 17.68        C
ATOM   1809  CG2 VAL B  73      -5.919  -6.906  82.305  1.00 19.65        C
ATOM   1810  N   VAL B  74      -4.657  -3.578  79.310  1.00 21.21        N
ATOM   1811  CA  VAL B  74      -4.824  -2.352  78.542  1.00 22.37        C
ATOM   1812  C   VAL B  74      -5.949  -2.488  77.491  1.00 24.19        C
ATOM   1813  O   VAL B  74      -6.021  -3.481  76.770  1.00 24.68        O
ATOM   1814  CB  VAL B  74      -3.515  -1.963  77.827  1.00 21.61        C
ATOM   1815  CG1 VAL B  74      -3.688  -0.666  77.105  1.00 20.37        C
ATOM   1816  CG2 VAL B  74      -2.399  -1.820  78.823  1.00 20.61        C
ATOM   1817  N   GLU B  75      -6.823  -1.483  77.428  1.00 26.60        N
ATOM   1818  CA  GLU B  75      -7.941  -1.449  76.477  1.00 29.66        C
ATOM   1819  C   GLU B  75      -7.975  -0.038  75.876  1.00 30.33        C
ATOM   1820  O   GLU B  75      -8.263   0.917  76.586  1.00 32.01        O
ATOM   1821  CB  GLU B  75      -9.260  -1.722  77.185  1.00 30.43        C
ATOM   1822  CG  GLU B  75      -9.271  -2.982  78.045  1.00 35.94        C
ATOM   1823  CD  GLU B  75      -9.778  -4.207  77.313  1.00 39.42        C
ATOM   1824  OE1 GLU B  75     -10.808  -4.085  76.601  1.00 43.71        O
ATOM   1825  OE2 GLU B  75      -9.177  -5.298  77.444  1.00 39.81        O
ATOM   1826  N   ALA B  76      -7.698   0.091  74.583  1.00 30.93        N
ATOM   1827  CA  ALA B  76      -7.680   1.392  73.946  1.00 33.80        C
ATOM   1828  C   ALA B  76      -8.639   1.461  72.771  1.00 36.71        C
ATOM   1829  O   ALA B  76      -8.558   0.654  71.844  1.00 37.57        O
ATOM   1830  CB  ALA B  76      -6.266   1.745  73.481  1.00 33.29        C
ATOM   1831  N   GLN B  77      -9.548   2.428  72.816  1.00 39.33        N
ATOM   1832  CA  GLN B  77     -10.516   2.628  71.762  1.00 41.16        C
ATOM   1833  C   GLN B  77     -10.319   4.010  71.166  1.00 42.83        C
ATOM   1834  O   GLN B  77     -10.333   5.015  71.875  1.00 41.75        O
ATOM   1835  CB  GLN B  77     -11.925   2.478  72.316  1.00 42.02        C
ATOM   1836  CG  GLN B  77     -12.197   1.082  72.832  1.00 45.11        C
ATOM   1837  CD  GLN B  77     -13.652   0.683  72.699  1.00 47.38        C
ATOM   1838  OE1 GLN B  77     -14.497   1.104  73.491  1.00 49.70        O
ATOM   1839  NE2 GLN B  77     -13.959  -0.123  71.681  1.00 46.60        N
ATOM   1840  N   GLY B  78     -10.133   4.051  69.851  1.00 45.23        N
ATOM   1841  CA  GLY B  78      -9.908   5.313  69.178  1.00 47.78        C
ATOM   1842  C   GLY B  78     -10.999   5.738  68.221  1.00 49.77        C
ATOM   1843  O   GLY B  78     -10.715   6.192  67.110  1.00 51.48        O
ATOM   1844  N   LYS B  79     -12.246   5.582  68.640  1.00 50.31        N
ATOM   1845  CA  LYS B  79     -13.388   5.987  67.829  1.00 50.85        C
ATOM   1846  C   LYS B  79     -13.117   6.011  66.320  1.00 49.98        C
ATOM   1847  O   LYS B  79     -12.771   7.050  65.754  1.00 49.90        O
ATOM   1848  CB  LYS B  79     -13.867   7.382  68.279  1.00 52.65        C
ATOM   1849  CG  LYS B  79     -13.036   8.044  69.399  1.00 53.98        C
ATOM   1850  CD  LYS B  79     -13.355   7.452  70.773  1.00 54.06        C
ATOM   1851  CE  LYS B  79     -12.190   7.595  71.752  1.00 54.11        C
ATOM   1852  NZ  LYS B  79     -11.762   9.005  71.973  1.00 53.73        N
ATOM   1853  N   GLY B  80     -13.277   4.868  65.666  1.00 49.05        N
ATOM   1854  CA  GLY B  80     -13.056   4.812  64.231  1.00 45.78        C
ATOM   1855  C   GLY B  80     -12.654   3.417  63.804  1.00 44.57        C
ATOM   1856  O   GLY B  80     -11.958   3.248  62.808  1.00 43.84        O
```

FIG. 7 (con't)

```
ATOM  345  CD  LYS A  79   23.073 -13.019 82.677 1.00 51.68   C
ATOM  346  CE  LYS A  79   23.911 -14.171 83.226 1.00 52.59   C
ATOM  347  NZ  LYS A  79   24.647 -14.889 82.136 1.00 52.97   N
ATOM  348  N   GLY A  80   18.946 -10.916 85.929 1.00 45.59   N
ATOM  349  CA  GLY A  80   18.833 -10.307 87.244 1.00 44.46   C
ATOM  350  C   GLY A  80   17.492 -10.592 87.901 1.00 44.04   C
ATOM  351  O   GLY A  80   17.178 -10.068 88.976 1.00 43.95   O
ATOM  352  N   GLY A  81   16.698 -11.435 87.243 1.00 42.18   N
ATOM  353  CA  GLY A  81   15.386 -11.780 87.753 1.00 39.56   C
ATOM  354  C   GLY A  81   14.273 -10.915 87.178 1.00 37.50   C
ATOM  355  O   GLY A  81   13.125 -11.016 87.607 1.00 36.38   O
ATOM  356  N   GLN A  82   14.614 -10.058 86.216 1.00 36.01   N
ATOM  357  CA  GLN A  82   13.637  -9.176 85.576 1.00 34.06   C
ATOM  358  C   GLN A  82   12.914  -9.936 84.459 1.00 31.83   C
ATOM  359  O   GLN A  82   13.543 -10.467 83.543 1.00 30.92   O
ATOM  360  CB  GLN A  82   14.347  -7.954 84.988 1.00 34.17   C
ATOM  361  CG  GLN A  82   15.445  -7.422 85.880 1.00 37.64   C
ATOM  362  CD  GLN A  82   16.589  -6.827 85.093 1.00 37.58   C
ATOM  363  OE1 GLN A  82   16.474  -5.742 84.533 1.00 36.42   O
ATOM  364  NE2 GLN A  82   17.710  -7.552 85.044 1.00 38.46   N
ATOM  365  N   VAL A  83   11.594 -10.010 84.542 1.00 29.61   N
ATOM  366  CA  VAL A  83   10.839 -10.710 83.514 1.00 28.42   C
ATOM  367  C   VAL A  83    9.544  -9.992 83.170 1.00 27.22   C
ATOM  368  O   VAL A  83    8.797  -9.590 84.056 1.00 27.49   O
ATOM  369  CB  VAL A  83   10.500 -12.148 83.959 1.00 28.55   C
ATOM  370  CG1 VAL A  83    9.763 -12.873 82.842 1.00 26.97   C
ATOM  371  CG2 VAL A  83   11.771 -12.891 84.340 1.00 26.81   C
ATOM  372  N   GLN A  84    9.289  -9.819 81.879 1.00 26.91   N
ATOM  373  CA  GLN A  84    8.056  -9.176 81.425 1.00 26.48   C
ATOM  374  C   GLN A  84    7.473  -9.964 80.266 1.00 26.36   C
ATOM  375  O   GLN A  84    8.163 -10.194 79.284 1.00 27.52   O
ATOM  376  CB  GLN A  84    8.332  -7.763 80.960 1.00 25.82   C
ATOM  377  CG  GLN A  84    9.002  -6.933 81.994 1.00 27.92   C
ATOM  378  CD  GLN A  84    9.488  -5.648 81.414 1.00 28.14   C
ATOM  379  OE1 GLN A  84    8.984  -5.198 80.385 1.00 29.64   O
ATOM  380  NE2 GLN A  84   10.470  -5.040 82.060 1.00 29.61   N
ATOM  381  N   ALA A  85    6.211 -10.383 80.372 1.00 26.56   N
ATOM  382  CA  ALA A  85    5.563 -11.124 79.289 1.00 25.59   C
ATOM  383  C   ALA A  85    4.106 -10.680 79.131 1.00 25.48   C
ATOM  384  O   ALA A  85    3.255 -11.027 79.942 1.00 26.61   O
ATOM  385  CB  ALA A  85    5.619 -12.622 79.554 1.00 24.51   C
ATOM  386  N   SER A  86    3.822  -9.912 78.091 1.00 24.49   N
ATOM  387  CA  SER A  86    2.463  -9.453 77.881 1.00 23.75   C
ATOM  388  C   SER A  86    1.939 -10.044 76.588 1.00 23.67   C
ATOM  389  O   SER A  86    2.695 -10.656 75.838 1.00 25.50   O
ATOM  390  CB  SER A  86    2.431  -7.933 77.785 1.00 23.36   C
ATOM  391  OG  SER A  86    3.031  -7.527 76.577 1.00 21.66   O
ATOM  392  N   ARG A  87    0.652  -9.856 76.325 1.00 22.22   N
ATOM  393  CA  ARG A  87    0.046 -10.385 75.113 1.00 20.45   C
ATOM  394  C   ARG A  87   -1.204  -9.597 74.767 1.00 18.82   C
ATOM  395  O   ARG A  87   -1.997  -9.256 75.645 1.00 18.95   O
ATOM  396  CB  ARG A  87   -0.308 -11.861 75.336 1.00 22.14   C
ATOM  397  CG  ARG A  87   -0.837 -12.553 74.110 1.00 23.90   C
ATOM  398  CD  ARG A  87   -0.979 -14.024 74.392 1.00 27.83   C
ATOM  399  NE  ARG A  87   -2.177 -14.318 75.165 1.00 29.95   N
ATOM  400  CZ  ARG A  87   -2.262 -15.290 76.062 1.00 31.20   C
ATOM  401  NH1 ARG A  87   -1.204 -16.064 76.311 1.00 31.83   N
ATOM  402  NH2 ARG A  87   -3.403 -15.490 76.702 1.00 30.33   N
ATOM  403  N   GLY A  88   -1.384  -9.295 73.496 1.00 17.26   N
ATOM  404  CA  GLY A  88   -2.550  -8.535 73.107 1.00 15.71   C
ATOM  405  C   GLY A  88   -2.742  -8.447 71.609 1.00 16.65   C
ATOM  406  O   GLY A  88   -2.199  -9.258 70.863 1.00 15.58   O
ATOM  407  N   TYR A  89   -3.500  -7.446 71.161 1.00 16.10   N
ATOM  408  CA  TYR A  89   -3.769  -7.281 69.747 1.00 15.92   C
ATOM  409  C   TYR A  89   -4.153  -5.840 69.420 1.00 15.73   C
ATOM  410  O   TYR A  89   -4.422  -5.046 70.317 1.00 15.36   O
ATOM  411  CB  TYR A  89   -4.896  -8.218 69.325 1.00 15.20   C
ATOM  412  CG  TYR A  89   -6.246  -7.564 69.254 1.00 14.21   C
ATOM  413  CD1 TYR A  89   -6.793  -7.197 68.032 1.00 14.43   C
ATOM  414  CD2 TYR A  89   -6.991  -7.339 70.407 1.00 14.75   C
ATOM  415  CE1 TYR A  89   -8.048  -6.633 67.956 1.00 15.39   C
ATOM  416  CE2 TYR A  89   -8.247  -6.776 70.345 1.00 13.17   C
ATOM  417  CZ  TYR A  89   -8.771  -6.431 69.119 1.00 14.99   C
ATOM  418  OH  TYR A  89  -10.032  -5.893 69.054 1.00 14.53   O
ATOM  419  N   LEU A  90   -4.212  -5.531 68.134 1.00 16.33   N
ATOM  420  CA  LEU A  90   -4.512  -4.191 67.689 1.00 19.09   C
ATOM  421  C   LEU A  90   -5.234  -4.225 66.350 1.00 20.18   C
ATOM  422  O   LEU A  90   -4.891  -5.034 65.486 1.00 19.77   O
ATOM  423  CB  LEU A  90   -3.210  -3.420 67.546 1.00 22.45   C
ATOM  424  CG  LEU A  90   -2.651  -2.151 66.724 1.00 26.97   C
ATOM  425  CD1 LEU A  90   -4.163  -1.092 67.399 1.00 28.71   C
ATOM  426  CD2 LEU A  90   -1.811  -1.659 66.549 1.00 27.47   C
ATOM  427  N   GLU A  91   -6.230  -3.360 66.173 1.00 20.86   N
ATOM  428  CA  GLU A  91   -6.979  -3.300 64.924 1.00 23.59   C
ATOM  429  C   GLU A  91   -7.515  -1.906 64.634 1.00 25.15   C
ATOM  430  O   GLU A  91   -7.628  -1.073 65.533 1.00 26.09   O

ATOM 1857  N   GLY B  81  -13.109  2.419 64.557 1.00 43.43   N
ATOM 1858  CA  GLY B  81  -12.767  1.044 64.257 1.00 41.67   C
ATOM 1859  C   GLY B  81  -11.477  0.587 64.939 1.00 40.48   C
ATOM 1860  O   GLY B  81  -11.248 -0.612 65.102 1.00 40.35   O
ATOM 1861  N   GLN B  82  -10.643  1.545 65.343 1.00 38.32   N
ATOM 1862  CA  GLN B  82   -9.369  1.247 65.988 1.00 37.07   C
ATOM 1863  C   GLN B  82   -9.536  0.827 67.442 1.00 34.54   C
ATOM 1864  O   GLN B  82   -9.903  1.626 68.299 1.00 32.52   O
ATOM 1865  CB  GLN B  82   -8.425  2.440 65.884 1.00 38.26   C
ATOM 1866  CG  GLN B  82   -9.085  3.770 66.137 1.00 42.25   C
ATOM 1867  CD  GLN B  82   -8.311  4.913 65.518 1.00 45.54   C
ATOM 1868  OE1 GLN B  82   -7.092  5.010 65.674 1.00 46.80   O
ATOM 1869  NE2 GLN B  82   -9.018  5.792 64.812 1.00 47.43   N
ATOM 1870  N   VAL B  83   -9.271 -0.453 67.691 1.00 31.57   N
ATOM 1871  CA  VAL B  83   -9.386 -1.036 69.010 1.00 29.10   C
ATOM 1872  C   VAL B  83   -8.035 -1.629 69.423 1.00 27.71   C
ATOM 1873  O   VAL B  83   -7.285 -2.104 68.580 1.00 26.66   O
ATOM 1874  CB  VAL B  83  -10.441 -2.146 69.021 1.00 28.90   C
ATOM 1875  CG1 VAL B  83  -10.574 -2.726 70.407 1.00 28.59   C
ATOM 1876  CG2 VAL B  83  -11.773 -1.597 68.539 1.00 30.37   C
ATOM 1877  N   GLN B  84   -7.730 -1.605 70.718 1.00 26.59   N
ATOM 1878  CA  GLN B  84   -6.462 -2.137 71.198 1.00 24.94   C
ATOM 1879  C   GLN B  84   -6.683 -2.831 72.526 1.00 24.71   C
ATOM 1880  O   GLN B  84   -7.332 -2.278 73.410 1.00 25.50   O
ATOM 1881  CB  GLN B  84   -5.483 -0.997 71.371 1.00 25.06   C
ATOM 1882  CG  GLN B  84   -4.109 -1.289 70.897 1.00 25.16   C
ATOM 1883  CD  GLN B  84   -3.364 -0.019 70.592 1.00 26.22   C
ATOM 1884  OE1 GLN B  84   -3.681  0.686 69.632 1.00 25.01   O
ATOM 1885  NE2 GLN B  84   -2.374  0.296 71.416 1.00 28.41   N
ATOM 1886  N   ALA B  85   -6.151 -4.036 72.689 1.00 23.24   N
ATOM 1887  CA  ALA B  85   -6.335 -4.756 73.950 1.00 22.14   C
ATOM 1888  C   ALA B  85   -5.139 -5.649 74.246 1.00 21.37   C
ATOM 1889  O   ALA B  85   -4.564 -6.239 73.338 1.00 22.65   O
ATOM 1890  CB  ALA B  85   -7.631 -5.583 73.896 1.00 20.69   C
ATOM 1891  N   SER B  86   -4.758 -5.749 75.512 1.00 21.18   N
ATOM 1892  CA  SER B  86   -3.630 -6.595 75.902 1.00 21.56   C
ATOM 1893  C   SER B  86   -3.618 -6.820 77.395 1.00 21.21   C
ATOM 1894  O   SER B  86   -4.322 -6.136 78.134 1.00 21.89   O
ATOM 1895  CB  SER B  86   -2.291 -5.958 75.488 1.00 21.65   C
ATOM 1896  OG  SER B  86   -2.095 -4.675 76.077 1.00 21.09   O
ATOM 1897  N   ARG B  87   -2.822 -7.786 77.835 1.00 22.70   N
ATOM 1898  CA  ARG B  87   -2.679 -8.053 79.264 1.00 24.84   C
ATOM 1899  C   ARG B  87   -1.325 -8.730 79.562 1.00 24.05   C
ATOM 1900  O   ARG B  87   -0.981 -9.742 78.959 1.00 24.65   O
ATOM 1901  CB  ARG B  87   -3.844 -8.908 79.761 1.00 26.91   C
ATOM 1902  CG  ARG B  87   -3.808 -10.333 79.289 1.00 30.39   C
ATOM 1903  CD  ARG B  87   -5.146 -11.015 79.496 1.00 35.17   C
ATOM 1904  NE  ARG B  87   -4.979 -12.451 79.694 1.00 38.13   N
ATOM 1905  CZ  ARG B  87   -5.863 -13.368 79.319 1.00 39.59   C
ATOM 1906  NH1 ARG B  87   -6.984 -13.004 78.714 1.00 40.31   N
ATOM 1907  NH2 ARG B  87   -5.628 -14.657 79.556 1.00 40.28   N
ATOM 1908  N   GLY B  88   -0.550 -8.151 80.473 1.00 22.82   N
ATOM 1909  CA  GLY B  88    0.730 -8.740 80.813 1.00 20.92   C
ATOM 1910  C   GLY B  88    1.085 -8.528 82.273 1.00 20.97   C
ATOM 1911  O   GLY B  88    0.209 -8.293 83.111 1.00 19.06   O
ATOM 1912  N   TYR B  89    2.373 -8.608 82.586 1.00 20.84   N
ATOM 1913  CA  TYR B  89    2.820 -8.397 83.953 1.00 21.58   C
ATOM 1914  C   TYR B  89    4.312 -8.055 83.996 1.00 23.15   C
ATOM 1915  O   TYR B  89    5.009 -8.215 83.004 1.00 19.77   O
ATOM 1916  CB  TYR B  89    2.543 -9.652 84.786 1.00 21.43   C
ATOM 1917  CG  TYR B  89    3.631 -10.680 84.696 1.00 21.53   C
ATOM 1918  CD1 TYR B  89    4.393 -11.007 85.816 1.00 22.29   C
ATOM 1919  CD2 TYR B  89    3.917 -11.315 83.494 1.00 21.95   C
ATOM 1920  CE1 TYR B  89    5.417 -11.945 85.747 1.00 22.65   C
ATOM 1921  CE2 TYR B  89    4.940 -12.257 83.407 1.00 23.15   C
ATOM 1922  CZ  TYR B  89    5.688 -12.571 84.545 1.00 23.51   C
ATOM 1923  OH  TYR B  89    6.683 -13.528 84.504 1.00 22.15   O
ATOM 1924  N   LEU B  90    4.772 -7.583 85.153 1.00 22.66   N
ATOM 1925  CA  LEU B  90    6.165 -7.179 85.362 1.00 23.09   C
ATOM 1926  C   LEU B  90    6.627 -7.794 86.648 1.00 23.32   C
ATOM 1927  O   LEU B  90    5.830 -7.987 87.571 1.00 23.38   O
ATOM 1928  CB  LEU B  90    6.265 -5.655 85.528 1.00 24.70   C
ATOM 1929  CG  LEU B  90    5.642 -4.797 84.436 1.00 28.23   C
ATOM 1930  CD1 LEU B  90    5.962 -3.301 84.666 1.00 27.79   C
ATOM 1931  CD2 LEU B  90    6.174 -5.305 83.074 1.00 29.19   C
ATOM 1932  N   GLU B  91    7.917 -8.083 86.723 1.00 23.69   N
ATOM 1933  CA  GLU B  91    8.488 -8.646 87.927 1.00 23.61   C
ATOM 1934  C   GLU B  91   10.015 -8.494 87.922 1.00 23.57   C
ATOM 1935  O   GLU B  91   10.676 -8.689 86.900 1.00 21.44   O
ATOM 1936  CB  GLU B  91    8.088 -10.112 88.068 1.00 24.92   C
ATOM 1937  CG  GLU B  91    8.812 -11.055 87.143 1.00 26.61   C
ATOM 1938  CD  GLU B  91    8.754 -12.507 87.621 1.00 29.63   C
ATOM 1939  OE1 GLU B  91    9.308 -12.815 88.698 1.00 30.15   O
ATOM 1940  OE2 GLU B  91    8.151 -13.350 86.921 1.00 30.07   O
ATOM 1941  N   ASP B  92   10.554 -8.113 89.073 1.00 23.55   N
ATOM 1942  CA  ASP B  92   11.984 -7.930 89.225 1.00 25.71   C
```

FIG. 7 (con't)

```
ATOM  431  CB  GLU A  91    -8.157  -4.288 64.942 1.00 23.40    C
ATOM  432  CG  GLU A  91    -9.400  -3.797 65.674 1.00 23.71    C
ATOM  433  CD  GLU A  91   -10.604  -4.727 65.504 1.00 25.29    C
ATOM  434  OE1 GLU A  91   -11.062  -4.945 64.365 1.00 25.45    O
ATOM  435  OE2 GLU A  91   -11.112  -5.246 66.520 1.00 27.19    O
ATOM  436  N   ASP A  92    -7.849  -1.651 63.377 1.00 27.65    N
ATOM  437  CA  ASP A  92    -8.386  -0.348 62.979 1.00 31.86    C
ATOM  438  C   ASP A  92    -9.185  -0.509 61.692 1.00 32.85    C
ATOM  439  O   ASP A  92    -8.824  -1.309 60.837 1.00 32.71    O
ATOM  440  CB  ASP A  92    -7.245   0.656 62.733 1.00 34.56    C
ATOM  441  CG  ASP A  92    -7.705   2.120 62.793 1.00 38.54    C
ATOM  442  OD1 ASP A  92    -8.902   2.414 62.523 1.00 39.55    O
ATOM  443  OD2 ASP A  92    -6.858   2.991 63.099 1.00 38.84    O
ATOM  444  N   GLU A  93   -10.267   0.252 61.558 1.00 35.55    N
ATOM  445  CA  GLU A  93   -11.098   0.175 60.360 1.00 37.34    C
ATOM  446  C   GLU A  93   -10.422   0.899 59.216 1.00 37.68    C
ATOM  447  O   GLU A  93   -10.396   0.413 58.088 1.00 36.49    O
ATOM  448  CB  GLU A  93   -12.478   0.794 60.596 1.00 39.79    C
ATOM  449  CG  GLU A  93   -13.497  -0.128 61.271 1.00 43.84    C
ATOM  450  CD  GLU A  93   -14.909   0.456 61.285 1.00 45.13    C
ATOM  451  OE1 GLU A  93   -15.389   0.844 60.199 1.00 46.73    O
ATOM  452  OE2 GLU A  93   -15.539   0.520 62.367 1.00 45.51    O
ATOM  453  N   HIS A  94    -9.876   2.071 59.509 1.00 39.10    N
ATOM  454  CA  HIS A  94    -9.205   2.868 58.494 1.00 40.87    C
ATOM  455  C   HIS A  94    -8.008   3.552 59.110 1.00 41.00    C
ATOM  456  O   HIS A  94    -8.024   4.758 59.337 1.00 41.86    O
ATOM  457  CB  HIS A  94   -10.164   3.915 57.927 1.00 42.66    C
ATOM  458  CG  HIS A  94   -10.944   3.438 56.743 1.00 45.89    C
ATOM  459  ND1 HIS A  94   -10.400   3.335 55.482 1.00 47.73    N
ATOM  460  CD2 HIS A  94   -12.232   3.013 56.632 1.00 46.71    C
ATOM  461  CE1 HIS A  94   -11.311   2.872 54.641 1.00 48.84    C
ATOM  462  NE2 HIS A  94   -12.429   2.670 55.320 1.00 48.36    N
ATOM  463  N   ALA A  95    -6.968   2.774 59.375 1.00 41.11    N
ATOM  464  CA  ALA A  95    -5.757   3.302 59.983 1.00 41.64    C
ATOM  465  C   ALA A  95    -4.867   3.992 58.961 1.00 41.21    C
ATOM  466  O   ALA A  95    -4.741   3.543 57.831 1.00 41.52    O
ATOM  467  CB  ALA A  95    -4.983   2.190 60.663 1.00 41.38    C
ATOM  468  N   ALA A  96    -4.238   5.083 59.381 1.00 40.46    N
ATOM  469  CA  ALA A  96    -3.354   5.828 58.508 1.00 39.29    C
ATOM  470  C   ALA A  96    -2.059   5.044 58.308 1.00 37.94    C
ATOM  471  O   ALA A  96    -1.487   5.008 57.213 1.00 37.83    O
ATOM  472  CB  ALA A  96    -3.055   7.169 59.123 1.00 40.86    C
ATOM  473  N   ALA A  97    -1.600   4.415 59.380 1.00 34.87    N
ATOM  474  CA  ALA A  97    -0.386   3.620 59.323 1.00 33.04    C
ATOM  475  C   ALA A  97    -0.726   2.132 59.354 1.00 31.16    C
ATOM  476  O   ALA A  97    -1.761   1.735 59.870 1.00 29.76    O
ATOM  477  CB  ALA A  97     0.523   3.960 60.499 1.00 33.02    C
ATOM  478  N   HIS A  98     0.163   1.317 58.798 1.00 30.47    N
ATOM  479  CA  HIS A  98    -0.029  -0.122 58.791 1.00 29.55    C
ATOM  480  C   HIS A  98     0.287  -0.752 60.164 1.00 29.61    C
ATOM  481  O   HIS A  98     1.007  -0.177 60.989 1.00 27.88    O
ATOM  482  CB  HIS A  98     0.843  -0.757 57.712 1.00 29.13    C
ATOM  483  CG  HIS A  98     0.572  -0.240 56.331 1.00 30.25    C
ATOM  484  ND1 HIS A  98     1.027  -0.888 55.203 1.00 31.62    N
ATOM  485  CD2 HIS A  98    -0.108   0.845 55.898 1.00 30.54    C
ATOM  486  CE1 HIS A  98     0.636  -0.218 54.131 1.00 31.59    C
ATOM  487  NE2 HIS A  98    -0.054   0.836 54.520 1.00 30.92    N
ATOM  488  N   ALA A  99    -0.250  -1.947 60.392 1.00 29.60    N
ATOM  489  CA  ALA A  99    -0.052  -2.656 61.644 1.00 30.33    C
ATOM  490  C   ALA A  99     1.398  -2.605 62.093 1.00 31.77    C
ATOM  491  O   ALA A  99     1.682  -2.344 63.262 1.00 31.22    O
ATOM  492  CB  ALA A  99    -0.504  -4.092 61.500 1.00 29.64    C
ATOM  493  N   GLU A 100     2.316  -2.839 61.163 1.00 33.41    N
ATOM  494  CA  GLU A 100     3.743  -2.820 61.476 1.00 35.26    C
ATOM  495  C   GLU A 100     4.174  -1.498 62.107 1.00 35.17    C
ATOM  496  O   GLU A 100     4.966  -1.473 63.046 1.00 34.71    O
ATOM  497  CB  GLU A 100     4.574  -3.064 60.212 1.00 37.51    C
ATOM  498  CG  GLU A 100     4.406  -4.445 59.539 1.00 39.79    C
ATOM  499  CD  GLU A 100     3.025  -4.708 58.914 1.00 41.46    C
ATOM  500  OE1 GLU A 100     2.307  -3.745 58.537 1.00 42.28    O
ATOM  501  OE2 GLU A 100     2.662  -5.896 58.780 1.00 41.23    O
ATOM  502  N   ALA A 101     3.654  -0.396 61.581 1.00 35.32    N
ATOM  503  CA  ALA A 101     4.020   0.912 62.099 1.00 34.70    C
ATOM  504  C   ALA A 101     3.433   1.153 63.471 1.00 33.76    C
ATOM  505  O   ALA A 101     4.165   1.454 64.417 1.00 34.89    O
ATOM  506  CB  ALA A 101     3.546   2.005 61.144 1.00 37.37    C
ATOM  507  CG  ALA A 101     4.112   1.899 59.729 1.00 41.75    C
ATOM  508  CD  ALA A 101     3.635   3.024 58.806 1.00 43.89    C
ATOM  509  OE1 ALA A 101     2.728   2.798 57.968 1.00 44.04    O
ATOM  510  OE2 ALA A 101     4.174   4.146 58.928 1.00 44.93    O
ATOM  511  N   ALA A 102     2.113   1.023 63.587 1.00 30.60    N
ATOM  512  CA  ALA A 102     1.425   1.245 64.854 1.00 28.41    C
ATOM  513  C   ALA A 102     2.069   0.511 66.021 1.00 28.14    C
ATOM  514  O   ALA A 102     2.104   1.024 67.146 1.00 29.70    O
ATOM  515  CB  ALA A 102    -0.055   0.826 64.740 1.00 25.71    C
ATOM  516  N   PHE A 103     2.574  -0.692 65.762 1.00 26.55    N

ATOM 1943  C   ASP B  92    12.314  -8.240 90.680 1.00 27.32    C
ATOM 1944  O   ASP B  92    11.456  -8.098 91.556 1.00 27.13    O
ATOM 1945  CB  ASP B  92    12.373  -6.486 88.892 1.00 24.87    C
ATOM 1946  CG  ASP B  92    13.839  -6.333 88.612 1.00 24.80    C
ATOM 1947  OD1 ASP B  92    14.615  -7.194 89.085 1.00 27.35    O
ATOM 1948  OD2 ASP B  92    14.225  -5.356 87.928 1.00 23.80    O
ATOM 1949  N   GLU B  93    13.545  -8.673 90.934 1.00 29.32    N
ATOM 1950  CA  GLU B  93    13.983  -9.002 92.292 1.00 31.14    C
ATOM 1951  C   GLU B  93    15.003  -7.962 92.783 1.00 31.81    C
ATOM 1952  O   GLU B  93    15.283  -7.862 93.980 1.00 32.87    O
ATOM 1953  CB  GLU B  93    14.593 -10.404 92.304 1.00 32.68    C
ATOM 1954  CG  GLU B  93    14.796 -10.987 93.695 1.00 35.81    C
ATOM 1955  CD  GLU B  93    13.495 -11.115 94.463 1.00 37.16    C
ATOM 1956  OE1 GLU B  93    12.509 -11.587 93.861 1.00 37.11    O
ATOM 1957  OE2 GLU B  93    13.468 -10.757 95.666 1.00 36.62    O
ATOM 1958  N   HIS B  94    15.545  -7.183 91.852 1.00 31.80    N
ATOM 1959  CA  HIS B  94    16.513  -6.160 92.191 1.00 32.24    C
ATOM 1960  C   HIS B  94    16.165  -4.858 91.476 1.00 31.69    C
ATOM 1961  O   HIS B  94    17.043  -4.132 91.021 1.00 32.87    O
ATOM 1962  CB  HIS B  94    17.916  -6.628 91.795 1.00 32.09    C
ATOM 1963  CG  HIS B  94    18.269  -7.978 92.335 1.00 33.63    C
ATOM 1964  ND1 HIS B  94    18.398  -8.229 93.686 1.00 34.75    N
ATOM 1965  CD2 HIS B  94    18.506  -9.152 91.708 1.00 34.17    C
ATOM 1966  CE1 HIS B  94    18.704  -9.501 93.865 1.00 34.41    C
ATOM 1967  NE2 HIS B  94    18.776 -10.088 92.684 1.00 33.98    N
ATOM 1968  N   ALA B  95    14.879  -4.568 91.374 1.00 31.25    N
ATOM 1969  CA  ALA B  95    14.448  -3.344 90.702 1.00 30.66    C
ATOM 1970  C   ALA B  95    14.876  -2.081 91.465 1.00 29.97    C
ATOM 1971  O   ALA B  95    14.831  -2.022 92.696 1.00 30.16    O
ATOM 1972  CB  ALA B  95    12.927  -3.362 90.500 1.00 29.25    C
ATOM 1973  N   ALA B  96    15.299  -1.067 90.728 1.00 28.62    N
ATOM 1974  CA  ALA B  96    15.702   0.178 91.340 1.00 28.40    C
ATOM 1975  C   ALA B  96    14.472   1.043 91.654 1.00 29.99    C
ATOM 1976  O   ALA B  96    14.553   2.002 92.419 1.00 30.71    O
ATOM 1977  CB  ALA B  96    16.621   0.919 90.416 1.00 27.25    C
ATOM 1978  N   ALA B  97    13.331   0.821 91.065 1.00 30.19    N
ATOM 1979  CA  ALA B  97    12.094   1.440 91.273 1.00 30.32    C
ATOM 1980  C   ALA B  97    10.928   0.493 91.544 1.00 30.58    C
ATOM 1981  O   ALA B  97    11.045  -0.710 91.322 1.00 30.24    O
ATOM 1982  CB  ALA B  97    11.799   2.285 90.047 1.00 29.28    C
ATOM 1983  N   HIS B  98     9.804   1.037 92.024 1.00 31.20    N
ATOM 1984  CA  HIS B  98     8.615   0.228 92.307 1.00 30.17    C
ATOM 1985  C   HIS B  98     7.869  -0.086 91.026 1.00 29.50    C
ATOM 1986  O   HIS B  98     8.022   0.614 90.021 1.00 28.00    O
ATOM 1987  CB  HIS B  98     7.689   0.940 93.283 1.00 30.91    C
ATOM 1988  CG  HIS B  98     8.319   1.196 94.617 1.00 33.22    C
ATOM 1989  ND1 HIS B  98     7.587   1.489 95.749 1.00 32.52    N
ATOM 1990  CD2 HIS B  98     9.620   1.206 94.999 1.00 32.97    C
ATOM 1991  CE1 HIS B  98     8.408   1.665 96.767 1.00 32.55    C
ATOM 1992  NE2 HIS B  98     9.649   1.499 96.337 1.00 32.87    N
ATOM 1993  N   ALA B  99     7.061  -1.145 91.080 1.00 29.92    N
ATOM 1994  CA  ALA B  99     6.272  -1.613 89.941 1.00 29.60    C
ATOM 1995  C   ALA B  99     5.508  -0.490 89.272 1.00 29.58    C
ATOM 1996  O   ALA B  99     5.412  -0.449 88.043 1.00 30.39    O
ATOM 1997  CB  ALA B  99     5.311  -2.728 90.386 1.00 29.03    C
ATOM 1998  N   GLU B 100     4.968   0.425 90.069 1.00 30.76    N
ATOM 1999  CA  GLU B 100     4.199   1.556 89.536 1.00 32.10    C
ATOM 2000  C   GLU B 100     5.035   2.453 88.615 1.00 32.56    C
ATOM 2001  O   GLU B 100     4.548   2.941 87.593 1.00 31.67    O
ATOM 2002  CB  GLU B 100     3.606   2.380 90.691 1.00 32.94    C
ATOM 2003  CG  GLU B 100     2.484   1.657 91.470 1.00 33.25    C
ATOM 2004  CD  GLU B 100     2.967   0.946 92.732 1.00 32.63    C
ATOM 2005  OE1 GLU B 100     4.173   0.655 92.830 1.00 30.43    O
ATOM 2006  OE2 GLU B 100     2.121   0.668 93.623 1.00 34.00    O
ATOM 2007  N   GLU B 101     6.296   2.656 88.973 1.00 33.19    N
ATOM 2008  CA  GLU B 101     7.181   3.493 88.186 1.00 33.91    C
ATOM 2009  C   GLU B 101     7.598   2.744 86.931 1.00 33.21    C
ATOM 2010  O   GLU B 101     7.593   3.294 85.826 1.00 34.04    O
ATOM 2011  CB  GLU B 101     8.427   3.859 88.999 1.00 35.98    C
ATOM 2012  CG  GLU B 101     8.149   4.490 90.380 1.00 40.27    C
ATOM 2013  CD  GLU B 101     9.406   4.590 91.262 1.00 43.83    C
ATOM 2014  OE1 GLU B 101    10.412   5.139 90.760 1.00 46.44    O
ATOM 2015  OE2 GLU B 101     9.399   4.139 92.439 1.00 42.52    O
ATOM 2016  N   ALA B 102     7.955   1.478 87.106 1.00 31.56    N
ATOM 2017  CA  ALA B 102     8.406   0.652 85.993 1.00 29.65    C
ATOM 2018  C   ALA B 102     7.385   0.551 84.881 1.00 28.86    C
ATOM 2019  O   ALA B 102     7.747   0.467 83.710 1.00 28.47    O
ATOM 2020  CB  ALA B 102     8.758  -0.750 86.494 1.00 30.14    C
ATOM 2021  N   PHE B 103     6.105   0.552 85.240 1.00 27.81    N
ATOM 2022  CA  PHE B 103     5.059   0.430 84.245 1.00 27.36    C
ATOM 2023  C   PHE B 103     5.030   1.591 83.266 1.00 28.18    C
ATOM 2024  O   PHE B 103     5.189   1.398 82.064 1.00 28.58    O
ATOM 2025  CB  PHE B 103     3.695   0.306 84.923 1.00 26.13    C
ATOM 2026  CG  PHE B 103     2.559   0.132 83.959 1.00 25.25    C
ATOM 2027  CD1 PHE B 103     2.296  -1.108 83.386 1.00 23.58    C
ATOM 2028  CD2 PHE B 103     1.755   1.217 83.608 1.00 25.36    C
```

*FIG. 7 (con't)*

```
ATOM   517  CA  PHE A 103      3.180  -1.501  66.810  1.00 25.13      C
ATOM   518  C   PHE A 103      4.383  -0.817  67.442  1.00 24.36      C
ATOM   519  O   PHE A 103      4.473  -0.709  68.665  1.00 23.47      O
ATOM   520  CB  PHE A 103      3.605  -2.864  66.256  1.00 23.54      C
ATOM   521  CG  PHE A 103      4.077  -3.813  67.315  1.00 21.94      C
ATOM   522  CD1 PHE A 103      3.169  -4.415  68.177  1.00 22.73      C
ATOM   523  CD2 PHE A 103      5.426  -4.085  67.476  1.00 21.49      C
ATOM   524  CE1 PHE A 103      3.602  -5.277  69.185  1.00 22.49      C
ATOM   525  CE2 PHE A 103      5.873  -4.945  68.484  1.00 21.79      C
ATOM   526  CZ  PHE A 103      4.958  -5.542  69.336  1.00 21.63      C
ATOM   527  N   PHE A 104      5.298  -0.357  66.600  1.00 24.45      N
ATOM   528  CA  PHE A 104      6.498   0.319  67.090  1.00 25.83      C
ATOM   529  C   PHE A 104      6.297   1.806  67.412  1.00 26.83      C
ATOM   530  O   PHE A 104      7.257   2.492  67.749  1.00 27.82      O
ATOM   531  CB  PHE A 104      7.631   0.182  66.070  1.00 21.81      C
ATOM   532  CG  PHE A 104      8.097  -1.222  65.871  1.00 17.73      C
ATOM   533  CD1 PHE A 104      7.961  -1.843  64.641  1.00 16.65      C
ATOM   534  CD2 PHE A 104      8.673  -1.930  66.915  1.00 17.77      C
ATOM   535  CE1 PHE A 104      8.391  -3.138  64.442  1.00 14.86      C
ATOM   536  CE2 PHE A 104      9.102  -3.231  66.726  1.00 16.29      C
ATOM   537  CZ  PHE A 104      8.960  -3.833  65.484  1.00 15.13      C
ATOM   538  N   ASN A 105      5.064   2.293  67.325  1.00 28.02      N
ATOM   539  CA  ASN A 105      4.805   3.684  67.614  1.00 30.45      C
ATOM   540  C   ASN A 105      4.001   3.903  68.871  1.00 31.79      C
ATOM   541  O   ASN A 105      4.047   4.985  69.447  1.00 34.01      O
ATOM   542  CB  ASN A 105      4.093   4.373  66.442  1.00 31.94      C
ATOM   543  CG  ASN A 105      4.997   4.561  65.240  1.00 33.98      C
ATOM   544  OD1 ASN A 105      6.189   4.855  65.388  1.00 35.96      O
ATOM   545  ND2 ASN A 105      4.439   4.413  64.049  1.00 33.43      N
ATOM   546  N   THR A 106      3.270   2.890  69.316  1.00 32.65      N
ATOM   547  CA  THR A 106      2.457   3.040  70.522  1.00 33.94      C
ATOM   548  C   THR A 106      2.464   1.841  71.447  1.00 33.85      C
ATOM   549  O   THR A 106      2.267   1.985  72.655  1.00 34.59      O
ATOM   550  CB  THR A 106      1.018   3.359  70.169  1.00 34.54      C
ATOM   551  OG1 THR A 106      0.611   2.531  69.067  1.00 36.21      O
ATOM   552  CG2 THR A 106      0.880   4.826  69.801  1.00 35.14      C
ATOM   553  N   ILE A 107      2.678   0.657  70.884  1.00 33.30      N
ATOM   554  CA  ILE A 107      2.705  -0.562  71.681  1.00 32.40      C
ATOM   555  C   ILE A 107      4.080  -0.848  72.288  1.00 31.75      C
ATOM   556  O   ILE A 107      4.194  -1.179  73.467  1.00 31.71      O
ATOM   557  CB  ILE A 107      2.272  -1.765  70.843  1.00 32.26      C
ATOM   558  CG1 ILE A 107      0.919  -1.476  70.214  1.00 32.28      C
ATOM   559  CG2 ILE A 107      2.151  -3.007  71.719  1.00 31.74      C
ATOM   560  CD1 ILE A 107      0.487  -2.531  69.277  1.00 34.74      C
ATOM   561  N   LEU A 108      5.124  -0.706  71.485  1.00 30.92      N
ATOM   562  CA  LEU A 108      6.464  -0.975  71.964  1.00 30.03      C
ATOM   563  C   LEU A 108      7.365   0.166  71.515  1.00 30.38      C
ATOM   564  O   LEU A 108      8.233  -0.018  70.668  1.00 31.35      O
ATOM   565  CB  LEU A 108      6.935  -2.298  71.377  1.00 29.78      C
ATOM   566  CG  LEU A 108      8.019  -3.058  72.126  1.00 31.17      C
ATOM   567  CD1 LEU A 108      7.601  -3.299  73.559  1.00 30.95      C
ATOM   568  CD2 LEU A 108      8.250  -4.373  71.431  1.00 31.92      C
ATOM   569  N   PRO A 109      7.160   1.372  72.075  1.00 31.40      N
ATOM   570  CA  PRO A 109      7.921   2.589  71.764  1.00 31.13      C
ATOM   571  C   PRO A 109      9.409   2.478  72.022  1.00 31.04      C
ATOM   572  O   PRO A 109     10.212   2.779  71.144  1.00 31.29      O
ATOM   573  CB  PRO A 109      7.271   3.640  72.657  1.00 31.39      C
ATOM   574  CG  PRO A 109      5.883   3.161  72.781  1.00 32.99      C
ATOM   575  CD  PRO A 109      6.077   1.685  73.024  1.00 32.10      C
ATOM   576  N   ALA A 110      9.782   2.063  73.225  1.00 31.49      N
ATOM   577  CA  ALA A 110     11.204   1.940  73.552  1.00 33.30      C
ATOM   578  C   ALA A 110     11.562   0.627  74.247  1.00 33.23      C
ATOM   579  O   ALA A 110     10.705  -0.044  74.820  1.00 33.66      O
ATOM   580  CB  ALA A 110     11.630   3.134  74.424  1.00 33.91      C
ATOM   581  N   PHE A 111     12.839   0.263  74.191  1.00 33.53      N
ATOM   582  CA  PHE A 111     13.313  -0.969  74.832  1.00 34.05      C
ATOM   583  C   PHE A 111     14.467  -0.636  75.774  1.00 35.38      C
ATOM   584  O   PHE A 111     15.323   0.173  75.424  1.00 36.35      O
ATOM   585  CB  PHE A 111     13.833  -1.964  73.789  1.00 30.80      C
ATOM   586  CG  PHE A 111     12.958  -2.100  72.581  1.00 28.32      C
ATOM   587  CD1 PHE A 111     12.847  -1.064  71.662  1.00 28.58      C
ATOM   588  CD2 PHE A 111     12.225  -3.258  72.369  1.00 26.83      C
ATOM   589  CE1 PHE A 111     12.014  -1.181  70.548  1.00 27.64      C
ATOM   590  CE2 PHE A 111     11.391  -3.385  71.260  1.00 26.13      C
ATOM   591  CZ  PHE A 111     11.286  -2.345  70.350  1.00 26.71      C
ATOM   592  N   ASP A 112     14.504  -1.253  76.953  1.00 35.63      N
ATOM   593  CA  ASP A 112     15.606  -0.999  77.878  1.00 37.37      C
ATOM   594  C   ASP A 112     16.730  -2.012  77.597  1.00 36.28      C
ATOM   595  O   ASP A 112     16.506  -3.223  77.576  1.00 35.18      O
ATOM   596  CB  ASP A 112     15.131  -1.098  79.336  1.00 40.34      C
ATOM   597  CG  ASP A 112     15.006   2.521  79.810  1.00 42.74      C
ATOM   598  OD1 ASP A 112     14.360  -3.328  79.106  1.00 45.41      O
ATOM   599  OD2 ASP A 112     15.549  -2.823  80.886  1.00 42.72      O
ATOM   600  N   PRO A 113     17.950  -1.512  77.360  1.00 35.36      N
ATOM   601  CA  PRO A 113     19.132  -2.327  77.066  1.00 33.92      C
ATOM   602  C   PRO A 113     19.319  -3.551  77.944  1.00 32.23      C
ATOM  2029  CE1 PHE B 103      1.256  -1.272  82.482  1.00 22.52      C
ATOM  2030  CE2 PHE B 103      0.706   1.068  82.706  1.00 23.78      C
ATOM  2031  CZ  PHE B 103      0.457  -0.181  82.142  1.00 24.57      C
ATOM  2032  N   PHE B 104      4.825   2.798  83.786  1.00 29.24      N
ATOM  2033  CA  PHE B 104      4.757   3.998  82.956  1.00 29.26      C
ATOM  2034  C   PHE B 104      6.073   4.406  82.308  1.00 31.16      C
ATOM  2035  O   PHE B 104      6.114   5.365  81.533  1.00 31.26      O
ATOM  2036  CB  PHE B 104      4.202   5.160  83.771  1.00 26.65      C
ATOM  2037  CG  PHE B 104      2.738   5.037  84.082  1.00 25.20      C
ATOM  2038  CD1 PHE B 104      2.274   5.216  85.381  1.00 22.70      C
ATOM  2039  CD2 PHE B 104      1.819   4.778  83.072  1.00 24.69      C
ATOM  2040  CE1 PHE B 104      0.917   5.138  85.669  1.00 23.29      C
ATOM  2041  CE2 PHE B 104      0.458   4.701  83.354  1.00 24.22      C
ATOM  2042  CZ  PHE B 104      0.007   4.880  84.658  1.00 22.70      C
ATOM  2043  N   ASN B 105      7.151   3.689  82.611  1.00 33.67      N
ATOM  2044  CA  ASN B 105      8.446   4.025  82.020  1.00 35.86      C
ATOM  2045  C   ASN B 105      8.912   3.075  80.926  1.00 36.14      C
ATOM  2046  O   ASN B 105      9.816   3.411  80.168  1.00 35.61      O
ATOM  2047  CB  ASN B 105      9.515   4.122  83.104  1.00 38.40      C
ATOM  2048  CG  ASN B 105      9.315   5.321  84.009  1.00 41.32      C
ATOM  2049  OD1 ASN B 105      8.419   6.141  83.788  1.00 42.54      O
ATOM  2050  ND2 ASN B 105     10.157   5.438  85.032  1.00 41.83      N
ATOM  2051  N   THR B 106      8.299   1.901  80.833  1.00 37.38      N
ATOM  2052  CA  THR B 106      8.690   0.943  79.809  1.00 39.06      C
ATOM  2053  C   THR B 106      7.518   0.239  79.144  1.00 39.10      C
ATOM  2054  O   THR B 106      7.571  -0.049  77.952  1.00 39.32      O
ATOM  2055  CB  THR B 106      9.624  -0.131  80.384  1.00 40.61      C
ATOM  2056  OG1 THR B 106      9.098  -0.605  81.624  1.00 41.74      O
ATOM  2057  CG2 THR B 106     11.013   0.437  80.608  1.00 41.42      C
ATOM  2058  N   ILE B 107      6.465  -0.039  79.912  1.00 38.64      N
ATOM  2059  CA  ILE B 107      5.287  -0.711  79.376  1.00 39.05      C
ATOM  2060  C   ILE B 107      4.437   0.240  78.528  1.00 39.47      C
ATOM  2061  O   ILE B 107      4.186  -0.032  77.359  1.00 39.91      O
ATOM  2062  CB  ILE B 107      4.424  -1.314  80.507  1.00 39.08      C
ATOM  2063  CG1 ILE B 107      5.316  -2.095  81.473  1.00 38.43      C
ATOM  2064  CG2 ILE B 107      3.334  -2.222  79.920  1.00 37.59      C
ATOM  2065  CD1 ILE B 107      6.278  -3.037  80.793  1.00 38.27      C
ATOM  2066  N   LEU B 108      4.008   1.355  79.112  1.00 39.98      N
ATOM  2067  CA  LEU B 108      3.203   2.336  78.391  1.00 40.78      C
ATOM  2068  C   LEU B 108      3.876   3.697  78.412  1.00 42.16      C
ATOM  2069  O   LEU B 108      3.363   4.654  79.001  1.00 41.46      O
ATOM  2070  CB  LEU B 108      1.819   2.453  79.023  1.00 41.19      C
ATOM  2071  CG  LEU B 108      0.689   1.639  78.418  1.00 40.26      C
ATOM  2072  CD1 LEU B 108     -0.632   2.021  79.073  1.00 39.76      C
ATOM  2073  CD2 LEU B 108      0.635   1.925  76.937  1.00 41.10      C
ATOM  2074  N   PRO B 109      5.049   3.799  77.784  1.00 43.67      N
ATOM  2075  CA  PRO B 109      5.765   5.072  77.757  1.00 44.76      C
ATOM  2076  C   PRO B 109      5.033   6.063  76.891  1.00 45.07      C
ATOM  2077  O   PRO B 109      4.930   7.231  77.237  1.00 45.84      O
ATOM  2078  CB  PRO B 109      7.118   4.698  77.159  1.00 45.21      C
ATOM  2079  CG  PRO B 109      7.277   3.265  77.544  1.00 46.15      C
ATOM  2080  CD  PRO B 109      5.903   2.716  77.274  1.00 44.82      C
ATOM  2081  N   ALA B 110      4.518   5.587  75.763  1.00 45.59      N
ATOM  2082  CA  ALA B 110      3.813   6.453  74.832  1.00 46.09      C
ATOM  2083  C   ALA B 110      2.304   6.203  74.817  1.00 45.65      C
ATOM  2084  O   ALA B 110      1.846   5.108  75.129  1.00 45.08      O
ATOM  2085  CB  ALA B 110      4.386   6.269  73.431  1.00 46.57      C
ATOM  2086  N   PHE B 111      1.544   7.233  74.452  1.00 44.98      N
ATOM  2087  CA  PHE B 111      0.097   7.130  74.376  1.00 44.99      C
ATOM  2088  C   PHE B 111     -0.409   7.738  73.073  1.00 45.71      C
ATOM  2089  O   PHE B 111     -0.007   8.840  72.694  1.00 47.07      O
ATOM  2090  CB  PHE B 111     -0.574   7.854  75.556  1.00 43.75      C
ATOM  2091  CG  PHE B 111     -0.272   7.249  76.904  1.00 43.28      C
ATOM  2092  CD1 PHE B 111      0.734   7.775  77.710  1.00 42.73      C
ATOM  2093  CD2 PHE B 111     -0.986   6.140  77.365  1.00 43.11      C
ATOM  2094  CE1 PHE B 111      1.027   7.205  78.955  1.00 42.37      C
ATOM  2095  CE2 PHE B 111     -0.702   5.562  78.613  1.00 42.95      C
ATOM  2096  CZ  PHE B 111      0.306   6.079  79.407  1.00 42.32      C
ATOM  2097  N   ASP B 112     -1.283   7.022  72.379  1.00 45.74      N
ATOM  2098  CA  ASP B 112     -1.846   7.523  71.138  1.00 45.60      C
ATOM  2099  C   ASP B 112     -2.956   8.523  71.479  1.00 45.23      C
ATOM  2100  O   ASP B 112     -4.040   8.135  71.903  1.00 43.83      O
ATOM  2101  CB  ASP B 112     -2.438   6.369  70.332  1.00 47.51      C
ATOM  2102  CG  ASP B 112     -2.799   6.771  68.918  1.00 48.52      C
ATOM  2103  OD1 ASP B 112     -3.347   7.878  68.735  1.00 49.31      O
ATOM  2104  OD2 ASP B 112     -2.538   5.970  67.996  1.00 49.15      O
ATOM  2105  N   PRO B 113     -2.696   9.829  71.289  1.00 45.48      N
ATOM  2106  CA  PRO B 113     -3.659  10.906  71.576  1.00 44.02      C
ATOM  2107  C   PRO B 113     -5.046  10.679  71.006  1.00 42.57      C
ATOM  2108  O   PRO B 113     -6.010  11.309  71.438  1.00 43.23      O
ATOM  2109  CB  PRO B 113      2.976  12.134  70.982  1.00 44.42      C
ATOM  2110  CG  PRO B 113     -1.513  11.833  71.236  1.00 46.02      C
ATOM  2111  CD  PRO B 113     -1.425  10.390  70.786  1.00 45.45      C
ATOM  2112  N   ALA B 114     -5.152   9.774  70.043  1.00 41.43      N
ATOM  2113  CA  ALA B 114     -6.438   9.486  69.416  1.00 39.56      C
ATOM  2114  C   ALA B 114     -7.229   8.456  70.195  1.00 38.00      C
```

FIG. 7 (con't)

| | | | | | | |
|---|---|---|---|---|---|---|
| ATOM | 603 | O PRO A 113 | 19.763 | -4.597 | 77.475 | 1.00 31.02 | O |
| ATOM | 604 | CB PRO A 113 | 20.271 | -1.327 | 77.225 | 1.00 34.30 | C |
| ATOM | 605 | CG PRO A 113 | 19.656 | -0.082 | 76.700 | 1.00 35.20 | C |
| ATOM | 606 | CD PRO A 113 | 18.302 | -0.081 | 77.378 | 1.00 34.86 | C |
| ATOM | 607 | N ALA A 114 | 18.963 | -3.410 | 79.212 | 1.00 31.30 | N |
| ATOM | 608 | CA ALA A 114 | 19.127 | -4.487 | 80.173 | 1.00 30.48 | C |
| ATOM | 609 | C ALA A 114 | 18.255 | -5.696 | 79.905 | 1.00 29.74 | C |
| ATOM | 610 | O ALA A 114 | 18.401 | -6.726 | 80.559 | 1.00 30.20 | O |
| ATOM | 611 | CB ALA A 114 | 18.861 | -3.965 | 81.578 | 1.00 30.69 | C |
| ATOM | 612 | N LEU A 115 | 17.354 | -5.588 | 78.943 | 1.00 28.59 | N |
| ATOM | 613 | CA LEU A 115 | 16.477 | -6.702 | 78.639 | 1.00 26.74 | C |
| ATOM | 614 | C LEU A 115 | 16.606 | -7.184 | 77.211 | 1.00 26.21 | C |
| ATOM | 615 | O LEU A 115 | 17.075 | -6.463 | 76.325 | 1.00 25.99 | O |
| ATOM | 616 | CB LEU A 115 | 15.020 | -6.317 | 78.909 | 1.00 25.62 | C |
| ATOM | 617 | CG LEU A 115 | 14.537 | -6.198 | 80.349 | 1.00 25.20 | C |
| ATOM | 618 | CD1 LEU A 115 | 13.091 | -5.725 | 80.379 | 1.00 24.76 | C |
| ATOM | 619 | CD2 LEU A 115 | 14.664 | -7.545 | 81.029 | 1.00 25.97 | C |
| ATOM | 620 | N ARG A 116 | 16.178 | -8.419 | 76.998 | 1.00 25.26 | N |
| ATOM | 621 | CA ARG A 116 | 16.194 | -9.010 | 75.679 | 1.00 25.16 | C |
| ATOM | 622 | C ARG A 116 | 14.753 | -9.378 | 75.322 | 1.00 23.32 | C |
| ATOM | 623 | O ARG A 116 | 14.142 | -10.222 | 75.967 | 1.00 22.07 | O |
| ATOM | 624 | CB ARG A 116 | 17.096 | -10.239 | 75.673 | 1.00 27.53 | C |
| ATOM | 625 | CG ARG A 116 | 18.555 | -9.909 | 75.966 | 1.00 31.30 | C |
| ATOM | 626 | CD ARG A 116 | 19.485 | -10.803 | 75.152 | 1.00 36.39 | C |
| ATOM | 627 | NE ARG A 116 | 19.176 | -10.717 | 73.720 | 1.00 39.38 | N |
| ATOM | 628 | CZ ARG A 116 | 19.794 | -11.406 | 72.762 | 1.00 39.62 | C |
| ATOM | 629 | NH1 ARG A 116 | 20.775 | -12.246 | 73.063 | 1.00 39.78 | N |
| ATOM | 630 | NH2 ARG A 116 | 19.417 | -11.257 | 71.497 | 1.00 39.62 | N |
| ATOM | 631 | N TYR A 117 | 14.215 | -8.729 | 74.294 | 1.00 22.29 | N |
| ATOM | 632 | CA TYR A 117 | 12.843 | -8.961 | 73.861 | 1.00 22.17 | C |
| ATOM | 633 | C TYR A 117 | 12.675 | -10.063 | 72.810 | 1.00 22.68 | C |
| ATOM | 634 | O TYR A 117 | 13.499 | -10.215 | 71.903 | 1.00 23.33 | O |
| ATOM | 635 | CB TYR A 117 | 12.241 | -7.662 | 73.332 | 1.00 22.44 | C |
| ATOM | 636 | CG TYR A 117 | 12.235 | -6.524 | 74.332 | 1.00 24.66 | C |
| ATOM | 637 | CD1 TYR A 117 | 13.421 | -5.889 | 74.702 | 1.00 25.81 | C |
| ATOM | 638 | CD2 TYR A 117 | 11.048 | -6.080 | 74.912 | 1.00 25.52 | C |
| ATOM | 639 | CE1 TYR A 117 | 13.426 | -4.849 | 75.620 | 1.00 26.80 | C |
| ATOM | 640 | CE2 TYR A 117 | 11.038 | 5.037 | 75.831 | 1.00 26.04 | C |
| ATOM | 641 | CZ TYR A 117 | 12.226 | -4.431 | 76.179 | 1.00 27.59 | C |
| ATOM | 642 | OH TYR A 117 | 12.215 | -3.417 | 77.108 | 1.00 29.37 | O |
| ATOM | 643 | N ASN A 118 | 11.592 | -10.823 | 72.937 | 1.00 23.61 | N |
| ATOM | 644 | CA ASN A 118 | 11.255 | -11.900 | 72.009 | 1.00 23.56 | C |
| ATOM | 645 | C ASN A 118 | 9.843 | -11.643 | 71.584 | 1.00 22.14 | C |
| ATOM | 646 | O ASN A 118 | 8.895 | -12.204 | 72.086 | 1.00 22.31 | O |
| ATOM | 647 | CB ASN A 118 | 11.291 | -13.239 | 72.725 | 1.00 26.22 | C |
| ATOM | 648 | CG ASN A 118 | 12.268 | -14.180 | 72.110 | 1.00 30.40 | C |
| ATOM | 649 | OD1 ASN A 118 | 13.483 | -14.005 | 72.246 | 1.00 34.07 | O |
| ATOM | 650 | ND2 ASN A 118 | 11.764 | -15.181 | 71.406 | 1.00 32.12 | N |
| ATOM | 651 | N VAL A 119 | 9.702 | -10.804 | 70.519 | 1.00 20.48 | N |
| ATOM | 652 | CA VAL A 119 | 8.382 | -10.442 | 70.009 | 1.00 17.96 | C |
| ATOM | 653 | C VAL A 119 | 7.909 | -11.427 | 68.988 | 1.00 16.86 | C |
| ATOM | 654 | O VAL A 119 | 8.702 | -11.928 | 68.205 | 1.00 18.02 | O |
| ATOM | 655 | CB VAL A 119 | 8.415 | -9.044 | 69.366 | 1.00 17.77 | C |
| ATOM | 656 | CG1 VAL A 119 | 7.032 | -8.702 | 68.832 | 1.00 18.50 | C |
| ATOM | 657 | CG2 VAL A 119 | 8.895 | -7.997 | 70.382 | 1.00 18.24 | C |
| ATOM | 658 | N THR A 120 | 6.616 | -11.712 | 68.989 | 1.00 16.23 | N |
| ATOM | 659 | CA THR A 120 | 6.046 | -12.637 | 68.018 | 1.00 15.49 | C |
| ATOM | 660 | C THR A 120 | 4.757 | -12.046 | 67.439 | 1.00 15.95 | C |
| ATOM | 661 | O THR A 120 | 3.865 | -11.725 | 68.205 | 1.00 16.29 | O |
| ATOM | 662 | CB THR A 120 | 5.746 | -13.952 | 68.672 | 1.00 14.15 | C |
| ATOM | 663 | OG1 THR A 120 | 6.970 | -14.531 | 69.104 | 1.00 14.89 | O |
| ATOM | 664 | CG2 THR A 120 | 5.043 | -14.881 | 67.706 | 1.00 14.01 | C |
| ATOM | 665 | N TRP A 121 | 4.670 | -11.904 | 66.105 | 1.00 15.04 | N |
| ATOM | 666 | CA TRP A 121 | 3.474 | -11.351 | 65.451 | 1.00 14.59 | C |
| ATOM | 667 | C TRP A 121 | 2.629 | -12.417 | 64.762 | 1.00 14.80 | C |
| ATOM | 668 | O TRP A 121 | 3.140 | -13.450 | 64.357 | 1.00 14.85 | O |
| ATOM | 669 | CB TRP A 121 | 3.828 | -10.321 | 64.372 | 1.00 13.65 | C |
| ATOM | 670 | CG TRP A 121 | 4.371 | -9.027 | 64.860 | 1.00 12.34 | C |
| ATOM | 671 | CD1 TRP A 121 | 4.413 | -8.581 | 66.151 | 1.00 10.88 | C |
| ATOM | 672 | CD2 TRP A 121 | 5.008 | -8.026 | 64.060 | 1.00 11.77 | C |
| ATOM | 673 | NE1 TRP A 121 | 5.047 | -7.359 | 66.206 | 1.00 9.27 | N |
| ATOM | 674 | CE2 TRP A 121 | 5.423 | -6.994 | 64.935 | 1.00 11.56 | C |
| ATOM | 675 | CE3 TRP A 121 | 5.273 | -7.899 | 62.687 | 1.00 11.99 | C |
| ATOM | 676 | CZ2 TRP A 121 | 6.096 | -5.845 | 64.482 | 1.00 11.62 | C |
| ATOM | 677 | CZ3 TRP A 121 | 5.948 | -6.749 | 62.236 | 1.00 15.58 | C |
| ATOM | 678 | CH2 TRP A 121 | 6.346 | -5.741 | 63.130 | 1.00 12.25 | C |
| ATOM | 679 | N TYR A 122 | 1.335 | -12.133 | 64.614 | 1.00 15.12 | N |
| ATOM | 680 | CA TYR A 122 | 0.399 | -13.048 | 63.969 | 1.00 14.52 | C |
| ATOM | 681 | C TYR A 122 | -0.485 | -12.199 | 63.081 | 1.00 14.18 | C |
| ATOM | 682 | O TYR A 122 | -1.467 | -11.628 | 63.554 | 1.00 15.95 | O |
| ATOM | 683 | CB TYR A 122 | -0.466 | -13.758 | 65.008 | 1.00 15.40 | C |
| ATOM | 684 | CG TYR A 122 | 0.257 | -14.791 | 65.846 | 1.00 15.65 | C |
| ATOM | 685 | CD1 TYR A 122 | 0.770 | -14.475 | 67.101 | 1.00 16.26 | C |
| ATOM | 686 | CD2 TYR A 122 | 0.386 | -16.108 | 65.400 | 1.00 16.74 | C |
| ATOM | 687 | CE1 TYR A 122 | 1.388 | -15.453 | 67.902 | 1.00 17.44 | C |
| ATOM | 688 | CE2 TYR A 122 | 0.999 | -17.095 | 66.188 | 1.00 14.89 | C |

| | | | | | | |
|---|---|---|---|---|---|---|
| ATOM | 2115 | O ALA B 114 | -8.424 | 8.611 | 70.414 | 1.00 38.59 | O |
| ATOM | 2116 | CB ALA B 114 | -6.217 | 8.998 | 68.014 | 1.00 38.88 | C |
| ATOM | 2117 | N LEU B 115 | -6.554 | 7.390 | 70.598 | 1.00 36.47 | N |
| ATOM | 2118 | CA LEU B 115 | -7.194 | 6.322 | 71.343 | 1.00 34.00 | C |
| ATOM | 2119 | C LEU B 115 | -7.471 | 6.720 | 72.796 | 1.00 31.90 | C |
| ATOM | 2120 | O LEU B 115 | -6.732 | 7.497 | 73.394 | 1.00 31.23 | O |
| ATOM | 2121 | CB LEU B 115 | -6.294 | 5.096 | 71.333 | 1.00 34.26 | C |
| ATOM | 2122 | CG LEU B 115 | -5.716 | 4.669 | 69.992 | 1.00 34.14 | C |
| ATOM | 2123 | CD1 LEU B 115 | -4.615 | 3.622 | 70.185 | 1.00 33.90 | C |
| ATOM | 2124 | CD2 LEU B 115 | -6.846 | 4.143 | 69.144 | 1.00 34.56 | C |
| ATOM | 2125 | N ARG B 116 | -8.538 | 6.173 | 73.368 | 1.00 31.01 | N |
| ATOM | 2126 | CA ARG B 116 | -8.884 | 6.437 | 74.758 | 1.00 28.60 | C |
| ATOM | 2127 | C ARG B 116 | -8.410 | 5.220 | 75.548 | 1.00 26.76 | C |
| ATOM | 2128 | O ARG B 116 | -8.929 | 4.122 | 75.363 | 1.00 25.42 | O |
| ATOM | 2129 | CB ARG B 116 | -10.382 | 6.563 | 74.898 | 1.00 32.04 | C |
| ATOM | 2130 | CG ARG B 116 | -10.825 | 7.721 | 75.738 | 1.00 37.33 | C |
| ATOM | 2131 | CD ARG B 116 | -10.236 | 7.705 | 77.139 | 1.00 38.69 | C |
| ATOM | 2132 | NE ARG B 116 | -11.059 | 8.488 | 78.062 | 1.00 41.96 | N |
| ATOM | 2133 | CZ ARG B 116 | -12.246 | 8.096 | 78.523 | 1.00 43.72 | C |
| ATOM | 2134 | NH1 ARG B 116 | -12.753 | 6.926 | 78.154 | 1.00 45.48 | N |
| ATOM | 2135 | NH2 ARG B 116 | -12.927 | 8.869 | 79.357 | 1.00 45.09 | N |
| ATOM | 2136 | N TYR B 117 | -7.450 | 5.409 | 76.439 | 1.00 24.66 | N |
| ATOM | 2137 | CA TYR B 117 | -6.914 | 4.290 | 77.195 | 1.00 24.15 | C |
| ATOM | 2138 | C TYR B 117 | -7.606 | 3.969 | 78.504 | 1.00 23.87 | C |
| ATOM | 2139 | O TYR B 117 | -7.944 | 4.865 | 79.270 | 1.00 25.73 | O |
| ATOM | 2140 | CB TYR B 117 | -5.421 | 4.511 | 77.476 | 1.00 22.85 | C |
| ATOM | 2141 | CG TYR B 117 | -4.537 | 4.460 | 76.246 | 1.00 21.61 | C |
| ATOM | 2142 | CD1 TYR B 117 | -4.443 | 5.542 | 75.370 | 1.00 21.30 | C |
| ATOM | 2143 | CD2 TYR B 117 | -3.814 | 3.315 | 75.949 | 1.00 22.98 | C |
| ATOM | 2144 | CE1 TYR B 117 | -3.641 | 5.475 | 74.217 | 1.00 22.30 | C |
| ATOM | 2145 | CE2 TYR B 117 | -3.016 | 3.237 | 74.810 | 1.00 24.43 | C |
| ATOM | 2146 | CZ TYR B 117 | -2.934 | 4.321 | 73.951 | 1.00 23.77 | C |
| ATOM | 2147 | OH TYR B 117 | -2.139 | 4.228 | 72.823 | 1.00 26.97 | O |
| ATOM | 2148 | N ASN B 118 | -7.805 | 2.681 | 78.756 | 1.00 23.52 | N |
| ATOM | 2149 | CA ASN B 118 | -8.420 | 2.194 | 79.986 | 1.00 23.33 | C |
| ATOM | 2150 | C ASN B 118 | -7.495 | 1.133 | 80.601 | 1.00 22.78 | C |
| ATOM | 2151 | O ASN B 118 | -7.534 | -0.037 | 80.217 | 1.00 23.03 | O |
| ATOM | 2152 | CB ASN B 118 | -9.770 | 1.582 | 79.673 | 1.00 24.96 | C |
| ATOM | 2153 | CG ASN B 118 | -10.905 | 2.489 | 80.033 | 1.00 26.13 | C |
| ATOM | 2154 | OD1 ASN B 118 | -11.543 | 2.293 | 81.058 | 1.00 29.62 | O |
| ATOM | 2155 | ND2 ASN B 118 | -11.167 | 3.496 | 79.203 | 1.00 27.07 | N |
| ATOM | 2156 | N VAL B 119 | -6.667 | 1.541 | 81.556 | 1.00 20.63 | N |
| ATOM | 2157 | CA VAL B 119 | -5.735 | 0.632 | 82.192 | 1.00 18.93 | C |
| ATOM | 2158 | C VAL B 119 | -6.242 | 0.102 | 83.520 | 1.00 19.43 | C |
| ATOM | 2159 | O VAL B 119 | -6.872 | 0.828 | 84.291 | 1.00 20.90 | O |
| ATOM | 2160 | CB VAL B 119 | -4.384 | 1.305 | 82.427 | 1.00 17.41 | C |
| ATOM | 2161 | CG1 VAL B 119 | -3.398 | 0.335 | 83.011 | 1.00 15.86 | C |
| ATOM | 2162 | CG2 VAL B 119 | -3.852 | 1.843 | 81.132 | 1.00 17.10 | C |
| ATOM | 2163 | N THR B 120 | -5.956 | -1.172 | 83.783 | 1.00 18.85 | N |
| ATOM | 2164 | CA THR B 120 | -6.353 | -1.825 | 85.021 | 1.00 18.06 | C |
| ATOM | 2165 | C THR B 120 | -5.153 | -2.547 | 85.643 | 1.00 18.23 | C |
| ATOM | 2166 | O THR B 120 | -4.524 | -3.382 | 85.006 | 1.00 18.08 | O |
| ATOM | 2167 | CB THR B 120 | -7.451 | -2.846 | 84.765 | 1.00 18.34 | C |
| ATOM | 2168 | OG1 THR B 120 | -8.562 | -2.203 | 84.127 | 1.00 20.38 | O |
| ATOM | 2169 | CG2 THR B 120 | -7.903 | -3.456 | 86.067 | 1.00 18.11 | C |
| ATOM | 2170 | N TRP B 121 | -4.829 | -2.237 | 86.890 | 1.00 17.12 | N |
| ATOM | 2171 | CA TRP B 121 | -3.703 | -2.903 | 87.515 | 1.00 15.87 | C |
| ATOM | 2172 | C TRP B 121 | -4.143 | -3.908 | 88.568 | 1.00 16.14 | C |
| ATOM | 2173 | O TRP B 121 | -5.226 | -3.796 | 89.140 | 1.00 15.96 | O |
| ATOM | 2174 | CB TRP B 121 | -2.763 | -1.897 | 88.183 | 1.00 13.51 | C |
| ATOM | 2175 | CG TRP B 121 | -2.022 | -0.999 | 87.255 | 1.00 14.95 | C |
| ATOM | 2176 | CD1 TRP B 121 | -1.879 | -1.139 | 85.907 | 1.00 15.66 | C |
| ATOM | 2177 | CD2 TRP B 121 | -1.183 | 0.106 | 87.626 | 1.00 15.87 | C |
| ATOM | 2178 | NE1 TRP B 121 | -1.013 | -0.198 | 85.414 | 1.00 13.06 | N |
| ATOM | 2179 | CE2 TRP B 121 | -0.574 | 0.589 | 86.444 | 1.00 13.64 | C |
| ATOM | 2180 | CE3 TRP B 121 | -0.896 | 0.756 | 88.846 | 1.00 15.19 | C |
| ATOM | 2181 | CZ2 TRP B 121 | 0.319 | 1.658 | 86.439 | 1.00 13.13 | C |
| ATOM | 2182 | CZ3 TRP B 121 | -0.003 | 1.828 | 88.838 | 1.00 12.86 | C |
| ATOM | 2183 | CH2 TRP B 121 | 0.580 | 2.273 | 87.640 | 1.00 13.34 | C |
| ATOM | 2184 | N TYR B 122 | -3.286 | -4.900 | 88.804 | 1.00 15.44 | N |
| ATOM | 2185 | CA TYR B 122 | -3.519 | -5.892 | 89.851 | 1.00 15.97 | C |
| ATOM | 2186 | C TYR B 122 | -2.222 | -5.959 | 90.660 | 1.00 16.17 | C |
| ATOM | 2187 | O TYR B 122 | -1.266 | -6.613 | 90.250 | 1.00 16.08 | O |
| ATOM | 2188 | CB TYR B 122 | -3.837 | -7.256 | 89.263 | 1.00 16.33 | C |
| ATOM | 2189 | CG TYR B 122 | -5.192 | -7.342 | 88.608 | 1.00 16.18 | C |
| ATOM | 2190 | CD1 TYR B 122 | -5.356 | -7.073 | 87.250 | 1.00 16.99 | C |
| ATOM | 2191 | CD2 TYR B 122 | -6.307 | -7.724 | 89.342 | 1.00 16.95 | C |
| ATOM | 2192 | CE1 TYR B 122 | -6.611 | -7.193 | 86.638 | 1.00 18.46 | C |
| ATOM | 2193 | CE2 TYR B 122 | -7.560 | -7.845 | 88.754 | 1.00 16.77 | C |
| ATOM | 2194 | CZ TYR B 122 | -7.711 | -7.581 | 87.403 | 1.00 19.17 | C |
| ATOM | 2195 | OH TYR B 122 | -8.962 | -7.703 | 86.837 | 1.00 18.02 | O |
| ATOM | 2196 | N VAL B 123 | -2.190 | -5.276 | 91.799 | 1.00 16.34 | N |
| ATOM | 2197 | CA VAL B 123 | -1.012 | -5.252 | 92.647 | 1.00 16.27 | C |
| ATOM | 2198 | C VAL B 123 | -1.342 | -5.837 | 93.997 | 1.00 17.21 | C |
| ATOM | 2199 | O VAL B 123 | -2.515 | -5.954 | 94.351 | 1.00 17.42 | O |
| ATOM | 2200 | CB VAL B 123 | -0.468 | -3.818 | 92.883 | 1.00 14.39 | C |

FIG. 7 (con't)

```
ATOM   689  CZ  TYR A 122    1.491 -16.760 67.439 1.00 16.76   C
ATOM   690  OH  TYR A 122    2.055 -17.721 68.248 1.00 15.81   O
ATOM   691  N   VAL A 123   -0.139 -12.104 61.807 1.00 14.48   N
ATOM   692  CA  VAL A 123   -0.893 -11.304 60.854 1.00 16.35   C
ATOM   693  C   VAL A 123   -1.402 -12.152 59.701 1.00 16.04   C
ATOM   694  O   VAL A 123   -0.873 -13.232 59.458 1.00 18.44   O
ATOM   695  CB  VAL A 123   -0.031 -10.177 60.256 1.00 17.58   C
ATOM   696  CG1 VAL A 123    0.060  -9.039 61.233 1.00 18.57   C
ATOM   697  CG2 VAL A 123    1.365 -10.710 59.928 1.00 19.50   C
ATOM   698  N   SER A 124   -2.394 -11.636 58.982 1.00 15.27   N
ATOM   699  CA  SER A 124   -2.992 -12.358 57.860 1.00 15.80   C
ATOM   700  C   SER A 124   -2.039 -12.583 56.693 1.00 15.80   C
ATOM   701  O   SER A 124   -2.115 -13.615 56.034 1.00 18.18   O
ATOM   702  CB  SER A 124   -4.234 -11.623 57.334 1.00 13.04   C
ATOM   703  OG  SER A 124   -3.910 -10.400 56.695 1.00 12.72   O
ATOM   704  N   SER A 125   -1.159 -11.631 56.427 1.00 14.87   N
ATOM   705  CA  SER A 125   -0.246 -11.783 55.327 1.00 16.64   C
ATOM   706  C   SER A 125    1.087 -11.084 55.593 1.00 16.05   C
ATOM   707  O   SER A 125    1.182 -10.263 56.498 1.00 16.72   O
ATOM   708  CB  SER A 125   -0.845 -11.213 54.050 1.00 19.25   C
ATOM   709  OG  SER A 125   -0.613  -9.817 53.997 1.00 24.71   O
ATOM   710  N   SER A 126    2.106 -11.414 54.795 1.00 15.34   N
ATOM   711  CA  SER A 126    3.430 -10.816 54.922 1.00 15.00   C
ATOM   712  C   SER A 126    3.368  -9.311 54.658 1.00 14.82   C
ATOM   713  O   SER A 126    2.517  -8.825 53.928 1.00 14.74   O
ATOM   714  CB  SER A 126    4.395 -11.471 53.950 1.00 15.19   C
ATOM   715  OG  SER A 126    3.776 -11.601 52.683 1.00 17.28   O
ATOM   716  N   PRO A 127    4.300  -8.560 55.243 1.00 16.07   N
ATOM   717  CA  PRO A 127    4.353  -7.105 55.092 1.00 17.03   C
ATOM   718  C   PRO A 127    4.677  -6.581 53.688 1.00 19.08   C
ATOM   719  O   PRO A 127    5.199  -7.307 52.834 1.00 18.40   O
ATOM   720  CB  PRO A 127    5.405  -6.704 56.113 1.00 17.23   C
ATOM   721  CG  PRO A 127    6.367  -7.845 56.044 1.00 16.41   C
ATOM   722  CD  PRO A 127    5.461  -9.054 56.014 1.00 17.60   C
ATOM   723  N   CYS A 128    4.352  -5.315 53.455 1.00 19.18   N
ATOM   724  CA  CYS A 128    4.613  -4.691 52.171 1.00 20.22   C
ATOM   725  C   CYS A 128    6.074  -4.286 52.122 1.00 21.46   C
ATOM   726  O   CYS A 128    6.763  -4.328 53.146 1.00 21.23   O
ATOM   727  CB  CYS A 128    3.729  -3.441 52.002 1.00 19.67   C
ATOM   728  SG  CYS A 128    4.103  -2.059 53.134 1.00 19.62   S
ATOM   729  N   ALA A 129    6.548  -3.893 50.938 1.00 22.22   N
ATOM   730  CA  ALA A 129    7.941  -3.477 50.754 1.00 22.51   C
ATOM   731  C   ALA A 129    8.317  -2.378 51.741 1.00 23.45   C
ATOM   732  O   ALA A 129    9.341  -2.475 52.420 1.00 23.51   O
ATOM   733  CB  ALA A 129    8.162  -2.997 49.313 1.00 22.20   C
ATOM   734  N   ALA A 130    7.498  -1.333 51.830 1.00 24.79   N
ATOM   735  CA  ALA A 130    7.770  -0.219 52.749 1.00 25.79   C
ATOM   736  C   ALA A 130    7.877  -0.691 54.195 1.00 27.57   C
ATOM   737  O   ALA A 130    8.851  -0.392 54.885 1.00 27.60   O
ATOM   738  CB  ALA A 130    6.681   0.837 52.640 1.00 23.96   C
ATOM   739  N   CYS A 131    6.853  -1.399 54.664 1.00 28.78   N
ATOM   740  CA  CYS A 131    6.839  -1.916 56.027 1.00 29.65   C
ATOM   741  C   CYS A 131    8.092  -2.765 56.323 1.00 29.09   C
ATOM   742  O   CYS A 131    8.683  -2.684 57.409 1.00 28.45   O
ATOM   743  CB  CYS A 131    5.572  -2.752 56.254 1.00 30.64   C
ATOM   744  SG  CYS A 131    4.096  -1.825 56.740 1.00 33.86   S
ATOM   745  N   ALA A 132    8.492  -3.582 55.358 1.00 28.98   N
ATOM   746  CA  ALA A 132    9.674  -4.400 55.539 1.00 29.57   C
ATOM   747  C   ALA A 132   10.839  -3.502 55.922 1.00 30.73   C
ATOM   748  O   ALA A 132   11.499  -3.755 56.924 1.00 31.49   O
ATOM   749  CB  ALA A 132   10.003  -5.156 54.278 1.00 27.72   C
ATOM   750  N   ASP A 133   11.081  -2.446 55.136 1.00 31.97   N
ATOM   751  CA  ASP A 133   12.180  -1.516 55.405 1.00 32.50   C
ATOM   752  C   ASP A 133   12.073  -0.945 56.798 1.00 31.96   C
ATOM   753  O   ASP A 133   13.068  -0.847 57.512 1.00 32.73   O
ATOM   754  CB  ASP A 133   12.219  -0.379 54.376 1.00 34.69   C
ATOM   755  CG  ASP A 133   13.063  -0.755 53.122 1.00 37.68   C
ATOM   756  OD1 ASP A 133   12.507  -1.574 52.314 1.00 37.51   O
ATOM   757  OD2 ASP A 133   14.129  -0.237 52.954 1.00 40.18   O
ATOM   758  N   ARG A 134   10.865  -0.569 57.195 1.00 31.15   N
ATOM   759  CA  ARG A 134   10.669  -0.030 58.528 1.00 30.86   C
ATOM   760  C   ARG A 134   11.077  -1.033 59.599 1.00 30.17   C
ATOM   761  O   ARG A 134   11.688  -0.659 60.598 1.00 29.88   O
ATOM   762  CB  ARG A 134    9.214   0.379 58.727 1.00 32.61   C
ATOM   763  CG  ARG A 134    8.863   1.708 58.085 1.00 36.85   C
ATOM   764  CD  ARG A 134    7.496   2.210 58.563 1.00 39.90   C
ATOM   765  NE  ARG A 134    6.377   1.630 57.825 1.00 42.27   N
ATOM   766  CZ  ARG A 134    6.079   1.937 56.564 1.00 43.86   C
ATOM   767  NH1 ARG A 134    6.820   2.820 55.913 1.00 44.43   N
ATOM   768  NH2 ARG A 134    5.057   1.346 55.948 1.00 43.80   N
ATOM   769  N   ILE A 135   10.744  -2.304 59.392 1.00 29.88   N
ATOM   770  CA  ILE A 135   11.091  -3.351 60.356 1.00 28.44   C
ATOM   771  C   ILE A 135   12.592  -3.547 60.582 1.00 28.03   C
ATOM   772  O   ILE A 135   13.170  -3.786 61.442 1.00 28.10   O
ATOM   773  CB  ILE A 135   10.431  -4.699 59.983 1.00 28.64   C
ATOM   774  CG1 ILE A 135    8.912  -4.565 60.045 1.00 27.00   C

ATOM  2201  CG1 VAL B 123    0.824  -3.634 92.155 1.00 13.34   C
ATOM  2202  CG2 VAL B 123   -1.460  -2.789 92.414 1.00 13.79   C
ATOM  2203  N   SER B 124   -0.299  -6.179 94.755 1.00 17.17   N
ATOM  2204  CA  SER B 124   -0.451  -6.765 96.086 1.00 17.43   C
ATOM  2205  C   SER B 124   -0.827  -5.711 97.119 1.00 17.04   C
ATOM  2206  O   SER B 124   -1.564  -5.991 98.065 1.00 18.00   O
ATOM  2207  CB  SER B 124    0.850  -7.469 96.498 1.00 16.15   C
ATOM  2208  OG  SER B 124    1.941  -6.563 96.576 1.00 14.06   O
ATOM  2209  N   SER B 125   -0.334  -4.499 96.931 1.00 17.34   N
ATOM  2210  CA  SER B 125   -0.632  -3.436 97.873 1.00 17.65   C
ATOM  2211  C   SER B 125   -0.738  -2.103 97.160 1.00 16.78   C
ATOM  2212  O   SER B 125   -0.131  -1.909 96.107 1.00 17.41   O
ATOM  2213  CB  SER B 125    0.465  -3.347 98.921 1.00 19.10   C
ATOM  2214  OG  SER B 125    1.689  -2.970 98.303 1.00 23.89   O
ATOM  2215  N   SER B 126   -1.495  -1.189 97.753 1.00 16.73   N
ATOM  2216  CA  SER B 126   -1.676   0.156 97.218 1.00 16.16   C
ATOM  2217  C   SER B 126   -0.321   0.846 97.102 1.00 15.14   C
ATOM  2218  O   SER B 126    0.621   0.482 97.784 1.00 14.33   O
ATOM  2219  CB  SER B 126   -2.580   0.982 98.146 1.00 16.63   C
ATOM  2220  OG  SER B 126   -1.949   1.285 99.393 1.00 18.88   O
ATOM  2221  N   PRO B 127   -0.226   1.866 96.243 1.00 16.79   N
ATOM  2222  CA  PRO B 127    1.024   2.613 96.033 1.00 18.72   C
ATOM  2223  C   PRO B 127    1.465   3.449 97.249 1.00 19.06   C
ATOM  2224  O   PRO B 127    0.657   3.785 98.121 1.00 18.57   O
ATOM  2225  CB  PRO B 127    0.708   3.471 94.807 1.00 18.56   C
ATOM  2226  CG  PRO B 127   -0.770   3.751 94.973 1.00 19.12   C
ATOM  2227  CD  PRO B 127   -1.315   2.408 95.402 1.00 18.60   C
ATOM  2228  N   CYS B 128    2.752   3.759 97.309 1.00 20.85   N
ATOM  2229  CA  CYS B 128    3.280   4.540 98.403 1.00 22.90   C
ATOM  2230  C   CYS B 128    3.070   6.012 98.085 1.00 23.71   C
ATOM  2231  O   CYS B 128    2.570   6.354 97.011 1.00 23.05   O
ATOM  2232  CB  CYS B 128    4.774   4.246 98.622 1.00 23.04   C
ATOM  2233  SG  CYS B 128    5.891   4.647 97.240 1.00 24.18   S
ATOM  2234  N   ALA B 129    3.453   6.867 99.024 1.00 24.79   N
ATOM  2235  CA  ALA B 129    3.289   8.299 98.861 1.00 25.62   C
ATOM  2236  C   ALA B 129    3.940   8.779 97.589 1.00 25.75   C
ATOM  2237  O   ALA B 129    3.333   9.515 96.813 1.00 26.64   O
ATOM  2238  CB  ALA B 129    3.878   9.017 100.050 1.00 27.15   C
ATOM  2239  N   ALA B 130    5.177   8.359 97.368 1.00 26.43   N
ATOM  2240  CA  ALA B 130    5.914   8.763 96.178 1.00 27.45   C
ATOM  2241  C   ALA B 130    5.293   8.216 94.891 1.00 28.53   C
ATOM  2242  O   ALA B 130    5.138   8.947 93.915 1.00 29.62   O
ATOM  2243  CB  ALA B 130    7.358   8.322 96.293 1.00 25.77   C
ATOM  2244  N   CYS B 131    4.954   6.932 94.881 1.00 28.75   N
ATOM  2245  CA  CYS B 131    4.354   6.333 93.701 1.00 29.91   C
ATOM  2246  C   CYS B 131    3.021   6.987 93.328 1.00 29.50   C
ATOM  2247  O   CYS B 131    2.719   7.184 92.152 1.00 28.24   O
ATOM  2248  CB  CYS B 131    4.159   4.832 93.920 1.00 30.09   C
ATOM  2249  SG  CYS B 131    5.693   3.919 93.746 1.00 32.76   S
ATOM  2250  N   ALA B 132    2.237   7.332 94.339 1.00 29.93   N
ATOM  2251  CA  ALA B 132    0.959   7.975 94.110 1.00 31.40   C
ATOM  2252  C   ALA B 132    1.163   9.281 93.332 1.00 31.89   C
ATOM  2253  O   ALA B 132    0.409   9.583 92.410 1.00 32.31   O
ATOM  2254  CB  ALA B 132    0.286   8.251 95.427 1.00 30.62   C
ATOM  2255  N   ASP B 133    2.187  10.044 93.695 1.00 32.98   N
ATOM  2256  CA  ASP B 133    2.459  11.292 93.005 1.00 35.62   C
ATOM  2257  C   ASP B 133    2.791  11.055 91.545 1.00 36.66   C
ATOM  2258  O   ASP B 133    2.246  11.722 90.663 1.00 37.83   O
ATOM  2259  CB  ASP B 133    3.612  12.054 93.662 1.00 37.11   C
ATOM  2260  CG  ASP B 133    3.202  12.736 94.947 1.00 38.64   C
ATOM  2261  OD1 ASP B 133    2.028  13.170 95.052 1.00 39.37   O
ATOM  2262  OD2 ASP B 133    4.050  12.858 95.849 1.00 40.21   O
ATOM  2263  N   ARG B 134    3.691  10.117 91.282 1.00 37.48   N
ATOM  2264  CA  ARG B 134    4.064   9.783 89.908 1.00 38.09   C
ATOM  2265  C   ARG B 134    2.794   9.472 89.135 1.00 36.52   C
ATOM  2266  O   ARG B 134    2.585   9.976 88.034 1.00 37.99   O
ATOM  2267  CB  ARG B 134    4.963   8.549 89.883 1.00 41.14   C
ATOM  2268  CG  ARG B 134    6.206   8.649 90.748 1.00 44.82   C
ATOM  2269  CD  ARG B 134    6.614   7.270 91.281 1.00 47.86   C
ATOM  2270  NE  ARG B 134    7.848   7.315 92.062 1.00 48.00   N
ATOM  2271  CZ  ARG B 134    9.037   7.537 91.525 1.00 47.68   C
ATOM  2272  NH1 ARG B 134    9.125   7.722 90.215 1.00 48.22   N
ATOM  2273  NH2 ARG B 134   10.125   7.578 92.283 1.00 47.56   N
ATOM  2274  N   ILE B 135    1.952   8.622 89.712 1.00 33.49   N
ATOM  2275  CA  ILE B 135    0.698   8.245 89.076 1.00 31.24   C
ATOM  2276  C   ILE B 135   -0.140   9.495 88.769 1.00 30.81   C
ATOM  2277  O   ILE B 135   -0.653   9.657 87.666 1.00 30.33   O
ATOM  2278  CB  ILE B 135   -0.109   7.282 89.988 1.00 29.47   C
ATOM  2279  CG1 ILE B 135    0.680   5.983 90.187 1.00 27.46   C
ATOM  2280  CG2 ILE B 135   -1.474   6.987 89.316 1.00 27.90   C
ATOM  2281  CD1 ILE B 135    0.092   5.059 91.228 1.00 26.02   C
ATOM  2282  N   ILE B 136   -0.253  10.382 89.752 1.00 30.45   N
ATOM  2283  CA  ILE B 136   -1.022  11.610 89.603 1.00 30.68   C
ATOM  2284  C   ILE B 136   -0.440  12.518 88.510 1.00 32.06   C
ATOM  2285  O   ILE B 136   -1.170  13.070 87.674 1.00 31.72   O
ATOM  2286  CB  ILE B 136   -1.072  12.369 90.950 1.00 28.90   C
```

FIG. 7 (con't)

| | | | | | | |
|---|---|---|---|---|---|---|
| ATOM | 775 | CG2 ILE A 135 | 10.915 | -5.809 | 60.924 1.00 27.75 | C |
| ATOM | 776 | CD1 ILE A 135 | 8.199 | -5.761 | 59.448 1.00 27.14 | C |
| ATOM | 777 | N ILE A 136 | 13.227 | -3.451 | 59.215 1.00 27.77 | N |
| ATOM | 778 | CA ILE A 136 | 14.674 | -3.627 | 59.110 1.00 27.53 | C |
| ATOM | 779 | C ILE A 136 | 15.442 | -2.518 | 59.830 1.00 28.11 | C |
| ATOM | 780 | O ILE A 136 | 16.451 | -2.771 | 60.488 1.00 26.28 | O |
| ATOM | 781 | CB ILE A 136 | 15.117 | -3.680 | 57.629 1.00 26.65 | C |
| ATOM | 782 | CG1 ILE A 136 | 14.520 | -4.915 | 56.961 1.00 26.41 | C |
| ATOM | 783 | CG2 ILE A 136 | 16.641 | -3.749 | 57.536 1.00 25.54 | C |
| ATOM | 784 | CD1 ILE A 136 | 14.764 | -4.984 | 55.472 1.00 25.91 | C |
| ATOM | 785 | N LYS A 137 | 14.952 | -1.290 | 59.701 1.00 29.45 | N |
| ATOM | 786 | CA LYS A 137 | 15.596 | -0.170 | 60.361 1.00 31.31 | C |
| ATOM | 787 | C LYS A 137 | 15.402 | -0.218 | 61.868 1.00 31.84 | C |
| ATOM | 788 | O LYS A 137 | 16.213 | 0.321 | 62.605 1.00 31.84 | O |
| ATOM | 789 | CB LYS A 137 | 15.071 | 1.156 | 59.818 1.00 33.70 | C |
| ATOM | 790 | CG LYS A 137 | 15.645 | 1.532 | 58.462 1.00 39.43 | C |
| ATOM | 791 | CD LYS A 137 | 15.388 | 2.999 | 58.136 1.00 43.11 | C |
| ATOM | 792 | CE LYS A 137 | 16.000 | 3.406 | 56.799 1.00 45.83 | C |
| ATOM | 793 | NZ LYS A 137 | 15.793 | 4.861 | 56.510 1.00 48.23 | N |
| ATOM | 794 | N THR A 138 | 14.328 | -0.860 | 62.322 1.00 30.57 | N |
| ATOM | 795 | CA THR A 138 | 14.032 | -0.951 | 63.754 1.00 30.73 | C |
| ATOM | 796 | C THR A 138 | 14.922 | -2.020 | 64.403 1.00 30.12 | C |
| ATOM | 797 | O THR A 138 | 15.541 | -1.795 | 65.450 1.00 30.61 | O |
| ATOM | 798 | CB THR A 138 | 12.515 | -1.302 | 64.008 1.00 30.33 | C |
| ATOM | 799 | OG1 THR A 138 | 11.669 | -0.289 | 63.449 1.00 30.91 | O |
| ATOM | 800 | CG2 THR A 138 | 12.218 | -1.380 | 65.479 1.00 28.73 | C |
| ATOM | 801 | N LEU A 139 | 14.991 | -3.184 | 63.773 1.00 29.17 | N |
| ATOM | 802 | CA LEU A 139 | 15.783 | -4.281 | 64.295 1.00 28.33 | C |
| ATOM | 803 | C LEU A 139 | 17.247 | -3.894 | 64.327 1.00 30.34 | C |
| ATOM | 804 | O LEU A 139 | 18.014 | -4.361 | 65.176 1.00 31.18 | O |
| ATOM | 805 | CB LEU A 139 | 15.595 | -5.532 | 63.429 1.00 25.69 | C |
| ATOM | 806 | CG LEU A 139 | 14.240 | -6.248 | 63.490 1.00 24.30 | C |
| ATOM | 807 | CD1 LEU A 139 | 14.165 | -7.334 | 62.421 1.00 21.25 | C |
| ATOM | 808 | CD2 LEU A 139 | 14.045 | -6.845 | 64.875 1.00 22.30 | C |
| ATOM | 809 | N SER A 140 | 17.627 | -3.023 | 63.404 1.00 31.22 | N |
| ATOM | 810 | CA SER A 140 | 18.998 | -2.570 | 63.293 1.00 32.50 | C |
| ATOM | 811 | C SER A 140 | 19.363 | -1.595 | 64.404 1.00 33.09 | C |
| ATOM | 812 | O SER A 140 | 20.539 | -1.456 | 64.751 1.00 32.74 | O |
| ATOM | 813 | CB SER A 140 | 19.214 | -1.910 | 61.933 1.00 32.90 | C |
| ATOM | 814 | OG SER A 140 | 20.591 | -1.753 | 61.665 1.00 36.45 | O |
| ATOM | 815 | N LYS A 141 | 18.355 | -0.925 | 64.958 1.00 33.24 | N |
| ATOM | 816 | CA LYS A 141 | 18.571 | 0.028 | 66.033 1.00 34.11 | C |
| ATOM | 817 | C LYS A 141 | 18.419 | -0.661 | 67.377 1.00 32.46 | C |
| ATOM | 818 | O LYS A 141 | 18.945 | -0.193 | 68.371 1.00 33.08 | O |
| ATOM | 819 | CB LYS A 141 | 17.575 | 1.188 | 65.945 1.00 36.83 | C |
| ATOM | 820 | CG LYS A 141 | 17.646 | 1.960 | 64.639 1.00 40.47 | C |
| ATOM | 821 | CD LYS A 141 | 19.006 | 2.652 | 64.442 1.00 44.25 | C |
| ATOM | 822 | CE LYS A 141 | 19.230 | 3.861 | 65.378 1.00 45.65 | C |
| ATOM | 823 | NZ LYS A 141 | 20.507 | 4.615 | 65.089 1.00 45.95 | N |
| ATOM | 824 | N THR A 142 | 17.699 | -1.772 | 67.408 1.00 31.67 | N |
| ATOM | 825 | CA THR A 142 | 17.512 | -2.493 | 68.659 1.00 30.34 | C |
| ATOM | 826 | C THR A 142 | 18.053 | -3.906 | 68.519 1.00 28.69 | C |
| ATOM | 827 | O THR A 142 | 17.358 | -4.801 | 68.036 1.00 28.84 | O |
| ATOM | 828 | CB THR A 142 | 16.028 | -2.553 | 69.046 1.00 31.00 | C |
| ATOM | 829 | OG1 THR A 142 | 15.244 | -2.703 | 67.864 1.00 32.61 | O |
| ATOM | 830 | CG2 THR A 142 | 15.610 | -1.292 | 69.747 1.00 31.79 | C |
| ATOM | 831 | N LYS A 143 | 19.295 | -4.091 | 68.946 1.00 27.28 | N |
| ATOM | 832 | CA LYS A 143 | 19.968 | -5.379 | 68.862 1.00 26.57 | C |
| ATOM | 833 | C LYS A 143 | 19.382 | -6.377 | 69.844 1.00 24.70 | C |
| ATOM | 834 | O LYS A 143 | 19.449 | -7.589 | 69.626 1.00 24.78 | O |
| ATOM | 835 | CB LYS A 143 | 21.461 | -5.214 | 69.156 1.00 27.13 | C |
| ATOM | 836 | CG LYS A 143 | 22.188 | -4.191 | 68.298 1.00 27.80 | C |
| ATOM | 837 | CD LYS A 143 | 22.277 | -4.625 | 66.851 1.00 28.75 | C |
| ATOM | 838 | CE LYS A 143 | 23.135 | -3.656 | 66.055 1.00 28.49 | C |
| ATOM | 839 | NZ LYS A 143 | 23.275 | -4.094 | 64.642 1.00 29.43 | N |
| ATOM | 840 | N ASN A 144 | 18.813 | -5.862 | 70.926 1.00 21.82 | N |
| ATOM | 841 | CA ASN A 144 | 18.236 | -6.702 | 71.967 1.00 20.08 | C |
| ATOM | 842 | C ASN A 144 | 16.789 | -7.046 | 71.672 1.00 18.62 | C |
| ATOM | 843 | O ASN A 144 | 16.017 | -7.368 | 72.574 1.00 16.24 | O |
| ATOM | 844 | CB ASN A 144 | 18.352 | -5.999 | 73.321 1.00 20.53 | C |
| ATOM | 845 | CG ASN A 144 | 17.702 | -4.627 | 73.326 1.00 22.83 | C |
| ATOM | 846 | OD1 ASN A 144 | 17.656 | -3.942 | 72.302 1.00 23.33 | O |
| ATOM | 847 | ND2 ASN A 144 | 17.210 | -4.208 | 74.490 1.00 23.75 | N |
| ATOM | 848 | N LEU A 145 | 16.430 | -6.990 | 70.396 1.00 17.97 | N |
| ATOM | 849 | CA LEU A 145 | 15.070 | -7.296 | 69.974 1.00 17.00 | C |
| ATOM | 850 | C LEU A 145 | 15.061 | -8.408 | 68.934 1.00 16.69 | C |
| ATOM | 851 | O LEU A 145 | 15.667 | -8.253 | 67.882 1.00 16.00 | O |
| ATOM | 852 | CB LEU A 145 | 14.431 | -6.039 | 69.364 1.00 16.89 | C |
| ATOM | 853 | CG LEU A 145 | 13.170 | -6.234 | 68.495 1.00 15.84 | C |
| ATOM | 854 | CD1 LEU A 145 | 12.052 | -6.869 | 69.294 1.00 14.43 | C |
| ATOM | 855 | CD2 LEU A 145 | 12.722 | -4.880 | 67.968 1.00 16.07 | C |
| ATOM | 856 | N ARG A 146 | 14.394 | -9.515 | 69.235 1.00 16.48 | N |
| ATOM | 857 | CA ARG A 146 | 14.273 | -10.622 | 68.272 1.00 17.03 | C |
| ATOM | 858 | C ARG A 146 | 12.813 | -10.646 | 67.799 1.00 15.61 | C |
| ATOM | 859 | O ARG A 146 | 11.889 | -10.581 | 68.622 1.00 15.69 | O |
| ATOM | 860 | CB ARG A 146 | 14.627 | -11.952 | 68.935 1.00 19.21 | C |
| ATOM | 2287 | CG1 ILE B 136 | -1.927 | 11.589 | 91.948 1.00 27.80 | C |
| ATOM | 2288 | CG2 ILE B 136 | -1.638 | 13.753 | 90.764 1.00 29.12 | C |
| ATOM | 2289 | CD1 ILE B 136 | -1.834 | 12.103 | 93.356 1.00 26.90 | C |
| ATOM | 2290 | N LYS B 137 | 0.874 | 12.659 | 88.506 1.00 32.68 | N |
| ATOM | 2291 | CA LYS B 137 | 1.507 | 13.508 | 87.517 1.00 35.72 | C |
| ATOM | 2292 | C LYS B 137 | 1.298 | 12.973 | 86.105 1.00 35.76 | C |
| ATOM | 2293 | O LYS B 137 | 1.099 | 13.745 | 85.164 1.00 35.63 | O |
| ATOM | 2294 | CB LYS B 137 | 3.007 | 13.657 | 87.822 1.00 37.87 | C |
| ATOM | 2295 | CG LYS B 137 | 3.293 | 14.233 | 89.218 1.00 41.24 | C |
| ATOM | 2296 | CD LYS B 137 | 4.701 | 14.825 | 89.350 1.00 42.17 | C |
| ATOM | 2297 | CE LYS B 137 | 4.902 | 15.485 | 90.717 1.00 45.82 | C |
| ATOM | 2298 | NZ LYS B 137 | 6.179 | 16.245 | 90.796 1.00 45.43 | N |
| ATOM | 2299 | N THR B 138 | 1.335 | 11.651 | 85.962 1.00 35.39 | N |
| ATOM | 2300 | CA THR B 138 | 1.129 | 11.019 | 84.666 1.00 35.04 | C |
| ATOM | 2301 | C THR B 138 | -0.340 | 11.174 | 84.266 1.00 33.96 | C |
| ATOM | 2302 | O THR B 138 | -0.642 | 11.537 | 83.138 1.00 32.49 | O |
| ATOM | 2303 | CB THR B 138 | 1.494 | 9.523 | 84.710 1.00 34.86 | C |
| ATOM | 2304 | OG1 THR B 138 | 2.878 | 9.380 | 85.029 1.00 34.79 | O |
| ATOM | 2305 | CG2 THR B 138 | 1.236 | 8.877 | 83.361 1.00 34.43 | C |
| ATOM | 2306 | N LEU B 139 | -1.237 | 10.892 | 85.205 1.00 34.40 | N |
| ATOM | 2307 | CA LEU B 139 | -2.662 | 11.026 | 84.952 1.00 35.51 | C |
| ATOM | 2308 | C LEU B 139 | -2.976 | 12.474 | 84.590 1.00 36.91 | C |
| ATOM | 2309 | O LEU B 139 | -3.926 | 12.746 | 83.862 1.00 37.56 | O |
| ATOM | 2310 | CB LEU B 139 | -3.470 | 10.624 | 86.185 1.00 34.03 | C |
| ATOM | 2311 | CG LEU B 139 | -3.743 | 9.139 | 86.390 1.00 33.41 | C |
| ATOM | 2312 | CD1 LEU B 139 | -4.416 | 8.898 | 87.737 1.00 32.54 | C |
| ATOM | 2313 | CD2 LEU B 139 | -4.627 | 8.659 | 85.263 1.00 33.87 | C |
| ATOM | 2314 | N SER B 140 | -2.170 | 13.397 | 85.108 1.00 38.70 | N |
| ATOM | 2315 | CA SER B 140 | -2.345 | 14.823 | 84.850 1.00 40.17 | C |
| ATOM | 2316 | C SER B 140 | -1.921 | 15.192 | 83.421 1.00 40.74 | C |
| ATOM | 2317 | O SER B 140 | -2.573 | 15.999 | 82.749 1.00 39.59 | O |
| ATOM | 2318 | CB SER B 140 | -1.538 | 15.628 | 85.859 1.00 41.74 | C |
| ATOM | 2319 | OG SER B 140 | -1.453 | 16.987 | 85.466 1.00 43.44 | O |
| ATOM | 2320 | N LYS B 141 | -0.822 | 14.602 | 82.970 1.00 42.10 | N |
| ATOM | 2321 | CA LYS B 141 | -0.324 | 14.843 | 81.622 1.00 43.45 | C |
| ATOM | 2322 | C LYS B 141 | -1.271 | 14.301 | 80.559 1.00 43.29 | C |
| ATOM | 2323 | O LYS B 141 | -1.801 | 15.066 | 79.763 1.00 44.45 | O |
| ATOM | 2324 | CB LYS B 141 | 1.048 | 14.195 | 81.423 1.00 44.76 | C |
| ATOM | 2325 | CG LYS B 141 | 2.173 | 14.873 | 82.168 1.00 47.52 | C |
| ATOM | 2326 | CD LYS B 141 | 3.488 | 14.131 | 81.968 1.00 50.79 | C |
| ATOM | 2327 | CE LYS B 141 | 4.652 | 14.809 | 82.706 1.00 52.67 | C |
| ATOM | 2328 | NZ LYS B 141 | 5.036 | 16.149 | 82.151 1.00 54.39 | N |
| ATOM | 2329 | N THR B 142 | -1.482 | 12.983 | 80.538 1.00 42.75 | N |
| ATOM | 2330 | CA THR B 142 | -2.359 | 12.355 | 79.544 1.00 42.17 | C |
| ATOM | 2331 | C THR B 142 | -3.813 | 12.336 | 80.008 1.00 41.50 | C |
| ATOM | 2332 | O THR B 142 | -4.161 | 11.627 | 80.952 1.00 42.71 | O |
| ATOM | 2333 | CB THR B 142 | -1.927 | 10.903 | 79.258 1.00 41.90 | C |
| ATOM | 2334 | OG1 THR B 142 | -2.305 | 10.076 | 80.358 1.00 44.46 | O |
| ATOM | 2335 | CG2 THR B 142 | -0.421 | 10.816 | 79.098 1.00 42.21 | C |
| ATOM | 2336 | N LYS B 143 | -4.660 | 13.109 | 79.338 1.00 40.08 | N |
| ATOM | 2337 | CA LYS B 143 | -6.070 | 13.189 | 79.701 1.00 38.21 | C |
| ATOM | 2338 | C LYS B 143 | -6.869 | 12.077 | 79.060 1.00 35.50 | C |
| ATOM | 2339 | O LYS B 143 | -8.017 | 11.833 | 79.421 1.00 33.75 | O |
| ATOM | 2340 | CB LYS B 143 | -6.661 | 14.540 | 79.265 1.00 40.79 | C |
| ATOM | 2341 | CG LYS B 143 | -5.993 | 15.776 | 79.869 1.00 43.12 | C |
| ATOM | 2342 | CD LYS B 143 | -4.890 | 16.338 | 78.970 1.00 46.16 | C |
| ATOM | 2343 | CE LYS B 143 | -4.301 | 17.631 | 79.528 1.00 48.14 | C |
| ATOM | 2344 | NZ LYS B 143 | -5.343 | 18.665 | 79.813 1.00 48.76 | N |
| ATOM | 2345 | N ASN B 144 | -6.257 | 11.400 | 78.097 1.00 34.11 | N |
| ATOM | 2346 | CA ASN B 144 | -6.936 | 10.314 | 77.405 1.00 31.65 | C |
| ATOM | 2347 | C ASN B 144 | -6.702 | 8.979 | 78.094 1.00 30.66 | C |
| ATOM | 2348 | O ASN B 144 | -7.057 | 7.938 | 77.552 1.00 30.15 | O |
| ATOM | 2349 | CB ASN B 144 | -6.468 | 10.230 | 75.965 1.00 31.74 | C |
| ATOM | 2350 | CG ASN B 144 | -4.977 | 9.983 | 75.844 1.00 31.40 | C |
| ATOM | 2351 | OD1 ASN B 144 | -4.496 | 9.617 | 74.773 1.00 31.14 | O |
| ATOM | 2352 | ND2 ASN B 144 | -4.241 | 10.185 | 76.930 1.00 29.98 | N |
| ATOM | 2353 | N LEU B 145 | -6.102 | 9.027 | 79.285 1.00 29.02 | N |
| ATOM | 2354 | CA LEU B 145 | -5.794 | 8.080 | 80.075 1.00 27.76 | C |
| ATOM | 2355 | C LEU B 145 | -6.658 | 7.733 | 81.334 1.00 27.57 | C |
| ATOM | 2356 | O LEU B 145 | -6.814 | 8.705 | 82.072 1.00 27.04 | O |
| ATOM | 2357 | CB LEU B 145 | -4.326 | 7.861 | 80.497 1.00 28.45 | C |
| ATOM | 2358 | CG LEU B 145 | -3.873 | 6.823 | 81.534 1.00 28.94 | C |
| ATOM | 2359 | CD1 LEU B 145 | -3.750 | 5.460 | 80.890 1.00 29.85 | C |
| ATOM | 2360 | CD2 LEU B 145 | -2.532 | 7.231 | 82.100 1.00 28.94 | C |
| ATOM | 2361 | N ARG B 146 | -7.196 | 6.541 | 81.588 1.00 26.96 | N |
| ATOM | 2362 | CA ARG B 146 | -8.031 | 6.290 | 82.760 1.00 26.21 | C |
| ATOM | 2363 | C ARG B 146 | -7.457 | 5.065 | 83.464 1.00 25.46 | C |
| ATOM | 2364 | O ARG B 146 | -7.346 | 4.002 | 82.862 1.00 25.45 | O |
| ATOM | 2365 | CB ARG B 146 | -9.474 | 6.019 | 82.337 1.00 27.96 | C |
| ATOM | 2366 | CG ARG B 146 | -10.521 | 6.703 | 83.214 1.00 29.77 | C |
| ATOM | 2367 | CD ARG B 146 | -11.108 | 7.951 | 82.562 1.00 29.46 | C |
| ATOM | 2368 | NE ARG B 146 | -10.091 | 8.955 | 82.261 1.00 30.14 | N |
| ATOM | 2369 | CZ ARG B 146 | -10.346 | 10.135 | 81.702 1.00 28.25 | C |
| ATOM | 2370 | NH1 ARG B 146 | -11.586 | 10.455 | 81.384 1.00 27.95 | N |
| ATOM | 2371 | NH2 ARG B 146 | -9.360 | 10.980 | 81.453 1.00 28.19 | N |
| ATOM | 2372 | N LEU B 147 | -7.104 | 5.210 | 84.744 1.00 24.29 | N |

FIG. 7 (con't)

```
ATOM    861  CG  ARG A 146    14.568 -13.132  67.997  1.00 24.03    C
ATOM    862  CD  ARG A 146    14.865 -14.443  68.721  1.00 28.94    C
ATOM    863  NE  ARG A 146    15.194 -15.531  67.791  1.00 32.64    N
ATOM    864  CZ  ARG A 146    14.373 -16.051  66.872  1.00 34.91    C
ATOM    865  NH1 ARG A 146    13.127 -15.612  66.725  1.00 32.12    N
ATOM    866  NH2 ARG A 146    14.824 -17.005  66.063  1.00 34.18    N
ATOM    867  N   LEU A 147    12.599 -10.736  66.491  1.00 12.70    N
ATOM    868  CA  LEU A 147    11.247 -10.717  65.943  1.00 10.85    C
ATOM    869  C   LEU A 147    10.882 -11.969  65.120  1.00  9.49    C
ATOM    870  O   LEU A 147    11.653 -12.438  64.300  1.00  7.48    O
ATOM    871  CB  LEU A 147    11.044  -9.447  65.091  1.00  9.95    C
ATOM    872  CG  LEU A 147     9.647  -9.236  64.447  1.00  9.67    C
ATOM    873  CD1 LEU A 147     8.635  -9.077  65.544  1.00  8.41    C
ATOM    874  CD2 LEU A 147     9.593  -8.016  63.552  1.00  5.99    C
ATOM    875  N   LEU A 148     9.692 -12.504  65.373  1.00  9.19    N
ATOM    876  CA  LEU A 148     9.230 -13.675  64.662  1.00  9.00    C
ATOM    877  C   LEU A 148     7.878 -13.326  64.104  1.00  9.20    C
ATOM    878  O   LEU A 148     6.950 -13.078  64.873  1.00 11.01    O
ATOM    879  CB  LEU A 148     9.077 -14.860  65.604  1.00 10.33    C
ATOM    880  CG  LEU A 148     8.230 -16.050  65.088  1.00 10.56    C
ATOM    881  CD1 LEU A 148     8.841 -16.613  63.825  1.00  9.10    C
ATOM    882  CD2 LEU A 148     8.187 -17.133  66.143  1.00 11.52    C
ATOM    883  N   ILE A 149     7.753 -13.301  62.785  1.00  8.64    N
ATOM    884  CA  ILE A 149     6.489 -12.963  62.165  1.00  9.20    C
ATOM    885  C   ILE A 149     5.856 -14.200  61.520  1.00  9.56    C
ATOM    886  O   ILE A 149     6.428 -14.776  60.597  1.00  9.65    O
ATOM    887  CB  ILE A 149     6.651 -11.875  61.058  1.00  8.35    C
ATOM    888  CG1 ILE A 149     7.413 -10.661  61.600  1.00 10.66    C
ATOM    889  CG2 ILE A 149     5.296 -11.378  60.619  1.00  7.82    C
ATOM    890  CD1 ILE A 149     7.611  -9.529  60.579  1.00  5.95    C
ATOM    891  N   LEU A 150     4.687 -14.605  62.024  1.00 10.12    N
ATOM    892  CA  LEU A 150     3.933 -15.744  61.483  1.00 10.54    C
ATOM    893  C   LEU A 150     2.753 -15.206  60.656  1.00 11.69    C
ATOM    894  O   LEU A 150     1.836 -14.576  61.197  1.00 12.15    O
ATOM    895  CB  LEU A 150     3.432 -16.649  62.607  1.00  8.05    C
ATOM    896  CG  LEU A 150     4.502 -17.414  63.395  1.00 10.15    C
ATOM    897  CD1 LEU A 150     3.850 -18.297  64.421  1.00 14.11    C
ATOM    898  CD2 LEU A 150     5.324 -18.279  62.481  1.00 10.62    C
ATOM    899  N   VAL A 151     2.765 -15.466  59.347  1.00 11.63    N
ATOM    900  CA  VAL A 151     1.717 -14.974  58.446  1.00 11.45    C
ATOM    901  C   VAL A 151     0.764 -16.051  57.953  1.00 11.20    C
ATOM    902  O   VAL A 151     1.159 -17.198  57.796  1.00 11.78    O
ATOM    903  CB  VAL A 151     2.349 -14.282  57.177  1.00 12.48    C
ATOM    904  CG1 VAL A 151     3.324 -13.180  57.607  1.00 10.25    C
ATOM    905  CG2 VAL A 151     3.047 -15.326  56.280  1.00 10.68    C
ATOM    906  N   GLY A 152    -0.492 -15.677  57.703  1.00 11.01    N
ATOM    907  CA  GLY A 152    -1.477 -16.638  57.219  1.00 12.05    C
ATOM    908  C   GLY A 152    -1.152 -17.036  55.794  1.00 13.47    C
ATOM    909  O   GLY A 152    -1.331 -18.190  55.392  1.00 13.66    O
ATOM    910  N   ARG A 153     0.688 -16.061  55.020  1.00 14.21    N
ATOM    911  CA  ARG A 153    -0.282 -16.303  53.644  1.00 16.23    C
ATOM    912  C   ARG A 153     0.666 -15.197  53.178  1.00 17.21    C
ATOM    913  O   ARG A 153     0.937 -14.247  53.909  1.00 18.17    O
ATOM    914  CB  ARG A 153    -1.508 -16.371  52.725  1.00 18.09    C
ATOM    915  CG  ARG A 153    -2.280 -15.073  52.616  1.00 18.56    C
ATOM    916  CD  ARG A 153    -3.178 -15.123  51.407  1.00 20.48    C
ATOM    917  NE  ARG A 153    -4.129 -14.020  51.345  1.00 23.75    N
ATOM    918  CZ  ARG A 153    -3.825 -12.756  51.064  1.00 23.54    C
ATOM    919  NH1 ARG A 153    -2.573 -12.397  50.807  1.00 24.38    N
ATOM    920  NH2 ARG A 153    -4.792 -11.849  51.022  1.00 24.43    N
ATOM    921  N   LEU A 154     1.192 -15.333  51.971  1.00 18.41    N
ATOM    922  CA  LEU A 154     2.103 -14.337  51.424  1.00 18.83    C
ATOM    923  C   LEU A 154     1.341 -13.247  50.674  1.00 19.96    C
ATOM    924  O   LEU A 154     0.268 -13.492  50.118  1.00 20.86    O
ATOM    925  CB  LEU A 154     3.105 -15.011  50.489  1.00 18.36    C
ATOM    926  CG  LEU A 154     4.491 -15.351  51.036  1.00 17.98    C
ATOM    927  CD1 LEU A 154     4.422 -15.661  52.518  1.00 17.77    C
ATOM    928  CD2 LEU A 154     5.068 -16.508  50.231  1.00 18.19    C
ATOM    929  N   PHE A 155     1.910 -12.046  50.665  1.00 20.98    N
ATOM    930  CA  PHE A 155     1.320 -10.887  49.998  1.00 20.88    C
ATOM    931  C   PHE A 155     2.172 -10.479  48.793  1.00 21.47    C
ATOM    932  O   PHE A 155     3.349 -10.151  48.946  1.00 21.49    O
ATOM    933  CB  PHE A 155     1.240  -9.733  50.985  1.00 19.60    C
ATOM    934  CG  PHE A 155     0.755  -8.464  50.376  1.00 19.16    C
ATOM    935  CD1 PHE A 155    -0.521  -8.380  49.862  1.00 16.14    C
ATOM    936  CD2 PHE A 155     1.581  -7.339  50.325  1.00 18.69    C
ATOM    937  CE1 PHE A 155    -0.984  -7.203  49.305  1.00 14.95    C
ATOM    938  CE2 PHE A 155     1.121  -6.150  49.765  1.00 17.26    C
ATOM    939  CZ  PHE A 155    -0.163  -6.085  49.256  1.00 16.12    C
ATOM    940  N   MET A 156     1.562 -10.476  47.609  1.00 22.57    N
ATOM    941  CA  MET A 156     2.263 -10.143  46.366  1.00 23.38    C
ATOM    942  C   MET A 156     3.595 -10.870  46.309  1.00 23.86    C
ATOM    943  O   MET A 156     4.602 -10.301  45.889  1.00 23.96    O
ATOM    944  CB  MET A 156     2.525  -8.648  46.267  1.00 23.99    C
ATOM    945  CG  MET A 156     1.297  -7.796  46.275  1.00 26.95    C
ATOM    946  SD  MET A 156     1.682  -6.167  45.590  1.00 29.35    S

ATOM   2373  CA  LEU B 147    -6.496   4.127  85.505  1.00 21.79    C
ATOM   2374  C   LEU B 147    -7.366   3.543  86.617  1.00 20.79    C
ATOM   2375  O   LEU B 147    -8.088   4.261  87.299  1.00 20.53    O
ATOM   2376  CB  LEU B 147    -5.168   4.601  86.098  1.00 21.66    C
ATOM   2377  CG  LEU B 147    -4.371   3.566  86.901  1.00 21.65    C
ATOM   2378  CD1 LEU B 147    -4.022   2.396  85.997  1.00 21.64    C
ATOM   2379  CD2 LEU B 147    -3.110   4.195  87.472  1.00 19.04    C
ATOM   2380  N   LEU B 148    -7.261   2.221  86.783  1.00 19.06    N
ATOM   2381  CA  LEU B 148    -7.996   1.465  87.788  1.00 15.72    C
ATOM   2382  C   LEU B 148    -7.025   0.553  88.525  1.00 16.09    C
ATOM   2383  O   LEU B 148    -6.465  -0.382  87.946  1.00 15.26    O
ATOM   2384  CB  LEU B 148    -9.078   0.616  87.127  1.00 14.89    C
ATOM   2385  CG  LEU B 148    -9.660  -0.531  87.972  1.00 14.68    C
ATOM   2386  CD1 LEU B 148   -10.299   0.089  89.246  1.00 14.36    C
ATOM   2387  CD2 LEU B 148   -10.688  -1.282  87.151  1.00 13.45    C
ATOM   2388  N   ILE B 149    -6.826   0.818  89.806  1.00 14.70    N
ATOM   2389  CA  ILE B 149    -5.917   0.005  90.581  1.00 14.28    C
ATOM   2390  C   ILE B 149    -6.664  -0.922  91.534  1.00 15.06    C
ATOM   2391  O   ILE B 149    -7.431  -0.475  92.382  1.00 15.28    O
ATOM   2392  CB  ILE B 149    -4.968   0.888  91.390  1.00 14.06    C
ATOM   2393  CG1 ILE B 149    -4.332   1.936  90.471  1.00 14.16    C
ATOM   2394  CG2 ILE B 149    -3.868   0.058  91.981  1.00 12.52    C
ATOM   2395  CD1 ILE B 149    -3.366   2.818  91.182  1.00 12.01    C
ATOM   2396  N   LEU B 150    -6.446  -2.223  91.377  1.00 15.28    N
ATOM   2397  CA  LEU B 150    -7.071  -3.215  92.239  1.00 15.89    C
ATOM   2398  C   LEU B 150    -6.003  -3.785  93.202  1.00 16.63    C
ATOM   2399  O   LEU B 150    -5.248  -4.680  92.840  1.00 19.24    O
ATOM   2400  CB  LEU B 150    -7.675  -4.325  91.378  1.00 15.36    C
ATOM   2401  CG  LEU B 150    -8.906  -3.901  90.569  1.00 18.61    C
ATOM   2402  CD1 LEU B 150    -9.327  -5.019  89.629  1.00 18.25    C
ATOM   2403  CD2 LEU B 150   -10.044  -3.567  91.530  1.00 18.95    C
ATOM   2404  N   VAL B 151    -5.937  -3.270  94.420  1.00 16.49    N
ATOM   2405  CA  VAL B 151    -4.928  -3.735  95.371  1.00 15.56    C
ATOM   2406  C   VAL B 151    -5.398  -4.909  96.231  1.00 16.31    C
ATOM   2407  O   VAL B 151    -6.591  -5.039  96.511  1.00 16.59    O
ATOM   2408  CB  VAL B 151    -4.524  -2.589  96.280  1.00 12.13    C
ATOM   2409  CG1 VAL B 151    -4.213  -1.380  95.432  1.00  9.75    C
ATOM   2410  CG2 VAL B 151    -5.663  -2.259  97.228  1.00 11.08    C
ATOM   2411  N   GLY B 152    -4.462  -5.759  96.648  1.00 17.30    N
ATOM   2412  CA  GLY B 152    -4.800  -6.903  97.488  1.00 17.76    C
ATOM   2413  C   GLY B 152    -4.986  -6.472  98.932  1.00 19.59    C
ATOM   2414  O   GLY B 152    -5.694  -7.100  99.725  1.00 16.62    O
ATOM   2415  N   ARG B 153    -4.327  -5.371  99.275  1.00 20.99    N
ATOM   2416  CA  ARG B 153    -4.417  -4.835 100.616  1.00 22.11    C
ATOM   2417  C   ARG B 153    -3.953  -3.389 100.602  1.00 20.94    C
ATOM   2418  O   ARG B 153    -3.360  -2.928  99.633  1.00 19.83    O
ATOM   2419  CB  ARG B 153    -3.542  -5.639 101.565  1.00 25.36    C
ATOM   2420  CG  ARG B 153    -2.065  -5.461 101.287  1.00 31.57    C
ATOM   2421  CD  ARG B 153    -1.213  -6.276 102.253  1.00 36.23    C
ATOM   2422  NE  ARG B 153     0.210  -5.945 102.117  1.00 41.06    N
ATOM   2423  CZ  ARG B 153     1.042  -5.788 103.146  1.00 42.13    C
ATOM   2424  NH1 ARG B 153     0.602  -5.942 104.389  1.00 40.06    N
ATOM   2425  NH2 ARG B 153     2.306  -5.436 102.927  1.00 42.40    N
ATOM   2426  N   LEU B 154    -4.221  -2.678 101.690  1.00 20.33    N
ATOM   2427  CA  LEU B 154    -3.814  -1.286 101.795  1.00 20.87    C
ATOM   2428  C   LEU B 154    -2.421  -1.166 102.402  1.00 21.95    C
ATOM   2429  O   LEU B 154     2.180  -1.604 103.528  1.00 20.15    O
ATOM   2430  CB  LEU B 154    -4.820  -0.519 102.637  1.00 20.32    C
ATOM   2431  CG  LEU B 154    -5.528   0.630 101.934  1.00 20.10    C
ATOM   2432  CD1 LEU B 154    -5.810   0.220 100.515  1.00 17.57    C
ATOM   2433  CD2 LEU B 154    -6.815   0.985 102.669  1.00 19.17    C
ATOM   2434  N   PHE B 155    -1.517  -0.561 101.637  1.00 23.13    N
ATOM   2435  CA  PHE B 155    -0.134  -0.375 102.064  1.00 24.44    C
ATOM   2436  C   PHE B 155    -0.026   0.732 103.090  1.00 24.13    C
ATOM   2437  O   PHE B 155    -0.103   1.918 102.748  1.00 24.25    O
ATOM   2438  CB  PHE B 155     0.745  -0.026 100.851  1.00 26.25    C
ATOM   2439  CG  PHE B 155     2.224   0.065 101.170  1.00 25.81    C
ATOM   2440  CD1 PHE B 155     2.942  -1.075 101.510  1.00 26.50    C
ATOM   2441  CD2 PHE B 155     2.902   1.285 101.094  1.00 27.32    C
ATOM   2442  CE1 PHE B 155     4.322  -1.019 101.762  1.00 25.85    C
ATOM   2443  CE2 PHE B 155     4.291   1.358 101.350  1.00 26.84    C
ATOM   2444  CZ  PHE B 155     4.996   0.200 101.679  1.00 26.23    C
ATOM   2445  N   MET B 156     0.149   0.342 104.343  1.00 25.15    N
ATOM   2446  CA  MET B 156     0.279   1.281 105.448  1.00 25.67    C
ATOM   2447  C   MET B 156    -0.818   2.343 105.487  1.00 25.77    C
ATOM   2448  O   MET B 156    -0.538   3.545 105.470  1.00 24.32    O
ATOM   2449  CB  MET B 156     1.647   1.961 105.385  1.00 26.82    C
ATOM   2450  CG  MET B 156     2.817   1.019 105.629  1.00 28.39    C
ATOM   2451  SD  MET B 156     4.430   1.843 105.481  1.00 32.72    S
ATOM   2452  CE  MET B 156     5.482   0.656 106.223  1.00 30.63    C
ATOM   2453  N   TRP B 157    -2.064   1.881 105.550  1.00 25.51    N
ATOM   2454  CA  TRP B 157    -3.226   2.756 105.595  1.00 25.32    C
ATOM   2455  C   TRP B 157    -3.266   3.612 106.857  1.00 26.75    C
ATOM   2456  O   TRP B 157    -3.969   4.615 106.897  1.00 26.48    O
ATOM   2457  CB  TRP B 157    -4.509   1.928 105.526  1.00 24.55    C
ATOM   2458  CG  TRP B 157    -4.661   0.949 106.659  1.00 23.68    C
```

FIG. 7 (con't)

```
ATOM    947  CE  MET A 156      2.577  -5.461  46.847  1.00 28.03      C
ATOM    948  N   TRP A 157      3.610 -12.132  46.730  1.00 24.70      N
ATOM    949  CA  TRP A 157      4.856 -12.899  46.741  1.00 27.04      C
ATOM    950  C   TRP A 157      5.566 -13.003  45.389  1.00 28.65      C
ATOM    951  O   TRP A 157      6.796 -13.024  45.330  1.00 30.30      O
ATOM    952  CB  TRP A 157      4.609 -14.299  47.272  1.00 25.35      C
ATOM    953  CG  TRP A 157      3.794 -15.107  46.387  1.00 25.33      C
ATOM    954  CD1 TRP A 157      2.440 -15.175  46.370  1.00 25.36      C
ATOM    955  CD2 TRP A 157      4.262 -16.038  45.405  1.00 25.45      C
ATOM    956  NE1 TRP A 157      2.027 -16.097  45.441  1.00 26.01      N
ATOM    957  CE2 TRP A 157      3.124 -16.637  44.831  1.00 26.09      C
ATOM    958  CE3 TRP A 157      5.532 -16.413  44.951  1.00 26.55      C
ATOM    959  CZ2 TRP A 157      3.213 -17.613  43.840  1.00 26.76      C
ATOM    960  CZ3 TRP A 157      5.626 -17.384  43.956  1.00 26.18      C
ATOM    961  CH2 TRP A 157      4.469 -17.965  43.410  1.00 27.75      C
ATOM    962  N   GLU A 158      4.788 -13.072  44.312  1.00 31.14      N
ATOM    963  CA  GLU A 158      5.336 -13.183  42.968  1.00 30.86      C
ATOM    964  C   GLU A 158      6.114 -11.944  42.519  1.00 29.33      C
ATOM    965  O   GLU A 158      7.014 -12.040  41.682  1.00 29.42      O
ATOM    966  CB  GLU A 158      4.212 -13.496  41.963  1.00 32.67      C
ATOM    967  CG  GLU A 158      2.972 -12.617  42.094  1.00 36.58      C
ATOM    968  CD  GLU A 158      1.913 -13.237  42.955  1.00 36.70      C
ATOM    969  OE1 GLU A 158      1.829 -12.911  44.165  1.00 37.61      O
ATOM    970  OE2 GLU A 158      1.178 -14.081  42.393  1.00 37.46      O
ATOM    971  N   GLU A 159      5.795 -10.779  43.072  1.00 28.03      N
ATOM    972  CA  GLU A 159      6.492  -9.557  42.679  1.00 26.60      C
ATOM    973  C   GLU A 159      7.945  -9.507  43.155  1.00 26.46      C
ATOM    974  O   GLU A 159      8.253  -9.801  44.309  1.00 26.25      O
ATOM    975  CB  GLU A 159      5.739  -8.330  43.190  1.00 25.49      C
ATOM    976  CG  GLU A 159      4.291  -8.265  42.719  1.00 24.92      C
ATOM    977  CD  GLU A 159      4.126  -8.441  41.214  1.00 25.00      C
ATOM    978  OE1 GLU A 159      4.706  -7.652  40.435  1.00 24.10      O
ATOM    979  OE2 GLU A 159      3.398  -9.380  40.807  1.00 26.07      O
ATOM    980  N   PRO A 160      8.866  -9.130  42.258  1.00 26.09      N
ATOM    981  CA  PRO A 160     10.281  -9.051  42.624  1.00 25.59      C
ATOM    982  C   PRO A 160     10.586  -8.029  43.713  1.00 24.98      C
ATOM    983  O   PRO A 160     11.552  -8.189  44.471  1.00 25.95      O
ATOM    984  CB  PRO A 160     10.956  -8.715  41.296  1.00 25.48      C
ATOM    985  CG  PRO A 160      9.900  -7.934  40.577  1.00 25.14      C
ATOM    986  CD  PRO A 160      8.666  -8.746  40.847  1.00 24.60      C
ATOM    987  N   GLU A 161      9.785  -6.982  43.802  1.00 23.99      N
ATOM    988  CA  GLU A 161     10.022  -5.972  44.830  1.00 23.98      C
ATOM    989  C   GLU A 161      9.806  -6.580  46.205  1.00 22.39      C
ATOM    990  O   GLU A 161     10.596  -6.363  47.118  1.00 22.10      O
ATOM    991  CB  GLU A 161      9.065  -4.788  44.675  1.00 25.40      C
ATOM    992  CG  GLU A 161      9.422  -3.777  43.602  1.00 26.04      C
ATOM    993  CD  GLU A 161      9.464  -4.357  42.202  1.00 27.64      C
ATOM    994  OE1 GLU A 161      8.656  -5.257  41.885  1.00 28.55      O
ATOM    995  OE2 GLU A 161     10.305  -3.888  41.409  1.00 30.68      O
ATOM    996  N   ILE A 162      8.721  -7.333  46.346  1.00 20.89      N
ATOM    997  CA  ILE A 162      8.388  -7.968  47.609  1.00 19.10      C
ATOM    998  C   ILE A 162      9.440  -9.014  47.982  1.00 19.76      C
ATOM    999  O   ILE A 162      9.856  -9.110  49.144  1.00 19.28      O
ATOM   1000  CB  ILE A 162      6.982  -8.624  47.528  1.00 17.30      C
ATOM   1001  CG1 ILE A 162      5.934  -7.545  47.240  1.00 17.11      C
ATOM   1002  CG2 ILE A 162      6.621  -9.323  48.825  1.00 14.85      C
ATOM   1003  CD1 ILE A 162      5.804  -6.510  48.348  1.00 15.95      C
ATOM   1004  N   GLN A 163      9.883  -9.779  46.989  1.00 18.99      N
ATOM   1005  CA  GLN A 163     10.870 -10.823  47.220  1.00 19.77      C
ATOM   1006  C   GLN A 163     12.178 -10.262  47.714  1.00 19.64      C
ATOM   1007  O   GLN A 163     12.851 -10.857  48.556  1.00 20.89      O
ATOM   1008  CB  GLN A 163     11.099 -11.651  45.949  1.00 19.69      C
ATOM   1009  CG  GLN A 163      9.959 -12.608  45.651  1.00 20.76      C
ATOM   1010  CD  GLN A 163     10.224 -13.518  44.477  1.00 20.36      C
ATOM   1011  OE1 GLN A 163     11.353 -13.973  44.272  1.00 23.17      O
ATOM   1012  NE2 GLN A 163      9.189 -13.810  43.711  1.00 21.56      N
ATOM   1013  N   ALA A 164     12.550  -9.105  47.199  1.00 20.11      N
ATOM   1014  CA  ALA A 164     13.793  -8.488  47.617  1.00 18.05      C
ATOM   1015  C   ALA A 164     13.653  -8.024  49.055  1.00 18.24      C
ATOM   1016  O   ALA A 164     14.574  -8.142  49.873  1.00 19.10      O
ATOM   1017  CB  ALA A 164     14.107  -7.325  46.716  1.00 16.51      C
ATOM   1018  N   ALA A 165     12.483  -7.502  49.379  1.00 16.67      N
ATOM   1019  CA  ALA A 165     12.254  -7.012  50.724  1.00 16.07      C
ATOM   1020  C   ALA A 165     12.256  -8.145  51.770  1.00 16.35      C
ATOM   1021  O   ALA A 165     12.763  -7.969  52.879  1.00 15.23      O
ATOM   1022  CB  ALA A 165     10.961  -6.240  50.746  1.00 13.13      C
ATOM   1023  N   LEU A 166     11.707  -9.304  51.398  1.00 17.26      N
ATOM   1024  CA  LEU A 166     11.666 -10.459  52.296  1.00 18.54      C
ATOM   1025  C   LEU A 166     13.067 -11.003  52.576  1.00 19.58      C
ATOM   1026  O   LEU A 166     13.351 -11.447  53.683  1.00 18.09      O
ATOM   1027  CB  LEU A 166     10.794 -11.578  51.713  1.00 18.23      C
ATOM   1028  CG  LEU A 166      9.287 -11.252  51.607  1.00 19.45      C
ATOM   1029  CD1 LEU A 166      8.534 -12.452  51.116  1.00 19.88      C
ATOM   1030  CD2 LEU A 166      8.741 -10.876  52.953  1.00 18.88      C
ATOM   1031  N   LYS A 167     13.943 -10.968  51.569  1.00 20.96      N
ATOM   1032  CA  LYS A 167     15.310 -11.450  51.743  1.00 22.76      C

ATOM   2459  CD1 TRP B 157     -4.102  -0.301 106.753  1.00 22.81      C
ATOM   2460  CD2 TRP B 157     -5.454   1.124 107.840  1.00 23.50      C
ATOM   2461  NE1 TRP B 157     -4.504  -0.910 107.917  1.00 23.45      N
ATOM   2462  CE2 TRP B 157     -5.326  -0.060 108.607  1.00 22.56      C
ATOM   2463  CE3 TRP B 157     -6.244   2.169 108.328  1.00 23.04      C
ATOM   2464  CZ2 TRP B 157     -5.981  -0.231 109.825  1.00 22.23      C
ATOM   2465  CZ3 TRP B 157     -6.897   1.998 109.545  1.00 22.69      C
ATOM   2466  CH2 TRP B 157     -6.753   0.806 110.282  1.00 23.45      C
ATOM   2467  N   GLU B 158     -2.527   3.208 107.890  1.00 28.38      N
ATOM   2468  CA  GLU B 158     -2.495   3.964 109.140  1.00 28.90      C
ATOM   2469  C   GLU B 158     -1.742   5.296 109.002  1.00 30.21      C
ATOM   2470  O   GLU B 158     -2.019   6.249 109.731  1.00 29.61      O
ATOM   2471  CB  GLU B 158     -1.844   3.138 110.252  1.00 28.21      C
ATOM   2472  CG  GLU B 158     -2.660   1.967 110.739  1.00 26.97      C
ATOM   2473  CD  GLU B 158     -1.913   1.129 111.762  1.00 27.15      C
ATOM   2474  OE1 GLU B 158     -1.570   1.647 112.847  1.00 26.39      O
ATOM   2475  OE2 GLU B 158     -1.670  -0.059 111.469  1.00 27.94      O
ATOM   2476  N   GLU B 159     -0.785   5.356 108.084  1.00 31.94      N
ATOM   2477  CA  GLU B 159     -0.026   6.587 107.881  1.00 35.28      C
ATOM   2478  C   GLU B 159     -0.906   7.689 107.330  1.00 36.39      C
ATOM   2479  O   GLU B 159     -1.585   7.505 106.321  1.00 36.78      O
ATOM   2480  CB  GLU B 159      1.124   6.387 106.895  1.00 36.81      C
ATOM   2481  CG  GLU B 159      2.395   5.837 107.489  1.00 41.62      C
ATOM   2482  CD  GLU B 159      3.523   5.751 106.476  1.00 45.62      C
ATOM   2483  OE1 GLU B 159      4.046   6.811 106.049  1.00 46.78      O
ATOM   2484  OE2 GLU B 159      3.885   4.615 106.095  1.00 47.98      O
ATOM   2485  N   PRO B 160     -0.904   8.860 107.980  1.00 37.22      N
ATOM   2486  CA  PRO B 160     -1.722   9.978 107.504  1.00 37.55      C
ATOM   2487  C   PRO B 160     -1.232  10.455 106.136  1.00 37.63      C
ATOM   2488  O   PRO B 160     -2.003  11.000 105.344  1.00 37.49      O
ATOM   2489  CB  PRO B 160     -1.544  11.022 108.610  1.00 37.77      C
ATOM   2490  CG  PRO B 160     -0.177  10.733 109.125  1.00 38.32      C
ATOM   2491  CD  PRO B 160     -0.165   9.231 109.198  1.00 37.29      C
ATOM   2492  N   GLU B 161      0.055  10.225 105.865  1.00 38.14      N
ATOM   2493  CA  GLU B 161      0.661  10.604 104.590  1.00 37.55      C
ATOM   2494  C   GLU B 161      0.106   9.710 103.491  1.00 35.52      C
ATOM   2495  O   GLU B 161     -0.111  10.158 102.375  1.00 35.44      O
ATOM   2496  CB  GLU B 161      2.188  10.468 104.645  1.00 39.10      C
ATOM   2497  CG  GLU B 161      2.863  11.330 105.709  1.00 42.24      C
ATOM   2498  CD  GLU B 161      2.934  10.651 107.068  1.00 45.01      C
ATOM   2499  OE1 GLU B 161      2.352   9.554 107.221  1.00 46.39      O
ATOM   2500  OE2 GLU B 161      3.571  11.215 107.990  1.00 47.20      O
ATOM   2501  N   ILE B 162     -0.116   8.443 103.812  1.00 34.28      N
ATOM   2502  CA  ILE B 162     -0.659   7.491 102.860  1.00 33.22      C
ATOM   2503  C   ILE B 162     -2.136   7.803 102.578  1.00 32.21      C
ATOM   2504  O   ILE B 162     -2.602   7.734 101.439  1.00 31.82      O
ATOM   2505  CB  ILE B 162     -0.543   6.054 103.409  1.00 33.32      C
ATOM   2506  CG1 ILE B 162      0.927   5.654 103.502  1.00 33.19      C
ATOM   2507  CG2 ILE B 162     -1.310   5.089 102.535  1.00 33.61      C
ATOM   2508  CD1 ILE B 162      1.615   5.598 102.168  1.00 32.61      C
ATOM   2509  N   GLN B 163     -2.877   8.149 103.621  1.00 31.22      N
ATOM   2510  CA  GLN B 163     -4.282   8.457 103.445  1.00 30.19      C
ATOM   2511  C   GLN B 163     -4.427   9.673 102.537  1.00 30.24      C
ATOM   2512  O   GLN B 163     -5.408   9.797 101.805  1.00 29.02      O
ATOM   2513  CB  GLN B 163     -4.965   8.735 104.782  1.00 28.72      C
ATOM   2514  CG  GLN B 163     -4.764   7.652 105.830  1.00 29.23      C
ATOM   2515  CD  GLN B 163     -5.767   7.735 106.978  1.00 30.35      C
ATOM   2516  OE1 GLN B 163     -5.583   7.108 108.020  1.00 29.29      O
ATOM   2517  NE2 GLN B 163     -6.843   8.501 106.782  1.00 30.60      N
ATOM   2518  N   ALA B 164     -3.442  10.564 102.594  1.00 30.02      N
ATOM   2519  CA  ALA B 164     -3.442  11.772 101.777  1.00 29.62      C
ATOM   2520  C   ALA B 164     -3.206  11.430 100.315  1.00 29.76      C
ATOM   2521  O   ALA B 164     -3.779  12.049  99.422  1.00 29.19      O
ATOM   2522  CB  ALA B 164     -2.366  12.711 102.246  1.00 29.66      C
ATOM   2523  N   ALA B 165     -2.344  10.451 100.076  1.00 30.25      N
ATOM   2524  CA  ALA B 165     -2.041  10.045  98.715  1.00 30.76      C
ATOM   2525  C   ALA B 165     -3.265   9.401  98.080  1.00 30.90      C
ATOM   2526  O   ALA B 165     -3.663   9.768  96.981  1.00 30.01      O
ATOM   2527  CB  ALA B 165     -0.876   9.074  98.708  1.00 30.96      C
ATOM   2528  N   LEU B 166     -3.861   8.442  98.783  1.00 31.51      N
ATOM   2529  CA  LEU B 166     -5.041   7.767  98.270  1.00 33.05      C
ATOM   2530  C   LEU B 166     -6.121   8.768  97.861  1.00 34.58      C
ATOM   2531  O   LEU B 166     -6.714   8.648  96.789  1.00 34.70      O
ATOM   2532  CB  LEU B 166     -5.606   6.804  99.312  1.00 32.37      C
ATOM   2533  CG  LEU B 166     -4.771   5.555  99.598  1.00 32.84      C
ATOM   2534  CD1 LEU B 166     -5.451   4.689 100.640  1.00 33.14      C
ATOM   2535  CD2 LEU B 166     -4.602   4.785  98.316  1.00 32.37      C
ATOM   2536  N   LYS B 167     -6.369   9.760  98.719  1.00 35.76      N
ATOM   2537  CA  LYS B 167     -7.384  10.775  98.449  1.00 34.98      C
ATOM   2538  C   LYS B 167     -6.980  11.603  97.244  1.00 34.26      C
ATOM   2539  O   LYS B 167     -7.795  11.859  96.365  1.00 34.25      O
ATOM   2540  CB  LYS B 167     -7.593  11.688  99.654  1.00 35.97      C
ATOM   2541  CG  LYS B 167     -8.142  10.985 100.880  1.00 38.58      C
ATOM   2542  CD  LYS B 167     -8.372  11.955 102.030  1.00 39.92      C
ATOM   2543  CE  LYS B 167     -8.142  11.268 103.367  1.00 41.16      C
ATOM   2544  NZ  LYS B 167     -8.204  12.216 104.506  1.00 43.44      N
```

FIG. 7 (con't)

| | | | | | |
|---|---|---|---|---|---|
| ATOM | 1033 C LYS A 167 | 16.064 -10.528 52.715 1.00 23.03 | C |
| ATOM | 1034 O LYS A 167 | 16.680 -10.994 53.675 1.00 22.49 | O |
| ATOM | 1035 CB LYS A 167 | 16.041 -11.496 50.402 1.00 23.99 | C |
| ATOM | 1036 CG LYS A 167 | 15.381 -12.381 49.352 1.00 27.53 | C |
| ATOM | 1037 CD LYS A 167 | 16.089 -12.261 48.007 1.00 30.15 | C |
| ATOM | 1038 CE LYS A 167 | 15.226 -12.800 46.872 1.00 32.48 | C |
| ATOM | 1039 NZ LYS A 167 | 15.755 -12.464 45.512 1.00 33.18 | N |
| ATOM | 1040 N LYS A 168 | 15.998 -9.221 52.459 1.00 22.85 | N |
| ATOM | 1041 CA LYS A 168 | 16.670 -8.230 53.280 1.00 22.23 | C |
| ATOM | 1042 C LYS A 168 | 16.155 -8.347 54.691 1.00 21.82 | C |
| ATOM | 1043 O LYS A 168 | 16.884 -8.126 55.666 1.00 20.73 | O |
| ATOM | 1044 CB LYS A 168 | 16.408 -6.827 52.748 1.00 23.31 | C |
| ATOM | 1045 CG LYS A 168 | 17.026 -6.567 51.396 1.00 27.42 | C |
| ATOM | 1046 CD LYS A 168 | 16.788 -5.124 50.973 1.00 32.41 | C |
| ATOM | 1047 CE LYS A 168 | 17.440 -4.789 49.628 1.00 35.51 | C |
| ATOM | 1048 NZ LYS A 168 | 17.186 -3.377 49.177 1.00 35.22 | N |
| ATOM | 1049 N LEU A 169 | 14.882 -8.707 54.785 1.00 21.82 | N |
| ATOM | 1050 CA LEU A 169 | 14.221 -8.875 56.071 1.00 21.28 | C |
| ATOM | 1051 C LEU A 169 | 14.805 -10.086 56.794 1.00 19.82 | C |
| ATOM | 1052 O LEU A 169 | 15.084 -9.996 57.978 1.00 20.17 | O |
| ATOM | 1053 CB LEU A 169 | 12.712 -9.059 55.874 1.00 22.53 | C |
| ATOM | 1054 CG LEU A 169 | 11.818 -9.066 57.128 1.00 22.31 | C |
| ATOM | 1055 CD1 LEU A 169 | 11.822 -7.695 57.754 1.00 22.18 | C |
| ATOM | 1056 CD2 LEU A 169 | 10.400 -9.453 56.747 1.00 24.04 | C |
| ATOM | 1057 N LYS A 170 | 14.976 -11.199 56.088 1.00 19.32 | N |
| ATOM | 1058 CA LYS A 170 | 15.546 -12.397 56.674 1.00 20.07 | C |
| ATOM | 1059 C LYS A 170 | 17.015 -12.115 57.057 1.00 21.35 | C |
| ATOM | 1060 O LYS A 170 | 17.527 -12.623 58.055 1.00 20.49 | O |
| ATOM | 1061 CB LYS A 170 | 15.495 -13.555 55.671 1.00 20.11 | C |
| ATOM | 1062 CG LYS A 170 | 16.239 -14.788 56.122 1.00 21.04 | C |
| ATOM | 1063 CD LYS A 170 | 16.704 -15.633 54.954 1.00 21.57 | C |
| ATOM | 1064 CE LYS A 170 | 17.460 -16.841 55.461 1.00 21.76 | C |
| ATOM | 1065 NZ LYS A 170 | 18.099 -17.565 54.346 1.00 23.42 | N |
| ATOM | 1066 N GLU A 171 | 17.673 -11.285 56.256 1.00 20.13 | N |
| ATOM | 1067 CA GLU A 171 | 19.062 -10.915 56.496 1.00 20.40 | C |
| ATOM | 1068 C GLU A 171 | 19.214 -10.001 57.712 1.00 19.22 | C |
| ATOM | 1069 O GLU A 171 | 20.280 -9.925 58.330 1.00 16.62 | O |
| ATOM | 1070 CB GLU A 171 | 19.634 -10.227 55.259 1.00 21.63 | C |
| ATOM | 1071 CG GLU A 171 | 19.617 -11.101 54.019 1.00 26.74 | C |
| ATOM | 1072 CD GLU A 171 | 20.277 -10.429 52.830 1.00 30.58 | C |
| ATOM | 1073 OE1 GLU A 171 | 20.883 -9.355 53.041 1.00 29.90 | O |
| ATOM | 1074 OE2 GLU A 171 | 20.197 -10.981 51.696 1.00 30.64 | O |
| ATOM | 1075 N ALA A 172 | 18.141 -9.301 58.049 1.00 18.37 | N |
| ATOM | 1076 CA ALA A 172 | 18.190 -8.413 59.192 1.00 17.49 | C |
| ATOM | 1077 C ALA A 172 | 18.045 -9.205 60.480 1.00 17.60 | C |
| ATOM | 1078 O ALA A 172 | 18.132 -8.634 61.557 1.00 16.96 | O |
| ATOM | 1079 CB ALA A 172 | 17.094 -7.367 59.098 1.00 17.02 | C |
| ATOM | 1080 N GLY A 173 | 17.814 -10.520 60.349 1.00 18.65 | N |
| ATOM | 1081 CA GLY A 173 | 17.657 -11.400 61.505 1.00 17.60 | C |
| ATOM | 1082 C GLY A 173 | 16.200 -11.720 61.840 1.00 18.07 | C |
| ATOM | 1083 O GLY A 173 | 15.911 -12.487 62.763 1.00 17.73 | O |
| ATOM | 1084 N CYS A 174 | 15.281 -11.121 61.092 1.00 16.33 | N |
| ATOM | 1085 CA CYS A 174 | 13.863 -11.346 61.313 1.00 16.16 | C |
| ATOM | 1086 C CYS A 174 | 13.444 -12.696 60.733 1.00 16.33 | C |
| ATOM | 1087 O CYS A 174 | 13.542 -12.929 59.534 1.00 15.43 | O |
| ATOM | 1088 CB CYS A 174 | 13.037 -10.241 60.674 1.00 15.16 | C |
| ATOM | 1089 SG CYS A 174 | 11.279 -10.569 60.787 1.00 17.07 | S |
| ATOM | 1090 N LYS A 175 | 12.965 -13.584 61.596 1.00 17.50 | N |
| ATOM | 1091 CA LYS A 175 | 12.562 -14.905 61.163 1.00 19.73 | C |
| ATOM | 1092 C LYS A 175 | 11.126 -14.846 60.677 1.00 20.26 | C |
| ATOM | 1093 O LYS A 175 | 10.240 -14.472 61.434 1.00 20.74 | O |
| ATOM | 1094 CB LYS A 175 | 12.691 -15.874 62.323 1.00 19.81 | C |
| ATOM | 1095 CG LYS A 175 | 12.463 -17.322 61.953 1.00 24.58 | C |
| ATOM | 1096 CD LYS A 175 | 12.440 -18.213 63.188 1.00 27.49 | C |
| ATOM | 1097 CE LYS A 175 | 12.425 -19.693 62.839 1.00 29.10 | C |
| ATOM | 1098 NZ LYS A 175 | 12.336 -20.492 64.092 1.00 32.01 | N |
| ATOM | 1099 N LEU A 176 | 10.892 -15.217 59.419 1.00 21.18 | N |
| ATOM | 1100 CA LEU A 176 | 9.540 -15.182 58.866 1.00 22.24 | C |
| ATOM | 1101 C LEU A 176 | 9.067 -16.586 58.499 1.00 21.94 | C |
| ATOM | 1102 O LEU A 176 | 9.784 -17.311 57.819 1.00 22.52 | O |
| ATOM | 1103 CB LEU A 176 | 9.522 -14.298 57.615 1.00 23.01 | C |
| ATOM | 1104 CG LEU A 176 | 8.270 -13.438 57.397 1.00 25.46 | C |
| ATOM | 1105 CD1 LEU A 176 | 8.463 -12.617 56.140 1.00 27.46 | C |
| ATOM | 1106 CD2 LEU A 176 | 7.024 -14.296 57.279 1.00 24.28 | C |
| ATOM | 1107 N ARG A 177 | 7.866 -16.967 58.932 1.00 21.87 | N |
| ATOM | 1108 CA ARG A 177 | 7.317 -18.291 58.638 1.00 22.85 | C |
| ATOM | 1109 C ARG A 177 | 5.819 -18.255 58.322 1.00 22.84 | C |
| ATOM | 1110 O ARG A 177 | 5.128 -17.284 58.638 1.00 22.66 | O |
| ATOM | 1111 CB ARG A 177 | 7.560 -19.237 59.825 1.00 25.46 | C |
| ATOM | 1112 CG ARG A 177 | 9.038 -19.554 60.090 1.00 29.18 | C |
| ATOM | 1113 CD ARG A 177 | 9.666 -20.394 58.968 1.00 33.66 | C |
| ATOM | 1114 NE ARG A 177 | 11.076 -20.735 59.231 1.00 38.67 | N |
| ATOM | 1115 CZ ARG A 177 | 12.117 -19.936 58.987 1.00 39.65 | C |
| ATOM | 1116 NH1 ARG A 177 | 11.940 -18.733 58.457 1.00 39.33 | N |
| ATOM | 1117 NH2 ARG A 177 | 13.342 -20.341 59.293 1.00 40.65 | N |
| ATOM | 1118 N ILE A 178 | 5.311 -19.310 57.681 1.00 22.35 | N |

| | | | | | |
|---|---|---|---|---|---|
| ATOM | 2545 N LYS B 168 | -5.732 12.035 97.189 1.00 33.17 | N |
| ATOM | 2546 CA LYS B 168 | -5.300 12.825 96.049 1.00 33.56 | C |
| ATOM | 2547 C LYS B 168 | -5.328 11.995 94.761 1.00 32.49 | C |
| ATOM | 2548 O LYS B 168 | -5.523 12.533 93.666 1.00 32.99 | O |
| ATOM | 2549 CB LYS B 168 | -3.890 13.371 96.280 1.00 34.72 | C |
| ATOM | 2550 CG LYS B 168 | -3.836 14.529 97.258 1.00 36.85 | C |
| ATOM | 2551 CD LYS B 168 | -2.406 14.848 97.678 1.00 39.47 | C |
| ATOM | 2552 CE LYS B 168 | -2.391 15.952 98.731 1.00 40.85 | C |
| ATOM | 2553 NZ LYS B 168 | -1.052 16.123 99.360 1.00 42.89 | N |
| ATOM | 2554 N LEU B 169 | -5.134 10.687 94.899 1.00 30.29 | N |
| ATOM | 2555 CA LEU B 169 | -5.143 9.780 93.763 1.00 27.74 | C |
| ATOM | 2556 C LEU B 169 | -6.557 9.771 93.183 1.00 26.16 | C |
| ATOM | 2557 O LEU B 169 | -6.730 9.781 91.969 1.00 25.12 | O |
| ATOM | 2558 CB LEU B 169 | -4.735 8.372 94.198 1.00 28.13 | C |
| ATOM | 2559 CG LEU B 169 | -3.870 7.573 93.222 1.00 27.91 | C |
| ATOM | 2560 CD1 LEU B 169 | -2.564 8.286 92.987 1.00 28.10 | C |
| ATOM | 2561 CD2 LEU B 169 | -3.594 6.203 93.794 1.00 28.49 | C |
| ATOM | 2562 N LYS B 170 | -7.557 9.756 94.058 1.00 24.78 | N |
| ATOM | 2563 CA LYS B 170 | -8.947 9.784 93.630 1.00 24.87 | C |
| ATOM | 2564 C LYS B 170 | -9.275 11.138 93.005 1.00 26.04 | C |
| ATOM | 2565 O LYS B 170 | -10.122 11.232 92.122 1.00 25.01 | O |
| ATOM | 2566 CB LYS B 170 | -9.884 9.548 94.805 1.00 24.63 | C |
| ATOM | 2567 CG LYS B 170 | -11.340 9.808 94.494 1.00 22.59 | C |
| ATOM | 2568 CD LYS B 170 | -12.205 9.556 95.717 1.00 21.73 | C |
| ATOM | 2569 CE LYS B 170 | -13.649 9.955 95.456 1.00 22.54 | C |
| ATOM | 2570 NZ LYS B 170 | -14.600 9.349 96.430 1.00 25.72 | N |
| ATOM | 2571 N GLU B 171 | -8.618 12.188 93.505 1.00 27.99 | N |
| ATOM | 2572 CA GLU B 171 | -8.786 13.548 92.993 1.00 27.48 | C |
| ATOM | 2573 C GLU B 171 | -8.338 13.582 91.529 1.00 26.08 | C |
| ATOM | 2574 O GLU B 171 | -8.991 14.192 90.686 1.00 24.94 | O |
| ATOM | 2575 CB GLU B 171 | -7.927 14.536 93.785 1.00 30.21 | C |
| ATOM | 2576 CG GLU B 171 | -8.189 14.592 95.286 1.00 34.50 | C |
| ATOM | 2577 CD GLU B 171 | -9.619 14.957 95.622 1.00 38.27 | C |
| ATOM | 2578 OE1 GLU B 171 | -10.282 15.601 94.772 1.00 38.88 | O |
| ATOM | 2579 OE2 GLU B 171 | -10.074 14.612 96.740 1.00 38.33 | O |
| ATOM | 2580 N ALA B 172 | -7.207 12.934 91.244 1.00 24.56 | N |
| ATOM | 2581 CA ALA B 172 | -6.653 12.889 89.890 1.00 23.01 | C |
| ATOM | 2582 C ALA B 172 | -7.522 12.075 88.933 1.00 22.36 | C |
| ATOM | 2583 O ALA B 172 | -7.236 11.996 87.737 1.00 22.84 | O |
| ATOM | 2584 CB ALA B 172 | -5.245 12.325 89.922 1.00 21.63 | C |
| ATOM | 2585 N GLY B 173 | -8.576 11.466 89.470 1.00 21.96 | N |
| ATOM | 2586 CA GLY B 173 | -9.486 10.680 88.660 1.00 22.00 | C |
| ATOM | 2587 C GLY B 173 | -9.176 9.197 88.624 1.00 22.85 | C |
| ATOM | 2588 O GLY B 173 | -9.741 8.452 87.818 1.00 24.08 | O |
| ATOM | 2589 N CYS B 174 | -8.280 8.760 89.501 1.00 21.81 | N |
| ATOM | 2590 CA CYS B 174 | -7.887 7.364 89.566 1.00 20.51 | C |
| ATOM | 2591 C CYS B 174 | -8.872 6.566 90.396 1.00 20.55 | C |
| ATOM | 2592 O CYS B 174 | -9.296 7.006 91.467 1.00 20.68 | O |
| ATOM | 2593 CB CYS B 174 | -6.486 7.246 90.168 1.00 19.92 | C |
| ATOM | 2594 SG CYS B 174 | -5.858 5.557 90.295 1.00 18.22 | S |
| ATOM | 2595 N LYS B 175 | -9.243 5.394 89.904 1.00 20.69 | N |
| ATOM | 2596 CA LYS B 175 | -10.186 4.550 90.627 1.00 22.91 | C |
| ATOM | 2597 C LYS B 175 | -9.448 3.489 91.420 1.00 22.03 | C |
| ATOM | 2598 O LYS B 175 | -8.685 2.704 90.861 1.00 23.44 | O |
| ATOM | 2599 CB LYS B 175 | -11.158 3.877 89.646 1.00 25.46 | C |
| ATOM | 2600 CG LYS B 175 | -12.175 4.811 88.973 1.00 30.51 | C |
| ATOM | 2601 CD LYS B 175 | -13.176 5.364 89.978 1.00 33.81 | C |
| ATOM | 2602 CE LYS B 175 | -14.317 6.106 89.302 1.00 36.20 | C |
| ATOM | 2603 NZ LYS B 175 | -15.331 6.520 90.317 1.00 38.39 | N |
| ATOM | 2604 N LEU B 176 | -9.669 3.463 92.724 1.00 21.01 | N |
| ATOM | 2605 CA LEU B 176 | -9.018 2.469 93.575 1.00 20.17 | C |
| ATOM | 2606 C LEU B 176 | -10.038 1.497 94.162 1.00 20.32 | C |
| ATOM | 2607 O LEU B 176 | -11.115 1.919 94.579 1.00 20.75 | O |
| ATOM | 2608 CB LEU B 176 | -8.282 3.172 94.710 1.00 19.98 | C |
| ATOM | 2609 CG LEU B 176 | -7.216 4.171 94.305 1.00 21.46 | C |
| ATOM | 2610 CD1 LEU B 176 | -6.848 5.022 95.507 1.00 23.30 | C |
| ATOM | 2611 CD2 LEU B 176 | -6.008 3.439 93.754 1.00 21.32 | C |
| ATOM | 2612 N ARG B 177 | -9.702 0.211 94.184 1.00 19.61 | N |
| ATOM | 2613 CA ARG B 177 | -10.576 -0.824 94.759 1.00 21.31 | C |
| ATOM | 2614 C ARG B 177 | -9.799 -1.997 95.348 1.00 21.44 | C |
| ATOM | 2615 O ARG B 177 | -8.702 -2.344 94.898 1.00 21.85 | O |
| ATOM | 2616 CB ARG B 177 | -11.567 -1.368 93.732 1.00 23.36 | C |
| ATOM | 2617 CG ARG B 177 | -12.673 -0.420 93.330 1.00 26.92 | C |
| ATOM | 2618 CD ARG B 177 | -13.772 -1.189 92.581 1.00 32.18 | C |
| ATOM | 2619 NE ARG B 177 | -13.281 -1.911 91.402 1.00 36.46 | N |
| ATOM | 2620 CZ ARG B 177 | -14.028 -2.692 90.615 1.00 37.62 | C |
| ATOM | 2621 NH1 ARG B 177 | -15.319 -2.867 90.871 1.00 39.00 | N |
| ATOM | 2622 NH2 ARG B 177 | -13.486 -3.300 89.566 1.00 36.59 | N |
| ATOM | 2623 N ILE B 178 | -10.372 -2.618 96.362 1.00 21.30 | N |
| ATOM | 2624 CA ILE B 178 | -9.715 -3.740 96.992 1.00 20.29 | C |
| ATOM | 2625 C ILE B 178 | -10.089 -5.000 96.219 1.00 21.29 | C |
| ATOM | 2626 O ILE B 178 | -11.259 -5.242 95.935 1.00 21.66 | O |
| ATOM | 2627 CB ILE B 178 | -10.160 -3.878 98.459 1.00 18.23 | C |
| ATOM | 2628 CG1 ILE B 178 | -10.068 -2.518 99.172 1.00 18.67 | C |
| ATOM | 2629 CG2 ILE B 178 | -9.306 -4.899 99.150 1.00 16.05 | C |
| ATOM | 2630 CD1 ILE B 178 | -8.685 -1.924 99.237 1.00 17.16 | C |

FIG. 7 (con't)

```
ATOM  1119  CA  ILE A 178    3.894 -19.400  57.349  1.00 20.34    C
ATOM  1120  C   ILE A 178    3.126 -20.056  58.494  1.00 21.15    C
ATOM  1121  O   ILE A 178    3.629 -20.974  59.137  1.00 21.86    O
ATOM  1122  CB  ILE A 178    3.686 -20.223  56.084  1.00 19.73    C
ATOM  1123  CG1 ILE A 178    4.491 -19.615  54.939  1.00 19.71    C
ATOM  1124  CG2 ILE A 178    2.217 -20.261  55.733  1.00 18.35    C
ATOM  1125  CD1 ILE A 178    4.197 -18.140  54.691  1.00 17.93    C
ATOM  1126  N   MET A 179    1.908 -19.587  58.749  1.00 21.52    N
ATOM  1127  CA  MET A 179    1.086 -20.127  59.836  1.00 21.73    C
ATOM  1128  C   MET A 179    0.525 -21.491  59.469  1.00 21.63    C
ATOM  1129  O   MET A 179   -0.090 -21.648  58.415  1.00 21.49    O
ATOM  1130  CB  MET A 179   -0.073 -19.181  60.132  1.00 21.14    C
ATOM  1131  CG  MET A 179    0.043 -18.312  61.379  1.00 21.98    C
ATOM  1132  SD  MET A 179   -1.463 -17.320  61.574  1.00 20.07    S
ATOM  1133  CE  MET A 179   -1.024 -16.022  60.719  1.00 19.83    C
ATOM  1134  N   LYS A 180    0.729 -22.462  60.346  1.00 20.59    N
ATOM  1135  CA  LYS A 180    0.212 -23.802  60.108  1.00 21.79    C
ATOM  1136  C   LYS A 180   -1.073 -23.983  60.906  1.00 21.48    C
ATOM  1137  O   LYS A 180   -1.427 -23.127  61.719  1.00 21.37    O
ATOM  1138  CB  LYS A 180    1.272 -24.843  60.505  1.00 22.90    C
ATOM  1139  CG  LYS A 180    1.847 -24.646  61.875  1.00 23.11    C
ATOM  1140  CD  LYS A 180    2.929 -25.666  62.152  1.00 23.25    C
ATOM  1141  CE  LYS A 180    4.112 -25.505  61.215  1.00 24.25    C
ATOM  1142  NZ  LYS A 180    5.208 -26.468  61.539  1.00 24.93    N
ATOM  1143  N   PRO A 181   -1.816 -25.075  60.657  1.00 21.00    N
ATOM  1144  CA  PRO A 181   -3.060 -25.315  61.382  1.00 20.19    C
ATOM  1145  C   PRO A 181   -2.969 -25.075  62.882  1.00 19.75    C
ATOM  1146  O   PRO A 181   -3.862 -24.461  63.464  1.00 18.22    O
ATOM  1147  CB  PRO A 181   -3.385 -26.751  61.016  1.00 20.40    C
ATOM  1148  CG  PRO A 181   -2.975 -26.788  59.595  1.00 20.15    C
ATOM  1149  CD  PRO A 181   -1.606 -26.120  59.645  1.00 21.32    C
ATOM  1150  N   GLN A 182   -1.890 -25.543  63.507  1.00 21.37    N
ATOM  1151  CA  GLN A 182   -1.722 -25.357  64.957  1.00 21.62    C
ATOM  1152  C   GLN A 182   -1.689 -23.887  65.346  1.00 20.06    C
ATOM  1153  O   GLN A 182   -2.182 -23.515  66.412  1.00 19.52    O
ATOM  1154  CB  GLN A 182   -0.462 -26.067  65.455  1.00 22.77    C
ATOM  1155  CG  GLN A 182   -0.466 -27.554  65.139  1.00 28.65    C
ATOM  1156  CD  GLN A 182    0.125 -27.868  63.767  1.00 31.78    C
ATOM  1157  OE1 GLN A 182    1.343 -27.985  63.635  1.00 34.11    O
ATOM  1158  NE2 GLN A 182   -0.726 -28.000  62.750  1.00 30.20    N
ATOM  1159  N   ASP A 183   -1.123 -23.057  64.472  1.00 19.76    N
ATOM  1160  CA  ASP A 183   -1.025 -21.623  64.724  1.00 18.68    C
ATOM  1161  C   ASP A 183   -2.383 -20.959  64.777  1.00 18.25    C
ATOM  1162  O   ASP A 183   -2.651 -20.181  65.685  1.00 16.97    O
ATOM  1163  CB  ASP A 183   -0.172 -20.942  63.669  1.00 19.59    C
ATOM  1164  CG  ASP A 183    1.273 -21.414  63.705  1.00 18.01    C
ATOM  1165  OD1 ASP A 183    1.867 -21.456  64.790  1.00 17.51    O
ATOM  1166  OD2 ASP A 183    1.807 -21.737  62.630  1.00 22.87    O
ATOM  1167  N   PHE A 184   -3.238 -21.248  63.797  1.00 17.75    N
ATOM  1168  CA  PHE A 184   -4.571 -20.665  63.782  1.00 17.68    C
ATOM  1169  C   PHE A 184   -5.315 -21.064  65.046  1.00 19.64    C
ATOM  1170  O   PHE A 184   -5.949 -20.232  65.685  1.00 19.95    O
ATOM  1171  CB  PHE A 184   -5.356 -21.111  62.565  1.00 15.70    C
ATOM  1172  CG  PHE A 184   -4.855 -20.525  61.295  1.00 14.98    C
ATOM  1173  CD1 PHE A 184   -3.972 -21.232  60.488  1.00 14.41    C
ATOM  1174  CD2 PHE A 184   -5.258 -19.261  60.900  1.00 13.40    C
ATOM  1175  CE1 PHE A 184   -3.503 -20.683  59.305  1.00 13.56    C
ATOM  1176  CE2 PHE A 184   -4.798 -18.708  59.721  1.00 12.12    C
ATOM  1177  CZ  PHE A 184   -3.917 -19.419  58.921  1.00 12.15    C
ATOM  1178  N   GLU A 185   -5.247 -22.343  65.407  1.00 20.76    N
ATOM  1179  CA  GLU A 185   -5.910 -22.820  66.611  1.00 22.07    C
ATOM  1180  C   GLU A 185   -5.384 -22.066  67.853  1.00 22.23    C
ATOM  1181  O   GLU A 185   -6.151 -21.662  68.736  1.00 22.55    O
ATOM  1182  CB  GLU A 185   -5.688 -24.320  66.766  1.00 23.80    C
ATOM  1183  CG  GLU A 185   -6.165 -24.892  68.086  1.00 29.28    C
ATOM  1184  CD  GLU A 185   -5.965 -26.402  68.195  1.00 33.31    C
ATOM  1185  OE1 GLU A 185   -4.847 -26.895  67.926  1.00 34.86    O
ATOM  1186  OE2 GLU A 185   -6.928 -27.106  68.564  1.00 36.20    O
ATOM  1187  N   TYR A 186   -4.073 -21.881  67.912  1.00 20.95    N
ATOM  1188  CA  TYR A 186   -3.445 -21.172  69.011  1.00 20.20    C
ATOM  1189  C   TYR A 186   -4.031 -19.752  69.151  1.00 20.26    C
ATOM  1190  O   TYR A 186   -4.536 -19.361  70.220  1.00 19.28    O
ATOM  1191  CB  TYR A 186   -1.938 -21.085  68.764  1.00 21.30    C
ATOM  1192  CG  TYR A 186   -1.192 -20.365  69.858  1.00 23.68    C
ATOM  1193  CD1 TYR A 186   -0.987 -20.969  71.099  1.00 23.12    C
ATOM  1194  CD2 TYR A 186   -0.747 -19.051  69.683  1.00 22.52    C
ATOM  1195  CE1 TYR A 186   -0.362 -20.284  72.141  1.00 22.83    C
ATOM  1196  CE2 TYR A 186   -0.123 -18.354  70.721  1.00 22.50    C
ATOM  1197  CZ  TYR A 186    0.066 -18.982  71.950  1.00 23.41    C
ATOM  1198  OH  TYR A 186    0.700 -18.331  72.987  1.00 24.95    O
ATOM  1199  N   VAL A 187   -3.966 -18.988  68.065  1.00 18.99    N
ATOM  1200  CA  VAL A 187   -4.450 -17.617  68.033  1.00 19.66    C
ATOM  1201  C   VAL A 187   -5.924 -17.528  68.422  1.00 21.19    C
ATOM  1202  O   VAL A 187   -6.343 -16.627  69.156  1.00 20.67    O
ATOM  1203  CB  VAL A 187   -4.285 -16.989  66.606  1.00 20.33    C
ATOM  1204  CG1 VAL A 187   -4.710 -15.541  66.623  1.00 18.54    C

ATOM  2631  N   MET B 179   -9.086  -5.787  95.850  1.00 21.50    N
ATOM  2632  CA  MET B 179   -9.326  -7.020  95.133  1.00 20.80    C
ATOM  2633  C   MET B 179  -10.294  -7.916  95.897  1.00 22.36    C
ATOM  2634  O   MET B 179  -10.061  -8.252  97.061  1.00 22.01    O
ATOM  2635  CB  MET B 179   -8.008  -7.763  94.913  1.00 20.69    C
ATOM  2636  CG  MET B 179   -7.030  -7.034  94.001  1.00 20.79    C
ATOM  2637  SD  MET B 179   -5.491  -7.940  93.683  1.00 18.03    S
ATOM  2638  CE  MET B 179   -6.095  -9.300  92.817  1.00 20.76    C
ATOM  2639  N   LYS B 180  -11.392  -8.291  95.237  1.00 23.05    N
ATOM  2640  CA  LYS B 180  -12.392  -9.188  95.818  1.00 23.33    C
ATOM  2641  C   LYS B 180  -11.916 -10.629  95.575  1.00 22.45    C
ATOM  2642  O   LYS B 180  -11.054 -10.871  94.735  1.00 22.97    O
ATOM  2643  CB  LYS B 180  -13.743  -8.973  95.130  1.00 25.72    C
ATOM  2644  CG  LYS B 180  -14.116  -7.509  94.934  1.00 28.31    C
ATOM  2645  CD  LYS B 180  -15.589  -7.338  94.600  1.00 26.92    C
ATOM  2646  CE  LYS B 180  -15.918  -7.864  93.214  1.00 28.09    C
ATOM  2647  NZ  LYS B 180  -15.387  -6.995  92.122  1.00 28.03    N
ATOM  2648  N   PRO B 181  -12.464 -11.599  96.310  1.00 22.63    N
ATOM  2649  CA  PRO B 181  -12.048 -12.997  96.112  1.00 22.85    C
ATOM  2650  C   PRO B 181  -12.092 -13.411  94.630  1.00 23.80    C
ATOM  2651  O   PRO B 181  -11.226 -14.155  94.139  1.00 23.89    O
ATOM  2652  CB  PRO B 181  -13.037 -13.762  96.985  1.00 23.10    C
ATOM  2653  CG  PRO B 181  -13.225 -12.798  98.159  1.00 21.37    C
ATOM  2654  CD  PRO B 181  -13.377 -11.464  97.463  1.00 21.27    C
ATOM  2655  N   GLN B 182  -13.092 -12.913  93.909  1.00 24.02    N
ATOM  2656  CA  GLN B 182  -13.245 -13.201  92.485  1.00 23.93    C
ATOM  2657  C   GLN B 182  -12.048 -12.671  91.681  1.00 23.19    C
ATOM  2658  O   GLN B 182  -11.661 -13.250  90.660  1.00 24.42    O
ATOM  2659  CB  GLN B 182  -14.536 -12.561  91.953  1.00 26.36    C
ATOM  2660  CG  GLN B 182  -15.850 -13.123  92.516  1.00 30.15    C
ATOM  2661  CD  GLN B 182  -16.011 -12.948  94.029  1.00 33.78    C
ATOM  2662  OE1 GLN B 182  -15.879 -11.842  94.566  1.00 35.18    O
ATOM  2663  NE2 GLN B 182  -16.318 -14.043  94.719  1.00 35.02    N
ATOM  2664  N   ASP B 183  -11.468 -11.566  92.138  1.00 20.73    N
ATOM  2665  CA  ASP B 183  -10.324 -10.946  91.477  1.00 19.23    C
ATOM  2666  C   ASP B 183   -9.083 -11.845  91.517  1.00 19.89    C
ATOM  2667  O   ASP B 183   -8.400 -12.028  90.504  1.00 18.48    O
ATOM  2668  CB  ASP B 183  -10.028  -9.589  92.137  1.00 18.49    C
ATOM  2669  CG  ASP B 183  -11.128  -8.566  91.880  1.00 17.42    C
ATOM  2670  OD1 ASP B 183  -11.559  -7.868  92.831  1.00 15.93    O
ATOM  2671  OD2 ASP B 183  -11.559  -8.463  90.716  1.00 15.46    O
ATOM  2672  N   PHE B 184   -8.792 -12.413  92.679  1.00 20.46    N
ATOM  2673  CA  PHE B 184   -7.637 -13.291  92.794  1.00 23.62    C
ATOM  2674  C   PHE B 184   -7.782 -14.488  91.848  1.00 24.21    C
ATOM  2675  O   PHE B 184   -6.808 -14.945  91.251  1.00 24.85    O
ATOM  2676  CB  PHE B 184   -7.469 -13.796  94.242  1.00 23.00    C
ATOM  2677  CG  PHE B 184   -7.009 -12.730  95.210  1.00 22.04    C
ATOM  2678  CD1 PHE B 184   -7.937 -11.890  95.835  1.00 20.18    C
ATOM  2679  CD2 PHE B 184   -5.643 -12.549  95.479  1.00 21.35    C
ATOM  2680  CE1 PHE B 184   -7.525 -10.886  96.714  1.00 19.54    C
ATOM  2681  CE2 PHE B 184   -5.210 -11.546  96.361  1.00 20.02    C
ATOM  2682  CZ  PHE B 184   -6.156 -10.710  96.983  1.00 20.43    C
ATOM  2683  N   GLU B 185   -9.007 -14.981  91.719  1.00 25.70    N
ATOM  2684  CA  GLU B 185   -9.287 -16.099  90.847  1.00 25.87    C
ATOM  2685  C   GLU B 185   -9.147 -15.646  89.406  1.00 24.28    C
ATOM  2686  O   GLU B 185   -8.745 -16.411  88.542  1.00 24.15    O
ATOM  2687  CB  GLU B 185  -10.717 -16.599  91.081  1.00 28.62    C
ATOM  2688  CG  GLU B 185  -11.116 -17.762  90.193  1.00 32.44    C
ATOM  2689  CD  GLU B 185  -12.590 -18.114  90.312  1.00 35.88    C
ATOM  2690  OE1 GLU B 185  -13.433 -17.210  90.113  1.00 38.50    O
ATOM  2691  OE2 GLU B 185  -12.921 -19.288  90.588  1.00 37.99    O
ATOM  2692  N   TYR B 186   -9.483 -14.397  89.142  1.00 23.63    N
ATOM  2693  CA  TYR B 186   -9.366 -13.888  87.786  1.00 23.72    C
ATOM  2694  C   TYR B 186   -7.883 -13.796  87.365  1.00 23.05    C
ATOM  2695  O   TYR B 186   -7.495 -14.217  86.272  1.00 21.29    O
ATOM  2696  CB  TYR B 186  -10.031 -12.513  87.689  1.00 25.73    C
ATOM  2697  CG  TYR B 186   -9.904 -11.866  86.330  1.00 29.26    C
ATOM  2698  CD1 TYR B 186  -10.689 -12.290  85.251  1.00 29.67    C
ATOM  2699  CD2 TYR B 186   -8.963 -10.855  86.105  1.00 29.20    C
ATOM  2700  CE1 TYR B 186  -10.534 -11.716  83.974  1.00 31.05    C
ATOM  2701  CE2 TYR B 186   -8.800 -10.280  84.840  1.00 31.40    C
ATOM  2702  CZ  TYR B 186   -9.584 -10.707  83.788  1.00 32.24    C
ATOM  2703  OH  TYR B 186   -9.416 -10.080  82.567  1.00 35.03    O
ATOM  2704  N   VAL B 187   -7.063 -13.246  88.246  1.00 21.12    N
ATOM  2705  CA  VAL B 187   -5.651 -13.103  87.968  1.00 20.71    C
ATOM  2706  C   VAL B 187   -4.990 -14.476  87.865  1.00 22.47    C
ATOM  2707  O   VAL B 187   -4.059 -14.698  87.075  1.00 23.30    O
ATOM  2708  CB  VAL B 187   -4.961 -12.282  89.071  1.00 18.25    C
ATOM  2709  CG1 VAL B 187   -3.466 -12.300  88.888  1.00 17.39    C
ATOM  2710  CG2 VAL B 187   -5.458 -10.850  89.029  1.00 16.85    C
ATOM  2711  N   TRP B 188   -5.488 -15.419  88.640  1.00 22.99    N
ATOM  2712  CA  TRP B 188   -4.913 -16.743  88.641  1.00 24.97    C
ATOM  2713  C   TRP B 188   -5.180 -17.541  87.382  1.00 27.24    C
ATOM  2714  O   TRP B 188   -4.318 -18.291  86.914  1.00 29.11    O
ATOM  2715  CB  TRP B 188   -5.398 -17.515  89.867  1.00 23.34    C
ATOM  2716  CG  TRP B 188   -4.918 -18.934  89.929  1.00 23.16    C
```

FIG. 7 (con't)

```
ATOM   1205  CG2 VAL A 187      -2.836 -17.079  66.154  1.00 17.64           C
ATOM   1206  N   TRP A 188      -6.704 -18.481  67.933  1.00 21.81           N
ATOM   1207  CA  TRP A 188      -8.117 -18.527  68.212  1.00 23.01           C
ATOM   1208  C   TRP A 188      -8.424 -18.740  69.675  1.00 26.07           C
ATOM   1209  O   TRP A 188      -9.231 -18.020  70.259  1.00 28.04           O
ATOM   1210  CB  TRP A 188      -8.783 -19.645  67.410  1.00 22.14           C
ATOM   1211  CG  TRP A 188     -10.266 -19.784  67.664  1.00 21.24           C
ATOM   1212  CD1 TRP A 188     -10.895 -20.759  68.396  1.00 19.15           C
ATOM   1213  CD2 TRP A 188     -11.301 -18.918  67.184  1.00 18.71           C
ATOM   1214  NE1 TRP A 188     -12.252 -20.555  68.387  1.00 17.30           N
ATOM   1215  CE2 TRP A 188     -12.531 -19.431  67.650  1.00 18.92           C
ATOM   1216  CE3 TRP A 188     -11.312 -17.756  66.399  1.00 18.39           C
ATOM   1217  CZ2 TRP A 188     -13.762 -18.823  67.362  1.00 19.31           C
ATOM   1218  CZ3 TRP A 188     -12.534 -17.149  66.109  1.00 17.90           C
ATOM   1219  CH2 TRP A 188     -13.740 -17.686  66.585  1.00 18.35           C
ATOM   1220  N   GLN A 189      -7.786 -19.731  70.282  1.00 28.68           N
ATOM   1221  CA  GLN A 189      -8.053 -20.026  71.683  1.00 30.60           C
ATOM   1222  C   GLN A 189      -7.348 -19.117  72.679  1.00 31.17           C
ATOM   1223  O   GLN A 189      -7.698 -19.102  73.857  1.00 30.63           O
ATOM   1224  CB  GLN A 189      -7.685 -21.476  71.982  1.00 32.34           C
ATOM   1225  CG  GLN A 189      -8.116 -22.445  70.909  1.00 34.32           C
ATOM   1226  CD  GLN A 189      -7.782 -23.881  71.259  1.00 36.97           C
ATOM   1227  OE1 GLN A 189      -6.727 -24.168  71.838  1.00 35.41           O
ATOM   1228  NE2 GLN A 189      -8.673 -24.798  70.895  1.00 36.12           N
ATOM   1229  N   ASN A 190      -6.371 -18.349  72.203  1.00 31.77           N
ATOM   1230  CA  ASN A 190      -5.614 -17.463  73.090  1.00 31.59           C
ATOM   1231  C   ASN A 190      -5.810 -15.973  72.877  1.00 29.99           C
ATOM   1232  O   ASN A 190      -5.622 -15.192  73.801  1.00 28.93           O
ATOM   1233  CB  ASN A 190      -4.129 -17.800  72.979  1.00 34.39           C
ATOM   1234  CG  ASN A 190      -3.774 -19.108  73.648  1.00 36.68           C
ATOM   1235  OD1 ASN A 190      -3.706 -19.184  74.871  1.00 38.40           O
ATOM   1236  ND2 ASN A 190      -3.552 -20.150  72.847  1.00 38.16           N
ATOM   1237  N   PHE A 191      -6.187 -15.577  71.666  1.00 29.38           N
ATOM   1238  CA  PHE A 191      -6.378 -14.162  71.374  1.00 28.28           C
ATOM   1239  C   PHE A 191      -7.856 -13.812  71.218  1.00 28.17           C
ATOM   1240  O   PHE A 191      -8.272 -12.680  71.455  1.00 27.98           O
ATOM   1241  CB  PHE A 191      -5.605 -13.798  70.107  1.00 27.26           C
ATOM   1242  CG  PHE A 191      -4.127 -13.640  70.325  1.00 28.00           C
ATOM   1243  CD1 PHE A 191      -3.599 -12.420  70.731  1.00 26.92           C
ATOM   1244  CD2 PHE A 191      -3.255 -14.718  70.140  1.00 28.21           C
ATOM   1245  CE1 PHE A 191      -2.233 -12.266  70.949  1.00 28.38           C
ATOM   1246  CE2 PHE A 191      -1.881 -14.573  70.360  1.00 27.03           C
ATOM   1247  CZ  PHE A 191      -1.370 -13.346  70.763  1.00 27.77           C
ATOM   1248  N   VAL A 192      -8.649 -14.793  70.820  1.00 28.18           N
ATOM   1249  CA  VAL A 192     -10.059 -14.559  70.639  1.00 30.52           C
ATOM   1250  C   VAL A 192     -10.803 -14.871  71.925  1.00 32.74           C
ATOM   1251  O   VAL A 192     -10.789 -16.007  72.393  1.00 31.06           O
ATOM   1252  CB  VAL A 192     -10.642 -15.431  69.525  1.00 29.42           C
ATOM   1253  CG1 VAL A 192     -12.146 -15.227  69.425  1.00 27.45           C
ATOM   1254  CG2 VAL A 192      -9.956 -15.105  68.209  1.00 27.82           C
ATOM   1255  N   GLU A 193     -11.448 -13.849  72.485  1.00 34.96           N
ATOM   1256  CA  GLU A 193     -12.209 -13.989  73.714  1.00 38.93           C
ATOM   1257  C   GLU A 193     -13.417 -14.905  73.563  1.00 41.77           C
ATOM   1258  O   GLU A 193     -14.224 -14.741  72.647  1.00 41.55           O
ATOM   1259  CB  GLU A 193     -12.696 -12.622  74.196  1.00 39.47           C
ATOM   1260  CG  GLU A 193     -13.705 -12.706  75.339  1.00 41.69           C
ATOM   1261  CD  GLU A 193     -14.272 -11.357  75.780  1.00 42.68           C
ATOM   1262  OE1 GLU A 193     -13.550 -10.590  76.451  1.00 43.65           O
ATOM   1263  OE2 GLU A 193     -15.440 -11.059  75.452  1.00 42.03           O
ATOM   1264  N   GLN A 194     -13.562 -15.837  74.499  1.00 46.22           N
ATOM   1265  CA  GLN A 194     -14.673 -16.783  74.522  1.00 50.57           C
ATOM   1266  C   GLN A 194     -15.498 -16.435  75.763  1.00 53.36           C
ATOM   1267  O   GLN A 194     -15.106 -15.571  76.546  1.00 54.46           O
ATOM   1268  CB  GLN A 194     -14.140 -18.208  74.660  1.00 51.86           C
ATOM   1269  CG  GLN A 194     -12.820 -18.487  73.926  1.00 53.59           C
ATOM   1270  CD  GLN A 194     -12.985 -18.653  72.420  1.00 54.54           C
ATOM   1271  OE1 GLN A 194     -13.627 -19.595  71.955  1.00 54.99           O
ATOM   1272  NE2 GLN A 194     -12.399 -17.738  71.651  1.00 55.33           N
ATOM   1273  N   GLU A 195     -16.617 -17.121  75.968  1.00 56.13           N
ATOM   1274  CA  GLU A 195     -17.447 -16.851  77.141  1.00 59.03           C
ATOM   1275  C   GLU A 195     -17.857 -18.134  77.879  1.00 59.59           C
ATOM   1276  O   GLU A 195     -17.995 -18.142  79.107  1.00 59.77           O
ATOM   1277  CB  GLU A 195     -18.696 -16.077  76.716  1.00 60.67           C
ATOM   1278  CG  GLU A 195     -18.415 -14.833  75.884  1.00 63.08           C
ATOM   1279  CD  GLU A 195     -19.430 -14.654  74.763  1.00 64.67           C
ATOM   1280  OE1 GLU A 195     -20.637 -14.507  75.054  1.00 66.01           O
ATOM   1281  OE2 GLU A 195     -19.015 -14.663  73.586  1.00 65.30           O
ATOM   1282  N   GLU A 196     -18.042 -19.213  77.121  1.00 59.97           N
ATOM   1283  CA  GLU A 196     -18.453 -20.499  77.692  1.00 59.86           C
ATOM   1284  C   GLU A 196     -17.401 -21.032  78.668  1.00 59.57           C
ATOM   1285  O   GLU A 196     -17.669 -21.936  79.464  1.00 58.23           O
ATOM   1286  CB  GLU A 196     -18.716 -21.526  76.555  1.00 58.96           C
ATOM   1287  N   ALA A 201     -14.693 -25.334  70.791  1.00 41.42           N
ATOM   1288  CA  ALA A 201     -13.676 -26.193  70.198  1.00 41.96           C
ATOM   1289  C   ALA A 201     -13.301 -25.743  68.780  1.00 42.33           C
ATOM   1290  O   ALA A 201     -14.155 -25.673  67.893  1.00 42.50           O

ATOM   2717  CD1 TRP B 188      -5.587 -20.042  89.501  1.00 22.79           C
ATOM   2718  CD2 TRP B 188      -3.662 -19.397  90.437  1.00 22.35           C
ATOM   2719  NE1 TRP B 188      -4.829 -21.167  89.707  1.00 22.57           N
ATOM   2720  CE2 TRP B 188      -3.637 -20.798  90.272  1.00 22.63           C
ATOM   2721  CE3 TRP B 188      -2.543 -18.764  90.997  1.00 22.96           C
ATOM   2722  CZ2 TRP B 188      -2.549 -21.583  90.670  1.00 21.99           C
ATOM   2723  CZ3 TRP B 188      -1.463 -19.541  91.392  1.00 23.43           C
ATOM   2724  CH2 TRP B 188      -1.472 -20.940  91.215  1.00 23.30           C
ATOM   2725  N   GLN B 189      -6.361 -17.370  86.815  1.00 28.12           N
ATOM   2726  CA  GLN B 189       6.724 -18.116  85.628  1.00 29.70           C
ATOM   2727  C   GLN B 189      -6.514 -17.353  84.328  1.00 28.64           C
ATOM   2728  O   GLN B 189      -6.815 -17.862  83.254  1.00 31.14           O
ATOM   2729  CB  GLN B 189      -8.187 -18.580  85.753  1.00 32.03           C
ATOM   2730  CG  GLN B 189      -8.430 -19.579  86.903  1.00 37.20           C
ATOM   2731  CD  GLN B 189      -9.898 -19.988  87.063  1.00 40.80           C
ATOM   2732  OE1 GLN B 189     -10.208 -20.963  87.760  1.00 42.46           O
ATOM   2733  NE2 GLN B 189     -10.805 -19.242  86.433  1.00 41.54           N
ATOM   2734  N   ASN B 190      -5.980 -16.148  84.396  1.00 26.37           N
ATOM   2735  CA  ASN B 190      -5.790 -15.399  83.172  1.00 24.53           C
ATOM   2736  C   ASN B 190      -4.388 -14.859  83.035  1.00 25.67           C
ATOM   2737  O   ASN B 190      -4.043 -14.293  82.003  1.00 26.47           O
ATOM   2738  CB  ASN B 190      -6.776 -14.244  83.102  1.00 23.33           C
ATOM   2739  CG  ASN B 190      -8.186 -14.705  82.821  1.00 23.10           C
ATOM   2740  OD1 ASN B 190      -8.510 -15.102  81.703  1.00 21.83           O
ATOM   2741  ND2 ASN B 190      -9.038 -14.658  83.837  1.00 22.66           N
ATOM   2742  N   PHE B 191      -3.585 -15.012  84.084  1.00 25.47           N
ATOM   2743  CA  PHE B 191      -2.216 -14.537  84.062  1.00 25.85           C
ATOM   2744  C   PHE B 191      -1.238 -15.656  84.410  1.00 28.13           C
ATOM   2745  O   PHE B 191      -0.171 -15.767  83.816  1.00 29.21           O
ATOM   2746  CB  PHE B 191      -2.014 -13.363  85.037  1.00 22.38           C
ATOM   2747  CG  PHE B 191      -2.680 -12.085  84.612  1.00 19.64           C
ATOM   2748  CD1 PHE B 191      -4.058 -11.920  84.733  1.00 18.87           C
ATOM   2749  CD2 PHE B 191      -1.928 -11.041  84.081  1.00 18.00           C
ATOM   2750  CE1 PHE B 191      -4.673 -10.740  84.332  1.00 16.26           C
ATOM   2751  CE2 PHE B 191      -2.531  -9.861  83.680  1.00 16.59           C
ATOM   2752  CZ  PHE B 191      -3.908  -9.708  83.807  1.00 16.38           C
ATOM   2753  N   VAL B 192      -1.599 -16.495  85.368  1.00 31.82           N
ATOM   2754  CA  VAL B 192      -0.714 -17.577  85.764  1.00 34.59           C
ATOM   2755  C   VAL B 192      -0.885 -18.757  84.829  1.00 38.26           C
ATOM   2756  O   VAL B 192      -1.983 -19.297  84.684  1.00 39.28           O
ATOM   2757  CB  VAL B 192      -0.991 -18.013  87.197  1.00 33.12           C
ATOM   2758  CG1 VAL B 192      -0.116 -19.185  87.554  1.00 33.15           C
ATOM   2759  CG2 VAL B 192      -0.742 -16.847  88.143  1.00 32.22           C
ATOM   2760  N   GLU B 193       0.208 -19.162  84.201  1.00 41.91           N
ATOM   2761  CA  GLU B 193       0.164 -20.262  83.267  1.00 46.74           C
ATOM   2762  C   GLU B 193      -0.029 -21.592  83.957  1.00 50.07           C
ATOM   2763  O   GLU B 193       0.848 -22.055  84.686  1.00 50.30           O
ATOM   2764  CB  GLU B 193       1.459 -20.315  82.447  1.00 47.59           C
ATOM   2765  CG  GLU B 193       1.254 -20.636  80.965  1.00 49.55           C
ATOM   2766  CD  GLU B 193       2.563 -20.817  80.214  1.00 50.50           C
ATOM   2767  OE1 GLU B 193       3.306 -21.761  80.559  1.00 50.73           O
ATOM   2768  OE2 GLU B 193       2.853 -20.022  79.283  1.00 50.94           O
ATOM   2769  N   GLN B 194      -1.173 -22.216  83.680  1.00 54.47           N
ATOM   2770  CA  GLN B 194      -1.508 -23.541  84.208  1.00 58.83           C
ATOM   2771  C   GLN B 194      -0.657 -24.577  83.447  1.00 62.10           C
ATOM   2772  O   GLN B 194      -0.624 -24.573  82.211  1.00 61.64           O
ATOM   2773  CB  GLN B 194      -2.994 -23.852  83.979  1.00 58.57           C
ATOM   2774  CG  GLN B 194      -3.970 -22.932  84.686  1.00 57.78           C
ATOM   2775  CD  GLN B 194      -3.898 -23.058  86.191  1.00 57.30           C
ATOM   2776  OE1 GLN B 194      -2.868 -22.776  86.801  1.00 56.05           O
ATOM   2777  NE2 GLN B 194      -4.998 -23.487  86.800  1.00 57.45           N
ATOM   2778  N   GLU B 195       0.020 -25.455  84.193  1.00 65.80           N
ATOM   2779  CA  GLU B 195       0.881 -26.500  83.615  1.00 69.36           C
ATOM   2780  C   GLU B 195       0.114 -27.616  82.904  1.00 71.50           C
ATOM   2781  O   GLU B 195       0.618 -28.203  81.944  1.00 71.97           O
ATOM   2782  CB  GLU B 195       1.779 -27.123  84.702  1.00 70.03           C
ATOM   2783  CG  GLU B 195       2.992 -26.278  85.100  1.00 70.46           C
ATOM   2784  CD  GLU B 195       2.628 -24.858  85.509  1.00 70.61           C
ATOM   2785  OE1 GLU B 195       1.810 -24.688  86.439  1.00 70.55           O
ATOM   2786  OE2 GLU B 195       3.168 -23.906  84.900  1.00 70.44           O
ATOM   2787  N   GLU B 196      -1.100 -27.903  83.372  1.00 73.56           N
ATOM   2788  CA  GLU B 196      -1.929 -28.949  82.770  1.00 75.53           C
ATOM   2789  C   GLU B 196      -3.056 -28.409  81.886  1.00 76.70           C
ATOM   2790  O   GLU B 196      -4.103 -29.050  81.760  1.00 77.40           O
ATOM   2791  CB  GLU B 196      -2.516 -29.846  83.864  1.00 75.56           C
ATOM   2792  N   GLY B 197      -2.833 -27.241  81.280  1.00 77.63           N
ATOM   2793  CA  GLY B 197      -3.801 -26.588  80.394  1.00 78.37           C
ATOM   2794  C   GLY B 197      -5.125 -26.276  81.108  1.00 78.86           C
ATOM   2795  O   GLY B 197      -5.143 -25.592  82.135  1.00 79.40           O
ATOM   2796  N   GLU B 198      -6.228 -26.781  80.559  1.00 78.80           N
ATOM   2797  CA  GLU B 198      -7.551 -26.568  81.141  1.00 78.33           C
ATOM   2798  C   GLU B 198      -7.975 -27.732  82.058  1.00 77.79           C
ATOM   2799  O   GLU B 198      -8.937 -28.448  81.773  1.00 78.09           O
ATOM   2800  CB  GLU B 198      -8.586 -26.359  80.017  1.00 78.38           C
ATOM   2801  N   SER B 199      -7.248 -27.911  83.162  1.00 76.53           N
ATOM   2802  CA  SER B 199      -7.546 -28.970  84.127  1.00 74.80           C
```

FIG. 7 (con't)

```
ATOM   1291  CB  ALA A 201    -14.169 -27.643  70.181  1.00 42.56      C
ATOM   1292  N   PHE A 202    -12.019 -25.436  68.575  1.00 41.90      N
ATOM   1293  CA  PHE A 202    -11.517 -24.990  67.275  1.00 40.32      C
ATOM   1294  C   PHE A 202    -11.889 -25.978  66.181  1.00 40.67      C
ATOM   1295  O   PHE A 202    -12.007 -27.178  66.432  1.00 41.39      O
ATOM   1296  CB  PHE A 202     -9.991 -24.846  67.314  1.00 37.36      C
ATOM   1297  CG  PHE A 202     -9.394 -24.381  66.015  1.00 34.24      C
ATOM   1298  CD1 PHE A 202     -9.677 -23.114  65.516  1.00 32.73      C
ATOM   1299  CD2 PHE A 202     -8.554 -25.206  65.277  1.00 33.86      C
ATOM   1300  CE1 PHE A 202     -9.137 -22.681  64.301  1.00 29.90      C
ATOM   1301  CE2 PHE A 202     -8.008 -24.780  64.062  1.00 30.90      C
ATOM   1302  CZ  PHE A 202     -8.305 -23.515  63.576  1.00 29.55      C
ATOM   1303  N   GLN A 203    -12.067 -25.475  64.967  1.00 40.74      N
ATOM   1304  CA  GLN A 203    -12.414 -26.339  63.848  1.00 41.28      C
ATOM   1305  C   GLN A 203    -11.728 -25.880  62.564  1.00 39.69      C
ATOM   1306  O   GLN A 203    -11.906 -24.746  62.128  1.00 38.68      O
ATOM   1307  CB  GLN A 203    -13.930 -26.343  63.656  1.00 44.69      C
ATOM   1308  CG  GLN A 203    -14.706 -26.687  64.924  1.00 50.11      C
ATOM   1309  CD  GLN A 203    -16.200 -26.415  64.796  1.00 53.41      C
ATOM   1310  OE1 GLN A 203    -16.634 -25.259  64.730  1.00 55.20      O
ATOM   1311  NE2 GLN A 203    -16.994 -27.481  64.756  1.00 54.06      N
ATOM   1312  N   PRO A 204    -10.928 -26.762  61.946  1.00 38.73      N
ATOM   1313  CA  PRO A 204    -10.236 -26.399  60.709  1.00 37.82      C
ATOM   1314  C   PRO A 204    -11.225 -26.151  59.575  1.00 36.81      C
ATOM   1315  O   PRO A 204    -12.416 -26.410  59.715  1.00 36.26      O
ATOM   1316  CB  PRO A 204     -9.332 -27.603  60.454  1.00 38.41      C
ATOM   1317  CG  PRO A 204    -10.123 -28.733  61.024  1.00 37.88      C
ATOM   1318  CD  PRO A 204    -10.624 -28.152  62.326  1.00 38.35      C
ATOM   1319  N   TRP A 205    -10.733 -25.647  58.452  1.00 35.50      N
ATOM   1320  CA  TRP A 205    -11.616 -25.370  57.336  1.00 34.59      C
ATOM   1321  C   TRP A 205    -11.099 -25.925  56.024  1.00 36.17      C
ATOM   1322  O   TRP A 205    -10.033 -26.530  55.973  1.00 34.54      O
ATOM   1323  CB  TRP A 205    -11.846 -23.857  57.209  1.00 30.32      C
ATOM   1324  CG  TRP A 205    -10.581 -23.051  57.196  1.00 25.07      C
ATOM   1325  CD1 TRP A 205     -9.735 -22.859  56.140  1.00 22.63      C
ATOM   1326  CD2 TRP A 205     -9.998 -22.360  58.309  1.00 22.48      C
ATOM   1327  NE1 TRP A 205     -8.661 -22.098  56.527  1.00 21.07      N
ATOM   1328  CE2 TRP A 205     -8.793 -21.777  57.855  1.00 21.49      C
ATOM   1329  CE3 TRP A 205    -10.373 -22.182  59.651  1.00 19.62      C
ATOM   1330  CZ2 TRP A 205     -7.956 -21.021  58.698  1.00 20.40      C
ATOM   1331  CZ3 TRP A 205     -9.537 -21.428  60.488  1.00 20.31      C
ATOM   1332  CH2 TRP A 205     -8.343 -20.862  60.006  1.00 17.57      C
ATOM   1333  N   GLU A 206    -11.897 -25.696  54.979  1.00 39.70      N
ATOM   1334  CA  GLU A 206    -11.628 -26.130  53.607  1.00 42.71      C
ATOM   1335  C   GLU A 206    -10.214 -26.646  53.394  1.00 42.39      C
ATOM   1336  O   GLU A 206     -9.956 -27.843  53.509  1.00 43.48      O
ATOM   1337  CB  GLU A 206    -11.874 -24.977  52.615  1.00 46.46      C
ATOM   1338  CG  GLU A 206    -12.635 -23.748  53.145  1.00 50.39      C
ATOM   1339  CD  GLU A 206    -14.141 -23.889  53.000  1.00 53.17      C
ATOM   1340  OE1 GLU A 206    -14.807 -24.469  53.867  1.00 54.75      O
ATOM   1341  OE2 GLU A 206    -14.658 -23.303  51.999  1.00 55.04      O
ATOM   1342  N   ASP A 207     -9.312 -25.720  53.076  1.00 41.36      N
ATOM   1343  CA  ASP A 207     -7.912 -26.033  52.804  1.00 40.79      C
ATOM   1344  C   ASP A 207     -6.924 -25.334  53.757  1.00 38.08      C
ATOM   1345  O   ASP A 207     -6.011 -24.629  53.332  1.00 36.62      O
ATOM   1346  CB  ASP A 207     -7.593 -25.684  51.333  1.00 44.46      C
ATOM   1347  CG  ASP A 207     -8.330 -24.439  50.841  1.00 47.83      C
ATOM   1348  OD1 ASP A 207     -8.214 -23.379  51.499  1.00 49.50      O
ATOM   1349  OD2 ASP A 207     -9.017 -24.517  49.788  1.00 49.24      O
ATOM   1350  N   ILE A 208     -7.110 -25.542  55.054  1.00 34.07      N
ATOM   1351  CA  ILE A 208     -6.229 -24.926  56.016  1.00 31.01      C
ATOM   1352  C   ILE A 208     -4.824 -25.520  55.928  1.00 30.50      C
ATOM   1353  O   ILE A 208     -3.844 -26.548  56.148  1.00 29.03      O
ATOM   1354  CB  ILE A 208     -6.754 -25.105  57.431  1.00 29.12      C
ATOM   1355  CG1 ILE A 208     -5.871 -24.349  58.408  1.00 27.44      C
ATOM   1356  CG2 ILE A 208     -6.794 -26.577  57.777  1.00 28.10      C
ATOM   1357  CD1 ILE A 208     -6.366 -24.410  59.822  1.00 27.40      C
ATOM   1358  N   GLN A 209     -4.736 -26.805  55.582  1.00 31.26      N
ATOM   1359  CA  GLN A 209     -3.449 -27.497  55.477  1.00 31.70      C
ATOM   1360  C   GLN A 209     -2.759 -27.307  54.131  1.00 30.36      C
ATOM   1361  O   GLN A 209     -1.538 -27.201  54.078  1.00 31.41      O
ATOM   1362  CB  GLN A 209     -3.625 -28.994  55.753  1.00 33.07      C
ATOM   1363  CG  GLN A 209     -2.325 -29.796  55.835  1.00 35.17      C
ATOM   1364  CD  GLN A 209     -1.337 -29.226  56.840  1.00 37.16      C
ATOM   1365  OE1 GLN A 209     -1.644 -29.077  58.028  1.00 37.31      O
ATOM   1366  NE2 GLN A 209     -0.142 -28.908  56.369  1.00 37.65      N
ATOM   1367  N   GLU A 210     -3.529 -27.272  53.056  1.00 30.28      N
ATOM   1368  CA  GLU A 210     -2.945 -27.103  51.740  1.00 32.33      C
ATOM   1369  C   GLU A 210     -2.429 -25.687  51.528  1.00 31.79      C
ATOM   1370  O   GLU A 210     -1.398 -25.508  50.896  1.00 32.58      O
ATOM   1371  CB  GLU A 210     -3.946 -27.458  50.632  1.00 34.07      C
ATOM   1372  CG  GLU A 210     -5.334 -27.893  51.114  1.00 39.54      C
ATOM   1373  CD  GLU A 210     -5.314 -29.147  51.959  1.00 41.45      C
ATOM   1374  OE1 GLU A 210     -4.656 -30.118  51.514  1.00 44.53      O
ATOM   1375  OE2 GLU A 210     -5.952 -29.160  53.049  1.00 40.18      O
ATOM   1376  N   ASN A 211     -3.139 -24.685  52.049  1.00 31.96      N
ATOM   2803  C   SER B 199     -7.167 -28.556  85.558  1.00 73.65      C
ATOM   2804  O   SER B 199     -6.266 -29.137  86.170  1.00 73.64      O
ATOM   2805  CB  SER B 199     -6.819 -30.259  83.733  1.00 74.61      C
ATOM   2806  N   LYS B 200     -7.864 -27.546  86.077  1.00 71.97      N
ATOM   2807  CA  LYS B 200     -7.631 -27.029  87.427  1.00 70.16      C
ATOM   2808  C   LYS B 200     -8.581 -25.865  87.747  1.00 68.45      C
ATOM   2809  O   LYS B 200     -8.817 -24.990  86.908  1.00 68.69      O
ATOM   2810  CB  LYS B 200     -6.163 -26.576  87.581  1.00 70.88      C
ATOM   2811  N   ALA B 201     -9.128 -25.866  88.960  1.00 65.62      N
ATOM   2812  CA  ALA B 201    -10.047 -24.818  89.383  1.00 62.53      C
ATOM   2813  C   ALA B 201     -9.302 -23.756  90.174  1.00 60.59      C
ATOM   2814  O   ALA B 201     -8.252 -23.285  89.741  1.00 61.13      O
ATOM   2815  CB  ALA B 201    -11.167 -25.411  90.226  1.00 62.89      C
ATOM   2816  N   PHE B 202     -9.841 -23.389  91.340  1.00 56.77      N
ATOM   2817  CA  PHE B 202     -9.229 -22.366  92.188  1.00 52.31      C
ATOM   2818  C   PHE B 202     -9.393 -22.681  93.666  1.00 50.70      C
ATOM   2819  O   PHE B 202    -10.504 -22.920  94.134  1.00 50.58      O
ATOM   2820  CB  PHE B 202     -9.860 -21.002  91.912  1.00 49.87      C
ATOM   2821  CG  PHE B 202     -9.152 -19.861  92.592  1.00 46.65      C
ATOM   2822  CD1 PHE B 202     -7.979 -19.341  92.063  1.00 46.09      C
ATOM   2823  CD2 PHE B 202     -9.641 -19.322  93.769  1.00 45.52      C
ATOM   2824  CE1 PHE B 202     -7.306 -18.301  92.698  1.00 45.10      C
ATOM   2825  CE2 PHE B 202     -8.971 -18.283  94.406  1.00 45.12      C
ATOM   2826  CZ  PHE B 202     -7.802 -17.776  93.867  1.00 44.53      C
ATOM   2827  N   GLN B 203     -8.289 -22.655  94.403  1.00 49.07      N
ATOM   2828  CA  GLN B 203     -8.308 -22.934  95.834  1.00 47.94      C
ATOM   2829  C   GLN B 203     -8.048 -21.668  96.643  1.00 45.83      C
ATOM   2830  O   GLN B 203     -6.906 -21.284  96.886  1.00 46.43      O
ATOM   2831  CB  GLN B 203     -7.263 -23.995  96.179  1.00 50.66      C
ATOM   2832  CG  GLN B 203     -6.805 -23.987  97.640  1.00 55.39      C
ATOM   2833  CD  GLN B 203     -7.849 -24.520  98.616  1.00 58.12      C
ATOM   2834  OE1 GLN B 203     -9.021 -24.141  98.565  1.00 60.40      O
ATOM   2835  NE2 GLN B 203     -7.418 -25.393  99.524  1.00 58.74      N
ATOM   2836  N   PRO B 204     -9.122 -21.006  97.079  1.00 43.40      N
ATOM   2837  CA  PRO B 204     -8.981 -19.785  97.860  1.00 40.47      C
ATOM   2838  C   PRO B 204     -8.527 -20.085  99.275  1.00 37.19      C
ATOM   2839  O   PRO B 204     -8.652 -21.206  99.743  1.00 35.18      O
ATOM   2840  CB  PRO B 204    -10.385 -19.197  97.816  1.00 41.54      C
ATOM   2841  CG  PRO B 204    -11.237 -20.414  97.822  1.00 41.04      C
ATOM   2842  CD  PRO B 204    -10.546 -21.296  96.816  1.00 42.36      C
ATOM   2843  N   TRP B 205     -7.988 -19.067  99.943  1.00 34.58      N
ATOM   2844  CA  TRP B 205     -7.526 -19.220 101.309  1.00 31.36      C
ATOM   2845  C   TRP B 205     -8.591 -18.841 102.351  1.00 31.15      C
ATOM   2846  O   TRP B 205     -9.555 -18.123 102.072  1.00 28.26      O
ATOM   2847  CB  TRP B 205     -6.234 -18.421 101.518  1.00 29.43      C
ATOM   2848  CG  TRP B 205     -6.185 -17.103 100.778  1.00 26.83      C
ATOM   2849  CD1 TRP B 205     -6.383 -15.855 101.298  1.00 25.68      C
ATOM   2850  CD2 TRP B 205     -5.912 -16.919  99.386  1.00 26.29      C
ATOM   2851  NE1 TRP B 205     -6.253 -14.904 100.313  1.00 25.88      N
ATOM   2852  CE2 TRP B 205     -5.968 -15.530  99.127  1.00 26.01      C
ATOM   2853  CE3 TRP B 205     -5.633 -17.795  98.331  1.00 24.23      C
ATOM   2854  CZ2 TRP B 205     -5.748 -14.996  97.857  1.00 23.90      C
ATOM   2855  CZ3 TRP B 205     -5.416 -17.264  97.069  1.00 23.98      C
ATOM   2856  CH2 TRP B 205     -5.478 -15.881  96.843  1.00 23.72      C
ATOM   2857  N   GLU B 206     -8.393 -19.345 103.561  1.00 31.76      N
ATOM   2858  CA  GLU B 206     -9.303 -19.122 104.679  1.00 32.35      C
ATOM   2859  C   GLU B 206     -9.751 -17.675 104.959  1.00 31.10      C
ATOM   2860  O   GLU B 206    -10.937 -17.438 105.190  1.00 30.56      O
ATOM   2861  CB  GLU B 206     -8.683 -19.734 105.930  1.00 34.67      C
ATOM   2862  CG  GLU B 206     -9.555 -19.673 107.159  1.00 40.49      C
ATOM   2863  CD  GLU B 206     -8.918 -20.364 108.348  1.00 43.62      C
ATOM   2864  OE1 GLU B 206     -8.725 -21.599 108.281  1.00 46.07      O
ATOM   2865  OE2 GLU B 206     -8.600 -19.679 109.346  1.00 44.88      O
ATOM   2866  N   ASP B 207     -8.818 -16.722 104.948  1.00 29.35      N
ATOM   2867  CA  ASP B 207     -9.137 -15.316 105.212  1.00 29.51      C
ATOM   2868  C   ASP B 207     -9.279 -14.440 103.942  1.00 27.92      C
ATOM   2869  O   ASP B 207     -9.039 -13.236 103.973  1.00 28.27      O
ATOM   2870  CB  ASP B 207     -8.078 -14.703 106.148  1.00 32.41      C
ATOM   2871  CG  ASP B 207     -6.732 -14.486 105.457  1.00 36.44      C
ATOM   2872  OD1 ASP B 207     -6.342 -15.344 104.634  1.00 39.98      O
ATOM   2873  OD2 ASP B 207     -6.057 -13.469 105.739  1.00 37.23      O
ATOM   2874  N   ILE B 208     -9.683 -15.045 102.831  1.00 25.56      N
ATOM   2875  CA  ILE B 208     -9.830 -14.310 101.582  1.00 21.83      C
ATOM   2876  C   ILE B 208    -10.960 -13.259 101.606  1.00 21.54      C
ATOM   2877  O   ILE B 208    -10.883 -12.218 100.949  1.00 19.26      O
ATOM   2878  CB  ILE B 208    -10.044 -15.298 100.425  1.00 20.10      C
ATOM   2879  CG1 ILE B 208     -9.852 -14.593  99.099  1.00 19.54      C
ATOM   2880  CG2 ILE B 208    -11.425 -15.919 100.515  1.00 18.97      C
ATOM   2881  CD1 ILE B 208     -9.544 -15.518  97.985  1.00 20.20      C
ATOM   2882  N   GLN B 209    -12.005 -13.524 102.381  1.00 21.53      N
ATOM   2883  CA  GLN B 209    -13.094 -12.581 102.452  1.00 21.16      C
ATOM   2884  C   GLN B 209    -12.857 -11.504 103.516  1.00 21.89      C
ATOM   2885  O   GLN B 209    -13.084 -10.320 103.256  1.00 21.96      O
ATOM   2886  CB  GLN B 209    -14.412 -13.315 102.709  1.00 20.66      C
ATOM   2887  CG  GLN B 209    -15.626 -12.536 102.236  1.00 20.15      C
ATOM   2888  CD  GLN B 209    -16.907 -13.125 102.751  1.00 21.39      C
```

FIG. 7 (con't)

| | | | | | |
|---|---|---|---|---|---|
| ATOM | 1377 CA ASN A 211 | -2.716 -23.287 51.908 1.00 31.08 | C | ATOM | 2889 OE1 GLN B 209 | -16.897 -13.891 103.705 1.00 23.81 | O |
| ATOM | 1378 C ASN A 211 | -1.359 -23.115 52.609 1.00 29.91 | C | ATOM | 2890 NE2 GLN B 209 | -18.035 -12.759 102.134 1.00 21.90 | N |
| ATOM | 1379 O ASN A 211 | -0.442 -22.466 52.110 1.00 27.63 | O | ATOM | 2891 N GLU B 210 | -12.383 -11.914 104.692 1.00 23.22 | N |
| ATOM | 1380 CB ASN A 211 | -3.742 -22.314 52.524 1.00 33.88 | C | ATOM | 2892 CA GLU B 210 | -12.111 -10.980 105.790 1.00 24.14 | C |
| ATOM | 1381 CG ASN A 211 | -5.116 -22.368 51.831 1.00 38.73 | C | ATOM | 2893 C GLU B 210 | -11.165 -9.902 105.343 1.00 21.96 | C |
| ATOM | 1382 OD1 ASN A 211 | -5.264 -22.966 50.762 1.00 41.62 | O | ATOM | 2894 O GLU B 210 | -11.291 -8.765 105.761 1.00 21.89 | O |
| ATOM | 1383 ND2 ASN A 211 | -6.130 -21.737 52.443 1.00 38.00 | N | ATOM | 2895 CB GLU B 210 | -11.487 -11.704 106.983 1.00 27.49 | C |
| ATOM | 1384 N PHE A 212 | -1.256 -23.695 53.794 1.00 28.77 | N | ATOM | 2896 CG GLU B 210 | -12.149 -13.021 107.277 1.00 34.45 | C |
| ATOM | 1385 CA PHE A 212 | -0.027 -23.634 54.558 1.00 26.34 | C | ATOM | 2897 CD GLU B 210 | -11.750 -13.580 108.617 1.00 38.98 | C |
| ATOM | 1386 C PHE A 212 | 1.144 -24.194 53.731 1.00 25.80 | C | ATOM | 2898 OE1 GLU B 210 | -11.238 -12.793 109.449 1.00 40.42 | O |
| ATOM | 1387 O PHE A 212 | 2.110 -23.488 53.420 1.00 23.73 | O | ATOM | 2899 OE2 GLU B 210 | -11.963 -14.801 108.838 1.00 41.41 | O |
| ATOM | 1388 CB PHE A 212 | -0.206 -24.440 55.835 1.00 26.16 | C | ATOM | 2900 N ASN B 211 | -10.202 -10.282 104.510 1.00 21.86 | N |
| ATOM | 1389 CG PHE A 212 | 1.075 -24.843 56.489 1.00 25.80 | C | ATOM | 2901 CA ASN B 211 | -9.231 -9.349 103.975 1.00 21.74 | C |
| ATOM | 1390 CD1 PHE A 212 | 1.938 -23.883 56.998 1.00 26.05 | C | ATOM | 2902 C ASN B 211 | -9.909 -8.298 103.109 1.00 20.18 | C |
| ATOM | 1391 CD2 PHE A 212 | 1.411 -26.184 56.612 1.00 25.22 | C | ATOM | 2903 O ASN B 211 | -9.708 -7.104 103.311 1.00 20.13 | O |
| ATOM | 1392 CE1 PHE A 212 | 3.116 -24.248 57.626 1.00 25.73 | C | ATOM | 2904 CB ASN B 211 | -8.205 -10.083 103.131 1.00 24.37 | C |
| ATOM | 1393 CE2 PHE A 212 | 2.588 -26.559 57.232 1.00 26.75 | C | ATOM | 2905 CG ASN B 211 | -6.856 -10.098 103.771 1.00 28.07 | C |
| ATOM | 1394 CZ PHE A 212 | 3.444 -25.586 57.743 1.00 27.21 | C | ATOM | 2906 OD1 ASN B 211 | -6.257 -9.045 103.990 1.00 29.99 | O |
| ATOM | 1395 N LEU A 213 | 1.045 -25.469 53.372 1.00 23.96 | N | ATOM | 2907 ND2 ASN B 211 | -6.357 -11.292 104.083 1.00 29.35 | N |
| ATOM | 1396 CA LEU A 213 | 2.115 -26.102 52.626 1.00 22.98 | C | ATOM | 2908 N PHE B 212 | -10.688 -8.752 102.132 1.00 17.70 | N |
| ATOM | 1397 C LEU A 213 | 2.486 -25.338 51.364 1.00 21.49 | C | ATOM | 2909 CA PHE B 212 | -11.410 -7.840 101.253 1.00 18.18 | C |
| ATOM | 1398 O LEU A 213 | 3.659 -25.226 51.032 1.00 22.36 | O | ATOM | 2910 C PHE B 212 | -12.309 -6.885 102.075 1.00 18.14 | C |
| ATOM | 1399 CB LEU A 213 | 1.753 -27.550 52.282 1.00 23.27 | C | ATOM | 2911 O PHE B 212 | -12.209 -5.659 101.967 1.00 16.29 | O |
| ATOM | 1400 CG LEU A 213 | 1.717 -28.519 53.466 1.00 24.09 | C | ATOM | 2912 CB PHE B 212 | -12.294 -8.636 100.262 1.00 15.20 | C |
| ATOM | 1401 CD1 LEU A 213 | 1.033 -29.798 53.037 1.00 24.67 | C | ATOM | 2913 CG PHE B 212 | -13.353 -7.798 99.583 1.00 11.34 | C |
| ATOM | 1402 CD2 LEU A 213 | 3.116 -28.805 53.967 1.00 22.04 | C | ATOM | 2914 CD1 PHE B 212 | -13.006 -6.780 98.705 1.00 7.88 | C |
| ATOM | 1403 N TYR A 214 | 1.498 -24.797 50.673 1.00 19.45 | N | ATOM | 2915 CD2 PHE B 212 | -14.708 -8.000 99.877 1.00 12.66 | C |
| ATOM | 1404 CA TYR A 214 | 1.762 -24.053 49.467 1.00 18.74 | C | ATOM | 2916 CE1 PHE B 212 | -13.994 -5.956 98.130 1.00 9.56 | C |
| ATOM | 1405 C TYR A 214 | 2.675 -22.850 49.715 1.00 19.90 | C | ATOM | 2917 CE2 PHE B 212 | -15.709 -7.189 99.306 1.00 12.13 | C |
| ATOM | 1406 O TYR A 214 | 3.726 -22.704 49.078 1.00 21.76 | O | ATOM | 2918 CZ PHE B 212 | -15.352 -6.163 98.434 1.00 9.72 | C |
| ATOM | 1407 CB TYR A 214 | 0.472 -23.571 48.848 1.00 19.08 | C | ATOM | 2919 N LEU B 213 | -13.166 -7.487 102.892 1.00 17.90 | N |
| ATOM | 1408 CG TYR A 214 | 0.682 -22.727 47.621 1.00 19.97 | C | ATOM | 2920 CA LEU B 213 | -14.105 -6.750 103.733 1.00 19.47 | C |
| ATOM | 1409 CD1 TYR A 214 | 0.880 -23.302 46.374 1.00 19.30 | C | ATOM | 2921 C LEU B 213 | -13.374 -5.768 104.622 1.00 19.11 | C |
| ATOM | 1410 CD2 TYR A 214 | 0.719 -21.337 47.717 1.00 22.30 | C | ATOM | 2922 O LEU B 213 | -13.771 -4.606 104.755 1.00 19.13 | O |
| ATOM | 1411 CE1 TYR A 214 | 1.116 -22.505 45.232 1.00 21.38 | C | ATOM | 2923 CB LEU B 213 | -14.938 -7.731 104.584 1.00 19.21 | C |
| ATOM | 1412 CE2 TYR A 214 | 0.952 -20.536 46.597 1.00 23.24 | C | ATOM | 2924 CG LEU B 213 | -15.863 -8.679 103.775 1.00 18.64 | C |
| ATOM | 1413 CZ TYR A 214 | 1.152 -21.114 45.359 1.00 22.72 | C | ATOM | 2925 CD1 LEU B 213 | -16.137 -9.943 104.559 1.00 19.45 | C |
| ATOM | 1414 OH TYR A 214 | 1.396 -20.265 44.291 1.00 22.46 | O | ATOM | 2926 CD2 LEU B 213 | -17.175 -7.996 103.421 1.00 19.54 | C |
| ATOM | 1415 N TYR A 215 | 2.277 -21.981 50.635 1.00 18.41 | N | ATOM | 2927 N TYR B 214 | -12.284 -6.236 105.213 1.00 18.67 | N |
| ATOM | 1416 CA TYR A 215 | 3.044 -20.788 50.942 1.00 18.24 | C | ATOM | 2928 CA TYR B 214 | -11.490 -5.409 106.092 1.00 17.05 | C |
| ATOM | 1417 C TYR A 215 | 4.356 -21.048 51.674 1.00 18.83 | C | ATOM | 2929 C TYR B 214 | -10.993 -4.157 105.388 1.00 18.47 | C |
| ATOM | 1418 O TYR A 215 | 5.262 -20.204 51.671 1.00 18.60 | O | ATOM | 2930 O TYR B 214 | -11.227 -3.054 105.869 1.00 18.91 | O |
| ATOM | 1419 CB TYR A 215 | 2.198 -19.787 51.737 1.00 16.51 | C | ATOM | 2931 CB TYR B 214 | -10.300 -6.192 106.615 1.00 18.15 | C |
| ATOM | 1420 CG TYR A 215 | 1.214 -19.016 50.885 1.00 17.10 | C | ATOM | 2932 CG TYR B 214 | -9.400 -5.410 107.552 1.00 18.40 | C |
| ATOM | 1421 CD1 TYR A 215 | -0.135 -19.354 50.853 1.00 14.46 | C | ATOM | 2933 CD1 TYR B 214 | -9.711 -5.288 108.899 1.00 17.14 | C |
| ATOM | 1422 CD2 TYR A 215 | 1.644 -17.965 50.063 1.00 16.80 | C | ATOM | 2934 CD2 TYR B 214 | -8.220 -4.817 107.093 1.00 18.75 | C |
| ATOM | 1423 CE1 TYR A 215 | -1.035 -18.679 50.029 1.00 16.00 | C | ATOM | 2935 CE1 TYR B 214 | -8.874 -4.603 109.779 1.00 18.61 | C |
| ATOM | 1424 CE2 TYR A 215 | 0.755 -17.279 49.232 1.00 16.39 | C | ATOM | 2936 CE2 TYR B 214 | -7.367 -4.120 107.972 1.00 19.41 | C |
| ATOM | 1425 CZ TYR A 215 | -0.579 -17.646 49.215 1.00 18.26 | C | ATOM | 2937 CZ TYR B 214 | -7.710 -4.021 109.317 1.00 19.78 | C |
| ATOM | 1426 OH TYR A 215 | -1.447 -17.026 48.323 1.00 21.26 | O | ATOM | 2938 OH TYR B 214 | -6.914 -3.329 110.213 1.00 21.64 | O |
| ATOM | 1427 N GLU A 216 | 4.469 -22.206 52.300 1.00 19.52 | N | ATOM | 2939 N TYR B 215 | -10.312 -4.327 104.249 1.00 17.63 | N |
| ATOM | 1428 CA GLU A 216 | 5.681 -22.541 53.003 1.00 20.54 | C | ATOM | 2940 CA TYR B 215 | -9.747 -3.199 103.508 1.00 17.50 | C |
| ATOM | 1429 C GLU A 216 | 6.709 -22.785 51.931 1.00 22.53 | C | ATOM | 2941 C TYR B 215 | -10.722 -2.346 102.700 1.00 18.26 | C |
| ATOM | 1430 O GLU A 216 | 7.861 -22.372 52.059 1.00 24.00 | O | ATOM | 2942 O TYR B 215 | -10.389 -1.234 102.276 1.00 18.22 | O |
| ATOM | 1431 CB GLU A 216 | 5.499 -23.802 53.846 1.00 20.92 | C | ATOM | 2943 CB TYR B 215 | -8.599 -3.672 102.604 1.00 16.50 | C |
| ATOM | 1432 CG GLU A 216 | 6.771 -24.259 54.531 1.00 24.55 | C | ATOM | 2944 CG TYR B 215 | -7.338 -4.010 103.377 1.00 17.72 | C |
| ATOM | 1433 CD GLU A 216 | 6.586 -25.490 55.382 1.00 26.85 | C | ATOM | 2945 CD1 TYR B 215 | -7.000 -5.338 103.687 1.00 16.30 | C |
| ATOM | 1434 OE1 GLU A 216 | 6.191 -26.556 54.836 1.00 26.59 | O | ATOM | 2946 CD2 TYR B 215 | 6.510 3.000 103.877 1.00 17.88 | C |
| ATOM | 1435 OE2 GLU A 216 | 6.842 -25.386 56.605 1.00 27.10 | O | ATOM | 2947 CE1 TYR B 215 | -5.866 -5.651 104.484 1.00 11.85 | C |
| ATOM | 1436 N GLU A 217 | 6.286 -23.440 50.848 1.00 24.09 | N | ATOM | 2948 CE2 TYR B 215 | -5.379 -3.298 104.672 1.00 15.77 | C |
| ATOM | 1437 CA GLU A 217 | 7.187 -23.755 49.728 1.00 25.51 | C | ATOM | 2949 CZ TYR B 215 | -5.063 -4.622 104.971 1.00 14.06 | C |
| ATOM | 1438 C GLU A 217 | 7.688 -22.500 49.042 1.00 24.63 | C | ATOM | 2950 OH TYR B 215 | -3.937 -4.896 105.740 1.00 11.98 | O |
| ATOM | 1439 O GLU A 217 | 8.881 -22.340 48.816 1.00 22.91 | O | ATOM | 2951 N GLU B 216 | -11.927 -2.862 102.488 1.00 19.22 | N |
| ATOM | 1440 CB GLU A 217 | 6.473 -24.662 48.710 1.00 28.86 | C | ATOM | 2952 CA GLU B 216 | -12.929 -2.129 101.740 1.00 18.65 | C |
| ATOM | 1441 CG GLU A 217 | 7.077 -24.635 47.290 1.00 33.24 | C | ATOM | 2953 C GLU B 216 | -13.440 -0.999 102.612 1.00 20.05 | C |
| ATOM | 1442 CD GLU A 217 | 6.045 -24.280 46.222 1.00 38.07 | C | ATOM | 2954 O GLU B 216 | -13.668 0.114 102.133 1.00 19.98 | O |
| ATOM | 1443 OE1 GLU A 217 | 5.161 -23.433 46.499 1.00 39.02 | O | ATOM | 2955 CB GLU B 216 | -14.089 -3.045 101.340 1.00 16.09 | C |
| ATOM | 1444 OE2 GLU A 217 | 6.114 -24.829 45.097 1.00 40.85 | O | ATOM | 2956 CG GLU B 216 | -15.310 -2.275 100.837 1.00 18.00 | C |
| ATOM | 1445 N LYS A 218 | 6.750 -21.622 48.702 1.00 25.71 | N | ATOM | 2957 CD GLU B 216 | -16.406 -3.138 100.197 1.00 21.54 | C |
| ATOM | 1446 CA LYS A 218 | 7.071 -20.362 48.044 1.00 26.11 | C | ATOM | 2958 OE1 GLU B 216 | -16.961 -4.040 100.861 1.00 21.13 | O |
| ATOM | 1447 C LYS A 218 | 7.968 -19.475 48.904 1.00 24.92 | C | ATOM | 2959 OE2 GLU B 216 | -16.736 -2.898 99.006 1.00 21.35 | O |
| ATOM | 1448 O LYS A 218 | 8.900 -18.864 48.393 1.00 24.92 | O | ATOM | 2960 N GLU B 217 | -13.599 -1.299 103.904 1.00 22.30 | N |
| ATOM | 1449 CB LYS A 218 | 5.786 -19.607 47.731 1.00 27.40 | C | ATOM | 2961 CA GLU B 217 | -14.093 -0.335 104.895 1.00 23.96 | C |
| ATOM | 1450 CG LYS A 218 | 4.887 -20.318 46.753 1.00 29.84 | C | ATOM | 2962 C GLU B 217 | -13.101 0.835 105.018 1.00 22.43 | C |
| ATOM | 1451 CD LYS A 218 | 5.530 -20.433 45.379 1.00 28.91 | C | ATOM | 2963 O GLU B 217 | -13.510 2.001 105.018 1.00 20.15 | O |
| ATOM | 1452 CE LYS A 218 | 4.641 -21.240 44.443 1.00 30.13 | C | ATOM | 2964 CB GLU B 217 | -14.305 -1.044 106.252 1.00 25.99 | C |
| ATOM | 1453 NZ LYS A 218 | 5.200 -21.333 43.070 1.00 30.40 | N | ATOM | 2965 CG GLU B 217 | -15.320 -0.345 107.179 1.00 32.14 | C |
| ATOM | 1454 N LEU A 219 | 7.669 -19.387 50.199 1.00 23.72 | N | ATOM | 2966 CD GLU B 217 | -14.685 0.364 108.378 1.00 35.99 | C |
| ATOM | 1455 CA LEU A 219 | 8.467 -18.567 51.092 1.00 23.67 | C | ATOM | 2967 OE1 GLU B 217 | -13.676 1.086 108.208 1.00 38.81 | O |
| ATOM | 1456 C LEU A 219 | 9.863 -19.150 51.212 1.00 25.66 | C | ATOM | 2968 OE2 GLU B 217 | -15.211 0.213 109.499 1.00 37.92 | O |
| ATOM | 1457 O LEU A 219 | 10.830 -18.410 51.375 1.00 27.47 | O | ATOM | 2969 N LYS B 218 | -11.811 0.493 105.080 1.00 21.85 | N |
| ATOM | 1458 CB LEU A 219 | 7.830 -18.475 52.484 1.00 22.58 | C | ATOM | 2970 CA LYS B 218 | -10.718 1.468 105.203 1.00 23.65 | C |
| ATOM | 1459 CG LEU A 219 | 8.601 -17.721 53.582 1.00 20.97 | C | ATOM | 2971 C LYS B 218 | -10.700 2.428 104.021 1.00 23.83 | C |
| ATOM | 1460 CD1 LEU A 219 | 8.705 -16.262 53.212 1.00 20.14 | C | ATOM | 2972 O LYS B 218 | -10.919 3.625 104.184 1.00 25.41 | O |
| ATOM | 1461 CD2 LEU A 219 | 7.891 -17.853 54.920 1.00 21.69 | C | ATOM | 2973 CB LYS B 218 | -9.350 0.757 105.258 1.00 24.64 | C |
| ATOM | 1462 N ALA A 220 | 9.985 -20.473 51.135 1.00 26.23 | N | ATOM | 2974 CG LYS B 218 | -9.276 -0.470 106.159 1.00 24.37 | C |

FIG. 7 (con't)

```
ATOM  1463 CA  ALA A 220    11.296 -21.122 51.238 1.00 27.57    C
ATOM  1464 C   ALA A 220    12.142 -20.913 49.974 1.00 29.46    C
ATOM  1465 O   ALA A 220    13.355 -20.709 50.054 1.00 29.16    O
ATOM  1466 CB  ALA A 220    11.133 -22.605 51.515 1.00 24.98    C
ATOM  1467 N   ASP A 221    11.500 -20.969 48.811 1.00 30.65    N
ATOM  1468 CA  ASP A 221    12.197 -20.770 47.549 1.00 32.42    C
ATOM  1469 C   ASP A 221    12.841 -19.395 47.468 1.00 32.14    C
ATOM  1470 O   ASP A 221    14.002 -19.252 47.079 1.00 31.87    O
ATOM  1471 CB  ASP A 221    11.244 -20.933 46.368 1.00 34.87    C
ATOM  1472 CG  ASP A 221    11.065 -22.375 45.966 1.00 38.82    C
ATOM  1473 OD1 ASP A 221    11.883 -23.215 46.396 1.00 40.17    O
ATOM  1474 OD2 ASP A 221    10.113 -22.667 45.208 1.00 42.34    O
ATOM  1475 N   ILE A 222    12.079 -18.376 47.838 1.00 31.44    N
ATOM  1476 CA  ILE A 222    12.571 -17.015 47.790 1.00 32.16    C
ATOM  1477 C   ILE A 222    13.616 -16.736 48.867 1.00 31.34    C
ATOM  1478 O   ILE A 222    14.640 -16.107 48.597 1.00 30.55    O
ATOM  1479 CB  ILE A 222    11.411 -16.007 47.934 1.00 31.93    C
ATOM  1480 CG1 ILE A 222    11.973 -14.617 48.225 1.00 31.99    C
ATOM  1481 CG2 ILE A 222    10.468 -16.472 48.999 1.00 33.78    C
ATOM  1482 CD1 ILE A 222    11.014 -13.677 48.846 1.00 32.26    C
ATOM  1483 N   LEU A 223    13.360 -17.211 50.074 1.00 32.73    N
ATOM  1484 CA  LEU A 223    14.280 -16.977 51.178 1.00 35.39    C
ATOM  1485 C   LEU A 223    15.564 -17.790 51.105 1.00 37.03    C
ATOM  1486 O   LEU A 223    16.499 -17.536 51.856 1.00 37.69    O
ATOM  1487 CB  LEU A 223    13.588 -17.235 52.518 1.00 33.88    C
ATOM  1488 CG  LEU A 223    12.968 -16.033 53.224 1.00 32.85    C
ATOM  1489 CD1 LEU A 223    12.038 -15.275 52.278 1.00 32.57    C
ATOM  1490 CD2 LEU A 223    12.227 -16.529 54.461 1.00 32.42    C
ATOM  1491 N   LYS A 224    15.618 -18.759 50.203 1.00 39.82    N
ATOM  1492 CA  LYS A 224    16.808 -19.582 50.077 1.00 42.13    C
ATOM  1493 C   LYS A 224    16.886 -20.133 48.674 1.00 43.06    C
ATOM  1494 O   LYS A 224    17.537 -19.471 47.839 1.00 43.58    O
ATOM  1495 CB  LYS A 224    16.758 -20.741 51.087 1.00 44.93    C
ATOM  1496 CG  LYS A 224    16.896 -20.320 52.549 1.00 46.58    C
ATOM  1497 CD  LYS A 224    16.737 -21.505 53.504 1.00 47.58    C
ATOM  1498 CE  LYS A 224    17.818 -22.569 53.300 1.00 48.37    C
ATOM  1499 NZ  LYS A 224    17.606 -23.755 54.190 1.00 50.33    N
ATOM  1500 OXT LYS A 224    16.278 -21.200 48.427 1.00 43.78    O
TER   1501     LYS A 224
ATOM  1502 N   GLY B 35    -10.627 -21.550 77.712 1.00 65.95    N
ATOM  1503 CA  GLY B 35    -11.789 -20.604 77.728 1.00 65.74    C
ATOM  1504 C   GLY B 35    -11.777 -19.666 78.924 1.00 65.88    C
ATOM  1505 O   GLY B 35    -12.113 -18.482 78.804 1.00 65.82    O
ATOM  1506 N   SER B 36    -11.391 -20.196 80.084 1.00 65.25    N
ATOM  1507 CA  SER B 36    -11.332 -19.406 81.316 1.00 64.34    C
ATOM  1508 C   SER B 36    -10.181 -18.403 81.291 1.00 63.25    C
ATOM  1509 O   SER B 36    -10.320 -17.280 81.782 1.00 63.83    O
ATOM  1510 CB  SER B 36    -11.194 -20.325 82.537 1.00 64.89    C
ATOM  1511 OG  SER B 36    -12.357 -21.122 82.705 1.00 65.58    O
ATOM  1512 N   GLY B 37     -9.048 -18.815 80.719 1.00 61.08    N

ATOM  2975 CD  LYS B 218    -9.560  -0.156 107.610 1.00 21.91   C
ATOM  2976 CE  LYS B 218    -9.364  -1.406 108.432 1.00 22.06   C
ATOM  2977 NZ  LYS B 218    -9.899  -1.270 109.802 1.00 20.19   N
ATOM  2978 N   LEU B 219   -10.437   1.889 102.833 1.00 21.86   N
ATOM  2979 CA  LEU B 219   -10.373   2.684 101.616 1.00 20.85   C
ATOM  2980 C   LEU B 219   -11.591   3.593 101.480 1.00 22.27   C
ATOM  2981 O   LEU B 219   -11.497   4.715 100.979 1.00 19.24   O
ATOM  2982 CB  LEU B 219   -10.273   1.747 100.408 1.00 18.92   C
ATOM  2983 CG  LEU B 219   -10.051   2.379  99.042 1.00 16.09   C
ATOM  2984 CD1 LEU B 219    -8.661   2.983  99.026 1.00 13.42   C
ATOM  2985 CD2 LEU B 219   -10.224   1.333  97.936 1.00 16.07   C
ATOM  2986 N   ALA B 220   -12.736   3.097 101.952 1.00 25.41   N
ATOM  2987 CA  ALA B 220   -13.988   3.846 101.884 1.00 28.52   C
ATOM  2988 C   ALA B 220   -13.892   5.113 102.723 1.00 30.96   C
ATOM  2989 O   ALA B 220   -14.068   6.217 102.210 1.00 30.08   O
ATOM  2990 CB  ALA B 220   -15.150   2.977 102.365 1.00 26.98   C
ATOM  2991 N   ASP B 221   -13.599   4.941 104.009 1.00 33.78   N
ATOM  2992 CA  ASP B 221   -13.505   6.077 104.916 1.00 37.59   C
ATOM  2993 C   ASP B 221   -12.552   7.128 104.368 1.00 38.11   C
ATOM  2994 O   ASP B 221   -12.830   8.321 104.433 1.00 38.48   O
ATOM  2995 CB  ASP B 221   -13.028   5.635 106.315 1.00 40.16   C
ATOM  2996 CG  ASP B 221   -14.006   4.695 107.005 1.00 43.53   C
ATOM  2997 OD1 ASP B 221   -15.233   4.963 106.965 1.00 46.44   O
ATOM  2998 OD2 ASP B 221   -13.559   3.688 107.606 1.00 45.17   O
ATOM  2999 N   ILE B 222   -11.435   6.668 103.818 1.00 38.63   N
ATOM  3000 CA  ILE B 222   -10.425   7.559 103.277 1.00 40.29   C
ATOM  3001 C   ILE B 222   -10.914   8.352 102.083 1.00 42.08   C
ATOM  3002 O   ILE B 222   -10.880   9.583 102.089 1.00 42.27   O
ATOM  3003 CB  ILE B 222    -9.195   6.775 102.862 1.00 39.79   C
ATOM  3004 CG1 ILE B 222    -8.751   5.882 104.023 1.00 40.01   C
ATOM  3005 CG2 ILE B 222    -8.082   7.731 102.500 1.00 39.63   C
ATOM  3006 CD1 ILE B 222    -7.862   4.734 103.613 1.00 38.98   C
ATOM  3007 N   LEU B 223   -11.372   7.644 101.057 1.00 44.39   N
ATOM  3008 CA  LEU B 223   -11.859   8.290  99.843 1.00 46.41   C
ATOM  3009 C   LEU B 223   -13.179   9.056  99.993 1.00 48.87   C
ATOM  3010 O   LEU B 223   -13.501   9.891  99.151 1.00 49.25   O
ATOM  3011 CB  LEU B 223   -12.006   7.254  98.723 1.00 45.14   C
ATOM  3012 CG  LEU B 223   -10.752   6.854  97.936 1.00 43.65   C
ATOM  3013 CD1 LEU B 223    -9.676   6.365  98.874 1.00 41.82   C
ATOM  3014 CD2 LEU B 223   -11.112   5.771  96.939 1.00 42.54   C
ATOM  3015 N   LYS B 224   -13.936   8.791 101.054 1.00 51.02   N
ATOM  3016 CA  LYS B 224   -15.216   9.468 101.232 1.00 54.51   C
ATOM  3017 C   LYS B 224   -15.841   9.160 102.590 1.00 55.71   C
ATOM  3018 O   LYS B 224   -17.085   9.046 102.658 1.00 56.14   O
ATOM  3019 CB  LYS B 224   -16.177   9.021 100.115 1.00 56.73   C
ATOM  3020 CG  LYS B 224   -16.456   7.515 100.122 1.00 59.20   C
ATOM  3021 CD  LYS B 224   -16.664   6.952  98.723 1.00 61.17   C
ATOM  3022 CE  LYS B 224   -16.675   5.424  98.732 1.00 61.91   C
ATOM  3023 NZ  LYS B 224   -16.718   4.856  97.349 1.00 62.77   N
ATOM  3024 OXT LYS B 224   -15.079   9.047 103.571 1.00 57.28   O
TER   3025     LYS B 224
```

FIG. 8

| ATOM | 1 | N | SER A 36 | -3.298 -22.445 78.217 1.00 60.22 | N |
|---|---|---|---|---|---|
| ATOM | 2 | CA | SER A 36 | -4.662 -22.689 77.656 1.00 60.60 | C |
| ATOM | 3 | C | SER A 36 | -5.074 -21.622 76.656 1.00 60.33 | C |
| ATOM | 4 | O | SER A 36 | -4.865 -21.775 75.449 1.00 61.84 | O |
| ATOM | 5 | CB | SER A 36 | -5.695 -22.747 78.783 1.00 61.34 | C |
| ATOM | 6 | OG | SER A 36 | -7.013 -22.646 78.257 1.00 62.46 | O |
| ATOM | 7 | N | GLY A 37 | -5.677 -20.544 77.157 1.00 59.14 | N |
| ATOM | 8 | CA | GLY A 37 | -6.113 -19.448 76.300 1.00 56.40 | C |
| ATOM | 9 | C | GLY A 37 | -7.178 -18.571 76.925 1.00 54.50 | C |
| ATOM | 10 | O | GLY A 37 | -8.252 -19.053 77.281 1.00 54.69 | O |
| ATOM | 11 | N | GLY A 38 | -6.893 -17.275 77.041 1.00 53.40 | N |
| ATOM | 12 | CA | GLY A 38 | -7.845 -16.351 77.645 1.00 51.22 | C |
| ATOM | 13 | C | GLY A 38 | -8.510 -15.399 76.676 1.00 49.73 | C |
| ATOM | 14 | O | GLY A 38 | -8.236 -15.399 75.478 1.00 48.90 | O |
| ATOM | 15 | N | GLY A 39 | -9.397 -14.563 77.192 1.00 48.94 | N |
| ATOM | 16 | CA | GLY A 39 | -10.073 -13.635 76.305 1.00 46.33 | C |
| ATOM | 17 | C | GLY A 39 | -9.193 -12.455 75.954 1.00 44.17 | C |
| ATOM | 18 | O | GLY A 39 | -8.110 -12.307 76.510 1.00 46.03 | O |
| ATOM | 19 | N | MET A 40 | -9.659 -11.617 75.034 1.00 40.58 | N |
| ATOM | 20 | CA | MET A 40 | -8.912 -10.424 74.636 1.00 35.27 | C |
| ATOM | 21 | C | MET A 40 | -9.651 -9.680 73.524 1.00 32.75 | C |
| ATOM | 22 | O | MET A 40 | -10.150 -8.570 73.712 1.00 31.53 | O |
| ATOM | 23 | CB | MET A 40 | -7.544 -10.843 74.153 1.00 36.46 | C |
| ATOM | 24 | CG | MET A 40 | -6.560 -9.748 74.122 1.00 34.33 | C |
| ATOM | 25 | SD | MET A 40 | -5.122 -10.626 73.644 1.00 35.10 | S |
| ATOM | 26 | CE | MET A 40 | -4.743 -11.654 75.256 1.00 35.47 | C |
| ATOM | 27 | N | ILE A 41 | -9.716 -10.323 72.366 1.00 27.95 | N |
| ATOM | 28 | CA | ILE A 41 | -10.388 -9.766 71.211 1.00 25.80 | C |
| ATOM | 29 | C | ILE A 41 | -11.877 -10.047 71.277 1.00 24.30 | C |
| ATOM | 30 | O | ILE A 41 | -12.276 -11.209 71.304 1.00 23.96 | O |
| ATOM | 31 | CB | ILE A 41 | -9.867 -10.404 69.915 1.00 24.92 | C |
| ATOM | 32 | CG1 | ILE A 41 | -8.355 -10.185 69.796 1.00 25.08 | C |
| ATOM | 33 | CG2 | ILE A 41 | -10.568 -9.804 68.725 1.00 23.59 | C |
| ATOM | 34 | CD1 | ILE A 41 | -7.707 -10.772 68.525 1.00 20.84 | C |
| ATOM | 35 | N | VAL A 42 | -12.691 -8.994 71.305 1.00 23.41 | N |
| ATOM | 36 | CA | VAL A 42 | -14.155 -9.137 71.343 1.00 22.08 | C |
| ATOM | 37 | C | VAL A 42 | -14.679 -9.043 69.905 1.00 22.86 | C |
| ATOM | 38 | O | VAL A 42 | -14.486 -8.024 69.241 1.00 23.94 | O |
| ATOM | 39 | CB | VAL A 42 | -14.794 -8.024 72.217 1.00 20.15 | C |
| ATOM | 40 | CG1 | VAL A 42 | -16.297 -8.251 72.370 1.00 18.38 | C |
| ATOM | 41 | CG2 | VAL A 42 | -14.135 -8.000 73.579 1.00 18.94 | C |
| ATOM | 42 | N | THR A 43 | -15.322 -10.105 69.424 1.00 22.77 | N |
| ATOM | 43 | CA | THR A 43 | -15.881 -10.141 68.073 1.00 22.69 | C |
| ATOM | 44 | C | THR A 43 | -17.234 -10.827 68.032 1.00 23.62 | C |
| ATOM | 45 | O | THR A 43 | -17.581 -11.575 68.939 1.00 23.01 | O |
| ATOM | 46 | CB | THR A 43 | -14.996 -10.906 67.129 1.00 22.17 | C |
| ATOM | 47 | OG1 | THR A 43 | -13.646 -10.544 67.406 1.00 28.17 | O |
| ATOM | 48 | CG2 | THR A 43 | -15.309 -10.568 65.685 1.00 20.20 | C |
| ATOM | 49 | N | GLY A 44 | -17.978 -10.575 66.960 1.00 23.82 | N |
| ATOM | 50 | CA | GLY A 44 | -19.275 -11.182 66.813 1.00 24.08 | C |
| ATOM | 51 | C | GLY A 44 | -19.191 -12.501 66.067 1.00 25.62 | C |
| ATOM | 52 | O | GLY A 44 | -20.002 -13.398 66.283 1.00 25.79 | O |
| ATOM | 53 | N | GLU A 45 | -18.203 -12.625 65.190 1.00 25.75 | N |
| ATOM | 54 | CA | GLU A 45 | -18.038 -13.845 64.429 1.00 27.88 | C |
| ATOM | 55 | C | GLU A 45 | -17.896 -15.039 65.376 1.00 28.91 | C |
| ATOM | 56 | O | GLU A 45 | -17.236 -14.942 66.403 1.00 29.04 | O |
| ATOM | 57 | CB | GLU A 45 | -16.821 -13.735 63.520 1.00 28.04 | C |
| ATOM | 58 | CG | GLU A 45 | -16.651 -14.917 62.609 1.00 30.62 | C |
| ATOM | 59 | CD | GLU A 45 | -17.947 -15.312 61.937 1.00 31.52 | C |
| ATOM | 60 | OE1 | GLU A 45 | -18.569 -14.448 61.284 1.00 32.36 | O |
| ATOM | 61 | OE2 | GLU A 45 | -18.342 -16.497 62.066 1.00 32.94 | O |
| ATOM | 62 | N | ARG A 46 | -18.520 -16.159 65.028 1.00 30.75 | N |
| ATOM | 63 | CA | ARG A 46 | -18.474 -17.341 65.871 1.00 32.60 | C |
| ATOM | 64 | C | ARG A 46 | -17.531 -18.414 65.311 1.00 32.42 | C |
| ATOM | 65 | O | ARG A 46 | -16.793 -19.051 66.063 1.00 32.04 | O |
| ATOM | 66 | CB | ARG A 46 | -19.882 -17.923 65.998 1.00 36.08 | C |
| ATOM | 67 | CG | ARG A 46 | -20.144 -18.681 67.276 1.00 40.89 | C |
| ATOM | 68 | CD | ARG A 46 | -20.455 -17.716 68.408 1.00 45.55 | C |
| ATOM | 69 | NE | ARG A 46 | -20.654 -18.398 69.686 1.00 49.81 | N |
| ATOM | 70 | CZ | ARG A 46 | -21.637 -19.254 69.955 1.00 52.19 | C |
| ATOM | 71 | NH1 | ARG A 46 | -22.554 -19.555 69.037 1.00 52.84 | N |
| ATOM | 72 | NH2 | ARG A 46 | -21.689 -19.825 71.151 1.00 53.17 | N |
| ATOM | 73 | N | LEU A 47 | -17.567 -18.605 63.989 1.00 31.06 | N |
| ATOM | 74 | CA | LEU A 47 | -16.740 -19.604 63.308 1.00 30.16 | C |
| ATOM | 75 | C | LEU A 47 | -15.319 -19.108 63.042 1.00 28.29 | C |
| ATOM | 76 | O | LEU A 47 | -15.127 -17.987 62.571 1.00 27.10 | O |
| ATOM | 77 | CB | LEU A 47 | -17.388 -20.006 61.970 1.00 33.05 | C |
| ATOM | 78 | CG | LEU A 47 | -16.509 -20.838 61.010 1.00 37.28 | C |
| ATOM | 79 | CD1 | LEU A 47 | -16.346 -22.281 61.551 1.00 36.15 | C |
| ATOM | 80 | CD2 | LEU A 47 | -17.125 -20.806 59.591 1.00 35.68 | C |
| ATOM | 81 | N | PRO A 48 | -14.306 -19.941 63.349 1.00 26.74 | N |
| ATOM | 82 | CA | PRO A 48 | -12.898 -19.586 63.136 1.00 25.76 | C |
| ATOM | 83 | C | PRO A 48 | -12.624 -19.188 61.692 1.00 25.17 | C |
| ATOM | 84 | O | PRO A 48 | -12.045 -18.134 61.430 1.00 25.26 | O |
| ATOM | 85 | CB | PRO A 48 | -12.161 -20.861 63.521 1.00 23.74 | C |

| ATOM | 751 | CA | ASP A 133 | 12.180 -1.516 55.405 1.00 32.50 | C |
|---|---|---|---|---|---|
| ATOM | 752 | C | ASP A 133 | 12.073 -0.945 56.798 1.00 31.96 | C |
| ATOM | 753 | O | ASP A 133 | 13.068 -0.847 57.512 1.00 32.73 | O |
| ATOM | 754 | CB | ASP A 133 | 12.219 -0.379 54.376 1.00 34.69 | C |
| ATOM | 755 | CG | ASP A 133 | 13.003 -0.755 53.122 1.00 37.68 | C |
| ATOM | 756 | OD1 | ASP A 133 | 12.507 -1.574 52.314 1.00 37.51 | O |
| ATOM | 757 | OD2 | ASP A 133 | 14.129 -0.237 52.954 1.00 40.18 | O |
| ATOM | 758 | N | ARG A 134 | 10.865 -0.569 57.195 1.00 31.15 | N |
| ATOM | 759 | CA | ARG A 134 | 10.669 -0.030 58.528 1.00 30.86 | C |
| ATOM | 760 | C | ARG A 134 | 11.077 -1.033 59.599 1.00 30.17 | C |
| ATOM | 761 | O | ARG A 134 | 11.688 -0.659 60.598 1.00 29.88 | O |
| ATOM | 762 | CB | ARG A 134 | 9.214 0.379 58.727 1.00 32.61 | C |
| ATOM | 763 | CG | ARG A 134 | 8.863 1.708 58.085 1.00 36.85 | C |
| ATOM | 764 | CD | ARG A 134 | 7.496 2.210 58.563 1.00 39.90 | C |
| ATOM | 765 | NE | ARG A 134 | 6.377 1.630 57.825 1.00 42.27 | N |
| ATOM | 766 | CZ | ARG A 134 | 6.079 1.937 56.564 1.00 43.86 | C |
| ATOM | 767 | NH1 | ARG A 134 | 6.820 2.820 55.913 1.00 44.43 | N |
| ATOM | 768 | NH2 | ARG A 134 | 5.057 1.346 55.948 1.00 43.80 | N |
| ATOM | 769 | N | ILE A 135 | 10.744 -2.304 59.392 1.00 29.88 | N |
| ATOM | 770 | CA | ILE A 135 | 11.091 -3.351 60.356 1.00 28.44 | C |
| ATOM | 771 | C | ILE A 135 | 12.592 -3.547 60.382 1.00 28.03 | C |
| ATOM | 772 | O | ILE A 135 | 13.170 -3.786 61.442 1.00 28.10 | O |
| ATOM | 773 | CB | ILE A 135 | 10.431 -4.699 59.983 1.00 28.64 | C |
| ATOM | 774 | CG1 | ILE A 135 | 8.912 -4.565 60.045 1.00 27.00 | C |
| ATOM | 775 | CG2 | ILE A 135 | 10.915 -5.809 60.924 1.00 27.75 | C |
| ATOM | 776 | CD1 | ILE A 135 | 8.199 -5.761 59.448 1.00 27.14 | C |
| ATOM | 777 | N | ILE A 136 | 13.227 -3.451 59.215 1.00 27.77 | N |
| ATOM | 778 | CA | ILE A 136 | 14.674 -3.627 59.110 1.00 27.53 | C |
| ATOM | 779 | C | ILE A 136 | 15.442 -2.518 59.830 1.00 28.11 | C |
| ATOM | 780 | O | ILE A 136 | 16.451 -2.771 60.488 1.00 26.28 | O |
| ATOM | 781 | CB | ILE A 136 | 15.117 -3.680 57.629 1.00 26.65 | C |
| ATOM | 782 | CG1 | ILE A 136 | 14.520 -4.915 56.961 1.00 26.41 | C |
| ATOM | 783 | CG2 | ILE A 136 | 16.641 -3.749 57.536 1.00 25.54 | C |
| ATOM | 784 | CD1 | ILE A 136 | 14.764 -4.984 55.472 1.00 25.91 | C |
| ATOM | 785 | N | LYS A 137 | 14.952 -1.290 59.701 1.00 29.45 | N |
| ATOM | 786 | CA | LYS A 137 | 15.596 -0.170 60.361 1.00 31.31 | C |
| ATOM | 787 | C | LYS A 137 | 15.402 -0.218 61.868 1.00 31.05 | C |
| ATOM | 788 | O | LYS A 137 | 16.213 0.321 62.605 1.00 31.84 | O |
| ATOM | 789 | CB | LYS A 137 | 15.071 1.156 59.818 1.00 33.70 | C |
| ATOM | 790 | CG | LYS A 137 | 15.645 1.532 58.462 1.00 39.43 | C |
| ATOM | 791 | CD | LYS A 137 | 15.388 2.999 58.136 1.00 43.11 | C |
| ATOM | 792 | CE | LYS A 137 | 16.000 3.406 56.799 1.00 45.83 | C |
| ATOM | 793 | NZ | LYS A 137 | 15.793 4.861 56.510 1.00 48.23 | N |
| ATOM | 794 | N | THR A 138 | 14.328 -0.860 62.322 1.00 30.57 | N |
| ATOM | 795 | CA | THR A 138 | 14.032 -0.951 63.754 1.00 30.73 | C |
| ATOM | 796 | C | THR A 138 | 14.922 -2.020 64.403 1.00 30.12 | C |
| ATOM | 797 | O | THR A 138 | 15.541 -1.795 65.450 1.00 30.61 | O |
| ATOM | 798 | CB | THR A 138 | 12.515 -1.302 64.008 1.00 30.33 | C |
| ATOM | 799 | OG1 | THR A 138 | 11.669 -0.289 63.449 1.00 30.91 | O |
| ATOM | 800 | CG2 | THR A 138 | 12.218 -1.380 65.479 1.00 28.73 | C |
| ATOM | 801 | N | LEU A 139 | 14.991 -3.184 63.773 1.00 29.17 | N |
| ATOM | 802 | CA | LEU A 139 | 15.783 -4.281 64.295 1.00 28.33 | C |
| ATOM | 803 | C | LEU A 139 | 17.247 -3.894 64.327 1.00 30.34 | C |
| ATOM | 804 | O | LEU A 139 | 18.014 -4.361 65.176 1.00 31.18 | O |
| ATOM | 805 | CB | LEU A 139 | 15.595 -5.532 63.429 1.00 25.69 | C |
| ATOM | 806 | CG | LEU A 139 | 14.240 -6.248 63.490 1.00 24.30 | C |
| ATOM | 807 | CD1 | LEU A 139 | 14.165 -7.334 62.421 1.00 21.25 | C |
| ATOM | 808 | CD2 | LEU A 139 | 14.045 -6.845 64.875 1.00 22.30 | C |
| ATOM | 809 | N | SER A 140 | 17.627 -3.023 63.404 1.00 31.22 | N |
| ATOM | 810 | CA | SER A 140 | 18.998 -2.570 63.293 1.00 32.30 | C |
| ATOM | 811 | C | SER A 140 | 19.363 -1.595 64.404 1.00 33.09 | C |
| ATOM | 812 | O | SER A 140 | 20.539 -1.456 64.751 1.00 32.74 | O |
| ATOM | 813 | CB | SER A 140 | 19.214 -1.910 61.933 1.00 32.30 | C |
| ATOM | 814 | OG | SER A 140 | 20.591 -1.753 61.665 1.00 36.45 | O |
| ATOM | 815 | N | LYS A 141 | 18.355 -0.925 64.958 1.00 33.24 | N |
| ATOM | 816 | CA | LYS A 141 | 18.571 0.028 66.033 1.00 34.11 | C |
| ATOM | 817 | C | LYS A 141 | 18.419 -0.661 67.377 1.00 32.46 | C |
| ATOM | 818 | O | LYS A 141 | 18.945 -0.193 68.371 1.00 33.08 | O |
| ATOM | 819 | CB | LYS A 141 | 17.575 1.188 65.945 1.00 36.83 | C |
| ATOM | 820 | CG | LYS A 141 | 17.646 1.960 64.639 1.00 40.47 | C |
| ATOM | 821 | CD | LYS A 141 | 19.006 2.652 64.442 1.00 44.25 | C |
| ATOM | 822 | CE | LYS A 141 | 19.230 3.861 65.378 1.00 45.65 | C |
| ATOM | 823 | NZ | LYS A 141 | 20.507 4.615 65.089 1.00 45.95 | N |
| ATOM | 824 | N | THR A 142 | 17.699 -1.772 67.408 1.00 31.67 | N |
| ATOM | 825 | CA | THR A 142 | 17.512 -2.493 68.659 1.00 30.34 | C |
| ATOM | 826 | C | THR A 142 | 18.053 -3.906 68.519 1.00 28.69 | C |
| ATOM | 827 | O | THR A 142 | 17.358 -4.801 68.036 1.00 28.84 | O |
| ATOM | 828 | CB | THR A 142 | 16.028 -2.553 69.046 1.00 31.00 | C |
| ATOM | 829 | OG1 | THR A 142 | 15.244 -2.703 67.864 1.00 32.61 | O |
| ATOM | 830 | CG2 | THR A 142 | 15.610 -1.292 69.747 1.00 31.79 | C |
| ATOM | 831 | N | LYS A 143 | 19.295 -4.091 68.946 1.00 27.28 | N |
| ATOM | 832 | CA | LYS A 143 | 19.968 -5.379 68.862 1.00 26.57 | C |
| ATOM | 833 | C | LYS A 143 | 19.382 -6.337 69.844 1.00 24.70 | C |
| ATOM | 834 | O | LYS A 143 | 19.449 -7.589 69.626 1.00 24.78 | O |
| ATOM | 835 | CB | LYS A 143 | 21.461 -5.214 69.156 1.00 27.13 | C |

FIG. 8 (con't)

```
ATOM     86  CG  PRO A  48     -13.012 -21.405 64.605 1.00 22.93      C
ATOM     87  CD  PRO A  48     -14.399 -21.241 64.034 1.00 26.04      C
ATOM     88  N   ALA A  49     -13.050 -20.041 60.766 1.00 25.16      N
ATOM     89  CA  ALA A  49     -12.845 -19.805 59.340 1.00 24.41      C
ATOM     90  C   ALA A  49     -13.306 -18.437 58.904 1.00 23.89      C
ATOM     91  O   ALA A  49     -12.634 -17.782 58.119 1.00 24.84      O
ATOM     92  CB  ALA A  49     -13.552 -20.854 58.528 1.00 24.69      C
ATOM     93  N   ASN A  50     -14.469 -18.012 59.389 1.00 23.87      N
ATOM     94  CA  ASN A  50     -14.977 -16.689 59.039 1.00 21.61      C
ATOM     95  C   ASN A  50     -14.119 -15.593 59.677 1.00 20.06      C
ATOM     96  O   ASN A  50     -13.817 -14.589 59.044 1.00 19.10      O
ATOM     97  CB  ASN A  50     -16.424 -16.526 59.488 1.00 23.81      C
ATOM     98  CG  ASN A  50     -17.402 -17.156 58.527 1.00 25.17      C
ATOM     99  OD1 ASN A  50     -17.334 -16.923 57.321 1.00 27.07      O
ATOM    100  ND2 ASN A  50     -18.325 -17.950 59.053 1.00 27.29      N
ATOM    101  N   PHE A  51     -13.732 -15.775 60.936 1.00 18.54      N
ATOM    102  CA  PHE A  51     -12.919 -14.774 61.621 1.00 17.24      C
ATOM    103  C   PHE A  51     -11.605 -14.495 60.889 1.00 18.07      C
ATOM    104  O   PHE A  51     -11.316 -13.356 60.505 1.00 18.63      O
ATOM    105  CB  PHE A  51     -12.620 -15.226 63.043 1.00 15.20      C
ATOM    106  CG  PHE A  51     -11.610 -14.376 63.741 1.00 14.28      C
ATOM    107  CD1 PHE A  51     -11.955 -13.119 64.211 1.00 13.22      C
ATOM    108  CD2 PHE A  51     -10.299 -14.814 63.882 1.00 12.20      C
ATOM    109  CE1 PHE A  51     -11.010 -12.307 64.807 1.00 13.49      C
ATOM    110  CE2 PHE A  51      -9.345 -14.009 64.475 1.00 12.16      C
ATOM    111  CZ  PHE A  51      -9.700 -12.750 64.939 1.00 13.88      C
ATOM    112  N   PHE A  52     -10.806 -15.546 60.706 1.00 18.74      N
ATOM    113  CA  PHE A  52      -9.517 -15.431 60.040 1.00 19.25      C
ATOM    114  C   PHE A  52      -9.583 -15.020 58.579 1.00 21.22      C
ATOM    115  O   PHE A  52      -8.592 -14.543 58.039 1.00 21.77      O
ATOM    116  CB  PHE A  52      -8.721 -16.730 60.158 1.00 17.63      C
ATOM    117  CG  PHE A  52      -8.288 -17.036 61.549 1.00 16.54      C
ATOM    118  CD1 PHE A  52      -9.031 -17.901 62.332 1.00 15.12      C
ATOM    119  CD2 PHE A  52      -7.175 -16.400 62.099 1.00 15.65      C
ATOM    120  CE1 PHE A  52      -8.678 -18.127 63.644 1.00 17.35      C
ATOM    121  CE2 PHE A  52      -6.820 -16.622 63.420 1.00 17.05      C
ATOM    122  CZ  PHE A  52      -7.570 -17.487 64.199 1.00 15.92      C
ATOM    123  N   LYS A  53     -10.732 -15.209 57.933 1.00 22.58      N
ATOM    124  CA  LYS A  53     -10.860 -14.826 56.530 1.00 24.42      C
ATOM    125  C   LYS A  53     -11.376 -13.414 56.300 1.00 23.52      C
ATOM    126  O   LYS A  53     -11.255 -12.905 55.191 1.00 24.47      O
ATOM    127  CB  LYS A  53     -11.777 -15.798 55.763 1.00 26.77      C
ATOM    128  CG  LYS A  53     -11.058 -16.979 55.079 1.00 31.52      C
ATOM    129  CD  LYS A  53     -10.402 -17.973 56.080 1.00 32.24      C
ATOM    130  CE  LYS A  53      -8.853 -18.053 55.976 1.00 34.63      C
ATOM    131  NZ  LYS A  53      -8.352 -18.705 54.728 1.00 34.84      N
ATOM    132  N   PHE A  54     -11.957 -12.794 57.324 1.00 22.89      N
ATOM    133  CA  PHE A  54     -12.509 -11.441 57.205 1.00 22.84      C
ATOM    134  C   PHE A  54     -12.018 -10.471 58.294 1.00 23.16      C
ATOM    135  O   PHE A  54     -11.243  -9.546 58.019 1.00 24.84      O
ATOM    136  CB  PHE A  54     -14.051 -11.491 57.229 1.00 23.62      C
ATOM    137  CG  PHE A  54     -14.656 -12.322 56.114 1.00 24.14      C
ATOM    138  CD1 PHE A  54     -15.247 -13.556 56.380 1.00 23.43      C
ATOM    139  CD2 PHE A  54     -14.599 -11.879 54.796 1.00 23.29      C
ATOM    140  CE1 PHE A  54     -15.768 -14.337 55.347 1.00 24.86      C
ATOM    141  CE2 PHE A  54     -15.116 -12.652 53.760 1.00 23.63      C
ATOM    142  CZ  PHE A  54     -15.702 -13.884 54.034 1.00 24.34      C
ATOM    143  N   GLN A  55     -12.461 -10.682 59.527 1.00 21.78      N
ATOM    144  CA  GLN A  55     -12.076  -9.814 60.622 1.00 22.32      C
ATOM    145  C   GLN A  55     -10.579  -9.792 60.881 1.00 20.63      C
ATOM    146  O   GLN A  55     -10.023  -8.786 61.313 1.00 19.51      O
ATOM    147  CB  GLN A  55     -12.821 -10.215 61.913 1.00 25.16      C
ATOM    148  CG  GLN A  55     -14.342  -9.942 61.871 1.00 28.79      C
ATOM    149  CD  GLN A  55     -15.119 -11.002 61.093 1.00 31.13      C
ATOM    150  OE1 GLN A  55     -16.228 -10.750 60.600 1.00 31.89      O
ATOM    151  NE2 GLN A  55     -14.546 -12.193 60.993 1.00 30.90      N
ATOM    152  N   PHE A  56      -9.918 -10.902 60.581 1.00 19.44      N
ATOM    153  CA  PHE A  56      -8.491 -10.997 60.820 1.00 17.34      C
ATOM    154  C   PHE A  56      -7.653 -10.372 59.721 1.00 17.95      C
ATOM    155  O   PHE A  56      -6.437 -10.332 59.828 1.00 16.43      O
ATOM    156  CB  PHE A  56      -8.103 -12.459 60.984 1.00 17.88      C
ATOM    157  CG  PHE A  56      -6.681 -12.673 61.412 1.00 18.04      C
ATOM    158  CD1 PHE A  56      -6.242 -12.256 62.662 1.00 18.72      C
ATOM    159  CD2 PHE A  56      -5.785 -13.321 60.569 1.00 17.81      C
ATOM    160  CE1 PHE A  56      -4.935 -12.484 63.075 1.00 19.14      C
ATOM    161  CE2 PHE A  56      -4.474 -13.557 60.971 1.00 18.70      C
ATOM    162  CZ  PHE A  56      -4.052 -13.138 62.229 1.00 18.69      C
ATOM    163  N   ARG A  57      -8.291  -9.863 58.667 1.00 19.86      N
ATOM    164  CA  ARG A  57      -7.539  -9.291 57.553 1.00 19.81      C
ATOM    165  C   ARG A  57      -6.789  -8.007 57.847 1.00 20.16      C
ATOM    166  O   ARG A  57      -7.309  -7.082 58.467 1.00 19.74      O
ATOM    167  CB  ARG A  57      -8.448  -9.062 56.358 1.00 20.23      C
ATOM    168  CG  ARG A  57      -7.708  -8.585 55.121 1.00 20.97      C
ATOM    169  CD  ARG A  57      -8.483  -8.899 53.849 1.00 21.79      C
ATOM    170  NE  ARG A  57      -7.750  -8.497 52.656 1.00 26.71      N
ATOM    171  CZ  ARG A  57      -7.982  -7.378 51.970 1.00 28.62      C

ATOM    836  CG  LYS A 143      22.188  -4.191 68.298 1.00 27.80      C
ATOM    837  CD  LYS A 143      22.277  -4.625 66.851 1.00 28.75      C
ATOM    838  CE  LYS A 143      23.135  -3.656 66.055 1.00 28.49      C
ATOM    839  NZ  LYS A 143      23.275  -4.094 64.642 1.00 29.43      N
ATOM    840  N   ASN A 144      18.813  -5.862 70.926 1.00 21.82      N
ATOM    841  CA  ASN A 144      18.236  -6.702 71.967 1.00 20.08      C
ATOM    842  C   ASN A 144      16.789  -7.046 71.672 1.00 18.62      C
ATOM    843  O   ASN A 144      16.017  -7.368 72.574 1.00 16.24      O
ATOM    844  CB  ASN A 144      18.352  -5.999 73.321 1.00 20.53      C
ATOM    845  CG  ASN A 144      17.702  -4.627 73.326 1.00 22.83      C
ATOM    846  OD1 ASN A 144      17.656  -3.942 72.302 1.00 23.33      O
ATOM    847  ND2 ASN A 144      17.210  -4.208 74.490 1.00 23.75      N
ATOM    848  N   LEU A 145      16.430  -6.990 70.396 1.00 17.97      N
ATOM    849  CA  LEU A 145      15.070  -7.296 69.974 1.00 17.00      C
ATOM    850  C   LEU A 145      15.061  -8.408 68.934 1.00 16.69      C
ATOM    851  O   LEU A 145      15.667  -8.253 67.882 1.00 16.00      O
ATOM    852  CB  LEU A 145      14.431  -6.039 69.364 1.00 16.89      C
ATOM    853  CG  LEU A 145      13.170  -6.234 68.495 1.00 15.84      C
ATOM    854  CD1 LEU A 145      12.052  -6.880 69.294 1.00 14.43      C
ATOM    855  CD2 LEU A 145      12.722  -4.880 67.968 1.00 16.07      C
ATOM    856  N   ARG A 146      14.394  -9.515 69.235 1.00 16.48      N
ATOM    857  CA  ARG A 146      14.273 -10.622 68.272 1.00 17.03      C
ATOM    858  C   ARG A 146      12.813 -10.646 67.799 1.00 15.61      C
ATOM    859  O   ARG A 146      11.889 -10.581 68.622 1.00 15.69      O
ATOM    860  CB  ARG A 146      14.627 -11.952 68.935 1.00 19.21      C
ATOM    861  CG  ARG A 146      14.568 -13.132 67.997 1.00 24.03      C
ATOM    862  CD  ARG A 146      14.865 -14.443 68.721 1.00 28.94      C
ATOM    863  NE  ARG A 146      15.194 -15.531 67.791 1.00 32.64      N
ATOM    864  CZ  ARG A 146      14.373 -16.051 66.872 1.00 34.91      C
ATOM    865  NH1 ARG A 146      13.127 -15.612 66.725 1.00 32.12      N
ATOM    866  NH2 ARG A 146      14.824 -17.005 66.063 1.00 34.18      N
ATOM    867  N   LEU A 147      12.599 -10.736 66.491 1.00 12.70      N
ATOM    868  CA  LEU A 147      11.247 -10.717 65.943 1.00 10.85      C
ATOM    869  C   LEU A 147      10.882 -11.969 65.120 1.00  9.49      C
ATOM    870  O   LEU A 147      11.653 -12.438 64.300 1.00  7.48      O
ATOM    871  CB  LEU A 147      11.044  -9.447 65.091 1.00  9.95      C
ATOM    872  CG  LEU A 147       9.647  -9.236 64.447 1.00  9.67      C
ATOM    873  CD1 LEU A 147       8.635  -9.077 65.544 1.00  8.41      C
ATOM    874  CD2 LEU A 147       9.593  -8.016 63.552 1.00  5.99      C
ATOM    875  N   LEU A 148       9.692 -12.504 65.373 1.00  9.19      N
ATOM    876  CA  LEU A 148       9.230 -13.675 64.662 1.00  9.00      C
ATOM    877  C   LEU A 148       7.878 -13.326 64.104 1.00  9.20      C
ATOM    878  O   LEU A 148       6.950 -13.078 64.873 1.00 11.01      O
ATOM    879  CB  LEU A 148       9.077 -14.860 65.604 1.00 10.33      C
ATOM    880  CG  LEU A 148       8.230 -16.050 65.088 1.00 10.56      C
ATOM    881  CD1 LEU A 148       8.841 -16.613 63.825 1.00  9.10      C
ATOM    882  CD2 LEU A 148       8.187 -17.133 66.143 1.00 11.52      C
ATOM    883  N   ILE A 149       7.753 -13.301 62.785 1.00  8.64      N
ATOM    884  CA  ILE A 149       6.489 -12.963 62.165 1.00  9.20      C
ATOM    885  C   ILE A 149       5.856 -14.200 61.520 1.00  9.56      C
ATOM    886  O   ILE A 149       6.428 -14.776 60.597 1.00  9.65      O
ATOM    887  CB  ILE A 149       6.651 -11.875 61.058 1.00  8.35      C
ATOM    888  CG1 ILE A 149       7.413 -10.661 61.600 1.00 10.66      C
ATOM    889  CG2 ILE A 149       5.296 -11.378 60.619 1.00  7.82      C
ATOM    890  CD1 ILE A 149       7.611  -9.529 60.579 1.00  5.95      C
ATOM    891  N   LEU A 150       4.687 -14.605 62.024 1.00 10.12      N
ATOM    892  CA  LEU A 150       3.933 -15.744 61.483 1.00 10.54      C
ATOM    893  C   LEU A 150       2.753 -15.206 60.656 1.00 11.69      C
ATOM    894  O   LEU A 150       1.836 -14.576 61.197 1.00 12.15      O
ATOM    895  CB  LEU A 150       3.432 -16.649 62.607 1.00  8.05      C
ATOM    896  CG  LEU A 150       4.502 -17.414 63.395 1.00 10.15      C
ATOM    897  CD1 LEU A 150       3.850 -18.297 64.421 1.00 14.11      C
ATOM    898  CD2 LEU A 150       5.324 -18.279 62.481 1.00 10.62      C
ATOM    899  N   VAL A 151       2.765 -15.466 59.347 1.00 11.13      N
ATOM    900  CA  VAL A 151       1.717 -14.974 58.446 1.00 11.45      C
ATOM    901  C   VAL A 151       0.764 -16.051 57.953 1.00 11.20      C
ATOM    902  O   VAL A 151       1.159 -17.198 57.796 1.00 11.78      O
ATOM    903  CB  VAL A 151       2.349 -14.282 57.177 1.00 12.48      C
ATOM    904  CG1 VAL A 151       3.324 -13.180 57.607 1.00 10.25      C
ATOM    905  CG2 VAL A 151       3.047 -15.326 56.280 1.00 10.68      C
ATOM    906  N   GLY A 152      -0.492 -15.677 57.703 1.00 11.01      N
ATOM    907  CA  GLY A 152      -1.477 -16.638 57.219 1.00 12.05      C
ATOM    908  C   GLY A 152      -1.152 -17.036 55.794 1.00 13.47      C
ATOM    909  O   GLY A 152      -1.331 -18.190 55.392 1.00 13.66      O
ATOM    910  N   ARG A 153      -0.688 -16.061 55.020 1.00 14.21      N
ATOM    911  CA  ARG A 153      -0.282 -16.303 53.644 1.00 16.23      C
ATOM    912  C   ARG A 153       0.666 -15.197 53.178 1.00 17.21      C
ATOM    913  O   ARG A 153       0.937 -14.247 53.909 1.00 18.17      O
ATOM    914  CB  ARG A 153      -1.508 -16.371 52.725 1.00 18.09      C
ATOM    915  CG  ARG A 153      -2.280 -15.073 52.616 1.00 18.56      C
ATOM    916  CD  ARG A 153      -3.178 -15.123 51.407 1.00 20.48      C
ATOM    917  NE  ARG A 153      -4.129 -14.020 51.345 1.00 23.75      N
ATOM    918  CZ  ARG A 153      -3.825 -12.756 51.064 1.00 23.54      C
ATOM    919  NH1 ARG A 153      -2.573 -12.397 50.807 1.00 24.38      N
ATOM    920  NH2 ARG A 153      -4.792 -11.849 51.022 1.00 24.43      N
ATOM    921  N   LEU A 154       1.192 -15.333 51.971 1.00 18.41      N
```

FIG. 8 (con't)

```
ATOM  172 NH1 ARG A  57   -8.940 -6.555 52.352 1.00 29.91    N
ATOM  173 NH2 ARG A  57   -7.234 -7.067 50.914 1.00 28.18    N
ATOM  174 N   ASN A  58   -5.558 -7.945 57.363 1.00 21.19    N
ATOM  175 CA  ASN A  58   -4.723 -6.779 57.556 1.00 22.52    C
ATOM  176 C   ASN A  58   -4.239 -6.319 56.187 1.00 24.20    C
ATOM  177 O   ASN A  58   -3.344 -6.919 55.606 1.00 22.98    O
ATOM  178 CB  ASN A  58   -3.532 -7.123 58.437 1.00 20.93    C
ATOM  179 CG  ASN A  58   -2.642 -5.925 58.700 1.00 19.59    C
ATOM  180 OD1 ASN A  58   -3.043 -4.980 59.372 1.00 17.63    O
ATOM  181 ND2 ASN A  58   -1.425 -5.959 58.158 1.00 16.30    N
ATOM  182 N   VAL A  59   -4.842 -5.240 55.690 1.00 27.67    N
ATOM  183 CA  VAL A  59   -4.504 -4.691 54.383 1.00 29.73    C
ATOM  184 C   VAL A  59   -3.124 -4.054 54.377 1.00 31.35    C
ATOM  185 O   VAL A  59   -2.786 -3.290 55.277 1.00 33.05    O
ATOM  186 CB  VAL A  59   -5.545 -3.634 53.953 1.00 28.58    C
ATOM  187 CG1 VAL A  59   -5.318 -3.221 52.501 1.00 27.60    C
ATOM  188 CG2 VAL A  59   -6.948 -4.193 54.143 1.00 29.31    C
ATOM  189 N   GLU A  60   -2.339 -4.370 53.348 1.00 33.94    N
ATOM  190 CA  GLU A  60   -0.983 -3.844 53.179 1.00 35.88    C
ATOM  191 C   GLU A  60   -0.848 -3.086 51.856 1.00 37.65    C
ATOM  192 O   GLU A  60    0.258 -2.886 51.348 1.00 38.68    O
ATOM  193 CB  GLU A  60    0.020 -5.005 53.214 1.00 35.18    C
ATOM  194 CG  GLU A  60    0.181 -5.650 54.584 1.00 36.90    C
ATOM  195 CD  GLU A  60    0.980 -4.773 55.518 1.00 36.90    C
ATOM  196 OE1 GLU A  60    2.100 -4.412 55.106 1.00 37.75    O
ATOM  197 OE2 GLU A  60    0.511 -4.451 56.635 1.00 35.89    O
ATOM  198 N   TYR A  61   -1.973 -2.663 51.293 1.00 39.37    N
ATOM  199 CA  TYR A  61   -1.953 -1.941 50.027 1.00 41.81    C
ATOM  200 C   TYR A  61   -0.999 -0.753 50.059 1.00 43.72    C
ATOM  201 O   TYR A  61   -1.111  0.129 50.910 1.00 43.48    O
ATOM  202 CB  TYR A  61   -3.360 -1.474 49.654 1.00 41.53    C
ATOM  203 CG  TYR A  61   -4.253 -2.571 49.098 1.00 41.89    C
ATOM  204 CD1 TYR A  61   -5.647 -2.455 49.142 1.00 41.24    C
ATOM  205 CD2 TYR A  61   -3.707 -3.717 48.510 1.00 41.74    C
ATOM  206 CE1 TYR A  61   -6.472 -3.456 48.612 1.00 41.75    C
ATOM  207 CE2 TYR A  61   -4.522 -4.719 47.978 1.00 41.34    C
ATOM  208 CZ  TYR A  61   -5.900 -4.584 48.031 1.00 41.37    C
ATOM  209 OH  TYR A  61   -6.695 -5.566 47.491 1.00 41.05    O
ATOM  210 N   SER A  62   -0.064 -0.752 49.113 1.00 46.36    N
ATOM  211 CA  SER A  62    0.930  0.300 48.978 1.00 48.19    C
ATOM  212 C   SER A  62    0.378  1.729 49.082 1.00 49.20    C
ATOM  213 O   SER A  62    1.119  2.661 49.397 1.00 49.70    O
ATOM  214 CB  SER A  62    1.696  0.119 47.648 1.00 49.01    C
ATOM  215 OG  SER A  62    0.839 -0.197 46.558 1.00 48.98    O
ATOM  216 N   SER A  63   -0.919  1.908 48.835 1.00 49.37    N
ATOM  217 CA  SER A  63   -1.521  3.236 48.895 1.00 49.02    C
ATOM  218 C   SER A  63   -2.820  3.248 49.694 1.00 49.71    C
ATOM  219 O   SER A  63   -3.379  2.196 50.011 1.00 49.73    O
ATOM  220 CB  SER A  63   -1.795  3.760 47.481 1.00 49.63    C
ATOM  221 OG  SER A  63   -2.844  3.037 46.854 1.00 50.54    O
ATOM  222 N   GLY A  64   -3.295  4.450 50.016 1.00 49.23    N
ATOM  223 CA  GLY A  64   -4.521  4.591 50.769 1.00 48.21    C
ATOM  224 C   GLY A  64   -4.366  4.295 52.245 1.00 48.41    C
ATOM  225 O   GLY A  64   -3.271  4.004 52.733 1.00 48.61    O
ATOM  226 N   ARG A  65   -5.479  4.371 52.965 1.00 47.82    N
ATOM  227 CA  ARG A  65   -5.480  4.111 54.393 1.00 47.49    C
ATOM  228 C   ARG A  65   -6.564  3.086 54.676 1.00 45.38    C
ATOM  229 O   ARG A  65   -7.634  3.441 55.142 1.00 44.85    O
ATOM  230 CB  ARG A  65   -5.797  5.395 55.153 1.00 50.26    C
ATOM  231 CG  ARG A  65   -5.415  6.655 54.397 1.00 54.10    C
ATOM  232 CD  ARG A  65   -5.595  7.920 55.242 1.00 56.61    C
ATOM  233 NE  ARG A  65   -6.914  8.021 55.870 1.00 58.58    N
ATOM  234 CZ  ARG A  65   -7.194  7.597 57.102 1.00 60.03    C
ATOM  235 NH1 ARG A  65   -6.247  7.045 57.848 1.00 60.37    N
ATOM  236 NH2 ARG A  65   -8.425  7.719 57.590 1.00 59.58    N
ATOM  237 N   ASN A  66   -6.273  1.820 54.387 1.00 43.47    N
ATOM  238 CA  ASN A  66   -7.229  0.741 54.589 1.00 40.09    C
ATOM  239 C   ASN A  66   -7.260  0.287 56.044 1.00 38.08    C
ATOM  240 O   ASN A  66   -6.776  0.990 56.937 1.00 38.39    O
ATOM  241 CB  ASN A  66   -6.875 -0.442 53.698 1.00 41.22    C
ATOM  242 CG  ASN A  66   -6.352 -0.005 52.336 1.00 42.59    C
ATOM  243 OD1 ASN A  66   -5.217  0.467 52.209 1.00 41.35    O
ATOM  244 ND2 ASN A  66   -7.180 -0.155 51.311 1.00 44.16    N
ATOM  245 N   LYS A  67   -7.812 -0.901 56.279 1.00 34.15    N
ATOM  246 CA  LYS A  67   -7.915 -1.428 57.618 1.00 30.52    C
ATOM  247 C   LYS A  67   -6.671 -2.187 58.037 1.00 29.04    C
ATOM  248 O   LYS A  67   -5.863 -2.604 57.208 1.00 28.64    O
ATOM  249 CB  LYS A  67   -9.129 -2.360 57.756 1.00 30.06    C
ATOM  250 CG  LYS A  67   -8.969 -3.694 57.062 1.00 28.54    C
ATOM  251 CD  LYS A  67  -10.015 -4.695 57.511 1.00 27.36    C
ATOM  252 CE  LYS A  67   -9.788 -5.110 58.953 1.00 29.78    C
ATOM  253 NZ  LYS A  67  -10.707 -6.204 59.367 1.00 28.57    N
ATOM  254 N   THR A  68   -6.507 -2.357 59.344 1.00 26.40    N
ATOM  255 CA  THR A  68   -5.357 -3.065 59.854 1.00 23.50    C
ATOM  256 C   THR A  68   -5.749 -3.981 61.004 1.00 20.98    C
ATOM  257 O   THR A  68   -6.721 -3.721 61.708 1.00 20.99    O
ATOM  922 CA  LEU A 154    2.103 -14.337 51.424 1.00 18.83    C
ATOM  923 C   LEU A 154    1.341 -13.247 50.674 1.00 19.96    C
ATOM  924 O   LEU A 154    0.268 -13.492 50.118 1.00 20.86    O
ATOM  925 CB  LEU A 154    3.105 -15.011 50.489 1.00 18.36    C
ATOM  926 CG  LEU A 154    4.491 -15.351 51.036 1.00 17.98    C
ATOM  927 CD1 LEU A 154    4.422 -15.661 52.518 1.00 17.77    C
ATOM  928 CD2 LEU A 154    5.068 -16.508 50.231 1.00 18.19    C
ATOM  929 N   PHE A 155    1.910 -12.046 50.665 1.00 20.98    N
ATOM  930 CA  PHE A 155    1.320 -10.887 49.998 1.00 20.88    C
ATOM  931 C   PHE A 155    2.172 -10.479 48.793 1.00 21.47    C
ATOM  932 O   PHE A 155    3.349 -10.151 48.946 1.00 21.49    O
ATOM  933 CB  PHE A 155    1.240  -9.733 50.985 1.00 19.60    C
ATOM  934 CG  PHE A 155    0.755  -8.464 50.376 1.00 19.16    C
ATOM  935 CD1 PHE A 155   -0.521  -8.380 49.862 1.00 16.14    C
ATOM  936 CD2 PHE A 155    1.581  -7.339 50.325 1.00 18.69    C
ATOM  937 CE1 PHE A 155   -0.984  -7.203 49.305 1.00 14.95    C
ATOM  938 CE2 PHE A 155    1.121  -6.150 49.765 1.00 17.26    C
ATOM  939 CZ  PHE A 155   -0.163  -6.085 49.256 1.00 16.12    C
ATOM  940 N   MET A 156    1.562 -10.476 47.609 1.00 22.57    N
ATOM  941 CA  MET A 156    2.263 -10.143 46.366 1.00 23.38    C
ATOM  942 C   MET A 156    3.595 -10.870 46.309 1.00 23.86    C
ATOM  943 O   MET A 156    4.602 -10.301 45.889 1.00 23.96    O
ATOM  944 CB  MET A 156    2.525  -8.648 46.267 1.00 23.99    C
ATOM  945 CG  MET A 156    1.297  -7.796 46.275 1.00 26.95    C
ATOM  946 SD  MET A 156    1.682  -6.167 45.590 1.00 29.35    S
ATOM  947 CE  MET A 156    2.577  -5.461 46.847 1.00 28.03    C
ATOM  948 N   TRP A 157    3.610 -12.132 46.730 1.00 24.70    N
ATOM  949 CA  TRP A 157    4.856 -12.899 46.741 1.00 27.04    C
ATOM  950 C   TRP A 157    5.566 -13.003 45.389 1.00 28.65    C
ATOM  951 O   TRP A 157    6.796 -13.024 45.330 1.00 30.30    O
ATOM  952 CB  TRP A 157    4.609 -14.299 47.272 1.00 25.35    C
ATOM  953 CG  TRP A 157    3.794 -15.107 46.387 1.00 25.33    C
ATOM  954 CD1 TRP A 157    2.440 -15.175 46.370 1.00 25.36    C
ATOM  955 CD2 TRP A 157    4.262 -16.038 45.405 1.00 25.45    C
ATOM  956 NE1 TRP A 157    2.027 -16.097 45.441 1.00 26.01    N
ATOM  957 CE2 TRP A 157    3.124 -16.637 44.831 1.00 26.09    C
ATOM  958 CE3 TRP A 157    5.532 -16.413 44.951 1.00 26.55    C
ATOM  959 CZ2 TRP A 157    3.213 -17.613 43.840 1.00 26.76    C
ATOM  960 CZ3 TRP A 157    5.626 -17.384 43.956 1.00 26.18    C
ATOM  961 CH2 TRP A 157    4.469 -17.965 43.410 1.00 27.75    C
ATOM  962 N   GLU A 158    4.788 -13.072 44.312 1.00 31.14    N
ATOM  963 CA  GLU A 158    5.336 -13.183 42.968 1.00 30.86    C
ATOM  964 C   GLU A 158    6.114 -11.944 42.519 1.00 29.33    C
ATOM  965 O   GLU A 158    7.014 -12.040 41.682 1.00 29.42    O
ATOM  966 CB  GLU A 158    4.212 -13.496 41.963 1.00 32.67    C
ATOM  967 CG  GLU A 158    2.972 -12.617 42.094 1.00 36.58    C
ATOM  968 CD  GLU A 158    1.913 -13.237 42.955 1.00 36.70    C
ATOM  969 OE1 GLU A 158    1.829 -12.911 44.165 1.00 37.61    O
ATOM  970 OE2 GLU A 158    1.178 -14.081 42.393 1.00 37.46    O
ATOM  971 N   GLU A 159    5.795 -10.779 43.072 1.00 28.03    N
ATOM  972 CA  GLU A 159    6.492  -9.557 42.679 1.00 26.60    C
ATOM  973 C   GLU A 159    7.945  -9.507 43.155 1.00 26.46    C
ATOM  974 O   GLU A 159    8.253  -9.801 44.309 1.00 26.25    O
ATOM  975 CB  GLU A 159    5.739  -8.330 43.190 1.00 25.49    C
ATOM  976 CG  GLU A 159    4.291  -8.265 42.719 1.00 24.92    C
ATOM  977 CD  GLU A 159    4.126  -8.441 41.214 1.00 25.09    C
ATOM  978 OE1 GLU A 159    4.706  -7.652 40.435 1.00 24.10    O
ATOM  979 OE2 GLU A 159    3.398  -9.380 40.807 1.00 26.07    O
ATOM  980 N   PRO A 160    8.866  -9.130 42.258 1.00 26.09    N
ATOM  981 CA  PRO A 160   10.281  -9.051 42.624 1.00 25.59    C
ATOM  982 C   PRO A 160   10.586  -8.029 43.713 1.00 24.98    C
ATOM  983 O   PRO A 160   11.552  -8.189 44.471 1.00 25.95    O
ATOM  984 CB  PRO A 160   10.956  -8.715 41.296 1.00 25.83    C
ATOM  985 CG  PRO A 160    9.900  -7.934 40.577 1.00 25.14    C
ATOM  986 CD  PRO A 160    8.666  -8.746 40.847 1.00 24.60    C
ATOM  987 N   GLU A 161    9.785  -6.982 43.802 1.00 23.99    N
ATOM  988 CA  GLU A 161   10.022  -5.972 44.830 1.00 23.98    C
ATOM  989 C   GLU A 161    9.806  -6.580 46.205 1.00 22.39    C
ATOM  990 O   GLU A 161   10.596  -6.363 47.118 1.00 22.10    O
ATOM  991 CB  GLU A 161    9.065  -4.788 44.675 1.00 25.40    C
ATOM  992 CG  GLU A 161    9.422  -3.777 43.602 1.00 26.04    C
ATOM  993 CD  GLU A 161    9.464  -4.357 42.202 1.00 27.64    C
ATOM  994 OE1 GLU A 161    8.656  -5.257 41.885 1.00 28.55    O
ATOM  995 OE2 GLU A 161   10.305  -3.888 41.409 1.00 30.68    O
ATOM  996 N   ILE A 162    8.721  -7.333 46.346 1.00 20.89    N
ATOM  997 CA  ILE A 162    8.388  -7.968 47.609 1.00 19.10    C
ATOM  998 C   ILE A 162    9.440  -9.014 47.982 1.00 19.76    C
ATOM  999 O   ILE A 162    9.856  -9.110 49.144 1.00 19.28    O
ATOM 1000 CB  ILE A 162    6.982  -8.624 47.528 1.00 17.30    C
ATOM 1001 CG1 ILE A 162    5.934  -7.545 47.240 1.00 17.11    C
ATOM 1002 CG2 ILE A 162    6.621  -9.323 48.825 1.00 14.85    C
ATOM 1003 CD1 ILE A 162    5.804  -6.510 48.348 1.00 15.95    C
ATOM 1004 N   GLN A 163    9.883  -9.779 46.989 1.00 18.99    N
ATOM 1005 CA  GLN A 163   10.870 -10.823 47.220 1.00 19.77    C
ATOM 1006 C   GLN A 163   12.178 -10.262 47.714 1.00 19.64    C
ATOM 1007 O   GLN A 163   12.851 -10.857 48.556 1.00 20.89    O
```

FIG. 8 (con't)

```
ATOM    258  CB  THR A  68      -4.285  -2.080  60.339  1.00 23.83       C
ATOM    259  OG1 THR A  68      -4.820  -1.286  61.394  1.00 26.02       O
ATOM    260  CG2 THR A  68      -3.862  -1.161  59.216  1.00 24.72       C
ATOM    261  N   PHE A  69      -5.000  -5.061  61.187  1.00 18.62       N
ATOM    262  CA  PHE A  69      -5.275  -6.001  62.274  1.00 16.84       C
ATOM    263  C   PHE A  69      -3.961  -6.696  62.627  1.00 16.13       C
ATOM    264  O   PHE A  69      -3.172  -6.995  61.741  1.00 14.51       O
ATOM    265  CB  PHE A  69      -6.306  -7.042  61.838  1.00 14.21       C
ATOM    266  CG  PHE A  69      -6.970  -7.756  62.983  1.00 12.89       C
ATOM    267  CD1 PHE A  69      -8.220  -7.362  63.434  1.00 11.28       C
ATOM    268  CD2 PHE A  69      -6.324  -8.819  63.619  1.00 13.47       C
ATOM    269  CE1 PHE A  69      -8.833  -8.002  64.493  1.00 10.96       C
ATOM    270  CE2 PHE A  69      -6.930  -9.473  64.685  1.00 12.99       C
ATOM    271  CZ  PHE A  69      -8.185  -9.065  65.119  1.00 13.34       C
ATOM    272  N   LEU A  70      -3.727  -6.950  63.916  1.00 15.36       N
ATOM    273  CA  LEU A  70      -2.485  -7.604  64.327  1.00 14.51       C
ATOM    274  C   LEU A  70      -2.484  -8.078  65.768  1.00 14.76       C
ATOM    275  O   LEU A  70      -2.736  -7.301  66.686  1.00 15.16       O
ATOM    276  CB  LEU A  70      -1.306  -6.665  64.115  1.00 12.51       C
ATOM    277  CG  LEU A  70       0.095  -7.134  64.525  1.00 12.29       C
ATOM    278  CD1 LEU A  70       1.121  -6.381  63.741  1.00 11.90       C
ATOM    279  CD2 LEU A  70       0.318  -6.871  65.970  1.00 12.92       C
ATOM    280  N   CYS A  71      -2.185  -9.360  65.968  1.00 14.57       N
ATOM    281  CA  CYS A  71      -2.082  -9.923  67.313  1.00 13.24       C
ATOM    282  C   CYS A  71      -0.621 -10.058  67.600  1.00 14.34       C
ATOM    283  O   CYS A  71       0.164 -10.323  66.688  1.00 14.18       O
ATOM    284  CB  CYS A  71      -2.659 -11.317  67.371  1.00 13.28       C
ATOM    285  SG  CYS A  71      -4.380 -11.421  66.933  1.00 11.98       S
ATOM    286  N   TYR A  72      -0.240  -9.942  68.870  1.00 15.75       N
ATOM    287  CA  TYR A  72       1.184 -10.060  69.234  1.00 13.62       C
ATOM    288  C   TYR A  72       1.445 -10.705  70.581  1.00 13.66       C
ATOM    289  O   TYR A  72       0.538 -10.934  71.401  1.00 13.43       O
ATOM    290  CB  TYR A  72       1.846  -8.682  69.181  1.00 11.98       C
ATOM    291  CG  TYR A  72       1.307  -7.690  70.187  1.00 14.01       C
ATOM    292  CD1 TYR A  72       1.694  -7.746  71.532  1.00 14.85       C
ATOM    293  CD2 TYR A  72       0.370  -6.725  69.817  1.00 14.44       C
ATOM    294  CE1 TYR A  72       1.164  -6.874  72.470  1.00 15.52       C
ATOM    295  CE2 TYR A  72      -0.172  -5.849  70.750  1.00 15.43       C
ATOM    296  CZ  TYR A  72       0.233  -5.931  72.077  1.00 16.16       C
ATOM    297  OH  TYR A  72      -0.287  -5.083  73.027  1.00 18.77       O
ATOM    298  N   VAL A  73       2.713 -10.997  70.810  1.00 13.41       N
ATOM    299  CA  VAL A  73       3.168 -11.590  72.065  1.00 14.19       C
ATOM    300  C   VAL A  73       4.544 -11.042  72.374  1.00 13.66       C
ATOM    301  O   VAL A  73       5.429 -11.079  71.526  1.00 14.27       O
ATOM    302  CB  VAL A  73       3.259 -13.136  71.973  1.00 13.10       C
ATOM    303  CG1 VAL A  73       3.946 -13.688  73.209  1.00 11.85       C
ATOM    304  CG2 VAL A  73       1.883 -13.732  71.898  1.00 13.20       C
ATOM    305  N   VAL A  74       4.723 -10.528  73.584  1.00 15.31       N
ATOM    306  CA  VAL A  74       6.021  -9.994  73.988  1.00 16.34       C
ATOM    307  C   VAL A  74       6.554 -10.683  75.239  1.00 17.68       C
ATOM    308  O   VAL A  74       5.816 -10.899  76.200  1.00 18.39       O
ATOM    309  CB  VAL A  74       5.935  -8.489  74.240  1.00 14.55       C
ATOM    310  CG1 VAL A  74       7.279  -7.959  74.708  1.00 13.50       C
ATOM    311  CG2 VAL A  74       5.510  -7.792  72.977  1.00 13.44       C
ATOM    312  N   GLU A  75       7.829 -11.029  75.214  1.00 20.54       N
ATOM    313  CA  GLU A  75       8.476 -11.676  76.350  1.00 24.00       C
ATOM    314  C   GLU A  75       9.895 -11.151  76.484  1.00 25.05       C
ATOM    315  O   GLU A  75      10.723 -11.363  75.601  1.00 24.19       O
ATOM    316  CB  GLU A  75       8.499 -13.187  76.153  1.00 26.10       C
ATOM    317  CG  GLU A  75       7.120 -13.784  76.018  1.00 31.35       C
ATOM    318  CD  GLU A  75       7.135 -15.291  76.085  1.00 35.63       C
ATOM    319  OE1 GLU A  75       7.964 -15.912  75.374  1.00 37.54       O
ATOM    320  OE2 GLU A  75       6.321 -15.866  76.842  1.00 38.67       O
ATOM    321  N   ALA A  76      10.173 -10.459  77.585  1.00 26.87       N
ATOM    322  CA  ALA A  76      11.496  -9.891  77.825  1.00 28.77       C
ATOM    323  C   ALA A  76      12.165 -10.557  79.019  1.00 30.78       C
ATOM    324  O   ALA A  76      11.543 -10.751  80.061  1.00 31.11       O
ATOM    325  CB  ALA A  76      11.374  -8.406  78.053  1.00 27.76       C
ATOM    326  N   GLN A  77      13.434 -10.908  78.853  1.00 34.96       N
ATOM    327  CA  GLN A  77      14.225 -11.564  79.899  1.00 38.74       C
ATOM    328  C   GLN A  77      15.412 -10.672  80.259  1.00 39.88       C
ATOM    329  O   GLN A  77      16.013 -10.051  79.385  1.00 40.01       O
ATOM    330  CB  GLN A  77      14.725 -12.927  79.386  1.00 41.39       C
ATOM    331  CG  GLN A  77      16.074 -13.383  79.973  1.00 46.84       C
ATOM    332  CD  GLN A  77      16.960 -14.119  78.958  1.00 49.73       C
ATOM    333  OE1 GLN A  77      18.133 -14.416  79.228  1.00 51.56       O
ATOM    334  NE2 GLN A  77      16.400 -14.416  77.789  1.00 50.92       N
ATOM    335  N   GLY A  78      15.741 -10.606  81.544  1.00 40.74       N
ATOM    336  CA  GLY A  78      16.865  -9.797  81.981  1.00 41.57       C
ATOM    337  C   GLY A  78      17.694 -10.533  83.015  1.00 43.22       C
ATOM    338  O   GLY A  78      17.158 -11.072  83.987  1.00 43.14       O
ATOM    339  N   LYS A  79      19.003 -10.562  82.802  1.00 44.77       N
ATOM    340  CA  LYS A  79      19.907 -11.246  83.718  1.00 46.43       C
ATOM    341  C   LYS A  79      19.885 -10.529  85.066  1.00 46.17       C
ATOM    342  O   LYS A  79      20.693  -9.638  85.306  1.00 47.25       O
ATOM    343  CB  LYS A  79      21.334 -11.261  83.145  1.00 47.07       C
ATOM   1008  CB  GLN A 163      11.099 -11.651  45.949  1.00 19.69       C
ATOM   1009  CG  GLN A 163       9.959 -12.608  45.651  1.00 20.76       C
ATOM   1010  CD  GLN A 163      10.224 -13.518  44.477  1.00 20.36       C
ATOM   1011  OE1 GLN A 163      11.353 -13.973  44.272  1.00 23.17       O
ATOM   1012  NE2 GLN A 163       9.189 -13.810  43.711  1.00 21.56       N
ATOM   1013  N   ALA A 164      12.550  -9.105  47.199  1.00 20.11       N
ATOM   1014  CA  ALA A 164      13.793  -8.488  47.617  1.00 18.05       C
ATOM   1015  C   ALA A 164      13.653  -8.024  49.055  1.00 18.24       C
ATOM   1016  O   ALA A 164      14.574  -8.142  49.873  1.00 19.10       O
ATOM   1017  CB  ALA A 164      14.107  -7.325  46.716  1.00 16.51       C
ATOM   1018  N   ALA A 165      12.483  -7.502  49.379  1.00 16.67       N
ATOM   1019  CA  ALA A 165      12.254  -7.012  50.724  1.00 16.07       C
ATOM   1020  C   ALA A 165      12.256  -8.145  51.770  1.00 16.35       C
ATOM   1021  O   ALA A 165      12.763  -7.969  52.879  1.00 15.23       O
ATOM   1022  CB  ALA A 165      10.961  -6.240  50.746  1.00 13.13       C
ATOM   1023  N   LEU A 166      11.707  -9.304  51.398  1.00 17.26       N
ATOM   1024  CA  LEU A 166      11.666 -10.459  52.296  1.00 18.54       C
ATOM   1025  C   LEU A 166      13.067 -11.003  52.576  1.00 19.58       C
ATOM   1026  O   LEU A 166      13.351 -11.447  53.683  1.00 18.09       O
ATOM   1027  CB  LEU A 166      10.794 -11.578  51.713  1.00 18.23       C
ATOM   1028  CG  LEU A 166       9.287 -11.252  51.607  1.00 19.45       C
ATOM   1029  CD1 LEU A 166       8.534 -12.452  51.116  1.00 19.88       C
ATOM   1030  CD2 LEU A 166       8.741 -10.876  52.953  1.00 18.88       C
ATOM   1031  N   LYS A 167      13.943 -10.968  51.569  1.00 20.96       N
ATOM   1032  CA  LYS A 167      15.310 -11.450  51.743  1.00 22.76       C
ATOM   1033  C   LYS A 167      16.064 -10.528  52.715  1.00 23.03       C
ATOM   1034  O   LYS A 167      16.680 -10.994  53.675  1.00 22.49       O
ATOM   1035  CB  LYS A 167      16.041 -11.496  50.402  1.00 23.99       C
ATOM   1036  CG  LYS A 167      15.381 -12.381  49.352  1.00 27.53       C
ATOM   1037  CD  LYS A 167      16.089 -12.261  48.007  1.00 30.15       C
ATOM   1038  CE  LYS A 167      15.226 -12.800  46.872  1.00 32.48       C
ATOM   1039  NZ  LYS A 167      15.755 -12.464  45.512  1.00 33.18       N
ATOM   1040  N   LYS A 168      15.998  -9.221  52.459  1.00 22.85       N
ATOM   1041  CA  LYS A 168      16.670  -8.230  53.280  1.00 22.23       C
ATOM   1042  C   LYS A 168      16.155  -8.347  54.691  1.00 21.82       C
ATOM   1043  O   LYS A 168      16.884  -8.126  55.666  1.00 20.73       O
ATOM   1044  CB  LYS A 168      16.408  -6.827  52.748  1.00 23.31       C
ATOM   1045  CG  LYS A 168      17.026  -6.567  51.396  1.00 27.42       C
ATOM   1046  CD  LYS A 168      16.788  -5.124  50.973  1.00 32.41       C
ATOM   1047  CE  LYS A 168      17.440  -4.789  49.628  1.00 35.51       C
ATOM   1048  NZ  LYS A 168      17.186  -3.377  49.177  1.00 35.22       N
ATOM   1049  N   LEU A 169      14.882  -8.707  54.785  1.00 21.82       N
ATOM   1050  CA  LEU A 169      14.221  -8.875  56.071  1.00 21.28       C
ATOM   1051  C   LEU A 169      14.805 -10.086  56.794  1.00 19.82       C
ATOM   1052  O   LEU A 169      15.084  -9.996  57.978  1.00 20.17       O
ATOM   1053  CB  LEU A 169      12.712  -9.059  55.874  1.00 22.53       C
ATOM   1054  CG  LEU A 169      11.818  -9.066  57.128  1.00 22.31       C
ATOM   1055  CD1 LEU A 169      11.822  -7.695  57.754  1.00 22.18       C
ATOM   1056  CD2 LEU A 169      10.400  -9.453  56.747  1.00 24.04       C
ATOM   1057  N   LYS A 170      14.976 -11.199  56.088  1.00 19.73       N
ATOM   1058  CA  LYS A 170      15.546 -12.397  56.674  1.00 20.07       C
ATOM   1059  C   LYS A 170      17.015 -12.115  57.057  1.00 21.35       C
ATOM   1060  O   LYS A 170      17.527 -12.623  58.055  1.00 20.49       O
ATOM   1061  CB  LYS A 170      15.495 -13.555  55.671  1.00 20.11       C
ATOM   1062  CG  LYS A 170      16.239 -14.788  56.122  1.00 21.04       C
ATOM   1063  CD  LYS A 170      16.704 -15.633  54.954  1.00 21.57       C
ATOM   1064  CE  LYS A 170      17.460 -16.841  55.461  1.00 21.76       C
ATOM   1065  NZ  LYS A 170      18.099 -17.565  54.346  1.00 23.42       N
ATOM   1066  N   GLU A 171      17.673 -11.285  56.256  1.00 20.61       N
ATOM   1067  CA  GLU A 171      19.062 -10.915  56.496  1.00 20.40       C
ATOM   1068  C   GLU A 171      19.214 -10.001  57.712  1.00 19.22       C
ATOM   1069  O   GLU A 171      20.280  -9.925  58.330  1.00 16.62       O
ATOM   1070  CB  GLU A 171      19.634 -10.227  55.259  1.00 21.63       C
ATOM   1071  CG  GLU A 171      19.617 -11.101  54.010  1.00 26.73       C
ATOM   1072  CD  GLU A 171      20.277 -10.429  52.830  1.00 30.58       C
ATOM   1073  OE1 GLU A 171      20.883  -9.355  53.041  1.00 29.90       O
ATOM   1074  OE2 GLU A 171      20.197 -10.981  51.696  1.00 30.64       O
ATOM   1075  N   ALA A 172      18.141  -9.301  58.049  1.00 18.37       N
ATOM   1076  CA  ALA A 172      18.190  -8.413  59.192  1.00 17.49       C
ATOM   1077  C   ALA A 172      18.045  -9.205  60.480  1.00 17.60       C
ATOM   1078  O   ALA A 172      18.132  -8.634  61.557  1.00 16.96       O
ATOM   1079  CB  ALA A 172      17.094  -7.367  59.098  1.00 17.02       C
ATOM   1080  N   GLY A 173      17.814 -10.520  60.349  1.00 18.65       N
ATOM   1081  CA  GLY A 173      17.657 -11.400  61.505  1.00 17.60       C
ATOM   1082  C   GLY A 173      16.200 -11.720  61.840  1.00 18.07       C
ATOM   1083  O   GLY A 173      15.911 -12.487  62.763  1.00 17.73       O
ATOM   1084  N   CYS A 174      15.281 -11.121  61.092  1.00 16.33       N
ATOM   1085  CA  CYS A 174      13.863 -11.346  61.313  1.00 16.16       C
ATOM   1086  C   CYS A 174      13.444 -12.696  60.733  1.00 16.33       C
ATOM   1087  O   CYS A 174      13.542 -12.929  59.534  1.00 15.43       O
ATOM   1088  CB  CYS A 174      13.037 -10.241  60.674  1.00 15.16       C
ATOM   1089  SG  CYS A 174      11.279 -10.569  60.787  1.00 17.07       S
ATOM   1090  N   LYS A 175      12.965 -13.584  61.596  1.00 17.50       N
ATOM   1091  CA  LYS A 175      12.562 -14.905  61.163  1.00 19.73       C
ATOM   1092  C   LYS A 175      11.126 -14.846  60.677  1.00 20.26       C
ATOM   1093  O   LYS A 175      10.240 -14.472  61.434  1.00 20.74       O
```

FIG. 8 (con't)

| | | | | | |
|---|---|---|---|---|---|
| ATOM | 344 | CG LYS A 79 | 22.268 -12.307 83.763 1.00 48.81 | C |
| ATOM | 345 | CD LYS A 79 | 23.073 -13.019 82.677 1.00 51.68 | C |
| ATOM | 346 | CE LYS A 79 | 23.911 -14.171 83.226 1.00 52.59 | C |
| ATOM | 347 | NZ LYS A 79 | 24.647 -14.889 82.136 1.00 52.97 | N |
| ATOM | 348 | N  GLY A 80 | 18.946 -10.916 85.929 1.00 45.59 | N |
| ATOM | 349 | CA GLY A 80 | 18.833 -10.307 87.244 1.00 44.46 | C |
| ATOM | 350 | C  GLY A 80 | 17.492 -10.592 87.901 1.00 44.04 | C |
| ATOM | 351 | O  GLY A 80 | 17.178 -10.068 88.976 1.00 43.95 | O |
| ATOM | 352 | N  GLY A 81 | 16.698 -11.435 87.243 1.00 42.18 | N |
| ATOM | 353 | CA GLY A 81 | 15.386 -11.780 87.753 1.00 39.56 | C |
| ATOM | 354 | C  GLY A 81 | 14.273 -10.915 87.178 1.00 37.50 | C |
| ATOM | 355 | O  GLY A 81 | 13.125 -11.016 87.607 1.00 36.38 | O |
| ATOM | 356 | N  GLN A 82 | 14.614 -10.058 86.216 1.00 36.01 | N |
| ATOM | 357 | CA GLN A 82 | 13.637 -9.176 85.576 1.00 34.06 | C |
| ATOM | 358 | C  GLN A 82 | 12.914 -9.936 84.459 1.00 31.83 | C |
| ATOM | 359 | O  GLN A 82 | 13.543 -10.467 83.543 1.00 30.92 | O |
| ATOM | 360 | CB GLN A 82 | 14.347 -7.954 84.988 1.00 34.17 | C |
| ATOM | 361 | CG GLN A 82 | 15.445 -7.422 85.880 1.00 37.64 | C |
| ATOM | 362 | CD GLN A 82 | 16.589 -6.827 85.093 1.00 37.58 | C |
| ATOM | 363 | OE1 GLN A 82 | 16.474 -5.742 84.533 1.00 36.42 | O |
| ATOM | 364 | NE2 GLN A 82 | 17.710 -7.552 85.044 1.00 38.46 | N |
| ATOM | 365 | N  VAL A 83 | 11.594 -10.010 84.542 1.00 29.61 | N |
| ATOM | 366 | CA VAL A 83 | 10.839 -10.710 83.514 1.00 28.42 | C |
| ATOM | 367 | C  VAL A 83 | 9.544 -9.992 83.170 1.00 27.22 | C |
| ATOM | 368 | O  VAL A 83 | 8.797 -9.590 84.056 1.00 27.49 | O |
| ATOM | 369 | CB VAL A 83 | 10.500 -12.148 83.959 1.00 28.55 | C |
| ATOM | 370 | CG1 VAL A 83 | 9.763 -12.873 82.842 1.00 26.97 | C |
| ATOM | 371 | CG2 VAL A 83 | 11.771 -12.891 84.340 1.00 26.81 | C |
| ATOM | 372 | N  GLN A 84 | 9.289 -9.819 81.879 1.00 26.91 | N |
| ATOM | 373 | CA GLN A 84 | 8.056 -9.176 81.425 1.00 26.48 | C |
| ATOM | 374 | C  GLN A 84 | 7.473 -9.964 80.266 1.00 26.36 | C |
| ATOM | 375 | O  GLN A 84 | 8.163 -10.194 79.284 1.00 27.52 | O |
| ATOM | 376 | CB GLN A 84 | 8.332 -7.763 80.960 1.00 25.82 | C |
| ATOM | 377 | CG GLN A 84 | 9.002 -6.933 81.994 1.00 27.92 | C |
| ATOM | 378 | CD GLN A 84 | 9.488 -5.668 81.414 1.00 28.14 | C |
| ATOM | 379 | OE1 GLN A 84 | 8.984 -5.198 80.385 1.00 29.64 | O |
| ATOM | 380 | NE2 GLN A 84 | 10.470 -5.040 82.060 1.00 29.61 | N |
| ATOM | 381 | N  ALA A 85 | 6.211 -10.383 80.372 1.00 26.56 | N |
| ATOM | 382 | CA ALA A 85 | 5.563 -11.124 79.289 1.00 25.59 | C |
| ATOM | 383 | C  ALA A 85 | 4.106 -10.680 79.131 1.00 25.48 | C |
| ATOM | 384 | O  ALA A 85 | 3.255 -11.027 79.942 1.00 26.61 | O |
| ATOM | 385 | CB ALA A 85 | 5.619 -12.622 79.554 1.00 24.51 | C |
| ATOM | 386 | N  SER A 86 | 3.822 -9.912 78.091 1.00 24.49 | N |
| ATOM | 387 | CA SER A 86 | 2.463 -9.453 77.881 1.00 23.75 | C |
| ATOM | 388 | C  SER A 86 | 1.939 -10.044 76.588 1.00 23.67 | C |
| ATOM | 389 | O  SER A 86 | 2.695 -10.656 75.838 1.00 25.50 | O |
| ATOM | 390 | CB SER A 86 | 2.431 -7.933 77.785 1.00 23.36 | C |
| ATOM | 391 | OG SER A 86 | 3.031 -7.527 76.577 1.00 21.66 | O |
| ATOM | 392 | N  ARG A 87 | 0.652 -9.856 76.325 1.00 22.22 | N |
| ATOM | 393 | CA ARG A 87 | 0.046 -10.385 75.113 1.00 20.45 | C |
| ATOM | 394 | C  ARG A 87 | -1.204 -9.597 74.767 1.00 18.82 | C |
| ATOM | 395 | O  ARG A 87 | -1.997 -9.256 75.645 1.00 18.95 | O |
| ATOM | 396 | CB ARG A 87 | -0.308 -11.861 75.336 1.00 22.14 | C |
| ATOM | 397 | CG ARG A 87 | -0.837 -12.553 74.110 1.00 23.90 | C |
| ATOM | 398 | CD ARG A 87 | -0.979 -14.024 74.392 1.00 27.83 | C |
| ATOM | 399 | NE ARG A 87 | -2.177 -14.318 75.165 1.00 29.95 | N |
| ATOM | 400 | CZ ARG A 87 | -2.262 -15.290 76.062 1.00 31.20 | C |
| ATOM | 401 | NH1 ARG A 87 | -1.204 -16.064 76.311 1.00 31.83 | N |
| ATOM | 402 | NH2 ARG A 87 | -3.403 -15.490 76.702 1.00 30.33 | N |
| ATOM | 403 | N  GLY A 88 | -1.384 -9.295 73.496 1.00 17.26 | N |
| ATOM | 404 | CA GLY A 88 | -2.550 -8.535 73.107 1.00 15.71 | C |
| ATOM | 405 | C  GLY A 88 | -2.742 -8.447 71.609 1.00 16.65 | C |
| ATOM | 406 | O  GLY A 88 | -2.199 -9.258 70.863 1.00 15.58 | O |
| ATOM | 407 | N  TYR A 89 | -3.500 -7.446 71.161 1.00 16.10 | N |
| ATOM | 408 | CA TYR A 89 | -3.769 -7.281 69.747 1.00 15.92 | C |
| ATOM | 409 | C  TYR A 89 | -4.153 -5.840 69.420 1.00 15.73 | C |
| ATOM | 410 | O  TYR A 89 | -4.422 -5.046 70.317 1.00 15.36 | O |
| ATOM | 411 | CB TYR A 89 | -4.896 -8.218 69.325 1.00 15.20 | C |
| ATOM | 412 | CG TYR A 89 | -6.246 -7.564 69.254 1.00 14.21 | C |
| ATOM | 413 | CD1 TYR A 89 | -6.793 -7.197 68.032 1.00 14.43 | C |
| ATOM | 414 | CD2 TYR A 89 | -6.991 -7.339 70.407 1.00 14.75 | C |
| ATOM | 415 | CE1 TYR A 89 | -8.048 -6.633 67.956 1.00 15.39 | C |
| ATOM | 416 | CE2 TYR A 89 | -8.247 -6.776 70.345 1.00 13.17 | C |
| ATOM | 417 | CZ TYR A 89 | -8.771 -6.431 69.119 1.00 14.99 | C |
| ATOM | 418 | OH TYR A 89 | -10.032 -5.893 69.054 1.00 14.53 | O |
| ATOM | 419 | N  LEU A 90 | -4.212 -5.531 68.134 1.00 16.33 | N |
| ATOM | 420 | CA LEU A 90 | -4.512 -4.191 67.689 1.00 19.09 | C |
| ATOM | 421 | C  LEU A 90 | -5.234 -4.225 66.350 1.00 20.18 | C |
| ATOM | 422 | O  LEU A 90 | -4.891 -5.034 65.486 1.00 19.77 | O |
| ATOM | 423 | CB LEU A 90 | -3.210 -3.420 67.546 1.00 22.45 | C |
| ATOM | 424 | CG LEU A 90 | -3.251 -2.151 66.724 1.00 26.97 | C |
| ATOM | 425 | CD1 LEU A 90 | -4.163 -1.092 67.399 1.00 28.71 | C |
| ATOM | 426 | CD2 LEU A 90 | -1.811 -1.659 66.549 1.00 27.47 | C |
| ATOM | 427 | N  GLU A 91 | -6.230 -3.360 66.173 1.00 20.86 | N |
| ATOM | 428 | CA GLU A 91 | -6.979 -3.300 64.924 1.00 23.59 | C |
| ATOM | 429 | C  GLU A 91 | -7.515 -1.906 64.634 1.00 25.15 | C |
| ATOM | 1094 | CB LYS A 175 | 12.691 -15.874 62.323 1.00 19.81 | C |
| ATOM | 1095 | CG LYS A 175 | 12.463 -17.322 61.953 1.00 24.58 | C |
| ATOM | 1096 | CD LYS A 175 | 12.440 -18.213 63.188 1.00 27.49 | C |
| ATOM | 1097 | CE LYS A 175 | 12.425 -19.693 62.839 1.00 29.10 | C |
| ATOM | 1098 | NZ LYS A 175 | 12.336 -20.492 64.092 1.00 32.01 | N |
| ATOM | 1099 | N  LEU A 176 | 10.892 -15.217 59.419 1.00 21.18 | N |
| ATOM | 1100 | CA LEU A 176 | 9.540 -15.182 58.866 1.00 22.24 | C |
| ATOM | 1101 | C  LEU A 176 | 9.067 -16.586 58.499 1.00 21.94 | C |
| ATOM | 1102 | O  LEU A 176 | 9.784 -17.311 57.819 1.00 22.52 | O |
| ATOM | 1103 | CB LEU A 176 | 9.522 -14.298 57.615 1.00 23.01 | C |
| ATOM | 1104 | CG LEU A 176 | 8.270 -13.438 57.397 1.00 25.46 | C |
| ATOM | 1105 | CD1 LEU A 176 | 8.463 -12.617 56.140 1.00 27.46 | C |
| ATOM | 1106 | CD2 LEU A 176 | 7.024 -14.296 57.279 1.00 24.28 | C |
| ATOM | 1107 | N  ARG A 177 | 7.866 -16.967 58.932 1.00 21.87 | N |
| ATOM | 1108 | CA ARG A 177 | 7.317 -18.291 58.638 1.00 22.85 | C |
| ATOM | 1109 | C  ARG A 177 | 5.819 -18.255 58.322 1.00 22.84 | C |
| ATOM | 1110 | O  ARG A 177 | 5.128 -17.284 58.638 1.00 22.66 | O |
| ATOM | 1111 | CB ARG A 177 | 7.560 -19.237 59.825 1.00 25.24 | C |
| ATOM | 1112 | CG ARG A 177 | 9.038 -19.554 60.090 1.00 29.18 | C |
| ATOM | 1113 | CD ARG A 177 | 9.666 -20.394 58.968 1.00 33.66 | C |
| ATOM | 1114 | NE ARG A 177 | 11.076 -20.735 59.231 1.00 38.67 | N |
| ATOM | 1115 | CZ ARG A 177 | 12.117 -19.936 58.987 1.00 39.65 | C |
| ATOM | 1116 | NH1 ARG A 177 | 11.940 -18.733 58.457 1.00 39.33 | N |
| ATOM | 1117 | NH2 ARG A 177 | 13.342 -20.341 59.293 1.00 40.65 | N |
| ATOM | 1118 | N  ILE A 178 | 5.311 -19.310 57.681 1.00 22.35 | N |
| ATOM | 1119 | CA ILE A 178 | 3.894 -19.377 57.349 1.00 20.34 | C |
| ATOM | 1120 | C  ILE A 178 | 3.126 -20.056 58.494 1.00 21.15 | C |
| ATOM | 1121 | O  ILE A 178 | 3.629 -20.974 59.137 1.00 21.86 | O |
| ATOM | 1122 | CB ILE A 178 | 3.686 -20.223 56.084 1.00 19.73 | C |
| ATOM | 1123 | CG1 ILE A 178 | 4.491 -19.615 54.939 1.00 19.71 | C |
| ATOM | 1124 | CG2 ILE A 178 | 2.217 -20.261 55.733 1.00 18.35 | C |
| ATOM | 1125 | CD1 ILE A 178 | 4.197 -18.140 54.691 1.00 17.93 | C |
| ATOM | 1126 | N  MET A 179 | 1.908 -19.587 58.749 1.00 21.52 | N |
| ATOM | 1127 | CA MET A 179 | 1.086 -20.127 59.836 1.00 21.73 | C |
| ATOM | 1128 | C  MET A 179 | 0.525 -21.491 59.469 1.00 21.63 | C |
| ATOM | 1129 | O  MET A 179 | -0.090 -21.648 58.415 1.00 21.49 | O |
| ATOM | 1130 | CB MET A 179 | -0.073 -19.181 60.132 1.00 21.14 | C |
| ATOM | 1131 | CG MET A 179 | 0.043 -18.312 61.379 1.00 21.98 | C |
| ATOM | 1132 | SD MET A 179 | -1.463 -17.320 61.574 1.00 20.07 | S |
| ATOM | 1133 | CE MET A 179 | -1.024 -16.022 60.719 1.00 19.83 | C |
| ATOM | 1134 | N  LYS A 180 | 0.729 -22.462 60.346 1.00 20.59 | N |
| ATOM | 1135 | CA LYS A 180 | 0.212 -23.802 60.108 1.00 21.79 | C |
| ATOM | 1136 | C  LYS A 180 | -1.073 -23.983 60.906 1.00 21.48 | C |
| ATOM | 1137 | O  LYS A 180 | -1.427 -23.127 61.719 1.00 21.37 | O |
| ATOM | 1138 | CB LYS A 180 | 1.272 -24.843 60.505 1.00 22.90 | C |
| ATOM | 1139 | CG LYS A 180 | 1.847 -24.646 61.875 1.00 23.11 | C |
| ATOM | 1140 | CD LYS A 180 | 2.929 -25.666 62.152 1.00 23.25 | C |
| ATOM | 1141 | CE LYS A 180 | 4.112 -25.505 61.215 1.00 24.25 | C |
| ATOM | 1142 | NZ LYS A 180 | 5.208 -26.468 61.539 1.00 24.93 | N |
| ATOM | 1143 | N  PRO A 181 | -1.816 -25.070 60.657 1.00 21.00 | N |
| ATOM | 1144 | CA PRO A 181 | -3.060 -25.315 61.382 1.00 20.19 | C |
| ATOM | 1145 | C  PRO A 181 | -2.969 -25.075 62.882 1.00 19.75 | C |
| ATOM | 1146 | O  PRO A 181 | -3.862 -24.461 63.464 1.00 18.22 | O |
| ATOM | 1147 | CB PRO A 181 | -3.385 -26.751 61.016 1.00 20.40 | C |
| ATOM | 1148 | CG PRO A 181 | -2.975 -26.788 59.595 1.00 20.15 | C |
| ATOM | 1149 | CD PRO A 181 | -1.606 -26.120 59.645 1.00 21.32 | C |
| ATOM | 1150 | N  GLN A 182 | -1.890 -25.543 63.507 1.00 21.37 | N |
| ATOM | 1151 | CA GLN A 182 | -1.722 -25.357 64.957 1.00 21.62 | C |
| ATOM | 1152 | C  GLN A 182 | -1.689 -23.887 65.346 1.00 20.06 | C |
| ATOM | 1153 | O  GLN A 182 | -2.182 -23.515 66.412 1.00 19.52 | O |
| ATOM | 1154 | CB GLN A 182 | -0.462 -26.067 65.455 1.00 22.77 | C |
| ATOM | 1155 | CG GLN A 182 | -0.466 -27.554 65.139 1.00 28.65 | C |
| ATOM | 1156 | CD GLN A 182 | 0.125 -27.868 63.767 1.00 31.78 | C |
| ATOM | 1157 | OE1 GLN A 182 | 1.343 -27.985 63.635 1.00 34.11 | O |
| ATOM | 1158 | NE2 GLN A 182 | -0.726 -28.000 62.753 1.00 30.20 | N |
| ATOM | 1159 | N  ASP A 183 | -1.123 -23.057 64.472 1.00 19.76 | N |
| ATOM | 1160 | CA ASP A 183 | -1.025 -21.623 64.724 1.00 18.68 | C |
| ATOM | 1161 | C  ASP A 183 | -2.383 -20.959 64.777 1.00 18.25 | C |
| ATOM | 1162 | O  ASP A 183 | -2.651 -20.181 65.685 1.00 16.97 | O |
| ATOM | 1163 | CB ASP A 183 | -0.172 -20.942 63.669 1.00 19.59 | C |
| ATOM | 1164 | CG ASP A 183 | 1.273 -21.414 63.705 1.00 18.01 | C |
| ATOM | 1165 | OD1 ASP A 183 | 1.867 -21.456 64.790 1.00 17.51 | O |
| ATOM | 1166 | OD2 ASP A 183 | 1.807 -21.737 62.630 1.00 22.87 | O |
| ATOM | 1167 | N  PHE A 184 | -3.238 -21.248 63.797 1.00 17.75 | N |
| ATOM | 1168 | CA PHE A 184 | -4.571 -20.665 63.782 1.00 17.68 | C |
| ATOM | 1169 | C  PHE A 184 | -5.315 -21.064 65.046 1.00 19.64 | C |
| ATOM | 1170 | O  PHE A 184 | -5.949 -20.232 65.685 1.00 19.95 | O |
| ATOM | 1171 | CB PHE A 184 | -5.356 -21.111 62.565 1.00 15.70 | C |
| ATOM | 1172 | CG PHE A 184 | -4.855 -20.525 61.295 1.00 14.98 | C |
| ATOM | 1173 | CD1 PHE A 184 | -3.972 -21.232 60.488 1.00 14.41 | C |
| ATOM | 1174 | CD2 PHE A 184 | -5.258 -19.261 60.900 1.00 13.40 | C |
| ATOM | 1175 | CE1 PHE A 184 | -3.503 -20.683 59.305 1.00 13.56 | C |
| ATOM | 1176 | CE2 PHE A 184 | -4.798 -18.708 59.721 1.00 12.12 | C |
| ATOM | 1177 | CZ PHE A 184 | -3.917 -19.419 58.921 1.00 12.15 | C |
| ATOM | 1178 | N  GLU A 185 | -5.247 -22.343 65.407 1.00 20.76 | N |
| ATOM | 1179 | CA GLU A 185 | -5.910 -22.820 66.611 1.00 22.07 | C |

FIG. 8 (con't)

```
ATOM  430  O   GLU A  91    -7.628  -1.073 65.533 1.00 26.09  O
ATOM  431  CB  GLU A  91    -8.157  -4.288 64.942 1.00 23.40  C
ATOM  432  CG  GLU A  91    -9.400  -3.797 65.674 1.00 23.71  C
ATOM  433  CD  GLU A  91   -10.604  -4.727 65.504 1.00 25.29  C
ATOM  434  OE1 GLU A  91   -11.062  -4.945 64.365 1.00 25.45  O
ATOM  435  OE2 GLU A  91   -11.112  -5.246 66.520 1.00 27.19  O
ATOM  436  N   ASP A  92    -7.849  -1.651 63.377 1.00 27.65  N
ATOM  437  CA  ASP A  92    -8.386  -0.348 62.979 1.00 31.86  C
ATOM  438  C   ASP A  92    -9.185  -0.509 61.692 1.00 32.85  C
ATOM  439  O   ASP A  92    -8.824  -1.309 60.837 1.00 32.71  O
ATOM  440  CB  ASP A  92    -7.245   0.656 62.733 1.00 34.56  C
ATOM  441  CG  ASP A  92    -7.705   2.120 62.793 1.00 38.54  C
ATOM  442  OD1 ASP A  92    -8.902   2.414 62.523 1.00 39.55  O
ATOM  443  OD2 ASP A  92    -6.858   2.991 63.099 1.00 38.84  O
ATOM  444  N   GLU A  93   -10.267   0.252 61.558 1.00 35.55  N
ATOM  445  CA  GLU A  93   -11.098   0.175 60.360 1.00 37.34  C
ATOM  446  C   GLU A  93   -10.422   0.899 59.216 1.00 37.68  C
ATOM  447  O   GLU A  93   -10.396   0.413 58.088 1.00 36.49  O
ATOM  448  CB  GLU A  93   -12.478   0.794 60.596 1.00 39.79  C
ATOM  449  CG  GLU A  93   -13.497  -0.128 61.271 1.00 43.84  C
ATOM  450  CD  GLU A  93   -14.909   0.456 61.285 1.00 45.13  C
ATOM  451  OE1 GLU A  93   -15.389   0.844 60.199 1.00 46.73  O
ATOM  452  OE2 GLU A  93   -15.539   0.520 62.367 1.00 45.51  O
ATOM  453  N   HIS A  94    -9.876   2.071 59.509 1.00 39.10  N
ATOM  454  CA  HIS A  94    -9.205   2.868 58.494 1.00 40.87  C
ATOM  455  C   HIS A  94    -8.008   3.552 59.110 1.00 41.00  C
ATOM  456  O   HIS A  94    -8.024   4.758 59.337 1.00 41.86  O
ATOM  457  CB  HIS A  94   -10.164   3.915 57.927 1.00 42.66  C
ATOM  458  CG  HIS A  94   -10.944   3.438 56.743 1.00 45.89  C
ATOM  459  ND1 HIS A  94   -10.400   3.335 55.482 1.00 47.73  N
ATOM  460  CD2 HIS A  94   -12.232   3.013 56.632 1.00 46.71  C
ATOM  461  CE1 HIS A  94   -11.311   2.872 54.641 1.00 48.84  C
ATOM  462  NE2 HIS A  94   -12.429   2.670 55.320 1.00 48.36  N
ATOM  463  N   ALA A  95    -6.968   2.774 59.375 1.00 41.11  N
ATOM  464  CA  ALA A  95    -5.757   3.302 59.983 1.00 41.64  C
ATOM  465  C   ALA A  95    -4.867   3.992 58.961 1.00 41.21  C
ATOM  466  O   ALA A  95    -4.741   3.543 57.831 1.00 41.52  O
ATOM  467  CB  ALA A  95    -4.983   2.190 60.663 1.00 41.38  C
ATOM  468  N   ALA A  96    -4.238   5.083 59.381 1.00 40.46  N
ATOM  469  CA  ALA A  96    -3.354   5.828 58.508 1.00 39.29  C
ATOM  470  C   ALA A  96    -2.059   5.044 58.308 1.00 37.94  C
ATOM  471  O   ALA A  96    -1.487   5.008 57.213 1.00 37.83  O
ATOM  472  CB  ALA A  96    -3.055   7.169 59.123 1.00 40.86  C
ATOM  473  N   ALA A  97    -1.600   4.415 59.380 1.00 34.87  N
ATOM  474  CA  ALA A  97    -0.386   3.620 59.323 1.00 33.04  C
ATOM  475  C   ALA A  97    -0.726   2.132 59.354 1.00 31.16  C
ATOM  476  O   ALA A  97    -1.761   1.735 59.870 1.00 29.76  O
ATOM  477  CB  ALA A  97     0.523   3.960 60.499 1.00 33.02  C
ATOM  478  N   HIS A  98     0.163   1.317 58.798 1.00 30.47  N
ATOM  479  CA  HIS A  98    -0.029  -0.122 58.791 1.00 29.55  C
ATOM  480  C   HIS A  98     0.287  -0.752 60.164 1.00 29.61  C
ATOM  481  O   HIS A  98     1.007  -0.177 60.989 1.00 27.88  O
ATOM  482  CB  HIS A  98     0.843  -0.757 57.712 1.00 29.13  C
ATOM  483  CG  HIS A  98     0.572  -0.240 56.331 1.00 30.25  C
ATOM  484  ND1 HIS A  98     1.027  -0.888 55.203 1.00 31.62  N
ATOM  485  CD2 HIS A  98    -0.108   0.845 55.898 1.00 30.54  C
ATOM  486  CE1 HIS A  98     0.636  -0.218 54.131 1.00 31.59  C
ATOM  487  NE2 HIS A  98    -0.054   0.836 54.520 1.00 30.92  N
ATOM  488  N   ALA A  99    -0.250  -1.947 60.392 1.00 29.60  N
ATOM  489  CA  ALA A  99    -0.052  -2.656 61.644 1.00 30.33  C
ATOM  490  C   ALA A  99     1.398  -2.605 62.093 1.00 31.77  C
ATOM  491  O   ALA A  99     1.682  -2.344 63.262 1.00 31.22  O
ATOM  492  CB  ALA A  99    -0.504  -4.092 61.500 1.00 29.64  C
ATOM  493  N   GLU A 100     2.316  -2.839 61.163 1.00 33.41  N
ATOM  494  CA  GLU A 100     3.743  -2.820 61.476 1.00 35.26  C
ATOM  495  C   GLU A 100     4.174  -1.498 62.107 1.00 35.17  C
ATOM  496  O   GLU A 100     4.966  -1.473 63.046 1.00 34.71  O
ATOM  497  CB  GLU A 100     4.574  -3.064 60.212 1.00 37.51  C
ATOM  498  CG  GLU A 100     4.406  -4.445 59.539 1.00 39.79  C
ATOM  499  CD  GLU A 100     3.025  -4.708 58.914 1.00 41.46  C
ATOM  500  OE1 GLU A 100     2.307  -3.745 58.537 1.00 42.28  O
ATOM  501  OE2 GLU A 100     2.662  -5.896 58.780 1.00 41.23  O
ATOM  502  N   GLU A 101     3.654  -0.396 61.581 1.00 35.32  N
ATOM  503  CA  GLU A 101     4.020   0.912 62.099 1.00 34.70  C
ATOM  504  C   GLU A 101     3.433   1.153 63.471 1.00 33.76  C
ATOM  505  O   GLU A 101     4.165   1.454 64.417 1.00 34.89  O
ATOM  506  CB  GLU A 101     3.546   2.005 61.144 1.00 37.37  C
ATOM  507  CG  GLU A 101     4.112   1.899 59.729 1.00 41.75  C
ATOM  508  CD  GLU A 101     3.635   3.024 58.806 1.00 43.89  C
ATOM  509  OE1 GLU A 101     2.728   2.798 57.968 1.00 44.04  O
ATOM  510  OE2 GLU A 101     4.174   4.146 58.928 1.00 44.93  O
ATOM  511  N   ALA A 102     2.113   1.023 63.587 1.00 30.60  N
ATOM  512  CA  ALA A 102     1.425   1.245 64.854 1.00 28.41  C
ATOM  513  C   ALA A 102     2.069   0.511 66.021 1.00 28.14  C
ATOM  514  O   ALA A 102     2.104   1.024 67.146 1.00 29.70  O
ATOM  515  CB  ALA A 102    -0.055   0.826 64.740 1.00 25.71  C
ATOM 1180  C   GLU A 185    -5.384 -22.066 67.853 1.00 22.23  C
ATOM 1181  O   GLU A 185    -6.151 -21.662 68.736 1.00 22.55  O
ATOM 1182  CB  GLU A 185    -5.688 -24.320 66.766 1.00 23.80  C
ATOM 1183  CG  GLU A 185    -6.165 -24.892 68.086 1.00 29.28  C
ATOM 1184  CD  GLU A 185    -5.965 -26.402 68.195 1.00 33.31  C
ATOM 1185  OE1 GLU A 185    -4.847 -26.895 67.926 1.00 34.86  O
ATOM 1186  OE2 GLU A 185    -6.928 -27.106 68.564 1.00 36.20  O
ATOM 1187  N   TYR A 186    -4.073 -21.881 67.912 1.00 20.95  N
ATOM 1188  CA  TYR A 186    -3.445 -21.172 69.011 1.00 20.20  C
ATOM 1189  C   TYR A 186    -4.031 -19.752 69.151 1.00 20.26  C
ATOM 1190  O   TYR A 186    -4.536 -19.361 70.220 1.00 19.28  O
ATOM 1191  CB  TYR A 186    -1.938 -21.085 68.764 1.00 21.30  C
ATOM 1192  CG  TYR A 186    -1.192 -20.365 69.858 1.00 23.68  C
ATOM 1193  CD1 TYR A 186    -0.987 -20.969 71.099 1.00 23.12  C
ATOM 1194  CD2 TYR A 186    -0.747 -19.051 69.683 1.00 22.52  C
ATOM 1195  CE1 TYR A 186    -0.362 -20.284 72.141 1.00 22.83  C
ATOM 1196  CE2 TYR A 186    -0.123 -18.354 70.721 1.00 22.50  C
ATOM 1197  CZ  TYR A 186     0.066 -18.982 71.950 1.00 23.41  C
ATOM 1198  OH  TYR A 186     0.700 -18.331 72.987 1.00 24.95  O
ATOM 1199  N   VAL A 187    -3.966 -18.988 68.065 1.00 18.99  N
ATOM 1200  CA  VAL A 187    -4.450 -17.617 68.033 1.00 19.66  C
ATOM 1201  C   VAL A 187    -5.924 -17.528 68.422 1.00 21.19  C
ATOM 1202  O   VAL A 187    -6.343 -16.627 69.156 1.00 20.67  O
ATOM 1203  CB  VAL A 187    -4.285 -16.989 66.606 1.00 20.33  C
ATOM 1204  CG1 VAL A 187    -4.710 -15.541 66.623 1.00 18.54  C
ATOM 1205  CG2 VAL A 187    -2.836 -17.079 66.154 1.00 17.64  C
ATOM 1206  N   TRP A 188    -6.704 -18.481 67.933 1.00 21.81  N
ATOM 1207  CA  TRP A 188    -8.117 -18.527 68.212 1.00 23.01  C
ATOM 1208  C   TRP A 188    -8.424 -18.740 69.675 1.00 26.07  C
ATOM 1209  O   TRP A 188    -9.231 -18.020 70.259 1.00 28.04  O
ATOM 1210  CB  TRP A 188    -8.783 -19.645 67.410 1.00 22.14  C
ATOM 1211  CG  TRP A 188   -10.266 -19.784 67.664 1.00 21.24  C
ATOM 1212  CD1 TRP A 188   -10.895 -20.759 68.396 1.00 19.15  C
ATOM 1213  CD2 TRP A 188   -11.301 -18.918 67.184 1.00 18.71  C
ATOM 1214  NE1 TRP A 188   -12.252 -20.555 68.387 1.00 17.30  N
ATOM 1215  CE2 TRP A 188   -12.531 -19.431 67.650 1.00 18.92  C
ATOM 1216  CE3 TRP A 188   -11.312 -17.756 66.399 1.00 18.39  C
ATOM 1217  CZ2 TRP A 188   -13.762 -18.823 67.362 1.00 19.31  C
ATOM 1218  CZ3 TRP A 188   -12.534 -17.149 66.109 1.00 17.90  C
ATOM 1219  CH2 TRP A 188   -13.740 -17.686 66.585 1.00 18.35  C
ATOM 1220  N   GLN A 189    -7.786 -19.731 70.282 1.00 28.68  N
ATOM 1221  CA  GLN A 189    -8.053 -20.026 71.683 1.00 30.60  C
ATOM 1222  C   GLN A 189    -7.348 -19.171 72.679 1.00 31.17  C
ATOM 1223  O   GLN A 189    -7.698 -19.102 73.857 1.00 30.63  O
ATOM 1224  CB  GLN A 189    -7.685 -21.476 71.982 1.00 32.34  C
ATOM 1225  CG  GLN A 189    -8.116 -22.445 70.909 1.00 34.32  C
ATOM 1226  CD  GLN A 189    -7.782 -23.881 71.259 1.00 36.97  C
ATOM 1227  OE1 GLN A 189    -6.727 -24.168 71.838 1.00 35.41  O
ATOM 1228  NE2 GLN A 189    -8.673 -24.798 70.895 1.00 36.12  N
ATOM 1229  N   ASN A 190    -6.371 -18.349 72.203 1.00 31.77  N
ATOM 1230  CA  ASN A 190    -5.614 -17.463 73.090 1.00 31.59  C
ATOM 1231  C   ASN A 190    -5.810 -15.973 72.877 1.00 29.99  C
ATOM 1232  O   ASN A 190    -5.622 -15.192 73.801 1.00 28.93  O
ATOM 1233  CB  ASN A 190    -4.129 -17.800 72.979 1.00 34.39  C
ATOM 1234  CG  ASN A 190    -3.774 -19.108 73.648 1.00 36.68  C
ATOM 1235  OD1 ASN A 190    -3.706 -19.184 74.871 1.00 38.40  O
ATOM 1236  ND2 ASN A 190    -3.552 -20.150 72.847 1.00 38.16  N
ATOM 1237  N   PHE A 191    -6.187 -15.577 71.666 1.00 28.18  N
ATOM 1238  CA  PHE A 191    -6.378 -14.162 71.374 1.00 28.28  C
ATOM 1239  C   PHE A 191    -7.856 -13.812 71.218 1.00 28.17  C
ATOM 1240  O   PHE A 191    -8.272 -12.680 71.455 1.00 27.98  O
ATOM 1241  CB  PHE A 191    -5.605 -13.798 70.107 1.00 27.26  C
ATOM 1242  CG  PHE A 191    -4.127 -13.640 70.325 1.00 28.00  C
ATOM 1243  CD1 PHE A 191    -3.599 -12.420 70.731 1.00 26.92  C
ATOM 1244  CD2 PHE A 191    -3.255 -14.718 70.140 1.00 28.21  C
ATOM 1245  CE1 PHE A 191    -2.233 -12.266 70.949 1.00 28.38  C
ATOM 1246  CE2 PHE A 191    -1.881 -14.573 70.360 1.00 27.03  C
ATOM 1247  CZ  PHE A 191    -1.370 -13.346 70.763 1.00 27.77  C
ATOM 1248  N   VAL A 192    -8.649 -14.793 70.820 1.00 28.18  N
ATOM 1249  CA  VAL A 192   -10.059 -14.559 70.639 1.00 30.52  C
ATOM 1250  C   VAL A 192   -10.803 -14.871 71.925 1.00 32.74  C
ATOM 1251  O   VAL A 192   -10.789 -16.007 72.393 1.00 31.06  O
ATOM 1252  CB  VAL A 192   -10.642 -15.431 69.525 1.00 29.42  C
ATOM 1253  CG1 VAL A 192   -12.146 -15.227 69.425 1.00 27.45  C
ATOM 1254  CG2 VAL A 192    -9.956 -15.105 68.209 1.00 27.82  C
ATOM 1255  N   GLU A 193   -11.448 -13.849 72.485 1.00 34.96  N
ATOM 1256  CA  GLU A 193   -12.209 -13.989 73.714 1.00 38.93  C
ATOM 1257  C   GLU A 193   -13.417 -14.905 73.563 1.00 41.77  C
ATOM 1258  O   GLU A 193   -14.224 -14.741 72.647 1.00 41.55  O
ATOM 1259  CB  GLU A 193   -12.696 -12.622 74.196 1.00 39.47  C
ATOM 1260  CG  GLU A 193   -13.705 -12.706 75.339 1.00 41.69  C
ATOM 1261  CD  GLU A 193   -14.272 -11.357 75.780 1.00 42.68  C
ATOM 1262  OE1 GLU A 193   -13.550 -10.590 76.451 1.00 43.65  O
ATOM 1263  OE2 GLU A 193   -15.440 -11.059 75.452 1.00 42.03  O
ATOM 1264  N   GLN A 194   -13.562 -15.837 74.499 1.00 46.22  N
ATOM 1265  CA  GLN A 194   -14.673 -16.783 74.522 1.00 50.57  C
```

FIG. 8 (con't)

| | | | | | | | | | | | | |
|---|---|---|---|---|---|---|---|---|---|---|---|---|
| ATOM | 516 | N | PHE A 103 | 2.574 | -0.692 | 65.762 | 1.00 | 26.55 | N | | | |
| ATOM | 517 | CA | PHE A 103 | 3.180 | -1.501 | 66.810 | 1.00 | 25.13 | C | | | |
| ATOM | 518 | C | PHE A 103 | 4.383 | -0.817 | 67.442 | 1.00 | 24.36 | C | | | |
| ATOM | 519 | O | PHE A 103 | 4.473 | -0.709 | 68.665 | 1.00 | 23.47 | O | | | |
| ATOM | 520 | CB | PHE A 103 | 3.605 | -2.864 | 66.256 | 1.00 | 23.54 | C | | | |
| ATOM | 521 | CG | PHE A 103 | 4.077 | -3.813 | 67.315 | 1.00 | 21.94 | C | | | |
| ATOM | 522 | CD1 | PHE A 103 | 3.169 | -4.415 | 68.177 | 1.00 | 22.73 | C | | | |
| ATOM | 523 | CD2 | PHE A 103 | 5.426 | -4.085 | 67.476 | 1.00 | 21.49 | C | | | |
| ATOM | 524 | CE1 | PHE A 103 | 3.602 | -5.277 | 69.185 | 1.00 | 22.49 | C | | | |
| ATOM | 525 | CE2 | PHE A 103 | 5.873 | -4.945 | 68.484 | 1.00 | 21.79 | C | | | |
| ATOM | 526 | CZ | PHE A 103 | 4.958 | -5.542 | 69.336 | 1.00 | 21.63 | C | | | |
| ATOM | 527 | N | PHE A 104 | 5.298 | -0.357 | 66.600 | 1.00 | 24.45 | N | | | |
| ATOM | 528 | CA | PHE A 104 | 6.498 | 0.319 | 67.090 | 1.00 | 25.83 | C | | | |
| ATOM | 529 | C | PHE A 104 | 6.297 | 1.806 | 67.412 | 1.00 | 26.83 | C | | | |
| ATOM | 530 | O | PHE A 104 | 7.257 | 2.492 | 67.749 | 1.00 | 27.82 | O | | | |
| ATOM | 531 | CB | PHE A 104 | 7.631 | 0.182 | 66.070 | 1.00 | 21.81 | C | | | |
| ATOM | 532 | CG | PHE A 104 | 8.097 | -1.222 | 65.871 | 1.00 | 17.73 | C | | | |
| ATOM | 533 | CD1 | PHE A 104 | 7.961 | -1.843 | 64.641 | 1.00 | 16.65 | C | | | |
| ATOM | 534 | CD2 | PHE A 104 | 8.673 | -1.930 | 66.915 | 1.00 | 17.77 | C | | | |
| ATOM | 535 | CE1 | PHE A 104 | 8.391 | -3.138 | 64.442 | 1.00 | 14.86 | C | | | |
| ATOM | 536 | CE2 | PHE A 104 | 9.102 | -3.231 | 66.726 | 1.00 | 16.29 | C | | | |
| ATOM | 537 | CZ | PHE A 104 | 8.960 | -3.833 | 65.484 | 1.00 | 15.13 | C | | | |
| ATOM | 538 | N | ASN A 105 | 5.064 | 2.293 | 67.325 | 1.00 | 28.02 | N | | | |
| ATOM | 539 | CA | ASN A 105 | 4.805 | 3.684 | 67.614 | 1.00 | 30.45 | C | | | |
| ATOM | 540 | C | ASN A 105 | 4.001 | 3.903 | 68.871 | 1.00 | 31.79 | C | | | |
| ATOM | 541 | O | ASN A 105 | 4.047 | 4.985 | 69.447 | 1.00 | 34.01 | O | | | |
| ATOM | 542 | CB | ASN A 105 | 4.093 | 4.373 | 66.442 | 1.00 | 31.94 | C | | | |
| ATOM | 543 | CG | ASN A 105 | 4.997 | 4.561 | 65.240 | 1.00 | 33.98 | C | | | |
| ATOM | 544 | OD1 | ASN A 105 | 6.189 | 4.855 | 65.388 | 1.00 | 35.96 | O | | | |
| ATOM | 545 | ND2 | ASN A 105 | 4.439 | 4.413 | 64.049 | 1.00 | 33.43 | N | | | |
| ATOM | 546 | N | THR A 106 | 3.270 | 2.890 | 69.316 | 1.00 | 32.65 | N | | | |
| ATOM | 547 | CA | THR A 106 | 2.457 | 3.040 | 70.522 | 1.00 | 33.94 | C | | | |
| ATOM | 548 | C | THR A 106 | 2.464 | 1.841 | 71.447 | 1.00 | 33.85 | C | | | |
| ATOM | 549 | O | THR A 106 | 2.267 | 1.985 | 72.655 | 1.00 | 34.59 | O | | | |
| ATOM | 550 | CB | THR A 106 | 1.018 | 3.359 | 70.169 | 1.00 | 34.54 | C | | | |
| ATOM | 551 | OG1 | THR A 106 | 0.611 | 2.531 | 69.067 | 1.00 | 36.21 | O | | | |
| ATOM | 552 | CG2 | THR A 106 | 0.880 | 4.826 | 69.801 | 1.00 | 35.14 | C | | | |
| ATOM | 553 | N | ILE A 107 | 2.678 | 0.657 | 70.884 | 1.00 | 33.30 | N | | | |
| ATOM | 554 | CA | ILE A 107 | 2.705 | -0.562 | 71.681 | 1.00 | 32.40 | C | | | |
| ATOM | 555 | C | ILE A 107 | 4.080 | -0.848 | 72.288 | 1.00 | 31.75 | C | | | |
| ATOM | 556 | O | ILE A 107 | 4.194 | -1.179 | 73.467 | 1.00 | 31.71 | O | | | |
| ATOM | 557 | CB | ILE A 107 | 2.272 | -1.765 | 70.843 | 1.00 | 32.26 | C | | | |
| ATOM | 558 | CG1 | ILE A 107 | 0.919 | -1.476 | 70.214 | 1.00 | 32.28 | C | | | |
| ATOM | 559 | CG2 | ILE A 107 | 2.151 | -3.007 | 71.719 | 1.00 | 31.74 | C | | | |
| ATOM | 560 | CD1 | ILE A 107 | 0.487 | -2.531 | 69.277 | 1.00 | 34.74 | C | | | |
| ATOM | 561 | N | LEU A 108 | 5.124 | -0.706 | 71.485 | 1.00 | 30.92 | N | | | |
| ATOM | 562 | CA | LEU A 108 | 6.464 | -0.975 | 71.964 | 1.00 | 30.03 | C | | | |
| ATOM | 563 | C | LEU A 108 | 7.365 | 0.166 | 71.515 | 1.00 | 30.38 | C | | | |
| ATOM | 564 | O | LEU A 108 | 8.233 | -0.018 | 70.668 | 1.00 | 31.35 | O | | | |
| ATOM | 565 | CB | LEU A 108 | 6.935 | -2.298 | 71.377 | 1.00 | 29.78 | C | | | |
| ATOM | 566 | CG | LEU A 108 | 8.019 | -3.058 | 72.126 | 1.00 | 31.17 | C | | | |
| ATOM | 567 | CD1 | LEU A 108 | 7.601 | -3.299 | 73.559 | 1.00 | 30.95 | C | | | |
| ATOM | 568 | CD2 | LEU A 108 | 8.250 | -4.373 | 71.431 | 1.00 | 31.92 | C | | | |
| ATOM | 569 | N | PRO A 109 | 7.160 | 1.372 | 72.075 | 1.00 | 31.40 | N | | | |
| ATOM | 570 | CA | PRO A 109 | 7.921 | 2.589 | 71.764 | 1.00 | 31.13 | C | | | |
| ATOM | 571 | C | PRO A 109 | 9.409 | 2.478 | 72.022 | 1.00 | 31.04 | C | | | |
| ATOM | 572 | O | PRO A 109 | 10.212 | 2.779 | 71.144 | 1.00 | 31.29 | O | | | |
| ATOM | 573 | CB | PRO A 109 | 7.271 | 3.640 | 72.657 | 1.00 | 31.39 | C | | | |
| ATOM | 574 | CG | PRO A 109 | 5.883 | 3.161 | 72.781 | 1.00 | 32.99 | C | | | |
| ATOM | 575 | CD | PRO A 109 | 6.077 | 1.685 | 73.024 | 1.00 | 32.10 | C | | | |
| ATOM | 576 | N | ALA A 110 | 9.782 | 2.063 | 73.225 | 1.00 | 31.49 | N | | | |
| ATOM | 577 | CA | ALA A 110 | 11.204 | 1.940 | 73.552 | 1.00 | 33.30 | C | | | |
| ATOM | 578 | C | ALA A 110 | 11.562 | 0.627 | 74.247 | 1.00 | 33.23 | C | | | |
| ATOM | 579 | O | ALA A 110 | 10.705 | -0.044 | 74.820 | 1.00 | 33.66 | O | | | |
| ATOM | 580 | CB | ALA A 110 | 11.630 | 3.134 | 74.424 | 1.00 | 33.91 | C | | | |
| ATOM | 581 | N | PHE A 111 | 12.839 | 0.263 | 74.191 | 1.00 | 33.53 | N | | | |
| ATOM | 582 | CA | PHE A 111 | 13.313 | -0.969 | 74.832 | 1.00 | 34.05 | C | | | |
| ATOM | 583 | C | PHE A 111 | 14.467 | -0.636 | 75.774 | 1.00 | 35.38 | C | | | |
| ATOM | 584 | O | PHE A 111 | 15.323 | 0.173 | 75.424 | 1.00 | 36.35 | O | | | |
| ATOM | 585 | CB | PHE A 111 | 13.833 | -1.964 | 73.789 | 1.00 | 30.80 | C | | | |
| ATOM | 586 | CG | PHE A 111 | 12.958 | -2.100 | 72.581 | 1.00 | 28.32 | C | | | |
| ATOM | 587 | CD1 | PHE A 111 | 12.847 | -1.064 | 71.662 | 1.00 | 28.58 | C | | | |
| ATOM | 588 | CD2 | PHE A 111 | 12.225 | -3.258 | 72.369 | 1.00 | 26.83 | C | | | |
| ATOM | 589 | CE1 | PHE A 111 | 12.014 | -1.181 | 70.548 | 1.00 | 27.64 | C | | | |
| ATOM | 590 | CE2 | PHE A 111 | 11.391 | -3.385 | 71.260 | 1.00 | 26.13 | C | | | |
| ATOM | 591 | CZ | PHE A 111 | 11.286 | -2.345 | 70.350 | 1.00 | 26.71 | C | | | |
| ATOM | 592 | N | ASP A 112 | 14.504 | -1.253 | 76.953 | 1.00 | 35.63 | N | | | |
| ATOM | 593 | CA | ASP A 112 | 15.606 | -0.999 | 77.878 | 1.00 | 37.37 | C | | | |
| ATOM | 594 | C | ASP A 112 | 16.730 | -2.012 | 77.597 | 1.00 | 36.28 | C | | | |
| ATOM | 595 | O | ASP A 112 | 16.506 | -3.223 | 77.576 | 1.00 | 35.18 | O | | | |
| ATOM | 596 | CB | ASP A 112 | 15.131 | -1.098 | 79.336 | 1.00 | 40.34 | C | | | |
| ATOM | 597 | CG | ASP A 112 | 15.006 | -2.521 | 79.810 | 1.00 | 42.74 | C | | | |
| ATOM | 598 | OD1 | ASP A 112 | 14.360 | -3.328 | 79.106 | 1.00 | 45.41 | O | | | |
| ATOM | 599 | OD2 | ASP A 112 | 15.549 | -2.823 | 80.886 | 1.00 | 42.72 | O | | | |
| ATOM | 600 | N | PRO A 113 | 17.950 | -1.512 | 77.360 | 1.00 | 35.36 | N | | | |
| ATOM | 601 | CA | PRO A 113 | 19.132 | -2.327 | 77.066 | 1.00 | 33.92 | C | | | |
| ATOM | 1266 | C | GLN A 194 | -15.498 | -16.435 | 75.763 | 1.00 | 53.36 | C | | | |
| ATOM | 1267 | O | GLN A 194 | -15.106 | -15.571 | 76.546 | 1.00 | 54.46 | O | | | |
| ATOM | 1268 | CB | GLN A 194 | -14.140 | -18.208 | 74.660 | 1.00 | 51.86 | C | | | |
| ATOM | 1269 | CG | GLN A 194 | -12.820 | -18.487 | 73.926 | 1.00 | 53.59 | C | | | |
| ATOM | 1270 | CD | GLN A 194 | -12.985 | -18.653 | 72.420 | 1.00 | 54.54 | C | | | |
| ATOM | 1271 | OE1 | GLN A 194 | -13.627 | -19.595 | 71.955 | 1.00 | 54.99 | O | | | |
| ATOM | 1272 | NE2 | GLN A 194 | -12.399 | -17.738 | 71.651 | 1.00 | 55.33 | N | | | |
| ATOM | 1273 | N | GLU A 195 | -16.617 | -17.121 | 75.968 | 1.00 | 56.13 | N | | | |
| ATOM | 1274 | CA | GLU A 195 | -17.447 | -16.851 | 77.141 | 1.00 | 59.03 | C | | | |
| ATOM | 1275 | C | GLU A 195 | -17.857 | -18.134 | 77.879 | 1.00 | 59.59 | C | | | |
| ATOM | 1276 | O | GLU A 195 | -17.995 | -18.142 | 79.107 | 1.00 | 59.77 | O | | | |
| ATOM | 1277 | CB | GLU A 195 | -18.696 | -16.077 | 76.716 | 1.00 | 60.67 | C | | | |
| ATOM | 1278 | CG | GLU A 195 | -18.415 | -14.833 | 75.884 | 1.00 | 63.08 | C | | | |
| ATOM | 1279 | CD | GLU A 195 | -19.430 | -14.654 | 74.763 | 1.00 | 64.67 | C | | | |
| ATOM | 1280 | OE1 | GLU A 195 | -20.637 | -14.507 | 75.054 | 1.00 | 66.01 | O | | | |
| ATOM | 1281 | OE2 | GLU A 195 | -19.015 | -14.663 | 73.586 | 1.00 | 65.30 | O | | | |
| ATOM | 1282 | N | GLU A 196 | -18.042 | -19.213 | 77.121 | 1.00 | 59.97 | N | | | |
| ATOM | 1283 | CA | GLU A 196 | -18.453 | -20.499 | 77.692 | 1.00 | 59.86 | C | | | |
| ATOM | 1284 | C | GLU A 196 | -17.401 | -21.032 | 78.668 | 1.00 | 59.57 | C | | | |
| ATOM | 1285 | O | GLU A 196 | -17.669 | -21.936 | 79.464 | 1.00 | 58.23 | O | | | |
| ATOM | 1286 | CB | GLU A 196 | -18.716 | -21.526 | 76.555 | 1.00 | 58.96 | C | | | |
| ATOM | 1287 | N | ALA A 201 | -14.693 | -25.334 | 70.791 | 1.00 | 41.42 | N | | | |
| ATOM | 1288 | CA | ALA A 201 | -13.676 | -26.193 | 70.198 | 1.00 | 41.96 | C | | | |
| ATOM | 1289 | C | ALA A 201 | -13.301 | -25.743 | 68.780 | 1.00 | 42.33 | C | | | |
| ATOM | 1290 | O | ALA A 201 | -14.155 | -25.673 | 67.893 | 1.00 | 42.50 | O | | | |
| ATOM | 1291 | CB | ALA A 201 | -14.169 | -27.643 | 70.181 | 1.00 | 42.56 | C | | | |
| ATOM | 1292 | N | PHE A 202 | -12.019 | -25.436 | 68.575 | 1.00 | 41.90 | N | | | |
| ATOM | 1293 | CA | PHE A 202 | -11.517 | -24.990 | 67.275 | 1.00 | 40.32 | C | | | |
| ATOM | 1294 | C | PHE A 202 | -11.889 | -25.978 | 66.181 | 1.00 | 40.67 | C | | | |
| ATOM | 1295 | O | PHE A 202 | -12.007 | -27.178 | 66.432 | 1.00 | 41.39 | O | | | |
| ATOM | 1296 | CB | PHE A 202 | -9.991 | -24.846 | 67.314 | 1.00 | 37.36 | C | | | |
| ATOM | 1297 | CG | PHE A 202 | -9.394 | -24.381 | 66.015 | 1.00 | 34.24 | C | | | |
| ATOM | 1298 | CD1 | PHE A 202 | -9.677 | -23.114 | 65.516 | 1.00 | 32.73 | C | | | |
| ATOM | 1299 | CD2 | PHE A 202 | -8.554 | -25.206 | 65.277 | 1.00 | 33.86 | C | | | |
| ATOM | 1300 | CE1 | PHE A 202 | -9.137 | -22.681 | 64.301 | 1.00 | 29.90 | C | | | |
| ATOM | 1301 | CE2 | PHE A 202 | -8.008 | -24.780 | 64.062 | 1.00 | 30.90 | C | | | |
| ATOM | 1302 | CZ | PHE A 202 | -8.305 | -23.515 | 63.576 | 1.00 | 29.55 | C | | | |
| ATOM | 1303 | N | GLN A 203 | -12.067 | -25.475 | 64.967 | 1.00 | 40.74 | N | | | |
| ATOM | 1304 | CA | GLN A 203 | -12.414 | -26.339 | 63.848 | 1.00 | 40.13 | C | | | |
| ATOM | 1305 | C | GLN A 203 | -11.728 | -25.880 | 62.564 | 1.00 | 39.69 | C | | | |
| ATOM | 1306 | O | GLN A 203 | -11.906 | -24.746 | 62.128 | 1.00 | 38.68 | O | | | |
| ATOM | 1307 | CB | GLN A 203 | -13.930 | -26.343 | 63.656 | 1.00 | 44.69 | C | | | |
| ATOM | 1308 | CG | GLN A 203 | -14.706 | -26.687 | 64.924 | 1.00 | 50.11 | C | | | |
| ATOM | 1309 | CD | GLN A 203 | -16.200 | -26.415 | 64.796 | 1.00 | 53.41 | C | | | |
| ATOM | 1310 | OE1 | GLN A 203 | -16.634 | -25.259 | 64.730 | 1.00 | 55.20 | O | | | |
| ATOM | 1311 | NE2 | GLN A 203 | -16.994 | -27.481 | 64.756 | 1.00 | 54.06 | N | | | |
| ATOM | 1312 | N | PRO A 204 | -10.928 | -26.762 | 61.946 | 1.00 | 38.73 | N | | | |
| ATOM | 1313 | CA | PRO A 204 | -10.236 | -26.399 | 60.709 | 1.00 | 37.82 | C | | | |
| ATOM | 1314 | C | PRO A 204 | -11.225 | -26.151 | 59.575 | 1.00 | 36.81 | C | | | |
| ATOM | 1315 | O | PRO A 204 | -12.416 | -26.410 | 59.715 | 1.00 | 36.26 | O | | | |
| ATOM | 1316 | CB | PRO A 204 | -9.332 | -27.603 | 60.454 | 1.00 | 38.41 | C | | | |
| ATOM | 1317 | CG | PRO A 204 | -10.123 | -28.733 | 61.024 | 1.00 | 37.88 | C | | | |
| ATOM | 1318 | CD | PRO A 204 | -10.624 | -28.152 | 62.326 | 1.00 | 38.35 | C | | | |
| ATOM | 1319 | N | TRP A 205 | -10.733 | -25.647 | 58.452 | 1.00 | 35.50 | N | | | |
| ATOM | 1320 | CA | TRP A 205 | -11.616 | -25.370 | 57.336 | 1.00 | 34.59 | C | | | |
| ATOM | 1321 | C | TRP A 205 | -11.099 | -25.925 | 56.024 | 1.00 | 36.17 | C | | | |
| ATOM | 1322 | O | TRP A 205 | -10.033 | -26.530 | 55.973 | 1.00 | 34.54 | O | | | |
| ATOM | 1323 | CB | TRP A 205 | -11.846 | -23.857 | 57.209 | 1.00 | 30.32 | C | | | |
| ATOM | 1324 | CG | TRP A 205 | -10.581 | -23.051 | 57.196 | 1.00 | 25.07 | C | | | |
| ATOM | 1325 | CD1 | TRP A 205 | -9.735 | -22.859 | 56.140 | 1.00 | 22.63 | C | | | |
| ATOM | 1326 | CD2 | TRP A 205 | -9.998 | -22.380 | 58.309 | 1.00 | 22.48 | C | | | |
| ATOM | 1327 | NE1 | TRP A 205 | -8.661 | -22.098 | 56.527 | 1.00 | 21.07 | N | | | |
| ATOM | 1328 | CE2 | TRP A 205 | -8.793 | -21.777 | 57.855 | 1.00 | 21.49 | C | | | |
| ATOM | 1329 | CE3 | TRP A 205 | -10.373 | -22.182 | 59.651 | 1.00 | 19.62 | C | | | |
| ATOM | 1330 | CZ2 | TRP A 205 | -7.956 | -21.021 | 58.698 | 1.00 | 20.40 | C | | | |
| ATOM | 1331 | CZ3 | TRP A 205 | -9.537 | -21.428 | 60.488 | 1.00 | 20.31 | C | | | |
| ATOM | 1332 | CH2 | TRP A 205 | -8.343 | -20.862 | 60.006 | 1.00 | 17.57 | C | | | |
| ATOM | 1333 | N | GLU A 206 | -11.897 | -25.696 | 54.979 | 1.00 | 39.70 | N | | | |
| ATOM | 1334 | CA | GLU A 206 | -11.628 | -26.130 | 53.607 | 1.00 | 42.71 | C | | | |
| ATOM | 1335 | C | GLU A 206 | -10.214 | -26.646 | 53.394 | 1.00 | 42.39 | C | | | |
| ATOM | 1336 | O | GLU A 206 | -9.956 | -27.843 | 53.509 | 1.00 | 43.48 | O | | | |
| ATOM | 1337 | CB | GLU A 206 | -11.874 | -24.977 | 52.615 | 1.00 | 46.46 | C | | | |
| ATOM | 1338 | CG | GLU A 206 | -12.635 | -23.748 | 53.145 | 1.00 | 50.39 | C | | | |
| ATOM | 1339 | CD | GLU A 206 | -14.141 | -23.849 | 53.000 | 1.00 | 53.17 | C | | | |
| ATOM | 1340 | OE1 | GLU A 206 | -14.807 | -24.469 | 53.867 | 1.00 | 54.75 | O | | | |
| ATOM | 1341 | OE2 | GLU A 206 | -14.658 | -23.303 | 51.999 | 1.00 | 55.04 | O | | | |
| ATOM | 1342 | N | ASP A 207 | -9.312 | -25.720 | 53.076 | 1.00 | 41.36 | N | | | |
| ATOM | 1343 | CA | ASP A 207 | -7.912 | -26.033 | 52.804 | 1.00 | 40.79 | C | | | |
| ATOM | 1344 | C | ASP A 207 | -6.924 | -25.334 | 53.757 | 1.00 | 38.08 | C | | | |
| ATOM | 1345 | O | ASP A 207 | -6.011 | -24.629 | 53.332 | 1.00 | 36.62 | O | | | |
| ATOM | 1346 | CB | ASP A 207 | -7.593 | -25.684 | 51.333 | 1.00 | 44.46 | C | | | |
| ATOM | 1347 | CG | ASP A 207 | -8.330 | -24.439 | 50.841 | 1.00 | 47.83 | C | | | |
| ATOM | 1348 | OD1 | ASP A 207 | -8.214 | -23.379 | 51.499 | 1.00 | 49.50 | O | | | |
| ATOM | 1349 | OD2 | ASP A 207 | -9.017 | -24.517 | 49.788 | 1.00 | 49.24 | O | | | |
| ATOM | 1350 | N | ILE A 208 | -7.110 | -25.542 | 55.054 | 1.00 | 34.07 | N | | | |
| ATOM | 1351 | CA | ILE A 208 | -6.229 | -24.926 | 56.016 | 1.00 | 31.01 | C | | | |

FIG. 8 (con't)

```
ATOM   602  C   PRO A 113    19.319  -3.551 77.944 1.00 32.23    C
ATOM   603  O   PRO A 113    19.763  -4.597 77.475 1.00 31.02    O
ATOM   604  CB  PRO A 113    20.271  -1.327 77.225 1.00 34.30    C
ATOM   605  CG  PRO A 113    19.656  -0.082 76.700 1.00 35.20    C
ATOM   606  CD  PRO A 113    18.302  -0.081 77.378 1.00 34.86    C
ATOM   607  N   ALA A 114    18.963  -3.410 79.212 1.00 31.30    N
ATOM   608  CA  ALA A 114    19.127  -4.487 80.173 1.00 30.48    C
ATOM   609  C   ALA A 114    18.255  -5.696 79.905 1.00 29.74    C
ATOM   610  O   ALA A 114    18.401  -6.726 80.559 1.00 30.20    O
ATOM   611  CB  ALA A 114    18.861  -3.965 81.578 1.00 30.69    C
ATOM   612  N   LEU A 115    17.354  -5.588 78.943 1.00 28.59    N
ATOM   613  CA  LEU A 115    16.477  -6.702 78.639 1.00 26.74    C
ATOM   614  C   LEU A 115    16.606  -7.184 77.211 1.00 26.21    C
ATOM   615  O   LEU A 115    17.075  -6.463 76.325 1.00 25.99    O
ATOM   616  CB  LEU A 115    15.020  -6.317 78.909 1.00 25.62    C
ATOM   617  CG  LEU A 115    14.537  -6.198 80.349 1.00 25.20    C
ATOM   618  CD1 LEU A 115    13.091  -5.725 80.379 1.00 24.76    C
ATOM   619  CD2 LEU A 115    14.664  -7.545 81.029 1.00 25.97    C
ATOM   620  N   ARG A 116    16.178  -8.419 76.998 1.00 25.26    N
ATOM   621  CA  ARG A 116    16.194  -9.010 75.679 1.00 25.16    C
ATOM   622  C   ARG A 116    14.753  -9.378 75.322 1.00 23.32    C
ATOM   623  O   ARG A 116    14.142 -10.222 75.967 1.00 22.07    O
ATOM   624  CB  ARG A 116    17.096 -10.239 75.673 1.00 27.53    C
ATOM   625  CG  ARG A 116    18.555  -9.909 75.966 1.00 31.30    C
ATOM   626  CD  ARG A 116    19.485 -10.803 75.152 1.00 36.39    C
ATOM   627  NE  ARG A 116    19.176 -10.717 73.720 1.00 39.38    N
ATOM   628  CZ  ARG A 116    19.794 -11.406 72.762 1.00 39.62    C
ATOM   629  NH1 ARG A 116    20.775 -12.246 73.063 1.00 39.78    N
ATOM   630  NH2 ARG A 116    19.417 -11.257 71.497 1.00 39.62    N
ATOM   631  N   TYR A 117    14.215  -8.729 74.294 1.00 22.29    N
ATOM   632  CA  TYR A 117    12.843  -8.961 73.861 1.00 22.17    C
ATOM   633  C   TYR A 117    12.675 -10.063 72.810 1.00 22.68    C
ATOM   634  O   TYR A 117    13.499 -10.215 71.903 1.00 23.33    O
ATOM   635  CB  TYR A 117    12.241  -7.662 73.332 1.00 22.44    C
ATOM   636  CG  TYR A 117    12.235  -6.524 74.332 1.00 24.66    C
ATOM   637  CD1 TYR A 117    13.421  -5.889 74.702 1.00 25.81    C
ATOM   638  CD2 TYR A 117    11.048  -6.080 74.912 1.00 25.52    C
ATOM   639  CE1 TYR A 117    13.426  -4.849 75.620 1.00 26.80    C
ATOM   640  CE2 TYR A 117    11.038  -5.037 75.831 1.00 26.04    C
ATOM   641  CZ  TYR A 117    12.226  -4.431 76.179 1.00 27.59    C
ATOM   642  OH  TYR A 117    12.215  -3.417 77.108 1.00 29.37    O
ATOM   643  N   ASN A 118    11.592 -10.823 72.937 1.00 23.61    N
ATOM   644  CA  ASN A 118    11.255 -11.900 72.009 1.00 23.56    C
ATOM   645  C   ASN A 118     9.843 -11.643 71.538 1.00 22.14    C
ATOM   646  O   ASN A 118     8.895 -12.204 72.086 1.00 22.31    O
ATOM   647  CB  ASN A 118    11.291 -13.239 72.725 1.00 26.22    C
ATOM   648  CG  ASN A 118    12.268 -14.180 72.110 1.00 30.40    C
ATOM   649  OD1 ASN A 118    13.483 -14.005 72.246 1.00 34.07    O
ATOM   650  ND2 ASN A 118    11.764 -15.181 71.406 1.00 32.12    N
ATOM   651  N   VAL A 119     9.702 -10.804 70.519 1.00 20.48    N
ATOM   652  CA  VAL A 119     8.382 -10.442 70.009 1.00 17.96    C
ATOM   653  C   VAL A 119     7.909 -11.427 68.988 1.00 16.86    C
ATOM   654  O   VAL A 119     8.702 -11.928 68.205 1.00 18.02    O
ATOM   655  CB  VAL A 119     8.415  -9.044 69.366 1.00 17.77    C
ATOM   656  CG1 VAL A 119     7.032  -8.702 68.832 1.00 18.50    C
ATOM   657  CG2 VAL A 119     8.895  -7.997 70.382 1.00 18.24    C
ATOM   658  N   THR A 120     6.616 -11.712 68.989 1.00 16.23    N
ATOM   659  CA  THR A 120     6.046 -12.637 68.018 1.00 15.49    C
ATOM   660  C   THR A 120     4.757 -12.046 67.439 1.00 15.95    C
ATOM   661  O   THR A 120     3.865 -11.725 68.205 1.00 16.29    O
ATOM   662  CB  THR A 120     5.746 -13.952 68.672 1.00 14.15    C
ATOM   663  OG1 THR A 120     6.970 -14.531 69.104 1.00 14.89    O
ATOM   664  CG2 THR A 120     5.043 -14.881 67.706 1.00 14.01    C
ATOM   665  N   TRP A 121     4.670 -11.904 66.105 1.00 15.04    N
ATOM   666  CA  TRP A 121     3.474 -11.351 65.451 1.00 14.59    C
ATOM   667  C   TRP A 121     2.629 -12.417 64.762 1.00 14.80    C
ATOM   668  O   TRP A 121     3.140 -13.450 64.357 1.00 14.85    O
ATOM   669  CB  TRP A 121     3.828 -10.321 64.372 1.00 13.65    C
ATOM   670  CG  TRP A 121     4.371  -9.027 64.860 1.00 12.34    C
ATOM   671  CD1 TRP A 121     4.413  -8.581 66.151 1.00 10.88    C
ATOM   672  CD2 TRP A 121     5.008  -8.026 64.060 1.00 11.77    C
ATOM   673  NE1 TRP A 121     5.047  -7.359 66.206 1.00  9.27    N
ATOM   674  CE2 TRP A 121     5.423  -6.994 64.935 1.00 11.56    C
ATOM   675  CE3 TRP A 121     5.273  -7.899 62.687 1.00 11.99    C
ATOM   676  CZ2 TRP A 121     6.096  -5.845 64.482 1.00 11.62    C
ATOM   677  CZ3 TRP A 121     5.948  -6.749 62.236 1.00 15.58    C
ATOM   678  CH2 TRP A 121     6.346  -5.741 63.130 1.00 12.25    C
ATOM   679  N   TYR A 122     1.335 -12.133 64.614 1.00 15.12    N
ATOM   680  CA  TYR A 122     0.399 -13.048 63.969 1.00 14.52    C
ATOM   681  C   TYR A 122    -0.485 -12.199 63.081 1.00 14.18    C
ATOM   682  O   TYR A 122    -1.467 -11.628 63.554 1.00 15.95    O
ATOM   683  CB  TYR A 122    -0.466 -13.758 65.008 1.00 15.40    C
ATOM   684  CG  TYR A 122     0.257 -14.791 65.846 1.00 15.65    C
ATOM   685  CD1 TYR A 122     0.770 -14.475 67.101 1.00 16.26    C
ATOM   686  CD2 TYR A 122     0.386 -16.108 65.400 1.00 16.74    C
ATOM   687  CE1 TYR A 122     1.388 -15.453 67.902 1.00 17.44    C

ATOM  1352  C   ILE A 208    -4.824 -25.520 55.928 1.00 30.50    C
ATOM  1353  O   ILE A 208    -3.844 -24.819 56.148 1.00 29.03    O
ATOM  1354  CB  ILE A 208    -6.754 -25.105 57.431 1.00 29.12    C
ATOM  1355  CG1 ILE A 208    -5.871 -24.349 58.408 1.00 27.44    C
ATOM  1356  CG2 ILE A 208    -6.794 -26.577 57.777 1.00 28.10    C
ATOM  1357  CD1 ILE A 208    -6.366 -24.410 59.822 1.00 27.40    C
ATOM  1358  N   GLN A 209    -4.736 -26.805 55.582 1.00 31.26    N
ATOM  1359  CA  GLN A 209    -3.449 -27.497 55.477 1.00 31.70    C
ATOM  1360  C   GLN A 209    -2.759 -27.307 54.131 1.00 30.36    C
ATOM  1361  O   GLN A 209    -1.538 -27.201 54.078 1.00 31.41    O
ATOM  1362  CB  GLN A 209    -3.625 -28.994 55.753 1.00 33.07    C
ATOM  1363  CG  GLN A 209    -2.325 -29.796 55.835 1.00 35.17    C
ATOM  1364  CD  GLN A 209    -1.337 -29.226 56.840 1.00 37.16    C
ATOM  1365  OE1 GLN A 209    -1.644 -29.077 58.028 1.00 37.31    O
ATOM  1366  NE2 GLN A 209    -0.142 -28.908 56.369 1.00 37.65    N
ATOM  1367  N   GLU A 210    -3.529 -27.272 53.056 1.00 30.28    N
ATOM  1368  CA  GLU A 210    -2.945 -27.103 51.740 1.00 32.33    C
ATOM  1369  C   GLU A 210    -2.429 -25.687 51.528 1.00 31.79    C
ATOM  1370  O   GLU A 210    -1.398 -25.508 50.896 1.00 32.58    O
ATOM  1371  CB  GLU A 210    -3.946 -27.458 50.632 1.00 34.07    C
ATOM  1372  CG  GLU A 210    -5.334 -27.893 51.114 1.00 39.54    C
ATOM  1373  CD  GLU A 210    -5.314 -29.147 51.959 1.00 41.45    C
ATOM  1374  OE1 GLU A 210    -4.656 -30.118 51.514 1.00 44.53    O
ATOM  1375  OE2 GLU A 210    -5.952 -29.160 53.049 1.00 40.18    O
ATOM  1376  N   ASN A 211    -3.139 -24.685 52.049 1.00 31.96    N
ATOM  1377  CA  ASN A 211    -2.716 -23.287 51.908 1.00 31.08    C
ATOM  1378  C   ASN A 211    -1.359 -23.115 52.609 1.00 29.91    C
ATOM  1379  O   ASN A 211    -0.442 -22.466 52.110 1.00 27.63    O
ATOM  1380  CB  ASN A 211    -3.742 -22.314 52.524 1.00 33.88    C
ATOM  1381  CG  ASN A 211    -5.116 -22.368 51.831 1.00 38.73    C
ATOM  1382  OD1 ASN A 211    -5.264 -22.966 50.762 1.00 41.62    O
ATOM  1383  ND2 ASN A 211    -6.130 -21.737 52.443 1.00 38.00    N
ATOM  1384  N   PHE A 212    -1.256 -23.695 53.794 1.00 28.77    N
ATOM  1385  CA  PHE A 212    -0.027 -23.634 54.558 1.00 26.34    C
ATOM  1386  C   PHE A 212     1.144 -24.194 53.731 1.00 25.80    C
ATOM  1387  O   PHE A 212     2.110 -23.488 53.420 1.00 23.73    O
ATOM  1388  CB  PHE A 212    -0.206 -24.440 55.835 1.00 26.16    C
ATOM  1389  CG  PHE A 212     1.075 -24.843 56.489 1.00 25.80    C
ATOM  1390  CD1 PHE A 212     1.938 -23.883 56.998 1.00 26.05    C
ATOM  1391  CD2 PHE A 212     1.411 -26.184 56.612 1.00 25.22    C
ATOM  1392  CE1 PHE A 212     3.116 -24.248 57.626 1.00 25.73    C
ATOM  1393  CE2 PHE A 212     2.588 -26.559 57.232 1.00 26.75    C
ATOM  1394  CZ  PHE A 212     3.444 -25.586 57.743 1.00 27.21    C
ATOM  1395  N   LEU A 213     1.045 -25.469 53.372 1.00 23.96    N
ATOM  1396  CA  LEU A 213     2.115 -26.102 52.626 1.00 22.98    C
ATOM  1397  C   LEU A 213     2.486 -25.338 51.364 1.00 21.49    C
ATOM  1398  O   LEU A 213     3.659 -25.226 51.032 1.00 22.36    O
ATOM  1399  CB  LEU A 213     1.753 -27.550 52.282 1.00 23.27    C
ATOM  1400  CG  LEU A 213     1.717 -28.519 53.466 1.00 24.09    C
ATOM  1401  CD1 LEU A 213     1.033 -29.798 53.037 1.00 24.18    C
ATOM  1402  CD2 LEU A 213     3.116 -28.805 53.967 1.00 22.04    C
ATOM  1403  N   TYR A 214     1.498 -24.797 50.673 1.00 19.55    N
ATOM  1404  CA  TYR A 214     1.762 -24.053 49.467 1.00 18.74    C
ATOM  1405  C   TYR A 214     2.675 -22.850 49.715 1.00 19.00    C
ATOM  1406  O   TYR A 214     3.726 -22.704 49.078 1.00 21.76    O
ATOM  1407  CB  TYR A 214     0.472 -23.571 48.848 1.00 19.08    C
ATOM  1408  CG  TYR A 214     0.682 -22.727 47.621 1.00 19.97    C
ATOM  1409  CD1 TYR A 214     0.880 -23.302 46.374 1.00 19.30    C
ATOM  1410  CD2 TYR A 214     0.719 -21.337 47.717 1.00 22.30    C
ATOM  1411  CE1 TYR A 214     1.116 -22.505 45.232 1.00 21.38    C
ATOM  1412  CE2 TYR A 214     0.952 -20.536 46.597 1.00 23.24    C
ATOM  1413  CZ  TYR A 214     1.152 -21.114 45.359 1.00 22.72    C
ATOM  1414  OH  TYR A 214     1.396 -20.265 44.291 1.00 22.46    O
ATOM  1415  N   TYR A 215     2.277 -21.981 50.635 1.00 18.41    N
ATOM  1416  CA  TYR A 215     3.044 -20.788 50.942 1.00 18.24    C
ATOM  1417  C   TYR A 215     4.356 -21.048 51.674 1.00 18.83    C
ATOM  1418  O   TYR A 215     5.262 -20.204 51.671 1.00 18.60    O
ATOM  1419  CB  TYR A 215     2.198 -19.787 51.737 1.00 16.51    C
ATOM  1420  CG  TYR A 215     1.214 -19.016 50.885 1.00 17.10    C
ATOM  1421  CD1 TYR A 215    -0.135 -19.354 50.853 1.00 16.50    C
ATOM  1422  CD2 TYR A 215     1.644 -17.965 50.063 1.00 16.80    C
ATOM  1423  CE1 TYR A 215    -1.035 -18.679 50.029 1.00 16.00    C
ATOM  1424  CE2 TYR A 215     0.755 -17.279 49.232 1.00 16.39    C
ATOM  1425  CZ  TYR A 215    -0.579 -17.646 49.215 1.00 18.26    C
ATOM  1426  OH  TYR A 215    -1.447 -17.026 48.323 1.00 21.26    O
ATOM  1427  N   GLU A 216     4.469 -22.206 52.300 1.00 19.52    N
ATOM  1428  CA  GLU A 216     5.681 -22.541 53.003 1.00 20.54    C
ATOM  1429  C   GLU A 216     6.709 -22.785 51.931 1.00 22.53    C
ATOM  1430  O   GLU A 216     7.861 -22.372 52.059 1.00 24.00    O
ATOM  1431  CB  GLU A 216     5.499 -23.802 53.846 1.00 20.92    C
ATOM  1432  CG  GLU A 216     6.771 -24.259 54.531 1.00 24.55    C
ATOM  1433  CD  GLU A 216     6.586 -25.490 55.382 1.00 26.85    C
ATOM  1434  OE1 GLU A 216     6.191 -26.556 54.836 1.00 26.59    O
ATOM  1435  OE2 GLU A 216     6.842 -25.386 56.605 1.00 27.10    O
ATOM  1436  N   GLU A 217     6.286 -23.440 50.848 1.00 24.09    N
ATOM  1437  CA  GLU A 217     7.187 -23.755 49.728 1.00 25.51    C
```

FIG. 8 (con't)

| | | | | | |
|---|---|---|---|---|---|
| ATOM | 688 | CE2 TYR A 122 | 0.999 -17.095 66.188 1.00 14.89 | C |
| ATOM | 689 | CZ TYR A 122 | 1.491 -16.760 67.439 1.00 16.76 | C |
| ATOM | 690 | OH TYR A 122 | 2.055 -17.721 68.248 1.00 15.81 | O |
| ATOM | 691 | N VAL A 123 | -0.139 -12.104 61.807 1.00 14.48 | N |
| ATOM | 692 | CA VAL A 123 | -0.893 -11.304 60.854 1.00 16.35 | C |
| ATOM | 693 | C VAL A 123 | -1.402 -12.152 59.701 1.00 16.04 | C |
| ATOM | 694 | O VAL A 123 | -0.873 -13.232 59.458 1.00 18.44 | O |
| ATOM | 695 | CB VAL A 123 | -0.031 -10.177 60.256 1.00 17.58 | C |
| ATOM | 696 | CG1 VAL A 123 | 0.060 -9.039 61.233 1.00 18.57 | C |
| ATOM | 697 | CG2 VAL A 123 | 1.365 -10.710 59.928 1.00 19.50 | C |
| ATOM | 698 | N SER A 124 | -2.394 -11.636 58.982 1.00 15.27 | N |
| ATOM | 699 | CA SER A 124 | -2.992 -12.358 57.860 1.00 15.80 | C |
| ATOM | 700 | C SER A 124 | -2.039 -12.583 56.693 1.00 15.80 | C |
| ATOM | 701 | O SER A 124 | -2.115 -13.615 56.034 1.00 18.18 | O |
| ATOM | 702 | CB SER A 124 | -4.234 -11.623 57.334 1.00 13.04 | C |
| ATOM | 703 | OG SER A 124 | -3.910 -10.400 56.695 1.00 12.72 | O |
| ATOM | 704 | N SER A 125 | -1.159 -11.631 56.427 1.00 14.87 | N |
| ATOM | 705 | CA SER A 125 | -0.246 -11.783 55.327 1.00 16.64 | C |
| ATOM | 706 | C SER A 125 | 1.087 -11.084 55.593 1.00 16.05 | C |
| ATOM | 707 | O SER A 125 | 1.182 -10.263 56.498 1.00 16.72 | O |
| ATOM | 708 | CB SER A 125 | -0.843 -11.213 54.050 1.00 19.25 | C |
| ATOM | 709 | OG SER A 125 | -0.613 -9.817 53.997 1.00 24.71 | O |
| ATOM | 710 | N SER A 126 | 2.106 -11.414 54.795 1.00 15.34 | N |
| ATOM | 711 | CA SER A 126 | 3.430 -10.816 54.922 1.00 15.00 | C |
| ATOM | 712 | C SER A 126 | 3.368 -9.311 54.658 1.00 14.82 | C |
| ATOM | 713 | O SER A 126 | 2.517 -8.825 53.928 1.00 14.74 | O |
| ATOM | 714 | CB SER A 126 | 4.395 -11.471 53.950 1.00 15.19 | C |
| ATOM | 715 | OG SER A 126 | 3.776 -11.601 52.683 1.00 17.28 | O |
| ATOM | 716 | N PRO A 127 | 4.300 -8.560 55.243 1.00 16.07 | N |
| ATOM | 717 | CA PRO A 127 | 4.353 -7.105 55.092 1.00 17.03 | C |
| ATOM | 718 | C PRO A 127 | 4.677 -6.581 53.688 1.00 19.08 | C |
| ATOM | 719 | O PRO A 127 | 5.199 -7.307 52.834 1.00 18.40 | O |
| ATOM | 720 | CB PRO A 127 | 5.405 -6.704 56.113 1.00 17.23 | C |
| ATOM | 721 | CG PRO A 127 | 6.367 -7.845 56.044 1.00 16.41 | C |
| ATOM | 722 | CD PRO A 127 | 5.461 -9.054 56.014 1.00 17.60 | C |
| ATOM | 723 | N CYS A 128 | 4.352 -5.315 53.455 1.00 19.18 | N |
| ATOM | 724 | CA CYS A 128 | 4.613 -4.691 52.171 1.00 20.22 | C |
| ATOM | 725 | C CYS A 128 | 6.074 -4.286 52.122 1.00 21.46 | C |
| ATOM | 726 | O CYS A 128 | 6.763 -4.328 53.146 1.00 21.23 | O |
| ATOM | 727 | CB CYS A 128 | 3.729 -3.441 52.002 1.00 19.67 | C |
| ATOM | 728 | SG CYS A 128 | 4.103 -2.059 53.134 1.00 19.62 | S |
| ATOM | 729 | N ALA A 129 | 6.548 -3.893 50.938 1.00 22.22 | N |
| ATOM | 730 | CA ALA A 129 | 7.941 -3.477 50.754 1.00 22.51 | C |
| ATOM | 731 | C ALA A 129 | 8.317 -2.378 51.741 1.00 23.45 | C |
| ATOM | 732 | O ALA A 129 | 9.341 -2.475 52.420 1.00 23.51 | O |
| ATOM | 733 | CB ALA A 129 | 8.162 -2.997 49.313 1.00 22.20 | C |
| ATOM | 734 | N ALA A 130 | 7.498 -1.333 51.830 1.00 24.79 | N |
| ATOM | 735 | CA ALA A 130 | 7.770 -0.219 52.749 1.00 25.79 | C |
| ATOM | 736 | C ALA A 130 | 7.877 -0.691 54.195 1.00 27.57 | C |
| ATOM | 737 | O ALA A 130 | 8.851 -0.392 54.885 1.00 27.60 | O |
| ATOM | 738 | CB ALA A 130 | 6.681 0.837 52.640 1.00 23.96 | C |
| ATOM | 739 | N CYS A 131 | 6.853 -1.399 54.664 1.00 28.78 | N |
| ATOM | 740 | CA CYS A 131 | 6.839 -1.916 56.027 1.00 29.65 | C |
| ATOM | 741 | C CYS A 131 | 8.092 -2.765 56.323 1.00 29.09 | C |
| ATOM | 742 | O CYS A 131 | 8.683 -2.684 57.409 1.00 28.45 | O |
| ATOM | 743 | CB CYS A 131 | 5.572 -2.752 56.254 1.00 30.64 | C |
| ATOM | 744 | SG CYS A 131 | 4.096 -1.825 56.740 1.00 33.86 | S |
| ATOM | 745 | N ALA A 132 | 8.492 -3.582 55.358 1.00 28.98 | N |
| ATOM | 746 | CA ALA A 132 | 9.674 -4.400 55.539 1.00 29.57 | C |
| ATOM | 747 | C ALA A 132 | 10.839 -3.502 55.922 1.00 30.73 | C |
| ATOM | 748 | O ALA A 132 | 11.499 -3.755 56.924 1.00 31.49 | O |
| ATOM | 749 | CB ALA A 132 | 10.003 -5.156 54.278 1.00 27.72 | C |
| ATOM | 750 | N ASP A 133 | 11.081 -2.446 55.136 1.00 31.97 | N |
| ATOM | 1438 | C GLU A 217 | 7.688 -22.500 49.042 1.00 24.63 | C |
| ATOM | 1439 | O GLU A 217 | 8.881 -22.340 48.816 1.00 22.91 | O |
| ATOM | 1440 | CB GLU A 217 | 6.473 -24.662 48.710 1.00 28.86 | C |
| ATOM | 1441 | CG GLU A 217 | 7.077 -24.635 47.290 1.00 33.24 | C |
| ATOM | 1442 | CD GLU A 217 | 6.045 -24.280 46.222 1.00 38.07 | C |
| ATOM | 1443 | OE1 GLU A 217 | 5.161 -23.433 46.499 1.00 39.02 | O |
| ATOM | 1444 | OE2 GLU A 217 | 6.114 -24.829 45.097 1.00 40.85 | O |
| ATOM | 1445 | N LYS A 218 | 6.750 -21.622 48.702 1.00 25.71 | N |
| ATOM | 1446 | CA LYS A 218 | 7.071 -20.362 48.044 1.00 26.11 | C |
| ATOM | 1447 | C LYS A 218 | 7.968 -19.475 48.904 1.00 24.92 | C |
| ATOM | 1448 | O LYS A 218 | 8.900 -18.864 48.393 1.00 24.92 | O |
| ATOM | 1449 | CB LYS A 218 | 5.786 -19.607 47.731 1.00 27.40 | C |
| ATOM | 1450 | CG LYS A 218 | 4.887 -20.318 46.753 1.00 29.84 | C |
| ATOM | 1451 | CD LYS A 218 | 5.530 -20.433 45.379 1.00 28.91 | C |
| ATOM | 1452 | CE LYS A 218 | 4.641 -21.240 44.443 1.00 30.13 | C |
| ATOM | 1453 | NZ LYS A 218 | 5.200 -21.333 43.070 1.00 30.40 | N |
| ATOM | 1454 | N LEU A 219 | 7.669 -19.387 50.199 1.00 23.72 | N |
| ATOM | 1455 | CA LEU A 219 | 8.467 -18.567 51.092 1.00 23.67 | C |
| ATOM | 1456 | C LEU A 219 | 9.863 -19.150 51.212 1.00 25.66 | C |
| ATOM | 1457 | O LEU A 219 | 10.830 -18.410 51.375 1.00 27.47 | O |
| ATOM | 1458 | CB LEU A 219 | 7.830 -18.475 52.484 1.00 22.58 | C |
| ATOM | 1459 | CG LEU A 219 | 8.601 -17.721 53.582 1.00 20.97 | C |
| ATOM | 1460 | CD1 LEU A 219 | 8.705 -16.262 53.212 1.00 20.14 | C |
| ATOM | 1461 | CD2 LEU A 219 | 7.891 -17.853 54.920 1.00 21.69 | C |
| ATOM | 1462 | N ALA A 220 | 9.985 -20.473 51.135 1.00 26.23 | N |
| ATOM | 1463 | CA ALA A 220 | 11.296 -21.122 51.238 1.00 27.57 | C |
| ATOM | 1464 | C ALA A 220 | 12.142 -20.913 49.974 1.00 29.46 | C |
| ATOM | 1465 | O ALA A 220 | 13.355 -20.709 50.054 1.00 29.16 | O |
| ATOM | 1466 | CB ALA A 220 | 11.133 -22.603 51.515 1.00 24.98 | C |
| ATOM | 1467 | N ASP A 221 | 11.500 -20.969 48.811 1.00 30.65 | N |
| ATOM | 1468 | CA ASP A 221 | 12.197 -20.770 47.549 1.00 32.42 | C |
| ATOM | 1469 | C ASP A 221 | 12.841 -19.395 47.468 1.00 32.14 | C |
| ATOM | 1470 | O ASP A 221 | 14.002 -19.252 47.079 1.00 31.87 | O |
| ATOM | 1471 | CB ASP A 221 | 11.244 -20.933 46.368 1.00 34.87 | C |
| ATOM | 1472 | CG ASP A 221 | 11.065 -22.375 45.966 1.00 38.82 | C |
| ATOM | 1473 | OD1 ASP A 221 | 11.883 -23.215 46.396 1.00 40.17 | O |
| ATOM | 1474 | OD2 ASP A 221 | 10.113 -22.667 45.208 1.00 42.34 | O |
| ATOM | 1475 | N ILE A 222 | 12.079 -18.376 47.838 1.00 31.44 | N |
| ATOM | 1476 | CA ILE A 222 | 12.571 -17.015 47.790 1.00 32.16 | C |
| ATOM | 1477 | C ILE A 222 | 13.616 -16.736 48.867 1.00 31.34 | C |
| ATOM | 1478 | O ILE A 222 | 14.640 -16.107 48.597 1.00 30.55 | O |
| ATOM | 1479 | CB ILE A 222 | 11.411 -16.007 47.934 1.00 31.93 | C |
| ATOM | 1480 | CG1 ILE A 222 | 11.973 -14.617 48.225 1.00 31.99 | C |
| ATOM | 1481 | CG2 ILE A 222 | 10.468 -16.472 48.999 1.00 33.78 | C |
| ATOM | 1482 | CD1 ILE A 222 | 11.014 -13.677 48.846 1.00 32.26 | C |
| ATOM | 1483 | N LEU A 223 | 13.360 -17.211 50.074 1.00 32.73 | N |
| ATOM | 1484 | CA LEU A 223 | 14.280 -16.977 51.178 1.00 35.39 | C |
| ATOM | 1485 | C LEU A 223 | 15.564 -17.790 51.105 1.00 37.03 | C |
| ATOM | 1486 | O LEU A 223 | 16.499 -17.536 51.856 1.00 37.69 | O |
| ATOM | 1487 | CB LEU A 223 | 13.588 -17.235 52.518 1.00 33.88 | C |
| ATOM | 1488 | CG LEU A 223 | 12.968 -16.033 53.224 1.00 32.85 | C |
| ATOM | 1489 | CD1 LEU A 223 | 12.038 -15.275 52.278 1.00 32.57 | C |
| ATOM | 1490 | CD2 LEU A 223 | 12.227 -16.529 54.461 1.00 32.42 | C |
| ATOM | 1491 | N LYS A 224 | 15.618 -18.759 50.203 1.00 39.82 | N |
| ATOM | 1492 | CA LYS A 224 | 16.808 -19.582 50.077 1.00 42.13 | C |
| ATOM | 1493 | C LYS A 224 | 16.886 -20.133 48.674 1.00 43.06 | C |
| ATOM | 1494 | O LYS A 224 | 17.537 -19.471 47.839 1.00 43.58 | O |
| ATOM | 1495 | CB LYS A 224 | 16.758 -20.741 51.087 1.00 44.93 | C |
| ATOM | 1496 | CG LYS A 224 | 16.896 -20.320 52.549 1.00 46.58 | C |
| ATOM | 1497 | CD LYS A 224 | 16.737 -21.505 53.504 1.00 47.58 | C |
| ATOM | 1498 | CE LYS A 224 | 17.818 -22.569 53.300 1.00 48.37 | C |
| ATOM | 1499 | NZ LYS A 224 | 17.606 -23.755 54.190 1.00 50.33 | N |
| ATOM | 1500 | OXT LYS A 224 | 16.278 -21.200 48.427 1.00 43.78 | O |
| TER | 1501 | LYS A 224 | | |

FIG. 9

```
ATOM   1502  N   GLY B  35     -10.627 -21.550  77.712  1.00 65.95           N
ATOM   1503  CA  GLY B  35     -11.789 -20.604  77.728  1.00 65.74           C
ATOM   1504  C   GLY B  35     -11.777 -19.666  78.924  1.00 65.88           C
ATOM   1505  O   GLY B  35     -12.113 -18.482  78.804  1.00 65.82           O
ATOM   1506  N   SER B  36     -11.391 -20.196  80.084  1.00 65.25           N
ATOM   1507  CA  SER B  36     -11.332 -19.406  81.316  1.00 64.34           C
ATOM   1508  C   SER B  36     -10.181 -18.403  81.291  1.00 63.25           C
ATOM   1509  O   SER B  36     -10.320 -17.280  81.782  1.00 63.83           O
ATOM   1510  CB  SER B  36     -11.194 -20.325  82.537  1.00 64.89           C
ATOM   1511  OG  SER B  36     -12.357 -21.122  82.705  1.00 65.58           O
ATOM   1512  N   GLY B  37      -9.048 -18.815  80.719  1.00 61.08           N
ATOM   1513  CA  GLY B  37      -7.889 -17.940  80.622  1.00 58.37           C
ATOM   1514  C   GLY B  37      -6.627 -18.655  80.176  1.00 56.48           C
ATOM   1515  O   GLY B  37      -6.508 -19.870  80.341  1.00 56.22           O
ATOM   1516  N   GLY B  38      -5.683 -17.898  79.613  1.00 54.16           N
ATOM   1517  CA  GLY B  38      -4.428 -18.478  79.157  1.00 52.32           C
ATOM   1518  C   GLY B  38      -3.368 -18.471  80.239  1.00 51.43           C
ATOM   1519  O   GLY B  38      -3.421 -19.244  81.203  1.00 52.20           O
ATOM   1520  N   GLY B  39      -2.385 -17.596  80.084  1.00 49.18           N
ATOM   1521  CA  GLY B  39      -1.340 -17.519  81.085  1.00 47.03           C
ATOM   1522  C   GLY B  39       0.017 -17.121  80.494  1.00 45.63           C
ATOM   1523  O   GLY B  39       0.391 -17.656  79.462  1.00 46.65           O
ATOM   1524  N   MET B  40       0.648 -16.177  81.152  1.00 43.33           N
ATOM   1525  CA  MET B  40       1.952 -15.681  80.718  1.00 41.32           C
ATOM   1526  C   MET B  40       2.954 -15.760  81.860  1.00 39.92           C
ATOM   1527  O   MET B  40       4.154 -15.656  81.634  1.00 40.36           O
ATOM   1528  CB  MET B  40       1.831 -14.231  80.240  1.00 41.10           C
ATOM   1529  CG  MET B  40       1.284 -13.293  81.296  1.00 41.23           C
ATOM   1530  SD  MET B  40      -0.175 -12.424  80.751  1.00 41.22           S
ATOM   1531  CE  MET B  40      -1.319 -13.808  80.575  1.00 42.14           C
ATOM   1532  N   ILE B  41       2.455 -15.944  83.084  1.00 39.53           N
ATOM   1533  CA  ILE B  41       3.303 -16.047  84.270  1.00 38.14           C
ATOM   1534  C   ILE B  41       3.596 -17.508  84.578  1.00 38.77           C
ATOM   1535  O   ILE B  41       2.689 -18.340  84.581  1.00 38.59           O
ATOM   1536  CB  ILE B  41       2.617 -15.434  85.495  1.00 37.33           C
ATOM   1537  CG1 ILE B  41       2.187 -14.002  85.180  1.00 36.78           C
ATOM   1538  CG2 ILE B  41       3.563 -15.426  86.666  1.00 35.32           C
ATOM   1539  CD1 ILE B  41       1.348 -13.360  86.250  1.00 36.32           C
ATOM   1540  N   VAL B  42       4.860 -17.818  84.843  1.00 39.95           N
ATOM   1541  CA  VAL B  42       5.255 -19.186  85.154  1.00 41.19           C
ATOM   1542  C   VAL B  42       5.923 -19.284  86.521  1.00 42.18           C
ATOM   1543  O   VAL B  42       6.912 -18.603  86.788  1.00 41.93           O
ATOM   1544  CB  VAL B  42       6.231 -19.731  84.101  1.00 41.11           C
ATOM   1545  CG1 VAL B  42       6.532 -21.189  84.389  1.00 40.37           C
ATOM   1546  CG2 VAL B  42       5.637 -19.566  82.711  1.00 41.56           C
ATOM   1547  N   THR B  43       5.367 -20.136  87.379  1.00 43.82           N
ATOM   1548  CA  THR B  43       5.887 -20.353  88.723  1.00 45.39           C
ATOM   1549  C   THR B  43       5.739 -21.815  89.095  1.00 46.40           C
ATOM   1550  O   THR B  43       4.884 -22.525  88.557  1.00 45.59           O
ATOM   1551  CB  THR B  43       5.136 -19.517  89.778  1.00 45.76           C
ATOM   1552  OG1 THR B  43       3.761 -19.394  89.392  1.00 45.90           O
ATOM   1553  CG2 THR B  43       5.779 -18.136  89.940  1.00 47.70           C
ATOM   1554  N   GLY B  44       6.583 -22.261  90.021  1.00 46.95           N
ATOM   1555  CA  GLY B  44       6.533 -23.641  90.465  1.00 47.63           C
ATOM   1556  C   GLY B  44       5.504 -23.824  91.561  1.00 47.94           C
ATOM   1557  O   GLY B  44       5.351 -24.919  92.100  1.00 48.43           O
ATOM   1558  N   GLU B  45       4.786 -22.753  91.884  1.00 47.48           N
ATOM   1559  CA  GLU B  45       3.782 -22.811  92.927  1.00 47.90           C
ATOM   1560  C   GLU B  45       2.454 -23.313  92.373  1.00 47.93           C
ATOM   1561  O   GLU B  45       1.889 -22.740  91.443  1.00 45.94           O
ATOM   1562  CB  GLU B  45       3.601 -21.438  93.561  1.00 48.53           C
ATOM   1563  CG  GLU B  45       2.969 -21.498  94.929  1.00 50.43           C
ATOM   1564  CD  GLU B  45       3.864 -22.151  95.957  1.00 51.36           C
ATOM   1565  OE1 GLU B  45       4.830 -21.492  96.414  1.00 51.15           O
ATOM   1566  OE2 GLU B  45       3.598 -23.324  96.303  1.00 51.55           O
ATOM   1567  N   ARG B  46       1.958 -24.393  92.962  1.00 49.04           N
ATOM   1568  CA  ARG B  46       0.718 -24.985  92.509  1.00 49.97           C
ATOM   1569  C   ARG B  46      -0.484 -24.439  93.281  1.00 48.13           C
ATOM   1570  O   ARG B  46      -1.617 -24.540  92.821  1.00 47.87           O
ATOM   1571  CB  ARG B  46       0.797 -26.510  92.658  1.00 53.46           C
ATOM   1572  CG  ARG B  46       0.328 -27.308  91.427  1.00 58.32           C
ATOM   1573  CD  ARG B  46      -1.136 -26.997  91.023  1.00 61.93           C
ATOM   1574  NE  ARG B  46      -1.577 -27.757  89.841  1.00 64.77           N
ATOM   1575  CZ  ARG B  46      -2.772 -27.640  89.260  1.00 65.91           C
ATOM   1576  NH1 ARG B  46      -3.676 -26.789  89.737  1.00 66.29           N
ATOM   1577  NH2 ARG B  46      -3.066 -28.376  88.193  1.00 65.31           N
ATOM   1578  N   LEU B  47      -0.236 -23.853  94.444  1.00 46.05           N
ATOM   1579  CA  LEU B  47      -1.330 -23.313  95.246  1.00 44.88           C
ATOM   1580  C   LEU B  47      -1.357 -21.803  95.130  1.00 43.20           C
ATOM   1581  O   LEU B  47      -0.346 -21.147  95.360  1.00 44.01           O
ATOM   1582  CB  LEU B  47      -1.153 -23.700  96.714  1.00 44.69           C
ATOM   1583  CG  LEU B  47      -2.332 -23.410  97.648  1.00 45.22           C
ATOM   1584  CD1 LEU B  47      -3.494 -24.345  97.335  1.00 43.81           C
ATOM   1585  CD2 LEU B  47      -1.884 -23.601  99.087  1.00 44.57           C
ATOM   1586  N   PRO B  48      -2.518 -21.228  94.784  1.00 41.40           N
ATOM   1587  CA  PRO B  48      -2.646 -19.775  94.643  1.00 39.91           C
ATOM   2264  CA  ARG B 134       4.064   9.783  89.908  1.00 38.09           C
ATOM   2265  C   ARG B 134       2.794   9.472  89.135  1.00 36.52           C
ATOM   2266  O   ARG B 134       2.585   9.976  88.034  1.00 37.99           O
ATOM   2267  CB  ARG B 134       4.963   8.549  89.883  1.00 41.14           C
ATOM   2268  CG  ARG B 134       6.206   8.649  90.748  1.00 44.82           C
ATOM   2269  CD  ARG B 134       6.614   7.270  91.281  1.00 47.86           C
ATOM   2270  NE  ARG B 134       7.848   7.315  92.062  1.00 48.00           N
ATOM   2271  CZ  ARG B 134       9.037   7.537  91.525  1.00 47.68           C
ATOM   2272  NH1 ARG B 134       9.125   7.722  90.215  1.00 48.22           N
ATOM   2273  NH2 ARG B 134      10.125   7.578  92.283  1.00 47.56           N
ATOM   2274  N   ILE B 135       1.952   8.622  89.712  1.00 33.49           N
ATOM   2275  CA  ILE B 135       0.698   8.245  89.076  1.00 31.24           C
ATOM   2276  C   ILE B 135      -0.140   9.495  88.769  1.00 30.81           C
ATOM   2277  O   ILE B 135      -0.653   9.657  87.666  1.00 30.33           O
ATOM   2278  CB  ILE B 135      -0.109   7.282  89.988  1.00 29.47           C
ATOM   2279  CG1 ILE B 135       0.680   5.983  90.187  1.00 27.46           C
ATOM   2280  CG2 ILE B 135      -1.474   6.987  89.376  1.00 27.90           C
ATOM   2281  CD1 ILE B 135       0.092   5.059  91.228  1.00 26.02           C
ATOM   2282  N   ILE B 136      -0.253  10.382  89.752  1.00 30.45           N
ATOM   2283  CA  ILE B 136      -1.022  11.610  89.603  1.00 30.68           C
ATOM   2284  C   ILE B 136       0.440  12.518  88.510  1.00 32.06           C
ATOM   2285  O   ILE B 136      -1.170  13.070  87.674  1.00 31.72           O
ATOM   2286  CB  ILE B 136      -1.072  12.369  90.950  1.00 28.90           C
ATOM   2287  CG1 ILE B 136      -1.927  11.589  91.948  1.00 27.80           C
ATOM   2288  CG2 ILE B 136      -1.638  13.753  90.764  1.00 29.12           C
ATOM   2289  CD1 ILE B 136      -1.834  12.103  93.356  1.00 26.90           C
ATOM   2290  N   LYS B 137       0.874  12.659  88.506  1.00 32.68           N
ATOM   2291  CA  LYS B 137       1.507  13.508  87.517  1.00 35.72           C
ATOM   2292  C   LYS B 137       1.298  12.973  86.105  1.00 35.76           C
ATOM   2293  O   LYS B 137       1.099  13.745  85.164  1.00 35.63           O
ATOM   2294  CB  LYS B 137       3.007  13.657  87.822  1.00 37.87           C
ATOM   2295  CG  LYS B 137       3.293  14.233  89.218  1.00 41.24           C
ATOM   2296  CD  LYS B 137       4.701  14.825  89.350  1.00 42.17           C
ATOM   2297  CE  LYS B 137       4.902  15.483  90.717  1.00 43.82           C
ATOM   2298  NZ  LYS B 137       6.179  16.245  90.796  1.00 45.43           N
ATOM   2299  N   THR B 138       1.335  11.651  85.962  1.00 35.39           N
ATOM   2300  CA  THR B 138       1.129  11.019  84.666  1.00 35.04           C
ATOM   2301  C   THR B 138      -0.340  11.174  84.266  1.00 33.96           C
ATOM   2302  O   THR B 138      -0.642  11.537  83.138  1.00 32.49           O
ATOM   2303  CB  THR B 138       1.494   9.523  84.710  1.00 34.86           C
ATOM   2304  OG1 THR B 138       2.878   9.380  85.029  1.00 34.79           O
ATOM   2305  CG2 THR B 138       1.236   8.877  83.361  1.00 34.43           C
ATOM   2306  N   LEU B 139      -1.237  10.892  85.205  1.00 34.40           N
ATOM   2307  CA  LEU B 139      -2.662  11.026  84.952  1.00 35.51           C
ATOM   2308  C   LEU B 139      -2.976  12.474  84.590  1.00 36.91           C
ATOM   2309  O   LEU B 139      -3.926  12.746  83.862  1.00 37.56           O
ATOM   2310  CB  LEU B 139      -3.470  10.624  86.185  1.00 34.03           C
ATOM   2311  CG  LEU B 139      -3.743   9.139  86.390  1.00 33.41           C
ATOM   2312  CD1 LEU B 139      -4.416   8.898  87.737  1.00 32.54           C
ATOM   2313  CD2 LEU B 139      -4.627   8.659  85.263  1.00 33.87           C
ATOM   2314  N   SER B 140      -2.170  13.397  85.108  1.00 38.70           N
ATOM   2315  CA  SER B 140      -2.345  14.823  84.850  1.00 40.17           C
ATOM   2316  C   SER B 140      -1.921  15.192  83.421  1.00 40.74           C
ATOM   2317  O   SER B 140      -2.573  15.999  82.749  1.00 39.59           O
ATOM   2318  CB  SER B 140      -1.538  15.628  85.859  1.00 41.74           C
ATOM   2319  OG  SER B 140      -1.453  16.987  85.466  1.00 43.64           O
ATOM   2320  N   LYS B 141      -0.822  14.602  82.970  1.00 42.10           N
ATOM   2321  CA  LYS B 141      -0.324  14.843  81.622  1.00 43.45           C
ATOM   2322  C   LYS B 141      -1.271  14.301  80.559  1.00 43.29           C
ATOM   2323  O   LYS B 141      -1.801  15.066  79.763  1.00 44.45           O
ATOM   2324  CB  LYS B 141       1.048  14.195  81.423  1.00 45.78           C
ATOM   2325  CG  LYS B 141       2.173  14.873  82.168  1.00 47.52           C
ATOM   2326  CD  LYS B 141       3.488  14.131  81.968  1.00 50.79           C
ATOM   2327  CE  LYS B 141       4.652  14.809  82.706  1.00 52.67           C
ATOM   2328  NZ  LYS B 141       5.036  16.149  82.151  1.00 54.39           N
ATOM   2329  N   THR B 142      -1.482  12.983  80.538  1.00 42.75           N
ATOM   2330  CA  THR B 142      -2.359  12.355  79.544  1.00 42.17           C
ATOM   2331  C   THR B 142      -3.813  12.336  80.008  1.00 41.50           C
ATOM   2332  O   THR B 142      -4.161  11.627  80.952  1.00 42.71           O
ATOM   2333  CB  THR B 142      -1.927  10.903  79.258  1.00 41.90           C
ATOM   2334  OG1 THR B 142      -2.305  10.076  80.358  1.00 44.46           O
ATOM   2335  CG2 THR B 142      -0.421  10.816  79.098  1.00 42.21           C
ATOM   2336  N   LYS B 143      -4.660  13.109  79.338  1.00 40.08           N
ATOM   2337  CA  LYS B 143      -6.070  13.189  79.701  1.00 38.21           C
ATOM   2338  C   LYS B 143      -6.869  12.077  79.060  1.00 35.50           C
ATOM   2339  O   LYS B 143      -8.017  11.833  79.421  1.00 33.75           O
ATOM   2340  CB  LYS B 143      -6.661  14.540  79.265  1.00 40.79           C
ATOM   2341  CG  LYS B 143      -5.993  15.776  79.869  1.00 43.12           C
ATOM   2342  CD  LYS B 143      -4.890  16.331  78.970  1.00 46.16           C
ATOM   2343  CE  LYS B 143      -4.301  17.631  79.528  1.00 48.14           C
ATOM   2344  NZ  LYS B 143      -5.343  18.665  79.813  1.00 48.76           N
ATOM   2345  N   ASN B 144      -6.257  11.400  78.097  1.00 31.53           N
ATOM   2346  CA  ASN B 144      -6.936  10.314  77.405  1.00 31.65           C
ATOM   2347  C   ASN B 144      -6.702   8.979  78.094  1.00 30.66           C
ATOM   2348  O   ASN B 144      -7.057   7.938  77.552  1.00 30.15           O
ATOM   2349  CB  ASN B 144      -6.468  10.230  75.965  1.00 31.74           C
```

FIG. 9 (con't)

```
ATOM   1588  C   PRO B  48     -2.418 -19.024  95.943  1.00 38.63      C
ATOM   1589  O   PRO B  48     -1.992 -17.866  95.945  1.00 37.68      O
ATOM   1590  CB  PRO B  48     -4.064 -19.609  94.110  1.00 40.40      C
ATOM   1591  CG  PRO B  48     -4.780 -20.757  94.701  1.00 40.22      C
ATOM   1592  CD  PRO B  48     -3.803 -21.884  94.498  1.00 41.21      C
ATOM   1593  N   ALA B  49     -2.695 -19.699  97.051  1.00 37.40      N
ATOM   1594  CA  ALA B  49     -2.531 -19.103  98.361  1.00 36.74      C
ATOM   1595  C   ALA B  49     -1.077 -18.727  98.588  1.00 37.22      C
ATOM   1596  O   ALA B  49     -0.784 -17.745  99.272  1.00 37.92      O
ATOM   1597  CB  ALA B  49     -2.999 -20.072  99.425  1.00 35.73      C
ATOM   1598  N   ASN B  50     -0.164 -19.506  97.999  1.00 36.86      N
ATOM   1599  CA  ASN B  50      1.274 -19.261  98.148  1.00 35.55      C
ATOM   1600  C   ASN B  50      1.783 -18.268  97.115  1.00 34.57      C
ATOM   1601  O   ASN B  50      2.632 -17.425  97.412  1.00 34.74      O
ATOM   1602  CB  ASN B  50      2.054 -20.573  98.031  1.00 36.48      C
ATOM   1603  CG  ASN B  50      1.685 -21.572  99.111  1.00 37.81      C
ATOM   1604  OD1 ASN B  50      1.836 -21.304 100.305  1.00 38.68      O
ATOM   1605  ND2 ASN B  50      1.193 -22.730  98.695  1.00 38.96      N
ATOM   1606  N   PHE B  51      1.258 -18.377  95.901  1.00 32.25      N
ATOM   1607  CA  PHE B  51      1.634 -17.496  94.819  1.00 30.10      C
ATOM   1608  C   PHE B  51      1.309 -16.045  95.164  1.00 29.79      C
ATOM   1609  O   PHE B  51      2.101 -15.146  94.889  1.00 31.28      O
ATOM   1610  CB  PHE B  51      0.876 -17.882  93.548  1.00 29.23      C
ATOM   1611  CG  PHE B  51      1.063 -16.920  92.415  1.00 26.10      C
ATOM   1612  CD1 PHE B  51      2.274 -16.857  91.737  1.00 26.15      C
ATOM   1613  CD2 PHE B  51      0.042 -16.055  92.043  1.00 26.87      C
ATOM   1614  CE1 PHE B  51      2.471 -15.942  90.698  1.00 25.67      C
ATOM   1615  CE2 PHE B  51      0.229 -15.130  91.005  1.00 26.81      C
ATOM   1616  CZ  PHE B  51      1.448 -15.078  90.334  1.00 25.60      C
ATOM   1617  N   PHE B  52      0.150 -15.819  95.773  1.00 28.87      N
ATOM   1618  CA  PHE B  52     -0.267 -14.469  96.135  1.00 29.04      C
ATOM   1619  C   PHE B  52      0.308 -14.002  97.460  1.00 30.61      C
ATOM   1620  O   PHE B  52      0.124 -12.850  97.865  1.00 31.07      O
ATOM   1621  CB  PHE B  52     -1.801 -14.369  96.190  1.00 27.06      C
ATOM   1622  CG  PHE B  52     -2.459 -14.378  94.833  1.00 24.65      C
ATOM   1623  CD1 PHE B  52     -3.158 -15.493  94.397  1.00 22.56      C
ATOM   1624  CD2 PHE B  52     -2.351 -13.276  93.980  1.00 23.11      C
ATOM   1625  CE1 PHE B  52     -3.745 -15.528  93.138  1.00 20.90      C
ATOM   1626  CE2 PHE B  52     -2.937 -13.301  92.713  1.00 22.18      C
ATOM   1627  CZ  PHE B  52     -3.635 -14.432  92.295  1.00 21.66      C
ATOM   1628  N   LYS B  53      1.002 -14.902  98.138  1.00 32.05      N
ATOM   1629  CA  LYS B  53      1.613 -14.581  99.411  1.00 33.59      C
ATOM   1630  C   LYS B  53      3.082 -14.190  99.201  1.00 34.05      C
ATOM   1631  O   LYS B  53      3.578 -13.270  99.852  1.00 33.80      O
ATOM   1632  CB  LYS B  53      1.510 -15.785 100.354  1.00 35.16      C
ATOM   1633  CG  LYS B  53      2.068 -15.563 101.751  1.00 37.21      C
ATOM   1634  CD  LYS B  53      1.228 -14.553 102.520  1.00 40.42      C
ATOM   1635  CE  LYS B  53      1.651 -14.439 103.985  1.00 40.80      C
ATOM   1636  NZ  LYS B  53      0.818 -13.452 104.755  1.00 41.58      N
ATOM   1637  N   PHE B  54      3.759 -14.872  98.272  1.00 33.63      N
ATOM   1638  CA  PHE B  54      5.175 -14.609  98.004  1.00 33.84      C
ATOM   1639  C   PHE B  54      5.435 -13.950  96.655  1.00 32.83      C
ATOM   1640  O   PHE B  54      5.823 -12.781  96.580  1.00 34.43      O
ATOM   1641  CB  PHE B  54      5.985 -15.908  98.083  1.00 34.77      C
ATOM   1642  CG  PHE B  54      5.766 -16.690  99.353  1.00 37.23      C
ATOM   1643  CD1 PHE B  54      5.179 -17.956  99.315  1.00 37.86      C
ATOM   1644  CD2 PHE B  54      6.124 -16.158 100.589  1.00 37.44      C
ATOM   1645  CE1 PHE B  54      4.949 -18.674 100.495  1.00 39.19      C
ATOM   1646  CE2 PHE B  54      5.899 -16.868 101.777  1.00 38.15      C
ATOM   1647  CZ  PHE B  54      5.307 -18.128 101.729  1.00 38.53      C
ATOM   1648  N   GLN B  55      5.226 -14.698  95.590  1.00 30.82      N
ATOM   1649  CA  GLN B  55      5.484 -14.173  94.272  1.00 30.73      C
ATOM   1650  C   GLN B  55      4.766 -12.886  93.950  1.00 29.59      C
ATOM   1651  O   GLN B  55      5.377 -11.952  93.432  1.00 30.41      O
ATOM   1652  CB  GLN B  55      5.147 -15.203  93.203  1.00 32.98      C
ATOM   1653  CG  GLN B  55      6.262 -16.211  92.945  1.00 37.44      C
ATOM   1654  CD  GLN B  55      6.344 -17.313  93.997  1.00 39.61      C
ATOM   1655  OE1 GLN B  55      7.340 -18.039  94.079  1.00 40.35      O
ATOM   1656  NE2 GLN B  55      5.288 -17.452  94.794  1.00 40.46      N
ATOM   1657  N   PHE B  56      3.474 -12.826  94.258  1.00 27.72      N
ATOM   1658  CA  PHE B  56      2.664 -11.650  93.944  1.00 26.73      C
ATOM   1659  C   PHE B  56      3.033 -10.434  94.797  1.00 27.37      C
ATOM   1660  O   PHE B  56      2.701  -9.295  94.461  1.00 27.11      O
ATOM   1661  CB  PHE B  56      1.175 -11.992  94.115  1.00 23.65      C
ATOM   1662  CG  PHE B  56      0.238 -11.028  93.426  1.00 22.80      C
ATOM   1663  CD1 PHE B  56      0.158 -10.983  92.036  1.00 21.59      C
ATOM   1664  CD2 PHE B  56     -0.580 -10.178  94.168  1.00 22.28      C
ATOM   1665  CE1 PHE B  56     -0.722 -10.107  91.397  1.00 20.82      C
ATOM   1666  CE2 PHE B  56     -1.463  -9.297  93.539  1.00 21.92      C
ATOM   1667  CZ  PHE B  56     -1.533  -9.263  92.150  1.00 21.01      C
ATOM   1668  N   ARG B  57      3.756 -10.689  95.882  1.00 27.57      N
ATOM   1669  CA  ARG B  57      4.135  -9.644  96.815  1.00 28.14      C
ATOM   1670  C   ARG B  57      5.111  -8.601  96.266  1.00 25.87      C
ATOM   1671  O   ARG B  57      5.841  -8.861  95.318  1.00 24.30      O
ATOM   1672  CB  ARG B  57      4.731 -10.273  98.075  1.00 31.68      C
ATOM   1673  CG  ARG B  57      4.248  -9.645  99.385  1.00 37.55      C
ATOM   2350  CG  ASN B 144     -4.977  9.983  75.844  1.00 31.40      C
ATOM   2351  OD1 ASN B 144     -4.496  9.617  74.773  1.00 31.14      O
ATOM   2352  ND2 ASN B 144     -4.241 10.185  76.930  1.00 29.98      N
ATOM   2353  N   LEU B 145     -6.102  9.027  79.285  1.00 29.02      N
ATOM   2354  CA  LEU B 145     -5.794  7.839  80.075  1.00 27.76      C
ATOM   2355  C   LEU B 145     -6.658  7.733  81.334  1.00 27.57      C
ATOM   2356  O   LEU B 145     -6.814  8.705  82.072  1.00 27.04      O
ATOM   2357  CB  LEU B 145     -4.326  7.861  80.497  1.00 28.45      C
ATOM   2358  CG  LEU B 145     -3.873  6.822  81.534  1.00 28.94      C
ATOM   2359  CD1 LEU B 145     -3.750  5.460  80.890  1.00 29.85      C
ATOM   2360  CD2 LEU B 145     -2.532  7.231  82.100  1.00 28.94      C
ATOM   2361  N   ARG B 146     -7.196  6.541  81.588  1.00 26.96      N
ATOM   2362  CA  ARG B 146     -8.031  6.290  82.760  1.00 26.21      C
ATOM   2363  C   ARG B 146     -7.457  5.065  83.464  1.00 25.46      C
ATOM   2364  O   ARG B 146     -7.346  4.002  82.862  1.00 25.45      O
ATOM   2365  CB  ARG B 146     -9.474  6.019  82.337  1.00 27.96      C
ATOM   2366  CG  ARG B 146    -10.521  6.703  83.214  1.00 29.77      C
ATOM   2367  CD  ARG B 146    -11.108  7.951  82.562  1.00 29.46      C
ATOM   2368  NE  ARG B 146    -10.091  8.955  82.261  1.00 30.14      N
ATOM   2369  CZ  ARG B 146    -10.346 10.135  81.702  1.00 28.29      C
ATOM   2370  NH1 ARG B 146    -11.586 10.455  81.384  1.00 27.95      N
ATOM   2371  NH2 ARG B 146     -9.360 10.980  81.453  1.00 28.19      N
ATOM   2372  N   LEU B 147     -7.104  5.210  84.744  1.00 24.29      N
ATOM   2373  CA  LEU B 147     -6.496  4.127  85.505  1.00 21.79      C
ATOM   2374  C   LEU B 147     -7.366  3.543  86.617  1.00 20.79      C
ATOM   2375  O   LEU B 147     -8.088  4.261  87.299  1.00 20.53      O
ATOM   2376  CB  LEU B 147     -5.168  4.601  86.098  1.00 21.66      C
ATOM   2377  CG  LEU B 147     -4.371  3.566  86.901  1.00 21.65      C
ATOM   2378  CD1 LEU B 147     -4.022  2.396  85.997  1.00 21.64      C
ATOM   2379  CD2 LEU B 147     -3.110  4.195  87.472  1.00 19.04      C
ATOM   2380  N   LEU B 148     -7.261  2.221  86.783  1.00 19.06      N
ATOM   2381  CA  LEU B 148     -7.996  1.465  87.788  1.00 15.72      C
ATOM   2382  C   LEU B 148     -7.025  0.553  88.525  1.00 16.09      C
ATOM   2383  O   LEU B 148     -6.465 -0.382  87.946  1.00 15.26      O
ATOM   2384  CB  LEU B 148     -9.078  0.616  87.127  1.00 14.89      C
ATOM   2385  CG  LEU B 148     -9.660 -0.531  87.972  1.00 14.68      C
ATOM   2386  CD1 LEU B 148    -10.299  0.000  89.246  1.00 14.36      C
ATOM   2387  CD2 LEU B 148    -10.688 -1.282  87.151  1.00 13.45      C
ATOM   2388  N   ILE B 149     -6.826  0.818  89.806  1.00 14.70      N
ATOM   2389  CA  ILE B 149     -5.917  0.005  90.581  1.00 14.28      C
ATOM   2390  C   ILE B 149     -6.664 -0.922  91.534  1.00 15.06      C
ATOM   2391  O   ILE B 149     -7.431 -0.475  92.382  1.00 15.28      O
ATOM   2392  CB  ILE B 149     -4.968  0.888  91.399  1.00 14.06      C
ATOM   2393  CG1 ILE B 149     -4.332  1.936  90.471  1.00 14.16      C
ATOM   2394  CG2 ILE B 149     -3.868  0.058  91.981  1.00 12.52      C
ATOM   2395  CD1 ILE B 149     -3.366  2.818  91.182  1.00 12.01      C
ATOM   2396  N   LEU B 150     -6.446 -2.223  91.377  1.00 15.28      N
ATOM   2397  CA  LEU B 150     -7.071 -3.215  92.239  1.00 15.89      C
ATOM   2398  C   LEU B 150     -6.003 -3.785  93.202  1.00 16.63      C
ATOM   2399  O   LEU B 150     -5.248 -4.680  92.840  1.00 19.24      O
ATOM   2400  CB  LEU B 150     -7.675 -4.325  91.378  1.00 15.36      C
ATOM   2401  CG  LEU B 150     -8.906 -3.901  90.569  1.00 18.61      C
ATOM   2402  CD1 LEU B 150     -9.327 -5.019  89.629  1.00 18.25      C
ATOM   2403  CD2 LEU B 150    -10.044 -3.567  91.530  1.00 18.95      C
ATOM   2404  N   VAL B 151     -5.937 -3.270  94.420  1.00 16.49      N
ATOM   2405  CA  VAL B 151     -4.928 -3.735  95.371  1.00 15.56      C
ATOM   2406  C   VAL B 151     -5.398 -4.909  96.231  1.00 16.31      C
ATOM   2407  O   VAL B 151     -6.591 -5.039  96.511  1.00 16.59      O
ATOM   2408  CB  VAL B 151     -4.524 -2.589  96.280  1.00 12.13      C
ATOM   2409  CG1 VAL B 151     -4.213 -1.380  95.432  1.00  9.75      C
ATOM   2410  CG2 VAL B 151     -5.663 -2.259  97.228  1.00 11.08      C
ATOM   2411  N   GLY B 152     -4.462 -5.759  96.648  1.00 17.30      N
ATOM   2412  CA  GLY B 152     -4.800 -6.903  97.488  1.00 17.76      C
ATOM   2413  C   GLY B 152     -4.986 -6.472  98.932  1.00 19.59      C
ATOM   2414  O   GLY B 152     -5.694 -7.100  99.725  1.00 16.62      O
ATOM   2415  N   ARG B 153     -4.327 -5.371  99.275  1.00 20.99      N
ATOM   2416  CA  ARG B 153     -4.417 -4.835 100.616  1.00 22.11      C
ATOM   2417  C   ARG B 153     -3.953 -3.389 100.602  1.00 20.94      C
ATOM   2418  O   ARG B 153     -3.360 -2.928  99.633  1.00 19.83      O
ATOM   2419  CB  ARG B 153     -3.542 -5.639 101.565  1.00 25.36      C
ATOM   2420  CG  ARG B 153     -2.065 -5.461 101.287  1.00 31.57      C
ATOM   2421  CD  ARG B 153     -1.213 -6.276 102.253  1.00 36.23      C
ATOM   2422  NE  ARG B 153      0.210 -5.945 102.117  1.00 41.06      N
ATOM   2423  CZ  ARG B 153      1.042 -5.788 103.146  1.00 42.13      C
ATOM   2424  NH1 ARG B 153      0.602 -5.942 104.389  1.00 44.06      N
ATOM   2425  NH2 ARG B 153      2.306 -5.436 102.927  1.00 42.40      N
ATOM   2426  N   LEU B 154     -4.221 -2.678 101.690  1.00 20.33      N
ATOM   2427  CA  LEU B 154     -3.814 -1.286 101.795  1.00 20.87      C
ATOM   2428  C   LEU B 154     -2.421 -1.166 102.402  1.00 21.95      C
ATOM   2429  O   LEU B 154     -2.180 -1.604 103.528  1.00 20.15      O
ATOM   2430  CB  LEU B 154     -4.820 -0.519 102.637  1.00 20.32      C
ATOM   2431  CG  LEU B 154     -5.528  0.631 101.934  1.00 20.10      C
ATOM   2432  CD1 LEU B 154     -5.810  0.220 100.515  1.00 17.57      C
ATOM   2433  CD2 LEU B 154     -6.815  0.985 102.669  1.00 19.17      C
ATOM   2434  N   PHE B 155     -1.517 -0.561 101.637  1.00 23.13      N
ATOM   2435  CA  PHE B 155     -0.134 -0.375 102.064  1.00 24.44      C
```

FIG. 9 (con't)

```
ATOM   1674  CD  ARG B  57    2.853 -10.146  99.793 1.00 40.52    C
ATOM   1675  NE  ARG B  57    2.504  -9.769 101.161 1.00 43.37    N
ATOM   1676  CZ  ARG B  57    1.543 -10.343 101.879 1.00 46.49    C
ATOM   1677  NH1 ARG B  57    0.822 -11.331 101.362 1.00 48.70    N
ATOM   1678  NH2 ARG B  57    1.310  -9.941 103.125 1.00 47.88    N
ATOM   1679  N   ASN B  58    5.079  -7.412  96.860 1.00 24.69    N
ATOM   1680  CA  ASN B  58    5.970  -6.319  96.500 1.00 23.73    C
ATOM   1681  C   ASN B  58    6.692  -5.909  97.787 1.00 24.86    C
ATOM   1682  O   ASN B  58    6.048  -5.567  98.777 1.00 24.08    O
ATOM   1683  CB  ASN B  58    5.214  -5.097  95.975 1.00 22.38    C
ATOM   1684  CG  ASN B  58    4.900  -5.183  94.498 1.00 22.23    C
ATOM   1685  OD1 ASN B  58    3.965  -5.862  94.089 1.00 20.24    O
ATOM   1686  ND2 ASN B  58    5.692  -4.484  93.685 1.00 19.40    N
ATOM   1687  N   VAL B  59    8.025  -5.938  97.765 1.00 25.46    N
ATOM   1688  CA  VAL B  59    8.808  -5.586  98.943 1.00 25.97    C
ATOM   1689  C   VAL B  59   10.020  -4.718  98.620 1.00 26.99    C
ATOM   1690  O   VAL B  59   10.746  -4.968  97.656 1.00 26.55    O
ATOM   1691  CB  VAL B  59    9.322  -6.847  99.654 1.00 25.65    C
ATOM   1692  CG1 VAL B  59   10.098  -6.457 100.887 1.00 26.97    C
ATOM   1693  CG2 VAL B  59    8.168  -7.760 100.010 1.00 27.12    C
ATOM   1694  N   GLU B  60   10.245  -3.706  99.441 1.00 27.82    N
ATOM   1695  CA  GLU B  60   11.388  -2.829  99.247 1.00 29.19    C
ATOM   1696  C   GLU B  60   12.450  -3.149 100.300 1.00 28.80    C
ATOM   1697  O   GLU B  60   12.357  -2.674 101.431 1.00 28.69    O
ATOM   1698  CB  GLU B  60   10.956  -1.377  99.375 1.00 30.04    C
ATOM   1699  CG  GLU B  60   12.096  -0.400  99.244 1.00 33.08    C
ATOM   1700  CD  GLU B  60   11.666   1.026  99.505 1.00 35.77    C
ATOM   1701  OE1 GLU B  60   10.703   1.487  98.861 1.00 37.27    O
ATOM   1702  OE2 GLU B  60   12.291   1.691 100.357 1.00 37.28    O
ATOM   1703  N   TYR B  61   13.445  -3.955  99.925 1.00 27.51    N
ATOM   1704  CA  TYR B  61   14.523  -4.321 100.845 1.00 26.91    C
ATOM   1705  C   TYR B  61   15.384  -3.093 101.157 1.00 27.18    C
ATOM   1706  O   TYR B  61   15.601  -2.770 102.317 1.00 24.54    O
ATOM   1707  CB  TYR B  61   15.409  -5.424 100.241 1.00 25.34    C
ATOM   1708  CG  TYR B  61   14.644  -6.599  99.686 1.00 23.96    C
ATOM   1709  CD1 TYR B  61   14.470  -6.753  98.310 1.00 23.62    C
ATOM   1710  CD2 TYR B  61   14.059  -7.540 100.532 1.00 23.24    C
ATOM   1711  CE1 TYR B  61   13.737  -7.814  97.791 1.00 22.83    C
ATOM   1712  CE2 TYR B  61   13.321  -8.601 100.024 1.00 23.69    C
ATOM   1713  CZ  TYR B  61   13.167  -8.734  98.658 1.00 23.37    C
ATOM   1714  OH  TYR B  61   12.452  -9.808  98.175 1.00 23.82    O
ATOM   1715  N   SER B  62   15.854  -2.419 100.105 1.00 29.35    N
ATOM   1716  CA  SER B  62   16.691  -1.227 100.240 1.00 31.06    C
ATOM   1717  C   SER B  62   16.212  -0.133  99.296 1.00 31.66    C
ATOM   1718  O   SER B  62   15.354  -0.366  98.454 1.00 31.17    O
ATOM   1719  CB  SER B  62   18.153  -1.550  99.914 1.00 32.00    C
ATOM   1720  OG  SER B  62   18.978  -1.392 101.050 1.00 31.84    O
ATOM   1721  N   SER B  63   16.797   1.055  99.424 1.00 32.00    N
ATOM   1722  CA  SER B  63   16.409   2.187  98.596 1.00 32.39    C
ATOM   1723  C   SER B  63   16.284   1.847  97.102 1.00 31.21    C
ATOM   1724  O   SER B  63   15.239   2.082  96.482 1.00 33.08    O
ATOM   1725  CB  SER B  63   17.391   3.333  98.790 1.00 33.46    C
ATOM   1726  OG  SER B  63   18.667   2.991  98.266 1.00 37.88    O
ATOM   1727  N   GLY B  64   17.333   1.299  96.521 1.00 28.40    N
ATOM   1728  CA  GLY B  64   17.263   0.985  95.109 1.00 26.47    C
ATOM   1729  C   GLY B  64   17.292  -0.498  94.813 1.00 24.74    C
ATOM   1730  O   GLY B  64   17.810  -0.917  93.781 1.00 24.90    O
ATOM   1731  N   ARG B  65   16.747  -1.290  95.726 1.00 22.73    N
ATOM   1732  CA  ARG B  65   16.708  -2.730  95.556 1.00 22.68    C
ATOM   1733  C   ARG B  65   15.415  -3.266  96.138 1.00 22.62    C
ATOM   1734  O   ARG B  65   15.298  -3.484  97.342 1.00 22.28    O
ATOM   1735  CB  ARG B  65   17.905  -3.395  96.252 1.00 22.67    C
ATOM   1736  CG  ARG B  65   17.930  -4.927  96.171 1.00 21.91    C
ATOM   1737  CD  ARG B  65   19.177  -5.516  96.852 1.00 19.71    C
ATOM   1738  NE  ARG B  65   19.125  -5.420  98.303 1.00 21.30    N
ATOM   1739  CZ  ARG B  65   18.501  -6.289  99.095 1.00 22.37    C
ATOM   1740  NH1 ARG B  65   17.872  -7.338  98.580 1.00 23.22    N
ATOM   1741  NH2 ARG B  65   18.491  -6.101 100.409 1.00 23.11    N
ATOM   1742  N   ASN B  66   14.430  -3.473  95.282 1.00 23.50    N
ATOM   1743  CA  ASN B  66   13.170  -3.978  95.780 1.00 24.38    C
ATOM   1744  C   ASN B  66   12.524  -4.973  94.840 1.00 22.48    C
ATOM   1745  O   ASN B  66   12.683  -4.876  93.632 1.00 23.32    O
ATOM   1746  CB  ASN B  66   12.225  -2.808  96.057 1.00 25.89    C
ATOM   1747  CG  ASN B  66   12.275  -1.763  94.983 1.00 25.63    C
ATOM   1748  OD1 ASN B  66   13.293  -1.102  94.782 1.00 27.35    O
ATOM   1749  ND2 ASN B  66   11.170  -1.595  94.284 1.00 29.96    N
ATOM   1750  N   LYS B  67   11.817  -5.939  95.419 1.00 22.30    N
ATOM   1751  CA  LYS B  67   11.117  -6.974  94.666 1.00 21.90    C
ATOM   1752  C   LYS B  67    9.845  -6.372  94.096 1.00 22.07    C
ATOM   1753  O   LYS B  67    8.972  -5.947  94.852 1.00 22.80    O
ATOM   1754  CB  LYS B  67   10.730  -8.129  95.586 1.00 21.10    C
ATOM   1755  CG  LYS B  67   10.081  -9.302  94.875 1.00 21.44    C
ATOM   1756  CD  LYS B  67    8.796  -9.734  95.563 1.00 20.82    C
ATOM   1757  CE  LYS B  67    8.316 -11.064  95.016 1.00 23.26    C
ATOM   1758  NZ  LYS B  67    9.352 -12.091  95.303 1.00 23.48    N
ATOM   1759  N   THR B  68    9.741  -6.352  92.775 1.00 21.38    N
ATOM   2436  C   PHE B 155   -0.026   0.732 103.090 1.00 24.13    C
ATOM   2437  O   PHE B 155   -0.103   1.918 102.748 1.00 24.25    O
ATOM   2438  CB  PHE B 155    0.745  -0.026 100.851 1.00 26.25    C
ATOM   2439  CG  PHE B 155    2.224   0.065 101.170 1.00 25.81    C
ATOM   2440  CD1 PHE B 155    2.942  -1.075 101.510 1.00 26.50    C
ATOM   2441  CD2 PHE B 155    2.902   1.285 101.094 1.00 27.32    C
ATOM   2442  CE1 PHE B 155    4.322  -1.019 101.762 1.00 25.85    C
ATOM   2443  CE2 PHE B 155    4.291   1.358 101.350 1.00 26.84    C
ATOM   2444  CZ  PHE B 155    4.996   0.200 101.679 1.00 26.33    C
ATOM   2445  N   MET B 156    0.149   0.342 104.343 1.00 25.15    N
ATOM   2446  CA  MET B 156    0.279   1.281 105.448 1.00 25.67    C
ATOM   2447  C   MET B 156   -0.818   2.343 105.487 1.00 25.77    C
ATOM   2448  O   MET B 156   -0.538   3.545 105.470 1.00 24.32    O
ATOM   2449  CB  MET B 156    1.647   1.961 105.385 1.00 26.82    C
ATOM   2450  CG  MET B 156    2.817   1.019 105.629 1.00 28.39    C
ATOM   2451  SD  MET B 156    4.430   1.843 105.481 1.00 32.72    S
ATOM   2452  CE  MET B 156    5.482   0.656 106.223 1.00 30.63    C
ATOM   2453  N   TRP B 157   -2.064   1.881 105.550 1.00 25.51    N
ATOM   2454  CA  TRP B 157   -3.226   2.756 105.595 1.00 25.32    C
ATOM   2455  C   TRP B 157   -3.266   3.612 106.857 1.00 26.75    C
ATOM   2456  O   TRP B 157   -3.969   4.615 106.897 1.00 26.48    O
ATOM   2457  CB  TRP B 157   -4.509   1.928 105.526 1.00 24.55    C
ATOM   2458  CG  TRP B 157   -4.661   0.949 106.659 1.00 23.68    C
ATOM   2459  CD1 TRP B 157   -4.102  -0.301 106.753 1.00 22.81    C
ATOM   2460  CD2 TRP B 157   -5.454   1.124 107.840 1.00 23.50    C
ATOM   2461  NE1 TRP B 157   -4.504  -0.910 107.917 1.00 23.45    N
ATOM   2462  CE2 TRP B 157   -5.326  -0.060 108.607 1.00 22.56    C
ATOM   2463  CE3 TRP B 157   -6.244   2.169 108.328 1.00 23.04    C
ATOM   2464  CZ2 TRP B 157   -5.981  -0.231 109.825 1.00 22.23    C
ATOM   2465  CZ3 TRP B 157   -6.897   1.998 109.545 1.00 22.69    C
ATOM   2466  CH2 TRP B 157   -6.753   0.816 110.282 1.00 23.45    C
ATOM   2467  N   GLU B 158   -2.527   3.208 107.890 1.00 28.38    N
ATOM   2468  CA  GLU B 158   -2.495   3.964 109.140 1.00 28.90    C
ATOM   2469  C   GLU B 158   -1.742   5.296 109.002 1.00 30.21    C
ATOM   2470  O   GLU B 158   -2.019   6.249 109.731 1.00 29.61    O
ATOM   2471  CB  GLU B 158   -1.844   3.138 110.252 1.00 28.21    C
ATOM   2472  CG  GLU B 158   -2.660   1.967 110.739 1.00 26.97    C
ATOM   2473  CD  GLU B 158   -1.913   1.129 111.762 1.00 27.15    C
ATOM   2474  OE1 GLU B 158   -1.570   1.647 112.847 1.00 26.39    O
ATOM   2475  OE2 GLU B 158   -1.670  -0.059 111.469 1.00 27.94    O
ATOM   2476  N   GLU B 159   -0.785   5.356 108.084 1.00 31.94    N
ATOM   2477  CA  GLU B 159   -0.026   6.587 107.881 1.00 35.28    C
ATOM   2478  C   GLU B 159   -0.906   7.689 107.330 1.00 36.39    C
ATOM   2479  O   GLU B 159   -1.585   7.505 106.321 1.00 36.78    O
ATOM   2480  CB  GLU B 159    1.124   6.387 106.895 1.00 36.81    C
ATOM   2481  CG  GLU B 159    2.395   5.837 107.489 1.00 41.62    C
ATOM   2482  CD  GLU B 159    3.523   5.751 106.476 1.00 45.62    C
ATOM   2483  OE1 GLU B 159    4.046   6.811 106.049 1.00 46.78    O
ATOM   2484  OE2 GLU B 159    3.885   4.615 106.095 1.00 47.98    O
ATOM   2485  N   PRO B 160   -0.904   8.860 107.980 1.00 37.22    N
ATOM   2486  CA  PRO B 160   -1.722   9.978 107.504 1.00 37.55    C
ATOM   2487  C   PRO B 160   -1.232  10.455 106.136 1.00 37.63    C
ATOM   2488  O   PRO B 160   -2.003  11.000 105.344 1.00 37.49    O
ATOM   2489  CB  PRO B 160   -1.544  11.022 108.610 1.00 37.77    C
ATOM   2490  CG  PRO B 160   -0.177  10.733 109.125 1.00 38.32    C
ATOM   2491  CD  PRO B 160   -0.165   9.231 109.198 1.00 37.29    C
ATOM   2492  N   GLU B 161    0.055  10.225 105.865 1.00 38.14    N
ATOM   2493  CA  GLU B 161    0.661  10.604 104.590 1.00 37.35    C
ATOM   2494  C   GLU B 161    0.106   9.710 103.491 1.00 35.52    C
ATOM   2495  O   GLU B 161   -0.111  10.158 102.375 1.00 35.44    O
ATOM   2496  CB  GLU B 161    2.188  10.468 104.645 1.00 39.10    C
ATOM   2497  CG  GLU B 161    2.863  11.330 105.709 1.00 42.24    C
ATOM   2498  CD  GLU B 161    2.934  10.651 107.068 1.00 45.01    C
ATOM   2499  OE1 GLU B 161    2.352   9.554 107.221 1.00 46.39    O
ATOM   2500  OE2 GLU B 161    3.571  11.215 107.990 1.00 47.20    O
ATOM   2501  N   ILE B 162   -0.116   8.443 103.812 1.00 34.28    N
ATOM   2502  CA  ILE B 162   -0.659   7.491 102.860 1.00 33.22    C
ATOM   2503  C   ILE B 162   -2.136   7.803 102.578 1.00 32.21    C
ATOM   2504  O   ILE B 162   -2.602   7.734 101.439 1.00 32.19    O
ATOM   2505  CB  ILE B 162   -0.543   6.054 103.409 1.00 33.32    C
ATOM   2506  CG1 ILE B 162    0.927   5.654 103.502 1.00 33.19    C
ATOM   2507  CG2 ILE B 162   -1.310   5.089 102.535 1.00 33.61    C
ATOM   2508  CD1 ILE B 162    1.615   5.598 102.168 1.00 32.61    C
ATOM   2509  N   GLN B 163   -2.877   8.149 103.621 1.00 31.22    N
ATOM   2510  CA  GLN B 163   -4.282   8.457 103.445 1.00 30.19    C
ATOM   2511  C   GLN B 163   -4.427   9.673 102.537 1.00 30.24    C
ATOM   2512  O   GLN B 163   -5.408   9.797 101.805 1.00 29.02    O
ATOM   2513  CB  GLN B 163   -4.965   8.735 104.782 1.00 28.72    C
ATOM   2514  CG  GLN B 163   -4.764   7.652 105.830 1.00 29.23    C
ATOM   2515  CD  GLN B 163   -5.767   7.735 106.978 1.00 30.35    C
ATOM   2516  OE1 GLN B 163   -5.583   7.108 108.020 1.00 29.29    O
ATOM   2517  NE2 GLN B 163   -6.843   8.501 106.782 1.00 30.60    N
ATOM   2518  N   ALA B 164   -3.442  10.564 102.594 1.00 30.02    N
ATOM   2519  CA  ALA B 164   -3.442  11.772 101.777 1.00 29.62    C
ATOM   2520  C   ALA B 164   -3.206  11.430 100.315 1.00 29.76    C
ATOM   2521  O   ALA B 164   -3.779  12.049  99.422 1.00 29.19    O
```

FIG. 9 (con't)

```
ATOM 1760 CA  THR B 68    8.581  -5.792 92.092 1.00 21.28   C
ATOM 1761 C   THR B 68    7.728  -6.843 91.413 1.00 19.26   C
ATOM 1762 O   THR B 68    8.221  -7.894 91.008 1.00 18.73   O
ATOM 1763 CB  THR B 68    9.043  -4.750 91.044 1.00 23.67   C
ATOM 1764 OG1 THR B 68    8.885  -3.436 91.599 1.00 27.35   O
ATOM 1765 CG2 THR B 68    8.248  -4.851 89.756 1.00 24.64   C
ATOM 1766 N   PHE B 69    6.433  -6.563 91.313 1.00 19.46   N
ATOM 1767 CA  PHE B 69    5.505  -7.474 90.645 1.00 18.31   C
ATOM 1768 C   PHE B 69    4.191  -6.736 90.357 1.00 16.79   C
ATOM 1769 O   PHE B 69    3.571  -6.205 91.260 1.00 16.15   O
ATOM 1770 CB  PHE B 69    5.241  -8.716 91.493 1.00 17.28   C
ATOM 1771 CG  PHE B 69    4.606  -9.849 90.723 1.00 17.46   C
ATOM 1772 CD1 PHE B 69    5.388 -10.852 90.146 1.00 19.90   C
ATOM 1773 CD2 PHE B 69    3.231  -9.883 90.527 1.00 18.31   C
ATOM 1774 CE1 PHE B 69    4.805 -11.879 89.369 1.00 22.06   C
ATOM 1775 CE2 PHE B 69    2.634 -10.898 89.757 1.00 21.88   C
ATOM 1776 CZ  PHE B 69    3.427 -11.897 89.175 1.00 22.21   C
ATOM 1777 N   LEU B 70    3.767  -6.718 89.088 1.00 16.55   N
ATOM 1778 CA  LEU B 70    2.538  -6.036 88.733 1.00 15.10   C
ATOM 1779 C   LEU B 70    1.833  -6.652 87.532 1.00 16.49   C
ATOM 1780 O   LEU B 70    2.472  -6.932 86.508 1.00 15.21   O
ATOM 1781 CB  LEU B 70    2.831  -4.563 88.451 1.00 15.47   C
ATOM 1782 CG  LEU B 70    1.660  -3.602 88.247 1.00 17.39   C
ATOM 1783 CD1 LEU B 70    2.093  -2.184 88.562 1.00 19.71   C
ATOM 1784 CD2 LEU B 70    1.181  -3.688 86.818 1.00 16.56   C
ATOM 1785 N   CYS B 71    0.521  -6.886 87.661 1.00 16.69   N
ATOM 1786 CA  CYS B 71   -0.301  -7.417 86.567 1.00 17.53   C
ATOM 1787 C   CYS B 71   -1.159  -6.278 85.981 1.00 18.34   C
ATOM 1788 O   CYS B 71   -1.671  -5.415 86.704 1.00 18.50   O
ATOM 1789 CB  CYS B 71   -1.224  -8.543 87.047 1.00 18.69   C
ATOM 1790 SG  CYS B 71   -0.411 -10.128 87.416 1.00 20.26   S
ATOM 1791 N   TYR B 72   -1.350  -6.283 84.671 1.00 18.23   N
ATOM 1792 CA  TYR B 72   -2.113  -5.213 84.073 1.00 18.50   C
ATOM 1793 C   TYR B 72   -2.944  -5.650 82.883 1.00 19.73   C
ATOM 1794 O   TYR B 72   -2.817  -6.772 82.388 1.00 20.04   O
ATOM 1795 CB  TYR B 72   -1.176  -4.073 83.665 1.00 15.86   C
ATOM 1796 CG  TYR B 72   -0.206  -4.440 82.567 1.00 15.74   C
ATOM 1797 CD1 TYR B 72   -0.592  -4.407 81.223 1.00 17.04   C
ATOM 1798 CD2 TYR B 72    1.086  -4.850 82.861 1.00 12.50   C
ATOM 1799 CE1 TYR B 72    0.298  -4.776 80.212 1.00 15.53   C
ATOM 1800 CE2 TYR B 72    1.969  -5.216 81.866 1.00 12.74   C
ATOM 1801 CZ  TYR B 72    1.573  -5.174 80.547 1.00 13.77   C
ATOM 1802 OH  TYR B 72    2.490  -5.498 79.572 1.00 16.57   O
ATOM 1803 N   VAL B 73   -3.798  -4.739 82.432 1.00 19.50   N
ATOM 1804 CA  VAL B 73   -4.666  -4.967 81.300 1.00 19.35   C
ATOM 1805 C   VAL B 73   -4.850  -3.616 80.628 1.00 20.74   C
ATOM 1806 O   VAL B 73   -5.144  -2.627 81.294 1.00 20.41   O
ATOM 1807 CB  VAL B 73   -6.056  -5.510 81.731 1.00 19.58   C
ATOM 1808 CG1 VAL B 73   -7.004  -5.562 80.545 1.00 17.68   C
ATOM 1809 CG2 VAL B 73   -5.919  -6.906 82.305 1.00 19.65   C
ATOM 1810 N   VAL B 74   -4.657  -3.578 79.310 1.00 21.21   N
ATOM 1811 CA  VAL B 74   -4.824  -2.352 78.542 1.00 22.37   C
ATOM 1812 C   VAL B 74   -5.949  -2.488 77.491 1.00 24.19   C
ATOM 1813 O   VAL B 74   -6.021  -3.481 76.770 1.00 24.68   O
ATOM 1814 CB  VAL B 74   -3.515  -1.963 77.827 1.00 21.61   C
ATOM 1815 CG1 VAL B 74   -3.688  -0.666 77.105 1.00 20.37   C
ATOM 1816 CG2 VAL B 74   -2.399  -1.820 78.823 1.00 20.61   C
ATOM 1817 N   GLU B 75   -6.823  -1.483 77.428 1.00 26.60   N
ATOM 1818 CA  GLU B 75   -7.941  -1.449 76.477 1.00 29.66   C
ATOM 1819 C   GLU B 75   -7.975  -0.038 75.876 1.00 30.33   C
ATOM 1820 O   GLU B 75   -8.263   0.917 76.586 1.00 32.01   O
ATOM 1821 CB  GLU B 75   -9.260  -1.722 77.185 1.00 30.43   C
ATOM 1822 CG  GLU B 75   -9.271  -2.982 78.045 1.00 35.94   C
ATOM 1823 CD  GLU B 75   -9.778  -4.207 77.313 1.00 39.42   C
ATOM 1824 OE1 GLU B 75  -10.808  -4.085 76.601 1.00 43.71   O
ATOM 1825 OE2 GLU B 75   -9.177  -5.298 77.444 1.00 39.81   O
ATOM 1826 N   ALA B 76   -7.698   0.091 74.583 1.00 30.93   N
ATOM 1827 CA  ALA B 76   -7.680   1.392 73.946 1.00 33.80   C
ATOM 1828 C   ALA B 76   -8.639   1.461 72.771 1.00 36.71   C
ATOM 1829 O   ALA B 76   -8.558   0.654 71.844 1.00 37.57   O
ATOM 1830 CB  ALA B 76   -6.266   1.745 73.481 1.00 33.29   C
ATOM 1831 N   GLN B 77   -9.548   2.428 72.816 1.00 39.33   N
ATOM 1832 CA  GLN B 77  -10.516   2.628 71.762 1.00 41.16   C
ATOM 1833 C   GLN B 77  -10.319   4.010 71.166 1.00 42.83   C
ATOM 1834 O   GLN B 77  -10.333   5.015 71.875 1.00 41.75   O
ATOM 1835 CB  GLN B 77  -11.925   2.478 72.316 1.00 42.02   C
ATOM 1836 CG  GLN B 77  -12.197   1.082 72.832 1.00 45.11   C
ATOM 1837 CD  GLN B 77  -13.652   0.683 72.699 1.00 47.38   C
ATOM 1838 OE1 GLN B 77  -14.497   1.104 73.491 1.00 49.70   O
ATOM 1839 NE2 GLN B 77  -13.959  -0.123 71.681 1.00 46.60   N
ATOM 1840 N   GLY B 78  -10.133   4.051 69.851 1.00 45.23   N
ATOM 1841 CA  GLY B 78   -9.908   5.313 69.178 1.00 47.78   C
ATOM 1842 C   GLY B 78  -10.999   5.738 68.221 1.00 49.77   C
ATOM 1843 O   GLY B 78  -10.715   6.192 67.110 1.00 51.48   O
ATOM 1844 N   LYS B 79  -12.246   5.582 68.640 1.00 50.31   N
ATOM 1845 CA  LYS B 79  -13.388   5.987 67.829 1.00 50.85   C

ATOM 2522 CB  ALA B 164   -2.366 12.711 102.246 1.00 29.66   C
ATOM 2523 N   ALA B 165   -2.344 10.451 100.076 1.00 30.25   N
ATOM 2524 CA  ALA B 165   -2.041 10.045  98.715 1.00 30.76   C
ATOM 2525 C   ALA B 165   -3.265  9.401  98.080 1.00 30.90   C
ATOM 2526 O   ALA B 165   -3.663  9.768  96.981 1.00 30.01   O
ATOM 2527 CB  ALA B 165   -0.876  9.074  98.708 1.00 30.96   C
ATOM 2528 N   LEU B 166   -3.861  8.442  98.783 1.00 31.51   N
ATOM 2529 CA  LEU B 166   -5.041  7.767  98.270 1.00 33.05   C
ATOM 2530 C   LEU B 166   -6.121  8.768  97.861 1.00 34.58   C
ATOM 2531 O   LEU B 166   -6.714  8.648  96.789 1.00 34.70   O
ATOM 2532 CB  LEU B 166   -5.606  6.804  99.312 1.00 32.37   C
ATOM 2533 CG  LEU B 166   -4.771  5.555  99.598 1.00 32.84   C
ATOM 2534 CD1 LEU B 166   -5.451  4.689 100.640 1.00 33.14   C
ATOM 2535 CD2 LEU B 166   -4.602  4.785  98.316 1.00 32.37   C
ATOM 2536 N   LYS B 167   -6.369  9.760  98.719 1.00 35.76   N
ATOM 2537 CA  LYS B 167   -7.384 10.775  98.449 1.00 34.98   C
ATOM 2538 C   LYS B 167   -6.980 11.603  97.244 1.00 34.26   C
ATOM 2539 O   LYS B 167   -7.795 11.859  96.365 1.00 34.25   O
ATOM 2540 CB  LYS B 167   -7.593 11.688  99.654 1.00 35.97   C
ATOM 2541 CG  LYS B 167   -8.142 10.985 100.880 1.00 38.58   C
ATOM 2542 CD  LYS B 167   -8.372 11.955 102.030 1.00 39.92   C
ATOM 2543 CE  LYS B 167   -8.142 11.268 103.367 1.00 41.16   C
ATOM 2544 NZ  LYS B 167   -8.204 12.216 104.506 1.00 43.44   N
ATOM 2545 N   LYS B 168   -5.732 12.035  97.189 1.00 33.17   N
ATOM 2546 CA  LYS B 168   -5.300 12.825  96.049 1.00 33.56   C
ATOM 2547 C   LYS B 168   -5.328 11.995  94.761 1.00 32.49   C
ATOM 2548 O   LYS B 168   -5.523 12.533  93.666 1.00 32.99   O
ATOM 2549 CB  LYS B 168   -3.890 13.371  96.280 1.00 34.72   C
ATOM 2550 CG  LYS B 168   -3.836 14.529  97.258 1.00 36.85   C
ATOM 2551 CD  LYS B 168   -2.406 14.848  97.678 1.00 39.47   C
ATOM 2552 CE  LYS B 168   -2.391 15.952  98.731 1.00 40.85   C
ATOM 2553 NZ  LYS B 168   -1.052 16.123  99.360 1.00 43.44   N
ATOM 2554 N   LEU B 169   -5.134 10.687  94.899 1.00 30.29   N
ATOM 2555 CA  LEU B 169   -5.143  9.780  93.763 1.00 27.71   C
ATOM 2556 C   LEU B 169   -6.557  9.771  93.183 1.00 26.16   C
ATOM 2557 O   LEU B 169   -6.730  9.781  91.969 1.00 25.12   O
ATOM 2558 CB  LEU B 169   -4.735  8.372  94.198 1.00 28.13   C
ATOM 2559 CG  LEU B 169   -3.870  7.573  93.222 1.00 27.91   C
ATOM 2560 CD1 LEU B 169   -2.564  8.286  92.987 1.00 28.10   C
ATOM 2561 CD2 LEU B 169   -3.594  6.203  93.794 1.00 28.49   C
ATOM 2562 N   LYS B 170   -7.557  9.756  94.058 1.00 24.78   N
ATOM 2563 CA  LYS B 170   -8.947  9.784  93.630 1.00 24.87   C
ATOM 2564 C   LYS B 170   -9.275 11.138  93.005 1.00 26.04   C
ATOM 2565 O   LYS B 170  -10.122 11.232  92.122 1.00 25.01   O
ATOM 2566 CB  LYS B 170   -9.884  9.548  94.805 1.00 24.63   C
ATOM 2567 CG  LYS B 170  -11.340  9.808  94.494 1.00 22.59   C
ATOM 2568 CD  LYS B 170  -12.205  9.556  95.717 1.00 21.73   C
ATOM 2569 CE  LYS B 170  -13.649  9.955  95.456 1.00 22.54   C
ATOM 2570 NZ  LYS B 170  -14.600  9.349  96.430 1.00 25.72   N
ATOM 2571 N   GLU B 171   -8.618 12.188  93.505 1.00 27.99   N
ATOM 2572 CA  GLU B 171   -8.786 13.548  92.993 1.00 27.48   C
ATOM 2573 C   GLU B 171   -8.338 13.582  91.529 1.00 26.08   C
ATOM 2574 O   GLU B 171   -8.991 14.192  90.686 1.00 24.94   O
ATOM 2575 CB  GLU B 171   -7.927 14.536  93.785 1.00 30.21   C
ATOM 2576 CG  GLU B 171   -8.189 14.592  95.286 1.00 34.50   C
ATOM 2577 CD  GLU B 171   -9.619 14.957  95.622 1.00 38.27   C
ATOM 2578 OE1 GLU B 171  -10.282 15.601  94.772 1.00 38.88   O
ATOM 2579 OE2 GLU B 171  -10.074 14.612  96.740 1.00 38.33   O
ATOM 2580 N   ALA B 172   -7.207 12.934  91.244 1.00 24.56   N
ATOM 2581 CA  ALA B 172   -6.653 12.889  89.890 1.00 23.01   C
ATOM 2582 C   ALA B 172   -7.522 12.075  88.933 1.00 22.36   C
ATOM 2583 O   ALA B 172   -7.236 11.996  87.737 1.00 22.84   O
ATOM 2584 CB  ALA B 172   -5.245 12.325  89.922 1.00 21.63   C
ATOM 2585 N   GLY B 173   -8.576 11.466  89.470 1.00 21.96   N
ATOM 2586 CA  GLY B 173   -9.486 10.680  88.660 1.00 22.00   C
ATOM 2587 C   GLY B 173   -9.176  9.197  88.624 1.00 22.85   C
ATOM 2588 O   GLY B 173   -9.741  8.452  87.818 1.00 24.08   O
ATOM 2589 N   CYS B 174   -8.280  8.760  89.501 1.00 21.81   N
ATOM 2590 CA  CYS B 174   -7.887  7.364  89.566 1.00 20.51   C
ATOM 2591 C   CYS B 174   -8.872  6.566  90.396 1.00 20.55   C
ATOM 2592 O   CYS B 174   -9.296  7.006  91.467 1.00 20.68   O
ATOM 2593 CB  CYS B 174   -6.486  7.246  90.168 1.00 19.92   C
ATOM 2594 SG  CYS B 174   -5.858  5.557  90.295 1.00 18.22   S
ATOM 2595 N   LYS B 175   -9.243  5.394  89.904 1.00 20.69   N
ATOM 2596 CA  LYS B 175  -10.186  4.550  90.627 1.00 22.91   C
ATOM 2597 C   LYS B 175   -9.448  3.489  91.420 1.00 22.03   C
ATOM 2598 O   LYS B 175   -8.685  2.704  90.861 1.00 23.44   O
ATOM 2599 CB  LYS B 175  -11.158  3.877  89.646 1.00 25.46   C
ATOM 2600 CG  LYS B 175  -12.175  4.811  88.973 1.00 30.51   C
ATOM 2601 CD  LYS B 175  -13.176  5.364  89.978 1.00 33.81   C
ATOM 2602 CE  LYS B 175  -14.317  6.106  89.302 1.00 36.20   C
ATOM 2603 NZ  LYS B 175  -15.331  6.520  90.317 1.00 38.39   N
ATOM 2604 N   LEU B 176   -9.669  3.463  92.724 1.00 21.01   N
ATOM 2605 CA  LEU B 176   -9.018  2.469  93.575 1.00 20.17   C
ATOM 2606 C   LEU B 176  -10.038  1.497  94.162 1.00 20.32   C
ATOM 2607 O   LEU B 176  -11.115  1.919  94.579 1.00 20.75   O
```

FIG. 9 (con't)

```
ATOM  1846  C   LYS B  79   -13.117   6.011  66.320  1.00 49.98   C
ATOM  1847  O   LYS B  79   -12.771   7.050  65.754  1.00 49.90   O
ATOM  1848  CB  LYS B  79   -13.867   7.382  68.279  1.00 52.65   C
ATOM  1849  CG  LYS B  79   -13.036   8.044  69.399  1.00 53.98   C
ATOM  1850  CD  LYS B  79   -13.355   7.452  70.773  1.00 54.06   C
ATOM  1851  CE  LYS B  79   -12.190   7.595  71.752  1.00 54.11   C
ATOM  1852  NZ  LYS B  79   -11.762   9.005  71.973  1.00 53.73   N
ATOM  1853  N   GLY B  80   -13.277   4.868  65.666  1.00 49.05   N
ATOM  1854  CA  GLY B  80   -13.056   4.812  64.231  1.00 45.78   C
ATOM  1855  C   GLY B  80   -12.654   3.417  63.804  1.00 44.57   C
ATOM  1856  O   GLY B  80   -11.958   3.248  62.808  1.00 43.84   O
ATOM  1857  N   GLY B  81   -13.109   2.419  64.557  1.00 43.43   N
ATOM  1858  CA  GLY B  81   -12.767   1.044  64.257  1.00 41.67   C
ATOM  1859  C   GLY B  81   -11.477   0.587  64.939  1.00 40.48   C
ATOM  1860  O   GLY B  81   -11.248  -0.612  65.102  1.00 40.35   O
ATOM  1861  N   GLN B  82   -10.643   1.545  65.343  1.00 38.32   N
ATOM  1862  CA  GLN B  82    -9.369   1.247  65.988  1.00 37.07   C
ATOM  1863  C   GLN B  82    -9.536   0.827  67.442  1.00 34.54   C
ATOM  1864  O   GLN B  82    -9.903   1.626  68.299  1.00 32.52   O
ATOM  1865  CB  GLN B  82    -8.425   2.440  65.884  1.00 38.26   C
ATOM  1866  CG  GLN B  82    -9.085   3.770  66.137  1.00 42.25   C
ATOM  1867  CD  GLN B  82    -8.311   4.913  65.518  1.00 45.54   C
ATOM  1868  OE1 GLN B  82    -7.092   5.010  65.674  1.00 46.80   O
ATOM  1869  NE2 GLN B  82    -9.018   5.792  64.812  1.00 47.43   N
ATOM  1870  N   VAL B  83    -9.271  -0.453  67.691  1.00 31.57   N
ATOM  1871  CA  VAL B  83    -9.386  -1.036  69.010  1.00 29.10   C
ATOM  1872  C   VAL B  83    -8.035  -1.629  69.423  1.00 27.71   C
ATOM  1873  O   VAL B  83    -7.285  -2.104  68.580  1.00 26.66   O
ATOM  1874  CB  VAL B  83   -10.441  -2.146  69.021  1.00 28.90   C
ATOM  1875  CG1 VAL B  83   -10.574  -2.726  70.407  1.00 28.59   C
ATOM  1876  CG2 VAL B  83   -11.773  -1.597  68.539  1.00 30.37   C
ATOM  1877  N   GLN B  84    -7.730  -1.605  70.718  1.00 26.59   N
ATOM  1878  CA  GLN B  84    -6.462  -2.137  71.198  1.00 24.94   C
ATOM  1879  C   GLN B  84    -6.683  -2.831  72.526  1.00 24.72   C
ATOM  1880  O   GLN B  84    -7.332  -2.278  73.410  1.00 25.50   O
ATOM  1881  CB  GLN B  84    -5.483  -0.997  71.371  1.00 25.06   C
ATOM  1882  CG  GLN B  84    -4.109  -1.289  70.897  1.00 25.16   C
ATOM  1883  CD  GLN B  84    -3.364  -0.019  70.592  1.00 26.22   C
ATOM  1884  OE1 GLN B  84    -3.681   0.686  69.632  1.00 25.01   O
ATOM  1885  NE2 GLN B  84    -2.374   0.296  71.416  1.00 28.41   N
ATOM  1886  N   ALA B  85    -6.151  -4.036  72.689  1.00 23.24   N
ATOM  1887  CA  ALA B  85    -6.335  -4.756  73.950  1.00 22.14   C
ATOM  1888  C   ALA B  85    -5.139  -5.649  74.246  1.00 21.37   C
ATOM  1889  O   ALA B  85    -4.564  -6.239  73.338  1.00 22.65   O
ATOM  1890  CB  ALA B  85    -7.631  -5.583  73.896  1.00 20.00   C
ATOM  1891  N   SER B  86    -4.758  -5.749  75.512  1.00 21.18   N
ATOM  1892  CA  SER B  86    -3.630  -6.595  75.902  1.00 21.56   C
ATOM  1893  C   SER B  86    -3.618  -6.820  77.395  1.00 21.44   C
ATOM  1894  O   SER B  86    -4.322  -6.136  78.134  1.00 21.89   O
ATOM  1895  CB  SER B  86    -2.291  -5.958  75.488  1.00 21.65   C
ATOM  1896  OG  SER B  86    -2.095  -4.675  76.077  1.00 21.09   O
ATOM  1897  N   ARG B  87    -2.822  -7.786  77.835  1.00 22.70   N
ATOM  1898  CA  ARG B  87    -2.679  -8.053  79.264  1.00 24.84   C
ATOM  1899  C   ARG B  87    -1.325  -8.730  79.562  1.00 24.05   C
ATOM  1900  O   ARG B  87    -0.981  -9.742  78.959  1.00 24.65   O
ATOM  1901  CB  ARG B  87    -3.844  -8.908  79.761  1.00 26.91   C
ATOM  1902  CG  ARG B  87    -3.808 -10.333  79.289  1.00 30.39   C
ATOM  1903  CD  ARG B  87    -5.146 -11.015  79.496  1.00 35.17   C
ATOM  1904  NE  ARG B  87    -4.979 -12.451  79.694  1.00 38.13   N
ATOM  1905  CZ  ARG B  87    -5.863 -13.368  79.319  1.00 39.59   C
ATOM  1906  NH1 ARG B  87    -6.984 -13.004  78.714  1.00 40.31   N
ATOM  1907  NH2 ARG B  87    -5.628 -14.657  79.556  1.00 40.28   N
ATOM  1908  N   GLY B  88    -0.550  -8.151  80.473  1.00 22.82   N
ATOM  1909  CA  GLY B  88     0.730  -8.740  80.813  1.00 20.92   C
ATOM  1910  C   GLY B  88     1.085  -8.528  82.273  1.00 20.97   C
ATOM  1911  O   GLY B  88     0.209  -8.293  83.111  1.00 19.06   O
ATOM  1912  N   TYR B  89     2.373  -8.608  82.586  1.00 20.84   N
ATOM  1913  CA  TYR B  89     2.820  -8.397  83.953  1.00 21.58   C
ATOM  1914  C   TYR B  89     4.312  -8.055  83.996  1.00 21.11   C
ATOM  1915  O   TYR B  89     5.009  -8.215  83.004  1.00 19.77   O
ATOM  1916  CB  TYR B  89     2.543  -9.652  84.786  1.00 21.43   C
ATOM  1917  CG  TYR B  89     3.631 -10.680  84.696  1.00 21.53   C
ATOM  1918  CD1 TYR B  89     4.393 -11.007  85.816  1.00 22.29   C
ATOM  1919  CD2 TYR B  89     3.917 -11.315  83.494  1.00 21.95   C
ATOM  1920  CE1 TYR B  89     5.417 -11.945  85.747  1.00 22.65   C
ATOM  1921  CE2 TYR B  89     4.940 -12.257  83.407  1.00 23.15   C
ATOM  1922  CZ  TYR B  89     5.688 -12.571  84.545  1.00 23.51   C
ATOM  1923  OH  TYR B  89     6.683 -13.528  84.504  1.00 22.15   O
ATOM  1924  N   LEU B  90     4.772  -7.583  85.153  1.00 22.66   N
ATOM  1925  CA  LEU B  90     6.165  -7.179  85.362  1.00 23.09   C
ATOM  1926  C   LEU B  90     6.627  -7.794  86.648  1.00 23.80   C
ATOM  1927  O   LEU B  90     5.830  -7.987  87.571  1.00 23.38   O
ATOM  1928  CB  LEU B  90     6.265  -5.655  85.528  1.00 24.70   C
ATOM  1929  CG  LEU B  90     5.642  -4.797  84.436  1.00 28.23   C
ATOM  1930  CD1 LEU B  90     5.962  -3.301  84.666  1.00 27.79   C
ATOM  1931  CD2 LEU B  90     6.174  -5.305  83.074  1.00 29.19   C

ATOM  2608  CB  LEU B 176    -8.282   3.172  94.710  1.00 19.98   C
ATOM  2609  CG  LEU B 176    -7.216   4.171  94.305  1.00 21.46   C
ATOM  2610  CD1 LEU B 176    -6.848   5.022  95.507  1.00 23.30   C
ATOM  2611  CD2 LEU B 176    -6.008   3.439  93.754  1.00 21.32   C
ATOM  2612  N   ARG B 177    -9.702   0.211  94.184  1.00 19.61   N
ATOM  2613  CA  ARG B 177   -10.576  -0.824  94.759  1.00 21.31   C
ATOM  2614  C   ARG B 177    -9.799  -1.997  95.348  1.00 21.44   C
ATOM  2615  O   ARG B 177    -8.702  -2.344  94.898  1.00 21.85   O
ATOM  2616  CB  ARG B 177   -11.567  -1.368  93.732  1.00 23.36   C
ATOM  2617  CG  ARG B 177   -12.673  -0.420  93.330  1.00 26.92   C
ATOM  2618  CD  ARG B 177   -13.772  -1.189  92.581  1.00 32.18   C
ATOM  2619  NE  ARG B 177   -13.281  -1.911  91.402  1.00 36.46   N
ATOM  2620  CZ  ARG B 177   -14.028  -2.692  90.615  1.00 37.62   C
ATOM  2621  NH1 ARG B 177   -15.319  -2.867  90.871  1.00 39.00   N
ATOM  2622  NH2 ARG B 177   -13.486  -3.300  89.566  1.00 36.59   N
ATOM  2623  N   ILE B 178   -10.372  -2.618  96.362  1.00 21.30   N
ATOM  2624  CA  ILE B 178    -9.715  -3.740  96.992  1.00 20.29   C
ATOM  2625  C   ILE B 178   -10.089  -5.000  96.219  1.00 21.29   C
ATOM  2626  O   ILE B 178   -11.259  -5.242  95.935  1.00 21.66   O
ATOM  2627  CB  ILE B 178   -10.160  -3.878  98.459  1.00 18.23   C
ATOM  2628  CG1 ILE B 178   -10.068  -2.518  99.172  1.00 18.67   C
ATOM  2629  CG2 ILE B 178    -9.306  -4.899  99.150  1.00 16.05   C
ATOM  2630  CD1 ILE B 178    -8.685  -1.924  99.237  1.00 17.16   C
ATOM  2631  N   MET B 179    -9.086  -5.787  95.850  1.00 21.50   N
ATOM  2632  CA  MET B 179    -9.326  -7.020  95.133  1.00 20.80   C
ATOM  2633  C   MET B 179   -10.294  -7.916  95.897  1.00 22.36   C
ATOM  2634  O   MET B 179   -10.061  -8.252  97.061  1.00 22.01   O
ATOM  2635  CB  MET B 179    -8.008  -7.763  94.913  1.00 20.69   C
ATOM  2636  CG  MET B 179    -7.030  -7.034  94.001  1.00 20.79   C
ATOM  2637  SD  MET B 179    -5.491  -7.940  93.683  1.00 18.15   S
ATOM  2638  CE  MET B 179    -6.095  -9.300  92.817  1.00 20.76   C
ATOM  2639  N   LYS B 180   -11.392  -8.291  95.237  1.00 23.35   N
ATOM  2640  CA  LYS B 180   -12.392  -9.188  95.818  1.00 23.33   C
ATOM  2641  C   LYS B 180   -11.916 -10.629  95.575  1.00 22.45   C
ATOM  2642  O   LYS B 180   -11.054 -10.871  94.735  1.00 22.57   O
ATOM  2643  CB  LYS B 180   -13.743  -8.973  95.130  1.00 25.72   C
ATOM  2644  CG  LYS B 180   -14.116  -7.509  94.934  1.00 28.31   C
ATOM  2645  CD  LYS B 180   -15.589  -7.338  94.600  1.00 26.92   C
ATOM  2646  CE  LYS B 180   -15.918  -7.864  93.214  1.00 28.09   C
ATOM  2647  NZ  LYS B 180   -15.387  -6.995  92.122  1.00 28.03   N
ATOM  2648  N   PRO B 181   -12.464 -11.599  96.310  1.00 22.63   N
ATOM  2649  CA  PRO B 181   -12.048 -12.997  96.112  1.00 22.85   C
ATOM  2650  C   PRO B 181   -12.092 -13.411  94.630  1.00 23.80   C
ATOM  2651  O   PRO B 181   -11.226 -14.155  94.139  1.00 23.89   O
ATOM  2652  CB  PRO B 181   -13.037 -13.762  96.985  1.00 23.10   C
ATOM  2653  CG  PRO B 181   -13.225 -12.798  98.159  1.00 21.37   C
ATOM  2654  CD  PRO B 181   -13.377 -11.464  97.463  1.00 21.27   C
ATOM  2655  N   GLN B 182   -13.092 -12.913  93.909  1.00 24.02   N
ATOM  2656  CA  GLN B 182   -13.245 -13.201  92.485  1.00 23.93   C
ATOM  2657  C   GLN B 182   -12.048 -12.671  91.681  1.00 23.19   C
ATOM  2658  O   GLN B 182   -11.661 -13.250  90.660  1.00 24.42   O
ATOM  2659  CB  GLN B 182   -14.536 -12.561  91.953  1.00 26.36   C
ATOM  2660  CG  GLN B 182   -15.850 -13.123  92.516  1.00 30.15   C
ATOM  2661  CD  GLN B 182   -16.011 -12.948  94.029  1.00 33.78   C
ATOM  2662  OE1 GLN B 182   -15.879 -11.842  94.566  1.00 35.01   O
ATOM  2663  NE2 GLN B 182   -16.318 -14.043  94.719  1.00 35.02   N
ATOM  2664  N   ASP B 183   -11.468 -11.566  92.138  1.00 20.73   N
ATOM  2665  CA  ASP B 183   -10.324 -10.946  91.477  1.00 19.23   C
ATOM  2666  C   ASP B 183    -9.083 -11.845  91.517  1.00 19.89   C
ATOM  2667  O   ASP B 183    -8.400 -12.028  90.504  1.00 18.48   O
ATOM  2668  CB  ASP B 183   -10.028  -9.589  92.137  1.00 18.49   C
ATOM  2669  CG  ASP B 183   -11.128  -8.566  91.880  1.00 17.42   C
ATOM  2670  OD1 ASP B 183   -11.559  -7.868  92.831  1.00 15.93   O
ATOM  2671  OD2 ASP B 183   -11.559  -8.463  90.716  1.00 15.46   O
ATOM  2672  N   PHE B 184    -8.792 -12.413  92.679  1.00 20.46   N
ATOM  2673  CA  PHE B 184    -7.637 -13.291  92.794  1.00 23.62   C
ATOM  2674  C   PHE B 184    -7.782 -14.488  91.848  1.00 24.67   C
ATOM  2675  O   PHE B 184    -6.808 -14.945  91.251  1.00 24.85   O
ATOM  2676  CB  PHE B 184    -7.469 -13.796  94.242  1.00 23.00   C
ATOM  2677  CG  PHE B 184    -7.009 -12.730  95.210  1.00 22.04   C
ATOM  2678  CD1 PHE B 184    -7.937 -11.890  95.835  1.00 20.18   C
ATOM  2679  CD2 PHE B 184    -5.643 -12.549  95.479  1.00 21.35   C
ATOM  2680  CE1 PHE B 184    -7.525 -10.886  96.714  1.00 19.54   C
ATOM  2681  CE2 PHE B 184    -5.210 -11.546  96.361  1.00 20.02   C
ATOM  2682  CZ  PHE B 184    -6.156 -10.710  96.983  1.00 20.43   C
ATOM  2683  N   GLU B 185    -9.007 -14.981  91.719  1.00 25.70   N
ATOM  2684  CA  GLU B 185    -9.287 -16.099  90.847  1.00 25.87   C
ATOM  2685  C   GLU B 185    -9.147 -15.646  89.406  1.00 24.28   C
ATOM  2686  O   GLU B 185    -8.745 -16.411  88.542  1.00 24.15   O
ATOM  2687  CB  GLU B 185   -10.717 -16.599  91.081  1.00 28.62   C
ATOM  2688  CG  GLU B 185   -11.116 -17.762  90.193  1.00 32.44   C
ATOM  2689  CD  GLU B 185   -12.590 -18.114  90.312  1.00 35.88   C
ATOM  2690  OE1 GLU B 185   -13.433 -17.210  90.113  1.00 38.50   O
ATOM  2691  OE2 GLU B 185   -12.921 -19.288  90.588  1.00 37.99   O
ATOM  2692  N   TYR B 186    -9.483 -14.397  89.142  1.00 23.63   N
ATOM  2693  CA  TYR B 186    -9.366 -13.888  87.786  1.00 23.72   C
```

FIG. 9 (con't)

```
ATOM   1932  N   GLU B  91      7.917  -8.083  86.723  1.00 23.69      N
ATOM   1933  CA  GLU B  91      8.488  -8.646  87.927  1.00 23.61      C
ATOM   1934  C   GLU B  91     10.015  -8.494  87.922  1.00 23.57      C
ATOM   1935  O   GLU B  91     10.676  -8.689  86.900  1.00 21.44      O
ATOM   1936  CB  GLU B  91      8.088 -10.112  88.068  1.00 22.96      C
ATOM   1937  CG  GLU B  91      8.812 -11.055  87.143  1.00 26.61      C
ATOM   1938  CD  GLU B  91      8.754 -12.507  87.621  1.00 29.03      C
ATOM   1939  OE1 GLU B  91      9.308 -12.815  88.698  1.00 30.15      O
ATOM   1940  OE2 GLU B  91      8.151 -13.350  86.921  1.00 30.07      O
ATOM   1941  N   ASP B  92     10.554  -8.113  89.073  1.00 23.55      N
ATOM   1942  CA  ASP B  92     11.984  -7.930  89.225  1.00 25.71      C
ATOM   1943  C   ASP B  92     12.314  -8.240  90.680  1.00 27.32      C
ATOM   1944  O   ASP B  92     11.456  -8.098  91.556  1.00 27.13      O
ATOM   1945  CB  ASP B  92     12.373  -6.486  88.892  1.00 24.87      C
ATOM   1946  CG  ASP B  92     13.839  -6.333  88.612  1.00 24.80      C
ATOM   1947  OD1 ASP B  92     14.615  -7.194  89.085  1.00 27.35      O
ATOM   1948  OD2 ASP B  92     14.225  -5.356  87.928  1.00 23.80      O
ATOM   1949  N   GLU B  93     13.545  -8.673  90.934  1.00 29.32      N
ATOM   1950  CA  GLU B  93     13.983  -9.002  92.292  1.00 31.14      C
ATOM   1951  C   GLU B  93     15.003  -7.962  92.783  1.00 31.81      C
ATOM   1952  O   GLU B  93     15.283  -7.862  93.980  1.00 32.87      O
ATOM   1953  CB  GLU B  93     14.593 -10.404  92.304  1.00 32.68      C
ATOM   1954  CG  GLU B  93     14.796 -10.987  93.695  1.00 35.81      C
ATOM   1955  CD  GLU B  93     13.495 -11.115  94.463  1.00 37.16      C
ATOM   1956  OE1 GLU B  93     12.509 -11.587  93.861  1.00 37.11      O
ATOM   1957  OE2 GLU B  93     13.468 -10.757  95.666  1.00 36.62      O
ATOM   1958  N   HIS B  94     15.545  -7.183  91.852  1.00 31.80      N
ATOM   1959  CA  HIS B  94     16.513  -6.160  92.191  1.00 32.24      C
ATOM   1960  C   HIS B  94     16.165  -4.858  91.476  1.00 31.69      C
ATOM   1961  O   HIS B  94     17.043  -4.132  91.021  1.00 32.87      O
ATOM   1962  CB  HIS B  94     17.916  -6.628  91.795  1.00 32.09      C
ATOM   1963  CG  HIS B  94     18.269  -7.978  92.335  1.00 33.63      C
ATOM   1964  ND1 HIS B  94     18.398  -8.229  93.686  1.00 34.75      N
ATOM   1965  CD2 HIS B  94     18.506  -9.152  91.708  1.00 34.17      C
ATOM   1966  CE1 HIS B  94     18.704  -9.501  93.865  1.00 34.41      C
ATOM   1967  NE2 HIS B  94     18.776 -10.088  92.684  1.00 33.98      N
ATOM   1968  N   ALA B  95     14.879  -4.568  91.374  1.00 31.25      N
ATOM   1969  CA  ALA B  95     14.448  -3.344  90.702  1.00 30.66      C
ATOM   1970  C   ALA B  95     14.876  -2.081  91.465  1.00 29.97      C
ATOM   1971  O   ALA B  95     14.831  -2.022  92.696  1.00 30.16      O
ATOM   1972  CB  ALA B  95     12.927  -3.362  90.500  1.00 29.25      C
ATOM   1973  N   ALA B  96     15.299  -1.067  90.728  1.00 28.62      N
ATOM   1974  CA  ALA B  96     15.702   0.178  91.340  1.00 28.40      C
ATOM   1975  C   ALA B  96     14.472   1.043  91.654  1.00 29.99      C
ATOM   1976  O   ALA B  96     14.553   2.002  92.419  1.00 30.71      O
ATOM   1977  CB  ALA B  96     16.621   0.919  90.416  1.00 27.25      C
ATOM   1978  N   ALA B  97     13.331   0.692  91.065  1.00 30.19      N
ATOM   1979  CA  ALA B  97     12.094   1.440  91.273  1.00 30.32      C
ATOM   1980  C   ALA B  97     10.928   0.493  91.544  1.00 30.58      C
ATOM   1981  O   ALA B  97     11.045  -0.710  91.322  1.00 30.16      O
ATOM   1982  CB  ALA B  97     11.799   2.285  90.047  1.00 29.28      C
ATOM   1983  N   HIS B  98      9.804   1.037  92.024  1.00 31.20      N
ATOM   1984  CA  HIS B  98      8.615   0.228  92.307  1.00 30.17      C
ATOM   1985  C   HIS B  98      7.869  -0.086  91.026  1.00 29.50      C
ATOM   1986  O   HIS B  98      8.022   0.614  90.021  1.00 28.00      O
ATOM   1987  CB  HIS B  98      7.689   0.940  93.283  1.00 30.91      C
ATOM   1988  CG  HIS B  98      8.319   1.196  94.617  1.00 33.22      C
ATOM   1989  ND1 HIS B  98      7.587   1.489  95.749  1.00 32.52      N
ATOM   1990  CD2 HIS B  98      9.620   1.206  94.999  1.00 32.87      C
ATOM   1991  CE1 HIS B  98      8.408   1.665  96.767  1.00 32.55      C
ATOM   1992  NE2 HIS B  98      9.649   1.499  96.337  1.00 32.87      N
ATOM   1993  N   ALA B  99      7.061  -1.145  91.080  1.00 29.92      N
ATOM   1994  CA  ALA B  99      6.272  -1.613  89.941  1.00 29.60      C
ATOM   1995  C   ALA B  99      5.508  -0.490  89.272  1.00 29.58      C
ATOM   1996  O   ALA B  99      5.412  -0.449  88.043  1.00 30.39      O
ATOM   1997  CB  ALA B  99      5.311  -2.728  90.386  1.00 29.03      C
ATOM   1998  N   GLU B 100      4.968   0.425  90.069  1.00 30.76      N
ATOM   1999  CA  GLU B 100      4.199   1.556  89.536  1.00 32.16      C
ATOM   2000  C   GLU B 100      5.035   2.453  88.615  1.00 32.56      C
ATOM   2001  O   GLU B 100      4.548   2.941  87.593  1.00 31.67      O
ATOM   2002  CB  GLU B 100      3.606   2.380  90.691  1.00 32.94      C
ATOM   2003  CG  GLU B 100      2.484   1.657  91.470  1.00 33.25      C
ATOM   2004  CD  GLU B 100      2.967   0.946  92.732  1.00 32.63      C
ATOM   2005  OE1 GLU B 100      4.173   0.655  92.830  1.00 30.43      O
ATOM   2006  OE2 GLU B 100      2.121   0.668  93.623  1.00 34.00      O
ATOM   2007  N   GLU B 101      6.296   2.656  88.973  1.00 33.19      N
ATOM   2008  CA  GLU B 101      7.181   3.493  88.186  1.00 33.91      C
ATOM   2009  C   GLU B 101      7.598   2.744  86.931  1.00 33.21      C
ATOM   2010  O   GLU B 101      7.593   3.294  85.826  1.00 34.04      O
ATOM   2011  CB  GLU B 101      8.427   3.859  88.999  1.00 35.98      C
ATOM   2012  CG  GLU B 101      8.149   4.490  90.380  1.00 40.27      C
ATOM   2013  CD  GLU B 101      9.406   4.590  91.262  1.00 43.83      C
ATOM   2014  OE1 GLU B 101     10.412   5.139  90.760  1.00 46.44      O
ATOM   2015  OE2 GLU B 101      9.399   4.139  92.439  1.00 42.52      O
ATOM   2016  N   ALA B 102      7.955   1.478  87.106  1.00 31.56      N
ATOM   2017  CA  ALA B 102      8.406   0.652  85.993  1.00 29.65      C

ATOM   2694  C   TYR B 186     -7.883 -13.796  87.365  1.00 22.46      C
ATOM   2695  O   TYR B 186     -7.495 -14.217  86.272  1.00 21.29      O
ATOM   2696  CB  TYR B 186    -10.031 -12.513  87.689  1.00 25.73      C
ATOM   2697  CG  TYR B 186     -9.904 -11.866  86.330  1.00 29.26      C
ATOM   2698  CD1 TYR B 186    -10.689 -12.290  85.251  1.00 29.67      C
ATOM   2699  CD2 TYR B 186     -8.963 -10.855  86.105  1.00 29.80      C
ATOM   2700  CE1 TYR B 186    -10.534 -11.716  83.974  1.00 31.05      C
ATOM   2701  CE2 TYR B 186     -8.800 -10.280  84.840  1.00 31.40      C
ATOM   2702  CZ  TYR B 186     -9.584 -10.707  83.788  1.00 32.24      C
ATOM   2703  OH  TYR B 186     -9.416 -10.080  82.567  1.00 35.03      O
ATOM   2704  N   VAL B 187     -7.063 -13.246  88.246  1.00 21.12      N
ATOM   2705  CA  VAL B 187     -5.651 -13.103  87.968  1.00 20.71      C
ATOM   2706  C   VAL B 187     -4.990 -14.476  87.865  1.00 22.47      C
ATOM   2707  O   VAL B 187     -4.059 -14.698  87.075  1.00 23.30      O
ATOM   2708  CB  VAL B 187     -4.961 -12.282  89.071  1.00 18.25      C
ATOM   2709  CG1 VAL B 187     -3.466 -12.300  88.888  1.00 17.39      C
ATOM   2710  CG2 VAL B 187     -5.458 -10.850  89.029  1.00 16.85      C
ATOM   2711  N   TRP B 188     -5.488 -15.419  88.640  1.00 22.99      N
ATOM   2712  CA  TRP B 188     -4.913 -16.743  88.641  1.00 24.97      C
ATOM   2713  C   TRP B 188     -5.180 -17.541  87.382  1.00 27.24      C
ATOM   2714  O   TRP B 188     -4.318 -18.291  86.914  1.00 29.11      O
ATOM   2715  CB  TRP B 188     -5.398 -17.515  89.867  1.00 23.34      C
ATOM   2716  CG  TRP B 188     -4.918 -18.934  89.929  1.00 23.16      C
ATOM   2717  CD1 TRP B 188     -5.587 -20.042  89.501  1.00 22.79      C
ATOM   2718  CD2 TRP B 188     -3.662 -19.397  90.437  1.00 22.35      C
ATOM   2719  NE1 TRP B 188     -4.829  21.167  89.707  1.00 22.57      N
ATOM   2720  CE2 TRP B 188     -3.637 -20.798  90.272  1.00 22.63      C
ATOM   2721  CE3 TRP B 188     -2.543 -18.764  90.997  1.00 22.96      C
ATOM   2722  CZ2 TRP B 188     -2.549 -21.583  90.670  1.00 21.99      C
ATOM   2723  CZ3 TRP B 188     -1.463 -19.541  91.392  1.00 23.43      C
ATOM   2724  CH2 TRP B 188     -1.472 -20.940  91.215  1.00 23.30      C
ATOM   2725  N   GLN B 189     -6.361 -17.370  86.815  1.00 28.12      N
ATOM   2726  CA  GLN B 189     -6.724 -18.116  85.628  1.00 29.70      C
ATOM   2727  C   GLN B 189     -6.514 -17.353  84.328  1.00 28.64      C
ATOM   2728  O   GLN B 189     -6.815 -17.862  83.254  1.00 31.14      O
ATOM   2729  CB  GLN B 189     -8.187 -18.580  85.753  1.00 32.03      C
ATOM   2730  CG  GLN B 189     -8.430 -19.579  86.903  1.00 37.20      C
ATOM   2731  CD  GLN B 189     -9.898 -19.988  87.063  1.00 40.80      C
ATOM   2732  OE1 GLN B 189    -10.208 -20.963  87.760  1.00 42.46      O
ATOM   2733  NE2 GLN B 189    -10.805 -19.242  86.433  1.00 41.54      N
ATOM   2734  N   ASN B 190     -5.980 -16.148  84.396  1.00 26.37      N
ATOM   2735  CA  ASN B 190     -5.790 -15.399  83.172  1.00 24.53      C
ATOM   2736  C   ASN B 190     -4.388 -14.859  83.035  1.00 25.67      C
ATOM   2737  O   ASN B 190     -4.043 -14.293  82.003  1.00 26.47      O
ATOM   2738  CB  ASN B 190     -6.776 -14.244  83.102  1.00 23.33      C
ATOM   2739  CG  ASN B 190     -8.186 -14.705  82.821  1.00 23.10      C
ATOM   2740  OD1 ASN B 190     -8.510 -15.102  81.703  1.00 21.83      O
ATOM   2741  ND2 ASN B 190     -9.038 -14.658  83.837  1.00 22.66      N
ATOM   2742  N   PHE B 191     -3.585 -15.012  84.084  1.00 25.47      N
ATOM   2743  CA  PHE B 191     -2.216 -14.537  84.062  1.00 25.85      C
ATOM   2744  C   PHE B 191     -1.238 -15.656  84.410  1.00 28.13      C
ATOM   2745  O   PHE B 191     -0.171 -15.767  83.816  1.00 29.21      O
ATOM   2746  CB  PHE B 191     -2.014 -13.363  85.037  1.00 22.38      C
ATOM   2747  CG  PHE B 191     -2.680 -12.085  84.612  1.00 19.64      C
ATOM   2748  CD1 PHE B 191     -4.058 -11.920  84.733  1.00 18.87      C
ATOM   2749  CD2 PHE B 191     -1.928 -11.041  84.081  1.00 18.00      C
ATOM   2750  CE1 PHE B 191     -4.673 -10.740  84.332  1.00 16.26      C
ATOM   2751  CE2 PHE B 191      2.531  -9.861  83.680  1.00 16.59      C
ATOM   2752  CZ  PHE B 191     -3.908  -9.708  83.807  1.00 16.38      C
ATOM   2753  N   VAL B 192     -1.599 -16.495  85.368  1.00 31.82      N
ATOM   2754  CA  VAL B 192     -0.714 -17.577  85.764  1.00 34.59      C
ATOM   2755  C   VAL B 192     -0.885 -18.757  84.829  1.00 38.26      C
ATOM   2756  O   VAL B 192     -1.983 -19.297  84.684  1.00 39.28      O
ATOM   2757  CB  VAL B 192     -0.991 -18.013  87.197  1.00 33.12      C
ATOM   2758  CG1 VAL B 192     -0.116 -19.185  87.554  1.00 33.15      C
ATOM   2759  CG2 VAL B 192     -0.742 -16.847  88.143  1.00 32.22      C
ATOM   2760  N   GLU B 193      0.208 -19.162  84.201  1.00 41.91      N
ATOM   2761  CA  GLU B 193      0.164 -20.262  83.267  1.00 46.74      C
ATOM   2762  C   GLU B 193     -0.029 -21.592  83.957  1.00 50.07      C
ATOM   2763  O   GLU B 193      0.848 -22.055  84.686  1.00 50.30      O
ATOM   2764  CB  GLU B 193      1.459 -20.315  82.447  1.00 47.59      C
ATOM   2765  CG  GLU B 193      1.254 -20.636  80.965  1.00 49.55      C
ATOM   2766  CD  GLU B 193      2.563 -20.817  80.214  1.00 50.50      C
ATOM   2767  OE1 GLU B 193      3.306 -21.761  80.559  1.00 50.73      O
ATOM   2768  OE2 GLU B 193      2.853 -20.022  79.283  1.00 50.94      O
ATOM   2769  N   GLN B 194     -1.173 -22.216  83.680  1.00 54.47      N
ATOM   2770  CA  GLN B 194     -1.508 -23.541  84.208  1.00 58.83      C
ATOM   2771  C   GLN B 194     -0.657 -24.577  83.447  1.00 62.10      C
ATOM   2772  O   GLN B 194     -0.624 -24.573  82.211  1.00 61.64      O
ATOM   2773  CB  GLN B 194     -2.994 -23.852  83.979  1.00 58.57      C
ATOM   2774  CG  GLN B 194     -3.970 -22.932  84.686  1.00 57.78      C
ATOM   2775  CD  GLN B 194     -3.898 -23.058  86.191  1.00 57.30      C
ATOM   2776  OE1 GLN B 194     -2.868 -22.776  86.801  1.00 56.05      O
ATOM   2777  NE2 GLN B 194     -4.998 -23.487  86.800  1.00 57.45      N
ATOM   2778  N   GLU B 195      0.020 -25.455  84.193  1.00 65.80      N
ATOM   2779  CA  GLU B 195      0.881 -26.500  83.615  1.00 69.36      C
```

FIG. 9 (con't)

```
ATOM  2018  C   ALA B 102      7.385  0.551 84.881 1.00 28.86       C
ATOM  2019  O   ALA B 102      7.747  0.467 83.710 1.00 28.47       O
ATOM  2020  CB  ALA B 102      8.758 -0.750 86.494 1.00 30.14       C
ATOM  2021  N   PHE B 103      6.105  0.552 85.240 1.00 27.81       N
ATOM  2022  CA  PHE B 103      5.059  0.430 84.245 1.00 27.36       C
ATOM  2023  C   PHE B 103      5.030  1.591 83.266 1.00 28.18       C
ATOM  2024  O   PHE B 103      5.189  1.398 82.064 1.00 28.86       O
ATOM  2025  CB  PHE B 103      3.695  0.306 84.923 1.00 26.13       C
ATOM  2026  CG  PHE B 103      2.559  0.132 83.959 1.00 25.25       C
ATOM  2027  CD1 PHE B 103      2.296 -1.108 83.386 1.00 23.58       C
ATOM  2028  CD2 PHE B 103      1.755  1.217 83.608 1.00 25.36       C
ATOM  2029  CE1 PHE B 103      1.256 -1.272 82.482 1.00 22.52       C
ATOM  2030  CE2 PHE B 103      0.706  1.068 82.706 1.00 23.78       C
ATOM  2031  CZ  PHE B 103      0.457 -0.181 82.142 1.00 24.57       C
ATOM  2032  N   PHE B 104      4.825  2.798 83.786 1.00 29.24       N
ATOM  2033  CA  PHE B 104      4.757  3.998 82.956 1.00 29.26       C
ATOM  2034  C   PHE B 104      6.073  4.406 82.308 1.00 31.16       C
ATOM  2035  O   PHE B 104      6.114  5.365 81.533 1.00 31.26       O
ATOM  2036  CB  PHE B 104      4.202  5.160 83.771 1.00 26.65       C
ATOM  2037  CG  PHE B 104      2.738  5.037 84.082 1.00 25.20       C
ATOM  2038  CD1 PHE B 104      2.274  5.216 85.381 1.00 22.70       C
ATOM  2039  CD2 PHE B 104      1.819  4.778 83.072 1.00 24.69       C
ATOM  2040  CE1 PHE B 104      0.917  5.138 85.669 1.00 23.29       C
ATOM  2041  CE2 PHE B 104      0.458  4.701 83.354 1.00 24.22       C
ATOM  2042  CZ  PHE B 104      0.007  4.880 84.658 1.00 22.70       C
ATOM  2043  N   ASN B 105      7.151  3.689 82.611 1.00 33.67       N
ATOM  2044  CA  ASN B 105      8.446  4.025 82.020 1.00 35.86       C
ATOM  2045  C   ASN B 105      8.912  3.075 80.926 1.00 36.14       C
ATOM  2046  O   ASN B 105      9.816  3.411 80.168 1.00 35.61       O
ATOM  2047  CB  ASN B 105      9.515  4.122 83.104 1.00 38.40       C
ATOM  2048  CG  ASN B 105      9.315  5.321 84.009 1.00 41.32       C
ATOM  2049  OD1 ASN B 105      8.419  6.141 83.788 1.00 42.54       O
ATOM  2050  ND2 ASN B 105     10.157  5.438 85.032 1.00 41.83       N
ATOM  2051  N   THR B 106      8.299  1.901 80.833 1.00 37.38       N
ATOM  2052  CA  THR B 106      8.690  0.943 79.809 1.00 39.06       C
ATOM  2053  C   THR B 106      7.518  0.239 79.144 1.00 39.10       C
ATOM  2054  O   THR B 106      7.571 -0.049 77.952 1.00 39.32       O
ATOM  2055  CB  THR B 106      9.624 -0.131 80.384 1.00 40.61       C
ATOM  2056  OG1 THR B 106      9.098 -0.605 81.624 1.00 41.74       O
ATOM  2057  CG2 THR B 106     11.013  0.437 80.608 1.00 41.42       C
ATOM  2058  N   ILE B 107      6.465 -0.039 79.912 1.00 38.64       N
ATOM  2059  CA  ILE B 107      5.287 -0.711 79.376 1.00 39.05       C
ATOM  2060  C   ILE B 107      4.437  0.240 78.528 1.00 39.47       C
ATOM  2061  O   ILE B 107      4.186 -0.032 77.359 1.00 39.91       O
ATOM  2062  CB  ILE B 107      4.424 -1.314 80.507 1.00 39.08       C
ATOM  2063  CG1 ILE B 107      5.316 -2.095 81.473 1.00 38.43       C
ATOM  2064  CG2 ILE B 107      3.334 -2.222 79.920 1.00 37.59       C
ATOM  2065  CD1 ILE B 107      6.278 -3.037 80.793 1.00 38.27       C
ATOM  2066  N   LEU B 108      4.008  1.355 79.112 1.00 39.98       N
ATOM  2067  CA  LEU B 108      3.203  2.336 78.391 1.00 40.78       C
ATOM  2068  C   LEU B 108      3.876  3.697 78.412 1.00 42.16       C
ATOM  2069  O   LEU B 108      3.363  4.654 79.001 1.00 41.46       O
ATOM  2070  CB  LEU B 108      1.819  2.453 79.023 1.00 41.19       C
ATOM  2071  CG  LEU B 108      0.689  1.639 78.418 1.00 40.26       C
ATOM  2072  CD1 LEU B 108     -0.632  2.021 79.073 1.00 39.76       C
ATOM  2073  CD2 LEU B 108      0.635  1.925 76.937 1.00 41.10       C
ATOM  2074  N   PRO B 109      5.049  3.799 77.784 1.00 43.67       N
ATOM  2075  CA  PRO B 109      5.765  5.072 77.757 1.00 44.76       C
ATOM  2076  C   PRO B 109      5.033  6.063 76.891 1.00 45.07       C
ATOM  2077  O   PRO B 109      4.930  7.231 77.237 1.00 45.84       O
ATOM  2078  CB  PRO B 109      7.118  4.698 77.159 1.00 45.21       C
ATOM  2079  CG  PRO B 109      7.277  3.265 77.544 1.00 46.15       C
ATOM  2080  CD  PRO B 109      5.903  2.716 77.274 1.00 44.82       C
ATOM  2081  N   ALA B 110      4.518  5.587 75.763 1.00 45.59       N
ATOM  2082  CA  ALA B 110      3.813  6.453 74.832 1.00 46.09       C
ATOM  2083  C   ALA B 110      2.304  6.203 74.817 1.00 45.65       C
ATOM  2084  O   ALA B 110      1.846  5.108 75.129 1.00 45.08       O
ATOM  2085  CB  ALA B 110      4.386  6.269 73.431 1.00 46.57       C
ATOM  2086  N   PHE B 111      1.544  7.233 74.452 1.00 44.98       N
ATOM  2087  CA  PHE B 111      0.097  7.130 74.376 1.00 44.99       C
ATOM  2088  C   PHE B 111     -0.409  7.738 73.073 1.00 45.71       C
ATOM  2089  O   PHE B 111     -0.007  8.840 72.694 1.00 47.07       O
ATOM  2090  CB  PHE B 111     -0.574  7.854 75.556 1.00 43.75       C
ATOM  2091  CG  PHE B 111     -0.272  7.249 76.904 1.00 43.28       C
ATOM  2092  CD1 PHE B 111      0.734  7.775 77.710 1.00 42.73       C
ATOM  2093  CD2 PHE B 111     -0.986  6.140 77.365 1.00 43.11       C
ATOM  2094  CE1 PHE B 111      1.027  7.205 78.955 1.00 42.47       C
ATOM  2095  CE2 PHE B 111     -0.702  5.562 78.613 1.00 42.95       C
ATOM  2096  CZ  PHE B 111      0.306  6.089 79.407 1.00 42.32       C
ATOM  2097  N   ASP B 112     -1.283  7.022 72.379 1.00 45.74       N
ATOM  2098  CA  ASP B 112     -1.846  7.523 71.138 1.00 45.60       C
ATOM  2099  C   ASP B 112     -2.956  8.523 71.479 1.00 45.20       C
ATOM  2100  O   ASP B 112     -4.040  8.135 71.903 1.00 43.83       O
ATOM  2101  CB  ASP B 112     -2.438  6.369 70.332 1.00 47.51       C
ATOM  2102  CG  ASP B 112     -2.799  6.771 68.918 1.00 48.52       C
ATOM  2103  OD1 ASP B 112     -3.347  7.878 68.735 1.00 49.31       O
ATOM  2780  C   GLU B 195      0.114 -27.616 82.904 1.00 71.50      C
ATOM  2781  O   GLU B 195      0.618 -28.203 81.944 1.00 71.97      O
ATOM  2782  CB  GLU B 195      1.779 -27.123 84.702 1.00 70.03      C
ATOM  2783  CG  GLU B 195      2.992 -26.278 85.100 1.00 70.46      C
ATOM  2784  CD  GLU B 195      2.628 -24.858 85.509 1.00 70.61      C
ATOM  2785  OE1 GLU B 195      1.810 -24.688 86.439 1.00 70.55      O
ATOM  2786  OE2 GLU B 195      3.168 -23.906 84.900 1.00 70.44      O
ATOM  2787  N   GLU B 196     -1.100 -27.903 83.372 1.00 73.56      N
ATOM  2788  CA  GLU B 196     -1.929 -28.949 82.770 1.00 75.53      C
ATOM  2789  CB  GLU B 196     -3.056 -28.409 81.886 1.00 76.70      C
ATOM  2790  O   GLU B 196     -4.103 -29.050 81.760 1.00 77.40      O
ATOM  2791  CB  GLU B 196     -2.516 -29.846 83.864 1.00 75.56      C
ATOM  2792  N   GLY B 197     -2.833 -27.241 81.280 1.00 77.63      N
ATOM  2793  CA  GLY B 197     -3.801 -26.588 80.394 1.00 78.37      C
ATOM  2794  C   GLY B 197     -5.125 -26.276 81.108 1.00 78.85      C
ATOM  2795  O   GLY B 197     -5.143 -25.592 82.135 1.00 79.40      O
ATOM  2796  N   GLU B 198     -6.228 -26.781 80.559 1.00 78.80      N
ATOM  2797  CA  GLU B 198     -7.551 -26.568 81.141 1.00 78.33      C
ATOM  2798  C   GLU B 198     -7.975 -27.732 82.058 1.00 77.79      C
ATOM  2799  O   GLU B 198     -8.937 -28.448 81.773 1.00 78.09      O
ATOM  2800  CB  GLU B 198     -8.586 -26.359 80.017 1.00 78.38      C
ATOM  2801  N   SER B 199     -7.248 -27.911 83.162 1.00 76.53      N
ATOM  2802  CA  SER B 199     -7.546 -28.970 84.127 1.00 74.80      C
ATOM  2803  C   SER B 199     -7.167 -28.556 85.558 1.00 73.65      C
ATOM  2804  O   SER B 199     -6.266 -29.137 86.170 1.00 73.64      O
ATOM  2805  CB  SER B 199     -6.819 -30.259 83.733 1.00 74.61      C
ATOM  2806  N   LYS B 200     -7.864 -27.546 86.077 1.00 71.97      N
ATOM  2807  CA  LYS B 200     -7.631 -27.029 87.427 1.00 70.16      C
ATOM  2808  C   LYS B 200     -8.581 -25.865 87.747 1.00 68.45      C
ATOM  2809  O   LYS B 200     -8.817 -24.990 86.908 1.00 68.69      O
ATOM  2810  CB  LYS B 200     -6.163 -26.576 87.581 1.00 70.88      C
ATOM  2811  N   ALA B 201     -9.128 -25.866 88.960 1.00 65.62      N
ATOM  2812  CA  ALA B 201    -10.047 -24.818 89.383 1.00 62.53      C
ATOM  2813  C   ALA B 201     -9.302 -23.756 90.174 1.00 60.59      C
ATOM  2814  O   ALA B 201     -8.252 -23.285 89.741 1.00 61.13      O
ATOM  2815  CB  ALA B 201    -11.167 -25.411 90.226 1.00 62.89      C
ATOM  2816  N   PHE B 202     -9.841 -23.389 91.340 1.00 56.77      N
ATOM  2817  CA  PHE B 202     -9.229 -22.366 92.188 1.00 52.31      C
ATOM  2818  C   PHE B 202     -9.393 -22.681 93.666 1.00 50.70      C
ATOM  2819  O   PHE B 202    -10.504 -22.920 94.134 1.00 50.58      O
ATOM  2820  CB  PHE B 202     -9.860 -21.002 91.912 1.00 49.87      C
ATOM  2821  CG  PHE B 202     -9.152 -19.861 92.592 1.00 46.65      C
ATOM  2822  CD1 PHE B 202     -7.979 -19.341 92.063 1.00 46.09      C
ATOM  2823  CD2 PHE B 202     -9.641 -19.322 93.769 1.00 45.52      C
ATOM  2824  CE1 PHE B 202     -7.306 -18.301 92.698 1.00 45.10      C
ATOM  2825  CE2 PHE B 202     -8.971 -18.283 94.406 1.00 45.12      C
ATOM  2826  CZ  PHE B 202     -7.802 -17.776 93.867 1.00 44.53      C
ATOM  2827  N   GLN B 203     -8.289 -22.655 94.403 1.00 49.07      N
ATOM  2828  CA  GLN B 203     -8.308 -22.934 95.834 1.00 47.94      C
ATOM  2829  C   GLN B 203     -8.048 -21.668 96.643 1.00 45.83      C
ATOM  2830  O   GLN B 203     -6.906 -21.284 96.886 1.00 46.43      O
ATOM  2831  CB  GLN B 203     -7.263 -23.995 96.179 1.00 50.66      C
ATOM  2832  CG  GLN B 203     -6.805 -23.987 97.640 1.00 55.39      C
ATOM  2833  CD  GLN B 203     -7.849 -24.520 98.616 1.00 58.12      C
ATOM  2834  OE1 GLN B 203     -9.021 -24.141 98.565 1.00 60.40      O
ATOM  2835  NE2 GLN B 203     -7.418 -25.393 99.524 1.00 58.74      N
ATOM  2836  N   PRO B 204     -9.122 -21.006 97.079 1.00 43.40      N
ATOM  2837  CA  PRO B 204     -8.981 -19.785 97.860 1.00 40.47      C
ATOM  2838  C   PRO B 204     -8.527 -20.085 99.275 1.00 37.19      C
ATOM  2839  O   PRO B 204     -8.652 -21.206 99.743 1.00 35.18      O
ATOM  2840  CB  PRO B 204    -10.385 -19.197 97.816 1.00 41.54      C
ATOM  2841  CG  PRO B 204    -11.237 -20.414 97.822 1.00 41.04      C
ATOM  2842  CD  PRO B 204    -10.546 -21.296 96.816 1.00 42.36      C
ATOM  2843  N   TRP B 205     -7.988 -19.067 99.943 1.00 34.58      N
ATOM  2844  CA  TRP B 205     -7.526 -19.220 101.309 1.00 31.36     C
ATOM  2845  C   TRP B 205     -8.591 -18.841 102.351 1.00 31.15     C
ATOM  2846  O   TRP B 205     -9.555 -18.123 102.072 1.00 28.26     O
ATOM  2847  CB  TRP B 205     -6.234 -18.421 101.518 1.00 29.43     C
ATOM  2848  CG  TRP B 205     -6.185 -17.103 100.778 1.00 26.29     C
ATOM  2849  CD1 TRP B 205     -6.383 -15.855 101.298 1.00 25.68     C
ATOM  2850  CD2 TRP B 205     -5.912 -16.919 99.386 1.00 26.29      C
ATOM  2851  NE1 TRP B 205     -6.253 -14.904 100.313 1.00 25.88     N
ATOM  2852  CE2 TRP B 205     -5.968 -15.530 99.127 1.00 26.01      C
ATOM  2853  CE3 TRP B 205     -5.633 -17.795 98.331 1.00 24.23      C
ATOM  2854  CZ2 TRP B 205     -5.748 -14.996 97.857 1.00 23.90      C
ATOM  2855  CZ3 TRP B 205     -5.416 -17.264 97.069 1.00 23.98      C
ATOM  2856  CH2 TRP B 205     -5.478 -15.881 96.843 1.00 23.72      C
ATOM  2857  N   GLU B 206     -8.393 -19.345 103.561 1.00 31.76     N
ATOM  2858  CA  GLU B 206     -9.303 -19.122 104.679 1.00 32.35     C
ATOM  2859  C   GLU B 206     -9.751 -17.675 104.959 1.00 31.10     C
ATOM  2860  O   GLU B 206    -10.937 -17.438 105.190 1.00 30.56     O
ATOM  2861  CB  GLU B 206     -8.683 -19.734 105.930 1.00 34.67     C
ATOM  2862  CG  GLU B 206     -9.555 -19.673 107.159 1.00 40.19     C
ATOM  2863  CD  GLU B 206     -8.918 -20.364 108.348 1.00 43.62     C
ATOM  2864  OE1 GLU B 206     -8.725 -21.599 108.281 1.00 46.07     O
ATOM  2865  OE2 GLU B 206     -8.600 -19.679 109.346 1.00 44.88     O
```

FIG. 9 (con't)

| | | | | | | |
|---|---|---|---|---|---|---|
| ATOM | 2104 | OD2 ASP B 112 | -2.538 5.970 67.996 | 1.00 49.15 | O |
| ATOM | 2105 | N PRO B 113 | -2.696 9.829 71.289 | 1.00 45.48 | N |
| ATOM | 2106 | CA PRO B 113 | -3.659 10.906 71.576 | 1.00 44.02 | C |
| ATOM | 2107 | C PRO B 113 | -5.046 10.679 71.006 | 1.00 42.57 | C |
| ATOM | 2108 | O PRO B 113 | -6.010 11.309 71.438 | 1.00 43.23 | O |
| ATOM | 2109 | CB PRO B 113 | -2.976 12.134 70.982 | 1.00 44.42 | C |
| ATOM | 2110 | CG PRO B 113 | -1.513 11.833 71.236 | 1.00 46.02 | C |
| ATOM | 2111 | CD PRO B 113 | -1.425 10.390 70.786 | 1.00 45.45 | C |
| ATOM | 2112 | N ALA B 114 | -5.152 9.774 70.043 | 1.00 41.43 | N |
| ATOM | 2113 | CA ALA B 114 | -6.438 9.486 69.416 | 1.00 39.56 | C |
| ATOM | 2114 | C ALA B 114 | -7.229 8.456 70.195 | 1.00 38.00 | C |
| ATOM | 2115 | O ALA B 114 | -8.424 8.611 70.414 | 1.00 38.59 | O |
| ATOM | 2116 | CB ALA B 114 | -6.217 8.998 68.014 | 1.00 38.88 | C |
| ATOM | 2117 | N LEU B 115 | -6.554 7.390 70.598 | 1.00 36.47 | N |
| ATOM | 2118 | CA LEU B 115 | -7.194 6.322 71.343 | 1.00 34.00 | C |
| ATOM | 2119 | C LEU B 115 | -7.471 6.720 72.796 | 1.00 31.90 | C |
| ATOM | 2120 | O LEU B 115 | -6.732 7.497 73.394 | 1.00 31.23 | O |
| ATOM | 2121 | CB LEU B 115 | -6.294 5.096 71.333 | 1.00 34.26 | C |
| ATOM | 2122 | CG LEU B 115 | -5.716 4.669 69.992 | 1.00 34.14 | C |
| ATOM | 2123 | CD1 LEU B 115 | -4.615 3.622 70.185 | 1.00 33.90 | C |
| ATOM | 2124 | CD2 LEU B 115 | -6.846 4.143 69.144 | 1.00 34.56 | C |
| ATOM | 2125 | N ARG B 116 | -8.538 6.173 73.368 | 1.00 31.01 | N |
| ATOM | 2126 | CA ARG B 116 | -8.884 6.437 74.758 | 1.00 28.60 | C |
| ATOM | 2127 | C ARG B 116 | -8.410 5.220 75.548 | 1.00 26.76 | C |
| ATOM | 2128 | O ARG B 116 | -8.929 4.122 75.363 | 1.00 25.42 | O |
| ATOM | 2129 | CB ARG B 116 | -10.382 6.563 74.898 | 1.00 32.04 | C |
| ATOM | 2130 | CG ARG B 116 | -10.825 7.721 75.738 | 1.00 37.33 | C |
| ATOM | 2131 | CD ARG B 116 | -10.236 7.705 77.139 | 1.00 38.69 | C |
| ATOM | 2132 | NE ARG B 116 | -11.059 8.488 78.062 | 1.00 41.96 | N |
| ATOM | 2133 | CZ ARG B 116 | -12.246 8.096 78.523 | 1.00 43.72 | C |
| ATOM | 2134 | NH1 ARG B 116 | -12.753 6.926 78.154 | 1.00 45.48 | N |
| ATOM | 2135 | NH2 ARG B 116 | -12.927 8.869 79.357 | 1.00 45.09 | N |
| ATOM | 2136 | N TYR B 117 | -7.450 5.409 76.439 | 1.00 24.66 | N |
| ATOM | 2137 | CA TYR B 117 | -6.914 4.290 77.195 | 1.00 24.15 | C |
| ATOM | 2138 | C TYR B 117 | -7.606 3.969 78.504 | 1.00 23.87 | C |
| ATOM | 2139 | O TYR B 117 | -7.944 4.865 79.270 | 1.00 25.73 | O |
| ATOM | 2140 | CB TYR B 117 | -5.421 4.511 77.476 | 1.00 22.85 | C |
| ATOM | 2141 | CG TYR B 117 | -4.537 4.460 76.246 | 1.00 21.61 | C |
| ATOM | 2142 | CD1 TYR B 117 | -4.443 5.542 75.370 | 1.00 21.30 | C |
| ATOM | 2143 | CD2 TYR B 117 | -3.814 3.315 75.949 | 1.00 22.98 | C |
| ATOM | 2144 | CE1 TYR B 117 | -3.641 5.475 74.217 | 1.00 22.30 | C |
| ATOM | 2145 | CE2 TYR B 117 | -3.016 3.237 74.810 | 1.00 24.43 | C |
| ATOM | 2146 | CZ TYR B 117 | -2.934 4.321 73.951 | 1.00 23.77 | C |
| ATOM | 2147 | OH TYR B 117 | -2.139 4.228 72.823 | 1.00 26.97 | O |
| ATOM | 2148 | N ASN B 118 | -7.805 2.681 78.756 | 1.00 23.52 | N |
| ATOM | 2149 | CA ASN B 118 | -8.420 2.194 79.986 | 1.00 23.33 | C |
| ATOM | 2150 | C ASN B 118 | -7.495 1.133 80.601 | 1.00 22.78 | C |
| ATOM | 2151 | O ASN B 118 | -7.534 -0.037 80.217 | 1.00 23.03 | O |
| ATOM | 2152 | CB ASN B 118 | -9.770 1.582 79.673 | 1.00 24.96 | C |
| ATOM | 2153 | CG ASN B 118 | -10.905 2.489 80.033 | 1.00 26.13 | C |
| ATOM | 2154 | OD1 ASN B 118 | -11.543 2.293 81.058 | 1.00 29.62 | O |
| ATOM | 2155 | ND2 ASN B 118 | -11.167 3.496 79.203 | 1.00 27.07 | N |
| ATOM | 2156 | N VAL B 119 | -6.667 1.541 81.556 | 1.00 20.63 | N |
| ATOM | 2157 | CA VAL B 119 | -5.735 0.632 82.192 | 1.00 18.93 | C |
| ATOM | 2158 | C VAL B 119 | -6.242 0.102 83.520 | 1.00 19.43 | C |
| ATOM | 2159 | O VAL B 119 | -6.872 0.828 84.291 | 1.00 20.90 | O |
| ATOM | 2160 | CB VAL B 119 | -4.384 1.305 82.427 | 1.00 17.41 | C |
| ATOM | 2161 | CG1 VAL B 119 | -3.398 0.335 83.011 | 1.00 15.86 | C |
| ATOM | 2162 | CG2 VAL B 119 | -3.852 1.843 81.132 | 1.00 17.10 | C |
| ATOM | 2163 | N THR B 120 | -5.956 -1.172 83.783 | 1.00 18.85 | N |
| ATOM | 2164 | CA THR B 120 | -6.353 -1.825 85.021 | 1.00 18.06 | C |
| ATOM | 2165 | C THR B 120 | -5.153 -2.547 85.643 | 1.00 18.23 | C |
| ATOM | 2166 | O THR B 120 | -4.524 -3.382 85.006 | 1.00 18.08 | O |
| ATOM | 2167 | CB THR B 120 | -7.451 -2.846 84.765 | 1.00 18.34 | C |
| ATOM | 2168 | OG1 THR B 120 | -8.562 -2.203 84.127 | 1.00 20.38 | O |
| ATOM | 2169 | CG2 THR B 120 | -7.903 -3.456 86.067 | 1.00 18.11 | C |
| ATOM | 2170 | N TRP B 121 | -4.829 -2.237 86.890 | 1.00 17.12 | N |
| ATOM | 2171 | CA TRP B 121 | -3.703 -2.903 87.515 | 1.00 15.87 | C |
| ATOM | 2172 | C TRP B 121 | -4.143 -3.908 88.568 | 1.00 16.14 | C |
| ATOM | 2173 | O TRP B 121 | -5.226 -3.796 89.140 | 1.00 15.96 | O |
| ATOM | 2174 | CB TRP B 121 | -2.763 -1.897 88.183 | 1.00 13.51 | C |
| ATOM | 2175 | CG TRP B 121 | -2.022 -0.999 87.255 | 1.00 14.95 | C |
| ATOM | 2176 | CD1 TRP B 121 | 1.879 -1.139 85.907 | 1.00 15.66 | C |
| ATOM | 2177 | CD2 TRP B 121 | -1.183 0.106 87.626 | 1.00 15.87 | C |
| ATOM | 2178 | NE1 TRP B 121 | -1.013 -0.198 85.414 | 1.00 13.06 | N |
| ATOM | 2179 | CE2 TRP B 121 | -0.574 0.589 86.444 | 1.00 13.64 | C |
| ATOM | 2180 | CE3 TRP B 121 | -0.896 0.756 88.846 | 1.00 15.19 | C |
| ATOM | 2181 | CZ2 TRP B 121 | 0.319 1.658 86.439 | 1.00 13.41 | C |
| ATOM | 2182 | CZ3 TRP B 121 | -0.003 1.828 88.838 | 1.00 12.86 | C |
| ATOM | 2183 | CH2 TRP B 121 | 0.580 2.273 87.640 | 1.00 13.34 | C |
| ATOM | 2184 | N TYR B 122 | -3.286 -4.900 88.804 | 1.00 15.44 | N |
| ATOM | 2185 | CA TYR B 122 | -3.519 -5.892 89.851 | 1.00 15.97 | C |
| ATOM | 2186 | C TYR B 122 | -2.222 -5.959 90.660 | 1.00 16.17 | C |
| ATOM | 2187 | O TYR B 122 | -1.266 -6.613 90.250 | 1.00 16.08 | O |
| ATOM | 2188 | CB TYR B 122 | -3.837 -7.256 89.263 | 1.00 16.33 | C |
| ATOM | 2189 | CG TYR B 122 | -5.192 -7.342 88.608 | 1.00 16.18 | C |
| ATOM | 2866 | N ASP B 207 | -8.818 -16.722 104.948 | 1.00 29.35 | N |
| ATOM | 2867 | CA ASP B 207 | -9.137 -15.316 105.212 | 1.00 29.51 | C |
| ATOM | 2868 | C ASP B 207 | -9.279 -14.440 103.942 | 1.00 27.92 | C |
| ATOM | 2869 | O ASP B 207 | -9.039 -13.236 103.973 | 1.00 28.27 | O |
| ATOM | 2870 | CB ASP B 207 | -8.078 -14.703 106.148 | 1.00 32.41 | C |
| ATOM | 2871 | CG ASP B 207 | -6.732 -14.486 105.457 | 1.00 36.44 | C |
| ATOM | 2872 | OD1 ASP B 207 | -6.342 -15.344 104.634 | 1.00 39.98 | O |
| ATOM | 2873 | OD2 ASP B 207 | -6.057 -13.469 105.739 | 1.00 37.23 | O |
| ATOM | 2874 | N ILE B 208 | -9.683 -15.045 102.831 | 1.00 25.56 | N |
| ATOM | 2875 | CA ILE B 208 | -9.830 -14.310 101.582 | 1.00 21.83 | C |
| ATOM | 2876 | C ILE B 208 | -10.960 -13.259 101.606 | 1.00 21.54 | C |
| ATOM | 2877 | O ILE B 208 | -10.883 -12.218 100.949 | 1.00 19.26 | O |
| ATOM | 2878 | CB ILE B 208 | -10.044 -15.298 100.425 | 1.00 20.10 | C |
| ATOM | 2879 | CG1 ILE B 208 | -9.852 -14.593 99.099 | 1.00 19.54 | C |
| ATOM | 2880 | CG2 ILE B 208 | -11.425 -15.919 100.515 | 1.00 18.97 | C |
| ATOM | 2881 | CD1 ILE B 208 | -9.544 -15.518 97.985 | 1.00 20.20 | C |
| ATOM | 2882 | N GLN B 209 | -12.005 -13.524 102.381 | 1.00 21.53 | N |
| ATOM | 2883 | CA GLN B 209 | -13.094 -12.581 102.452 | 1.00 21.16 | C |
| ATOM | 2884 | C GLN B 209 | -12.857 -11.504 103.516 | 1.00 21.89 | C |
| ATOM | 2885 | O GLN B 209 | -13.084 -10.320 103.256 | 1.00 21.96 | O |
| ATOM | 2886 | CB GLN B 209 | -14.412 -13.315 102.709 | 1.00 20.66 | C |
| ATOM | 2887 | CG GLN B 209 | -15.626 -12.536 102.236 | 1.00 20.15 | C |
| ATOM | 2888 | CD GLN B 209 | -16.907 -13.125 102.751 | 1.00 21.39 | C |
| ATOM | 2889 | OE1 GLN B 209 | -16.897 -13.891 103.705 | 1.00 23.81 | O |
| ATOM | 2890 | NE2 GLN B 209 | -18.035 -12.759 102.134 | 1.00 21.90 | N |
| ATOM | 2891 | N GLU B 210 | -12.383 -11.914 104.692 | 1.00 23.22 | N |
| ATOM | 2892 | CA GLU B 210 | -12.111 -10.980 105.790 | 1.00 24.14 | C |
| ATOM | 2893 | C GLU B 210 | -11.165 -9.902 105.343 | 1.00 21.96 | C |
| ATOM | 2894 | O GLU B 210 | -11.291 -8.765 105.761 | 1.00 21.89 | O |
| ATOM | 2895 | CB GLU B 210 | -11.487 -11.704 106.983 | 1.00 27.49 | C |
| ATOM | 2896 | CG GLU B 210 | -12.149 -13.021 107.277 | 1.00 34.45 | C |
| ATOM | 2897 | CD GLU B 210 | -11.750 -13.580 108.617 | 1.00 38.98 | C |
| ATOM | 2898 | OE1 GLU B 210 | -11.238 -12.793 109.449 | 1.00 40.42 | O |
| ATOM | 2899 | OE2 GLU B 210 | -11.963 -14.801 108.838 | 1.00 41.41 | O |
| ATOM | 2900 | N ASN B 211 | -10.202 -10.282 104.510 | 1.00 21.86 | N |
| ATOM | 2901 | CA ASN B 211 | -9.231 -9.349 103.975 | 1.00 21.74 | C |
| ATOM | 2902 | C ASN B 211 | -9.909 -8.298 103.109 | 1.00 20.18 | C |
| ATOM | 2903 | O ASN B 211 | -9.708 -7.104 103.311 | 1.00 20.13 | O |
| ATOM | 2904 | CB ASN B 211 | -8.205 -10.083 103.131 | 1.00 24.37 | C |
| ATOM | 2905 | CG ASN B 211 | -6.856 -10.098 103.771 | 1.00 28.07 | C |
| ATOM | 2906 | OD1 ASN B 211 | -6.257 -9.045 103.990 | 1.00 29.99 | O |
| ATOM | 2907 | ND2 ASN B 211 | -6.352 -11.292 104.083 | 1.00 29.35 | N |
| ATOM | 2908 | N PHE B 212 | -10.688 -8.752 102.132 | 1.00 17.70 | N |
| ATOM | 2909 | CA PHE B 212 | -11.410 -7.840 101.253 | 1.00 18.18 | C |
| ATOM | 2910 | C PHE B 212 | -12.309 -6.885 102.075 | 1.00 18.14 | C |
| ATOM | 2911 | O PHE B 212 | -12.209 -5.659 101.967 | 1.00 16.29 | O |
| ATOM | 2912 | CB PHE B 212 | -12.294 -8.636 100.262 | 1.00 15.20 | C |
| ATOM | 2913 | CG PHE B 212 | -13.353 -7.798 99.583 | 1.00 11.34 | C |
| ATOM | 2914 | CD1 PHE B 212 | -13.006 -6.780 98.705 | 1.00 7.88 | C |
| ATOM | 2915 | CD2 PHE B 212 | -14.708 -8.000 99.877 | 1.00 12.66 | C |
| ATOM | 2916 | CE1 PHE B 212 | -13.994 -5.956 98.130 | 1.00 9.56 | C |
| ATOM | 2917 | CE2 PHE B 212 | -15.709 -7.189 99.306 | 1.00 12.13 | C |
| ATOM | 2918 | CZ PHE B 212 | -15.352 -6.163 98.434 | 1.00 9.72 | C |
| ATOM | 2919 | N LEU B 213 | -13.166 -7.487 102.892 | 1.00 17.90 | N |
| ATOM | 2920 | CA LEU B 213 | -14.105 -6.750 103.733 | 1.00 19.47 | C |
| ATOM | 2921 | C LEU B 213 | -13.374 -5.768 104.622 | 1.00 19.11 | C |
| ATOM | 2922 | O LEU B 213 | -13.771 -4.606 104.755 | 1.00 19.13 | O |
| ATOM | 2923 | CB LEU B 213 | -14.938 -7.731 104.584 | 1.00 19.21 | C |
| ATOM | 2924 | CG LEU B 213 | -15.863 -8.679 103.775 | 1.00 18.64 | C |
| ATOM | 2925 | CD1 LEU B 213 | -16.137 -9.943 104.559 | 1.00 19.45 | C |
| ATOM | 2926 | CD2 LEU B 213 | -17.175 -7.996 103.421 | 1.00 19.54 | C |
| ATOM | 2927 | N TYR B 214 | -12.284 -6.236 105.213 | 1.00 18.67 | N |
| ATOM | 2928 | CA TYR B 214 | -11.490 -5.409 106.092 | 1.00 17.05 | C |
| ATOM | 2929 | C TYR B 214 | -10.993 -4.157 105.388 | 1.00 18.47 | C |
| ATOM | 2930 | O TYR B 214 | -11.227 -3.054 105.869 | 1.00 18.91 | O |
| ATOM | 2931 | CB TYR B 214 | -10.300 -6.192 106.615 | 1.00 18.15 | C |
| ATOM | 2932 | CG TYR B 214 | -9.400 -5.410 107.552 | 1.00 18.40 | C |
| ATOM | 2933 | CD1 TYR B 214 | -9.711 -5.288 108.899 | 1.00 17.14 | C |
| ATOM | 2934 | CD2 TYR B 214 | -8.220 -4.817 107.093 | 1.00 18.75 | C |
| ATOM | 2935 | CE1 TYR B 214 | -8.874 -4.603 109.779 | 1.00 18.61 | C |
| ATOM | 2936 | CE2 TYR B 214 | -7.367 -4.120 107.972 | 1.00 19.41 | C |
| ATOM | 2937 | CZ TYR B 214 | -7.710 -4.021 109.317 | 1.00 19.98 | C |
| ATOM | 2938 | OH TYR B 214 | -6.914 -3.329 110.213 | 1.00 21.64 | O |
| ATOM | 2939 | N TYR B 215 | -10.312 -4.327 104.249 | 1.00 17.63 | N |
| ATOM | 2940 | CA TYR B 215 | -9.747 -3.199 103.508 | 1.00 17.50 | C |
| ATOM | 2941 | C TYR B 215 | -10.722 -2.346 102.700 | 1.00 18.26 | C |
| ATOM | 2942 | O TYR B 215 | -10.389 -1.234 102.276 | 1.00 18.22 | O |
| ATOM | 2943 | CB TYR B 215 | -8.599 -3.672 102.604 | 1.00 16.50 | C |
| ATOM | 2944 | CG TYR B 215 | -7.338 -4.010 103.377 | 1.00 17.72 | C |
| ATOM | 2945 | CD1 TYR B 215 | -7.000 -5.338 103.687 | 1.00 16.30 | C |
| ATOM | 2946 | CD2 TYR B 215 | -6.510 -3.000 103.877 | 1.00 17.88 | C |
| ATOM | 2947 | CE1 TYR B 215 | -5.866 -5.651 104.484 | 1.00 11.85 | C |
| ATOM | 2948 | CE2 TYR B 215 | -5.379 -3.298 104.672 | 1.00 15.77 | C |
| ATOM | 2949 | CZ TYR B 215 | -5.063 -4.622 104.971 | 1.00 14.06 | C |
| ATOM | 2950 | OH TYR B 215 | -3.937 -4.896 105.740 | 1.00 11.98 | O |
| ATOM | 2951 | N GLU B 216 | -11.927 -2.862 102.488 | 1.00 19.22 | N |

FIG. 9 (con't)

| | | | | | | | | | | | | |
|---|---|---|---|---|---|---|---|---|---|---|---|---|
| ATOM | 2190 | CD1 | TYR B 122 | -5.356 | -7.073 | 87.250 | 1.00 | 16.99 | | | | C |
| ATOM | 2191 | CD2 | TYR B 122 | -6.307 | -7.724 | 89.342 | 1.00 | 16.95 | | | | C |
| ATOM | 2192 | CE1 | TYR B 122 | -6.611 | -7.193 | 86.638 | 1.00 | 18.46 | | | | C |
| ATOM | 2193 | CE2 | TYR B 122 | -7.560 | -7.845 | 88.754 | 1.00 | 16.77 | | | | C |
| ATOM | 2194 | CZ | TYR B 122 | -7.711 | -7.581 | 87.403 | 1.00 | 19.17 | | | | C |
| ATOM | 2195 | OH | TYR B 122 | -8.962 | -7.703 | 86.837 | 1.00 | 18.02 | | | | O |
| ATOM | 2196 | N | VAL B 123 | -2.190 | -5.276 | 91.799 | 1.00 | 16.34 | | | | N |
| ATOM | 2197 | CA | VAL B 123 | -1.012 | -5.252 | 92.647 | 1.00 | 16.27 | | | | C |
| ATOM | 2198 | C | VAL B 123 | -1.342 | -5.837 | 93.997 | 1.00 | 17.21 | | | | C |
| ATOM | 2199 | O | VAL B 123 | -2.515 | -5.954 | 94.351 | 1.00 | 17.42 | | | | O |
| ATOM | 2200 | CB | VAL B 123 | -0.468 | -3.818 | 92.883 | 1.00 | 14.39 | | | | C |
| ATOM | 2201 | CG1 | VAL B 123 | 0.824 | -3.634 | 92.155 | 1.00 | 13.34 | | | | C |
| ATOM | 2202 | CG2 | VAL B 123 | -1.460 | -2.789 | 92.414 | 1.00 | 13.79 | | | | C |
| ATOM | 2203 | N | SER B 124 | -0.299 | -6.179 | 94.755 | 1.00 | 17.17 | | | | N |
| ATOM | 2204 | CA | SER B 124 | -0.451 | -6.765 | 96.086 | 1.00 | 17.43 | | | | C |
| ATOM | 2205 | C | SER B 124 | -0.827 | -5.711 | 97.119 | 1.00 | 17.04 | | | | C |
| ATOM | 2206 | O | SER B 124 | -1.564 | -5.991 | 98.065 | 1.00 | 18.00 | | | | O |
| ATOM | 2207 | CB | SER B 124 | 0.850 | -7.469 | 96.498 | 1.00 | 16.15 | | | | C |
| ATOM | 2208 | OG | SER B 124 | 1.941 | -6.563 | 96.576 | 1.00 | 14.06 | | | | O |
| ATOM | 2209 | N | SER B 125 | -0.334 | -4.499 | 96.931 | 1.00 | 17.34 | | | | N |
| ATOM | 2210 | CA | SER B 125 | -0.632 | -3.436 | 97.873 | 1.00 | 17.65 | | | | C |
| ATOM | 2211 | C | SER B 125 | -0.738 | -2.103 | 97.160 | 1.00 | 16.78 | | | | C |
| ATOM | 2212 | O | SER B 125 | -0.131 | -1.909 | 96.107 | 1.00 | 17.41 | | | | O |
| ATOM | 2213 | CB | SER B 125 | 0.465 | -3.347 | 98.921 | 1.00 | 19.10 | | | | C |
| ATOM | 2214 | OG | SER B 125 | 1.689 | -2.970 | 98.303 | 1.00 | 23.89 | | | | O |
| ATOM | 2215 | N | SER B 126 | -1.495 | -1.189 | 97.753 | 1.00 | 16.73 | | | | N |
| ATOM | 2216 | CA | SER B 126 | -1.676 | 0.156 | 97.218 | 1.00 | 16.16 | | | | C |
| ATOM | 2217 | C | SER B 126 | -0.321 | 0.846 | 97.102 | 1.00 | 15.14 | | | | C |
| ATOM | 2218 | O | SER B 126 | 0.621 | 0.482 | 97.784 | 1.00 | 14.33 | | | | O |
| ATOM | 2219 | CB | SER B 126 | -2.580 | 0.982 | 98.146 | 1.00 | 16.63 | | | | C |
| ATOM | 2220 | OG | SER B 126 | -1.949 | 1.285 | 99.393 | 1.00 | 18.88 | | | | O |
| ATOM | 2221 | N | PRO B 127 | -0.226 | 1.866 | 96.243 | 1.00 | 16.79 | | | | N |
| ATOM | 2222 | CA | PRO B 127 | 1.024 | 2.613 | 96.033 | 1.00 | 18.72 | | | | C |
| ATOM | 2223 | C | PRO B 127 | 1.465 | 3.449 | 97.249 | 1.00 | 19.06 | | | | C |
| ATOM | 2224 | O | PRO B 127 | 0.657 | 3.785 | 98.121 | 1.00 | 18.57 | | | | O |
| ATOM | 2225 | CB | PRO B 127 | 0.708 | 3.471 | 94.807 | 1.00 | 18.56 | | | | C |
| ATOM | 2226 | CG | PRO B 127 | -0.770 | 3.751 | 94.973 | 1.00 | 19.12 | | | | C |
| ATOM | 2227 | CD | PRO B 127 | -1.315 | 2.408 | 95.402 | 1.00 | 18.60 | | | | C |
| ATOM | 2228 | N | CYS B 128 | 2.752 | 3.759 | 97.309 | 1.00 | 20.85 | | | | N |
| ATOM | 2229 | CA | CYS B 128 | 3.280 | 4.540 | 98.403 | 1.00 | 22.90 | | | | C |
| ATOM | 2230 | C | CYS B 128 | 3.076 | 6.012 | 98.085 | 1.00 | 23.71 | | | | C |
| ATOM | 2231 | O | CYS B 128 | 2.570 | 6.354 | 97.011 | 1.00 | 23.05 | | | | O |
| ATOM | 2232 | CB | CYS B 128 | 4.774 | 4.246 | 98.622 | 1.00 | 23.04 | | | | C |
| ATOM | 2233 | SG | CYS B 128 | 5.891 | 4.647 | 97.240 | 1.00 | 24.18 | | | | S |
| ATOM | 2234 | N | ALA B 129 | 3.453 | 6.867 | 99.024 | 1.00 | 24.79 | | | | N |
| ATOM | 2235 | CA | ALA B 129 | 3.289 | 8.299 | 98.861 | 1.00 | 25.62 | | | | C |
| ATOM | 2236 | C | ALA B 129 | 3.940 | 8.779 | 97.589 | 1.00 | 25.75 | | | | C |
| ATOM | 2237 | O | ALA B 129 | 3.333 | 9.515 | 96.813 | 1.00 | 26.64 | | | | O |
| ATOM | 2238 | CB | ALA B 129 | 3.878 | 9.017 | 100.050 | 1.00 | 27.15 | | | | C |
| ATOM | 2239 | N | ALA B 130 | 5.177 | 8.359 | 97.368 | 1.00 | 26.43 | | | | N |
| ATOM | 2240 | CA | ALA B 130 | 5.914 | 8.763 | 96.178 | 1.00 | 27.45 | | | | C |
| ATOM | 2241 | C | ALA B 130 | 5.293 | 8.216 | 94.891 | 1.00 | 28.53 | | | | C |
| ATOM | 2242 | O | ALA B 130 | 5.138 | 8.947 | 93.915 | 1.00 | 29.62 | | | | O |
| ATOM | 2243 | CB | ALA B 130 | 7.358 | 8.322 | 96.293 | 1.00 | 25.77 | | | | C |
| ATOM | 2244 | N | CYS B 131 | 4.954 | 6.932 | 94.881 | 1.00 | 28.75 | | | | N |
| ATOM | 2245 | CA | CYS B 131 | 4.354 | 6.333 | 93.701 | 1.00 | 29.91 | | | | C |
| ATOM | 2246 | C | CYS B 131 | 3.021 | 6.987 | 93.328 | 1.00 | 29.50 | | | | C |
| ATOM | 2247 | O | CYS B 131 | 2.719 | 7.184 | 92.152 | 1.00 | 28.24 | | | | O |
| ATOM | 2248 | CB | CYS B 131 | 4.159 | 4.832 | 93.920 | 1.00 | 30.09 | | | | C |
| ATOM | 2249 | SG | CYS B 131 | 5.693 | 3.919 | 93.746 | 1.00 | 32.76 | | | | S |
| ATOM | 2250 | N | ALA B 132 | 2.237 | 7.332 | 94.339 | 1.00 | 29.93 | | | | N |
| ATOM | 2251 | CA | ALA B 132 | 0.959 | 7.975 | 94.110 | 1.00 | 31.40 | | | | C |
| ATOM | 2252 | C | ALA B 132 | 1.163 | 9.281 | 93.332 | 1.00 | 31.89 | | | | C |
| ATOM | 2253 | O | ALA B 132 | 0.409 | 9.583 | 92.410 | 1.00 | 32.31 | | | | O |
| ATOM | 2254 | CB | ALA B 132 | 0.286 | 8.251 | 95.427 | 1.00 | 30.62 | | | | C |
| ATOM | 2255 | N | ASP B 133 | 2.187 | 10.044 | 93.695 | 1.00 | 32.98 | | | | N |
| ATOM | 2256 | CA | ASP B 133 | 2.459 | 11.292 | 93.005 | 1.00 | 35.62 | | | | C |
| ATOM | 2257 | C | ASP B 133 | 2.791 | 11.055 | 91.545 | 1.00 | 36.66 | | | | C |
| ATOM | 2258 | O | ASP B 133 | 2.246 | 11.722 | 90.663 | 1.00 | 37.83 | | | | O |
| ATOM | 2259 | CB | ASP B 133 | 3.612 | 12.054 | 93.662 | 1.00 | 37.11 | | | | C |
| ATOM | 2260 | CG | ASP B 133 | 3.202 | 12.736 | 94.947 | 1.00 | 38.64 | | | | C |
| ATOM | 2261 | OD1 | ASP B 133 | 2.028 | 13.170 | 95.052 | 1.00 | 39.37 | | | | O |
| ATOM | 2262 | OD2 | ASP B 133 | 4.050 | 12.858 | 95.849 | 1.00 | 40.21 | | | | O |
| ATOM | 2263 | N | ARG B 134 | 3.691 | 10.117 | 91.282 | 1.00 | 37.48 | | | | N |
| ATOM | 2952 | CA | GLU B 216 | -12.929 | -2.129 | 101.740 | 1.00 | 18.65 | | | | C |
| ATOM | 2953 | C | GLU B 216 | -13.440 | -0.999 | 102.612 | 1.00 | 20.05 | | | | C |
| ATOM | 2954 | O | GLU B 216 | -13.668 | 0.114 | 102.133 | 1.00 | 19.98 | | | | O |
| ATOM | 2955 | CB | GLU B 216 | -14.089 | -3.045 | 101.340 | 1.00 | 16.09 | | | | C |
| ATOM | 2956 | CG | GLU B 216 | -15.310 | -2.275 | 100.837 | 1.00 | 18.00 | | | | C |
| ATOM | 2957 | CD | GLU B 216 | -16.406 | -3.138 | 100.197 | 1.00 | 21.54 | | | | C |
| ATOM | 2958 | OE1 | GLU B 216 | -16.961 | -4.040 | 100.861 | 1.00 | 21.13 | | | | O |
| ATOM | 2959 | OE2 | GLU B 216 | -16.736 | -2.898 | 99.006 | 1.00 | 21.35 | | | | O |
| ATOM | 2960 | N | GLU B 217 | -13.599 | -1.299 | 103.904 | 1.00 | 22.30 | | | | N |
| ATOM | 2961 | CA | GLU B 217 | -14.093 | -0.335 | 104.895 | 1.00 | 23.96 | | | | C |
| ATOM | 2962 | C | GLU B 217 | -13.101 | 0.835 | 105.018 | 1.00 | 22.43 | | | | C |
| ATOM | 2963 | O | GLU B 217 | -13.510 | 2.001 | 105.018 | 1.00 | 20.15 | | | | O |
| ATOM | 2964 | CB | GLU B 217 | -14.305 | -1.044 | 106.252 | 1.00 | 25.99 | | | | C |
| ATOM | 2965 | CG | GLU B 217 | -15.320 | -0.345 | 107.179 | 1.00 | 32.14 | | | | C |
| ATOM | 2966 | CD | GLU B 217 | -14.685 | 0.364 | 108.378 | 1.00 | 35.99 | | | | C |
| ATOM | 2967 | OE1 | GLU B 217 | -13.676 | 1.086 | 108.208 | 1.00 | 38.81 | | | | O |
| ATOM | 2968 | OE2 | GLU B 217 | -15.211 | 0.213 | 109.499 | 1.00 | 37.92 | | | | O |
| ATOM | 2969 | N | LYS B 218 | -11.811 | 0.493 | 105.080 | 1.00 | 21.85 | | | | N |
| ATOM | 2970 | CA | LYS B 218 | -10.718 | 1.468 | 105.203 | 1.00 | 23.65 | | | | C |
| ATOM | 2971 | C | LYS B 218 | -10.700 | 2.428 | 104.021 | 1.00 | 23.83 | | | | C |
| ATOM | 2972 | O | LYS B 218 | -10.919 | 3.625 | 104.184 | 1.00 | 25.41 | | | | O |
| ATOM | 2973 | CB | LYS B 218 | -9.350 | 0.757 | 105.258 | 1.00 | 24.64 | | | | C |
| ATOM | 2974 | CG | LYS B 218 | -9.276 | -0.470 | 106.159 | 1.00 | 24.37 | | | | C |
| ATOM | 2975 | CD | LYS B 218 | -9.560 | -0.156 | 107.610 | 1.00 | 21.91 | | | | C |
| ATOM | 2976 | CE | LYS B 218 | -9.364 | 1.406 | 108.432 | 1.00 | 22.06 | | | | C |
| ATOM | 2977 | NZ | LYS B 218 | -9.899 | -1.270 | 109.802 | 1.00 | 20.19 | | | | N |
| ATOM | 2978 | N | LEU B 219 | -10.437 | 1.889 | 102.833 | 1.00 | 21.86 | | | | N |
| ATOM | 2979 | CA | LEU B 219 | -10.373 | 2.684 | 101.616 | 1.00 | 20.85 | | | | C |
| ATOM | 2980 | C | LEU B 219 | -11.591 | 3.593 | 101.480 | 1.00 | 22.27 | | | | C |
| ATOM | 2981 | O | LEU B 219 | -11.497 | 4.715 | 100.979 | 1.00 | 19.24 | | | | O |
| ATOM | 2982 | CB | LEU B 219 | -10.273 | 1.747 | 100.408 | 1.00 | 18.92 | | | | C |
| ATOM | 2983 | CG | LEU B 219 | -10.051 | 2.379 | 99.042 | 1.00 | 16.09 | | | | C |
| ATOM | 2984 | CD1 | LEU B 219 | -8.661 | 2.983 | 99.026 | 1.00 | 13.42 | | | | C |
| ATOM | 2985 | CD2 | LEU B 219 | -10.224 | 1.333 | 97.936 | 1.00 | 16.07 | | | | C |
| ATOM | 2986 | N | ALA B 220 | -12.736 | 3.097 | 101.952 | 1.00 | 25.41 | | | | N |
| ATOM | 2987 | CA | ALA B 220 | -13.988 | 3.846 | 101.884 | 1.00 | 28.52 | | | | C |
| ATOM | 2988 | C | ALA B 220 | -13.892 | 5.113 | 102.723 | 1.00 | 30.96 | | | | C |
| ATOM | 2989 | O | ALA B 220 | -14.068 | 6.217 | 102.210 | 1.00 | 30.08 | | | | O |
| ATOM | 2990 | CB | ALA B 220 | -15.150 | 2.977 | 102.365 | 1.00 | 26.98 | | | | C |
| ATOM | 2991 | N | ASP B 221 | -13.599 | 4.941 | 104.009 | 1.00 | 33.78 | | | | N |
| ATOM | 2992 | CA | ASP B 221 | -13.505 | 6.077 | 104.916 | 1.00 | 37.59 | | | | C |
| ATOM | 2993 | C | ASP B 221 | -12.552 | 7.128 | 104.368 | 1.00 | 38.11 | | | | C |
| ATOM | 2994 | O | ASP B 221 | -12.830 | 8.321 | 104.433 | 1.00 | 38.48 | | | | O |
| ATOM | 2995 | CB | ASP B 221 | -13.028 | 5.635 | 106.315 | 1.00 | 40.16 | | | | C |
| ATOM | 2996 | CG | ASP B 221 | -14.006 | 4.635 | 107.005 | 1.00 | 43.53 | | | | C |
| ATOM | 2997 | OD1 | ASP B 221 | -15.233 | 4.963 | 106.965 | 1.00 | 46.44 | | | | O |
| ATOM | 2998 | OD2 | ASP B 221 | -13.559 | 3.688 | 107.606 | 1.00 | 45.17 | | | | O |
| ATOM | 2999 | N | ILE B 222 | -11.435 | 6.668 | 103.818 | 1.00 | 38.63 | | | | N |
| ATOM | 3000 | CA | ILE B 222 | -10.425 | 7.559 | 103.277 | 1.00 | 40.29 | | | | C |
| ATOM | 3001 | C | ILE B 222 | -10.914 | 8.352 | 102.083 | 1.00 | 42.08 | | | | C |
| ATOM | 3002 | O | ILE B 222 | -10.880 | 9.583 | 102.089 | 1.00 | 42.27 | | | | O |
| ATOM | 3003 | CB | ILE B 222 | -9.195 | 6.775 | 102.862 | 1.00 | 39.79 | | | | C |
| ATOM | 3004 | CG1 | ILE B 222 | -8.751 | 5.882 | 104.023 | 1.00 | 40.01 | | | | C |
| ATOM | 3005 | CG2 | ILE B 222 | -8.082 | 7.731 | 102.500 | 1.00 | 39.63 | | | | C |
| ATOM | 3006 | CD1 | ILE B 222 | -7.862 | 4.734 | 103.613 | 1.00 | 38.98 | | | | C |
| ATOM | 3007 | N | LEU B 223 | -11.372 | 7.644 | 101.057 | 1.00 | 44.39 | | | | N |
| ATOM | 3008 | CA | LEU B 223 | -11.859 | 8.290 | 99.843 | 1.00 | 46.41 | | | | C |
| ATOM | 3009 | C | LEU B 223 | -13.179 | 9.056 | 99.993 | 1.00 | 48.87 | | | | C |
| ATOM | 3010 | O | LEU B 223 | -13.501 | 9.891 | 99.151 | 1.00 | 49.25 | | | | O |
| ATOM | 3011 | CB | LEU B 223 | -12.006 | 7.254 | 98.723 | 1.00 | 45.14 | | | | C |
| ATOM | 3012 | CG | LEU B 223 | -10.752 | 6.854 | 97.936 | 1.00 | 43.65 | | | | C |
| ATOM | 3013 | CD1 | LEU B 223 | -9.676 | 6.365 | 98.874 | 1.00 | 41.82 | | | | C |
| ATOM | 3014 | CD2 | LEU B 223 | -11.112 | 5.771 | 96.939 | 1.00 | 42.54 | | | | C |
| ATOM | 3015 | N | LYS B 224 | -13.936 | 8.791 | 101.054 | 1.00 | 51.02 | | | | N |
| ATOM | 3016 | CA | LYS B 224 | -15.216 | 9.468 | 101.232 | 1.00 | 54.51 | | | | C |
| ATOM | 3017 | C | LYS B 224 | -15.841 | 9.160 | 102.590 | 1.00 | 55.71 | | | | C |
| ATOM | 3018 | O | LYS B 224 | -17.085 | 9.046 | 102.658 | 1.00 | 56.14 | | | | O |
| ATOM | 3019 | CB | LYS B 224 | -16.177 | 9.021 | 100.115 | 1.00 | 56.73 | | | | C |
| ATOM | 3020 | CG | LYS B 224 | -16.456 | 7.515 | 100.122 | 1.00 | 59.20 | | | | C |
| ATOM | 3021 | CD | LYS B 224 | -16.664 | 6.952 | 98.723 | 1.00 | 61.17 | | | | C |
| ATOM | 3022 | CE | LYS B 224 | -16.675 | 5.424 | 98.732 | 1.00 | 61.91 | | | | C |
| ATOM | 3023 | NZ | LYS B 224 | -16.718 | 4.856 | 97.349 | 1.00 | 62.77 | | | | N |
| ATOM | 3024 | OXT | LYS B 224 | -15.079 | 9.047 | 103.571 | 1.00 | 57.28 | | | | O |
| TER | 3025 | | LYS B 224 | | | | | | | | | |

THREE-DIMENSIONAL STRUCTURE OF THE APOBEC 2 STRUCTURE, USES THEREOF, AND METHODS FOR TREATING CHRONIC AND INFECTIOUS DISEASES

RELATED APPLICATION

This application claims the benefit of and priority to U.S. Provisional Application Ser. No. 61/016,172, filed Dec. 21, 2007, the contents of which are incorporated by reference herein in its entirety.

GOVERNMENT SUPPORT

This invention was made with government support under Contract No. AI055926 awarded by the National Institutes of Health. The government has certain rights in this invention.

BACKGROUND

Sequence Listing

This application contains a sequence listing, submitted in both paper and a Computer Readable Form (CRF) and filed electronically via EFS. The file is entitled "APO2. txt", is 6,779 bytes in size (measured in Windows XP) and was created on Dec. 19, 2008.

FILED OF DISCLOSURE

The present disclosure relates generally to the information provided by the three-dimensional structure of APOBEC-2 and other structure models of any APOBEC proteins obtained by computer modeling that bears similarity with a root-mean-square deviation (RMSD) of 2.0 with the APOBEC-2 monomer, dimer or tetramer. Additionally, the present disclosure relates to the uses of the three-dimensional structure of APOBEC-2 and models of APOBEC proteins particularly for structure-based drug design of compounds, peptides or mutant APOBEC proteins designed to treat Hyper-IgM-2 Syndrome, B cell lymphomas and lentivirus infections, particularly the human immunodeficiency virus (HIV) infection.

General Background

APOBEC-2 (APO2) belongs to the Apolioprotein B (APOB) mRNA-editing enzyme catalytic polypeptide (APOBEC) family of cytidine deaminases found exclusively in vertebrates (6). APOBEC nucleic acid deaminases modify genes by deaminating cytosines in mRNA coding sequences and in single-stranded DNA (6). Additionally, these enzymes can inhibit the replication of retroviruses, such as the human immunodeficiency virus (HIV) and hepatitis B virus (HBV), and retrotransposons. (4,5,6,7).

The APOBEC family is composed of APOBEC-1 (APO1), APOBEC-2, Activation Induced Cytidine Deaminase (AID), APOBEC-3 (3A, 3B, 3C, 3D, 3E, 3F, 3G, and 3H) and APOBEC-4 (2). APO1, the first member to be characterized, deaminates $C^{6666} \rightarrow U$ in the APOB mRNA thereby creating a premature stop codon, which results in a truncated APOB100 protein (APOB48) with a different function. Of the APOBEC3 subgroup of enzymes, APOBEC-3B (A3B), APOBEC-3F (A3F) and APOBEC-3G (A3G) have two cytidine deaminase domains (CDAs) and inhibit HIV-1 replication in the absence of the HIV viral infectivity factor protein (Vif) (4,5,6,7). In this setting, the APOBEC enzymes are incorporated into HIV virions and introduce multiple $dC \rightarrow dU$ deaminations on the minus strand of HIV viral cDNA formed during reverse transcription. Additionally, APOBEC enzymes inhibit HIV replication by a less characterized mechanism that is independent of deamination activity. APOBEC3 proteins also shield the human genome from the deleterious action of endogenous retrotransposons: A3A, A3B, A3C and A3F inhibit LINE 1 and Alu retrotransposition.

AID and APO2 have a single CDA homology domain and are phylogenetically the most ancient members of the APOBEC family (2). AID induces somatic hypermutation (SHM) and class switch recombination (CSR) in activated germinal center B cells (3). Specific point mutations in AID are responsible for an immunodeficiency disease, Hyper-IgM-2 (HIGM-2) syndrome, which is characterized by a deficiency in isotype-switched and high affinity antibody formation (14,15). Additionally, aberrant expression of AID can induce B cell lymphomas (1,29).

APO2, also known as ARCD-1, is ubiquitously expressed at low levels in both human and mouse and highly expressed in cardiac and skeletal muscle (16). APO2 can form heterodimers with APO1 and inhibit APOB mRNA deamination by APO1 (16). APO2 is encapsulated into HIV-1 virions when co-expressed with Δvif HIV-1 DNA in 293T cells (21). However, studies fail to show that APO2 inhibits HIV-1 viral replication (21).

The APOBEC proteins use the same deamination activity and RNA binding properties to achieve diverse human biological functions. A comprehension of the molecular mechanisms of the APOBEC enzymes has been limited by the lack of 3-dimensional structures. Therefore, there is a need in the art for solving a 3-dimensional structure of APOBEC-2 and creating 3-dimensional models of other APOBEC enzymes derived from the APOBEC-2 structure.

Patients diagnosed with Hyper-IgM-2 Syndrome suffer from severe and recurrent infections throughout their lifetime. Currently, the only cure for Hyper-IgM-2 Syndrome is a bone marrow transplant if it is possible. The only treatment available is lifelong immunoglobulin replacement therapy. Given that mutations in the gene encoding the APOBEC protein, AID, cause Hyper-IgM-2 Syndrome, there is a need in the art for using information provided by the 3-dimensional structure of an APOBEC protein (such as APOBEC-2) to design drugs or mutant AID enzymes to serve as a cure or treatment for this chronic disease.

There is a need in the art for using the information provided by the 3-dimensional structure of an APOBEC protein (such as APOBEC-2) to design drugs that can affect the deamination activity of APOBEC proteins. The aberrant expression and deamination activity of AID has been shown to result in B cell lymphoma (1,29). Drugs that can restore the proper function of APOBEC deaminases and the timing of their function could prevent or treat B cell lymphomas.

HIV is a human retrovirus which leads to the depletion of CD4+ T lymphocytes resulting in the acquired immunodeficiency syndrome (AIDS). AIDS is characterized by various pathological conditions, including immune incompetence, opportunistic infections, neurological dysfunctions, and neoplastic growth. HIV-1 relies on Vif (virion infectivity factor), a protein encoded by HIV-1 and many related primate lentiviruses, to evade the potent innate antiviral function of APOBEC3G (also known as CEM15) and APOBEC3F in vivo. Most of the APOBEC-3 proteins are DNA cytidine deaminases that are incorporated into virions and produce extensive hypermutation in newly synthesized viral DNA formed during reverse transcription. These proteins can also inhibit HIV replication by a less characterized mechanism that is independent of deamination activity but that involves RNA binding.

Despite the availability of a number of drugs to combat HIV infections, there is a need in the art for additional drugs that inhibit HIV replication, and which are suitable for treating HIV and other lentiviral infections. The present invention addresses this need by providing structure based methods for identifying agents that target APOBEC enzymes and prevent Vif mediated degradation of APOBEC3G, APOBEC3F or other APOBEC enzymes that can restrict HIV replication under certain conditions.

There is a need in the art for using the information provided by the 3-dimensional structure of an APOBEC protein (such as APOBEC-2) to design drugs that can affect the oligomerization of the APOBEC protein. It has been demonstrated that oligomerization of APOBEC proteins occurs in vivo and in vitro. Information provided by the APOBEC-2 structure suggests this oligomerization is important for the biological functions of these enzymes. Drugs designed to affect oligomerization of APOBEC enzymes may enhance or restrict their biological functions, such as, deamination activity, RNA binding properties and viral restriction.

There is a need in the art for designing or identifying compounds that mimic, enhance, disrupt or compete with the interactions of APOBEC proteins with their substrates and other cellular or viral proteins, such as HIV Vif. Knowledge of the three-dimensional structure of the protein enables a skilled artisan to design a compound that has a specific and appropriate conformation to achieve such an objective. Information from the three dimensional structure of the protein also enables a skilled artisan strategically select such a compound from available libraries of compounds. For example, knowledge of the three dimensional structure of APOBEC-2 enables one of skill in the art to design a compound that binds to APOBEC-2 or other APOBEC proteins that can inhibition interactions with the HIV Vif protein and restore the ability of APOBEC proteins to restrict HIV viral replication.

SUMMARY

One embodiment of the present disclosure provides structural information derived from the APOBEC-2 crystal structure and models of related APOBEC proteins obtained by computer modeling that bears similarity with a root-mean-square deviation (RMSD) of 2.0 with the APOBEC-2 monomer, dimer or tetramer. Additionally, other embodiments of the present disclosure provide methods for using this structural information to design drugs to treat chronic diseases, such as Hyper-IgM-2 Syndrome, B cell lymphomas, and infectious lentiviral infections, such as HIV. Yet other embodiments of the present disclosure drugs and related methods to affect the DNA or RNA binding properties, zinc coordination and/or oligomerization of APOBEC proteins. Additionally, yet other embodiments of the present disclosure include drugs and related methods to inhibit interactions with other cellular or viral proteins, including but not limited to, HIV Vif. The present disclosure provides these and other additional advantages described herein.

Definitions

According to the present disclosure, APOBEC-2 can be defined as a protein that is characterized by the amino acid sequence represented in FIG. 3a including amino acids 41-224. Additionally, APOBEC-2 can be defined as a protein including amino acids 1-224 filed in the NCBI Genebank data base(AAD45360; GI:5566287). According to the present disclosure, general reference to the APOBEC-2 protein is a protein that, at a minimum, includes an APOBEC-2 monomer, dimer or tetramer and may include other biologically active fragments of APOBEC proteins.

A "homologue" of an APOBEC protein, or "homologous" APOBEC protein, includes proteins which differ from a naturally occurring APOBEC protein in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). Preferably, an APOBEC homologue has a buried amino acid sequence that is at least 70% similar in chemical nature (such as polar or hydrophobic), if not identical, to the amino acid sequence of a naturally occurring APOBEC protein, and more preferably, at least about 75%, and more preferably, at least about 80%, and more preferably, at least about 85%, and more preferably, at least about 90%, and more preferably, at least about 95% identical to the amino acid sequence of a naturally occurring APOBEC protein. Preferred three-dimensional structural homologues of an APOBEC protein are described in detail below.

According to the present disclosure, an APOBEC "homologue", or a "homologous" APOBEC protein, preferably has, at a minimum, one or two cytidine deamination motifs that consists of H-X-E-$X_{23-28}$-P-C-$X_{24}$-C (H=Histidine; X=any amino acid; E=Glutamic Acid; P=Proline; and C=Cysteine) (SEC) ID NO: 64).

In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications of a protein, such as in a homologue or mimetic (discussed below), may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action of a protein. Similarly, modifications which result in an increase in protein expression or an increase in the activity of the protein can be referred to as amplification, overproduction, activation, enhancement, up-regulation or increased action of a protein. As used herein, a protein that has "biological activity" refers to a protein that has an activity that can include any one, and preferably more than one, of the following characteristics: (a) binds to the following APOBEC substrates: DNA, RNA or zinc; (b) deaminates cytosines to uracils in single-stranded DNA or RNA.

An isolated protein, according to the present disclosure, is a protein that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein, and particularly, an isolated APOBEC protein, is produced recombinantly.

Proteins of the present disclosure are preferably retrieved, obtained, and/or used in "substantially pure" form. As used herein, "substantially pure" refers to a purity that allows for the effective use of the protein in vitro, ex vivo or in vivo according to the present disclosure. For a protein to be useful in an in vitro, ex vivo or in vivo method according to the present disclosure, it is substantially free of contaminants, other proteins and/or chemicals that might interfere or that would interfere with its use in a method disclosed by the present disclosure, or that at least would be undesirable for inclusion with the protein when it is used in a method disclosed by the present disclosure. Preferably, a "substantially pure" protein, as referenced herein, is a protein that can be produced by any method (i.e., by direct purification from a natural source, recombinantly, or synthetically), and that has been purified from other protein components such that the protein comprises at least about 80% weight/weight of the total protein in a given composition (i.e., the protein is about 80% of the protein in a solution/composition/buffer), and more preferably, at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99%, weight/weight of the total protein in a given composition.

As used herein, a "structure" of a protein refers to the components and the manner of arrangement of the components to constitute the protein. The "three dimensional structure" or "tertiary structure" of the protein refers to the arrangement of the components of the protein in three dimensions. Such term is well known to those of skill in the art. It is also to be noted that the terms "tertiary" and "three dimensional" can be used interchangeably.

As used herein, the terms "crystalline APOBEC-2", "APOBEC-2 crystal", "APOBEC crystal" refer to crystallized APOBEC-2 or APOBEC protein and are intended to be used interchangeably. Preferably, a crystalline APOBEC is produced using the crystal formation method described herein, in particular according to the method disclosed in Example 1. An APOBEC-2 crystal of the present disclosure can comprise any crystal structure and preferably crystallizes as an orthorhombic crystal lattice. A suitable crystalline APOBEC-2 of the present disclosure includes a monomer or a dimer, or tetramer of APOBEC-2 protein. One preferred crystalline APOBEC-2 comprises between one and four APOBEC-2 proteins in an asymmetric unit. Preferably, a composition of the present disclosure includes APOBEC-2 protein molecules arranged in a crystalline manner in a space group $P2_12_12_1$ so as to form a unit cell of dimensions a=37.841 Å, b=89.41 Å, c=245.77 Å. A preferred crystal of the present disclosure provides X-ray diffraction data for determination of atomic coordinates of the APOBEC-2 protein to a resolution of about 4.0 Å, and preferably to about 3.0 Å, and more preferably to about 2.0 Å.

As used herein, the term "model" refers to a representation in a tangible medium of the three-dimensional structure of a protein, polypeptide or peptide. For example, a model can be a representation of the three dimensional structure in an electronic file, on a computer screen, on a piece of paper (i.e., on a two dimensional medium), and/or as a ball-and-stick figure. Physical three-dimensional models are tangible and include, but are not limited to, stick models and space-filling models. The phrase "imaging the model on a computer screen" refers to the ability to express (or represent) and manipulate the model on a computer screen using appropriate computer hardware and software technology known to those skilled in the art. Such technology is available from a variety of sources including, for example, Evans and Sutherland, Salt Lake City, Utah, and Biosym Technologies, San Diego, Calif. The phrase "providing a picture of the model" refers to the ability to generate a "hard copy" of the model. Hard copies include both motion and still pictures. Computer screen images and pictures of the model can be visualized in a number of formats including space-filling representations, a carbon traces, ribbon diagrams and electron density maps.

As used herein, the phrase "common amino acid side chains" refers to amino acid side chains that are common to both the structural homologue and to the structure that is actually represented by such atomic coordinates.

According to the present disclosure, the phrase "providing a three dimensional structure of APOBEC protein" is defined as any means of providing, supplying, accessing, displaying, retrieving, or otherwise making available the three dimensional structure of APOBEC-2 or a three dimensional computer generated structure model of an APOBEC protein. For example, the step of providing can include, but is not limited to, accessing the atomic coordinates for the structure from a database; importing the atomic coordinates for the structure into a computer or other database; displaying the atomic coordinates and/or a model of the structure in any manner, such as on a computer, on paper, etc.; and determining the three dimensional structure of APOBEC-2 de novo using the guidance provided herein.

As used herein, structure based drug design refers to the prediction of a conformation of a peptide, polypeptide, protein, or conformational of an interaction between a peptide or polypeptide, and a compound, using the three dimensional structure of the peptide, polypeptide or protein. Typically, structure based drug design is performed with a computer. For example, generally, for a protein to effectively interact with (or bind to) a compound, it is necessary that the three dimensional structure of the compound assume a compatible conformation that allows the compound to bind to the protein in such a manner that a desired result is obtained upon binding.

DRAWINGS

The patent or application file contains at least one drawing executed in color. Copies of this patent or patent application publication with color drawing(s) will be provided by the Office upon request and payment of the necessary fee.

The above-mentioned features and objects of the present disclosure will become more apparent with reference to the following description taken in conjunction with the accompanying drawings wherein like reference numerals denote like elements and in which:

FIG. 1 is the structure of APO2.

FIG. 1a is the APO2 tetramer structure. It has an end-to-end span of ~126.9 Å. Zn atoms in the active centers are shown as red spheres.

FIG. 2a is the APO2 active sites are accessible to DNA/RNA. Red spheres represent Zn.

FIG. 2b is the fntCDA active site is accessible only to free nucleotides.

FIG. 2c is the outer APO2 active sites show Zn coordination (yellow dashed lines) by three residues (H98, C128, C131) and a water molecule (blue sphere).

FIG. 2d is the middle APO2 active centre sites showing Zn coordination by a fourth residue, E60.

FIG. 2e shows the β1'-hairpin structure, the hydrophobic ring of Y61 interacting with the guanidine group of R65, stabilizing the conformation.

FIG. 2f shows the h1/β1 loop, the E60 coordinates with Zn. Y61 now rotates away from R65 and interacts with R57, facilitating the disruption of the β1'-hairpin and stabilizing the loop conformation.

FIG. 2g shows superimposed monomers show that the h1/β1 loop (purple) is pulled down, 8.5 Å towards the active site owing to the E60-Zn bond formation.

FIG. 3a shows a sequence alignment of APO2 and AID, showing significant homology. Red, identical residues; grey shading, buried residues; red squares, active centre residues; green dots, tetrameric interface residues; blue diamonds, dimeric interface residues; purple stars, HIGM mutated residues; and black triangles, mutated AID residues.

FIG. 3b shows mutated AID residues (in green) at the tetramer interface as modeled based on the APO2 structure.

Figure 3:
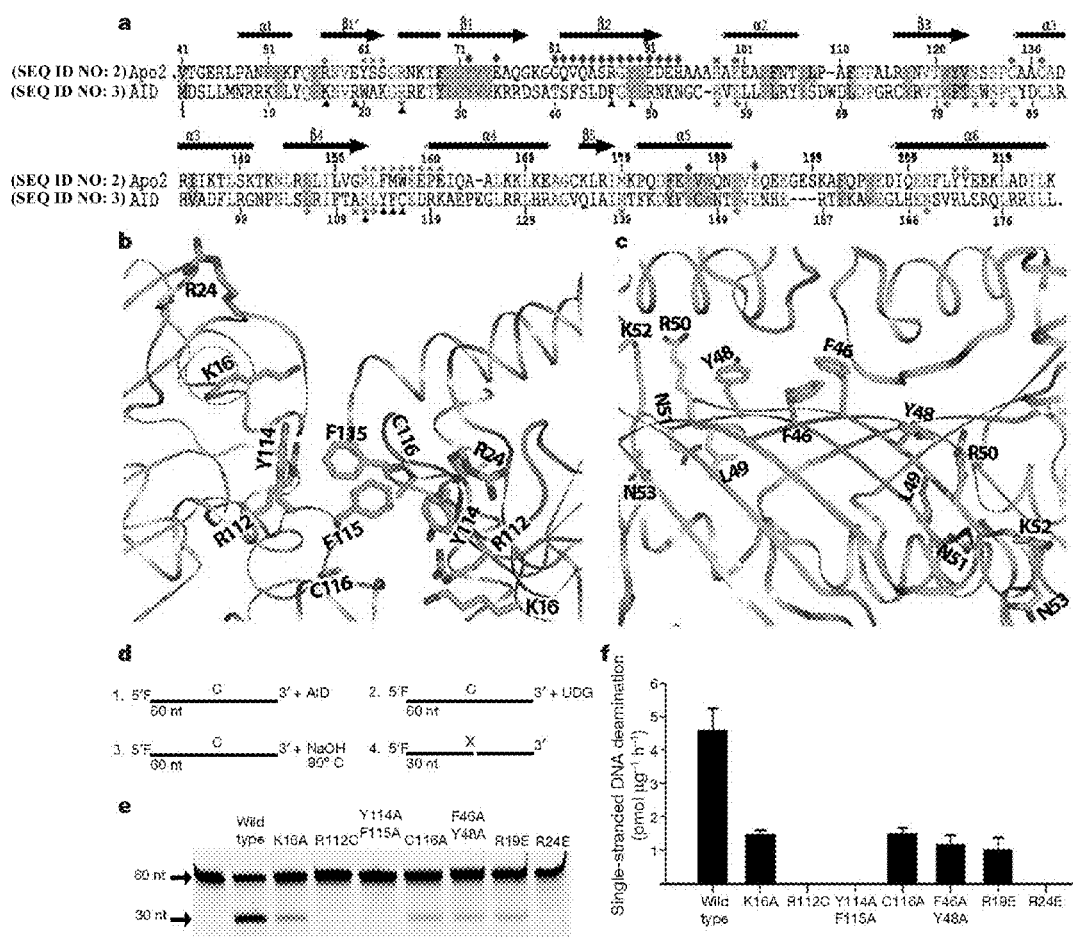
FIG. 3 shows how structurally guided mutagenesis of AID impairs deamination activity.

FIG. 3c, Mutated AID residues (in green) in the dimer interface as modeled based on the APO2 structure.

FIG. 3d shows a sketch describing the cytidine deamination assay. F, fluorescein; UDG, is uracil DNA glycosylase.

FIG. 3e shows a denaturing PAGE analysis of the deamination activity for wild-type and mutant AID proteins. The 30-nucleotide (nt) band indicates deamination activity.

FIG. 3f shows a bar representation of the specific activities for wildtype and mutant AID proteins.

Figure 4:
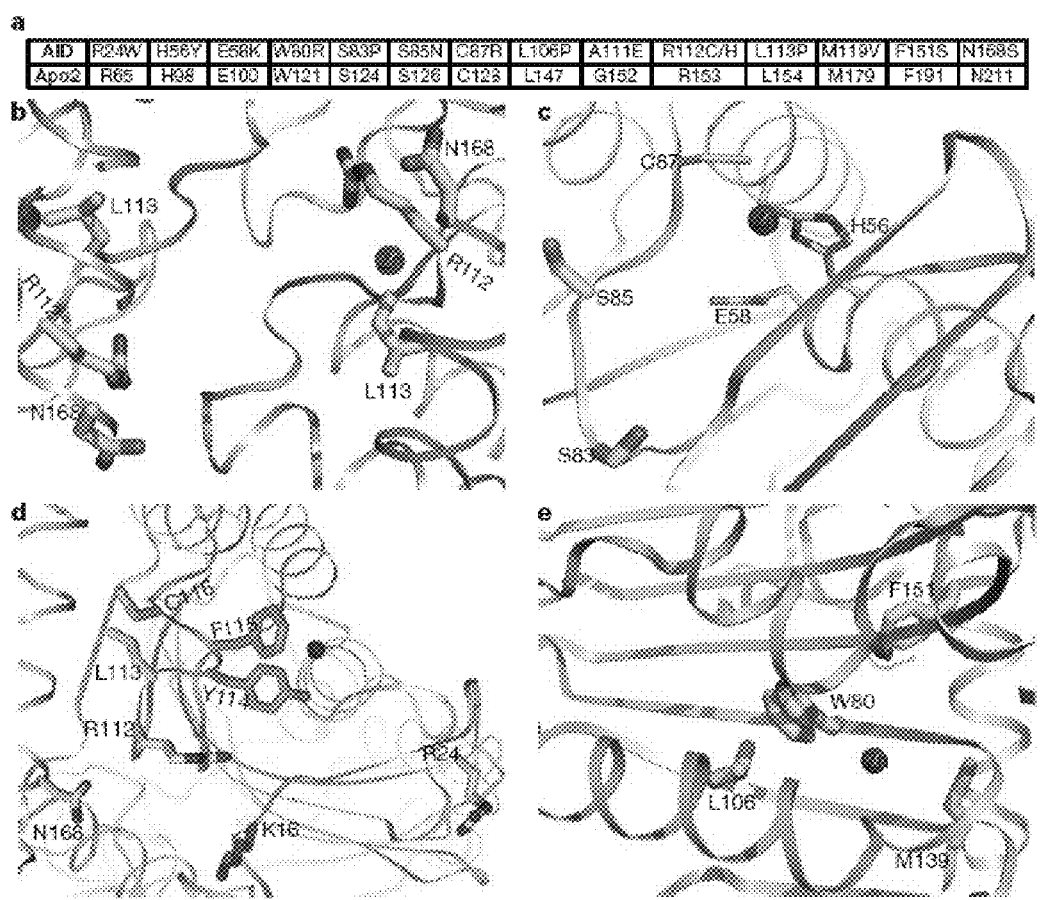

FIG. 4 shows AID HIGM-2 mutations.

FIG. 4a shows alignment of mutated residues of AID from HIGM-2 patients with the corresponding residues in APO2, showing high sequence conservation.

FIG. 4b maps the residues in AID HIGM-2 mutations (R112, L113, N168) to the tetramer interface as modeled from the APO2 structure.

FIG. 4c maps the AID HIGM-2 mutations, S83 and S85, near the active site.

FIG. 4d maps the AID mutations, K16, Y114/F115 and C116 (in green), to the exposed surface of an outer monomer. The HIGM-2 AID residues (R112, L113, N168, in yellow), which are at the tetramer interface (b), are also located on this exposed surface.

FIG. 4e maps AID HIGM-2 mutations, W80, L106, M139 and F151, to the interior core structure.

FIG. 5 refers to data collection, phasing and refinement statistics (MIR).

Figure 6:
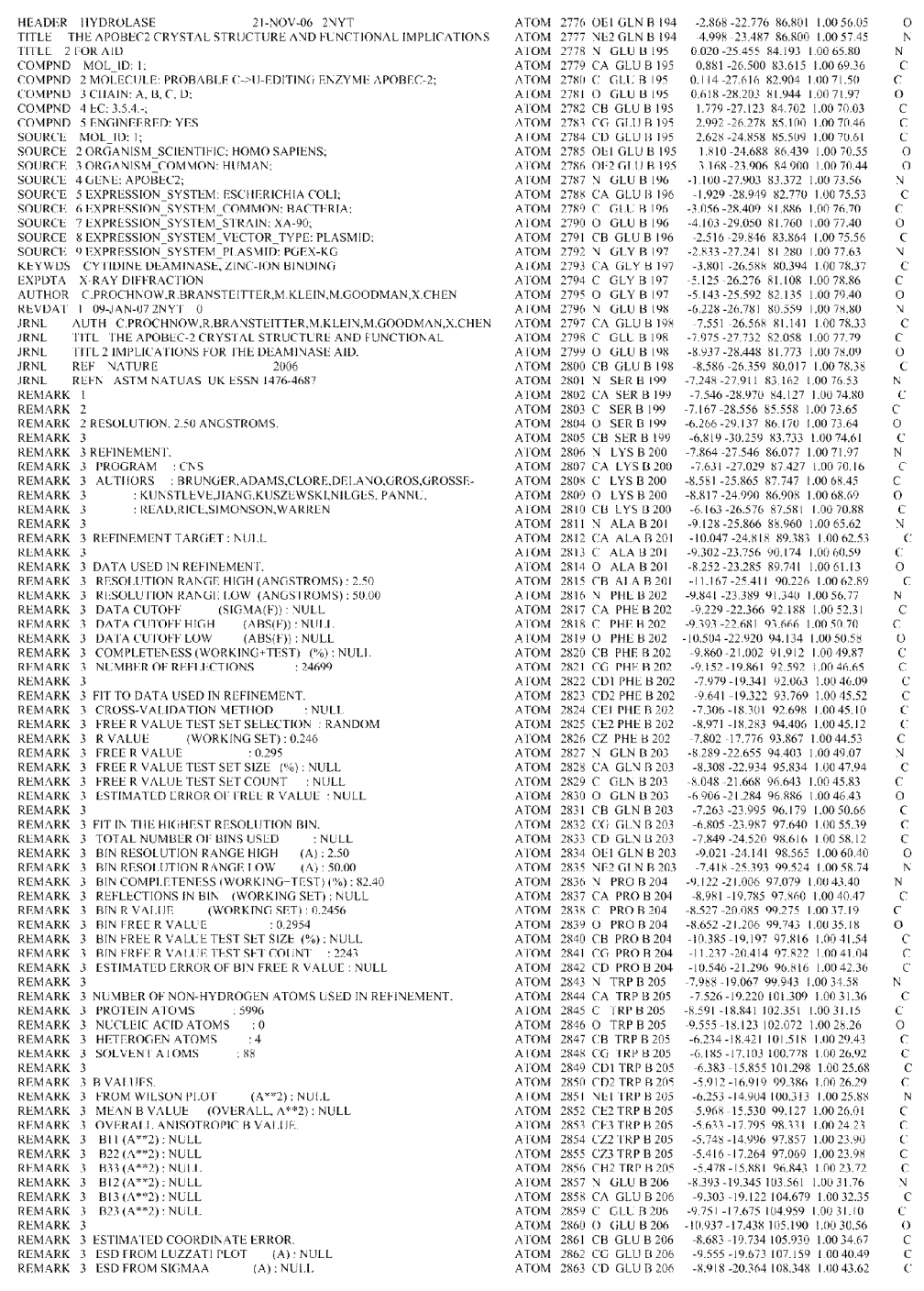
Figure 6:
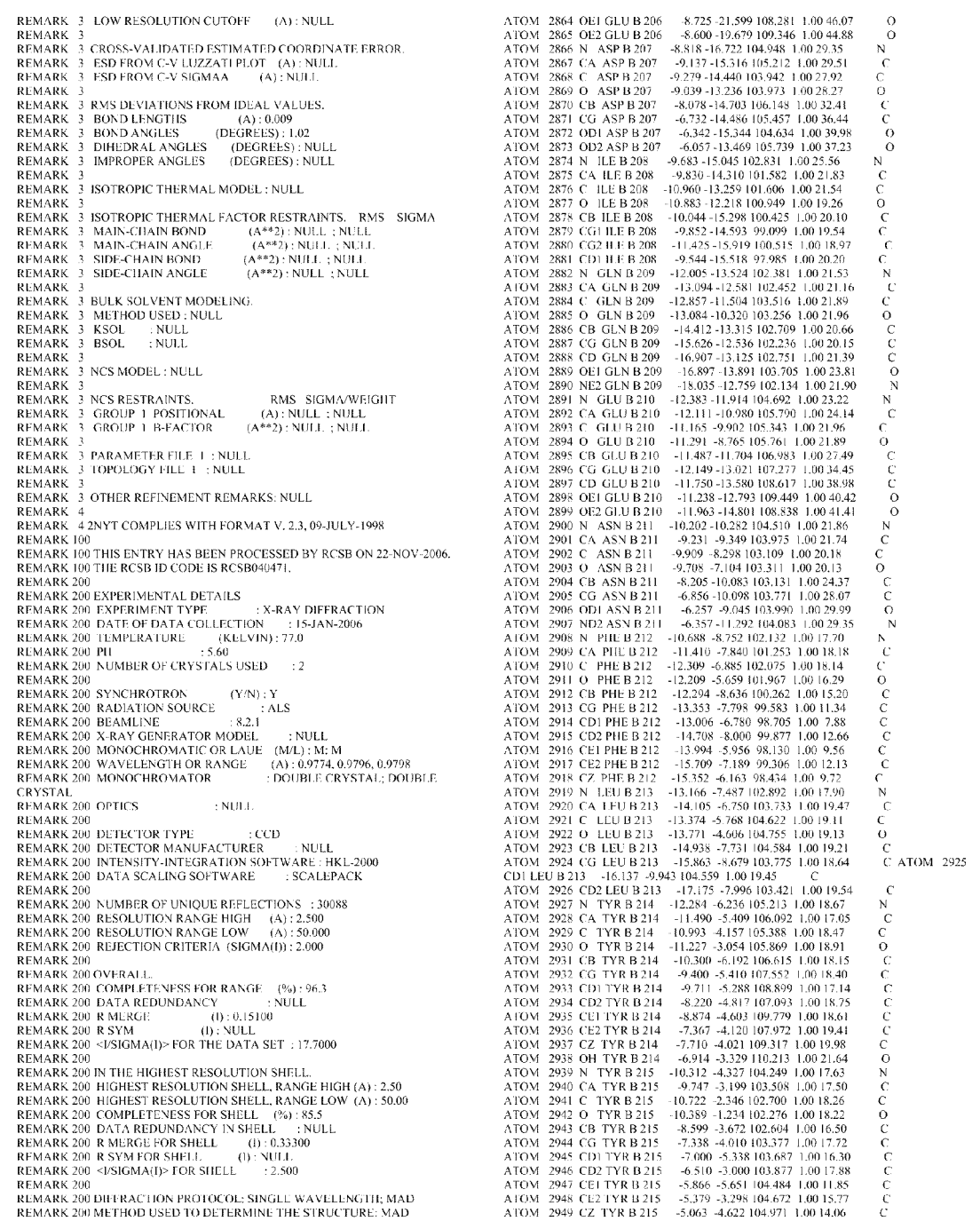
Figure 6:
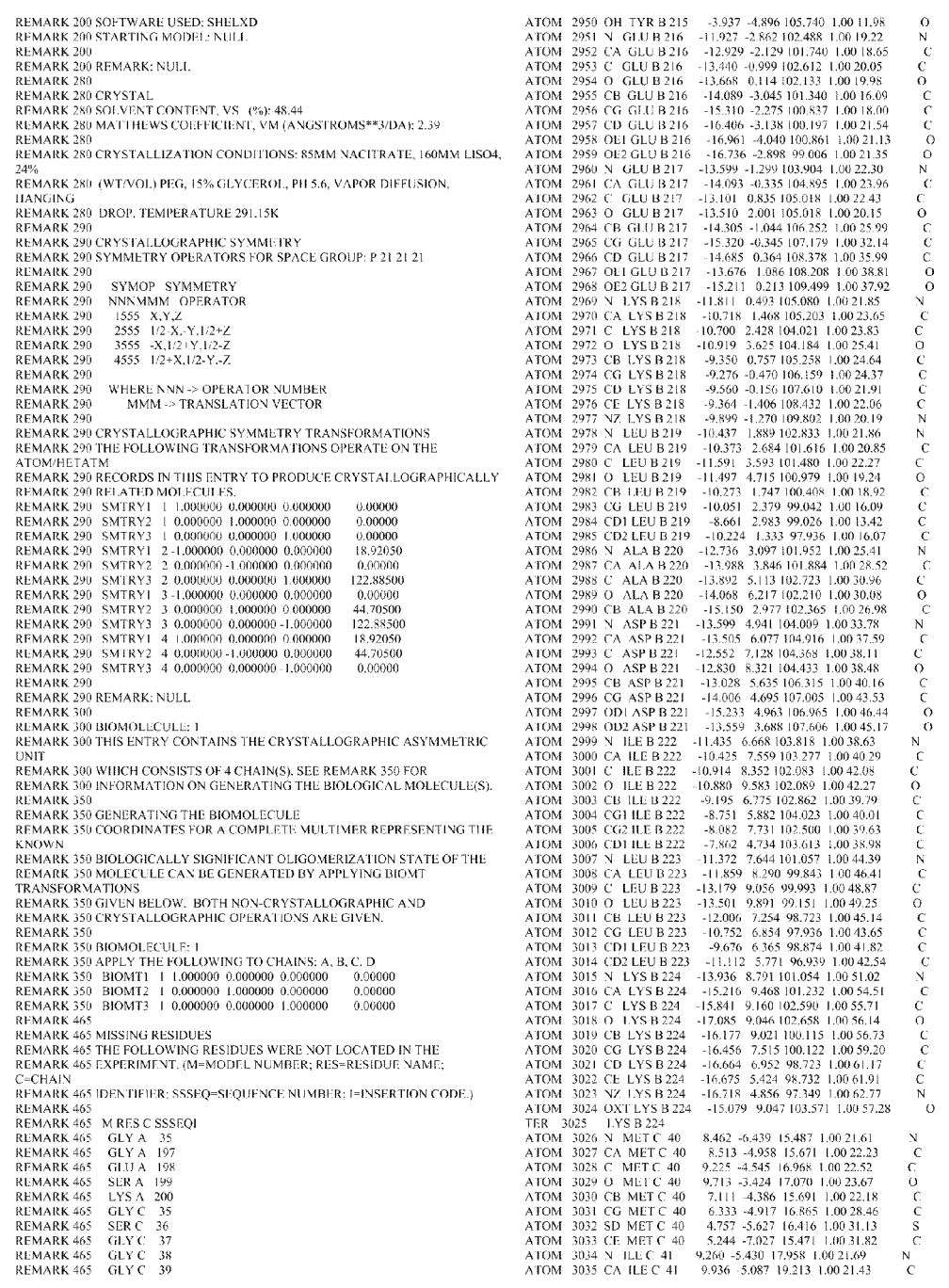
Figure 6:
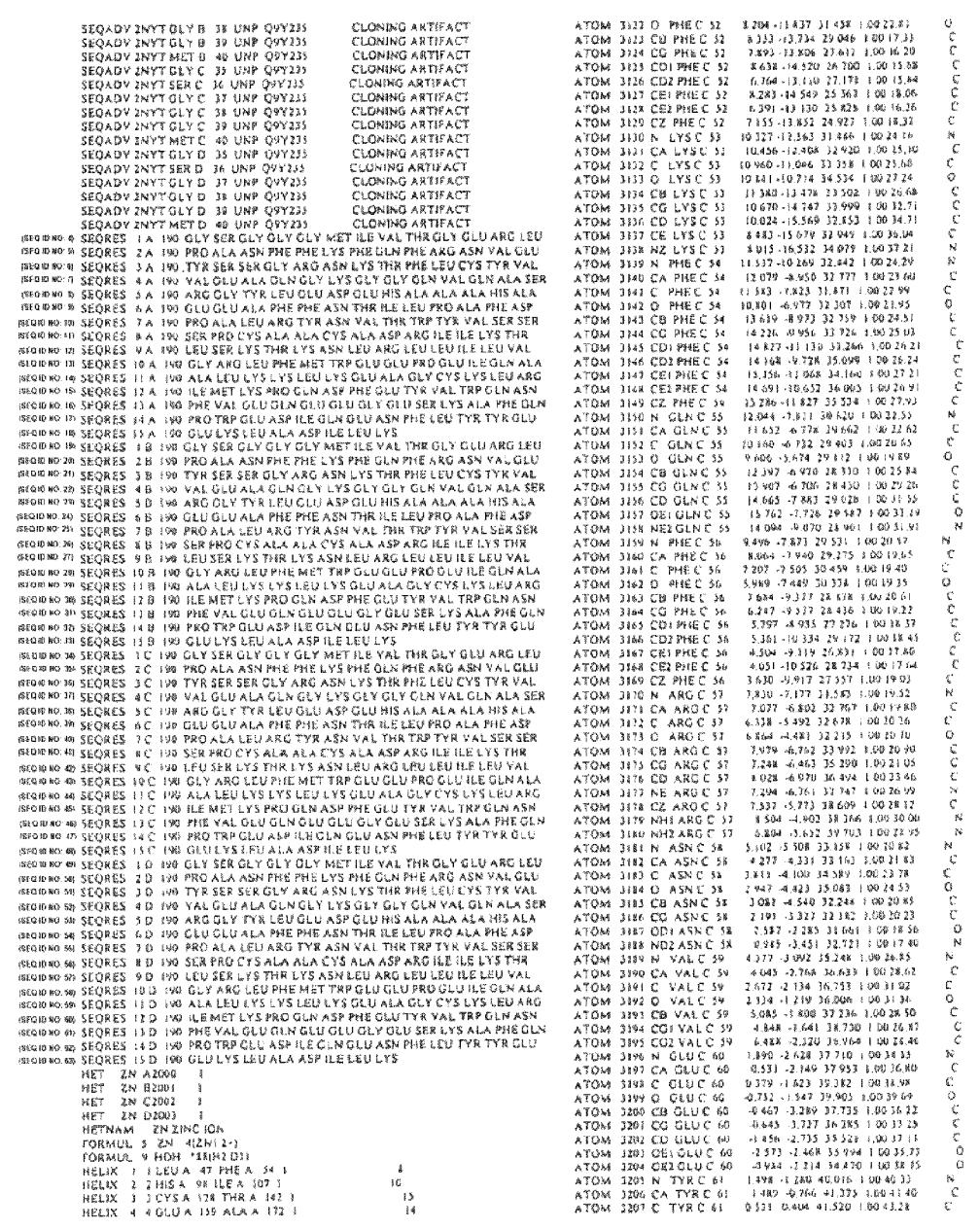
Figure 6:
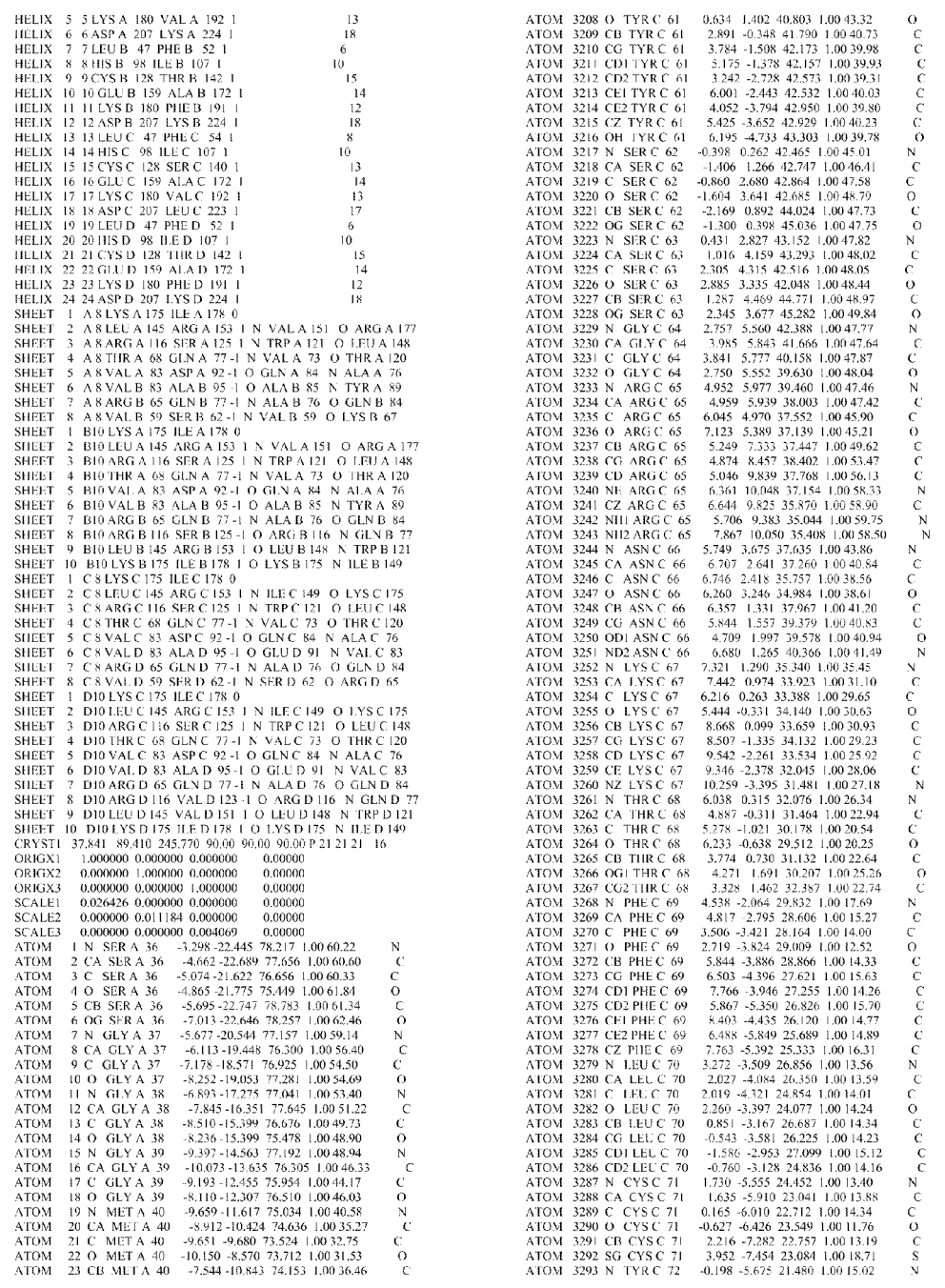

FIG. 6 shows the atomic coordinates of an APO2 Tetramer.
FIG. 7 shows the atomic coordinates of an APO2 Dimer.
FIG. 8 shows the atomic coordinates of APO2 Monomer A.
FIG. 9 shows the atomic coordinates of APO2 Monomer B.

DETAILED DESCRIPTION

One embodiment of the present disclosure relates to a three-dimensional structure of APOBEC-2 protein that is defined by atomic coordinates selected from FIGS. 6-9. Additionally, in another embodiment the three dimensional structure of APOBEC-2 is defined by atomic coordinates wherein at least 50% of the structure has an average root-mean-square deviation (RMSD) from backbone atoms in secondary structure elements in the three dimensional structure represented by the atomic coordinates selected from FIGS. 6-9 (shown below) of equal to or less than about 1.0 Å. In yet another embodiment, the three dimensional structure of APOBEC-2 can also be defined by atomic coordinates derived from APOBEC-2 protein molecules arranged in a crystalline manner in a space group $P2_12_12_1$ so as to form a unit cell of dimensions a=37.841 Å, b=89.41 Å, c=245.77 Å.

Another embodiment of the present disclosure relates to the information provided by the three-dimensional crystal structure of a human APOBEC protein, APOBEC-2, and other structure models of APOBEC proteins obtained by computer modeling that bear similarity with an APOBEC-2 monomer, dimer or tetramer and have a root-mean-square deviation (RMSD) of 2.0. Additionally, yet another embodiment of the present disclosure relates to how the information provided by the three-dimensional APOBEC-2 crystal structure and models of other homologous APOBECS can be used for drug discovery. Since APOBEC-2 shares sufficient sequence and structural similarities to all the other homologues included in the APOBEC protein family, it can be used for homology modeling to obtain computer models of other APOBEC proteins. For example, APOBEC-2 shares a sequence homology of 43% and buried residue homology of 83% with the N-terminal catalytic domain of APOBEC-3G. With the C-terminal catalytic domain of APOBEC-3G, APOBEC-2 shares a sequence homology of 46% and buried residue homology of 83%. The extent of homology between the two proteins indicates that the proteins are folded in a similar manner. Therefore, information provided by the APOBEC-2 crystal structure can be used to model the single domain APOBEC proteins (AID, APOBEC-1, APOBEC-3A, APOBEC-3C, APOBEC3H, APOBEC-4) and the double-domain APOBEC proteins (APOBEC3B, APOBEC-3DE, APOBEC3G and APOBEC3F).

Yet another embodiment of the present disclosure relates to the structural information pertaining to the unique features of an APOBEC active site, which is provided by the three-dimensional crystal structure of APOBEC-2 and other structure models of APOBEC proteins obtained by computer modeling that bear similarity with an APOBEC-2 monomer, dimer or tetramer and have a root-mean-square deviation (RMSD) of 2.0.

Yet another embodiment of the present disclosure relates to the structural information pertaining to unique features of APOBEC oligomerization, which is provided by the three-dimensional crystal structure of APOBEC-2 and other structure models of APOBEC proteins obtained by computer modeling that bear similarity with an APOBEC-2 monomer, dimer or tetramer and have a root-mean-square deviation (RMSD) of 2.0.

Yet another embodiment of the present disclosure relates to the structural information pertaining to the APOBEC residues which reside on the surface of APOBEC proteins, which is provided by the three-dimensional crystal structure of APOBEC-2 and other structure models of APOBEC proteins obtained by computer modeling that bear similarity with an APOBEC-2 monomer, dimer or tetramer and have a root-mean-square deviation (RMSD) of 2.0.

Yet another embodiment of the present disclosure relates to a method for the identification of compounds which inhibit APOBEC DNA or RNA binding and Zinc coordination within the APOBEC active site. Such compounds could be used to prevent or treat aberrant cytidine deamination activity of APOBEC enzymes causing chronic diseases, such as B cell lymphomas. Additionally, such compounds could enhance the anti-viral action of APOBEC enzymes. It has been demonstrated that APOBEC3G and APOBEC3F are associated with inhibitory RNA molecules and/or inhibitory ribonucleoprotein complexes in cells that are targets for HIV infection (4). Releasing APOBEC3G or APOBEC3F from these RNA complexes with a drug that inhibits RNA binding, while DNA binding remains intact, could restore their post entry HIV viral restriction properties. In this case, APOBEC3G or APOBEC3F would be able to inactivate the HIV provirus by introducing extensive cytidine deaminations onto the viral cDNA.

Yet another embodiment of the present disclosure includes a method including one or more steps of: (1) providing a three dimensional structure of an APOBEC protein or a model of a homologous APOBEC protein; and, (2) identifying a candidate compound that can affect DNA or RNA binding or zinc coordination within the APOBEC active sites via structure based drug design utilizing structural information provided in (1). The three dimensional structure of APOBEC-2 or a model(s) of homologous APOBEC proteins includes structures: (a) defined by atomic coordinates of a three dimensional structure of a crystalline APOBEC-2 protein with the atomic coordinates represented in tables 1 (tetramer), 2 (dimer), and 3 (monomer A), 4 (monomer B);(b) defined by atomic coordinates wherein at least 50% of the structure has an average root-mean-square deviation (RMSD) from backbone atoms in the secondary structure elements represented by the atomic coordinates of (a) of equal to or less than about 2.5 Å for main chain Ca carbon backbone; and (c) a structure defined by atomic coordinates derived from APOBEC-2 molecules arranged in a crystalline manner in a space group $P2_12_12_1$ so as to form a unit cell of dimensions: a=37.841 Å, b=89.41 Å, c=245.77 Å.

In another aspect of this embodiment, the methods described above further includes the step (3) of screening lead compounds identified in step (2) that inhibit the binding of an APOBEC protein to DNA, RNA or zinc. The step (3) of screening can include: (a) contacting the candidate compound identified in step (2) with an APOBEC protein or a fragment thereof or with the APOBEC substrates (DNA, RNA or zinc) under conditions in which the APOBEC protein can bind its substrate in the absence of the candidate compound; and (b) measuring the binding affinity of the APOBEC protein or fragment thereof to its substrates (DNA, RNA or zinc); wherein a candidate inhibitor compound is selected as a compound that inhibits the binding of the APOBEC protein to its substrate when there is a decrease in the binding affinity of the APOBEC protein or fragment thereof to its substrate (DNA, RNA or zinc), as compared to in the absence of the candidate inhibitor compound.

Another embodiment of the present disclosure relates to a method for the identification of compounds which enhance the ability of the APOBEC protein to bind DNA or RNA. Such compounds could potentially restore the function of AID in patients diagnosed with Hyper-IgM-2 syndrome. A subset of these patients has mutations in the gene encoding for AID that may impair DNA binding. Compounds that enhance the DNA binding capabilities of AID could potentially correct this defect. Additionally, these compounds may enhance the anti-viral properties of the APOBEC enzymes. This method includes the steps of: (1) providing a three dimensional structure of an APOBEC protein or a model of a homologous APOBEC protein as described in detail above; and, (2) identifying a candidate compound that can enhance DNA or RNA binding via structure based drug design utilizing structural information provided in (1). The step (3) of screening can include: (a) contacting the candidate compound identified in step (2) with an APOBEC protein or a fragment thereof or with the APOBEC substrates, DNA or RNA, under conditions in which the APOBEC protein can bind its substrate in the absence of the candidate compound; and (b) measuring the binding affinity of the APOBEC protein or fragment thereof to its substrates (DNA or RNA); wherein a lead compound is selected as a compound that enhances the binding of the APOBEC protein to its substrate (DNA or RNA) when there is an increase in the binding affinity of the APOBEC protein or fragment thereof to its substrate (DNA or RNA), as compared to in the absence of the lead compound.

Yet another embodiment of the present disclosure relates to a method for the identification of compounds which disrupt APOBEC protein oligomerization. Such compounds could be used to prevent or treat aberrant cytidine deamination activity of APOBEC enzymes causing chronic diseases, such as B cell lymphomas. Experimental evidence has been reported which suggests that APOBEC oligomerization can alter its deamination activity. Yet another embodiment related to a method including one or more of the steps of: (1) providing a three dimensional structure of an APOBEC protein or a model of a homologous APOBEC protein as described in detail above; and, (2) identifying a candidate compound that can disrupt oligomerization (for example, dimerization or tetramerization) via structure based drug design utilizing structural information provided in (1). The step (3) of screening can include: (a) contacting the candidate compound identified in step (2) with an APOBEC protein or a fragment thereof under conditions in which the APOBEC protein can oligomerize in the absence of the candidate compound; and (b) measuring the oligomerization of the APOBEC protein or fragment thereof; wherein a candidate inhibitor compound is selected as a compound that inhibits the oligomerization of the APOBEC protein when there is a decrease in the oligomerization of the APOBEC protein or fragment thereof, as compared to in the absence of the candidate inhibitor compound. APOBEC oligomerization can be measured by many techniques including, but not limited to: gel filtration, dynamic light scattering, native gel analysis, protein cross-linking, immunoprecipitation, FRET analysis or BIACore.

Yet another embodiment of the present disclosure relates to a method for the identification of compounds which enhance APOBEC protein oligomerization. Such compounds could be used to enhance the anti-viral activity of the APOBEC enzymes by increasing DNA deamination activity and RNA binding to the viral RNA. Further, such compounds could be used to repair the effects of mutations in the AID protein which disrupt AID oligomerization and cause Hyper-IgM-2 syndrome. In one aspect of the present disclosure, this method includes the steps of: (1) providing a three dimensional structure of an APOBEC protein or a model of a homologous APOBEC protein as described in detail above; and, (2) identifying a candidate compound that can enhance oligomerization (for example, dimerization or tetramerization) via structure based drug design utilizing structural information provided in (1). The step (3) of screening can include: (a) contacting the candidate compound identified in step (2) with an APOBEC protein or a fragment thereof under conditions in which the APOBEC protein can oligomerize in the absence of the candidate compound; and (b) measuring the oligomerization of the APOBEC protein or fragment thereof; wherein a lead compound is selected as a compound that enhances the oligomerization of the APOBEC protein when there is an increase in the oligomerization of the APOBEC protein or fragment thereof, as compared to in the absence of the lead compound. APOBEC oligomerization can be measured by many techniques including but not limited to: gel filtration, dynamic light scattering, native gel analysis, protein cross-linking, immunoprecipitation, FRET analysis or BIACore.

Yet another embodiment of the present disclosure relates to a method for the identification of compounds which inhibit HIV viral infectivity factor (Vif) protein from binding to an APOBEC protein. The HIV Vif protein can bind to most all of the APOBEC enzymes regardless of their ability to restrict HIV replication. For example, Vif can bind to AID and inhibit its deamination activity. In cells that are targets for HIV infection, Vif binds to APOBEC3G and APOBEC3F and targets it for ubiquitylation and proteasome mediated degradation. Compounds that can disrupt Vif and APOBEC protein interactions may serve as very effective anti-viral drugs.

In one aspect of the method described above, the steps include one or more of the following: (1) providing a three dimensional structure of an APOBEC protein or a model of a homologous APOBEC protein as described in detail above; and, (2) identifying a candidate compound that can disrupt Vif and APOBEC binding interactions via structure based drug design utilizing structural information provided in (1). The step (3) of screening can include: (a) contacting the candidate compound identified in step (2) with an APOBEC protein or a fragment thereof, or with Vif or a fragment thereof, under conditions in which the APOBEC protein and Vif can interact in the absence of the candidate compound; and (b) measuring the binding interactions of the APOBEC protein or fragment thereof with Vif or a fragment thereof; wherein a lead inhibitory compound is selected when there is a decrease in the binding interactions of the APOBEC protein or fragment thereof with Vif or a fragment thereof, as compared to in the absence of the lead compound.

Yet another embodiment of the present disclosure relates to a method for the identification of compounds which inhibit APOBEC ubiquitylation and proteasomal mediated degradation. In cells that are targets for HIV infection, Vif binds to APOBEC3G and APOBEC3F and targets it for ubiquitylation and proteasomal mediated degradation. Compounds that can disrupt APOBEC ubiquitlyation may serve as very effective anti-viral drugs. In one aspect of the methods described above, the method includes one or more of the steps of: (1) providing a three dimensional structure of an APOBEC protein or a model of a homologous APOBEC protein as described in detail above; and, (2) identifying a candidate compound that can disrupt Vif and APOBEC binding interactions via structure based drug design utilizing structural information provided in (1). The step (3) of screening can include: (a) contacting the candidate compound identified in step (2) with an APOBEC protein or a fragment thereof under conditions in which the APOBEC protein or a fragment thereof becomes ubiquitylated in the absence of the candidate compound; and (b) measuring the ubiquitlyation of the APOBEC protein of fragment thereof; wherein a lead inhibitory compound is selected when there is a decrease in ubiquitylation of the APOBEC protein or fragment thereof, as compared to in the absence of the lead compound. Ubiquitlyation can be measured by many techniques including, but not limited to: immunoprecipitation and western blot analysis with an antibody specific for ubiquitin and the APOBEC protein.

In yet another aspect of various embodiments of the present disclosure, the step (2) of identifying a compound in the method described above in this present disclosure can include any suitable method of drug design, drug screening or identification, including, but not limited to: directed drug design, random drug design, grid-based drug design, and/or computational screening of one or more databases of chemical compounds.

Yet another embodiment of the present disclosure relates to a method for preparing APOBEC proteins having modified biological activity. In one embodiment, the method includes the steps of: (1) providing a three dimensional structure of an APOBEC protein or a model of a homologous APOBEC protein as described in detail above; (2) utilizing the structural information provided by (1) to identify at least one or more sites in the structure contributing to the biological activity of an APOBEC protein; and (3) modifying at least one or more sites in an APOBEC protein to alter its biological activity. The mutant APOBEC protein comprises an amino acid sequence that differs from the wildtype sequence via amino acid substitutions. The APOBEC mutant protein includes mutations that can inhibit, reduce or enhance oligomerization, zinc coordination, binding to DNA or RNA substrates, binding to cellular co-factors or viral proteins including but not limited to HIV Vif, as compared to the wild-type APOBEC protein.

Yet another embodiment of the present disclosure includes a method for producing crystals of APOBEC-2. Native and selenium-methionine labeled protein is concentrated to 15 mg per ml in a buffer containing 25 mM Hepes, pH 7.0, 50 mM NaCl and 10 mM dithiothreitol. Crystals are grown at 18° C. by hanging-drop vapor diffusion from a reservoir solution of 85 mM Na-citrate, pH 5.6, 160 mM LiSO4, 24% (weight/volume) polyethylene glycol monomethyl ether and 15% glycerol.

Yet another embodiment of the present disclosure includes a representation, or model, of the three dimensional structure of an APOBEC protein, such as a computer model. A computer model of the present disclosure can be produced using any suitable software program, including, but not limited to, MOLSCRIPT 2.0 (Avatar Software AB, Heleneborgsgatan 21C, SE-11731 Stockholm, Sweden), the graphical display program 0 (Jones et. al., Acta Crystallography, vol. A47, p. 110, 1991), the graphical display program GRASP, or the graphical display program INSIGHT. Suitable computer hardware useful for producing an image of the present disclosure is known to those of skill in the art (e.g., a Silicon Graphics Workstation).

A representation, or model, of the three dimensional structure of the APOBEC-2 or any other APOBEC protein for which a crystal has been produced can also be determined using techniques which include molecular replacement or SIR/MIR (single/multiple isomorphous replacement). Methods of molecular replacement are generally known by those of skill in the art (generally described in Brunger, Meth. Enzym., vol. 276, pp. 558-580, 1997; Navaza and Saludjian, Meth. Enzym., vol. 276, pp. 581-594, 1997; Tong and Rossmann, Meth. Enzym., vol. 276, pp. 594-611, 1997; and Bentley, Meth. Enzym., vol. 276, pp. 611-619, 1997, each of which are incorporated by this reference herein in their entirety) and are performed in a software program including, for example, AmoRe (CCP4, Acta Cryst. D50, 760-763 (1994) or XPLOR. Briefly, X-ray diffraction data is collected from the crystal of a crystallized target structure.

The X-ray diffraction data is transformed to calculate a Patterson function. The Patterson function of the crystallized target structure is compared with a Patterson function calculated from a known structure (referred to herein as a search structure). The Patterson function of the crystallized target structure is rotated on the search structure Patterson function to determine the correct orientation of the crystallized target structure in the crystal. The translation function is then calculated to determine the location of the target structure with respect to the crystal axes. Once the crystallized target structure has been correctly positioned in the unit cell, initial phases for the experimental data can be calculated. These phases are necessary for calculation of an electron density map from which structural differences can be observed and for refinement of the structure. Preferably, the structural features (e.g., amino acid sequence, conserved di-sulphide bonds, and β-strands or β-sheets) of the search molecule are related to the crystallized target structure.

In yet another embodiment of the present disclosure, a three dimensional structure of an APOBEC-2 homologue protein includes a structure represented by atomic coordinates, wherein at least 50% of the structure has an average root-mean-square deviation (RMSD) from backbone atoms in secondary structure elements the three dimensional structure represented by the atomic coordinates of FIGS. 6-9 of equal to or less than about 1.0 Å. Such a structure can be referred to as a structural homologue of the APOBEC structures defined by FIGS. 6-9. Preferably, at least 50% of the structure has an RMSD from backbone atoms in secondary structure elements in the three dimensional structure represented by the atomic coordinates of FIGS. 6-9 of equal to or less than about 0.7 Å, equal to or less than about 0.5 Å, and most preferably, equal to or less than about 0.3 Å. In another embodiment, a three dimensional structure of an APOBEC-2 protein provided by the present disclosure includes a structure defined by atomic coordinates that define a three dimensional structure, wherein at least about 75% of such structure has the recited average RMSD value, and more preferably, at least about 90% of such structure has the recited average RMSD value, and most preferably, about 100% of such structure has the recited average RMSD value.

In yet another embodiment of the present disclosure, the RMSD of a structural homologue of APOBEC-2 can be extended to include atoms of amino acid side chains. As used herein, the phrase "common amino acid side chains" refers to amino acid side chains that are common to both the structural homologue and to the structure that is actually represented by such atomic coordinates. Preferably, at least 50% of the structure has an average RMSD from common amino acid side chains in the three dimensional structure represented by the atomic coordinates of FIGS. 6-9 of equal to or less than about 1.0 Å equal to or less than about 0.7 Å, equal to or less than about 0.5 Å, and most preferably, equal to or less than about 0.3 Å. In a more preferred embodiment, a three dimensional structure of an APOBEC-2 protein provided by the present disclosure includes a structure defined by atomic coordinates that define a three dimensional structure, wherein at least about 75% of such structure has the recited average RMSD value, and more preferably, at least about 90% of such structure has the recited average RMSD value, and most preferably, about 100% of such structure has the recited average RMSD value.

Suitable structures and models useful for structure based drug design are disclosed herein. Preferred target structures to use in a method of structure based drug design include any representations of structures produced by any modeling method disclosed herein, including molecular replacement and fold recognition related methods.

According to the present disclosure, the step of designing a compound for testing in a method of structure based identification of the present disclosure can include creating a new chemical compound or searching databases of libraries of known compounds (e.g., a compound listed in a computational screening database containing three dimensional structures of known compounds). Designing can also be performed by simulating chemical compounds having substitute moieties at certain structural features. The step of designing can include selecting a chemical compound based on a known function of the compound. A preferred step of designing comprises computational screening of one or more databases of compounds in which the three dimensional structure of the compound is known and is interacted (e.g., docked, aligned, matched, interfaced) with the three dimensional structure of an APOBEC protein by computer (e.g. as described by Humblet and Dunbar, Animal Reports in Medicinal Chemistry, vol. 28, pp. 275-283, 1993, M Venuti, ed., Academic Press). Methods to synthesize suitable chemical compounds are known to those of skill in the art and depend upon the structure of the chemical being synthesized. Methods to evaluate the bioactivity of the synthesized compound depend upon the bioactivity of the compound (e.g., inhibitory or stimulatory) and are disclosed herein.

Various other methods of structure-based drug design are disclosed in Maulik et al., 1997, Molecular Biotechnology: Therapeutic Applications and Strategies, Wiley-Liss, Inc., which is incorporated herein by reference in its entirety. Maulik et al. disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

In the present method of structure based drug design, it is not necessary to align a candidate chemical compound (i.e., a chemical compound being analyzed in, for example, a computational screening method of the present disclosure) to each residue in a target site (target sites will be discussed in detail below). Suitable candidate chemical compounds can align to a subset of residues described for a target site. Preferably, a candidate chemical compound comprises a conformation that promotes the formation of covalent or noncovalent cross-linking between the target site and the candidate chemical compound. Preferably, a candidate chemical compound binds to a surface adjacent to a target site to provide an additional site of interaction in a complex. When designing an antagonist (i.e., a chemical compound that inhibits the binding of a substrate for an APOBEC protein by blocking a binding site or interface), the antagonist should bind with sufficient affinity to the binding site or to substantially prohibit a substrate (i.e., a molecule that specifically binds to the target site) from binding to a target area. It will be appreciated by one of skill in the art that it is not necessary that the complementarity between a candidate chemical compound and a target site extend over all residues specified here in order to inhibit or promote binding of a ligand.

In general, the design of a chemical compound possessing stereochemical complementarity can be accomplished by techniques that optimize, chemically or geometrically, the "fit" between a chemical compound and a target site. Such techniques are disclosed by, for example, Sheridan and Venkataraghavan, Acc. Chem Res., vol. 20, p. 322, 1987: Goodford, J Med. Chem., vol. 27, p. 557, 1984; Beddell, Chem. Soc Reviews, vol. 279, 1985; Hol, Angew. Chem., vol. 25, p. 767, 1986; and Verlinde and Hol, Structure, vol. 2, p. 577, 1994, each of which are incorporated by this reference herein in their entirety.

One embodiment of the present disclosure for structure based drug design comprises identifying a chemical compound that complements the shape of an APOBEC protein, or a portion thereof. Such method is referred to herein as a "geometric approach". In a geometric approach, the number of internal degrees of freedom (and the corresponding local minima in the molecular conformation space) is reduced by considering only the geometric (hard-sphere) interactions of two rigid bodies, where one body (the active site) contains "pockets" or "grooves" that form binding sites for the second body (the complementing molecule, such as a ligand).

The geometric approach is described by Kuntz et al., J Mol. Biol., vol. 161, p. 269, 1982, which is incorporated by this reference herein in its entirety. The algorithm for chemical compound design can be implemented using the software program DOCK Package, Version 1.0 (available from the Regents of the University of California). Pursuant to the Kuntz algorithm, the shape of the cavity or groove on the surface of a structure (e.g., APOBEC-2) at a binding site or interface is defined as a series of overlapping spheres of different radii. One or more extant databases of crystallographic data (e.g., the Cambridge Structural Database System maintained by University Chemical Laboratory, Cambridge University, Lensfield Road, Cambridge CB2 1EW, U.K.) or the Protein Data Bank maintained by Brookhaven National Laboratory, is then searched for chemical compounds that approximate the shape thus defined. Chemical compounds identified by the geometric approach can be modified to satisfy criteria associated with chemical complementarity, such as hydrogen bonding, ionic interactions or Van der Waals interactions.

Yet another embodiment of the present disclosure for structure based identification of compounds comprises determining the interaction of chemical groups ("probes") with an active site at sample positions within and around a binding site or interface, resulting in an array of energy values from which three dimensional contour surfaces at selected energy levels can be generated. This method is referred to herein as a "chemical-probe approach." The chemical-probe approach to the design of a chemical compound of the present disclosure is described by, for example, Goodford, J Med Chem., vol. 28, p. 849, 1985, which is incorporated by this reference herein in its entirety, and is implemented using an appropriate software package, including for example, GRID (available from Molecular Discovery Ltd., Oxford OX2 9LL, U.K.). The chemical prerequisites for a site-complementing molecule can be identified at the outset, by probing the active site of an APOBEC protein, with different chemical probes, e.g., water, a methyl group, an amine nitrogen, a carboxyl oxygen and/or a hydroxyl. Preferred sites for interaction between an active site and a probe are determined. Putative complementary chemical compounds can be generated using the resulting three dimensional pattern of such sites According to the present disclosure, suitable candidate compounds to test using the method of the present disclosure include proteins, peptides or other organic molecules, and inorganic molecules. Suitable organic molecules include small organic molecules. Peptides refer to small molecular weight compounds yielding two or more amino acids upon hydrolysis. A polypeptide is comprised of two or more peptides. As used herein, a protein is comprised of one or more polypeptides. Preferred therapeutic compounds to design include peptides composed of "L" and/or "D" amino acids that are configured as normal or retroinverso peptides, peptidomimetic compounds, small organic molecules, or homo- or hetero-polymers thereof, in linear or branched configurations.

Preferably, a compound that is identified by the method of the present disclosure originates from a compound having chemical and/or stereochemical complementarity with an APOBEC protein. Such complementarity is characteristic of a compound that matches the surface of the protein either in shape or in distribution of chemical groups and binds to the APOBEC protein to promote or inhibit APOBEC ligand binding in a cell expressing an APOBEC protein upon the binding of the compound to the APOBEC protein. More preferably, a compound that binds to a ligand binding site of an APOBEC protein associates with an affinity of at least about 10-6 M, and more preferably with an affinity of at least about 10-7 M, and more preferably with an affinity of at least about 10-8 M.

Preferably, four general sites on an APOBEC protein are targets for structure based drug design (i.e., target sites), although other sites may become apparent to those of skill in the art. The four preferred sites include: (1) the interfaces between APOBEC monomers, dimers and tetramers; (2) the active site where zinc is coordinated and where cytosine to uracil deamination activity occurs on DNA or RNA substrates (3) the D128 residue on APOBEC3G or E159 on APOBEC-2 or D118 on AID (4) and DNA or RNA binding sites. Combinations of any of these general sites are also suitable target sites.

The following discussion provides specific detail on compound identification (i.e., drug design) using target sites of APOBEC proteins based on the APOBEC-2 three-dimensional structure. It is to be understood, however, that one of skill in the art, using the description of the APOBEC-2 structure provided herein, will be able to identify compounds that are potential candidates for inhibiting, stimulating or enhancing the interaction of APOBEC proteins with their other substrates, cellular co-factors and other viral accessory proteins.

A candidate compound for binding to an APOBEC protein, including one of the preferred target sites described above, is identified by one or more of the methods of structure-based identification discussed above. As used herein, a "candidate compound" or "lead compound" refers to a compound that is selected by a method of structure-based identification described herein as having a potential for binding to an APOBEC protein (or its substrate) on the basis of a predicted conformational interaction between the candidate compound and the target site of the APOBEC protein. The ability of the candidate compound to actually bind to an APOBEC protein can be determined using techniques known in the art, as discussed in some detail below. A "putative compound" is a compound with an unknown regulatory activity, at least with respect to the ability of such a compound to bind to and/or regulate an APOBEC protein as described herein. Therefore, a library of putative compounds can be screened using structure based identification methods as discussed herein, and from the putative compounds, one or more candidate compounds for binding to an APOBEC protein can be identified. Alternatively, a candidate compound for binding to an APOBEC protein can be designed de novo using structure based drug design, also as discussed above. Candidate compounds can be selected based on their predicted ability to inhibit the binding of an APOBEC protein to its substrate, cellular co-factor or a viral accessory protein, such as HIV Vif and to disrupt or enhance the oligomerization of APOBEC monomers or dimers.

In accordance with the present disclosure, a cell-based assay is conducted under conditions which are effective to screen for candidate compounds useful in the method of the present disclosure. Effective conditions include, but are not limited to, appropriate media, temperature, pH and oxygen conditions that permit the growth of the cell that expresses the receptor. An appropriate, or effective, medium refers to any medium in which a cell that naturally or recombinantly expresses an APOBEC protein, when cultured, is capable of cell growth and expression of the APOBEC protein. Such a medium is typically a solid or liquid medium comprising growth factors and assimilable carbon, nitrogen and phosphate sources, as well as appropriate salts, minerals, metals and other nutrients, such as vitamins. Culturing is carried out at a temperature, pH and oxygen content appropriate for the cell. Such culturing conditions are within the expertise of one of ordinary skill in the art.

Cells that are useful in the cell-based assays of the present disclosure include any cell that expresses an APOBEC protein and particularly, other proteins that are associated with that APOBEC protein. Such cells include bacterial cells. Additionally, certain cells may be induced to express an APOBEC protein recombinantly. Therefore, cells that express an APOBEC protein can include cells that naturally express an APOBEC protein, recombinantly express an APOBEC protein, or which can be induced to express an APOBEC protein. Cells useful in some embodiments can also include cells that can express the HIV Vif protein, such as Hela or 293T cells.

The assay of the present disclosure can also be a non-cell based assay. In this embodiment, the candidate compound can be directly contacted with an isolated APOBEC protein or fragment of that APOBEC protein, and the ability of the candidate compound to bind to the APOBEC protein can be evaluated by a binding assay. The assay can, if desired, additionally include the step of further analyzing whether candidate compounds which bind to a portion of the APOBEC protein are capable of increasing or decreasing the activity of the APOBEC protein or disrupting its interactions with the HIV Vif protein. Such further steps can be performed by cell-based assay, as described above, or by non-cell-based assay.

Alternatively, soluble APOBEC protein may be recombinantly expressed and utilized in non-cell based assays to identify compounds that bind to APOBEC proteins. Recombinantly expressed APOBEC polypeptides or fusion proteins containing one or more extracellular domains of an APOBEC protein can be used in the non-cell based screening assays. In non-cell based assays the recombinantly expressed APOBEC protein is attached to a solid substrate by means well known to those in the art. For example, APOBEC3G and/or cell lysates containing such proteins can be immobilized on a substrate such as: artificial membranes, organic supports, biopolymer supports and inorganic supports. The protein can be immobilized on the solid support by a variety of methods including adsorption, cross-linking (including covalent bonding), and entrapment. Adsorption can be through van del Waal's forces, hydrogen bonding, ionic bonding, or hydrophobic binding. Exemplary solid supports for adsorption immobilization include polymeric adsorbents and ion-exchange resins. Solid supports can be in any suitable form, including in a bead form, plate form, or well form. The test compounds are then assayed for their ability to bind to an APOBEC protein and disrupt interactions with their substrates, cellular co-factors or viral accessory proteins such as HIV Vif.

Yet another embodiment of the present disclosure relates to a therapeutic composition that, when administered to an animal, inhibits or prevents the degradation of an APOBEC protein by proteasome-mediated degradation. The therapeutic composition comprises a compound that inhibits the binding of HIV Vif protein to APOBEC3G or APOBEC3F. The method comprises: (a) providing a three dimensional structure or structure model of an APOBEC protein as previously described herein; (b) identifying a candidate compound for binding to the APOBEC protein by performing structure based drug design with the structure of (a) to identify a compound structure that binds to the three dimensional structure of the APOBEC protein; (c) synthesizing the candidate compound; and (d) selecting candidate compounds that inhibit HIV Vif binding to the APOBEC protein in the presence of the candidate compounds. Preferably, the compounds inhibit the formation of a complex between the APOBEC protein and HIV Vif.

Another embodiment of the present disclosure relates to a therapeutic composition that, when administered to an animal, inhibits or prevents the deamination activity of an APOBEC protein. One embodiment of the method comprises one or more of the following: (a) providing a three dimensional structure or structure model of an APOBEC protein as previously described herein; (b) identifying a candidate compound for binding to the APOBEC protein by performing structure based drug design with the structure of (a) to identify a compound structure that binds to the three dimensional structure of the APOBEC protein; (c) synthesizing the candidate compound; and (d) selecting candidate compounds that inhibit deamination activity of the APOBEC protein in the presence of the candidate compounds. Preferably, the compounds prevent or inhibit the formation of B cell lymphomas.

Methods of identifying candidate compounds and selecting compounds that bind to and activate or inhibit an APOBEC protein have been previously described herein. Candidate compounds can be synthesized using techniques known in the art, and depending on the type of compound. Synthesis techniques for the production of non-protein compounds, including organic and inorganic compounds are well known in the art.

For smaller peptides, chemical synthesis methods are preferred. For example, such methods include well-known chemical procedures, such as solution or solid-phase peptide synthesis, or semi-synthesis in solution beginning with protein fragments coupled through conventional solution methods. Such methods are well known in the art and may be found in general texts and articles in the area such as: Merrifield, 1997, Methods Enzymol. 289:3-13; Wade et al., 1993, Australas Biotechnol. 3(6):332-336; Wong et al., 1991, Experientia 47(11-12):1123-1129; Carey et al., 1991, Ciba Found Symp. 158:187-203; Plaueetal., 1990, Biologicals 18(3): 147-157; Bodanszky, 1985, Int. J. Pept. Protein Res. 25(5): 449-474; H. Dugas and C. Penney, BIOORGANIC CHEMISTRY, (1981) at pages 54-92, all of which are incorporated herein by reference in their entirety. For example, peptides may be synthesized by solid-phase methodology utilizing a commercially available peptide synthesizer and synthesis cycles supplied by the manufacturer. One skilled in the art recognizes that the solid phase synthesis could also be accomplished using the FMOC strategy and a TFA/scavenger cleavage mixture.

If larger quantities of a protein are desired, or if the protein is a larger polypeptide, the protein can be produced using recombinant DNA technology. A protein can be produced recombinantly by culturing a cell capable of expressing the protein (i.e., by expressing a recombinant nucleic acid molecule encoding the protein) under conditions effective to produce the protein, and recovering the protein. Effective culture conditions include, but are not limited to, effective media, bioreactor, temperature, pH and oxygen conditions that permit protein production. An effective medium refers to any medium in which a cell is cultured to produce the protein. Such medium typically comprises an aqueous medium having assimilable carbon, nitrogen and phosphate sources, and appropriate salts, minerals, metals and other nutrients, such as vitamins. Recombinant cells (i.e., cells expressing a nucleic acid molecule encoding the desired protein) can be cultured in conventional fermentation bioreactors, shake flasks, test tubes, microtiter dishes, and Petri plates. Culturing can be carried out at a temperature, pH and oxygen content appropriate for a recombinant cell. Such culturing conditions are within the expertise of one of ordinary skill in the art. Such techniques are well known in the art and are described, for example, in Sambrook et al., 1988, Molecular Cloning: A Laboratory Manual, Cold Spring Harbor Press, Cold Spring Harbor Laboratory, Cold Spring Harbor, N.Y. or Current Protocols in Molecular Biology (1989) and supplements.

As discussed above, a composition, and particularly a therapeutic composition, of the present disclosure generally includes the therapeutic compound (e.g., the compound identified by the structure based identification method) and a carrier, and preferably, a pharmaceutically acceptable carrier. Pharmaceutically acceptable carriers and preferred methods of administration of therapeutic compositions of the present disclosure have been described in detail above with regard to the administration of an inhibitor compound to a patient. Such carriers and administration protocols are applicable to this embodiment.

Another embodiment of the present disclosure relates to a computer for producing a three-dimensional model of a molecule or molecular structure, wherein the molecule or molecular structure comprises a three dimensional structure defined by atomic coordinates of APOBEC-2, or a three-dimensional model of a homologue of the molecule or molecular structure, wherein the homologue comprises a three dimensional structure that has an average root-mean-square deviation (RMSD) of equal to or less than about 2.0 Å for the backbone atoms in secondary structure elements in the APOBEC-2 protein, wherein the computer comprises: a) a computer-readable medium encoded with the atomic coordinates of the APOBEC-2 protein to create an electronic file; b) a working memory for storing a graphical display software program for processing the electronic file; c) a processor coupled to the working memory and to the computer-readable medium which is capable of representing the electronic file as the three dimensional model; and, d) a display coupled to the processor for visualizing the three dimensional model; wherein the three dimensional structure of the APOBEC protein is displayed on the computer.

EXAMPLE 1

The APOBEC2 Crystal Structure and Functional Implications for AID

The following example is put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec., second(s); min, minute (s); h or hr, hour(s); and the like.

Experimental Procedures

Protein Purification and Crystallization

Human APO2 containing residues 41-224 was cloned and expressed in Escherichia coli as a recombinant GST fusion protein. Following GST cleavage by thrombin, further purification of APO2 was achieved using Superdex-75 gel filtration chromatography. Native and selenium-methionine labeled protein was concentrated to 15 mg per ml in a buffer containing 25 mM Hepes, pH 7.0, 50 mM NaCl and 10 mM dithiothreitol. Crystals were grown at 18° C. by hanging-drop vapor diffusion from a reservoir solution of 85 mM Na-citrate, pH 5.6, 160 mM LiSO4, 24% (weight/volume) polyethylene glycol monomethyl ether and 15% glycerol.

Structure Determination and Refinement

Native and selenium-multiwavelength anomalous diffraction (MAD) data were collected at the synchrotron and processed using HKL200024 (FIG. 5). An initial solution was obtained at 3.5 Å using the program Solve25 and located eight selenium atoms using the peak wavelength data set. A search with SHELXD26 found four additional selenium atoms (totaling twelve) and, subsequently, the program SHARP identified four additional weaker anomalous scattering atoms, which were recognized as Zn atoms. Density modification schemes of solvent flattening and fourfold non-crystallographic symmetry (NCS) averaging were applied using the program RESOLVE27. Additionally, phase extension in RESOLVE was performed with the native data set to 2.5 Å resolution using the two-wavelength MAD phases calculated in SHARP. The molecular model was built based on this experimental map using the program "O" and was refined with the Crystallography and NMR System (CNS). A twofold NCS constrain was applied during the initial simulated annealing, but the final refinement was carried out without NCS constrain. The protein geometry is excellent when examined using the program PROCHECK.

Construction of AID Mutants

Mutant AID proteins were constructed by site-directed mutagenesis using the pGEX-KG-AID vector as the PCR template and primers specific for the respective mutations (5'-CTG AGG ATC TTC ACC GCG TGC CTC TAC TTC TGT GAG GAC-3' (SEQ ID NO: 65) (R112C), 5'-ATC TTC ACC GCG CGC CTC GCC GCC TGT GAG GAC CGC AAG GCT-3' (SEQ ID NO: 66) (Y114/Y115), 5'-GCG CGC CTC TAC TTC TGT GCG GCC CGC AAG GCT GAG CCC GAG-3' (SEQ ID NO: 67)(E117/E118A), 5'-AAG TTT CTT TAC CAA TTC GCA AAT GTC CGC TGG GCT AAG-3' (SEQ ID NO: 68)(K16A), 5'-ACC GCG CGC CTC TAG TIC OCT GAG GAC CGC AAG GCT GAG-3' SEQ ID NO: 69)(C116A), 5'-TAC CAA TTC AAA AAT GTC_GAG TGG GCT AAG GGT CGG CGT-3' (SEQ ID NO: 70)(R19E), and 5'-ACA TCC TTT TCA CTG GAC GCT GGT GCT CTT CGC AAT AAG AAC GGC-3' (SEQ ID NO: 71)(F46A/Y48A). Mutant constructs were verified by DNA sequencing.

Deamination Reactions

Deamination experiments were performed by incubating various concentrations of AID protein (in the range of 0.1 to 0.5 μg) with a 25 nM concentration of single-stranded DNA substrate and 2 units of Uracil DNA glycosylase enzyme in a buffer containing 25 mM Tris pH 8.0 and 50 mM NaCl. The total reaction volume was 20 μl and was incubated at 37° C. for 1 hour. Then 0.8 of 0.5 N NaOH and 0.4 μl of 0.5 M EDTA were added to the reaction. The reaction was heated to 95° C. for 7 minutes. Last, 10 μl of formamide was added. The reaction was loaded onto a 16% TBE-Urea-PAGE gel. Reaction products were visualized on a BioRad FX scanner. The deamination product ran as a lower 30-nt DNA band. The unreacted DNA substrate was visualized as the upper 60-nt band. The DNA substrate used was a fluorescein-dT incorporated single-stranded DNA substrate (5'-taa agg fluorescein -dTga aga gag gag aga gaa gta agc tga aga gag agg aag aga gtg aag gag-3' : SEQ ID NO: 72).

Results

Figure 1:
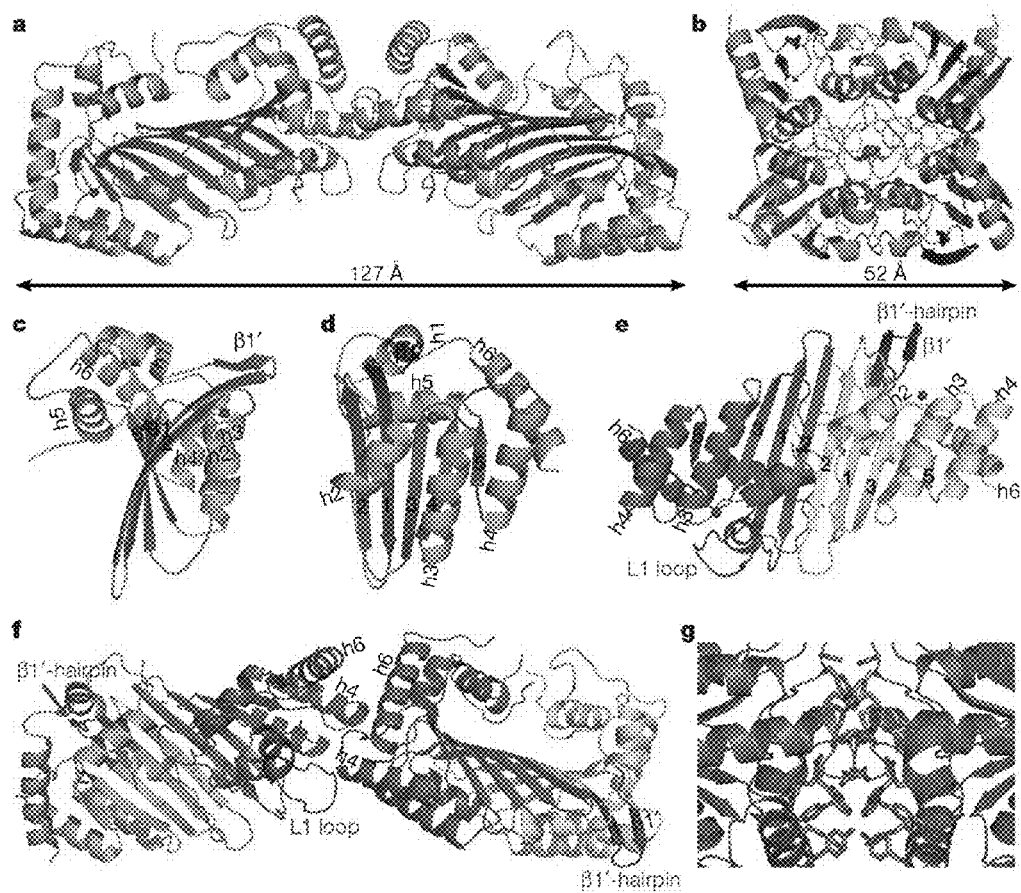
FIG. 1b is the square-shaped structure of human cytidine deaminase (PDB accession number: 1MQ0), a fntCDA.
FIGS. 1c and 1d are the APO2 monomer structure rotated by 90 degrees, showing the unique features of APO2: the short β1' strand and helices h4 and h6. h4 and h6 dictate how APO2 oligomerizes.
FIG. 1e is the APO2 dimer formed by two monomers (in purple and yellow). Each has a different conformation for the h1/β1-turn (in red): a loop (L1) and a hairpin.
FIG. 1f is the tetrameric interface, showing the extensive interactions mediated through h4, h6 and L1.
FIG. 1g is the stick model (hydrophobic, polar and charged amino acids in h4, h6 and L1) of the interactions at the tetramer interface.

APOBEC-2, which contains amino acid residues 41-224, was crystallized with four monomers in each asymmetric unit that form a tetramer with an atypical elongated shape (FIG. 1a). This tetramer assembles through two different monomer-monomer interfaces, in contrast to the canonical square shape of the free nucleotide cytidine deaminase (fntCDA) tetramer (FIG. 1b), in which all four monomers interact with each other. The elongated APO2 tetramer has the shape of a butterfly (FIG. 1a) with an end-to-end span of approximately 126.9 Å.

The APO2 monomer appears to adopt the typical core fold of the fntCDAs with a five-stranded β-sheet flanked by helices on both sides (FIGS. 1c, d). However, one new attribute is the additional α-helices surrounding the core β-sheet (FIGS. 1c, d); six long helices are present in the APO2 monomer whereas only three or four are observed in the fntCDA monomer (excluding the shorter $3_{10}$ helices). Helices h3 and h6 make extensive contacts with h4, stabilizing the position of the helices within the monomer subunit. On the basis of the close sequence homology of APO2 with other APOBEC proteins, the long helix (h4) probably serves as a structural signature of this family (FIGS. 1c, d).

The APO2 dimer is formed by pairing two long β-strands (β2) (FIG. 1e), joining two β-sheets sideways to form one wide β-sheet that resembles a rib cage (FIGS. 1a, e). Twelve residues (residues 82-93) on each β2 strand form 12 hydrogen bonds through main-chain atoms, providing the principal bonding force between the two monomers. The dimer interface is reinforced by the side-chain interactions occurring through the loops and helices located on both sides of the β-sheet. Ordered water molecules also help to stabilize this interface.

The dimer is nearly symmetrical (FIG. 1e) with six helices (h2, h3 and h4 of both molecules) located on one side of the augmented β-sheet and four helices (h1 and h5 of both monomers) on the other side. Capped on both edges of the β-sheet are h4 and h6. However, one part of the dimer shows obvious asymmetry at the turn between h1 and strand β1 (h1/β1-turn). This h1/β1-turn (residues 57-68) assumes a hairpin structure (β1'-hairpin) in one monomer, and a loop conformation (L1) in the other monomer (FIGS. 1e, f).

The APO2 tetramer is formed by two dimers joining through head-to-head interactions. The two dimers make extensive contacts via the residues from h4 and h6, as well as the loop L1 at the h1/β1-turn (FIG. 1f). Residues Y61, F155, M156, W157, P160, Y214 and Y215 from each side of the interface form extensive hydrophobic packing interactions, and residues R57, S62, S63, R153, E158, E159 and E161 establish salt bridges and hydrogen bonds (FIG. 1g). Some charged residues even use their aliphatic side chains to interact with hydrophobic residues. Thus, hydrophobic, polar and charged amino acid side chains are all involved in the tetramerization interactions. The total buried area is 1,745 Å$^2$ within the tetramer interface, where h4 and h6 play a major role forming the interface (FIG. 1f). h4 and h6 also sterically hinder the formation of the square-shaped fntCDA-type tetramer by occupying the space where another monomer would need to be. Therefore, h4 and h6 appear to determine directly the elongated tetramer formation.

Figure 2:
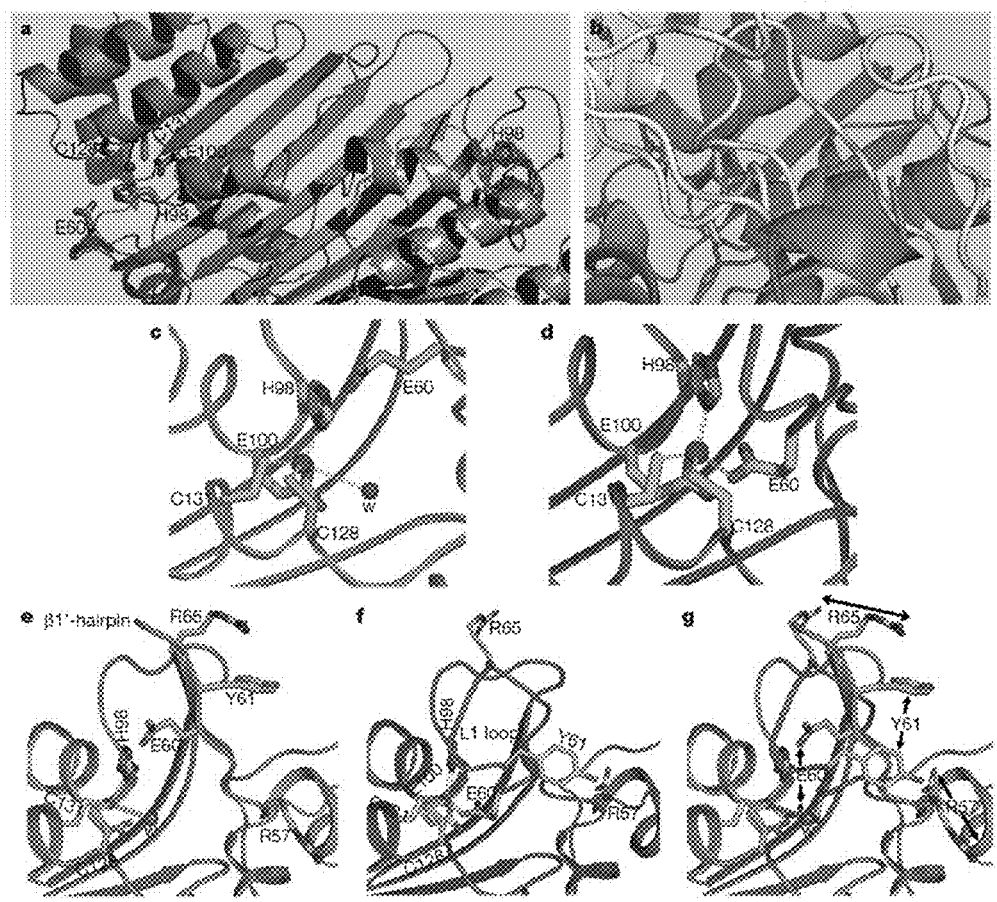
FIG. 2 is the APO2 active site.

A prominent feature of the APO2 tetramer distinctive from the fntCDA tetramer is that the active sites are accessible for large RNA or DNA substrates (FIG. 2a). In the square-shaped fntCDA tetramer, loops from two neighboring monomers cover the active sites so that only small free nucleotides can bind to the buried sites (FIG. 2b). Although the yeast fntCDA, CDD1, has been reported to deaminate the apolipoprotein BmRNA in vitro, its known biological substrate in vivo is a free nucleotide and the CDD1 structure is a canonical square-shaped tetramer.

In fntCDAs, the active centre Zn atom is coordinated by three residues (either three cysteines, or two cysteines+one histidine) and forms a fourth bond with a water molecule with a bond distance of ~3.0 Å (ref. 10). This type of Zn coordination is also present in APO2 (FIG. 2c), but only in the two outer monomers of the tetramer. Surprisingly, the active sites for the other two monomers in the middle of a tetramer contain an E60 residue, which replaces the water molecule and makes the fourth coordination bond with the Zn (FIG. 2d). This coordination of Zn by four residues is unexpected given that all known fntCDA structures have only three amino acid residues participating in Zn coordination.

A closer examination of the structure reveals a 'built-in' mechanism for a conformational switch between the two types of Zn coordination. The switch is mediated by sequences contained in the h1/β1-turn, in which E60 is located. The h1/β1-turn can adopt either a hairpin (β1'-hairpin, FIG. 2e) or a loop (L1) conformation (FIG. 2f), which controls whether or not E60 coordinates with Zn. The E60 is located 6 Å from the Zn when the h1/β1-turn is a β1'-hairpin (FIG. 2e). The β1'-hairpin is stabilized by main-chain hydrogen bonds within the β1'-hairpin and reinforced by interactions between Y61 and the guanidine group of R65. In the two middle monomers of an APO2 tetramer, the h1/β1-turn folds into a loop (L1, FIG. 1f). In this conformation, Y61 rotates its side chain to interact with R57 instead of the R65 (FIGS. 2f, g). The new pairing of Y61 with R57 destabilizes the β1'-hairpin while stabilizing the loop. In the loop conformation, the E60 is 2.2 Å from the Zn (FIG. 2f).

The hairpin-loop switch may have two important consequences. First, switching to the loop and forming the fourth Zn coordination by E60 prevents coordination by water and subsequent hydroxylation of Zn necessary for deamination (FIGS. 2d, f). Second, Zn coordination by E60 pulls the h1/β1-turn approximately 8.5 Å towards the active centre (FIG. 2g), which could restrict substrate access to the active centre. On the other hand, breaking of the fourth coordination of E60 may allow the loop to move away from the active centre to form the β1'-hairpin as observed in the outer monomers. The E60 would no longer prevent the Zn hydroxylation and nucleic acid substrate access to those active sites. Thus, the hairpin-loop switch can be a molecular mechanism for regulating substrate access and enzyme activity mediated through Zn coordination.

The APO2 fragment in the structure shares a 33.3% amino acid identity (44.6% homology) with AID, and the buried residues in APO2 share a 75% identity (96% homology) with AID (FIG. 3a). The highly conserved residues buried inside the structure and those located at the dimer/tetramer interfaces strongly suggest a structural conservation of AID with APO2. Thus, the APO2 crystal structure should provide functional insights for AID and other APOBEC family members, despite of the lack of the known biological activity of APO2. For this reason, we use AID as a surrogate to test how mutations guided by APO2 structure affect AID deamination activity.

We generated glutathione S-transferase (GST)-AID mutants with amino acid substitutions located at the tetrameric interface (FIG. 3b), and showed that the mutants either had no detectable or significantly reduced deaminase activity compared to wild-type GST-AID (FIGS. 3d-f). Mutants R112C and Y114A/F115A were inactive (FIGS. 3e, f), while mutants K16A and C116A had a 3.3-fold reduction in activity (FIGS. 3e, f).

AID mutations within the predicted dimerization domain, F46A/Y48A (FIG. 3c), displayed a four fold decrease in deamination activity (FIGS. 3e, f). The dimer interface is extensive, so two mutations should not completely disrupt dimeric AID. This explains why weak deamination activity was observed with this double AID mutant. These mutational results suggest that the residues within the predicted dimeric and tetrameric interfaces are important for deamination activity. One caveat is that the residues on the tetramer interface are also present on the exposed surface of the outer ends of the tetramer and thus could also be involved in an additional role beside tetramerization (FIGS. 3b, 4d). We noticed that in gel filtration assays the tetramer was a minor species when compared with the dimer, suggesting a stronger dimeric interaction. AID has an arginine (R19) at the equivalent position of the APO2 E60 residue (FIG. 3a) that may have a negative regulatory role for APO2 activity by blocking Zn hydroxylation and substrate access (FIG. 2f).

We showed that an AID R19E mutant mimicking APO2 E60 had a significantly decreased deamination activity (about 4.6-fold less than the wild type, FIGS. 3e, f). Similarly, the AID R24 residue is equivalent to APO2 R65, which interacts with Y61 of APO2 to stabilize the open β1'-hairpin conformation. We predicted that the disruption of the R65-Y61 interaction would collapse the β1'-hairpin into the closed loop conformation to block substrate access and impair deamination activity. Indeed, the AID R24E mutant was completely inactive on single-stranded DNA (FIGS. 3e, f). Mutations in human AID cause hyper-IgM-2 (HIGM-2) syndrome, characterized by an impaired production of high-affinity antibodies (14, 15). The mutated AID residues of HIGM-2 patients are highly conserved in APO2 (FIG. 4a). A plausible explanation for why and how HIGM-2 mutations disrupt AID function is given by the structure of APO2 (FIGS. 4b-e).

On the basis of the crystal structure, HIGM-2 AID mutations can be divided into four classes. The first mutant class (A111, R112, L113 and N168) occurs at the tetramerization interface (FIG. 4b). The second mutant class includes residues in and near the active centre (FIG. 4c), H56, E58, S83, S85 and C87, which are conserved among all APOBEC enzymes. The AID R24 residue is also mutated in HIGM-2 patients. As previously discussed, R24 may stabilize the β1'-hairpin, which keeps the active site open for DNA/RNA access. The third class consists of residues located on the enzyme surface (FIG. 4d), including those residues located at the tetramer interface (A111, R112, L113, N168; see FIG. 4d). A fourth class of HIGM-2 AID mutations are those with large hydrophobic side chains buried within the core (FIG. 4e), including W80, L106, M139 and F151. Three of these residues are located near the active centre. Mutating these residues should disrupt the folding and stability of AID.

Since many of the APOBEC enzymes are reported to form dimers and multimers, the APO2 structure may shed light on how these enzymes oligomerize. The elucidation of the APO2 structure, fortified by the structure-guided predictions for the activity of specific AID mutants, provides a structural basis to pursue further functional studies of APOBEC proteins with an eye towards developing therapeutic strategies to deal with deficiency in deaminating cytidine and to restrict retroviral replication.

While the information provided by the APOBEC-2 structure and other related APOBEC model structures, their uses and related methods have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures.

REFERENCES

1. Pham, P., Bransteitter, R. & Goodman, M. F. Reward versus Risk: DNA Cytidine Deaminases Triggering Immunity and Disease. *Biochemistry* 44, 2703-15 (2005).

2. Conticello, S. G., Thomas, C. J. F., Petersen-Mahrt, S. K. & Neuberger, M. S. Evolution of the AID/APOBEC Family of Polynucleotide (Deoxy)cytidine Deaminases. *Molecular Biology and Evolution* 22, 367-377 (2004).

3. Bransteitter, R., Sneeden, J. L., Allen, S., Pham, P. & Goodman, O. M. F. First AID (Activation-induced Cytidine Deaminase) Is Needed to Produce High Affinity Isotype-switched Antibodies. *Journal of Biological Chemistry* 281, 16833-6 (2006).

4. Chiu, Y. L. & Greene, W. C. Multifaceted antiviral actions of APOBEC3 cytidine deaminases. *Trends in Immunology* 27, 291-7 (2006).

5. Cullen, B. R. Role and Mechanism of Action of the APOBEC3 Family of Antiretroviral Resistance Factors. *Journal of Virology* 80, 1067-1076 (2006).

6. Franca, R., Spadari, S. & Maga, G. APOBEC deaminases as cellular antiviral factors: A novel natural host defense mechanism. *Med Sci Monit* 12, RA92-RA98 (2006).

7. Bonvin, M. et al. Interferon-inducible Expression of APOBEC3 Editing Enzymes in Human Hepatocytes and Inhibition of Hepatitis B Virus Replication. *Hepatology* 43, 1364-1374 (2006).

8. Johansson, E., Mejlhede, N., Neuhard, J. & Larsen, S. Crystal structure of the tetrameric cytidine deaminase from *Bacillus subtilis* at 2.0 Å resolution. *Biochemistry* 41, 2563-70 (2002).

9. Xie, K. et al. The structure of a yeast RNA-editing deaminase provides insight into the fold and function of activation-induced deaminase and APOBEC-1. *Proc. Natl. Acad. Sci.* 101, 8114-9 (2004).

10. Teh, A. et al. The 1.48 Å Resolution Crystal Structure of the Homotetrameric Cytidine Deaminase from Mouse. *Biochemistry* 45, 7825-33 (2006).

11. Chung, S. J., Fromme, J. C. & Verdine, G. L. Structure of human cytidine deaminase bound to a potent inhibitor. *Journal of Medicinal Chemistry* 48, 658-660 (2005).

12. Betts, L., Xiang, S., Short, S. A., Wolfenden, R. & Carter, C. W. Cytidine deaminase. The 2.3 Å crystal structure of an enzyme: transition-state analog complex. *Current Biology* 235, 635-656 (1994).

13. Smith, A. A., Carlow, D. C., Wolfenden, R. & Short, S. A. Mutations Affecting Transition-State Stabilization by Residues Coordinating Zinc at the Active Site of Cytidine Deaminase. *Biochemistry* 33, 6468-74 (1994).

14. Durandy, A., Peron, S. & Fischer, A. Hyper-IgM syndromes. *Current Opinion in Rheumatology* 18, 369-76 (2006).

15. Minegishi, Y. et al. Mutations in Activation-induced Cytidine Deaminase in Patients with Hyper IgM Syndrome. *Clinical Immunology* 97, 203-210 (2000).

16. Anant, S. et al. ARCD-1, an apobec-1-related cytidine deaminase, exerts a dominant negative effect on C to U RNA editing. *American Journal of Cell Physiology* 281, C1904-16 (2001).

17. Jarmuz, A. et al. An anthropoid-specific locus of orphan C to U RNA-editing enzymes on chromosome 22. *Genomics* 79, 285-296 (2002).

18. Shindo, K. et al. The enzymatic activity of CEM15/Apobec-3G is essential for the regulation of the infectivity of HIV-1 virion but not a sole determinant of its antiviral activity. *Journal of Biological Chemistry* 278, 44412-6 (2003).

19. Wiegand, H. L., Doehle, B. P., Bogerd, H. P. & Cullen, B. R. A second human antiretroviral factor, APOBEC3F, is suppressed by the HIV-1 and HIV-2 Vif proteins. *The EMBO Journal* 23, 2451-8 (2004).

20. Opi, S. et al. Monomeric APOBEC3G is catalytically active and has antiviral activity. *Journal of Virology* 80, 4673-4682 (2006).

21. Navarro, F. et al. Complementary function of the two catalytic domains of APOBEC3G. *Virology* 333, 374-386 (2005).

22. Wang, J. et al. Identification of a Specific Domain Required for Dimerization of Activation-induced Cytidine Deaminase. *Journal of Biological Chemistry*, in press (2006).

23. Teng, B. et al. Mutational analysis of apolipoprotein B mRNA editing enzyme (APOBEC1): structure-function relationships of RNA editing and dimerization. *Journal of Lipid Research* 40, 623-35 (1999).

24. Otwinowski, Z. & Minor, W. Processing of X-ray Diffraction Data Collected in Oscillation Mode. *Methods in Enzymology* 276, 307-326 (1997).

25. Terwilliger, T. C. & Berendzen, J. Automated MAD and MIR structure solution. *Acta Crystallographica* 55, 849-61 (1999).

26. Schneider, T. R. & Sheldrick, G. M. Substructure solution with SHELXD. *Acta Crystallographica* 58, 1772-9 (2002).

27. Terwilliger, T. C. Maximum-likelihood density modification. *Acta Crystallographica* 56, 965-72 (2000).

28. Bransteitter, R., Pham, P., Scharff, M. D. & Goodman, M. F. Activation-induced cytidine deaminase deaminates deoxycytidine on single-stranded DNA but requires the action of RNase. *Proc. Natl. Acad. Sci.* 100, 4102-7 (2003).

29. Okazaki, I. M., Kotani, A. & Honjo, T. Role of AID in Tumorogenesis. *Adv. Immunol.* 94, 245-73 (2007).

---

SEQUENCE LISTING

```
<160> NUMBER OF SEQ ID NOS: 72

<210> SEQ ID NO 1
<211> LENGTH: 736
<212> TYPE: PRT
<213> ORGANISM: Homo sapiens

<400> SEQUENCE: 1

Ile Val Thr Gly Glu Arg Leu Pro Ala Asn Phe Phe Lys Phe Gln Phe
1               5                   10                  15

Arg Asn Val Glu Tyr Ser Ser Gly Arg Asn Lys Thr Phe Leu Cys Tyr
            20                  25                  30

Val Val Glu Ala Gln Gly Lys Gly Gly Gln Val Gln Ala Ser Arg Gly
        35                  40                  45

Tyr Leu Glu Asp Glu His Ala Ala Ala His Ala Glu Glu Ala Phe Phe
    50                  55                  60

Asn Thr Ile Leu Pro Ala Phe Asp Pro Ala Leu Arg Tyr Asn Val Thr
65                  70                  75                  80

Trp Tyr Val Ser Ser Ser Pro Cys Ala Ala Cys Ala Asp Arg Ile Ile
                85                  90                  95

Lys Thr Leu Ser Lys Thr Lys Asn Leu Arg Leu Leu Ile Leu Val Gly
            100                 105                 110

Arg Leu Phe Met Trp Glu Glu Pro Glu Ile Gln Ala Ala Leu Lys Lys
        115                 120                 125

Leu Lys Glu Ala Gly Cys Lys Leu Arg Ile Met Lys Pro Gln Asp Phe
    130                 135                 140
```

```
Glu Tyr Val Trp Gln Asn Phe Val Glu Gln Glu Gly Glu Ser Lys
145                 150                 155                 160

Ala Phe Gln Pro Trp Glu Asp Ile Gln Glu Asn Phe Leu Tyr Tyr Glu
                165                 170                 175

Glu Lys Leu Ala Asp Ile Leu Lys Ile Val Thr Gly Glu Arg Leu Pro
            180                 185                 190

Ala Asn Phe Phe Lys Phe Gln Phe Arg Asn Val Glu Tyr Ser Ser Gly
        195                 200                 205

Arg Asn Lys Thr Phe Leu Cys Tyr Val Val Glu Ala Gln Gly Lys Gly
210                 215                 220

Gly Gln Val Gln Ala Ser Arg Gly Tyr Leu Glu Asp Glu His Ala Ala
225                 230                 235                 240

Ala His Ala Glu Glu Ala Phe Phe Asn Thr Ile Leu Pro Ala Phe Asp
                245                 250                 255

Pro Ala Leu Arg Tyr Asn Val Thr Trp Tyr Val Ser Ser Ser Pro Cys
            260                 265                 270

Ala Ala Cys Ala Asp Arg Ile Ile Lys Thr Leu Ser Lys Thr Lys Asn
        275                 280                 285

Leu Arg Leu Leu Ile Leu Val Gly Arg Leu Phe Met Trp Glu Glu Pro
290                 295                 300

Glu Ile Gln Ala Ala Leu Lys Lys Leu Lys Glu Ala Gly Cys Lys Leu
305                 310                 315                 320

Arg Ile Met Lys Pro Gln Asp Phe Glu Tyr Val Trp Gln Asn Phe Val
                325                 330                 335

Glu Gln Glu Glu Gly Glu Ser Lys Ala Phe Gln Pro Trp Glu Asp Ile
            340                 345                 350

Gln Glu Asn Phe Leu Tyr Tyr Glu Glu Lys Leu Ala Asp Ile Leu Lys
        355                 360                 365

Ile Val Thr Gly Glu Arg Leu Pro Ala Asn Phe Phe Lys Phe Gln Phe
370                 375                 380

Arg Asn Val Glu Tyr Ser Ser Gly Arg Asn Lys Thr Phe Leu Cys Tyr
385                 390                 395                 400

Val Val Glu Ala Gln Gly Lys Gly Gly Gln Val Gln Ala Ser Arg Gly
                405                 410                 415

Tyr Leu Glu Asp Glu His Ala Ala Ala His Ala Glu Glu Ala Phe Phe
            420                 425                 430

Asn Thr Ile Leu Pro Ala Phe Asp Pro Ala Leu Arg Tyr Asn Val Thr
        435                 440                 445

Trp Tyr Val Ser Ser Ser Pro Cys Ala Ala Cys Ala Asp Arg Ile Ile
450                 455                 460

Lys Thr Leu Ser Lys Thr Lys Asn Leu Arg Leu Leu Ile Leu Val Gly
465                 470                 475                 480

Arg Leu Phe Met Trp Glu Glu Pro Glu Ile Gln Ala Ala Leu Lys Lys
                485                 490                 495

Leu Lys Glu Ala Gly Cys Lys Leu Arg Ile Met Lys Pro Gln Asp Phe
            500                 505                 510

Glu Tyr Val Trp Gln Asn Phe Val Glu Gln Glu Gly Glu Ser Lys
        515                 520                 525

Ala Phe Gln Pro Trp Glu Asp Ile Gln Glu Asn Phe Leu Tyr Tyr Glu
                530                 535                 540

Glu Lys Leu Ala Asp Ile Leu Lys Ile Val Thr Gly Glu Arg Leu Pro
545                 550                 555                 560

Ala Asn Phe Phe Lys Phe Gln Phe Arg Asn Val Glu Tyr Ser Ser Gly
```

```
                   565                 570                 575
Arg Asn Lys Thr Phe Leu Cys Tyr Val Val Glu Ala Gln Gly Lys Gly
            580                 585                 590

Gly Gln Val Gln Ala Ser Arg Gly Tyr Leu Glu Asp Glu His Ala Ala
        595                 600                 605

Ala His Ala Glu Glu Ala Phe Phe Asn Thr Ile Leu Pro Ala Phe Asp
    610                 615                 620

Pro Ala Leu Arg Tyr Asn Val Thr Trp Tyr Val Ser Ser Pro Cys
625                 630                 635                 640

Ala Ala Cys Ala Asp Arg Ile Ile Lys Thr Leu Ser Lys Thr Lys Asn
                645                 650                 655

Leu Arg Leu Leu Ile Leu Val Gly Arg Leu Phe Met Trp Glu Glu Pro
            660                 665                 670

Glu Ile Gln Ala Ala Leu Lys Lys Leu Lys Glu Ala Gly Cys Lys Leu
        675                 680                 685

Arg Ile Met Lys Pro Gln Asp Phe Glu Tyr Val Trp Gln Asn Phe Val
    690                 695                 700

Glu Gln Glu Glu Gly Glu Ser Lys Ala Phe Gln Pro Trp Glu Asp Ile
705                 710                 715                 720

Gln Glu Asn Phe Leu Tyr Tyr Glu Lys Leu Ala Asp Ile Leu Lys
                725                 730                 735

<210> SEQ ID NO 2
<211> LENGTH: 183
<212> TYPE: PRT
<213> ORGANISM: unknown
<220> FEATURE:
<223> OTHER INFORMATION: mammal

<400> SEQUENCE: 2

Val Thr Gly Glu Arg Leu Pro Ala Asn Phe Phe Lys Phe Gln Phe Arg
1               5                   10                  15

Asn Val Glu Tyr Ser Ser Gly Arg Asn Lys Thr Phe Leu Cys Tyr Val
            20                  25                  30

Val Glu Ala Gln Gly Lys Gly Gly Gln Val Gln Ala Ser Arg Gly Tyr
        35                  40                  45

Leu Glu Asp Glu His Ala Ala His Ala Glu Glu Ala Phe Phe Asn
    50                  55                  60

Thr Ile Leu Pro Ala Phe Asp Pro Ala Leu Arg Tyr Asn Val Thr Trp
65                  70                  75                  80

Tyr Val Ser Ser Ser Pro Cys Ala Ala Cys Ala Asp Arg Ile Ile Lys
                85                  90                  95

Thr Leu Ser Lys Thr Lys Asn Leu Arg Leu Leu Ile Leu Val Gly Arg
            100                 105                 110

Leu Phe Met Trp Glu Glu Pro Glu Ile Gln Ala Ala Leu Lys Lys Leu
        115                 120                 125

Lys Glu Ala Gly Cys Lys Leu Arg Ile Met Lys Pro Gln Asp Phe Glu
    130                 135                 140

Tyr Val Trp Gln Asn Phe Val Glu Gln Glu Glu Gly Glu Ser Lys Ala
145                 150                 155                 160

Phe Gln Pro Trp Glu Asp Ile Gln Glu Asn Phe Leu Tyr Tyr Glu Glu
                165                 170                 175

Lys Leu Ala Asp Ile Leu Lys
            180

<210> SEQ ID NO 3
```

```
<211> LENGTH: 181
<212> TYPE: PRT
<213> ORGANISM: unknown
<220> FEATURE:
<223> OTHER INFORMATION: mammal

<400> SEQUENCE: 3

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu
            180

<210> SEQ ID NO 4
<211> LENGTH: 13
<212> TYPE: PRT
<213> ORGANISM: unknown
<220> FEATURE:
<223> OTHER INFORMATION: mammal

<400> SEQUENCE: 4

Gly Ser Gly Gly Gly Met Ile Val Thr Gly Glu Arg Leu
1               5                   10

<210> SEQ ID NO 5
<211> LENGTH: 13
<212> TYPE: PRT
<213> ORGANISM: unknown
<220> FEATURE:
<223> OTHER INFORMATION: mammal

<400> SEQUENCE: 5

Pro Ala Asn Phe Phe Lys Phe Gln Phe Arg Asn Val Glu
1               5                   10

<210> SEQ ID NO 6
<211> LENGTH: 13
<212> TYPE: PRT
<213> ORGANISM: unknown
<220> FEATURE:
<223> OTHER INFORMATION: mammal

<400> SEQUENCE: 6
```

-continued

```
Tyr Ser Ser Gly Arg Asn Lys Thr Phe Leu Cys Tyr Val
1               5                   10
```

<210> SEQ ID NO 7
<211> LENGTH: 13
<212> TYPE: PRT
<213> ORGANISM: unknown
<220> FEATURE:
<223> OTHER INFORMATION: mammal

<400> SEQUENCE: 7

```
Val Glu Ala Gln Gly Lys Gly Gly Gln Val Gln Ala Ser
1               5                   10
```

<210> SEQ ID NO 8
<211> LENGTH: 13
<212> TYPE: PRT
<213> ORGANISM: unknown
<220> FEATURE:
<223> OTHER INFORMATION: mammal

<400> SEQUENCE: 8

```
Arg Gly Tyr Leu Glu Asp Glu His Ala Ala His Ala
1               5                   10
```

<210> SEQ ID NO 9
<211> LENGTH: 13
<212> TYPE: PRT
<213> ORGANISM: unknown
<220> FEATURE:
<223> OTHER INFORMATION: mammal

<400> SEQUENCE: 9

```
Glu Glu Ala Phe Phe Asn Thr Ile Leu Pro Ala Phe Asp
1               5                   10
```

<210> SEQ ID NO 10
<211> LENGTH: 13
<212> TYPE: PRT
<213> ORGANISM: unknown
<220> FEATURE:
<223> OTHER INFORMATION: mammal

<400> SEQUENCE: 10

```
Pro Ala Leu Arg Tyr Asn Val Thr Trp Tyr Val Ser Ser
1               5                   10
```

<210> SEQ ID NO 11
<211> LENGTH: 13
<212> TYPE: PRT
<213> ORGANISM: unknown
<220> FEATURE:
<223> OTHER INFORMATION: mammal

<400> SEQUENCE: 11

```
Ser Pro Cys Ala Ala Cys Ala Asp Arg Ile Ile Lys Thr
1               5                   10
```

<210> SEQ ID NO 12
<211> LENGTH: 13
<212> TYPE: PRT
<213> ORGANISM: unknown
<220> FEATURE:
<223> OTHER INFORMATION: mammal

<400> SEQUENCE: 12

```
Leu Ser Lys Thr Lys Asn Leu Arg Leu Leu Ile Leu Val
1               5                   10
```

```
<210> SEQ ID NO 13
<211> LENGTH: 13
<212> TYPE: PRT
<213> ORGANISM: unknown
<220> FEATURE:
<223> OTHER INFORMATION: mammal

<400> SEQUENCE: 13

Gly Arg Leu Phe Met Trp Glu Glu Pro Glu Ile Gln Ala
1               5                   10

<210> SEQ ID NO 14
<211> LENGTH: 13
<212> TYPE: PRT
<213> ORGANISM: unknown
<220> FEATURE:
<223> OTHER INFORMATION: mammal

<400> SEQUENCE: 14

Ala Leu Lys Lys Leu Lys Glu Ala Gly Cys Lys Leu Arg
1               5                   10

<210> SEQ ID NO 15
<211> LENGTH: 13
<212> TYPE: PRT
<213> ORGANISM: unknown
<220> FEATURE:
<223> OTHER INFORMATION: mammal

<400> SEQUENCE: 15

Ile Met Lys Pro Gln Asp Phe Glu Tyr Val Trp Gln Asn
1               5                   10

<210> SEQ ID NO 16
<211> LENGTH: 13
<212> TYPE: PRT
<213> ORGANISM: unknown
<220> FEATURE:
<223> OTHER INFORMATION: mammal

<400> SEQUENCE: 16

Phe Val Glu Gln Glu Glu Gly Glu Ser Lys Ala Phe Gln
1               5                   10

<210> SEQ ID NO 17
<211> LENGTH: 13
<212> TYPE: PRT
<213> ORGANISM: unknown
<220> FEATURE:
<223> OTHER INFORMATION: mammal

<400> SEQUENCE: 17

Pro Trp Glu Asp Ile Gln Glu Asn Phe Leu Tyr Tyr Glu
1               5                   10

<210> SEQ ID NO 18
<211> LENGTH: 8
<212> TYPE: PRT
<213> ORGANISM: unknown
<220> FEATURE:
<223> OTHER INFORMATION: mammal

<400> SEQUENCE: 18

Glu Lys Leu Ala Asp Ile Leu Lys
1               5
```

-continued

```
<210> SEQ ID NO 19
<211> LENGTH: 13
<212> TYPE: PRT
<213> ORGANISM: unknown
<220> FEATURE:
<223> OTHER INFORMATION: mammal

<400> SEQUENCE: 19

Gly Ser Gly Gly Gly Met Ile Val Thr Gly Glu Arg Leu
1               5                   10

<210> SEQ ID NO 20
<211> LENGTH: 13
<212> TYPE: PRT
<213> ORGANISM: unknown
<220> FEATURE:
<223> OTHER INFORMATION: mammal

<400> SEQUENCE: 20

Pro Ala Asn Phe Phe Lys Phe Gln Phe Arg Asn Val Glu
1               5                   10

<210> SEQ ID NO 21
<211> LENGTH: 13
<212> TYPE: PRT
<213> ORGANISM: unknown
<220> FEATURE:
<223> OTHER INFORMATION: mammal

<400> SEQUENCE: 21

Tyr Ser Ser Gly Arg Asn Lys Thr Phe Leu Cys Tyr Val
1               5                   10

<210> SEQ ID NO 22
<211> LENGTH: 13
<212> TYPE: PRT
<213> ORGANISM: unknown
<220> FEATURE:
<223> OTHER INFORMATION: mammal

<400> SEQUENCE: 22

Val Glu Ala Gln Gly Lys Gly Gly Gln Val Gln Ala Ser
1               5                   10

<210> SEQ ID NO 23
<211> LENGTH: 13
<212> TYPE: PRT
<213> ORGANISM: unknown
<220> FEATURE:
<223> OTHER INFORMATION: mammal

<400> SEQUENCE: 23

Arg Gly Tyr Leu Glu Asp Glu His Ala Ala His Ala
1               5                   10

<210> SEQ ID NO 24
<211> LENGTH: 13
<212> TYPE: PRT
<213> ORGANISM: unknown
<220> FEATURE:
<223> OTHER INFORMATION: mammal

<400> SEQUENCE: 24

Glu Glu Ala Phe Phe Asn Thr Ile Leu Pro Ala Phe Asp
1               5                   10

<210> SEQ ID NO 25
<211> LENGTH: 13
```

```
<212> TYPE: PRT
<213> ORGANISM: unknown
<220> FEATURE:
<223> OTHER INFORMATION: mammal

<400> SEQUENCE: 25

Pro Ala Leu Arg Tyr Asn Val Thr Trp Tyr Val Ser Ser
1               5                   10

<210> SEQ ID NO 26
<211> LENGTH: 13
<212> TYPE: PRT
<213> ORGANISM: unknown
<220> FEATURE:
<223> OTHER INFORMATION: mammal

<400> SEQUENCE: 26

Ser Pro Cys Ala Ala Cys Ala Asp Arg Ile Ile Lys Thr
1               5                   10

<210> SEQ ID NO 27
<211> LENGTH: 13
<212> TYPE: PRT
<213> ORGANISM: unknown
<220> FEATURE:
<223> OTHER INFORMATION: mammal

<400> SEQUENCE: 27

Leu Ser Lys Thr Lys Asn Leu Arg Leu Leu Ile Leu Val
1               5                   10

<210> SEQ ID NO 28
<211> LENGTH: 13
<212> TYPE: PRT
<213> ORGANISM: unknown
<220> FEATURE:
<223> OTHER INFORMATION: mammal

<400> SEQUENCE: 28

Gly Arg Leu Phe Met Trp Glu Glu Pro Glu Ile Gln Ala
1               5                   10

<210> SEQ ID NO 29
<211> LENGTH: 13
<212> TYPE: PRT
<213> ORGANISM: unknown
<220> FEATURE:
<223> OTHER INFORMATION: mammal

<400> SEQUENCE: 29

Ala Leu Lys Lys Leu Lys Glu Ala Gly Cys Lys Leu Arg
1               5                   10

<210> SEQ ID NO 30
<211> LENGTH: 13
<212> TYPE: PRT
<213> ORGANISM: unknown
<220> FEATURE:
<223> OTHER INFORMATION: mammal

<400> SEQUENCE: 30

Ile Met Lys Pro Gln Asp Phe Glu Tyr Val Trp Gln Asn
1               5                   10

<210> SEQ ID NO 31
<211> LENGTH: 13
<212> TYPE: PRT
<213> ORGANISM: unknown
```

```
<220> FEATURE:
<223> OTHER INFORMATION: mammal

<400> SEQUENCE: 31

Phe Val Glu Gln Glu Glu Gly Glu Ser Lys Ala Phe Gln
1               5                   10

<210> SEQ ID NO 32
<211> LENGTH: 13
<212> TYPE: PRT
<213> ORGANISM: unknown
<220> FEATURE:
<223> OTHER INFORMATION: mammal

<400> SEQUENCE: 32

Pro Trp Glu Asp Ile Gln Glu Asn Phe Leu Tyr Tyr Glu
1               5                   10

<210> SEQ ID NO 33
<211> LENGTH: 8
<212> TYPE: PRT
<213> ORGANISM: unknown
<220> FEATURE:
<223> OTHER INFORMATION: mammal

<400> SEQUENCE: 33

Glu Lys Leu Ala Asp Ile Leu Lys
1               5

<210> SEQ ID NO 34
<211> LENGTH: 13
<212> TYPE: PRT
<213> ORGANISM: unknown
<220> FEATURE:
<223> OTHER INFORMATION: mammal

<400> SEQUENCE: 34

Gly Ser Gly Gly Gly Met Ile Val Thr Gly Glu Arg Leu
1               5                   10

<210> SEQ ID NO 35
<211> LENGTH: 13
<212> TYPE: PRT
<213> ORGANISM: unknown
<220> FEATURE:
<223> OTHER INFORMATION: mammal

<400> SEQUENCE: 35

Pro Ala Asn Phe Phe Lys Phe Gln Phe Arg Asn Val Glu
1               5                   10

<210> SEQ ID NO 36
<211> LENGTH: 13
<212> TYPE: PRT
<213> ORGANISM: unknown
<220> FEATURE:
<223> OTHER INFORMATION: mammal

<400> SEQUENCE: 36

Tyr Ser Ser Gly Arg Asn Lys Thr Phe Leu Cys Tyr Val
1               5                   10

<210> SEQ ID NO 37
<211> LENGTH: 13
<212> TYPE: PRT
<213> ORGANISM: unknown
<220> FEATURE:
<223> OTHER INFORMATION: mammal
```

<400> SEQUENCE: 37

Val Glu Ala Gln Gly Lys Gly Gly Gln Val Gln Ala Ser
1               5                   10

<210> SEQ ID NO 38
<211> LENGTH: 13
<212> TYPE: PRT
<213> ORGANISM: unknown
<220> FEATURE:
<223> OTHER INFORMATION: mammal

<400> SEQUENCE: 38

Arg Gly Tyr Leu Glu Asp Glu His Ala Ala Ala His Ala
1               5                   10

<210> SEQ ID NO 39
<211> LENGTH: 13
<212> TYPE: PRT
<213> ORGANISM: unknown
<220> FEATURE:
<223> OTHER INFORMATION: mammal

<400> SEQUENCE: 39

Glu Glu Ala Phe Phe Asn Thr Ile Leu Pro Ala Phe Asp
1               5                   10

<210> SEQ ID NO 40
<211> LENGTH: 13
<212> TYPE: PRT
<213> ORGANISM: unknown
<220> FEATURE:
<223> OTHER INFORMATION: mammal

<400> SEQUENCE: 40

Pro Ala Leu Arg Tyr Asn Val Thr Trp Tyr Val Ser Ser
1               5                   10

<210> SEQ ID NO 41
<211> LENGTH: 13
<212> TYPE: PRT
<213> ORGANISM: unknown
<220> FEATURE:
<223> OTHER INFORMATION: mammal

<400> SEQUENCE: 41

Ser Pro Cys Ala Ala Cys Ala Asp Arg Ile Ile Lys Thr
1               5                   10

<210> SEQ ID NO 42
<211> LENGTH: 13
<212> TYPE: PRT
<213> ORGANISM: unknown
<220> FEATURE:
<223> OTHER INFORMATION: mammal

<400> SEQUENCE: 42

Leu Ser Lys Thr Lys Asn Leu Arg Leu Leu Ile Leu Val
1               5                   10

<210> SEQ ID NO 43
<211> LENGTH: 13
<212> TYPE: PRT
<213> ORGANISM: unknown
<220> FEATURE:
<223> OTHER INFORMATION: mammal

<400> SEQUENCE: 43

```
Gly Arg Leu Phe Met Trp Glu Glu Pro Glu Ile Gln Ala
1               5                   10
```

<210> SEQ ID NO 44
<211> LENGTH: 13
<212> TYPE: PRT
<213> ORGANISM: unknown
<220> FEATURE:
<223> OTHER INFORMATION: mammal

<400> SEQUENCE: 44

```
Ala Leu Lys Lys Leu Lys Glu Ala Gly Cys Lys Leu Arg
1               5                   10
```

<210> SEQ ID NO 45
<211> LENGTH: 13
<212> TYPE: PRT
<213> ORGANISM: unknown
<220> FEATURE:
<223> OTHER INFORMATION: mammal

<400> SEQUENCE: 45

```
Ile Met Lys Pro Gln Asp Phe Glu Tyr Val Trp Gln Asn
1               5                   10
```

<210> SEQ ID NO 46
<211> LENGTH: 13
<212> TYPE: PRT
<213> ORGANISM: unknown
<220> FEATURE:
<223> OTHER INFORMATION: mammal

<400> SEQUENCE: 46

```
Phe Val Glu Gln Glu Glu Gly Glu Ser Lys Ala Phe Gln
1               5                   10
```

<210> SEQ ID NO 47
<211> LENGTH: 13
<212> TYPE: PRT
<213> ORGANISM: unknown
<220> FEATURE:
<223> OTHER INFORMATION: mammal

<400> SEQUENCE: 47

```
Pro Trp Glu Asp Ile Gln Glu Asn Phe Leu Tyr Tyr Glu
1               5                   10
```

<210> SEQ ID NO 48
<211> LENGTH: 8
<212> TYPE: PRT
<213> ORGANISM: unknown
<220> FEATURE:
<223> OTHER INFORMATION: mammal

<400> SEQUENCE: 48

```
Glu Lys Leu Ala Asp Ile Leu Lys
1               5
```

<210> SEQ ID NO 49
<211> LENGTH: 13
<212> TYPE: PRT
<213> ORGANISM: unknown
<220> FEATURE:
<223> OTHER INFORMATION: mammal

<400> SEQUENCE: 49

```
Gly Ser Gly Gly Gly Met Ile Val Thr Gly Glu Arg Leu
```

-continued

```
1               5                   10
```

<210> SEQ ID NO 50
<211> LENGTH: 13
<212> TYPE: PRT
<213> ORGANISM: unknown
<220> FEATURE:
<223> OTHER INFORMATION: mammal
<400> SEQUENCE: 50

```
Pro Ala Asn Phe Phe Lys Phe Gln Phe Arg Asn Val Glu
1               5                   10
```

<210> SEQ ID NO 51
<211> LENGTH: 13
<212> TYPE: PRT
<213> ORGANISM: unknown
<220> FEATURE:
<223> OTHER INFORMATION: mammal
<400> SEQUENCE: 51

```
Tyr Ser Ser Gly Arg Asn Lys Thr Phe Leu Cys Tyr Val
1               5                   10
```

<210> SEQ ID NO 52
<211> LENGTH: 13
<212> TYPE: PRT
<213> ORGANISM: unknown
<220> FEATURE:
<223> OTHER INFORMATION: mammal
<400> SEQUENCE: 52

```
Val Glu Ala Gln Gly Lys Gly Gly Gln Val Gln Ala Ser
1               5                   10
```

<210> SEQ ID NO 53
<211> LENGTH: 13
<212> TYPE: PRT
<213> ORGANISM: unknown
<220> FEATURE:
<223> OTHER INFORMATION: mammal
<400> SEQUENCE: 53

```
Arg Gly Tyr Leu Glu Asp Glu His Ala Ala His Ala
1               5                   10
```

<210> SEQ ID NO 54
<211> LENGTH: 13
<212> TYPE: PRT
<213> ORGANISM: unknown
<220> FEATURE:
<223> OTHER INFORMATION: mammal
<400> SEQUENCE: 54

```
Glu Glu Ala Phe Phe Asn Thr Ile Leu Pro Ala Phe Asp
1               5                   10
```

<210> SEQ ID NO 55
<211> LENGTH: 13
<212> TYPE: PRT
<213> ORGANISM: unknown
<220> FEATURE:
<223> OTHER INFORMATION: mammal
<400> SEQUENCE: 55

```
Pro Ala Leu Arg Tyr Asn Val Thr Trp Tyr Val Ser Ser
1               5                   10
```

-continued

```
<210> SEQ ID NO 56
<211> LENGTH: 13
<212> TYPE: PRT
<213> ORGANISM: unknown
<220> FEATURE:
<223> OTHER INFORMATION: mammal

<400> SEQUENCE: 56

Ser Pro Cys Ala Ala Cys Ala Asp Arg Ile Ile Lys Thr
1               5                   10

<210> SEQ ID NO 57
<211> LENGTH: 13
<212> TYPE: PRT
<213> ORGANISM: unknown
<220> FEATURE:
<223> OTHER INFORMATION: mammal

<400> SEQUENCE: 57

Leu Ser Lys Thr Lys Asn Leu Arg Leu Leu Ile Leu Val
1               5                   10

<210> SEQ ID NO 58
<211> LENGTH: 13
<212> TYPE: PRT
<213> ORGANISM: unknown
<220> FEATURE:
<223> OTHER INFORMATION: mammal

<400> SEQUENCE: 58

Gly Arg Leu Phe Met Trp Glu Glu Pro Glu Ile Gln Ala
1               5                   10

<210> SEQ ID NO 59
<211> LENGTH: 13
<212> TYPE: PRT
<213> ORGANISM: unknown
<220> FEATURE:
<223> OTHER INFORMATION: mammal

<400> SEQUENCE: 59

Ala Leu Lys Lys Leu Lys Glu Ala Gly Cys Lys Leu Arg
1               5                   10

<210> SEQ ID NO 60
<211> LENGTH: 13
<212> TYPE: PRT
<213> ORGANISM: unknown
<220> FEATURE:
<223> OTHER INFORMATION: mammal

<400> SEQUENCE: 60

Ile Met Lys Pro Gln Asp Phe Glu Tyr Val Trp Gln Asn
1               5                   10

<210> SEQ ID NO 61
<211> LENGTH: 13
<212> TYPE: PRT
<213> ORGANISM: unknown
<220> FEATURE:
<223> OTHER INFORMATION: mammal

<400> SEQUENCE: 61

Phe Val Glu Gln Glu Glu Gly Glu Ser Lys Ala Phe Gln
1               5                   10

<210> SEQ ID NO 62
```

```
<211> LENGTH: 13
<212> TYPE: PRT
<213> ORGANISM: unknown
<220> FEATURE:
<223> OTHER INFORMATION: mammal

<400> SEQUENCE: 62

Pro Trp Glu Asp Ile Gln Glu Asn Phe Leu Tyr Tyr Glu
1               5                   10

<210> SEQ ID NO 63
<211> LENGTH: 8
<212> TYPE: PRT
<213> ORGANISM: unknown
<220> FEATURE:
<223> OTHER INFORMATION: mammal

<400> SEQUENCE: 63

Glu Lys Leu Ala Asp Ile Leu Lys
1               5

<210> SEQ ID NO 64
<211> LENGTH: 58
<212> TYPE: PRT
<213> ORGANISM: unknown
<220> FEATURE:
<223> OTHER INFORMATION: mammal
<220> FEATURE:
<221> NAME/KEY: MISC_FEATURE
<222> LOCATION: (2)..(2)
<223> OTHER INFORMATION: wherein the "Xaa" represents any amino acid
<220> FEATURE:
<221> NAME/KEY: MISC_FEATURE
<222> LOCATION: (4)..(31)
<223> OTHER INFORMATION: wherein the "Xaa's" represent any amino acid,
      and a sequence of amino acids with a length of from 23 to 28
      residues
<220> FEATURE:
<221> NAME/KEY: MISC_FEATURE
<222> LOCATION: (34)..(57)
<223> OTHER INFORMATION: wherein the "Xaa's" represent any amino acid,
      and a sequence of amino acids with a length of 24 residues

<400> SEQUENCE: 64

His Xaa Glu Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Pro
                20                  25                  30

Cys Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Cys
    50                  55

<210> SEQ ID NO 65
<211> LENGTH: 39
<212> TYPE: DNA
<213> ORGANISM: unknown
<220> FEATURE:
<223> OTHER INFORMATION: mammal

<400> SEQUENCE: 65
ctgaggatct tcaccgcgtg cctctacttc tgtgaggac                      39

<210> SEQ ID NO 66
<211> LENGTH: 42
<212> TYPE: DNA
<213> ORGANISM: unknown
<220> FEATURE:
<223> OTHER INFORMATION: mammal
```

-continued

<400> SEQUENCE: 66
atcttcaccg cgcgcctcgc cgcctgtgag gaccgcaagg ct                42

<210> SEQ ID NO 67
<211> LENGTH: 42
<212> TYPE: DNA
<213> ORGANISM: unknown
<220> FEATURE:
<223> OTHER INFORMATION: mammal

<400> SEQUENCE: 67
gcgcgcctct acttctgtgc ggcccgcaag gctgagcccg ag                42

<210> SEQ ID NO 68
<211> LENGTH: 39
<212> TYPE: DNA
<213> ORGANISM: unknown
<220> FEATURE:
<223> OTHER INFORMATION: mammal

<400> SEQUENCE: 68
aagtttcttt accaattcgc aaatgtccgc tgggctaag                   39

<210> SEQ ID NO 69
<211> LENGTH: 39
<212> TYPE: DNA
<213> ORGANISM: unknown
<220> FEATURE:
<223> OTHER INFORMATION: mammal

<400> SEQUENCE: 69
accgcgcgcc tctacttcgc tgaggaccgc aaggctgag                   39

<210> SEQ ID NO 70
<211> LENGTH: 39
<212> TYPE: DNA
<213> ORGANISM: unknown
<220> FEATURE:
<223> OTHER INFORMATION: mammal

<400> SEQUENCE: 70
taccaattca aaaatgtcga gtgggctaag ggtcggcgt                   39

<210> SEQ ID NO 71
<211> LENGTH: 45
<212> TYPE: DNA
<213> ORGANISM: unknown
<220> FEATURE:
<223> OTHER INFORMATION: mammal

<400> SEQUENCE: 71
acatcctttt cactggacgc tggtgctctt cgcaataaga acggc            45

<210> SEQ ID NO 72
<211> LENGTH: 60
<212> TYPE: DNA
<213> ORGANISM: unknown
<220> FEATURE:
<223> OTHER INFORMATION: mammal
<220> FEATURE:
<221> NAME/KEY: misc_feature
<222> LOCATION: (7)..(7)

-continued

```
<223> OTHER INFORMATION: wherein deoxythymidine is covalently attached
      to fluorescein

<400> SEQUENCE: 72
taaaggtgaa gagaggagag agaagtaagc tgaagagaga gaaggaagag agtgaaggag          60
```

What is claimed is:

1. A method for identifying a compound that selectively binds to a target site of an Apolipoprotein B mRNA-editing enzyme catalytic polypeptide-2 (APOBEC-2) protein or a structural homologue of the Apolipoprotein B mRNA-editing enzyme catalytic polypeptide-2 (APOBEC-2) protein, the method comprising:
   (a) generating on a computer the three dimensional structural features of the Apolipoprotein B mRNA-editing enzyme catalytic polypeptide-2 (APOBEC-2) protein according to FIG. 6,
   wherein the three dimensional structural features comprise a tetramer of the Apolipoprotein B mRNA-editing enzyme catalytic polypeptide-2 (APOBEC-2) protein, wherein the tetramer is formed by combination of two dimers of the Apolipoprotein B mRNA-editing enzyme catalytic polypeptide-2 (APOBEC-2) protein joined through head-to-head interactions, and each dimer is formed by combination of two monomers;
   (b) designing a compound capable of selectively binding to the target site in the Apolipoprotein B mRNA-editing enzyme catalytic polypeptide-2 (APOBEC-2) protein or the structural homologue of the Apolipoprotein B mRNA-editing enzyme catalytic polypeptide-2 (APOBEC-2) protein;
   wherein the target site comprises an interface between the monomer, the dimer and the tetramer of the Apolipoprotein B mRNA-editing enzyme catalytic polypeptide-2 (APOBEC-2), the structural homologue of the Apolipoprotein B mRNA-editing enzyme catalytic polypeptide-2 (APOBEC-2) protein, an active site of the Apolipoprotein B mRNA-editing enzyme catalytic polypeptide-2 (APOBEC-2), or the structural homologue of the Apolipoprotein B mRNA-editing enzyme catalytic polypeptide-2 (APOBEC-2) protein,
   wherein zinc is coordinated within the active site of the Apolipoprotein B mRNA-editing enzyme catalytic polypeptide-2 (APOBEC-2),
   and wherein the three dimensional structural features of the dimers and the tetramer are necessary for deamination of deoxyribonucleic acid (DNA) or ribonucleic acid (RNA) substrates:
   (c) synthesizing the compound;
   (d) contacting the monomer, the dimer or the tetramer of the Apolipoprotein B mRNA-editing enzyme catalytic polypeptide-2 (APOBEC-2) protein or the structural homologue of the Apolipoprotein B mRNA-editing enzyme catalytic polypeptide-2 (APOBEC-2) protein with the compound; and
   (e) identifying a candidate compound that selectively binds to the target site, wherein selective binding of the candidate compound to the target site interferes with at least one biological activity of the Apolipoprotein B mRNA-editing enzyme catalytic polypeptide-2 (APOBEC-2) or the structural homologue of the Apolipoprotein B mRNA-editing enzyme catalytic polypeptide-2 (APOBEC-2).

2. The method of claim 1, further comprising measuring the biological activity of the Apolipoprotein B mRNA-editing enzyme catalytic polypeptide-2 (APOBEC-2) protein or the structural homologue of the Apolipoprotein B mRNA-editing enzyme catalytic polypeptide-2 (APOBEC-2)protein, when the Apolipoprotein B mRNA-editing enzyme catalytic polypeptide-2 (APOBEC-2) protein or the structural homologue of the Apolipoprotein B mRNA-editing enzyme catalytic polypeptide-2 (APOBEC-2) protein is contacted with the candidate compound.

3. The method of claim 2, further comprising comparing the biological activity of the Apolipoprotein B mRNA-editing enzyme catalytic polypeptide-2 (APOBEC-2) protein or the structural homologue of the Apolipoprotein B mRNA-editing enzyme catalytic polypeptide-2 (APOBEC-2), when the Apolipoprotein B mRNA-editing enzyme catalytic polypeptide-2 (APOBEC-2) protein or the structural homologue of the Apolipoprotein B mRNA-editing enzyme catalytic polypeptide-2 (APOBEC-2) protein is in the presence of and in the absence of the candidate compound.

4. The method of claim 1, further comprising contacting the candidate compound identified in step (c) with a cell that expresses the Apolipoprotein B mRNA-editing enzyme catalytic polypeptide-2 (APOBEC-2) protein or the structural homologue of the Apolipoprotein B mRNA-editing enzyme catalytic polypeptide-2 (APOBEC-2) and detecting a change in a phenotype of the cell when the candidate compound is present.

5. The method of claim 1, wherein the method further comprises steps for identifying an anti-viral agent capable of restricting replication of a retrovirus, method further comprising:
   (f) providing the candidate compound identified in step (c) to a solution or to a cell comprising an HIV viral infectivity factor (Vif) protein and the Apolipoprotein B mRNA-editing enzyme catalytic polypeptide-2 (APOBEC-2) or the structural homologue of the Apolipoprotein B mRNA-editing enzyme catalytic polypeptide-2 (APOBEC-2), wherein the solution or the cell is under a condition in which the HIV viral infectivity factor (Vif) protein and the Apolipoprotein B mRNA-editing enzyme catalytic polypeptide-2 (APOBEC-2) or the structural homologue of the Apolipoprotein B mRNA-editing enzyme catalytic polypeptide-2 (APOBEC-2) can interact in the absence of the candidate compound:
   (g) measuring binding of the HIV viral infectivity factor (Vif) protein and the Apolipoprotein B mRNA-editing enzyme catalytic polypeptide-2 (APOBEC-2) or the structural homologue of the Apolipoprotein B mRNA-editing enzyme catalytic polypeptide-2 (APOBEC-2), as compared to in the absence of the candidate compound; and
   (h) selecting the candidate compound that disrupts the binding interaction between the HIV viral infectivity factor (Vif) protein and the Apolipoprotein B mRNA-editing enzyme catalytic polypeptide-2 (APOBEC-2) or the structural homologue of the Apolipoprotein B mRNA-editing enzyme catalytic polypeptide-2 (APOBEC-2) as the anti-viral agent.

6. The method of claim 1, wherein the candidate compound treats Hyper-IgM-2 Syndrome, or a B cell lymphoma.

7. The method according to claim 1, wherein the structural homologue of the Apolipoprotein B mRNA-editing enzyme catalytic polypeptide-2 (APOBEC-2) bears similarity with a root-mean-square deviation (RMSD)) of about 2.0 Å or less with the monomer, the dimer, or the tetramer of the Apolipoprotein B mRNA-editing enzyme catalytic polypeptide-2 (APOBEC-2).

8. The method according to claim 1, wherein selective binding of the candidate compound to the target site is determined by a cell-based assay.

9. The method according to claim 1, wherein selective binding of the candidate compound to the target site is determined by a non-cell based assay.

10. The method according, to claim 1, wherein the at least one biological activity of the Apolipoprotein B mRNA-editing enzyme catalytic polypeptide-2 (APOBEC-2) or the structural homologue of the Apolipoprotein B mRNA-editing enzyme catalytic polypeptide-2 (APOBEC-2) is binding of the Apolipoprotein B mRNA-editing enzyme catalytic polypeptide-2 (APOBEC-2) or the structural homologue of the Apolipoprotein B mRNA-editing enzyme catalytic polypeptide-2 (APOBEC-2) to a substrate.

11. The method according to claim 10, wherein the substrate of the Apolipoprotein B mRNA-editing enzyme catalytic polypeptide-2 (APOBEC-2) or the structural homologue of the Apolipoprotein B mRNA-editing enzyme catalytic polypeptide-2 (APOBEC-2) comprises deoxyribonucleic acid (DNA), ribonucleic acid (RNA), or zinc.

12. The method according to claim 1, wherein the at least one biological activity of the Apolipoprotein B mRNA-editing enzyme catalytic polypeptide-2 (APOBEC-2) or the structural homologue of the Apolipoprotein B mRNA-editing enzyme catalytic polypeptide-2 (APOBEC-2) is deaminating cytosines to uracils in a single-stranded deoxyribonucleic acid (DNA) or ribonucleic acid (RNA) molecule.

13. The method according to claim 5, wherein the anti-viral agent identified from step (h) is capable of treating infections caused by retrovirus.

14. The method according to claim 13, wherein the retrovirus comprises hepatitis B virus and lentivirus.

15. The method according to claim 14, wherein the lentivirus is human immunodeficiency virus (HIV).

16. The method according to claim 1, wherein the three dimensional structural features of the Apolipoprotein B mRNA-editing enzyme catalytic polypeptide-2 (APOBEC-2) protein are defined by atomic coordinates derived from the Apolipoprotein B mRNA-editing enzyme catalytic polypeptide-2 (APOBEC-2) protein arranged in a crystalline manner in a space group $P2_12_12_1$ so as to form a unit cell of dimensions a=37.841 Å, b=89.41 Å, and c=245.77 Å.

17. The method according to claim 1, wherein the structural homologue of the Apolipoprotein B mRNA-editing enzyme catalytic polypeptide-2 (APOBEC-2) bears similarity with a root-mean-square deviation (RMSD) of about 1.0 Å or less with the monomer, the dimer, or the tetramer of the Apolipoprotein B mRNA-editing enzyme catalytic polypeptide-2 (APOBEC-2).

18. The method according to claim 1, wherein the structural homologue of the Apolipoprotein B mRNA-editing enzyme catalytic polypeptide-2 (APOBEC-2) bears similarity with a root-mean-square deviation (RMSD) of about 0.7 Å or less with the monomer, the dimer, or the tetramer of the Apolipoprotein B mRNA-editing enzyme catalytic polypeptide-2 (APOBEC-2).

19. The method according to claim 1, wherein the structural homologue of the Apolipoprotein B mRNA-editing enzyme catalytic polypeptide-2 (APOBEC-2) bears similarity with a root-mean-square deviation (RMSD) of about 0.5 Å or less with the monomer, the dimer, or the tetramer of the Apolipoprotein B mRNA-editing enzyme catalytic polypeptide-2 (APOBEC-2).

20. The method according to claim 1, wherein the structural homologue of the Apolipoprotein B mRNA-editing enzyme catalytic polypeptide-2 (APOBEC-2) bears similarity with a root-mean-square deviation (RMSD) of about 0.3 Å or less with the monomer, the dimer, or the tetramer of the Apolipoprotein B mRNA-editing enzyme catalytic polypeptide-2 (APOBEC-2).

* * * * *